US010112935B2

(12) United States Patent
Aicher et al.

(10) Patent No.: US 10,112,935 B2
(45) Date of Patent: Oct. 30, 2018

(54) INDAZOLYL THIADIAZOLAMINES AND RELATED COMPOUNDS FOR INHIBITION OF RHO-ASSOCIATED PROTEIN KINASE AND THE TREATMENT OF DISEASE

(71) Applicant: Lycera Corporation, Ann Arbor, MI (US)

(72) Inventors: Thomas Daniel Aicher, Ann Arbor, MI (US); Fernando Padilla, Ann Arbor, MI (US); Peter L. Toogood, Ann Arbor, MI (US); Shoujun Chen, Ann Arbor, MI (US)

(73) Assignee: Lycera Corporation, Ann Arbor, MI (US)

( * ) Notice: Subject to any disclaimer, the term of this patent is extended or adjusted under 35 U.S.C. 154(b) by 0 days.

(21) Appl. No.: 15/551,132

(22) PCT Filed: Feb. 26, 2016

(86) PCT No.: PCT/US2016/019678

§ 371 (c)(1),
(2) Date: Aug. 15, 2017

(87) PCT Pub. No.: WO2016/138335

PCT Pub. Date: Sep. 1, 2016

(65) Prior Publication Data

US 2018/0093978 A1 Apr. 5, 2018

Related U.S. Application Data

(60) Provisional application No. 62/121,636, filed on Feb. 27, 2015.

(51) Int. Cl.

| | |
|---|---|
| *C07D 417/12* | (2006.01) |
| *A61K 31/416* | (2006.01) |
| *A61K 31/433* | (2006.01) |
| *C07D 417/14* | (2006.01) |
| *C07D 471/04* | (2006.01) |
| *C07D 498/04* | (2006.01) |
| *C07D 513/04* | (2006.01) |
| *A61P 11/00* | (2006.01) |

(52) U.S. Cl.

CPC .......... *C07D 417/12* (2013.01); *A61K 31/416* (2013.01); *A61K 31/433* (2013.01); *A61P 11/00* (2018.01); *C07D 417/14* (2013.01); *C07D 471/04* (2013.01); *C07D 498/04* (2013.01); *C07D 513/04* (2013.01)

(58) Field of Classification Search

CPC ... C07D 417/12; A61K 31/416; A61K 31/433
See application file for complete search history.

(56) References Cited

U.S. PATENT DOCUMENTS

| | | | |
|---|---|---|---|
| 2009/0093452 | A1 | 4/2009 | Huang et al. |
| 2011/0190355 | A1 | 8/2011 | Klein et al. |

FOREIGN PATENT DOCUMENTS

| | | | |
|---|---|---|---|
| KR | 2013-0100587 | A | 9/2013 |
| WO | WO-2007/076161 | A2 | 7/2007 |
| WO | WO-2008/093674 | A1 | 8/2008 |
| WO | WO-2008/138448 | A2 | 11/2008 |
| WO | WO-2012/040499 | A2 | 3/2012 |
| WO | WO-2012/049161 | A1 | 4/2012 |
| WO | WO-2014/055996 | A2 | 4/2014 |
| WO | WO-2014/055999 | A2 | 4/2014 |

OTHER PUBLICATIONS

International Search Report and Written Opinion for PCT/US2016/019678 dated May 31, 2016. (9 pages).
Barbuceanu, S.-F. et al. "New heterocyclic compounds from 1,2,4-triazole and 1,3,4-thiadiazole class bearing diphenylsulfone moieties. Synthesis, characterization and antimicrobial activity evaluation," *Eur. J. Med. Chem.* (2012) vol. 49, pp. 417-423.
Khan, I. et al. "Synthesis, antioxidant activities and urease inhibition of some new 1,2,4-triazole and 1,3,4-thiadiazole derivatives," *Eur. J. Med. Chem.* (2010) vol. 45, pp. 5200-5207.
SciFinder Database Record for KR2013-0100587. (1 page).
Yang, S.-J. et al. "Regioselective Synthesis of 2-Amino-Substituted 1,3,4-Oxadiazole and 1,3,4-Thiadiazole Derivatives via Reagent-Based Cyclization of Thiosemicarbazide Intermediate," *J. Org. Chem.* (2013) vol. 78, pp. 438-444.

*Primary Examiner* — Rebecca L Anderson
*Assistant Examiner* — Karen Cheng
(74) *Attorney, Agent, or Firm* — Dechert LLP

(57) ABSTRACT

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds. An exemplary indazolyl thiadiazolamine compound is an N-(5-[5-[(1H4ndazol-5-yl)amino]-1,3,4-thiadiazol-2-yl]pyridin-3-yl)acetamide compound.

32 Claims, No Drawings

INDAZOLYL THIADIAZOLAMINES AND RELATED COMPOUNDS FOR INHIBITION OF RHO-ASSOCIATED PROTEIN KINASE AND THE TREATMENT OF DISEASE

CROSS-REFERENCE TO RELATED APPLICATIONS

This application is the national stage of International (PCT) Patent Application Serial No. PCT/US2016/019678, filed Feb. 26, 2016, which claims the benefit of and priority to U.S. Provisional Patent Application Ser. No. 62/121,636, filed Feb. 27, 2015, the contents of each of which are hereby incorporated by reference.

FIELD OF THE INVENTION

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds.

BACKGROUND

Rho-associated protein kinase (ROCK) is a member of the serine-threonine protein kinase family. ROCK, which exists in two isoforms, ROCK1 and ROCK2, is an effector molecule of RhoA, and the RhoA/ROCK signaling pathway is involved in a number of cellular functions, which include, for example, actin organization, cell adhesion, cell migration, and cytokinesis. In addition, the RhoA/ROCK signaling pathway is involved in regulating smooth muscle contraction. Inhibitors of ROCK have been reported to be useful for treating multiple medical disorders, such as fibrosis, inflammatory disorders, autoimmune disorders, and cardiovascular disorders.

Fibrosis is a condition featuring excess, fibrotic connective tissue, which may form in numerous types of bodily tissues, including, for example, skin, lung, kidney, heart, liver, and gastrointestinal tract. Exemplary fibrotic disorders include scleroderma, kidney fibrosis, pulmonary fibrosis, liver fibrosis, cardiac fibrosis, and skin fibrosis. Scleroderma is frequently characterized as featuring increased synthesis of collagen, and the disease typically features hardening of the skin, and in more severe forms of the disease may also affect internal organs. Pulmonary fibrosis involves scarring of lung tissue, which can occur when alveoli and interstitial tissue of the lungs become inflamed and develop scars in an attempt to repair themselves. Pulmonary fibrosis can be caused by various conditions which include chronic inflammatory processes, infections, environmental agents (e.g., asbestos or silica), exposure to ionizing radiation, and even certain medications (e.g., pingyangmycin, busulfan, methotrexate, and nitrofurantoin). Cystic fibrosis is a type of pulmonary fibrosis. Liver fibrosis typically involves excessive accumulation of extracellular matrix proteins in the liver, and the subsequent scarring process. Over time, advanced liver fibrosis can result in cirrhosis of the liver. Cardiac fibrosis can involve a disproportionate accumulation of fibrillated collagen that can occur after myocyte death, inflammation, enhanced workload, hypertrophy, and/or stimulation by a number of hormones, cytokines, and growth factors. Cardiac fibrosis may contribute to sudden cardiac death, ventricular tachyarrhythmia, left ventricular (LV) dysfunction, and heart failure.

Inflammatory disorders that continue to afflict a significant amount of people include psoriasis and nonalcoholic steatohepatitis. Psoriasis is a chronic, inflammatory, hyperproliferative skin condition. It has been reported that approximately 150,000 new cases of psoriasis and approximately 400 deaths from psoriasis are reported each year. See Stern, R. S. (1995) Dermatol. Clin. 13:717-722. Typical symptoms of psoriasis include skin lesions, redness, inflammation, or patches of skin that become dry, red, covered with silvery scales, cracked, and/or painful. Psoriasis can affect all parts of the skin, but it is more commonly seen on the skin of the trunk, scalp, elbows, knees, or in the fingernails or toenails. The symptoms of psoriasis may become worse in response to cuts, burns, insect bites or other skin injuries. The symptoms of psoriasis can also be more severe in patients having a deficient immune system, such as patients afflicted with AIDS or receiving cancer chemotherapy. Amongst the several types of psoriasis, the most common type of psoriasis is chronic plaque syndrome. This type of psoriasis consists of periods of remission and relapse during the course of the condition. If left untreated, plaque psoriasis can evolve into a more severe condition, such as pustular psoriasis or erythrodermic psoriasis. Current treatment options for psoriasis include acitretin, cyclosporine, methotrexate, apremilast, phototherapy, and biologics such as anti-TNF antibodies adalimumab, etanercept, and the anti-IL12/IL23 antibody ustekinumab. However, these treatments don't meet the needs of all patients suffering from psoriasis, and thus the need exists for new therapeutic agents for treating psoriasis and other inflammatory disorders.

Nonalcoholic steatohepatitis (NASH) is a liver disorder featuring inflammation and damage associated with buildup of fat in the liver. A significant percentage of patients suffering from NASH are approximately forty to fifty years old and also suffer from obesity, insulin resistance, high cholesterol, and/or metabolic syndrome. Diagnostic tests for identifying NASH include histological evaluation of a liver biopsy, and patients suffering from NASH may experience right upper quadrant pain, hepatomegaly, or non-specific symptoms such as abdominal discomfort, weakness, fatigue, and/or malaise. Treatment options for NASH are quite limited and new therapeutic agents are needed.

Accordingly, a need exists for improved treatments for inflammatory and other medical disorders. The present invention addresses this need and provides other related advantages.

SUMMARY

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds. In particular, one aspect of the invention provides a collection of indazolyl thiadiazolamines and related compounds, such as a compound represented by Formula I:

(I)

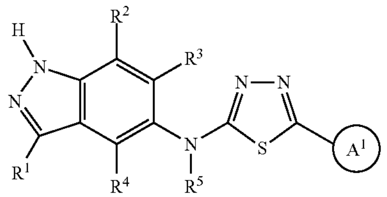

or a pharmaceutically acceptable salt thereof, or a solvate of the foregoing, where the variables are as defined in the detailed description. Another aspect of the invention provides a collection of indazolyl thiadiazolamines and related compounds represented by Formula II:

(II)

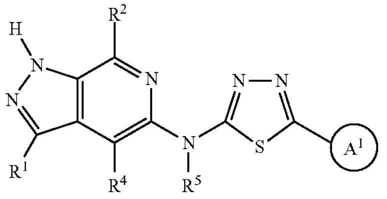

or a pharmaceutically acceptable salt thereof, or a solvate of the foregoing, where the variables are as defined in the detailed description. Further description of additional collections of indazolyl thiadiazolamines and related compounds are described in the detailed description. The compounds may be part of a pharmaceutical composition comprising a pharmaceutically acceptable carrier. Preferred embodiments utilize compounds described herein that are highly selective for inhibiting ROCK2, while having little inhibitory activity towards ROCK1. Such selective inhibition of ROCK2 provides multiple benefits when using the compounds in medical therapy.

Another aspect of the invention provides a method of treating a patient suffering from a medical disorder. The method comprises administering to the patient a therapeutically effective amount of one or more indazolyl thiadiazolamine or related compounds described herein, e.g., a compound of Formula I, I-A, I-1, I-1A, I-1B, II, II-1, II-1A, or II-1B, to treat the disorder. A large number of disorders can be treated using the indazolyl thiadiazolamine and related compounds described herein. For example, the compounds described herein can be used to treat an inflammatory disorder, immune disorder, fibrotic disorder, or cardiovascular disorder. In certain embodiments, the disorder is scleroderma, psoriasis, nonalcoholic steatohepatitis, giant cell arteritis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, ulcerative colitis, asthma, uveitis, rheumatoid arthritis, or epidermal hyperplasia. In yet other embodiments, the disorder is cystic fibrosis or idiopathic pulmonary fibrosis.

Another aspect of the invention provides a method of inhibiting Rho-associated protein kinase isoform 2. The method comprises exposing a Rho-associated protein kinase isoform 2 to an effective amount of one or more indazolyl thiadiazolamine or related compounds described herein, e.g., a compound of Formula I, I-A, I-1, I-1A, I-1B, II, II-1, II-1A, or II-1B, to inhibit said Rho-associated protein kinase isoform 2.

DETAILED DESCRIPTION

The invention provides indazolyl thiadiazolamines and related compounds, pharmaceutical compositions, methods of inhibiting Rho-associated protein kinase, and methods of treating inflammatory disorders, immune disorders, fibrotic disorders, and other medical disorders using such compounds. Preferred embodiments utilize compounds described herein that are highly selective for inhibiting ROCK2, while having little inhibitory activity towards ROCK1. Such selective inhibition of ROCK2 provides multiple benefits when using the compounds in medical therapy. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include $—CH_2—$, $—CH_2CH_2—$, and $—CH_2C(H)(CH_3)CH_2—$.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl.

The term "haloalkyl" refers to an alkyl group that is substituted with at least one halogen. Exemplary haloalkyl groups include $—CH_2F$, $—CHF_2$, $—CF_3$, $—CH_2CF_3$, $—CF_2CF_3$, and the like.

The term "hydroxyalkyl" refers to an alkyl group that is substituted with at least one hydroxyl group. Exemplary hydroxyalkyl groups include $—CH_2C(H_2)OH$, $—CH_2C(H)(OH)CH_3$, and the like.

The term "hydroxyalkylene" refers to a diradical of a hydroxyalkyl group. Exemplary hydroxyalkylene groups include $—CH_2C(H)(OH)—$, $—CH_2C(H)(OH)CH_2—$, and the like.

The term "aralkyl" refers to an alkyl group substituted with an aryl group. Exemplary aralkyl groups include

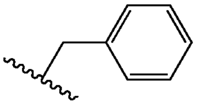 and 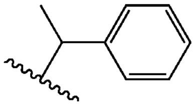.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group. The aryl group may be a 6-14 membered carbocyclic aromatic group, or a 6-10 membered carbocyclic aromatic group. In certain embodiments, the aryl group is not substituted (i.e., it is unsubstituted).

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocyclic ring or a 9-10 membered bicyclic ring. In certain embodiments, the heteroaryl is not substituted, i.e., it is unsubstituted.

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. The nonaromatic ring may be a saturated ring, or it may be a partially saturated ring (i.e., it contains one or more double bonds between ring atoms, but does not contain enough double bonds between ring atoms to qualify as aromatic). Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, oxo, sulfonyl, sulfonamido, sulfonamide, ketone, aldehyde, ester, heterocyclyl, aryl or heteroaryl moieties, —$CF_3$, —CN, or the like. In certain embodiments, the heterocyclyl group is a 3-7 membered ring that, unless specified otherwise, is substituted or unsubstituted. In certain embodiments, the heterocyclyl is not substituted, i.e., it is unsubstituted.

The term "heterocycloalkyl" refers to a saturated heterocyclyl group having, for example, 3-7 ring atoms (which may be C and one or more of O, N, and S). In certain embodiments, the heterocycloalkyl is not substituted, i.e., it is unsubstituted.

The term "oxo-heterocycloalkyl" refers to a heterocycloalkyl group substituted by an oxo group (i.e., =O).

The terms "amine" and "amino" are art-recognized and refer to both unsubstituted and substituted amines, e.g., a moiety that may be represented by the general formulas:

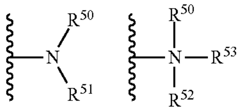

wherein $R^{50}$, $R^{51}$, $R^{52}$ and $R^{53}$ each independently represent a hydrogen, an alkyl, an alkenyl, —$(CH_2)_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—$(CH_2)_m$—$R^{61}$, where m and $R^{61}$ are described above.

The term "oxo" is art-recognized and refers to a "=O" substituent. For example, a cyclopentane substituted with an oxo group is cyclopentanone.

The symbol "∿∿" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound" or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Nonlimiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

The term "$IC_{50}$" is art-recognized and refers to the concentration of a compound that is required for 50% inhibition of its target.

The term "$EC_{50}$" is art-recognized and refers to the concentration of a compound that is required to achieve 50% of the maximum possible activation of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to N,N-dimethylformamide. The abbreviation "DMA" is art-recognized and refers to dimethylacetamide. The abbreviation "EDTA" is art-recognized and refers to ethylenediaminetetraacetic acid. The abbreviation "TFA" is art-recognized and refers to trifluoroacetic acid. The abbreviation "Ts" is art-recognized and refers to tosylate. The abbreviation "TBS" is art-recognized and refers to tert-butyldimethylsilyl. The abbreviation "DMSO" is art-recognized and refers to dimethylsulfoxide. The abbreviation "ACN" is art-recognized and refers to acetonitrile.

As a general matter, compositions specifying a percentage are by weight unless otherwise specified.

I. Indazolyl Thiadiazolamines and Related Compounds

The invention provides indazolyl thiadiazolamines and related compounds. Exemplary compounds are described in the following sections, along with exemplary procedures for making the compounds. Additional exemplary compounds and synthetic procedures are described in the Examples.

Another aspect of the provides a compound represented by Formula I:

(I)

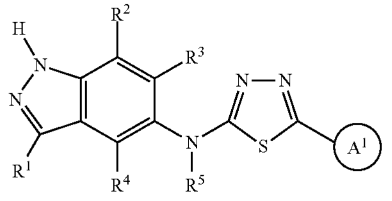

or a pharmaceutically acceptable salt thereof, or a solvate of the foregoing; wherein:

$R^1$ and $R^4$ each represent independently for each occurrence hydrogen, halogen, $C_1$-$C_3$ alkyl, $C_1$-$C_3$ haloalkyl, cyclopropyl, $C_2$-$C_4$ alkenyl, or cyano;

$R^2$ and $R^3$ each represent independently for each occurrence hydrogen, $C_1$-$C_3$ alkyl, cyclopropyl, or cyano;

$R^5$ is hydrogen, $C_1$-$C_6$ alkyl, $C_1$-$C_6$ hydroxyalkyl, or —$CO_2R^{12}$;

$R^6$ and $R^7$ each represent independently for each occurrence hydrogen, $C_1$-$C_6$ alkyl, $C_1$-$C_6$ hydroxyalkyl, or $C_3$-$C_6$ cycloalkyl; or $R^6$ and $R^7$ when attached to the same nitrogen atom may be taken together with the nitrogen atom to form a 3-7 membered ring optionally substituted with 1 or 2 $R^{12}$;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, —($C_1$-$C_6$ alkylene)-O—($C_1$-$C_6$ alkyl), or —($C_1$-$C_6$ alkylene)-N($R^6$)($R^7$); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N$(R^6)_2$, and —($C_1$-$C_6$ alkylene)-$CO_2R^6$;

$R^{10}$ represents independently for each occurrence $C_1$-$C_6$ alkyl, $C_1$-$C_6$ haloalkyl, $C_3$-$C_6$ cycloalkyl, $C_1$-$C_6$ hydroxyalkyl, —($C_1$-$C_6$ alkylene)-O—($C_1$-$C_6$ alkyl), —($C_1$-$C_6$ alkylene)-N($R^8$)($R^9$), —($C_1$-$C_6$ alkylene)-$CO_2R^6$, —($C_1$-$C_6$ alkylene)-(3-7 membered heterocycloalkyl), or 3-7 membered heterocycloalkyl; wherein said cycloalkyl is optionally substituted by 1 or 2 $C_1$-$C_6$ alkyl;

$R^{11}$ represents independently for each occurrence a 5-6 membered heteroaryl or 3-7 membered heterocycloalkyl, each of which is optionally substituted with 1 or 2 occurrences of $Y^1$;

$R^{12}$ represents independently for each occurrence $C_1$-$C_6$ alkyl or $C_3$-$C_6$ cycloalkyl;

$A^1$ is a cyclic group selected from:

(i)

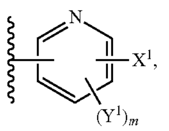

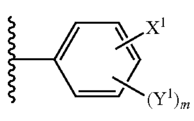

,

-continued

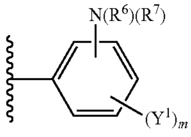

, or

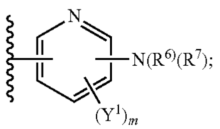

(ii)

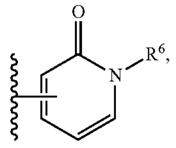

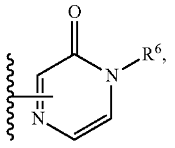

or dihydropyridinyl, each being optionally substituted by $X^1$ and 0, 1, 2, or 3 occurrences of $Y^1$;

(iii) a heteroaryl selected from the group consisting a 8-10 membered bicyclic heteroaryl, a 5-membered heteroaryl, and a 6-membered heteroaryl containing at least two ring nitrogen atoms; wherein said heteroaryl is optionally substituted by 1, 2, or 3 substituents independently selected from the group consisting of $X^1$, $Y^1$, —($C_1$-$C_6$alkylene)-$CO_2R^8$, —N($R^6$)($R^7$), —O-(3-7 membered heterocyclyl), a 3-7 membered heterocycloalkyl, and $C_6$ aryl;

(iv) a 3-7 membered heterocycloalkyl, $C_3$-$C_7$ cycloalkyl, or 8-10 membered bicyclic partially unsaturated heterocyclyl, each optionally substituted by oxo, $C_6$ aryl, $X^1$, and 0, 1, 2, or 3 occurrences of $Y^1$; or (v) aralkyl or heteroaralkyl, each being optionally substituted by a $C_6$ aryl, $X^1$, and 0, 1, 2, or 3 occurrences of $Y^1$;

$X^1$ represents independently for each occurrence:

—N($R^6$)C(O)-(3-7 membered heterocyclyl), —N($R^6$)C(O)-phenyl, —N($R^6$)C(O)-aralkyl, or —N($R^6$)C(O)-heteroaralkyl; each of which is optionally substituted by 1, 2, or 3 substituents independently selected from the group consisting of $Y^1$ and —N($R^8$)($R^9$);

—$CO_2R^8$, —C(O)N($R^8$)($R^9$), —C(O)$R^{11}$, —C(O)$R^{12}$, —C(O)-(3-7 membered heterocyclyl), —C(O)N($R^8$)($R^{10}$), —N($R^6$)C(O)$R^{10}$, —N($R^{10}$)C(O)$R^{10}$, —N($R^6$)$CO_2R^{10}$, —N($R^8$)$SO_2R^{10}$, —N($R^6$)—($C_1$-$C_6$ alkylene)-C(O)N($R^8$)($R^9$), —N($R^6$)—C(O)—($C_1$-$C_6$ hydroxyalkylene)-N($R^8$)($R^9$), —N($R^6$)—C(O)-(2-6 membered heteroalkyl), —N($R^6$)C(O)N($R^6$)($R^7$), or —$NO_2$;

—O—($C_1$-$C_6$alkylene)-$CO_2R^8$, —OC(O)$R^{12}$, —O—($C_1$-$C_6$ alkylene)-C(O)N($R^8$)($R^9$), —O—($C_1$-$C_6$ alkylene)-N($R^8$)($R^9$), —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;

—$SO_2R^{10}$, —$SO_2$N($R^8$)-heteroaryl, cyano, or —P(O)$(OR^8)_2$;

5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —N($R^6$)($R^7$); or —($C_2$-$C_6$ alkylene)-aryl, —($C_2$-$C_6$ alkylene)-heterocyclyl, or —($C_1$-$C_6$ alkylene)-$COR^{12}$;

$Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, $C_2$-$C_6$ alkenyl, cyano, hydroxyl, —$CO_2R^8$, —C(O)N($R^8$)($R^9$), —N($R^6$)C(O)

$R^{10}$, —$N(R^6)C(O)N(R^6)(R^7)$, —($C_1$-$C_6$ alkylene)-$CO_2R^8$, —($C_1$-$C_6$ alkylene)-O—($C_1$-$C_6$ alkyl), —($C_1$-$C_6$alkylene)-$N(R^6)(R^7)$, —($C_1$-$C_6$alkylene)-$N(R^6)S(O)_2R^{12}$, $C_6$ alkylene)-S—$C(O)R^{12}$, —S—$R^{12}$, or 3-7 membered heterocycloalkyl; and m is 0, 1, 2, or 3.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

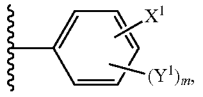

$X^1$ is —$N(R^6)C(O)$-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula I or a pharmaceutically acceptable salt thereof. In certain other embodiments, the compound is a compound of Formula I. In yet other embodiments, the compound is a compound of Formula I or a solvate thereof, such as $C_1$-$C_3$ haloalkanoic acid solvate.

The compound can be further characterized according to the definition of variables $R^1$ through $R^{10}$. Accordingly, in certain embodiments, $R^1$, $R^2$, and $R^3$ are independently hydrogen. In certain embodiments, $R^4$ is hydrogen. In certain other embodiments, $R^4$ is chloro. In certain embodiments, $R^5$ is hydrogen. In certain embodiments, $R^6$ and $R^7$ each represent independently for each occurrence hydrogen or $C_1$-$C_6$ alkyl. In certain embodiments, $R^8$ and $R^9$ each represent independently for each occurrence or $C_1$-$C_6$ alkyl. In certain embodiments, $R^8$ and $R^9$ each represent independently for each occurrence hydrogen, $C_1$-$C_6$ alkyl, $C_1$-$C_6$ hydroxyalkyl, or $C_3$-$C_6$ cycloalkyl. In certain embodiments, $R^{10}$ is $C_1$-$C_6$ alkyl, $C_1$-$C_6$ haloalkyl, $C_3$-$C_6$ cycloalkyl, or $C_1$-$C_6$ hydroxyalkyl. In certain embodiments, $R^{10}$ is $C_1$-$C_6$ alkyl.

The compound can be further characterized according to the definition of variable $A^1$. Accordingly, in certain embodiments, $A^1$ is

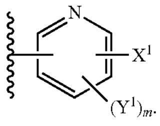

In certain embodiments, $A^1$ is

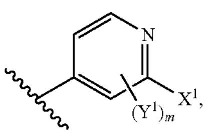

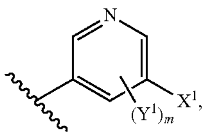

or

-continued

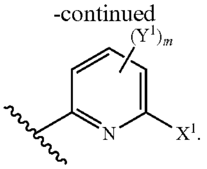

In certain embodiments, $A^1$ is

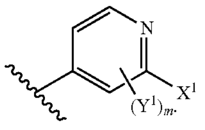

In certain embodiments, $A^1$ is

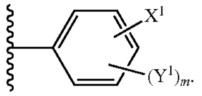

In certain embodiments, $A^1$ is

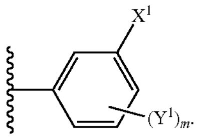

In certain embodiments, $A^1$ is

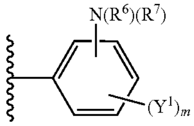

or

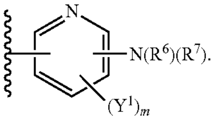

In certain embodiments, $A^1$ is

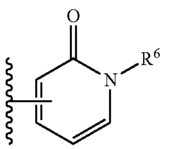

optionally substituted by $X^1$ and 0, 1, 2, or 3 occurrences of $Y^1$.

In certain embodiments, $A^1$ is a heteroaryl selected from the group consisting a 8-10 membered bicyclic heteroaryl, a 5-membered heteroaryl, and a 6-membered heteroaryl containing at least two ring nitrogen atoms; wherein said heteroaryl is optionally substituted by 1, 2, or 3 substituents independently selected from the group consisting of $X^1$, $Y^1$, —($C_1$-$C_6$ alkylene)-$CO_2R^8$, —$N(R^6)(R^7)$, —O-(3-7 membered heterocyclyl), a 3-7 membered heterocycloalkyl, and $C_6$ aryl. In certain embodiments, $A^1$ is a 8-10 membered bicyclic heteroaryl substituted by 1, 2, or 3 substituents independently selected from the group consisting of $X^1$, $Y^1$, —($C_1$-$C_6$ alkylene)-$CO_2R^8$, —O-(3-7 membered heterocyclyl), a 3-7 membered heterocycloalkyl, and $C_6$ aryl. In certain embodiments, $A^1$ is a 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo[d]oxazolyl, 1H-indazolyl, and oxazolo[5,4-b]pyridinyl, each being optionally substituted by 1, 2, or 3 substituents independently selected from the group consisting of $X^1$, $Y^1$, —($C_1$-$C_6$ alkylene)-$CO_2R^8$, —O-(3-7 membered heterocyclyl), a 3-7 membered heterocycloalkyl, and $C_6$ aryl. In certain embodiments, $A^1$ is a 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo[d]oxazolyl, 1H-indazolyl, and oxazolo[5,4-b]pyridinyl, each being optionally substituted by 1, 2, or 3 substituents independently selected from the group consisting of $Y^1$, a 3-7 membered heterocycloalkyl, and $C_6$ aryl. In certain embodiments, $A^1$ is a 3-7 membered heterocycloalkyl or a 8-10 membered bicyclic partially unsaturated heterocyclyl, each being optionally substituted by oxo, $C_6$ aryl, $X^1$, and 0, 1, 2, or 3 occurrences of $Y^1$.

The compound can be further characterized according to the definition of variable $X^1$. Accordingly, in certain embodiments, $X^1$ is —$N(R^6)C(O)$-(3-7 membered heterocyclyl) optionally substituted by 1, 2, or 3 substituents independently selected from the group consisting of $Y^1$ and —$N(R^8)(R^9)$. In certain embodiments, $X^1$ is —C(O)-(5 or 6-membered heteroaryl optionally substituted with 1 or 2 occurrences of $Y^1$). In certain embodiments, $X^1$ is —C(O)-phenyl optionally substituted by 1, 2, or 3 occurrences of $Y^1$. In certain embodiments, $X^1$ is —$CO_2R^8$, —$C(O)N(R^8)(R^9)$, —$C(O)R^{11}$, —$C(O)R^{12}$, —C(O)-(3-7 membered heterocyclyl), —$C(O)N(R^8)(R^{10})$, —$N(R^6)C(O)R^{10}$, —$N(R^{10})C(O)R^{10}$, —$N(R^6)CO_2R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), —$N(R^6)C(O)N(R^6)(R^7)$, or —$NO_2$. In certain embodiments, $X^1$ is —$CO_2R^8$ or —$C(O)N(R^8)(R^9)$. In certain embodiments, $X^1$ is —$N(R^6)C(O)R^{10}$, —$N(R^{10})C(O)R^{10}$, —$N(R^6)CO_2R^{10}$, or —$N(R^8)SO_2R^{10}$. In certain embodiments, $X^1$ is —$N(R^6)CO_2R^{10}$. In certain embodiments, $X^1$ is —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), or —$N(R^6)C(O)N(R^6)(R^7)$.

In certain embodiments, $X^1$ is —O—($C_1$-$C_6$alkylene)-$CO_2R^8$, —$OC(O)R^{12}$, —O—($C_1$-$C_6$ alkylene)-$C(O)N(R^8)(R^9)$, —O—($C_1$-$C_6$ alkylene)-$N(R^8)(R^9)$, —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl. In certain embodiments, $X^1$ is $SO_2R^{10}$, —$SO_2N(R^8)$-heteroaryl, cyano, or —$P(O)(OR^8)_2$.

In certain embodiments, $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —$N(R^6)(R^7)$. In certain embodiments, $X^1$ is a 5-6 membered heteroaryl optionally substituted with 1, 2, or 3 substituents independently selected from the group consisting of $Y^1$ and phenyl. In certain embodiments, $X^1$ is a 5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl, each being optionally substituted with 1, 2, or 3 occurrences of $Y^1$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, hydroxyl, or —($C_1$-$C_6$ alkylene)-$N(R^6)(R^7)$. In certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain other embodiments, $Y^1$ represents independently for each occurrence halogen or $C_1$-$C_6$ alkyl.

The compound can be further characterized according to the definition of variable m. Accordingly, in certain embodiments, m is 0. In certain other embodiments, m is 1 or 2.

The description above describes multiple embodiments relating to compounds of Formula I. The patent application specifically contemplates all combinations of the embodiments. For example, the invention contemplates a compound of Formula I wherein $A^1$ is

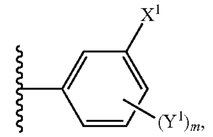

$X^1$ is —C(O)-(5-membered heteroaryl optionally substituted with 1 or 2 occurrences of $Y^1$), and m is 0.

Another aspect of the invention provides a compound represented by Formula I-A:

(I-A)

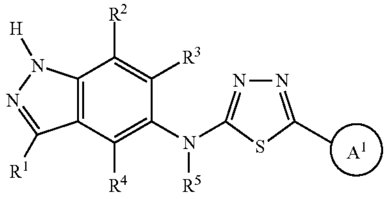

or a pharmaceutically acceptable salt thereof, or a solvate of the foregoing; wherein:

$R^1$, $R^2$, $R^3$, and $R^5$ are hydrogen;

$R^4$ is chloro or fluoro;

$R^6$ and $R^7$ each represent independently for each occurrence hydrogen or $C_1$-$C_3$ alkyl;

$R^8$ and $R^9$ each represent independently for each occurrence hydrogen or $C_1$-$C_3$ alkyl; or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, —$CO_2R^6$, —$N(R^6)_2$, and hydroxyl;

$R^{10}$ is $C_1$-$C_6$ alkyl, $C_1$-$C_6$ haloalkyl, $C_3$-$C_6$ cycloalkyl, or $C_1$-$C_6$ hydroxyalkyl;

$A^1$ is a cyclic group selected from:

(i)

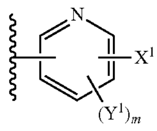

or

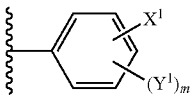

;

-continued (ii)

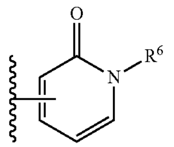

substituted by $X^1$ and 0, 1, 2, or 3 occurrences of $Y^1$; or (iii) a heteroaryl selected from the group consisting of a 8-10 membered bicyclic heteroaryl, a 5-membered heteroaryl, and a 6-membered heteroaryl containing at least two ring nitrogen atoms; wherein said heteroaryl is optionally substituted by 1, 2, or 3 substituents independently selected from the group consisting of $X^1$, $Y^1$, —($C_1$-$C_6$ alkylene)-$CO_2R^8$, —N($R^6$)($R^7$), —O-(3-7 membered heterocyclyl), a 3-7 membered heterocycloalkyl, and $C_6$ aryl;

$X^1$ represents independently for each occurrence:

—N($R^6$)C(O)-(3-7 membered heterocyclyl) or —N($R^6$)C(O)-phenyl, each of which is optionally substituted by 1, 2, or 3 substituents independently selected from the group consisting of $Y^1$ and —N($R^8$)($R^9$);

—$CO_2R^8$, —C(O)N($R^8$)($R^9$), —N($R^6$)C(O)$R^{10}$, —N($R^{10}$)C(O)$R^{10}$, —N($R^6$)$CO_2R^{10}$, or —N($R^8$)$SO_2R^{10}$;

—O—($C_1$-$C_6$alkylene)-$CO_2R^8$, —O—($C_1$-$C_6$ alkylene)-C(O)N($R^8$)($R^9$), —O—($C_1$-$C_6$ alkylene)-N($R^8$)($R^9$), or —O—($C_1$-$C_6$ alkyl); or 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —N($R^6$)($R^7$);

$Y^1$ represents independently for each occurrence halogen, $C_1$-$C_6$ alkyl, $C_1$-$C_6$ haloalkyl, $C_1$-$C_6$ hydroxyalkyl, —$CO_2R^8$, hydroxyl, or —($C_1$-$C_6$alkylene)-N($R^6$)($R^7$); and m is 0, 1, 2, or 3

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

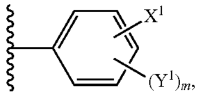

$X^1$ is —N($R^6$)C(O)-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula I-A or a pharmaceutically acceptable salt thereof. In certain other embodiments, the compound is a compound of Formula I-A. In yet other embodiments, the compound is a compound of Formula I-A or a solvate thereof, such as $C_1$-$C_3$ haloalkanoic acid solvate.

The compound can be further characterized according to the definition of variables $R^1$ through $R^{10}$. Accordingly, in certain embodiments, $R^4$ is chloro. In certain embodiments, $R^6$ and $R^7$ each represent independently for each occurrence hydrogen or $C_1$-$C_6$ alkyl. In certain embodiments, $R^8$ and $R^9$ each represent independently for each occurrence hydrogen or $C_1$-$C_6$ alkyl. In certain embodiments, $R^6$ and $R^7$ each represent independently for each occurrence hydrogen or $C_1$-$C_6$ alkyl; $R^8$ and $R^9$ each represent independently for each occurrence hydrogen or $C_1$-$C_6$ alkyl. In certain embodiments, $R^{10}$ is $C_1$-$C_6$ alkyl.

The compound can be further characterized according to the definition of variable $A^1$. Accordingly, in certain embodiments, $A^1$ is

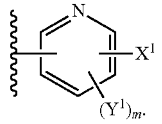

In certain embodiments, $A^1$ is

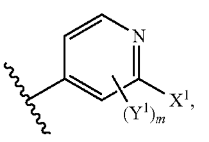

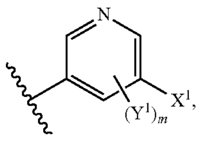

or

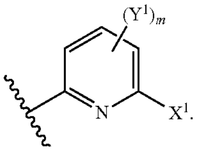

In certain embodiments, $A^1$ is

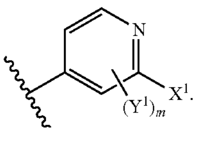

In certain embodiments, $A^1$ is

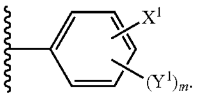

In certain embodiments, $A^1$ is

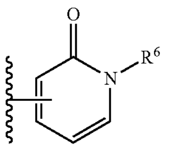

optionally substituted by $X^1$ and 0, 1, 2, or 3 occurrences of $Y^1$.

In certain embodiments, $A^1$ is a 8-10 membered bicyclic heteroaryl substituted by 1, 2, or 3 substituents independently selected from the group consisting of $X^1$, $Y^1$, —($C_1$-$C_6$ alkylene)-$CO_2R^8$, —O-(3-7 membered heterocyclyl), a 3-7 membered heterocycloalkyl, and $C_6$ aryl. In certain embodiments, $A^1$ is a 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo[d]oxazolyl, 1H-indazolyl, and oxazolo[5,4-b]pyridinyl, each being optionally substituted by 1, 2, or 3 substituents independently selected from the group consisting of $X^1$, $Y^1$, —($C_1$-$C_6$ alkylene)-$CO_2R^8$, —O-(3-7 membered heterocyclyl), a 3-7 membered heterocycloalkyl, and $C_6$ aryl. In certain embodiments, $A^1$ is a 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo[d]oxazolyl, 1H-indazolyl, and oxazolo[5,4-b]pyridinyl, each being optionally substituted by 1, 2, or 3 substituents independently selected from the group consisting of $Y^1$, a 3-7 membered heterocycloalkyl, and $C_6$ aryl.

The compound can be further characterized according to the definition of variable $X^1$. Accordingly, in certain embodiments, $X^1$ is —N($R^6$)C(O)-(3-7 membered heterocyclyl) optionally substituted by 1, 2, or 3 substituents independently selected from the group consisting of $Y^1$ and —N($R^8$)($R^9$). In certain embodiments, $X^1$ is —$CO_2R^8$ or —C(O)N($R^8$)($R^9$). In certain embodiments, $X^1$ is —N($R^6$)C(O)$R^{10}$, —N($R^{10}$)C(O)$R^{10}$, —N($R^6$)$CO_2R^{10}$, or —N($R^8$)$SO_2R^{10}$. In certain embodiments, $X^1$ is —N($R^6$)$CO_2R^{10}$.

In certain embodiments, $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —N($R^6$)($R^7$). In certain embodiments, $X^1$ is a 5-6 membered heteroaryl optionally substituted with 1, 2, or 3 substituents independently selected from the group consisting of $Y^1$ and phenyl. In certain embodiments, $X^1$ is a 5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl, each being optionally substituted with 1, 2, or 3 occurrences of $Y^1$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain embodiments, $Y^1$ represents independently for each occurrence halogen or $C_1$-$C_6$ alkyl.

The compound can be further characterized according to the definition of variable m. Accordingly, in certain embodiments, m is 0. In certain other embodiments, m is 1 or 2.

The description above describes multiple embodiments relating to compounds of Formula I-A. The patent application specifically contemplates all combinations of the embodiments. For example, the invention contemplates a compound of Formula I-A wherein $A^1$ is

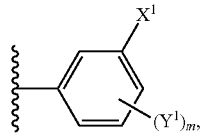

$X^1$ is —C(O)-(5-membered heteroaryl optionally substituted with 1 or 2 occurrences of $Y^1$), and m is 0.

In certain embodiments, invention provides a compound represented by Formula I-1:

(I-1)

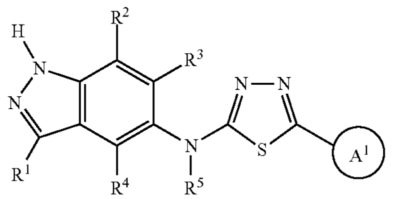

or a pharmaceutically acceptable salt thereof, or a solvate of the foregoing; wherein:

$R^1$ and $R^4$ each represent independently for each occurrence hydrogen, halogen, $C_1$-$C_3$ alkyl, $C_1$-$C_3$ haloalkyl, cyclopropyl, or cyano;

$R^2$ and $R^3$ each represent independently for each occurrence hydrogen, $C_1$-$C_3$ alkyl, cyclopropyl, or cyano;

$R^5$ is hydrogen, $C_1$-$C_6$ alkyl, or $C_1$-$C_6$ hydroxyalkyl;

$R^6$ and $R^7$ each represent independently for each occurrence hydrogen, $C_1$-$C_6$ alkyl, or $C_3$-$C_6$ cycloalkyl; or $R^6$ and $R^7$ when attached to the same nitrogen atom may be taken together with the nitrogen atom to form a 3-7 membered ring;

$R^8$ and $R^9$ each represent independently for each occurrence hydrogen, $C_1$-$C_6$ alkyl, $C_1$-$C_6$ hydroxyalkyl, $C_1$-$C_3$haloalkyl, $C_3$-$C_6$ cycloalkyl, or —($C_1$-$C_6$ alkylene)-O—($C_1$-$C_6$ alkyl); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N($R^6$)$_2$, and —($C_1$-$C_6$ alkylene)-$CO_2R^6$;

$R^{10}$ represents independently for each occurrence $C_1$-$C_6$ alkyl, $C_3$-$C_6$ cycloalkyl, $C_1$-$C_6$ hydroxyalkyl, or —($C_1$-$C_6$alkylene)-N($R^8$)($R^9$);

$R^{11}$ represents independently for each occurrence a 5-6 membered heteroaryl or 3-7 membered heterocycloalkyl, each of which is optionally substituted with 1 or 2 occurrences of $Y^1$;

$A^1$ is a cyclic group selected from:

(i)

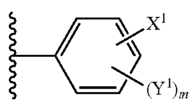
,
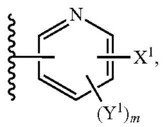

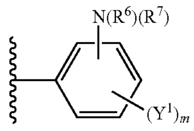
, or
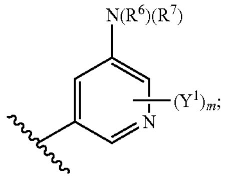

(ii) a heteroaryl selected from the group consisting a 8-10 membered bicyclic heteroaryl, a 5-membered heteroaryl, and a 6-membered heteroaryl containing at least two, ring nitrogen atoms; wherein said heteroaryl is optionally substituted by 1, 2, or 3 substituents independently selected from the group consisting of $X^1$, $Y^1$, —($C_1$-$C_6$alkylene)-$CO_2R^8$, —$N(R^6)(R^7)$, —O-(3-7 membered heterocyclyl), and a 3-7 membered heterocycloalkyl; or (iii) a 3-7 membered heterocycloalkyl optionally substituted by 1, 2, or 3 substituents independently selected from the group consisting of $X^1$ and $Y^1$;

$X^1$ represents independently for each occurrence:

—$N(R^6)C(O)$-(3-7 membered heterocyclyl), —$N(R^6)C(O)$-phenyl, —$N(R^6)C(O)$-aralkyl, or —$N(R^6)C(O)$-heteroaralkyl; each of which is optionally substituted by 1, 2, or 3 substituents independently selected from the group consisting of $Y^1$ and —$N(R^8)(R^9)$;

—$CO_2R^8$, —$C(O)N(R^8)(R^9)$, —$C(O)R^{11}$, —C(O)-(3-7 membered heterocyclyl), —$C(O)N(R^8)(R^{10})$, —$N(R^6)C(O)R^{10}$, —$N(R^6)CO_2R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), or —$NO_2$;

—O—($C_1$-$C_6$alkylene)-$CO_2R^8$, —O—($C_1$-$C_6$ alkylene)-$C(O)N(R^8)(R^9)$, —O—($C_1$-$C_6$ alkylene)-$N(R^8)(R^9)$, —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;

—$SO_2R^{10}$, —$SO_2N(R^8)$-heteroaryl, or —$P(O)(OR^8)_2$;

5-membered heteroaryl optionally substituted with 1, 2, or 3 occurrences of $Y^1$; or —($C_2$-$C_6$ alkylene)-aryl or —($C_2$-$C_6$ alkylene)-heteroaryl;

$Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^8$, —$C(O)N(R^8)(R^9)$, —$N(R^6)C(O)R^{10}$, —($C_1$-$C_6$ alkylene)-$CO_2R^8$, or —($C_1$-$C_6$ alkylene)-O—($C_1$-$C_6$ alkyl); and m is 0, 1, 2, or 3.

The definitions of variables in Formula I-1 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

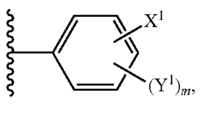

$X^1$ is —$N(R^6)C(O)$-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula I-1 or a pharmaceutically acceptable salt thereof. In certain other embodiments, the compound is a compound of Formula I-1. In yet other embodiments, the compound is a compound of Formula I-1 or a solvate thereof, such as $C_1$-$C_3$ haloalkanoic acid solvate.

The compound can be further characterized according to the definition of variables $R^1$ through $R^{10}$. Accordingly, in certain embodiments, $R^1$, $R^2$, and $R^3$ are independently hydrogen. In certain embodiments, $R^4$ is hydrogen. In certain other embodiments, $R^4$ is chloro. In certain embodiments, $R^5$ is hydrogen. In certain embodiments, $R^6$ and $R^7$ each represent independently for each occurrence hydrogen or $C_1$-$C_6$ alkyl. In certain embodiments, $R^8$ and $R^9$ each represent independently for each occurrence or $C_1$-$C_6$ alkyl. In certain embodiments, $R^{10}$ is $C_1$-$C_6$ alkyl.

The compound can be further characterized according to the definition of variable $A^1$. Accordingly, in certain embodiments, $A^1$ is

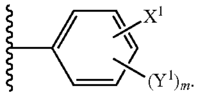

In certain other embodiments, $A^1$ is

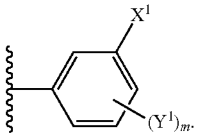

In certain other embodiments, $A^1$ is

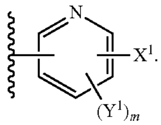

In certain other embodiments, $A^1$ is

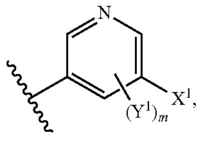

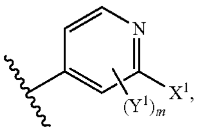

or

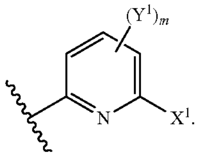

In certain other embodiments, $A^1$ is

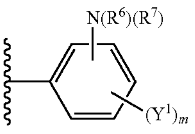

or

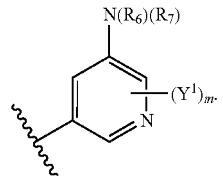

In certain other embodiments, $A^1$ is a heteroaryl selected from the group consisting a 8-10 membered bicyclic heteroaryl, a 5-membered heteroaryl, and a 6-membered heteroaryl containing at least two, ring nitrogen atoms; wherein said heteroaryl is optionally substituted by 1, 2, or 3 substituents independently selected from the group consisting of $X^1$, $Y^1$, —($C_1$-$C_6$alkylene)-$CO_2R^8$, —$N(R^6)(R^7)$, —O-(3-7 membered heterocyclyl), and a 3-7 membered heterocycloalkyl. In certain other embodiments, $A^1$ is a 3-7 membered heterocycloalkyl optionally substituted by 1, 2, or 3 substituents independently selected from the group consisting of $X^1$ and $Y^1$.

The compound can be further characterized according to the definition of variable $X^1$. Accordingly, in certain embodiments, $X^1$ is —$N(R^6)C(O)$-(3-7 membered heterocyclyl), —$N(R^6)C(O)$-phenyl, —$N(R^6)C(O)$-aralkyl, or —$N(R^6)C(O)$-heteroaralkyl; each of which is optionally substituted by 1, 2, or 3 substituents independently selected from the group consisting of $Y^1$ and —$N(R^8)(R^9)$. In certain embodiments, $X^1$ is —C(O)-(3-7 membered heterocyclyl optionally substituted by 1, 2, or 3 occurrences of $Y^1$). In certain other embodiments, $X^1$ is —C(O)-(5 or 6-membered heteroaryl optionally substituted with 1 or 2 occurrences of $Y^1$). In certain other embodiments, $X^1$ is —C(O)-phenyl optionally substituted by 1, 2, or 3 occurrences of $Y^1$.

In other embodiments, $X^1$ is —$CO_2R^8$, —$C(O)N(R^8)(R^9)$, —$C(O)R^{11}$, —C(O)-(3-7 membered heterocyclyl), —$C(O)N(R^8)(R^{10})$, —$N(R^6)C(O)R^{10}$, —$N(R^6)CO_2R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), or —$NO_2$. In other certain embodiments, $X^1$ is —$CO_2R^8$, —$C(O)N(R^8)(R^9)$, —$C(O)R^{11}$, —C(O)-(3-7 membered heterocyclyl), —$C(O)N(R^8)(R^{10})$, —$N(R^6)C(O)R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), or —$NO_2$. In certain other embodiments, $X^1$ is —$CO_2R^8$, —$C(O)N(R^8)(R^9)$, —$C(O)R^{11}$, —$N(R^6)C(O)R^{10}$, —$N(R^8)SO_2R^{10}$, —$N(R^6)$—C(O)—($C_1$-$C_6$ hydroxyalkylene)-$N(R^8)(R^9)$, —$N(R^6)$—C(O)-(2-6 membered heteroalkyl), or —$NO_2$. In certain other embodiments, $X^1$ is —$CO_2R^8$ or —$C(O)N(R^8)(R^9)$.

In certain embodiments, $X^1$ is —$N(R^6)C(O)R^{10}$, —$N(R^6)C(O)R^{11}$, —$N(R^8)SO_2R^{10}$, or —$N(R^8)SO_2R^{11}$. In certain other embodiments, $X^1$ is —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, or —$N(R^6)$—C(O)-(2-6 membered heteroalkyl). In certain other embodiments, $X^1$ is —O—($C_1$-$C_6$alkylene)-$CO_2R^8$, —O—($C_1$-$C_6$ alkylene)-$C(O)N(R^8)(R^9)$, —O—($C_1$-$C_6$ alkylene)-$N(R^8)(R^9)$, —O—($C_1$-$C_6$ alkyl), or —O-(3-7 membered heterocyclyl). In certain other embodiments, $X^1$ is —$SO_2R^{10}$, —$SO_2N(R^8)$-heteroaryl, or —$P(O)(OR^8)_2$. In certain other embodiments, $X^1$ is a 5-membered heteroaryl optionally substituted with 1, 2, or 3 occurrences of $Y^1$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain other embodiments, $Y^1$ represents independently for each occurrence halogen or $C_1$-$C_6$ alkyl.

The compound can be further characterized according to the definition of variable m. Accordingly, in certain embodiments, m is 0. In certain other embodiments, m is 1 or 2.

The description above describes multiple embodiments relating to compounds of Formula I-1. The patent application specifically contemplates all combinations of the embodiments. For example, the invention contemplates a compound of Formula I-1 wherein $A^1$ is

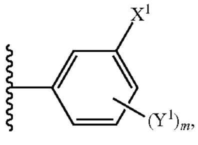

$X^1$ is —C(O)-(5-membered heteroaryl optionally substituted with 1 or 2 occurrences of $Y^1$), and m is 0.

Another aspect of the invention provides a compound represented by Formula I-1A:

(I-1A)

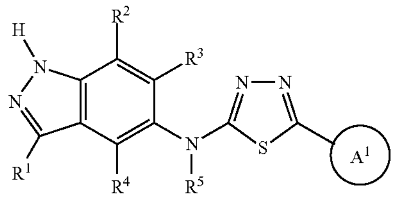

or a pharmaceutically acceptable salt thereof, or a solvate of the foregoing; wherein:

$R^1$, $R^2$, $R^3$, and $R^5$ are hydrogen;

$R^4$ is hydrogen or chloro;

$R^6$ and $R^7$ each represent independently for each occurrence hydrogen or $C_1$-$C_3$ alkyl;

$R^8$ and $R^9$ each represent independently for each occurrence hydrogen or $C_1$-$C_3$ alkyl; or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$haloalkyl, $C_1$-$C_6$ hydroxyalkyl, —$CO_2R^6$, —$N(R^6)_2$, and hydroxyl;

$R^{10}$ is $C_1$-$C_6$ alkyl;

$A^1$ is a cyclic group selected from:

(i)

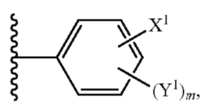 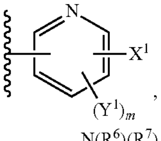 ,

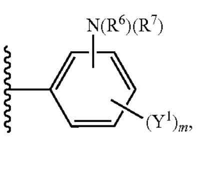 or 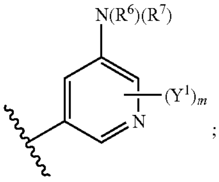 ;

(ii) a heteroaryl selected from the group consisting a 9-10 membered bicyclic heteroaryl, a 5-membered heteroaryl, and a 6-membered heteroaryl containing at least two, ring nitrogen atoms; wherein said heteroaryl is optionally substituted by 1, 2, or 3 substituents independently selected from the group consisting of $X^1$, $Y^1$, —($C_1$-$C_6$alkylene)-$CO_2R^8$, —$N(R^6)(R^7)$, —O-(3-7 membered heterocyclyl), and a 3-7 membered heterocycloalkyl; or (iii) a 3-7 membered heterocycloalkyl optionally substituted by 1, 2, or 3 substituents independently selected from the group consisting of $X^1$ and $Y^1$;

$X^1$ represents independently for each occurrence:

—$N(R^6)C(O)$-(3-7 membered heterocyclyl) or —$N(R^6)C(O)$-phenyl, each of which is optionally substituted by 1, 2, or 3 substituents independently selected from the group consisting of $Y^1$ and —$N(R^8)(R^9)$;

—$CO_2R^8$, —$C(O)N(R^8)(R^9)$, —$N(R^6)C(O)R^{10}$, or —$N(R^8)SO_2R^{10}$;

—O—($C_1$-$C_6$alkylene)-$CO_2R^8$, —O—($C_1$-$C_6$ alkylene)-$C(O)N(R^8)(R^9)$, —O—($C_1$-$C_6$ alkylene)-N($R^8$)($R^9$), or —O—($C_1$-$C_6$ alkyl); or 5-membered heteroaryl optionally substituted with 1, 2, or 3 occurrences of $Y^1$;

$Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl; and m is 0, 1, 2, or 3.

The definitions of variables in Formula I-1A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

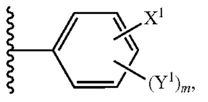

$X^1$ is —$N(R^6)C(O)$-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula I-1A or a pharmaceutically acceptable salt thereof. In certain other embodiments, the compound is a compound of Formula I-1A. In yet other embodiments, the compound is a compound of Formula I-1A or a solvate thereof, such as $C_1$-$C_3$ haloalkanoic acid solvate.

The compound can be further characterized according to the definition of variables $R^1$ through $R^{10}$. Accordingly, in certain embodiments, $R^4$ is hydrogen. In certain embodiments, $R^4$ is chloro. In certain embodiments, $R^6$ and $R^7$ each represent independently for each occurrence hydrogen or $C_1$-$C_6$ alkyl. In certain embodiments, $R^8$ and $R^9$ each represent independently for each occurrence hydrogen or $C_1$-$C_6$ alkyl. In certain embodiments, $R^{10}$ is $C_1$-$C_6$ alkyl.

The compound can be further characterized according to the definition of variable $A^1$. Accordingly, in certain embodiments, $A^1$ is

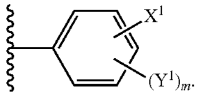

In certain other embodiments, $A^1$ is

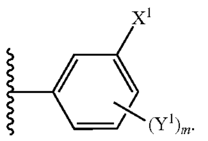

In certain other embodiments, $A^1$ is

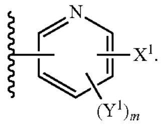

In certain other embodiments, $A^1$ is

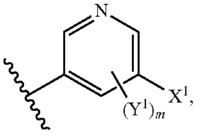

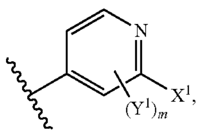

or

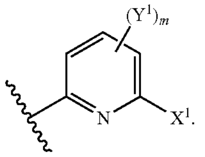

In certain other embodiments, $A^1$ is

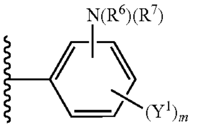

or

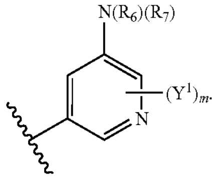

The compound can be further characterized according to the definition of variable $X^1$. Accordingly, in certain embodiments, $X^1$ is —C(O)-(3-7 membered heterocyclyl optionally substituted by 1, 2, or 3 occurrences of $Y^1$). In certain other embodiments, $X^1$ is —C(O)-(5-membered heteroaryl optionally substituted with 1 or 2 occurrences of $Y^1$). In certain other embodiments, $X^1$ is —$CO_2R^8$, —$C(O)N(R^8)(R^9)$, —$N(R^6)C(O)R^{10}$, or —$N(R^8)SO_2R^{10}$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain other embodiments, $Y^1$ represents independently for each occurrence halogen or $C_1$-$C_6$ alkyl.

The compound can be further characterized according to the definition of variable m. Accordingly, in certain embodiments, m is 0. In certain other embodiments, m is 1 or 2.

The description above describes multiple embodiments relating to compounds of Formula I-1A. The patent application specifically contemplates all combinations of the embodiments. For example, the invention contemplates a compound of Formula I-1A wherein $A^1$ is

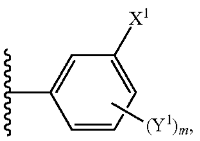

$X^1$ is —C(O)-(5-membered heteroaryl optionally substituted with 1 or 2 occurrences of $Y^1$), and m is 0.

Another aspect of the invention provides a compound represented by Formula I-1B:

(I-1B)

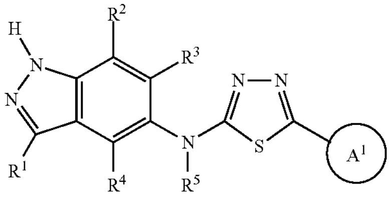

wherein:

$R^1$, $R^2$, $R^3$, and $R^5$ are hydrogen;

$R^4$ is hydrogen or chloro;

$R^6$ and $R^7$ each represent independently for each occurrence hydrogen or $C_1$-$C_3$ alkyl;

$R^8$ and $R^9$ are independently hydrogen or $C_1$-$C_3$ alkyl;

$R^{10}$ is $C_1$-$C_6$ alkyl;

$A^1$ is

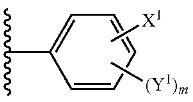

or

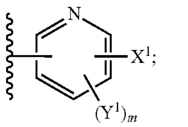

$X^1$ is one of the following:

—$N(R^6)C(O)$-(3-7 membered heteroaryl optionally substituted by 1, 2, or 3 substituents independently selected from the group consisting of $Y^1$ and —$N(R^8)(R^9)$);

—$CO_2R^8$, —$C(O)N(R^8)(R^9)$, —$N(R^6)C(O)R^{10}$, or —$N(R^8)SO_2R^{10}$;

—O—($C_1$-$C_6$alkylene)-$CO_2R^8$, —O—($C_1$-$C_6$ alkylene)-$C(O)N(R^8)(R^9)$, —O—($C_1$-$C_6$ alkylene)-$N(R^8)(R^9)$, or —O—($C_1$-$C_6$ alkyl);

$Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl; and m is 0, 1, 2, or 3.

The definitions of variables in Formula I-1B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

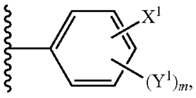

$X^1$ is —$N(R^6)C(O)$-(3-7 membered heteroaryl optionally substituted by 1 or 2 occurrences of $Y^1$), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is further selected from a pharmaceutically acceptable salt thereof of Formula I-1B. In certain other embodiments, the compound is a compound of Formula I-1B, a pharmaceutically acceptable salt thereof, or a solvate of the foregoing. In yet other embodiments, the compound is a compound of Formula I-1B or a solvate thereof, such as $C_1$-$C_3$ haloalkanoic acid solvate.

Another aspect of the invention provides a compound represented by Formula II:

(II)

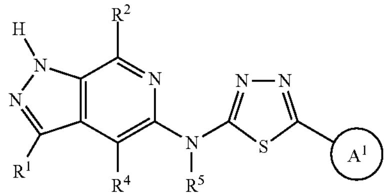

or a pharmaceutically acceptable salt thereof, or a solvate of the foregoing; wherein:

$R^1$ and $R^4$ each represent independently for each occurrence hydrogen, halogen, $C_1$-$C_3$ alkyl, $C_1$-$C_3$ haloalkyl, cyclopropyl, $C_2$-$C_4$ alkenyl, or cyano;

$R^2$ is hydrogen, $C_1$-$C_3$ alkyl, cyclopropyl, or cyano;

$R^5$ is hydrogen, $C_1$-$C_6$ alkyl, $C_1$-$C_6$ hydroxyalkyl, or —$CO_2R^{12}$;

$R^6$ and $R^7$ each represent independently for each occurrence hydrogen, $C_1$-$C_6$ alkyl, $C_1$-$C_6$ hydroxyalkyl, or $C_3$-$C_6$ cycloalkyl; or $R^6$ and $R^7$ when attached to the same nitrogen atom may be taken together with the nitrogen atom to form a 3-7 membered ring optionally substituted with 1 or 2 $R^{12}$;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, —($C_1$-$C_6$ alkylene)-O—($C_1$-$C_6$ alkyl), or —($C_1$-$C_6$ alkylene)-$N(R^6)(R^7)$; or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —$C(O)N(R^6)(R^7)$, —$N(R^6)C(O)R^6$, —$N(R^6)_2$, and —($C_1$-$C_6$ alkylene)-$CO_2R^6$;

$R^{10}$ represents independently for each occurrence $C_1$-$C_6$ alkyl, $C_1$-$C_6$ haloalkyl, $C_3$-$C_6$ cycloalkyl, $C_1$-$C_6$ hydroxyalkyl, —($C_1$-$C_6$ alkylene)-O—($C_1$-$C_6$ alkyl), —($C_1$-$C_6$alkylene)-$N(R^8)(R^9)$, —($C_1$-$C_6$ alkylene)-$CO_2R^6$, —($C_1$-$C_6$ alkylene)-(3-7 membered heterocycloalkyl), or 3-7 membered heterocycloalkyl; wherein said cycloalkyl is optionally substituted by 1 or 2 $C_1$-$C_6$ alkyl;

$R^{11}$ represents independently for each occurrence a 5-6 membered heteroaryl or 3-7 membered heterocycloalkyl, each of which is optionally substituted with 1 or 2 occurrences of $Y^1$;

$R^{12}$ represents independently for each occurrence $C_1$-$C_6$ alkyl or $C_3$-$C_6$ cycloalkyl;

$A^1$ is a cyclic group selected from:

(i)

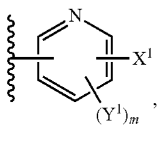

,

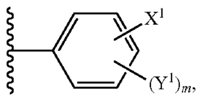

-continued

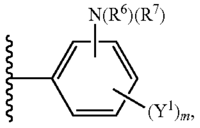

or

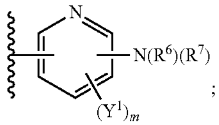

;

(ii)

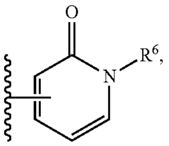

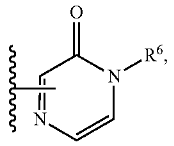

or dihydropyridinyl, each being optionally substituted by $X^1$ and 0, 1, 2, or 3 occurrences of $Y^1$;

(iii) a heteroaryl selected from the group consisting a 8-10 membered bicyclic heteroaryl, a 5-membered heteroaryl, and a 6-membered heteroaryl containing at least two ring nitrogen atoms; wherein said heteroaryl is optionally substituted by 1, 2, or 3 substituents independently selected from the group consisting of $X^1$, $Y^1$, —($C_1$-$C_6$alkylene)-$CO_2R^8$, —$N(R^6)(R^7)$, —O-(3-7 membered heterocyclyl), a 3-7 membered heterocycloalkyl, and $C_6$ aryl;

(iv) a 3-7 membered heterocycloalkyl, $C_3$-$C_7$ cycloalkyl, or 8-10 membered bicyclic partially unsaturated heterocyclyl, each optionally substituted by oxo, $C_6$ aryl, $X^1$, and 0, 1, 2, or 3 occurrences of $Y^1$; or (v) aralkyl or heteroaralkyl, each being optionally substituted by a $C_6$ aryl, $X^1$, and 0, 1, 2, or 3 occurrences of $Y^1$;

$X^1$ represents independently for each occurrence:

—$N(R^6)C(O)$-(3-7 membered heterocyclyl), —$N(R^6)C(O)$-phenyl, —$N(R^6)C(O)$-aralkyl, or —$N(R^6)C(O)$-heteroaralkyl; each of which is optionally substituted by 1, 2, or 3 substituents independently selected from the group consisting of $Y^1$ and —$N(R^8)(R^9)$;

—$CO_2R^8$, —$C(O)N(R^8)(R^9)$, —$C(O)R^{11}$, —$C(O)R^{12}$, —C(O)-(3-7 membered heterocyclyl), —$C(O)N(R^8)(R^{10})$, —$N(R^6)C(O)R^{10}$), —$N(R^{10})C(O)R^{10}$, —$N(R^6)CO_2R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), —$N(R^6)C(O)N(R^6)(R^7)$, or —$NO_2$;

—O—($C_1$-$C_6$alkylene)-$CO_2R^8$, —$OC(O)R^{12}$, —O—($C_1$-$C_6$ alkylene)-$C(O)N(R^8)(R^9)$, —O—($C_1$-$C_6$ alkylene)-$N(R^8)(R^9)$, —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;

—$SO_2R^{10}$, —$SO_2N(R^8)$-heteroaryl, cyano, or —$P(O)(OR^8)_2$;

5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —$N(R^6)(R^7)$; or —($C_2$-$C_6$ alkylene)-aryl, —($C_2$-$C_6$ alkylene)-heterocyclyl, or —($C_1$-$C_6$ alkylene)-$COR^{12}$;

$Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, $C_2$-$C_6$ alkenyl, cyano, hydroxyl, —$CO_2R^8$, —$C(O)N(R^8)(R^9)$, —$N(R^6)C(O)R^{10}$, —$N(R^6)C(O)N(R^6)(R^7)$, —($C_1$-$C_6$ alkylene)-$CO_2R^8$, —($C_1$-$C_6$ alkylene)-O—($C_1$-$C_6$ alkyl), —($C_1$-$C_6$alkylene)-$N(R^6)(R^7)$, —($C_1$-$C_6$ alkylene)-$N(R^6)S(O)_2R^{12}$, —($C_1$-$C_6$ alkylene)-S—$C(O)R^{12}$, —S—$R^{12}$, or 3-7 membered heterocycloalkyl; and m is 0, 1, 2, or 3.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

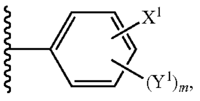

$X^1$ is —$N(R^6)C(O)$-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

The compound can be further characterized according to the definition of variables $R^1$ through $R^{10}$. Accordingly, in certain embodiments, $R^1$ and $R^2$ are independently hydrogen. In certain embodiments, $R^4$ is hydrogen. In certain other embodiments, $R^4$ is chloro. In certain embodiments, $R^5$ is hydrogen. In certain embodiments, $R^6$ and $R^7$ each represent independently for each occurrence hydrogen or $C_1$-$C_6$ alkyl. In certain embodiments, $R^8$ and $R^9$ each represent independently for each occurrence or $C_1$-$C_6$ alkyl. In certain embodiments, $R^8$ and $R^9$ each represent independently for each occurrence hydrogen, $C_1$-$C_6$ alkyl, $C_1$-$C_6$ hydroxyalkyl, or $C_3$-$C_6$ cycloalkyl. In certain embodiments, $R^{10}$ is $C_1$-$C_6$ alkyl, $C_1$-$C_6$ haloalkyl, $C_3$-$C_6$ cycloalkyl, or $C_1$-$C_6$ hydroxyalkyl. In certain embodiments, $R^{10}$ is $C_1$-$C_6$ alkyl.

The compound can be further characterized according to the definition of variable $A^1$. Accordingly, in certain embodiments, $A^1$ is

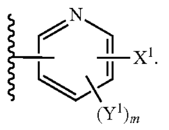

In certain embodiments, $A^1$ is

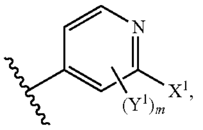

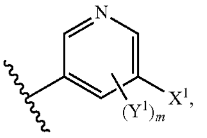

or

-continued

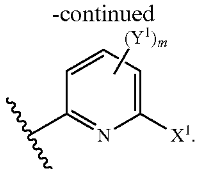

In certain embodiments, $A^1$ is

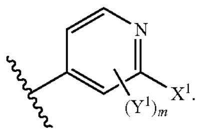

In certain embodiments, $A^1$ is

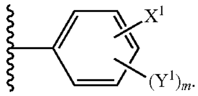

In certain embodiments, $A^1$ is

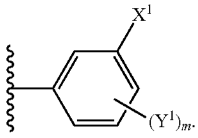

In certain embodiments, $A^1$ is

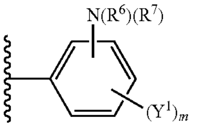

or

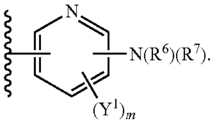

In certain embodiments, $A^1$ is

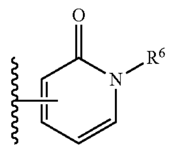

optionally substituted by $X^1$ and 0, 1, 2, or 3 occurrences of $Y^1$.

In certain embodiments, $A^1$ is a heteroaryl selected from the group consisting a 8-10 membered bicyclic heteroaryl, a 5-membered heteroaryl, and a 6-membered heteroaryl containing at least two ring nitrogen atoms; wherein said heteroaryl is optionally substituted by 1, 2, or 3 substituents independently selected from the group consisting of $X^1$, $Y^1$, —($C_1$-$C_6$ alkylene)-$CO_2R^8$, —$N(R^6)(R^7)$, —O-(3-7 membered heterocyclyl), a 3-7 membered heterocycloalkyl, and $C_6$ aryl. In certain embodiments, $A^1$ is a 8-10 membered bicyclic heteroaryl substituted by 1, 2, or 3 substituents independently selected from the group consisting of $X^1$, $Y^1$, —($C_1$-$C_6$alkylene)-$CO_2R^8$, —O-(3-7 membered heterocyclyl), a 3-7 membered heterocycloalkyl, and $C_6$ aryl. In certain embodiments, $A^1$ is a 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo[d]oxazolyl, 1H-indazolyl, and oxazolo[5,4-b]pyridinyl, each being optionally substituted by 1, 2, or 3 substituents independently selected from the group consisting of $X^1$, $Y^1$, —($C_1$-$C_6$ alkylene)-$CO_2R^8$, —O-(3-7 membered heterocyclyl), a 3-7 membered heterocycloalkyl, and $C_6$ aryl. In certain embodiments, $A^1$ is a 8-10 membered bicyclic heteroaryl selected from the group consisting of imidazo[1,2-a]pyridinyl, 1H-benzo[d]imidazolyl, 3H-imidazo[4,5-b]pyridinyl, benzo[d]thiazolyl, thiazolo[5,4-b]pyridinyl, benzo[d]oxazolyl, 1H-indazolyl, and oxazolo[5,4-b]pyridinyl, each being optionally substituted by 1, 2, or 3 substituents independently selected from the group consisting of $Y^1$, a 3-7 membered heterocycloalkyl, and $C_6$ aryl. In certain embodiments, $A^1$ is a 3-7 membered heterocycloalkyl or a 8-10 membered bicyclic partially unsaturated heterocyclyl, each being optionally substituted by oxo, $C_6$ aryl, $X^1$, and 0, 1, 2, or 3 occurrences of $Y^1$.

The compound can be further characterized according to the definition of variable $X^1$. Accordingly, in certain embodiments, $X^1$ is —$N(R^6)C(O)$-(3-7 membered heterocyclyl) optionally substituted by 1, 2, or 3 substituents independently selected from the group consisting of $Y^1$ and —$N(R^8)(R^9)$. In certain embodiments, $X^1$ is —C(O)-(5 or 6-membered heteroaryl optionally substituted with 1 or 2 occurrences of $Y^1$). In certain embodiments, $X^1$ is —C(O)-phenyl optionally substituted by 1, 2, or 3 occurrences of $Y^1$. In certain embodiments, $X^1$ is —$CO_2R^8$, —$C(O)N(R^8)(R^9)$, —$C(O)R^{11}$, —$C(O)R^{12}$, —C(O)-(3-7 membered heterocyclyl), —$C(O)N(R^8)(R^{10})$, —$N(R^6)C(O)R^{10}$, —$N(R^{10})C(O)R^{10}$, —$N(R^6)CO_2R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), —$N(R^6)C(O)N(R^6)(R^7)$, or —$NO_2$. In certain embodiments, $X^1$ is —$CO_2R^8$ or —$C(O)N(R^8)(R^9)$. In certain embodiments, $X^1$ is —$N(R^6)C(O)R^{10}$, —$N(R^{10})C(O)R^{10}$, —$N(R^6)CO_2R^{10}$, or —$N(R^8)SO_2R^{10}$. In certain embodiments, $X^1$ is —$N(R^6)CO_2R^{10}$. In certain embodiments, $X^1$ is —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), or —$N(R^6)C(O)N(R^6)(R^7)$.

In certain embodiments, $X^1$ is —O—($C_1$-$C_6$alkylene)-$CO_2R^8$, —$OC(O)R^{12}$, —O—($C_1$-$C_6$ alkylene)-$C(O)N(R^8)(R^9)$, —O—($C_1$-$C_6$ alkylene)-$N(R^8)(R^9)$, —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl. In certain embodiments, $X^1$ is $SO_2R^{10}$, —$SO_2N(R^8)$-heteroaryl, cyano, or —$P(O)(OR^8)_2$.

In certain embodiments, $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —$N(R^6)(R^7)$. In certain embodiments, $X^1$ is a 5-6 membered heteroaryl optionally substituted with 1, 2, or 3 substituents independently selected from the group consisting of $Y^1$ and phenyl. In certain embodiments, $X^1$ is a 5-6 membered heteroaryl selected from the group consisting of oxazolyl, imidazolyl, pyrazolyl, isoxazolyl, thiazolyl, pyrrolyl, furanyl, pyranyl, pyridinyl, pyrimidinyl, pyrazinyl, and thiophenyl, each being optionally substituted with 1, 2, or 3 occurrences of $Y^1$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, hydroxyl, or —($C_1$-$C_6$ alkylene)-N($R^6$)($R^7$). In certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain other embodiments, $Y^1$ represents independently for each occurrence halogen or $C_1$-$C_6$ alkyl.

The compound can be further characterized according to the definition of variable m. Accordingly, in certain embodiments, m is 0. In certain other embodiments, m is 1 or 2.

The description above describes multiple embodiments relating to compounds of Formula II. The patent application specifically contemplates all combinations of the embodiments.

Another aspect of the invention provides a compound represented by Formula II-1:

(II-1)

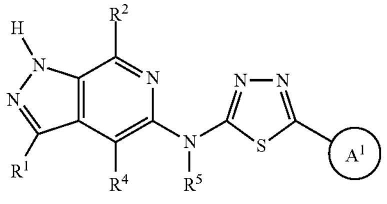

or a pharmaceutically acceptable salt thereof, or a solvate of the foregoing; wherein:

$R^1$ and $R^4$ each represent independently for each occurrence hydrogen, halogen, $C_1$-$C_3$ alkyl, $C_1$-$C_3$ haloalkyl, cyclopropyl, or cyano;

$R^2$ is hydrogen, $C_1$-$C_3$ alkyl, cyclopropyl, or cyano;

$R^5$ is hydrogen, $C_1$-$C_6$ alkyl, or $C_1$-$C_6$ hydroxyalkyl;

$R^6$ and $R^7$ each represent independently for each occurrence hydrogen, $C_1$-$C_6$ alkyl, or $C_3$-$C_6$ cycloalkyl; or $R^6$ and $R^7$ when attached to the same nitrogen atom may be taken together with the nitrogen atom to form a 3-7 membered ring;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, or —($C_1$-$C_6$ alkylene)-O—($C_1$-$C_6$ alkyl); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N$(R^6)_2$, and —($C_1$-$C_6$ alkylene)-$CO_2R^6$;

$R^{10}$ represents independently for each occurrence $C_1$-$C_6$ alkyl, $C_3$-$C_6$ cycloalkyl, $C_1$-$C_6$ hydroxyalkyl, or —($C_1$-$C_6$alkylene)-N($R^8$)($R^9$);

$R^{11}$ represents independently for each occurrence a 5-6 membered heteroaryl or 3-7 membered heterocycloalkyl, each of which is optionally substituted with 1 or 2 occurrences of $Y^1$;

$A^1$ is a cyclic group selected from:

(i)

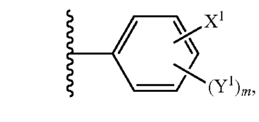 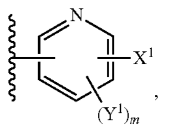 ,

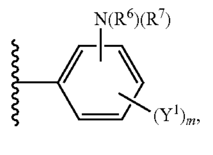 or 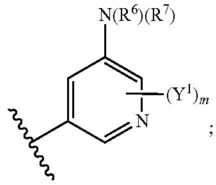 ;

(ii) a heteroaryl selected from the group consisting a 8-10 membered bicyclic heteroaryl, a 5-membered heteroaryl, and a 6-membered heteroaryl containing at least two, ring nitrogen atoms; wherein said heteroaryl is optionally substituted by 1, 2, or 3 substituents independently selected from the group consisting of $X^1$, $Y^1$, —($C_1$-$C_6$ alkylene)-$CO_2R^8$, —N($R^6$)($R^7$), —O-(3-7 membered heterocyclyl), and a 3-7 membered heterocycloalkyl; or (iii) a 3-7 membered heterocycloalkyl optionally substituted by 1, 2, or 3 substituents independently selected from the group consisting of $X^1$ and $Y^1$;

$X^1$ represents independently for each occurrence:

—N($R^6$)C(O)-(3-7 membered heterocyclyl), —N($R^6$)C(O)-phenyl, —N($R^6$)C(O)-aralkyl, or —N($R^6$)C(O)-heteroaralkyl; each of which is optionally substituted by 1, 2, or 3 substituents independently selected from the group consisting of $Y^1$ and —N($R^8$)($R^9$);

—$CO_2R^8$, —C(O)N($R^8$)($R^9$), —C(O)$R^{11}$, —C(O)-(3-7 membered heterocyclyl), —C(O)N($R^8$)($R^{10}$), —N($R^6$)C(O)$R^{10}$, —N($R^6$)$CO_2R^{10}$, —N($R^8$)$SO_2R^{10}$, —N($R^6$)—($C_1$-$C_6$ alkylene)-C(O)N($R^8$)($R^9$), —N($R^6$)—C(O)—($C_1$-$C_6$ hydroxyalkylene)-N($R^8$)($R^9$), —N($R^6$)—C(O)-(2-6 membered heteroalkyl), or —$NO_2$, —O—($C_1$-$C_6$alkylene)-$CO_2R^8$, —O—($C_1$-$C_6$ alkylene)-C(O)N($R^8$)($R^9$), —O—($C_1$-$C_6$ alkylene)-N($R^8$)($R^9$), —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;

—$SO_2R^{10}$, —$SO_2$N($R^8$)-heteroaryl, or —P(O)$(OR^8)_2$;

5-membered heteroaryl optionally substituted with 1, 2, or 3 occurrences of $Y^1$; or —($C_2$-$C_6$ alkylene)-aryl or —($C_2$-$C_6$ alkylene)-heteroaryl;

$Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^8$, —C(O)N($R^8$)($R^9$), —N($R^6$)C(O)$R^{10}$, —($C_1$-$C_6$ alkylene)-$CO_2R^8$, or —($C_1$-$C_6$ alkylene)-O—($C_1$-$C_6$ alkyl); and m is 0, 1, 2, or 3.

The definitions of variables in Formula II-1 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

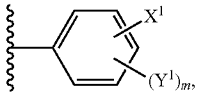

$X^1$ is —$N(R^6)C(O)$-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula II-1 or a pharmaceutically acceptable salt thereof. In certain other embodiments, the compound is a compound of Formula II-1. In yet other embodiments, the compound is a compound of Formula II-1 or a solvate thereof, such as $C_1$-$C_3$ haloalkanoic acid solvate.

The compound can be further characterized according to the definition of variables $R^1$ through $R^{10}$. Accordingly, in certain embodiments, $R^1$ is hydrogen. In certain embodiments, $R^4$ is hydrogen. In certain other embodiments, $R^4$ is chloro. In certain embodiments, $R^5$ is hydrogen. In certain embodiments, $R^6$ and $R^7$ each represent independently for each occurrence hydrogen or $C_1$-$C_6$ alkyl. In certain embodiments, $R^8$ and $R^9$ each represent independently for each occurrence hydrogen or $C_1$-$C_6$ alkyl. In certain embodiments, $R^{10}$ is $C_1$-$C_6$ alkyl.

The compound can be further characterized according to the definition of variable $A^1$. Accordingly, in certain embodiments, $A^1$ is

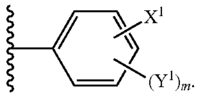

In certain other embodiments, $A^1$ is

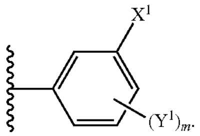

In certain other embodiments, $A^1$ is

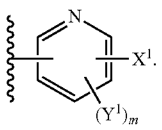

In certain other embodiments, $A^1$ is

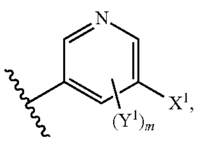
,
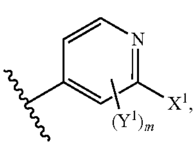
, or

-continued

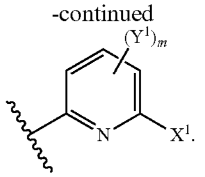

In certain other embodiments, $A^1$ is

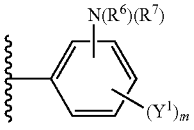
or
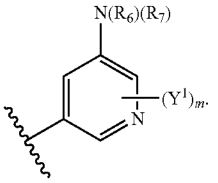

In certain other embodiments, $A^1$ is a heteroaryl selected from the group consisting a 8-10 membered bicyclic heteroaryl, a 5-membered heteroaryl, and a 6-membered heteroaryl containing at least two, ring nitrogen atoms; wherein said heteroaryl is optionally substituted by 1, 2, or 3 substituents independently selected from the group consisting of $X^1$, $Y^1$, —($C_1$-$C_6$alkylene)-$CO_2R^8$, —$N(R^6)(R^7)$, —O-(3-7 membered heterocyclyl), and a 3-7 membered heterocycloalkyl. In certain other embodiments, $A^1$ is a 3-7 membered heterocycloalkyl optionally substituted by 1, 2, or 3 substituents independently selected from the group consisting of $X^1$ and $Y^1$.

The compound can be further characterized according to the definition of variable $X^1$. Accordingly, in certain embodiments, $X^1$—$N(R^6)C(O)$-(3-7 membered heterocyclyl), —$N(R^6)C(O)$-phenyl, —$N(R^6)C(O)$-aralkyl, or —$N(R^6)C(O)$-heteroaralkyl; each of which is optionally substituted by 1, 2, or 3 substituents independently selected from the group consisting of $Y^1$ and —$N(R^8)(R^9)$. In certain embodiments, $X^1$ is —C(O)-(3-7 membered heterocyclyl optionally substituted by 1, 2, or 3 occurrences of $Y^1$). In certain other embodiments, $X^1$ is —C(O)-(5 or 6-membered heteroaryl optionally substituted with 1 or 2 occurrences of $Y^1$). In certain other embodiments, $X^1$ is —C(O)-phenyl optionally substituted by 1, 2, or 3 occurrences of $Y^1$.

In other embodiments, $X^1$ is —$CO_2R^8$, —$C(O)N(R^8)(R^9)$, —$C(O)R^{11}$, —C(O)-(3-7 membered heterocyclyl), —$C(O)N(R^8)(R^{10})$, —$N(R^6)C(O)R^{10}$, —$N(R^6)CO_2R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), or —$NO_2$. In other certain embodiments, $X^1$ is —$CO_2R^8$, —$C(O)N(R^8)(R^9)$, —$C(O)R^{11}$, —C(O)-(3-7 membered heterocyclyl), —$C(O)N(R^8)(R^{10})$, —$N(R^6)C(O)R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), or —$NO_2$. In certain other embodiments, $X^1$ is —$CO_2R^8$, —$C(O)N(R^8)(R^9)$, —$C(O)R^{11}$, —$N(R^6)C(O)R^{10}$, —$N(R^8)SO_2R^{10}$, —$N(R^6)$—C(O)—($C_1$-$C_6$ hydroxyalkylene)-$N(R^8)(R^9)$, —$N(R^6)$—C(O)-(2-6 membered heteroalkyl), or —$NO_2$. In certain other embodiments, $X^1$ is —$CO_2R^8$ or —$C(O)N(R^8)(R^9)$.

In certain embodiments, $X^1$ is —$N(R^6)C(O)R^{10}$, —$N(R^6)C(O)R^{11}$, —$N(R^8)SO_2R^{10}$, or —$N(R^8)SO_2R^{11}$. In certain other embodiments, $X^1$ is —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, or —$N(R^6)$—C(O)-(2-6 membered heteroalkyl). In certain other embodiments, $X^1$ is —O—($C_1$-$C_6$alkylene)-$CO_2R^8$, —O—($C_1$-$C_6$ alkylene)-$C(O)N(R^8)(R^9)$, —O—

($C_1$-$C_6$ alkylene)-N($R^8$)($R^9$), —O—($C_1$-$C_6$ alkyl), or —O-(3-7 membered heterocyclyl). In certain other embodiments, $X^1$ is —$SO_2R^{10}$, —$SO_2N(R^8)$-heteroaryl, or —P(O)($OR^8$)$_2$. In certain other embodiments, $X^1$ is a 5-membered heteroaryl optionally substituted with 1, 2, or 3 occurrences of $Y^1$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain other embodiments, $Y^1$ represents independently for each occurrence halogen or $C_1$-$C_6$ alkyl.

The compound can be further characterized according to the definition of variable m. Accordingly, in certain embodiments, m is 0. In certain other embodiments, m is 1 or 2.

The description above describes multiple embodiments relating to compounds of Formula II-1. The patent application specifically contemplates all combinations of the embodiments. For example, the invention contemplates a compound of Formula II-1 wherein $A^1$ is

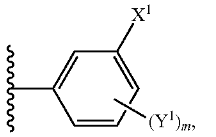

$X^1$ is —C(O)-(5-membered heteroaryl optionally substituted with 1 or 2 occurrences of $Y^1$), and m is 0.

Another aspect of the invention provides a compound represented by Formula II-1A:

(II-1A)

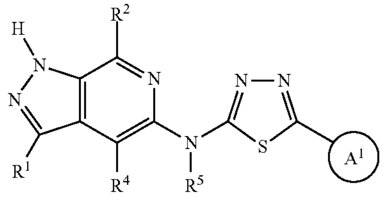

or a pharmaceutically acceptable salt thereof, or a solvate of the foregoing; wherein:

$R^1$, $R^2$, and $R^5$ are hydrogen;

$R^4$ is hydrogen or chloro;

$R^6$ and $R^7$ each represent independently for each occurrence hydrogen or $C_1$-$C_3$ alkyl;

$R^8$ and $R^9$ each represent independently for each occurrence hydrogen or $C_1$-$C_3$ alkyl; or $R^8$ and $R^9$ each represent independently for each occurrence hydrogen or $C_1$-$C_3$ alkyl; or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, —$CO_2R^6$, —N($R^6$)$_2$, and hydroxyl;

$R^{10}$ is $C_1$-$C_6$ alkyl;

$A^1$ is a cyclic group selected from:

(i)

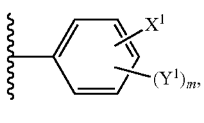

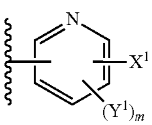

,

-continued

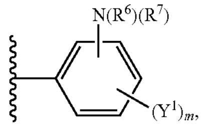

or

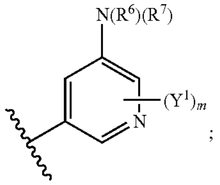

;

(ii) a heteroaryl selected from the group consisting a 9-10 membered bicyclic heteroaryl, a 5-membered heteroaryl, and a 6-membered heteroaryl containing at least two, ring nitrogen atoms; wherein said heteroaryl is optionally substituted by 1, 2, or 3 substituents independently selected from the group consisting of $X^1$, $Y^1$, —($C_1$-$C_6$ alkylene)-$CO_2R^8$, —N($R^6$)($R^7$), —O-(3-7 membered heterocyclyl), and a 3-7 membered heterocycloalkyl; or (iii) a 3-7 membered heterocycloalkyl optionally substituted by 1, 2, or 3 substituents independently selected from the group consisting of $X^1$ and $Y^1$;

$X^1$ represents independently for each occurrence:

—N($R^6$)C(O)-(3-7 membered heterocyclyl) or —N($R^6$)C(O)-phenyl, each of which is optionally substituted by 1, 2, or 3 substituents independently selected from the group consisting of $Y^1$ and —N($R^8$)($R^9$);

—$CO_2R^8$, —C(O)N($R^8$)($R^9$), —N($R^6$)C(O)$R^{10}$, or —N($R^8$)$SO_2R^{10}$;

—O—($C_1$-$C_6$alkylene)-$CO_2R^8$, —O—($C_1$-$C_6$ alkylene)-C(O)N($R^8$)($R^9$), —O—($C_1$-$C_6$ alkylene)-N($R^8$)($R^9$), or —O—($C_1$-$C_6$ alkyl); or 5-membered heteroaryl optionally substituted with 1, 2, or 3 occurrences of $Y^1$;

$Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl; and m is 0, 1, 2, or 3.

The definitions of variables in Formula II-1A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

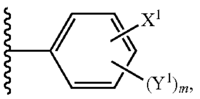

$X^1$ is —N($R^6$)C(O)-(3-7 membered heterocyclyl), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is a compound of Formula II-1A or a pharmaceutically acceptable salt thereof. In certain other embodiments, the compound is a compound of Formula II-1A. In yet other embodiments, the compound is a compound of Formula II-1A or a solvate thereof, such as $C_1$-$C_3$ haloalkanoic acid solvate.

The compound can be further characterized according to the definition of variables $R^1$ through $R^{10}$. Accordingly, in certain embodiments, $R^4$ is hydrogen. In certain embodiments, $R^4$ is chloro. In certain embodiments, $R^6$ and $R^7$ each represent independently for each occurrence hydrogen or $C_1$-$C_6$ alkyl. In certain embodiments, $R^8$ and $R^9$ each represent independently for each occurrence hydrogen or $C_1$-$C_6$ alkyl. In certain embodiments, $R^{10}$ is $C_1$-$C_6$ alkyl.

The compound can be further characterized according to the definition of variable $A^1$. Accordingly, in certain embodiments, $A^1$ is

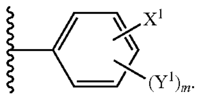

In certain other embodiments, $A^1$ is

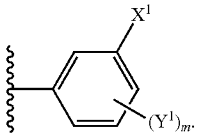

In certain other embodiments, $A^1$ is

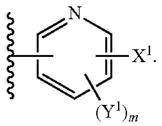

In certain other embodiments, $A^1$ is

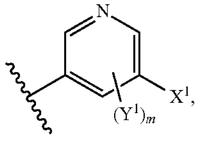
,
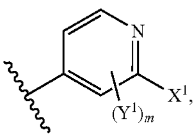
, or
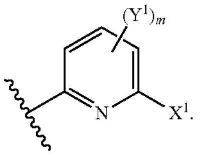

In certain other embodiments, $A^1$ is

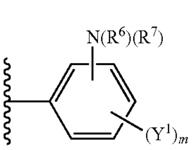
or
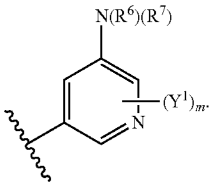

The compound can be further characterized according to the definition of variable $X^1$. Accordingly, in certain embodiments, $X^1$ is —C(O)-(3-7 membered heterocyclyl optionally substituted by 1, 2, or 3 occurrences of $Y^1$). In certain other embodiments, $X^1$ is —C(O)-(5-membered heteroaryl optionally substituted with 1 or 2 occurrences of $Y^1$). In certain other embodiments, $X^1$ is —$CO_2R^8$, —C(O)N($R^8$)($R^9$), —N($R^6$)C(O)$R^{10}$, or —N($R^8$)$SO_2R^{10}$.

The compound can be further characterized according to the definition of variable $Y^1$. Accordingly, in certain embodiments, $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl. In certain other embodiments, $Y^1$ represents independently for each occurrence halogen or $C_1$-$C_6$ alkyl.

The compound can be further characterized according to the definition of variable m. Accordingly, in certain embodiments, m is 0. In certain other embodiments, m is 1 or 2.

The description above describes multiple embodiments relating to compounds of Formula II-1A. The patent application specifically contemplates all combinations of the embodiments. For example, the invention contemplates a compound of Formula II-1A wherein $A^1$ is

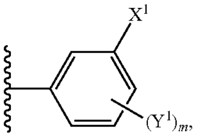

$X^1$ is —C(O)-(5-membered heteroaryl optionally substituted with 1 or 2 occurrences of $Y^1$), and m is 0.

Another aspect of the invention provides a compound represented by Formula II-1B:

(II-1B)

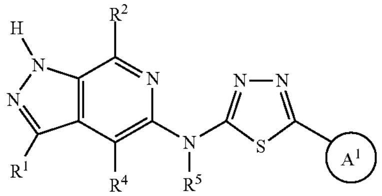

wherein:

$R^1$, $R^2$, and $R^5$ are hydrogen;

$R^4$ is hydrogen or chloro;

$R^6$ and $R^7$ each represent independently for each occurrence hydrogen or $C_1$-$C_3$ alkyl;

$R^8$ and $R^9$ each represent independently for each occurrence hydrogen or $C_1$-$C_3$ alkyl;

$R^{10}$ is $C_1$-$C_6$ alkyl;

$A^1$ is

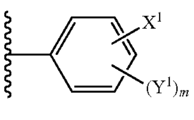
or
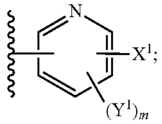

$X^1$ is one of the following:

—N($R^6$)C(O)-(3-7 membered heteroaryl optionally substituted by 1, 2, or 3 substituents independently selected from the group consisting of $Y^1$ and —N($R^8$)($R^9$));

—$CO_2R^8$, —C(O)N($R^8$)($R^9$), —N($R^6$)C(O)$R^{10}$, or —N($R^8$)$SO_2R^{10}$; or

—O—($C_1$-$C_6$alkylene)-$CO_2R^8$, —O—($C_1$-$C_6$ alkylene)-C(O)N($R^8$)($R^9$), —O—($C_1$-$C_6$ alkylene)-N($R^8$)($R^9$), or —O—($C_1$-$C_6$ alkyl);

$Y^1$ represents independently for each occurrence halogen, $C_1$-$C_6$ alkyl, $C_1$-$C_6$ haloalkyl, $C_1$-$C_6$ hydroxyalkyl, —$CO_2R^8$, or hydroxyl; and m is 0, 1, 2, or 3.

The definitions of variables in Formula II-1B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where $A^1$ is

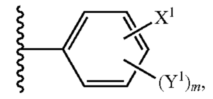

$X^1$ is —$N(R^6)C(O)$-(3-7 membered heteroaryl optionally substituted by 1 or 2 occurrences of $Y^1$), and $Y^1$ represents independently for each occurrence halogen, $C_1$-$C_6$ alkyl, $C_1$-$C_6$ haloalkyl, or $C_1$-$C_6$ hydroxyalkyl.

In certain embodiments, the compound is further selected from a pharmaceutically acceptable salt thereof of Formula II-1B. In certain other embodiments, the compound is a compound of Formula II-1B, a pharmaceutically acceptable salt thereof, or a solvate of the foregoing. In yet other embodiments, the compound is a compound of Formula II-1B or a solvate thereof, such as $C_1$-$C_3$haloalkanoic acid solvate.

In certain other embodiments, the compound is a compound in Table 1, or a pharmaceutically acceptable salt thereof.

TABLE 1

| No. | Compound |
|---|---|
| I-1 | 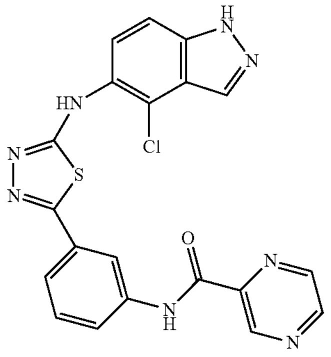 [SMILES: O=C(Nc1cccc(-c2nnc(Nc3ccc4[nH]ncc4c3Cl)s2)c1)c1cnccn1] |
| I-2 | 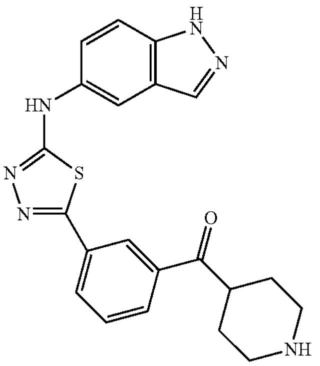 [SMILES: O=C(c1cccc(-c2nnc(Nc3ccc4[nH]ncc4c3)s2)c1)C1CCNCC1] |

TABLE 1-continued

| No. | Compound |
|---|---|
| I-3 | 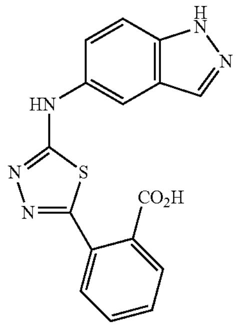 [SMILES: O=C(O)c1ccccc1-c1nnc(Nc2ccc3[nH]ncc3c2)s1] |
| I-4 | 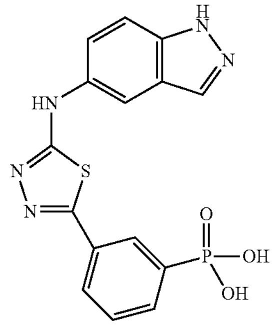 [SMILES: O=P(O)(O)c1cccc(-c2nnc(Nc3ccc4[nH]ncc4c3)s2)c1] |
| I-5 | 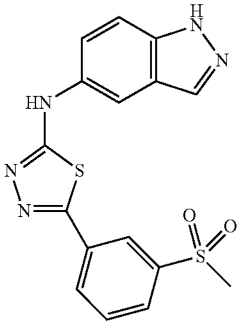 [SMILES: CS(=O)(=O)c1cccc(-c2nnc(Nc3ccc4[nH]ncc4c3)s2)c1] |
| I-6 | 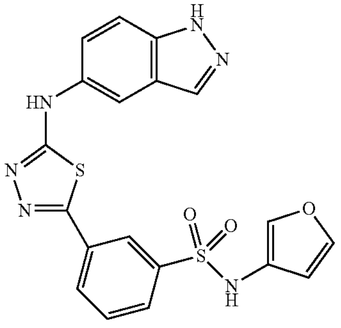 [SMILES: O=S(=O)(Nc1ccoc1)c1cccc(-c2nnc(Nc3ccc4[nH]ncc4c3)s2)c1] |

TABLE 1-continued
| No. | Compound |
| --- | --- |
| I-7 | 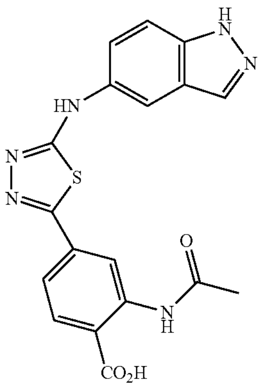 [SMILES: CC(=O)Nc1cc(-c2nnc(Nc3ccc4[nH]ncc4c3)s2)ccc1C(=O)O] |
| I-8 | 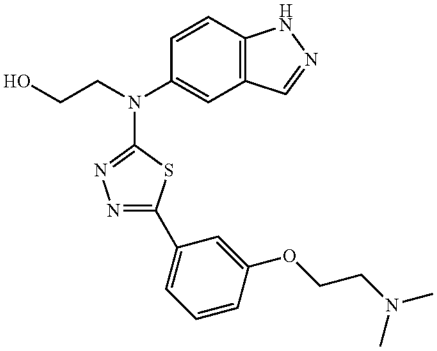 [SMILES: CN(C)CCOc1cccc(-c2nnc(N(CCO)c3ccc4[nH]ncc4c3)s2)c1] |
| I-9 | 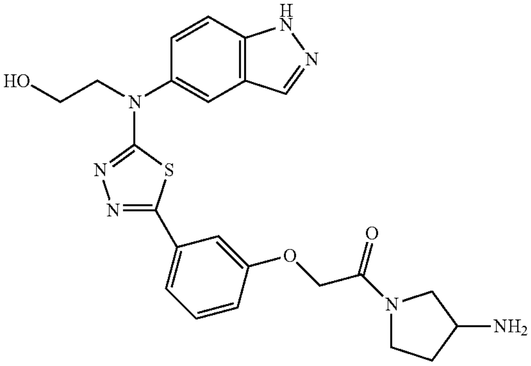 [SMILES: NC1CCN(C(=O)COc2cccc(-c3nnc(N(CCO)c4ccc5[nH]ncc5c4)s3)c2)C1] |
| I-10 | 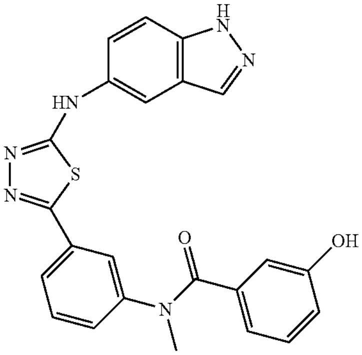 [SMILES: CN(C(=O)c1cccc(O)c1)c1cccc(-c2nnc(Nc3ccc4[nH]ncc4c3)s2)c1] |
| I-11 | 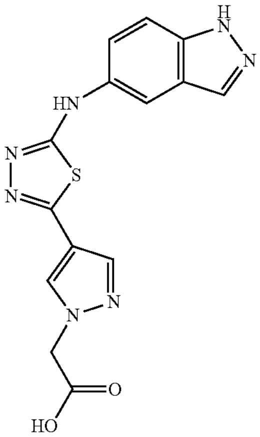 [SMILES: O=C(O)Cn1cc(-c2nnc(Nc3ccc4[nH]ncc4c3)s2)cn1] |
| I-12 | 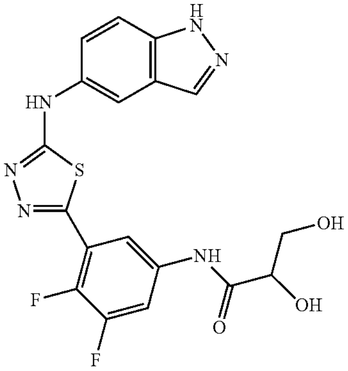 [SMILES: O=C(Nc1cc(F)c(F)c(-c2nnc(Nc3ccc4[nH]ncc4c3)s2)c1)C(O)CO] |
| I-13 | 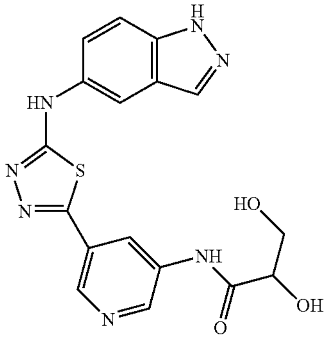 [SMILES: O=C(Nc1cncc(-c2nnc(Nc3ccc4[nH]ncc4c3)s2)c1)C(O)CO] |
| I-14 | 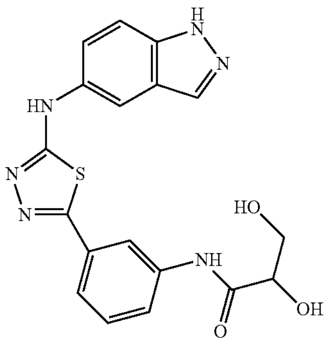 |

TABLE 1-continued
| No. | Compound |
|---|---|
| I-15 | 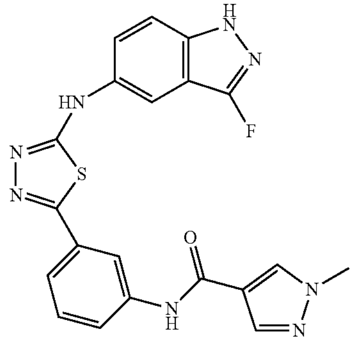 [SMILES: Cn1cc(C(=O)Nc2cccc(-c3nnc(Nc4ccc5[nH]nc(F)c5c4)s3)c2)cn1] |
| I-16 | 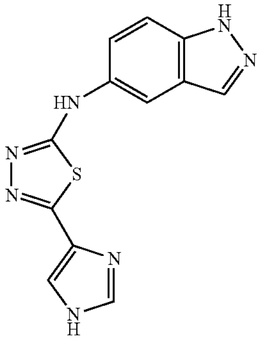 [SMILES: c1nc(-c2nnc(Nc3ccc4[nH]ncc4c3)s2)c[nH]1] |
| I-17 | 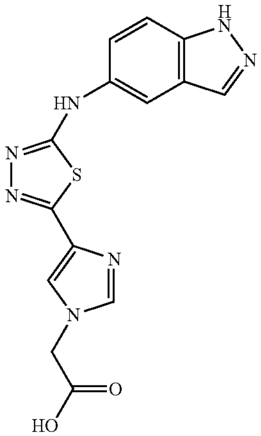 [SMILES: O=C(O)Cn1cnc(-c2nnc(Nc3ccc4[nH]ncc4c3)s2)c1] |
| I-18 | 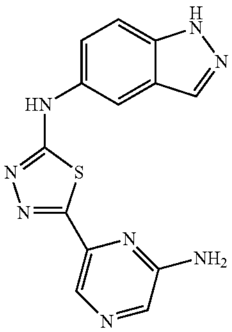 [SMILES: Nc1cncc(-c2nnc(Nc3ccc4[nH]ncc4c3)s2)n1] |
TABLE 1-continued
| No. | Compound |
|---|---|
| I-19 | 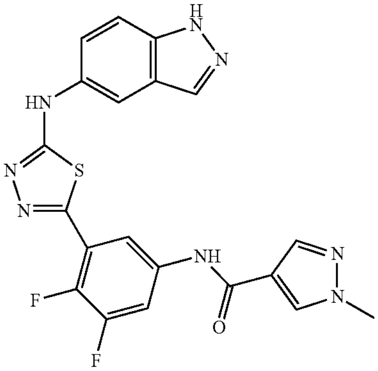 [SMILES: Cn1cc(C(=O)Nc2cc(F)c(F)c(-c3nnc(Nc4ccc5[nH]ncc5c4)s3)c2)cn1] |
| I-20 | 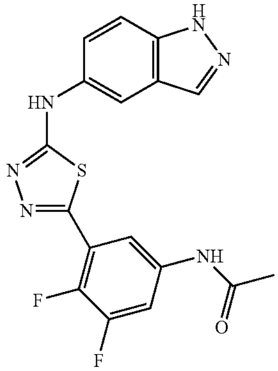 [SMILES: CC(=O)Nc1cc(F)c(F)c(-c2nnc(Nc3ccc4[nH]ncc4c3)s2)c1] |
| I-21 | 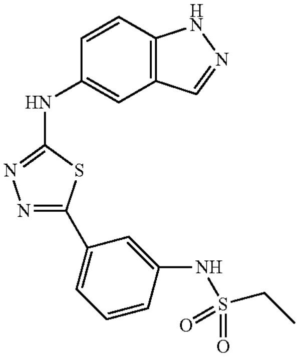 [SMILES: CCS(=O)(=O)Nc1cccc(-c2nnc(Nc3ccc4[nH]ncc4c3)s2)c1] |
| I-22 | 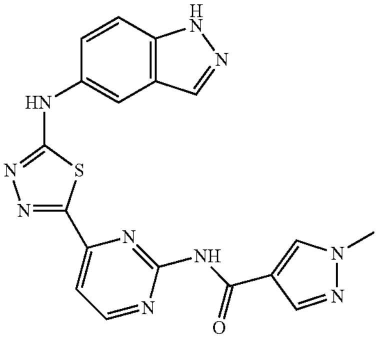 [SMILES: Cn1cc(C(=O)Nc2nccc(-c3nnc(Nc4ccc5[nH]ncc5c4)s3)n2)cn1] |

TABLE 1-continued
| No. | Compound |
|---|---|
| I-23 | 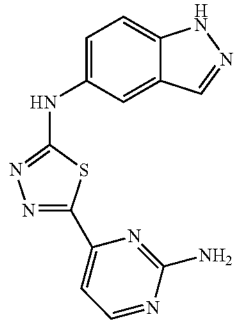 [SMILES: Nc1nccc(-c2nnc(Nc3ccc4[nH]ncc4c3)s2)n1] |
| I-24 | 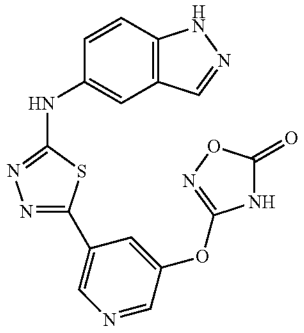 [SMILES: O=c1[nH]c(Oc2cncc(-c3nnc(Nc4ccc5[nH]ncc5c4)s3)c2)no1] |
| I-25 | 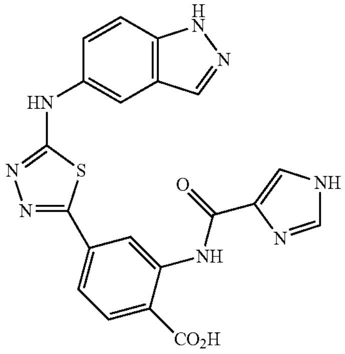 [SMILES: O=C(Nc1cc(-c2nnc(Nc3ccc4[nH]ncc4c3)s2)ccc1C(=O)O)c1c[nH]cn1] |
| I-26 | 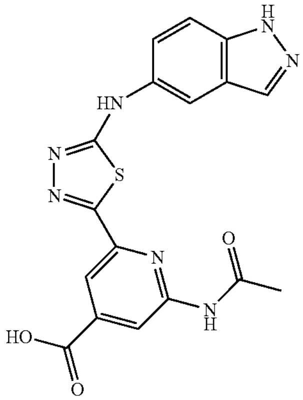 [SMILES: CC(=O)Nc1cc(C(=O)O)cc(-c2nnc(Nc3ccc4[nH]ncc4c3)s2)n1] |
TABLE 1-continued
| No. | Compound |
|---|---|
| I-27 | 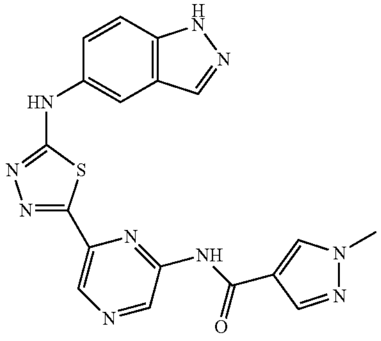 [SMILES: Cn1cc(C(=O)Nc2cncc(-c3nnc(Nc4ccc5[nH]ncc5c4)s3)n2)cn1] |
| I-28 | 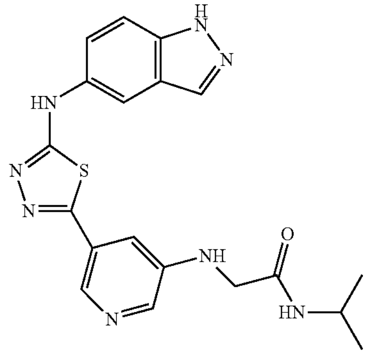 [SMILES: CC(C)NC(=O)CNc1cncc(-c2nnc(Nc3ccc4[nH]ncc4c3)s2)c1] |
| I-29 | 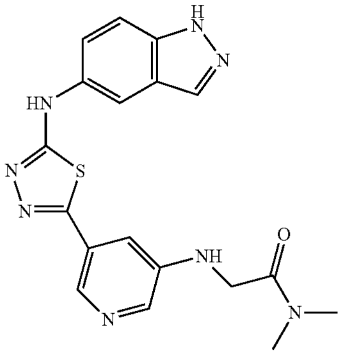 [SMILES: CN(C)C(=O)CNc1cncc(-c2nnc(Nc3ccc4[nH]ncc4c3)s2)c1] |
| I-30 | 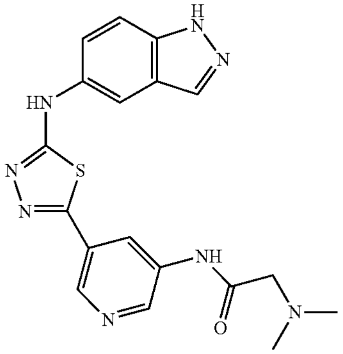 [SMILES: CN(C)CC(=O)Nc1cncc(-c2nnc(Nc3ccc4[nH]ncc4c3)s2)c1] |

TABLE 1-continued
| No. | Compound |
|---|---|
| I-31 | 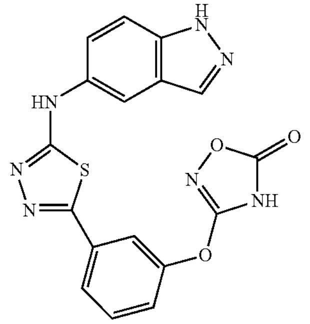 [SMILES: O=c1[nH]c(Oc2cccc(-c3nnc(Nc4ccc5[nH]ncc5c4)s3)c2)no1] |
| I-32 | 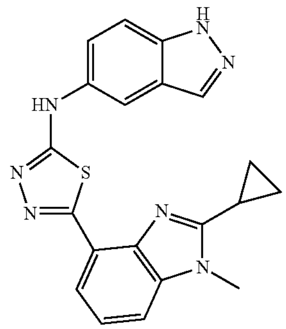 [SMILES: Cn1c(C2CC2)nc2c(-c3nnc(Nc4ccc5[nH]ncc5c4)s3)cccc21] |
| I-33 | 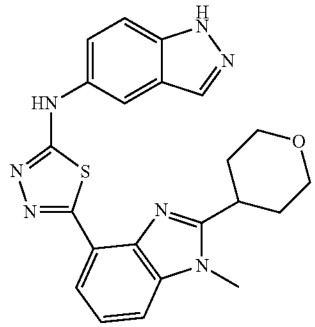 [SMILES: Cn1c(C2CCOCC2)nc2c(-c3nnc(Nc4ccc5[nH]ncc5c4)s3)cccc21] |
| I-34 | 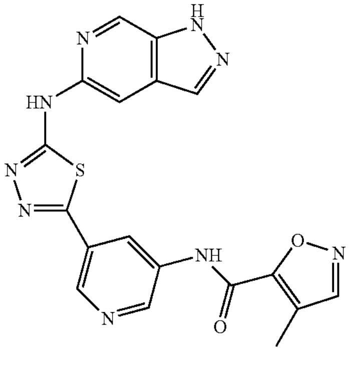 [SMILES: Cc1cnoc1C(=O)Nc1cncc(-c2nnc(Nc3cc4cn[nH]c4cn3)s2)c1] |
TABLE 1-continued
| No. | Compound |
|---|---|
| I-35 | 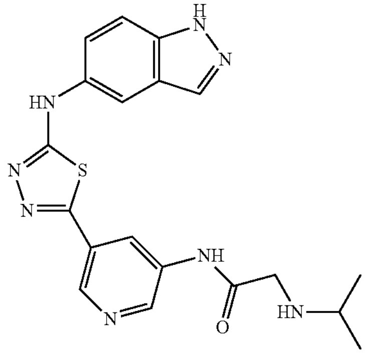 [SMILES: CC(C)NCC(=O)Nc1cncc(-c2nnc(Nc3ccc4[nH]ncc4c3)s2)c1] |
| I-36 | 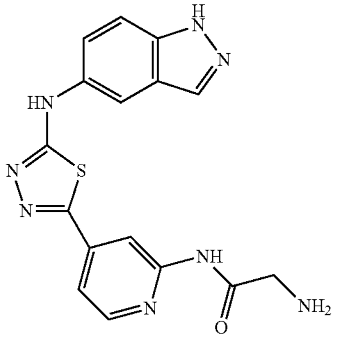 [SMILES: NCC(=O)Nc1cc(-c2nnc(Nc3ccc4[nH]ncc4c3)s2)ccn1] |
| I-37 | 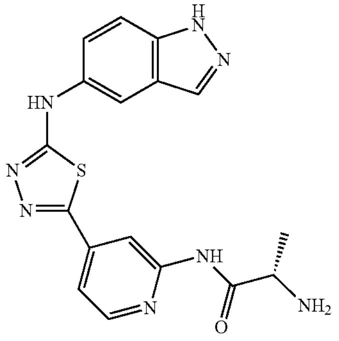 [SMILES: C[C@H](N)C(=O)Nc1cc(-c2nnc(Nc3ccc4[nH]ncc4c3)s2)ccn1] |
| I-38 | 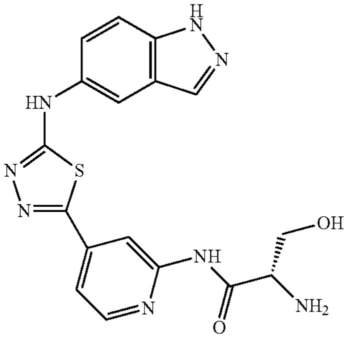 [SMILES: N[C@@H](CO)C(=O)Nc1cc(-c2nnc(Nc3ccc4[nH]ncc4c3)s2)ccn1] |

TABLE 1-continued
| No. | Compound |
|---|---|
| I-39 | 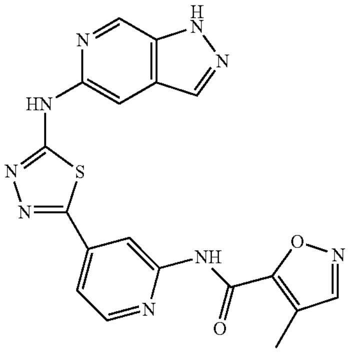 [SMILES: Cc1cnoc1C(=O)Nc1cc(-c2nnc(Nc3cc4cn[nH]c4cn3)s2)ccn1] |
| I-40 | 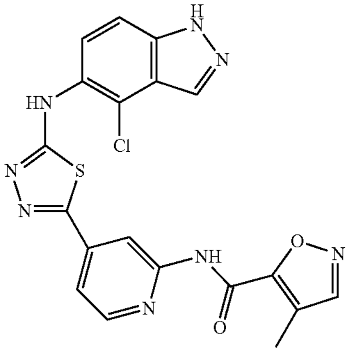 [SMILES: Cc1cnoc1C(=O)Nc1cc(-c2nnc(Nc3ccc4[nH]ncc4c3Cl)s2)ccn1] |
| I-41 | 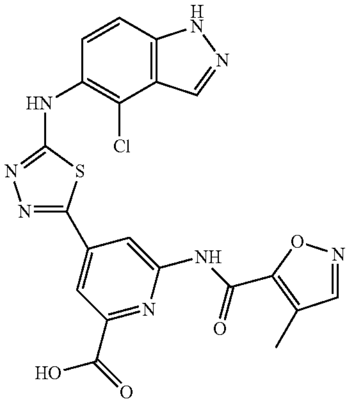 [SMILES: Cc1cnoc1C(=O)Nc1cc(-c2nnc(Nc3ccc4[nH]ncc4c3Cl)s2)cc(C(=O)O)n1] |
| I-42 | 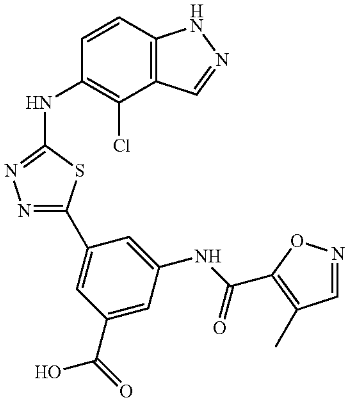 |
TABLE 1-continued
| No. | Compound |
|---|---|
| I-43 | 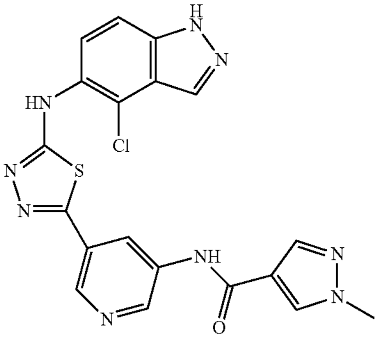 [SMILES: Cn1cc(C(=O)Nc2cncc(-c3nnc(Nc4ccc5[nH]ncc5c4Cl)s3)c2)cn1] |
| I-44 | 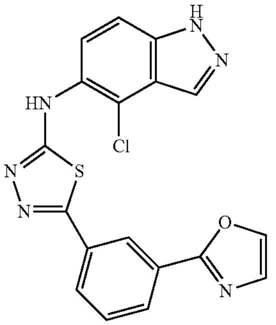 [SMILES: Clc1c(Nc2nnc(-c3cccc(-c4ncco4)c3)s2)ccc2[nH]ncc12] |
| I-45 | 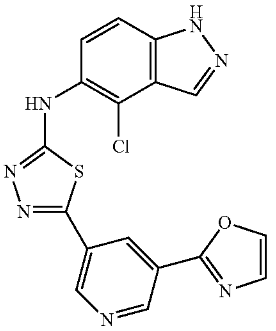 [SMILES: Clc1c(Nc2nnc(-c3cncc(-c4ncco4)c3)s2)ccc2[nH]ncc12] |
| I-46 | 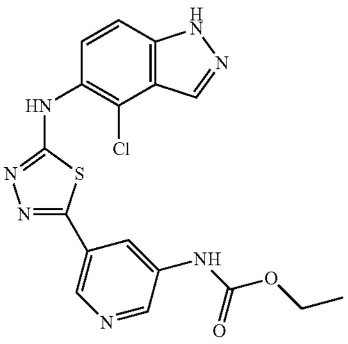 [SMILES: CCOC(=O)Nc1cncc(-c2nnc(Nc3ccc4[nH]ncc4c3Cl)s2)c1] |

TABLE 1-continued
| No. | Compound |
|---|---|
| I-47 | 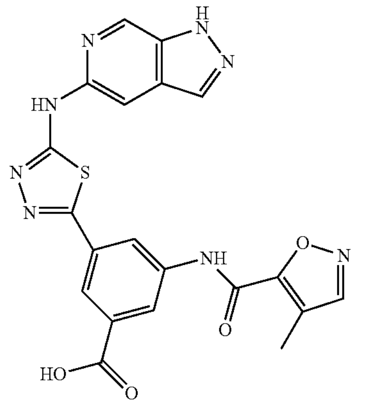 [SMILES: Cc1cnoc1C(=O)Nc1cc(C(=O)O)cc(-c2nnc(Nc3cc4cn[nH]c4cn3)s2)c1] |
| I-48 | 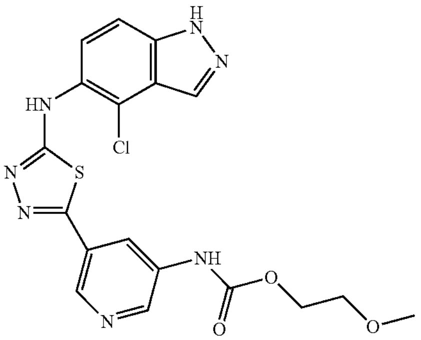 [SMILES: COCCOC(=O)Nc1cncc(-c2nnc(Nc3ccc4[nH]ncc4c3Cl)s2)c1] |
| I-49 | 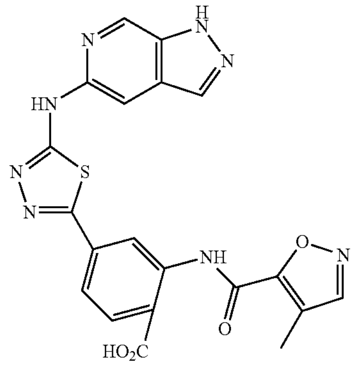 [SMILES: Cc1cnoc1C(=O)Nc1cc(-c2nnc(Nc3cc4cn[nH]c4cn3)s2)ccc1C(=O)O] |
| I-50 | 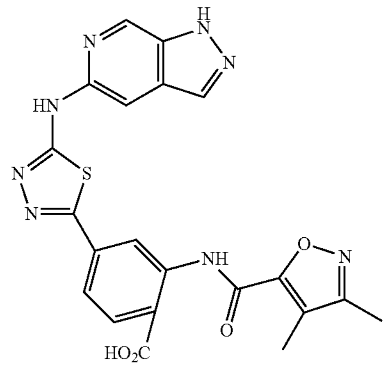 [SMILES: Cc1noc(C(=O)Nc2cc(-c3nnc(Nc4cc5cn[nH]c5cn4)s3)ccc2C(=O)O)c1C] |
TABLE 1-continued
| No. | Compound |
|---|---|
| I-51 | 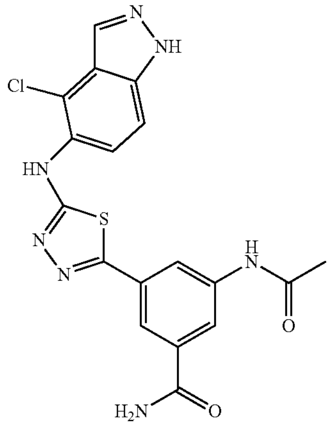 [SMILES: CC(=O)Nc1cc(C(N)=O)cc(-c2nnc(Nc3ccc4[nH]ncc4c3Cl)s2)c1] |
| I-52 | 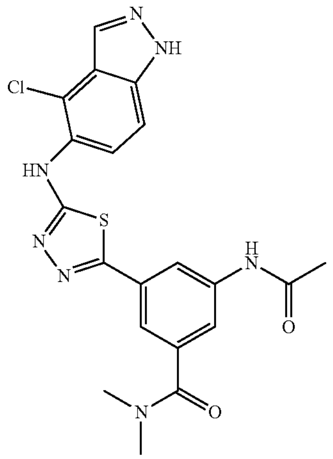 [SMILES: CC(=O)Nc1cc(C(=O)N(C)C)cc(-c2nnc(Nc3ccc4[nH]ncc4c3Cl)s2)c1] |
| I-53 | 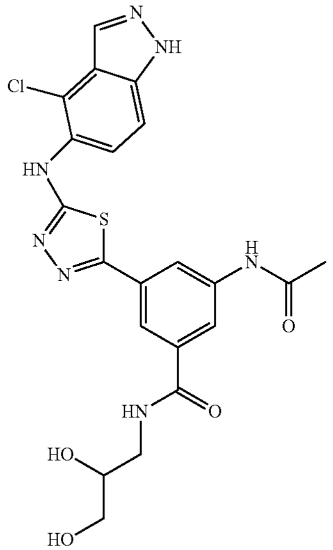 [SMILES: CC(=O)Nc1cc(C(=O)NCC(O)CO)cc(-c2nnc(Nc3ccc4[nH]ncc4c3Cl)s2)c1] |

TABLE 1-continued
| No. | Compound |
|---|---|
| I-54 | 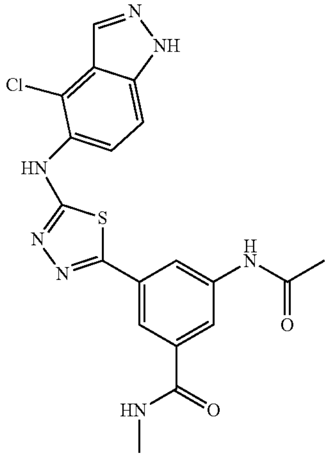 [SMILES: CNC(=O)c1cc(NC(C)=O)cc(-c2nnc(Nc3ccc4[nH]ncc4c3Cl)s2)c1] |
| I-55 | 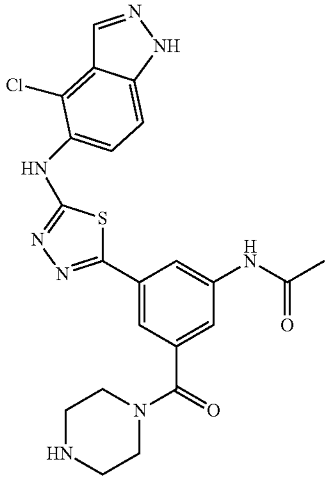 [SMILES: CC(=O)Nc1cc(C(=O)N2CCNCC2)cc(-c2nnc(Nc3ccc4[nH]ncc4c3Cl)s2)c1] |
| I-56 | 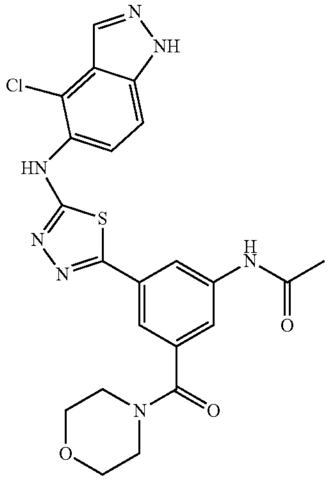 [SMILES: CC(=O)Nc1cc(C(=O)N2CCOCC2)cc(-c2nnc(Nc3ccc4[nH]ncc4c3Cl)s2)c1] |
| I-57 | 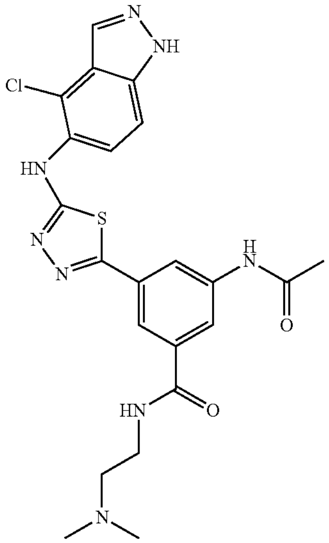 [SMILES: CC(=O)Nc1cc(C(=O)NCCN(C)C)cc(-c2nnc(Nc3ccc4[nH]ncc4c3Cl)s2)c1] |
| I-58 | 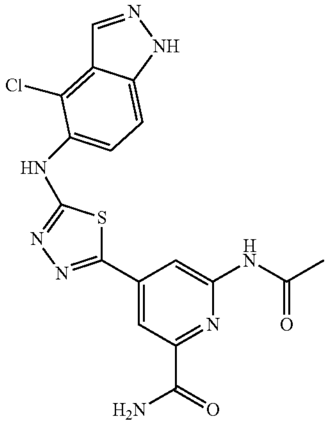 [SMILES: CC(=O)Nc1cc(-c2nnc(Nc3ccc4[nH]ncc4c3Cl)s2)cc(C(N)=O)n1] |
| I-59 | 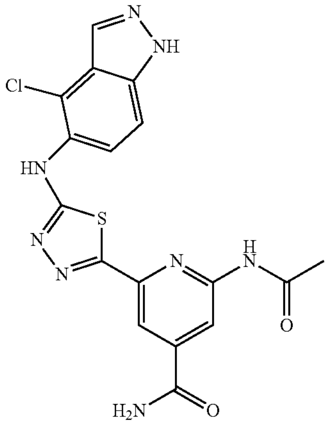 [SMILES: CC(=O)Nc1cc(C(N)=O)cc(-c2nnc(Nc3ccc4[nH]ncc4c3Cl)s2)n1] |

TABLE 1-continued
| No. | Compound |
| --- | --- |
| I-60 | 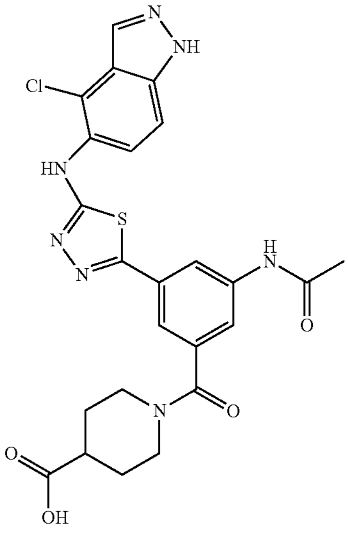 [SMILES: CC(=O)Nc1cc(C(=O)N2CCC(C(=O)O)CC2)cc(-c2nnc(Nc3ccc4[nH]ncc4c3Cl)s2)c1] |
| I-61 | 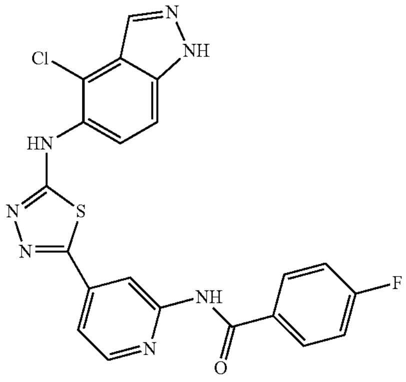 |
| I-62 | 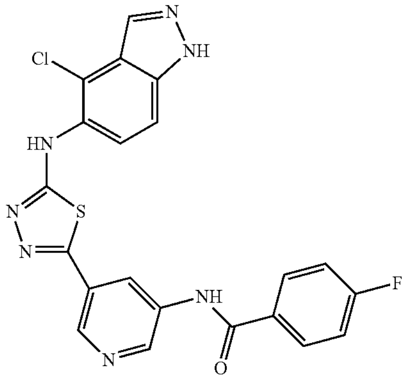 [SMILES: O=C(Nc1cncc(-c2nnc(Nc3ccc4[nH]ncc4c3Cl)s2)c1)c1ccc(F)cc1] |
TABLE 1-continued
| No. | Compound |
| --- | --- |
| I-63 | 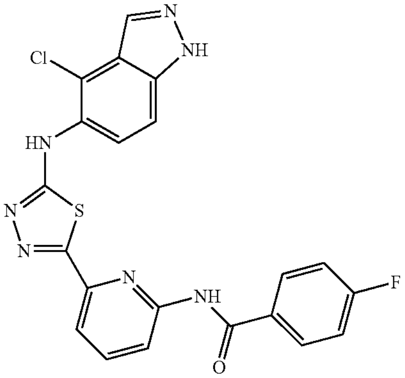 |
| I-64 | 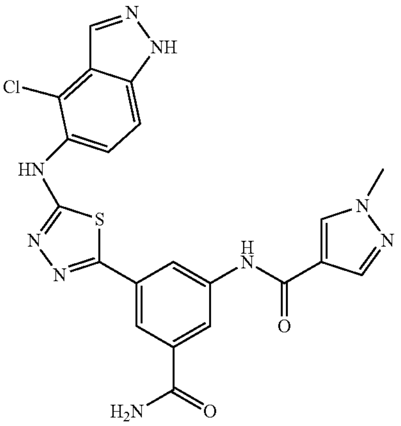 [SMILES: Cn1cc(C(=O)Nc2cc(C(N)=O)cc(-c3nnc(Nc4ccc5[nH]ncc5c4Cl)s3)c2)cn1] |
| I-65 | 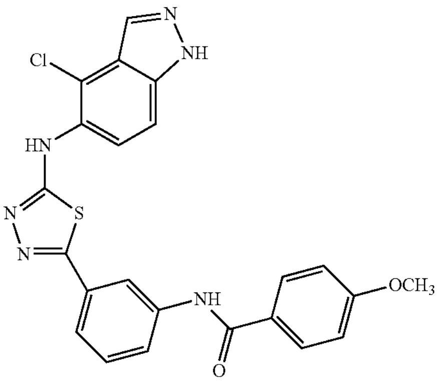 [SMILES: COc1ccc(C(=O)Nc2cccc(-c3nnc(Nc4ccc5[nH]ncc5c4Cl)s3)c2)cc1] |
| I-66 | 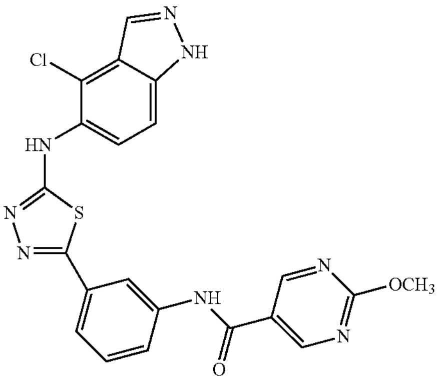 [SMILES: COc1ncc(C(=O)Nc2cccc(-c3nnc(Nc4ccc5[nH]ncc5c4Cl)s3)c2)cn1] |

TABLE 1-continued
| No. | Compound |
| --- | --- |
| I-67 | 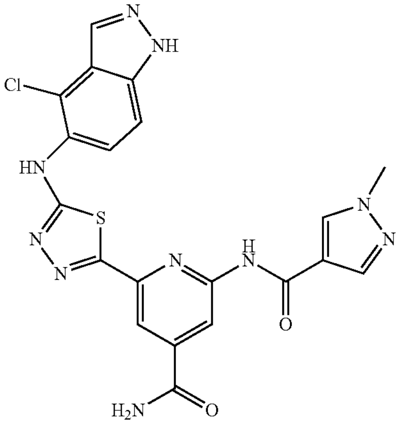 |
| I-68 | 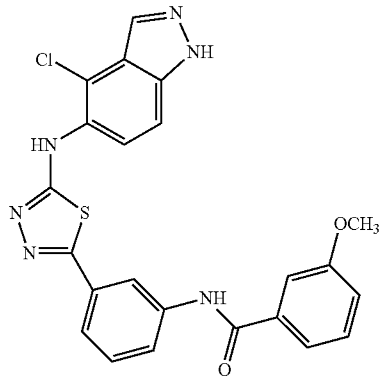 [SMILES: COc1cccc(C(=O)Nc2cccc(-c3nnc(Nc4ccc5[nH]ncc5c4Cl)s3)c2)c1] |
| I-69 | 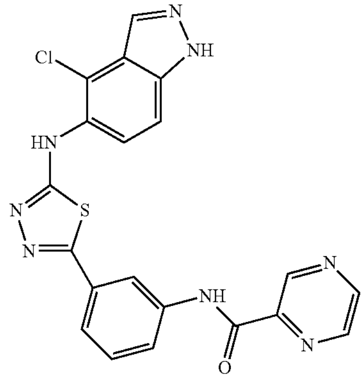 [SMILES: O=C(Nc1cccc(-c2nnc(Nc3ccc4[nH]ncc4c3Cl)s2)c1)c1cnccn1] |
| I-70 | 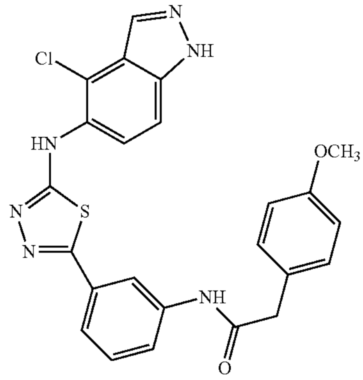 [SMILES: COc1ccc(CC(=O)Nc2cccc(-c3nnc(Nc4ccc5[nH]ncc5c4Cl)s3)c2)cc1] |
TABLE 1-continued
| No. | Compound |
| --- | --- |
| I-71 | 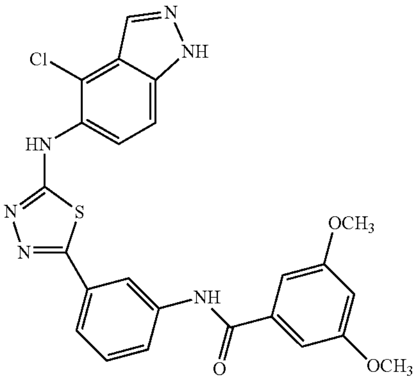 [SMILES: COc1cc(OC)cc(C(=O)Nc2cccc(-c3nnc(Nc4ccc5[nH]ncc5c4Cl)s3)c2)c1] |
| I-72 | 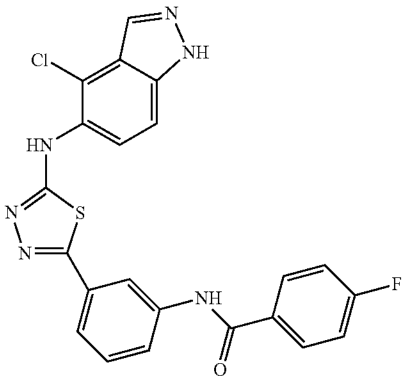 [SMILES: O=C(Nc1cccc(-c2nnc(Nc3ccc4[nH]ncc4c3Cl)s2)c1)c1ccc(F)cc1] |
| I-73 | 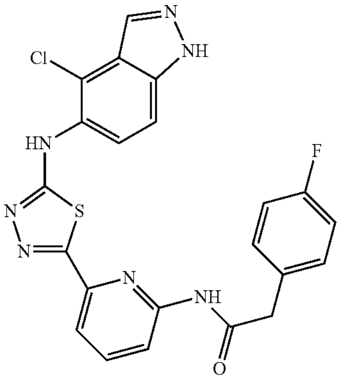 [SMILES: O=C(Cc1ccc(F)cc1)Nc1cccc(-c2nnc(Nc3ccc4[nH]ncc4c3Cl)s2)n1] |
| I-74 | 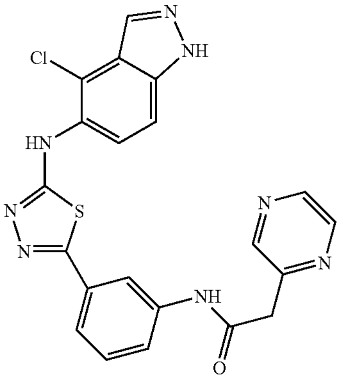 [SMILES: O=C(Cc1cnccn1)Nc1cccc(-c2nnc(Nc3ccc4[nH]ncc4c3Cl)s2)c1] |

TABLE 1-continued
| No. | Compound |
| --- | --- |
| I-75 | 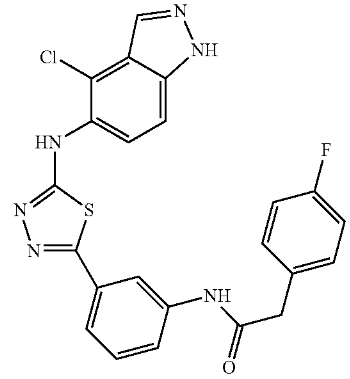 |
| I-76 | 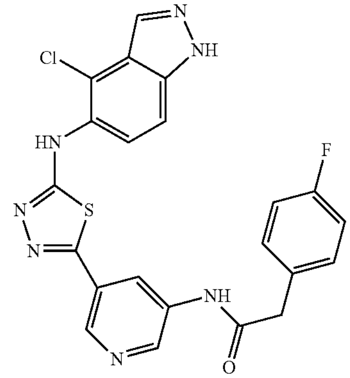 [SMILES: O=C(Cc1ccc(F)cc1)Nc1cncc(-c2nnc(Nc3ccc4[nH]ncc4c3Cl)s2)c1] |
| I-77 | 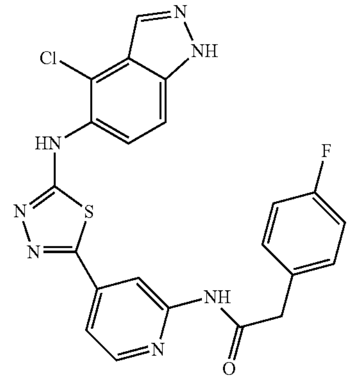 [SMILES: O=C(Cc1ccc(F)cc1)Nc1cc(-c2nnc(Nc3ccc4[nH]ncc4c3Cl)s2)ccn1] |
| I-78 | 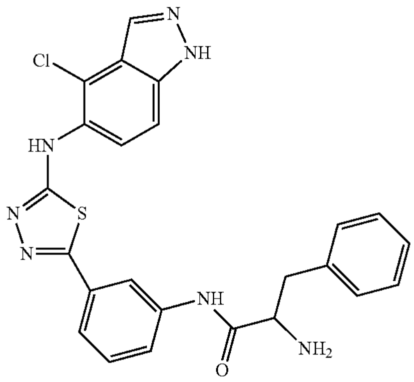 [SMILES: NC(Cc1ccccc1)C(=O)Nc1cccc(-c2nnc(Nc3ccc4[nH]ncc4c3Cl)s2)c1] |
TABLE 1-continued
| No. | Compound |
| --- | --- |
| I-79 | 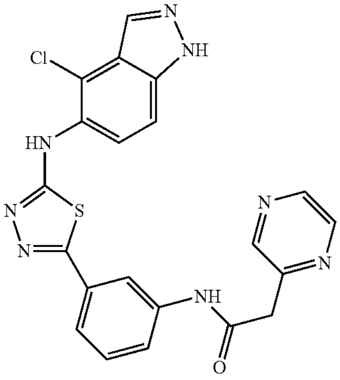 [SMILES: O=C(Cc1cnccn1)Nc1cccc(-c2nnc(Nc3ccc4[nH]ncc4c3Cl)s2)c1] |
| I-80 | 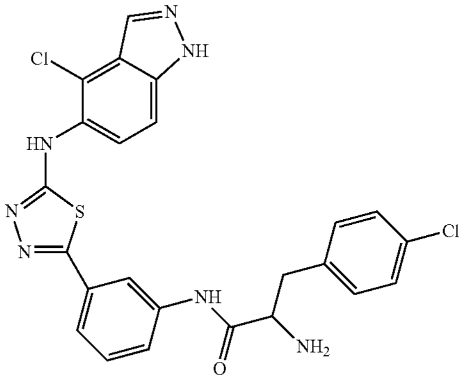 [SMILES: NC(Cc1ccc(Cl)cc1)C(=O)Nc1cccc(-c2nnc(Nc3ccc4[nH]ncc4c3Cl)s2)c1] |
| I-81 | 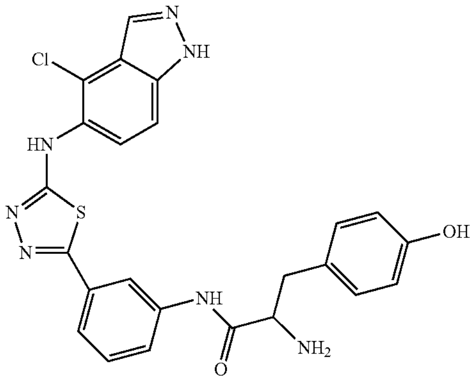 [SMILES: NC(Cc1ccc(O)cc1)C(=O)Nc1cccc(-c2nnc(Nc3ccc4[nH]ncc4c3Cl)s2)c1] |
| I-82 | 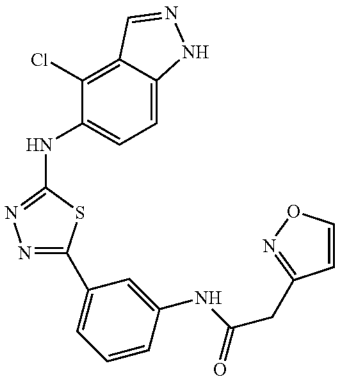 |

TABLE 1-continued
| No. | Compound |
|---|---|
| I-83 | 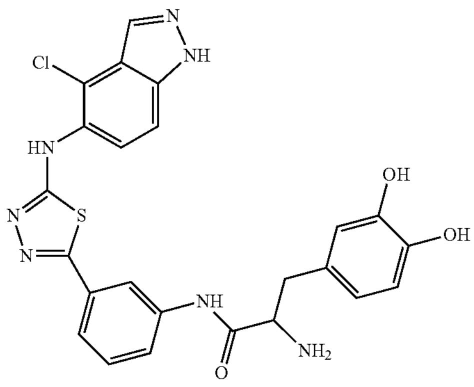 [SMILES: NC(Cc1ccc(O)c(O)c1)C(=O)Nc1cccc(-c2nnc(Nc3ccc4[nH]ncc4c3Cl)s2)c1] |
| I-84 | 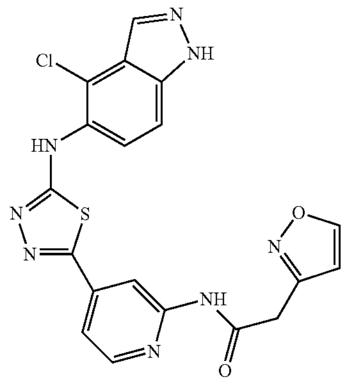 [SMILES: O=C(Cc1ccon1)Nc1cc(-c2nnc(Nc3ccc4[nH]ncc4c3Cl)s2)ccn1] |
| I-85 | 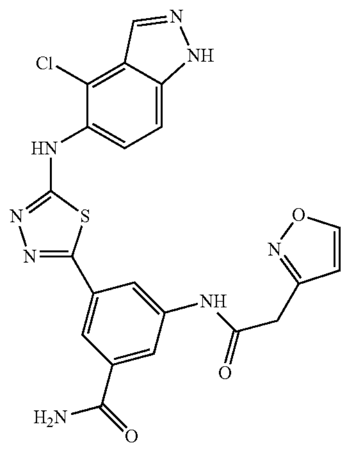 [SMILES: NC(=O)c1cc(NC(=O)Cc2ccon2)cc(-c2nnc(Nc3ccc4[nH]ncc4c3Cl)s2)c1] |
TABLE 1-continued
| No. | Compound |
|---|---|
| I-86 | 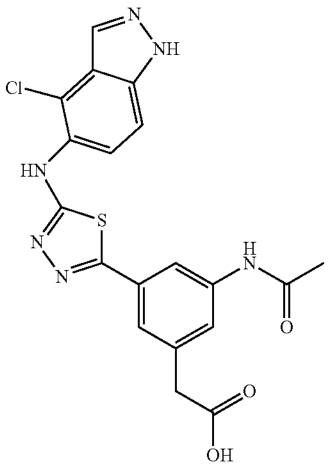 [SMILES: CC(=O)Nc1cc(CC(=O)O)cc(-c2nnc(Nc3ccc4[nH]ncc4c3Cl)s2)c1] |
| I-87 | 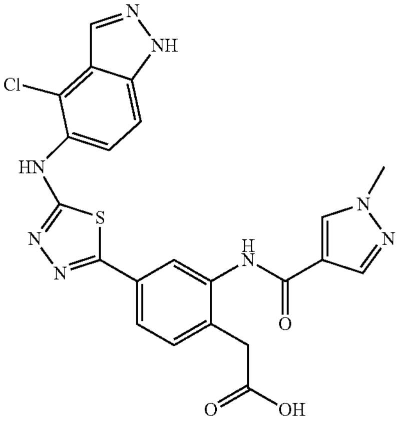 [SMILES: Cn1cc(C(=O)Nc2cc(-c3nnc(Nc4ccc5[nH]ncc5c4Cl)s3)ccc2CC(=O)O)cn1] |
| I-88 | 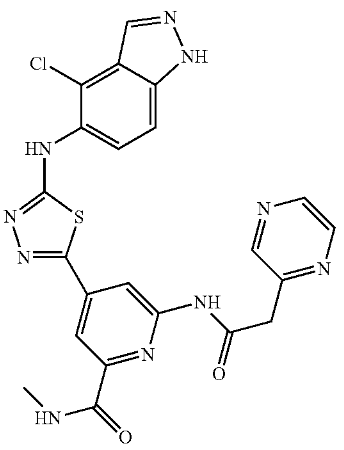 [SMILES: CNC(=O)c1cc(-c2nnc(Nc3ccc4[nH]ncc4c3Cl)s2)cc(NC(=O)Cc2cnccn2)n1] |

TABLE 1-continued
| No. | Compound |
|---|---|
| I-89 | 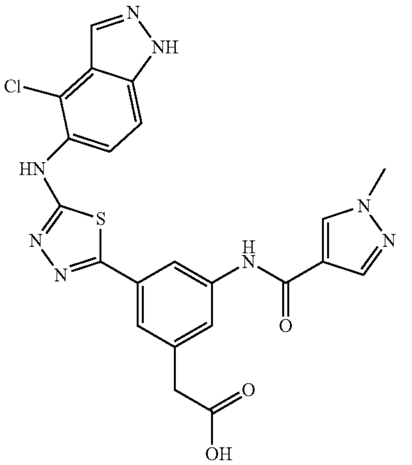 [SMILES: Cn1cc(C(=O)Nc2cc(CC(=O)O)cc(-c3nnc(Nc4ccc5[nH]ncc5c4Cl)s3)c2)cn1] |
| I-90 | 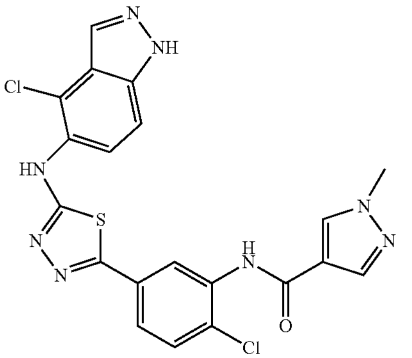 [SMILES: Cn1cc(C(=O)Nc2cc(-c3nnc(Nc4ccc5[nH]ncc5c4Cl)s3)ccc2Cl)cn1] |
In certain other embodiments, the compound is a compound in Table 2, or a pharmaceutically acceptable salt thereof.
TABLE 2
| Compound |
|---|
| 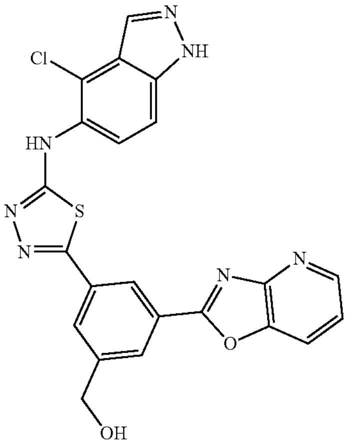 [SMILES: OCc1cc(-c2nc3ncccc3o2)cc(-c2nnc(Nc3ccc4[nH]ncc4c3Cl)s2)c1] |
TABLE 2-continued
| Compound |
|---|
| 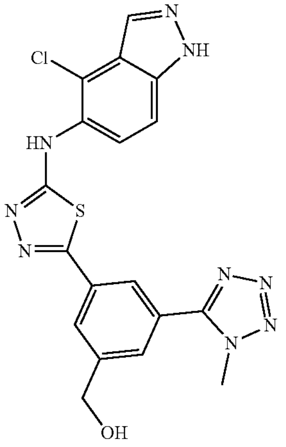 [SMILES: Cn1nnnc1-c1cc(CO)cc(-c2nnc(Nc3ccc4[nH]ncc4c3Cl)s2)c1] |
| 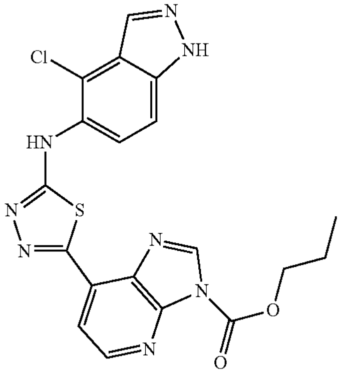 |
| 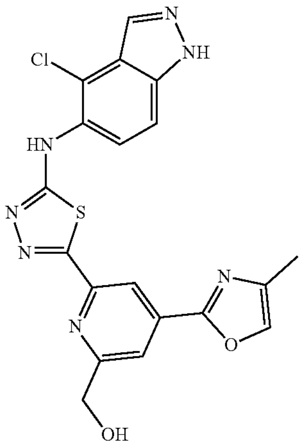 [SMILES: Cc1coc(-c2cc(CO)nc(-c3nnc(Nc4ccc5[nH]ncc5c4Cl)s3)c2)n1] |

TABLE 2-continued
| Compound |
| --- |
| 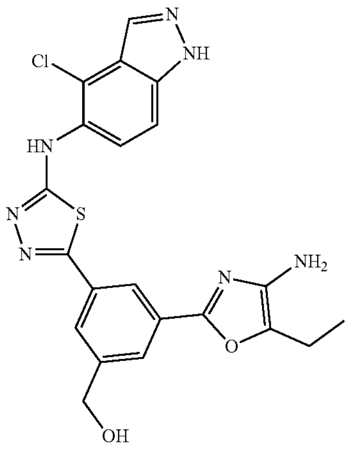 [SMILES: CCc1oc(-c2cc(CO)cc(-c3nnc(Nc4ccc5[nH]ncc5c4Cl)s3)c2)nc1N] |
| 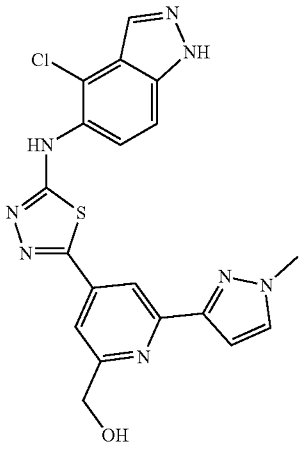 [SMILES: Cn1ccc(-c2cc(-c3nnc(Nc4ccc5[nH]ncc5c4Cl)s3)cc(CO)n2)n1] |
| 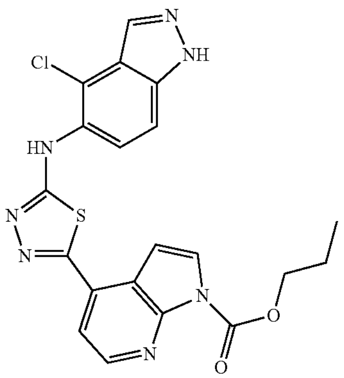 [SMILES: CCCOC(=O)n1ccc2c(-c3nnc(Nc4ccc5[nH]ncc5c4Cl)s3)ccnc21] |
TABLE 2-continued
| Compound |
| --- |
| 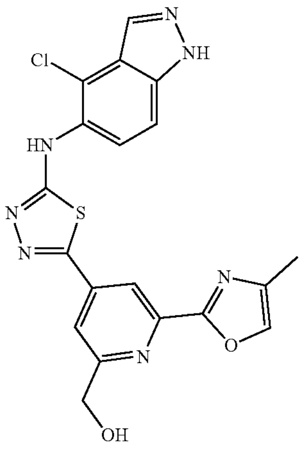 [SMILES: Cc1coc(-c2cc(-c3nnc(Nc4ccc5[nH]ncc5c4Cl)s3)cc(CO)n2)n1] |
| 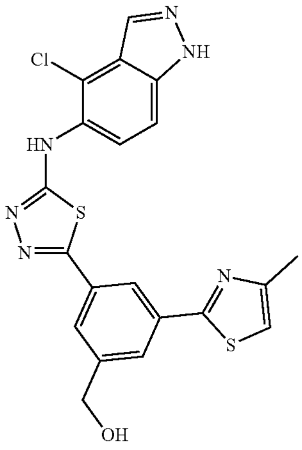 [SMILES: Cc1csc(-c2cc(CO)cc(-c3nnc(Nc4ccc5[nH]ncc5c4Cl)s3)c2)n1] |
| 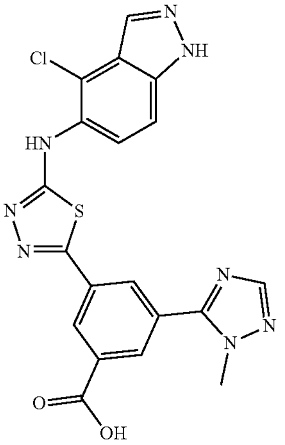 [SMILES: Cn1ncnc1-c1cc(C(=O)O)cc(-c2nnc(Nc3ccc4[nH]ncc4c3Cl)s2)c1] |

TABLE 2-continued
| Compound |
| --- |
| 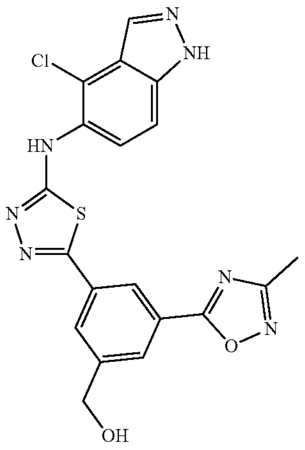 [SMILES: Cc1noc(-c2cc(CO)cc(-c3nnc(Nc4ccc5[nH]ncc5c4Cl)s3)c2)n1] |
| 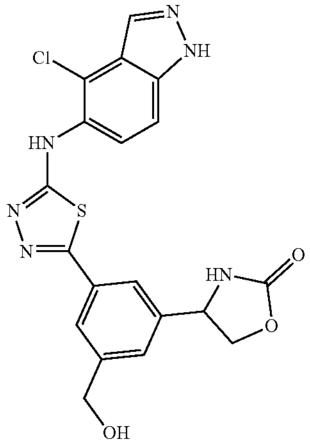 [SMILES: O=C1NC(c2cc(CO)cc(-c3nnc(Nc4ccc5[nH]ncc5c4Cl)s3)c2)CO1] |
| 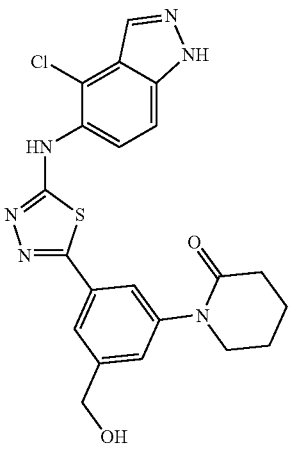 [SMILES: O=C1CCCCN1c1cc(CO)cc(-c2nnc(Nc3ccc4[nH]ncc4c3Cl)s2)c1] |
TABLE 2-continued
| Compound |
| --- |
| 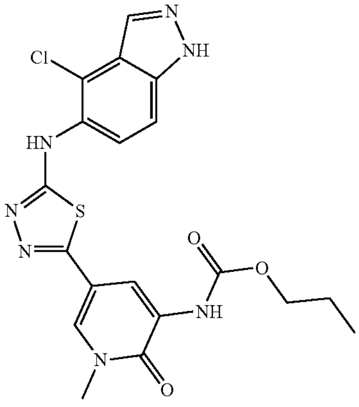 [SMILES: CCCOC(=O)Nc1cc(-c2nnc(Nc3ccc4[nH]ncc4c3Cl)s2)cn(C)c1=O] |
| 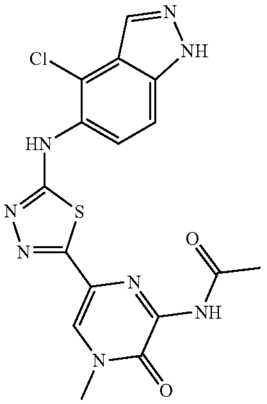 [SMILES: CC(=O)Nc1nc(-c2nnc(Nc3ccc4[nH]ncc4c3Cl)s2)cn(C)c1=O] |
| 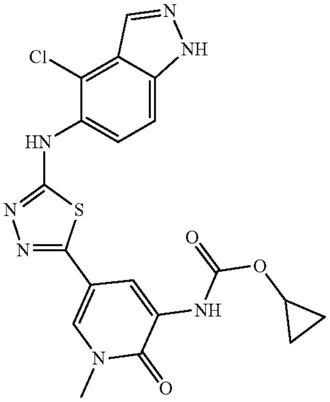 [SMILES: Cn1cc(-c2nnc(Nc3ccc4[nH]ncc4c3Cl)s2)cc(NC(=O)OC2CC2)c1=O] |

TABLE 2-continued
| Compound |
| --- |
| 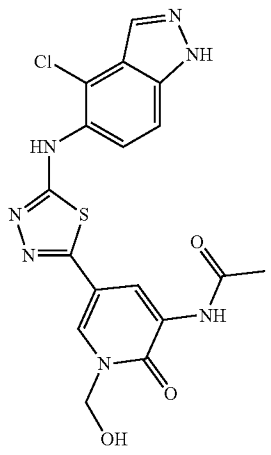 [SMILES: CC(=O)Nc1cc(-c2nnc(Nc3ccc4[nH]ncc4c3Cl)s2)cn(CO)c1=O] |
| 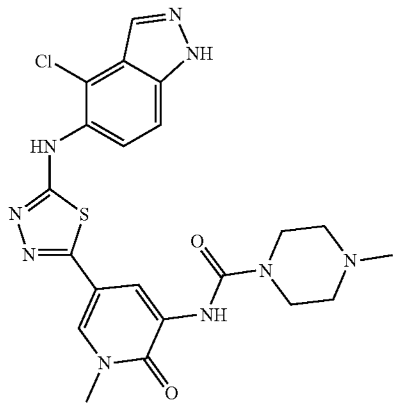 [SMILES: CN1CCN(C(=O)Nc2cc(-c3nnc(Nc4ccc5[nH]ncc5c4Cl)s3)cn(C)c2=O)CC1] |
| 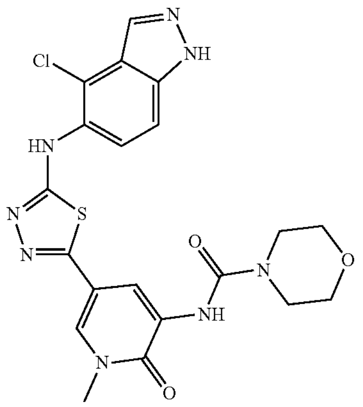 [SMILES: Cn1cc(-c2nnc(Nc3ccc4[nH]ncc4c3Cl)s2)cc(NC(=O)N2CCOCC2)c1=O] |
TABLE 2-continued
| Compound |
| --- |
| 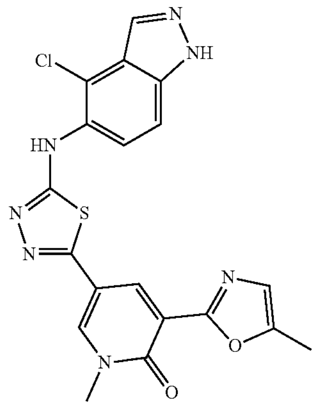 [SMILES: Cc1cnc(-c2cc(-c3nnc(Nc4ccc5[nH]ncc5c4Cl)s3)cn(C)c2=O)o1] |
| 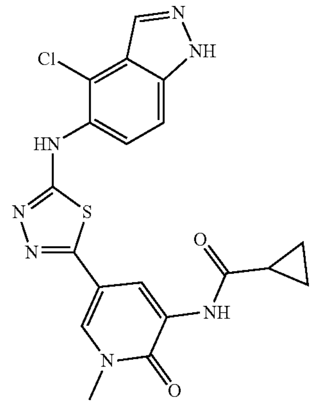 [SMILES: Cn1cc(-c2nnc(Nc3ccc4[nH]ncc4c3Cl)s2)cc(NC(=O)C2CC2)c1=O] |
| 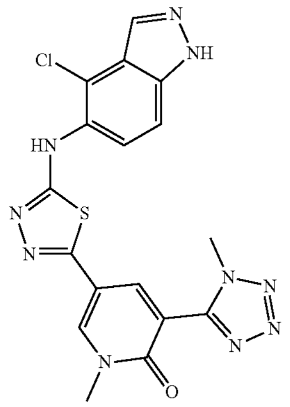 [SMILES: Cn1nnnc1-c1cc(-c2nnc(Nc3ccc4[nH]ncc4c3Cl)s2)cn(C)c1=O] |

TABLE 2-continued
| Compound |
| --- |
| 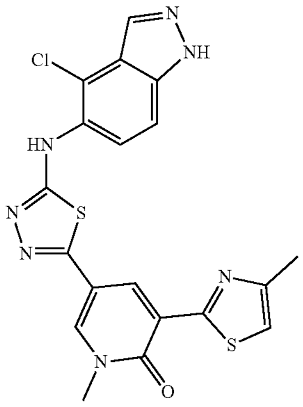 [SMILES: Cc1csc(-c2cc(-c3nnc(Nc4ccc5[nH]ncc5c4Cl)s3)cn(C)c2=O)n1] |
| 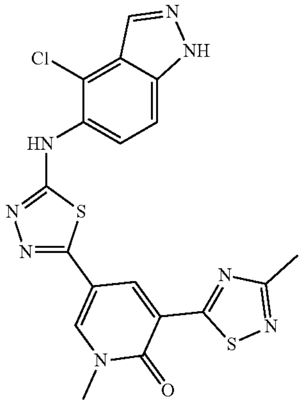 [SMILES: Cc1nsc(-c2cc(-c3nnc(Nc4ccc5[nH]ncc5c4Cl)s3)cn(C)c2=O)n1] |
| 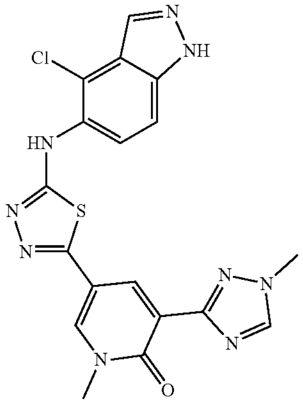 [SMILES: Cn1cnc(-c2cc(-c3nnc(Nc4ccc5[nH]ncc5c4Cl)s3)cn(C)c2=O)n1] |
| 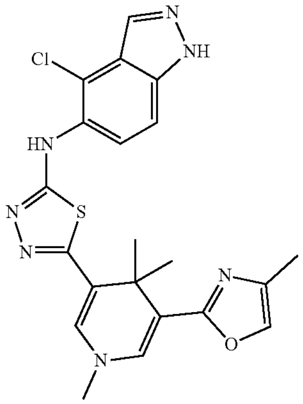 [SMILES: Cc1coc(C2=CN(C)C=C(c3nnc(Nc4ccc5[nH]ncc5c4Cl)s3)C2(C)C)n1] |
TABLE 2-continued
| Compound |
| --- |
| 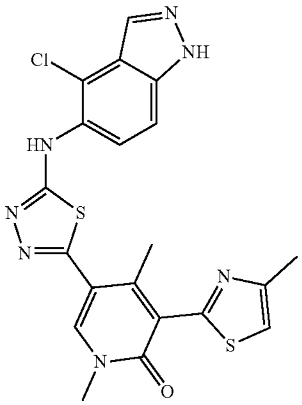 [SMILES: Cc1csc(-c2c(C)c(-c3nnc(Nc4ccc5[nH]ncc5c4Cl)s3)cn(C)c2=O)n1] |
| 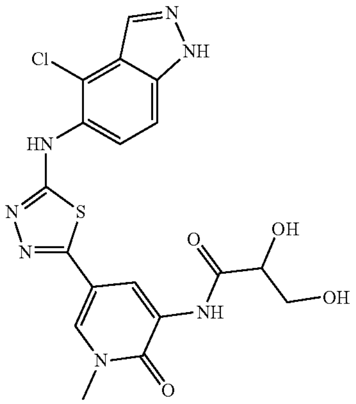 [SMILES: Cn1cc(-c2nnc(Nc3ccc4[nH]ncc4c3Cl)s2)cc(NC(=O)C(O)CO)c1=O] |
| 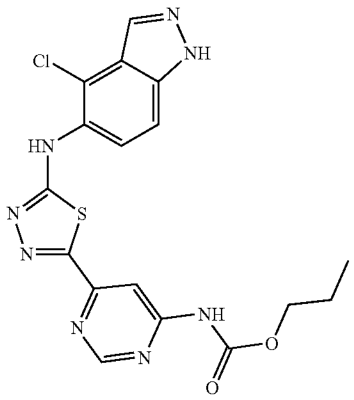 [SMILES: CCCOC(=O)Nc1cc(-c2nnc(Nc3ccc4[nH]ncc4c3Cl)s2)ncn1] |
| 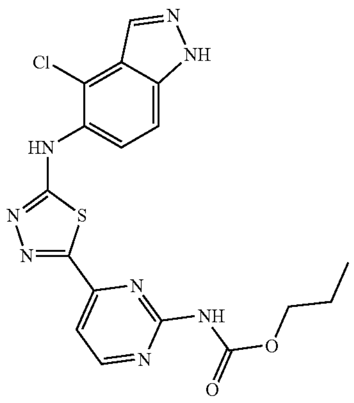 [SMILES: CCCOC(=O)Nc1nccc(-c2nnc(Nc3ccc4[nH]ncc4c3Cl)s2)n1] |

TABLE 2-continued
| Compound |
| --- |
| 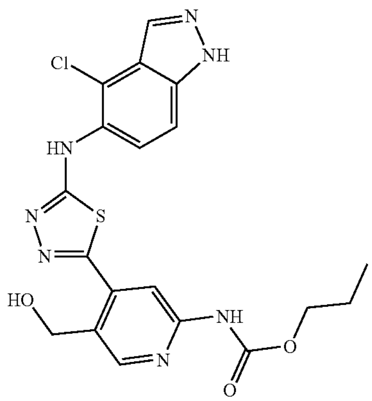 [SMILES: CCCOC(=O)Nc1cc(-c2nnc(Nc3ccc4[nH]ncc4c3Cl)s2)c(CO)cn1] |
| 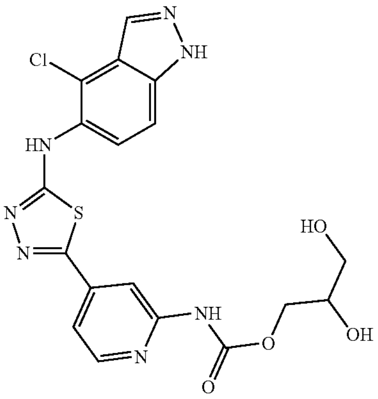 [SMILES: O=C(Nc1cc(-c2nnc(Nc3ccc4[nH]ncc4c3Cl)s2)ccn1)OCC(O)CO] |
| 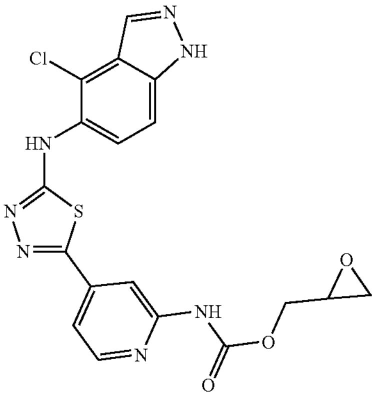 [SMILES: O=C(Nc1cc(-c2nnc(Nc3ccc4[nH]ncc4c3Cl)s2)ccn1)OCC1CO1] |
| 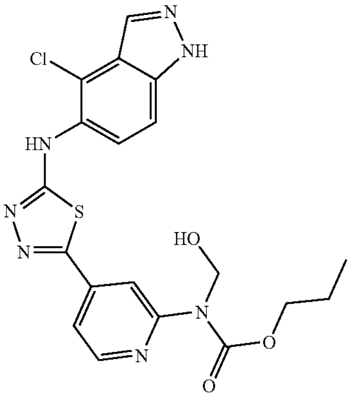 [SMILES: CCCOC(=O)N(CO)c1cc(-c2nnc(Nc3ccc4[nH]ncc4c3Cl)s2)ccn1] |
TABLE 2-continued
| Compound |
| --- |
| 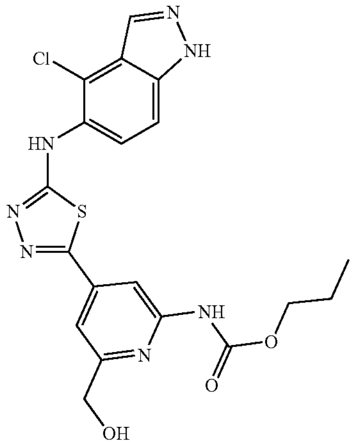 [SMILES: CCCOC(=O)Nc1cc(-c2nnc(Nc3ccc4[nH]ncc4c3Cl)s2)cc(CO)n1] |
| 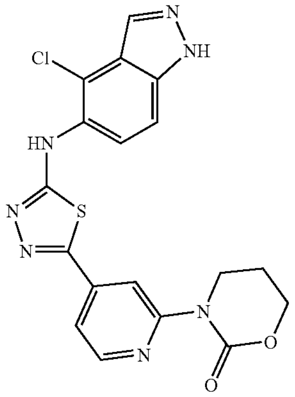 [SMILES: O=C1OCCCN1c1cc(-c2nnc(Nc3ccc4[nH]ncc4c3Cl)s2)ccn1] |
| 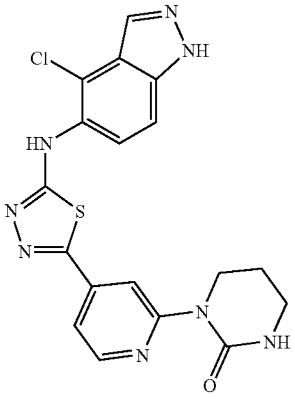 [SMILES: O=C1NCCCN1c1cc(-c2nnc(Nc3ccc4[nH]ncc4c3Cl)s2)ccn1] |

TABLE 2-continued
| Compound |
|---|
| 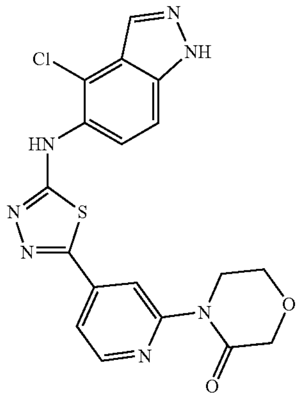 [SMILES: O=C1COCCN1c1cc(-c2nnc(Nc3ccc4[nH]ncc4c3Cl)s2)ccn1] |
| 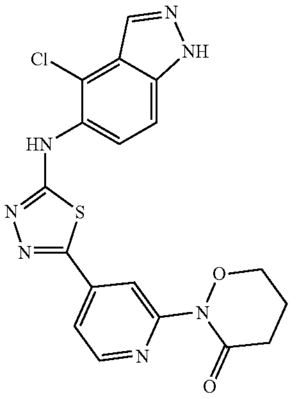 [SMILES: O=C1CCCON1c1cc(-c2nnc(Nc3ccc4[nH]ncc4c3Cl)s2)ccn1] |
| 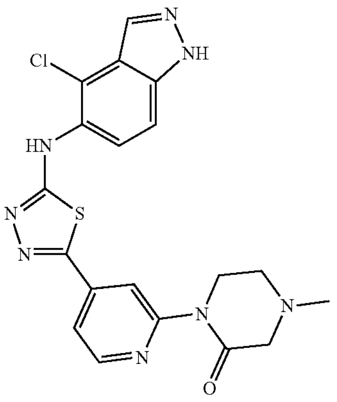 [SMILES: CN1CCN(c2cc(-c3nnc(Nc4ccc5[nH]ncc5c4Cl)s3)ccn2)C(=O)C1] |
| 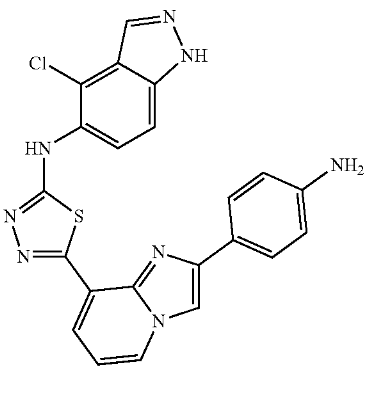 [SMILES: Nc1ccc(-c2cn3cccc(-c4nnc(Nc5ccc6[nH]ncc6c5Cl)s4)c3n2)cc1] |
TABLE 2-continued
| Compound |
|---|
| 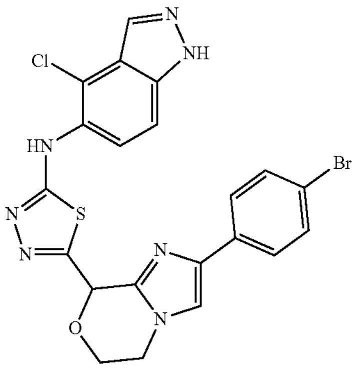 [SMILES: Clc1c(Nc2nnc(C3OCCn4cc(-c5ccc(Br)cc5)nc43)s2)ccc2[nH]ncc12] |
| 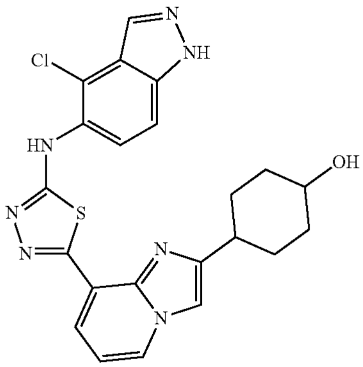 [SMILES: OC1CCC(c2cn3cccc(-c4nnc(Nc5ccc6[nH]ncc6c5Cl)s4)c3n2)CC1] |
| 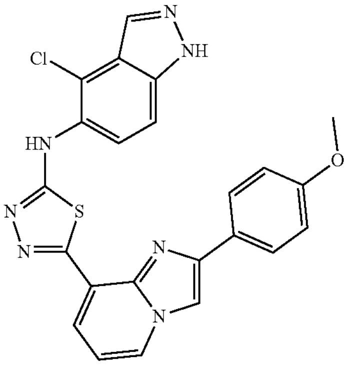 [SMILES: COc1ccc(-c2cn3cccc(-c4nnc(Nc5ccc6[nH]ncc6c5Cl)s4)c3n2)cc1] |
| 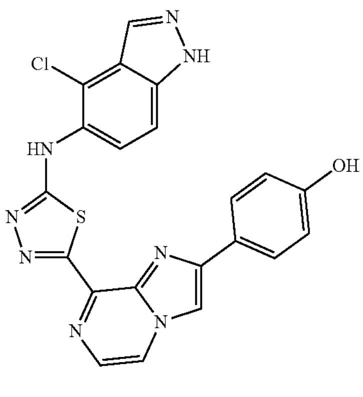 [SMILES: Oc1ccc(-c2cn3ccnc(-c4nnc(Nc5ccc6[nH]ncc6c5Cl)s4)c3n2)cc1]

| Compound |
| --- |
| 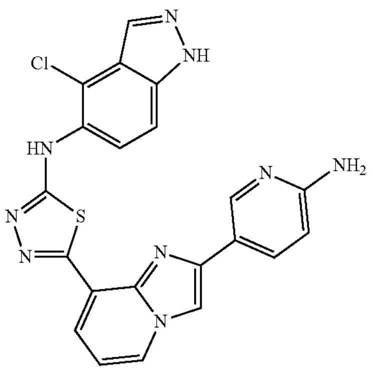 [SMILES: Nc1ccc(-c2cn3cccc(-c4nnc(Nc5ccc6[nH]ncc6c5Cl)s4)c3n2)cn1] |
| 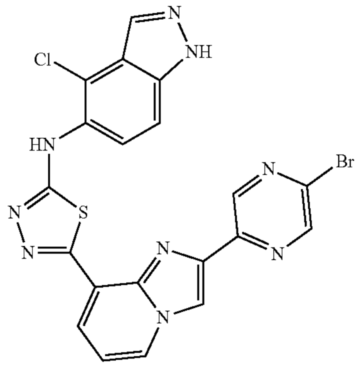 [SMILES: Clc1c(Nc2nnc(-c3cccn4cc(-c5cnc(Br)cn5)nc34)s2)ccc2[nH]ncc12] |
| 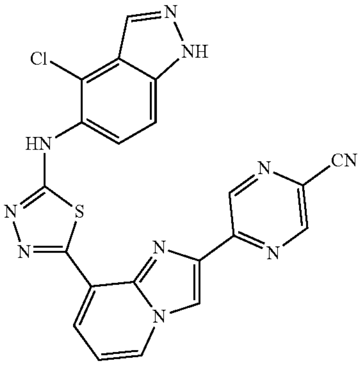 [SMILES: N#Cc1cnc(-c2cn3cccc(-c4nnc(Nc5ccc6[nH]ncc6c5Cl)s4)c3n2)cn1] |
| 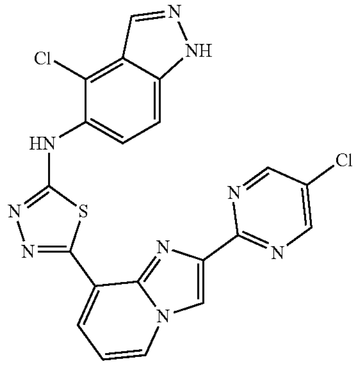 [SMILES: Clc1cnc(-c2cn3cccc(-c4nnc(Nc5ccc6[nH]ncc6c5Cl)s4)c3n2)nc1] |
| Compound |
| --- |
| 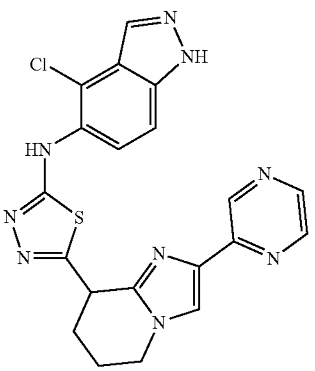 [SMILES: Clc1c(Nc2nnc(C3CCCn4cc(-c5cnccn5)nc43)s2)ccc2[nH]ncc12] |
| 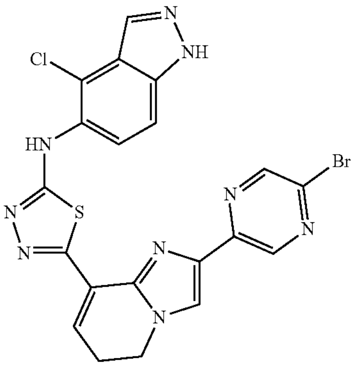 [SMILES: Clc1c(Nc2nnc(C3=CCCn4cc(-c5cnc(Br)cn5)nc43)s2)ccc2[nH]ncc12] |
| 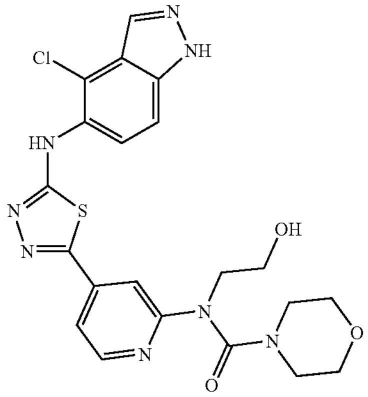 [SMILES: O=C(N1CCOCC1)N(CCO)c1cc(-c2nnc(Nc3ccc4[nH]ncc4c3Cl)s2)ccn1] |
| 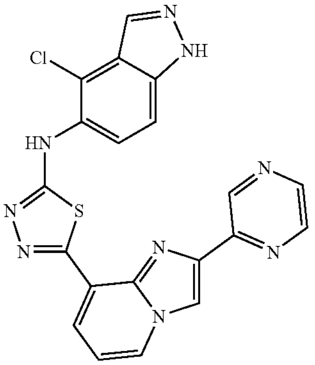 [SMILES: Clc1c(Nc2nnc(-c3cccn4cc(-c5cnccn5)nc34)s2)ccc2[nH]ncc12] |

TABLE 2-continued
| Compound |
| --- |
| 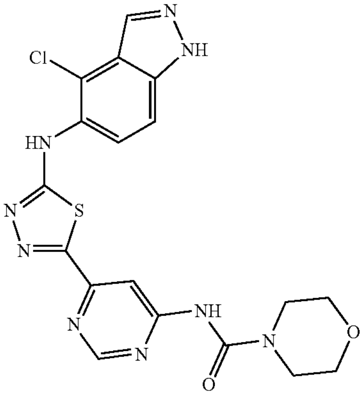 [SMILES: O=C(Nc1cc(-c2nnc(Nc3ccc4[nH]ncc4c3Cl)s2)ncn1)N1CCOCC1] |
| 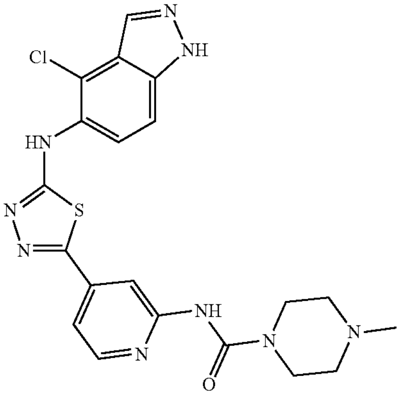 [SMILES: CN1CCN(C(=O)Nc2cc(-c3nnc(Nc4ccc5[nH]ncc5c4Cl)s3)ccn2)CC1] |
| 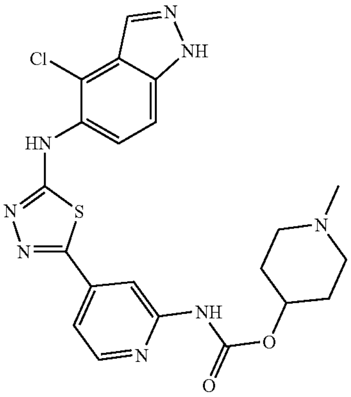 [SMILES: CN1CCC(OC(=O)Nc2cc(-c3nnc(Nc4ccc5[nH]ncc5c4Cl)s3)ccn2)CC1] |
| 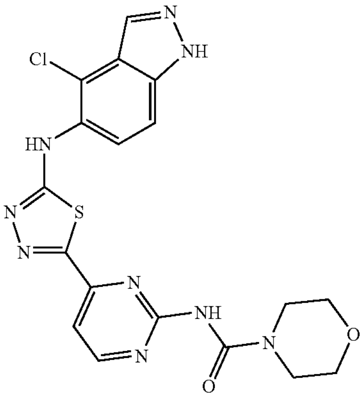 [SMILES: O=C(Nc1nccc(-c2nnc(Nc3ccc4[nH]ncc4c3Cl)s2)n1)N1CCOCC1] |
TABLE 2-continued
| Compound |
| --- |
| 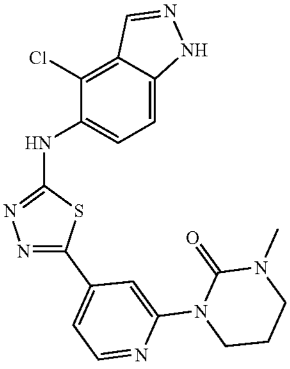 [SMILES: CN1CCCN(c2cc(-c3nnc(Nc4ccc5[nH]ncc5c4Cl)s3)ccn2)C1=O] |
| 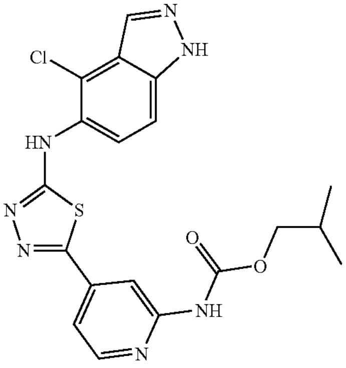 [SMILES: CC(C)COC(=O)Nc1cc(-c2nnc(Nc3ccc4[nH]ncc4c3Cl)s2)ccn1] |
| 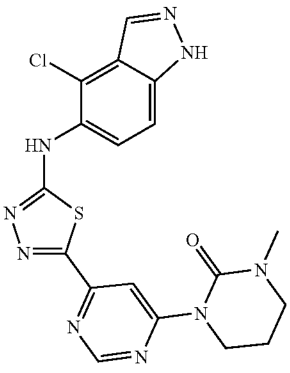 [SMILES: CN1CCCN(c2cc(-c3nnc(Nc4ccc5[nH]ncc5c4Cl)s3)ncn2)C1=O] |
| 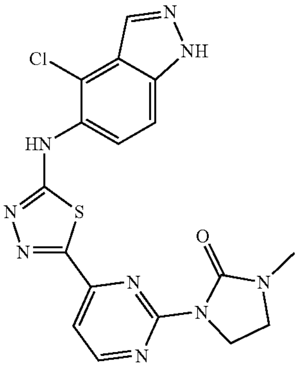 [SMILES: CN1CCN(c2nccc(-c3nnc(Nc4ccc5[nH]ncc5c4Cl)s3)n2)C1=O] |

TABLE 2-continued
| Compound |
| --- |
| 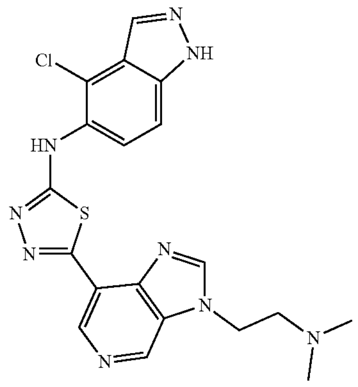 [SMILES: CN(C)CCn1cnc2c(-c3nnc(Nc4ccc5[nH]ncc5c4Cl)s3)cncc21] |
| 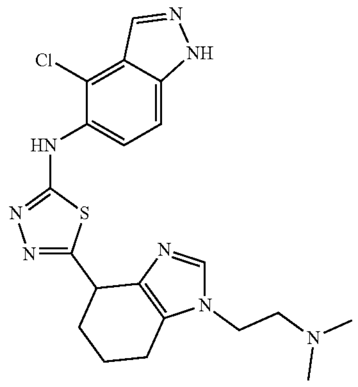 [SMILES: CN(C)CCn1cnc2c1CCCC2c1nnc(Nc2ccc3[nH]ncc3c2Cl)s1] |
| 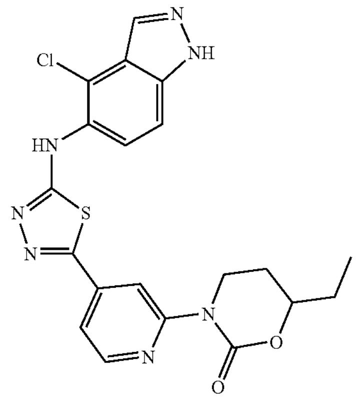 [SMILES: CCC1CCN(c2cc(-c3nnc(Nc4ccc5[nH]ncc5c4Cl)s3)ccn2)C(=O)O1] |
| 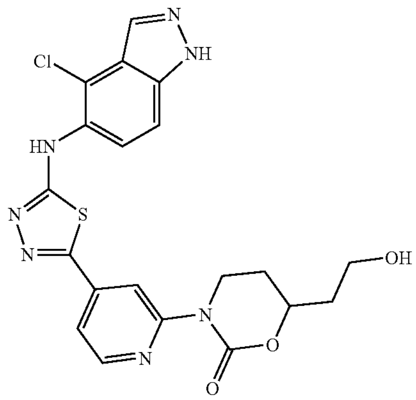 [SMILES: O=C1OC(CCO)CCN1c1cc(-c2nnc(Nc3ccc4[nH]ncc4c3Cl)s2)ccn1] |
TABLE 2-continued
| Compound |
| --- |
| 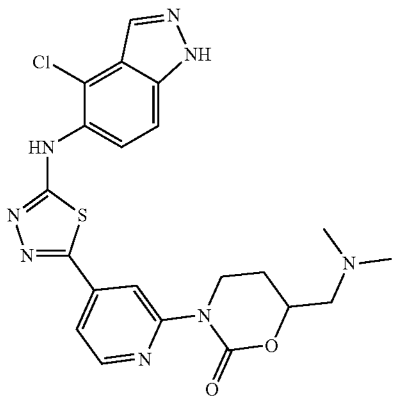 [SMILES: CN(C)CC1CCN(c2cc(-c3nnc(Nc4ccc5[nH]ncc5c4Cl)s3)ccn2)C(=O)O1] |
| 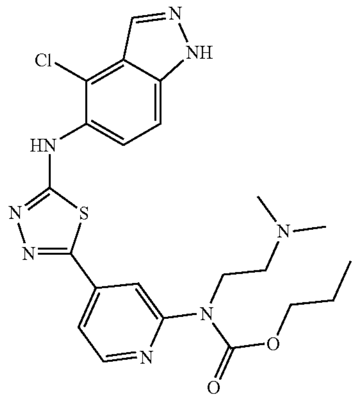 [SMILES: CCCOC(=O)N(CCN(C)C)c1cc(-c2nnc(Nc3ccc4[nH]ncc4c3Cl)s2)ccn1] |
| 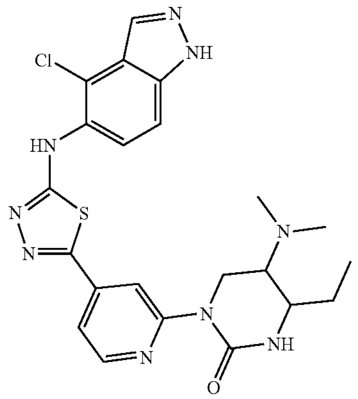 [SMILES: CCC1NC(=O)N(c2cc(-c3nnc(Nc4ccc5[nH]ncc5c4Cl)s3)ccn2)CC1N(C)C] |
| 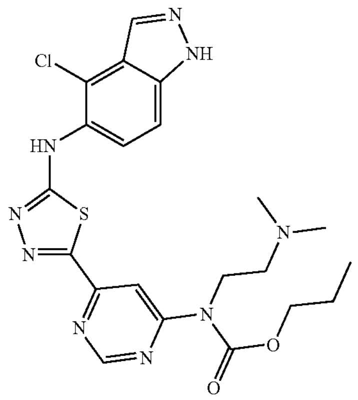 [SMILES: CCCOC(=O)N(CCN(C)C)c1cc(-c2nnc(Nc3ccc4[nH]ncc4c3Cl)s2)ncn1] |

TABLE 2-continued
| Compound |
| --- |
| 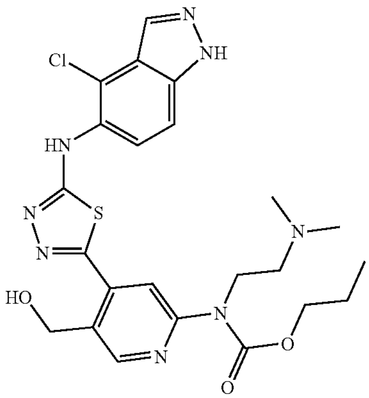 [SMILES: CCCOC(=O)N(CCN(C)C)c1cc(-c2nnc(Nc3ccc4[nH]ncc4c3Cl)s2)c(CO)cn1] |
| 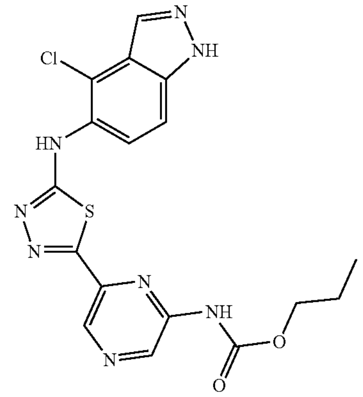 [SMILES: CCCOC(=O)Nc1cncc(-c2nnc(Nc3ccc4[nH]ncc4c3Cl)s2)n1] |
| 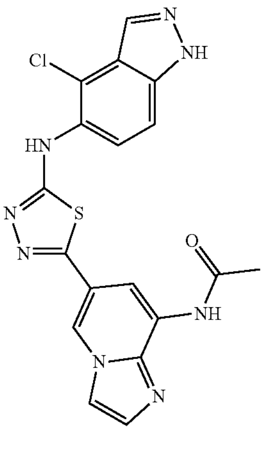 [SMILES: CC(=O)Nc1cc(-c2nnc(Nc3ccc4[nH]ncc4c3Cl)s2)cn2ccnc12] |
| 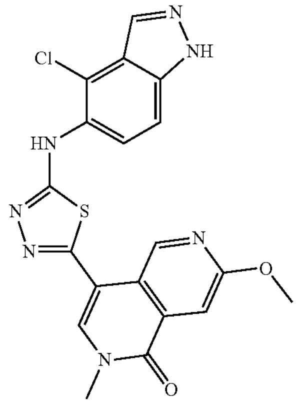 [SMILES: COc1cc2c(=O)n(C)cc(-c3nnc(Nc4ccc5[nH]ncc5c4Cl)s3)c2cn1] |
| 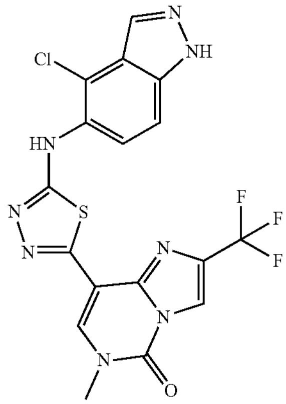 [SMILES: Cn1cc(-c2nnc(Nc3ccc4[nH]ncc4c3Cl)s2)c2nc(C(F)(F)F)cn2c1=O] |
| 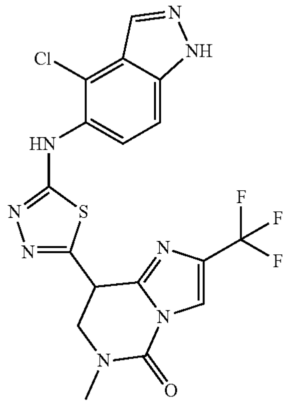 [SMILES: CN1CC(c2nnc(Nc3ccc4[nH]ncc4c3Cl)s2)c2nc(C(F)(F)F)cn2C1=O] |
| 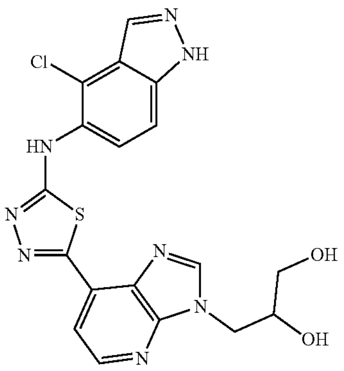 [SMILES: OCC(O)Cn1cnc2c(-c3nnc(Nc4ccc5[nH]ncc5c4Cl)s3)ccnc21] |

TABLE 2-continued
| Compound |
| --- |
| 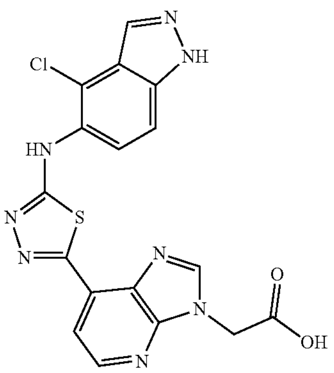 [SMILES: O=C(O)Cn1cnc2c(-c3nnc(Nc4ccc5[nH]ncc5c4Cl)s3)ccnc21] |
| 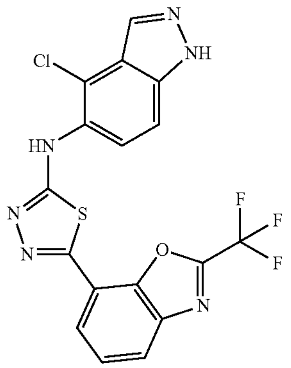 [SMILES: FC(F)(F)c1nc2cccc(-c3nnc(Nc4ccc5[nH]ncc5c4Cl)s3)c2o1] |
| 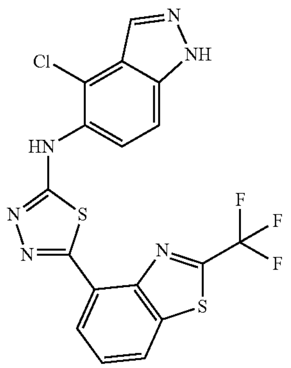 [SMILES: FC(F)(F)c1nc2c(-c3nnc(Nc4ccc5[nH]ncc5c4Cl)s3)cccc2s1] |
| 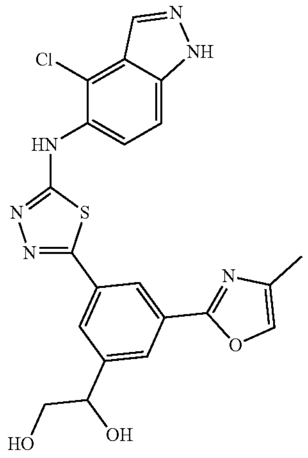 [SMILES: Cc1coc(-c2cc(-c3nnc(Nc4ccc5[nH]ncc5c4Cl)s3)cc(C(O)CO)c2)n1] |
TABLE 2-continued
| Compound |
| --- |
| 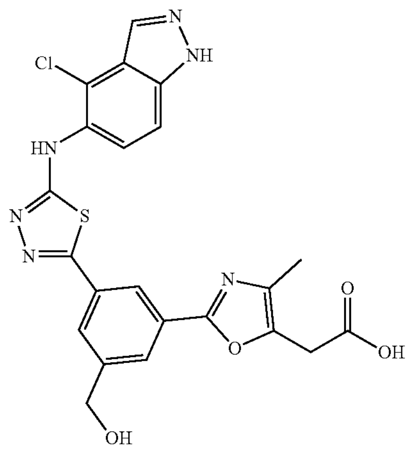 [SMILES: Cc1nc(-c2cc(CO)cc(-c3nnc(Nc4ccc5[nH]ncc5c4Cl)s3)c2)oc1CC(=O)O] |
| 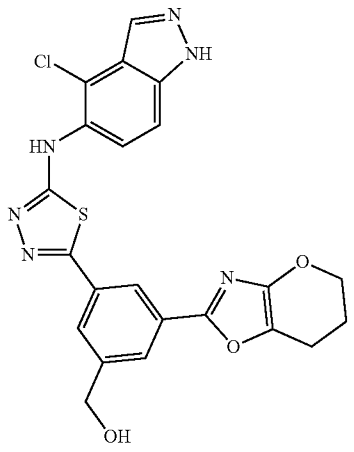 [SMILES: OCc1cc(-c2nc3c(o2)CCCO3)cc(-c2nnc(Nc3ccc4[nH]ncc4c3Cl)s2)c1] |
| 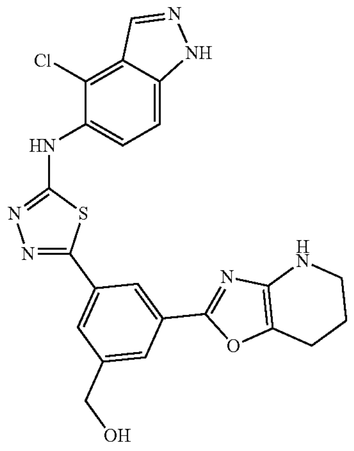 [SMILES: OCc1cc(-c2nc3c(o2)CCCN3)cc(-c2nnc(Nc3ccc4[nH]ncc4c3Cl)s2)c1] |

TABLE 2-continued
| Compound |
| --- |
| 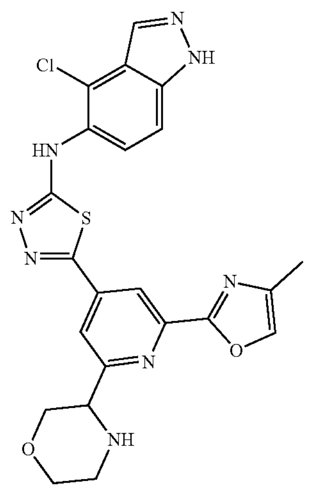 [SMILES: Cc1coc(-c2cc(-c3nnc(Nc4ccc5[nH]ncc5c4Cl)s3)cc(C3COCCN3)n2)n1] |
| 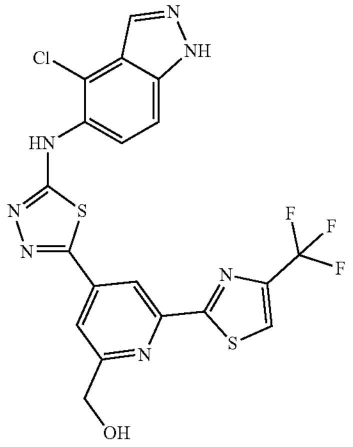 [SMILES: OCc1cc(-c2nnc(Nc3ccc4[nH]ncc4c3Cl)s2)cc(-c2nc(C(F)(F)F)cs2)n1] |
| 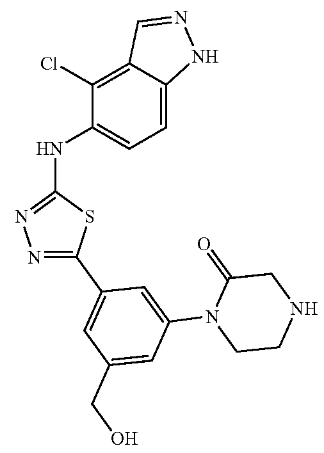 [SMILES: O=C1CNCCN1c1cc(CO)cc(-c2nnc(Nc3ccc4[nH]ncc4c3Cl)s2)c1] |
TABLE 2-continued
| Compound |
| --- |
| 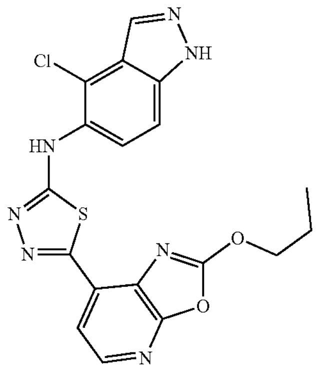 [SMILES: CCCOc1nc2c(-c3nnc(Nc4ccc5[nH]ncc5c4Cl)s3)ccnc2o1] |
| 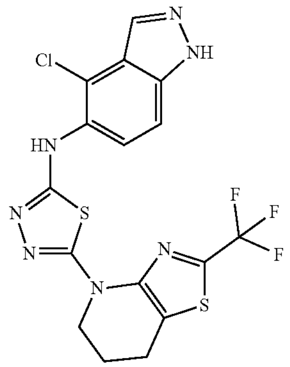 [SMILES: FC(F)(F)c1nc2c(s1)CCCN2c1nnc(Nc2ccc3[nH]ncc3c2Cl)s1] |
| 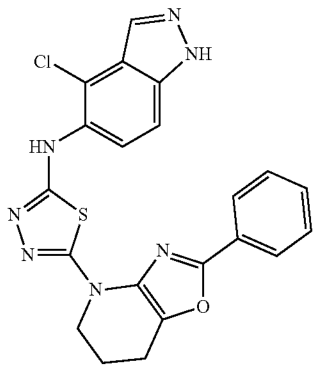 [SMILES: Clc1c(Nc2nnc(N3CCCc4oc(-c5ccccc5)nc43)s2)ccc2[nH]ncc12] |
| 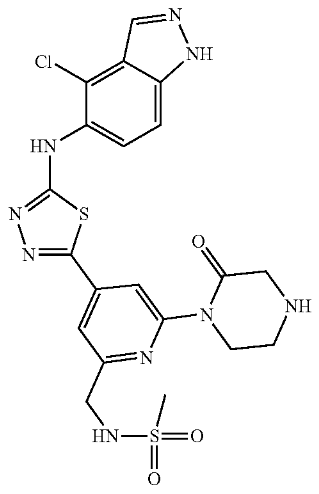 [SMILES: CS(=O)(=O)NCc1cc(-c2nnc(Nc3ccc4[nH]ncc4c3Cl)s2)cc(N2CCNCC2=O)n1] |

TABLE 2-continued
| Compound |
|---|
| 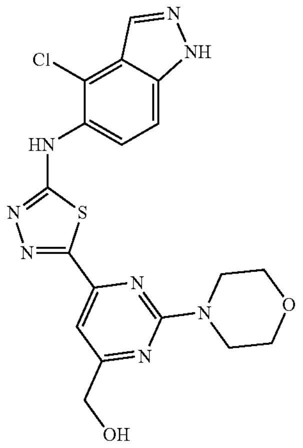 [SMILES: OCc1cc(-c2nnc(Nc3ccc4[nH]ncc4c3Cl)s2)nc(N2CCOCC2)n1] |
| 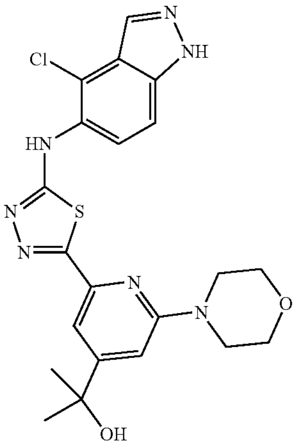 [SMILES: CC(C)(O)c1cc(-c2nnc(Nc3ccc4[nH]ncc4c3Cl)s2)nc(N2CCOCC2)c1] |
| 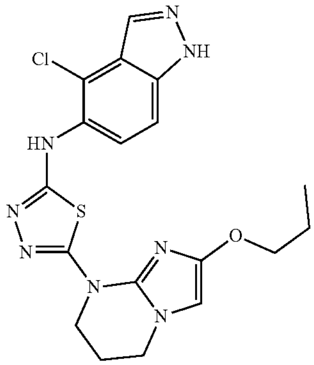 [SMILES: CCCOc1cn2c(n1)N(c1nnc(Nc3ccc4[nH]ncc4c3Cl)s1)CCC2] |
TABLE 2-continued
| Compound |
|---|
| 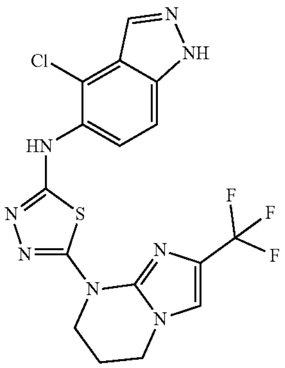 [SMILES: FC(F)(F)c1cn2c(n1)N(c1nnc(Nc3ccc4[nH]ncc4c3Cl)s1)CCC2] |
| 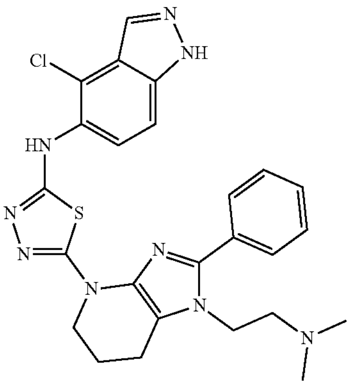 [SMILES: CN(C)CCn1c(-c2ccccc2)nc2c1CCCN2c1nnc(Nc2ccc3[nH]ncc3c2Cl)s1] |
| 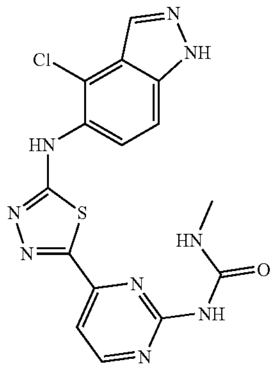 [SMILES: CNC(=O)Nc1nccc(-c2nnc(Nc3ccc4[nH]ncc4c3Cl)s2)n1] |
| 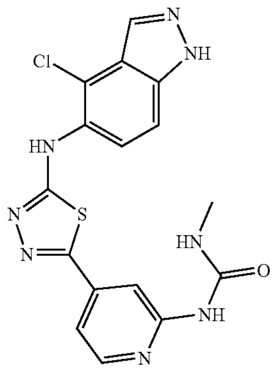 [SMILES: CNC(=O)Nc1cc(-c2nnc(Nc3ccc4[nH]ncc4c3Cl)s2)ccn1] |

TABLE 2-continued
| Compound |
|---|
| 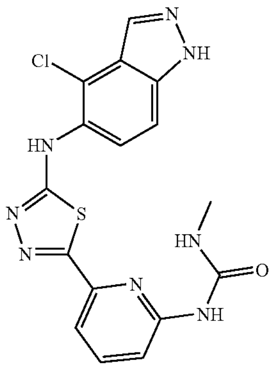 [SMILES: CNC(=O)Nc1cccc(-c2nnc(Nc3ccc4[nH]ncc4c3Cl)s2)n1] |
| 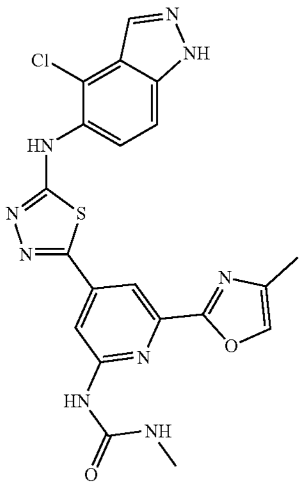 [SMILES: CNC(=O)Nc1cc(-c2nnc(Nc3ccc4[nH]ncc4c3Cl)s2)cc(-c2nc(C)co2)n1] |
| 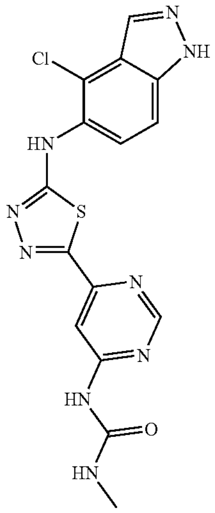 [SMILES: CNC(=O)Nc1cc(-c2nnc(Nc3ccc4[nH]ncc4c3Cl)s2)ncn1] |
TABLE 2-continued
| Compound |
|---|
| 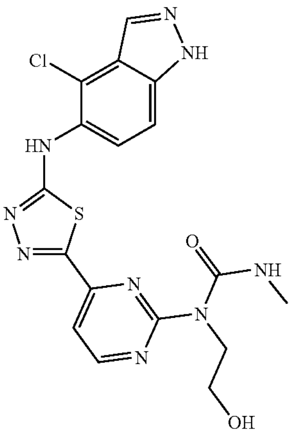 [SMILES: CNC(=O)N(CCO)c1nccc(-c2nnc(Nc3ccc4[nH]ncc4c3Cl)s2)n1] |
| 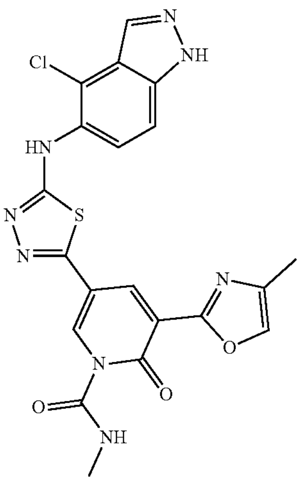 [SMILES: CNC(=O)n1cc(-c2nnc(Nc3ccc4[nH]ncc4c3Cl)s2)cc(-c2nc(C)co2)c1=O] |
| 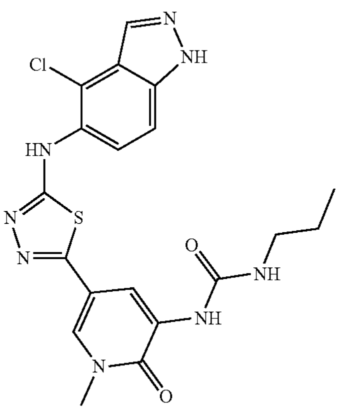 [SMILES: CCCNC(=O)Nc1cc(-c2nnc(Nc3ccc4[nH]ncc4c3Cl)s2)cn(C)c1=O]

TABLE 2-continued
| Compound |
| --- |
| 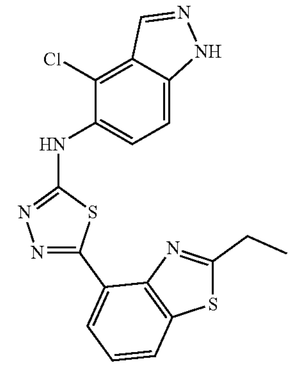 [SMILES: CCc1nc2c(-c3nnc(Nc4ccc5[nH]ncc5c4Cl)s3)cccc2s1] |
| 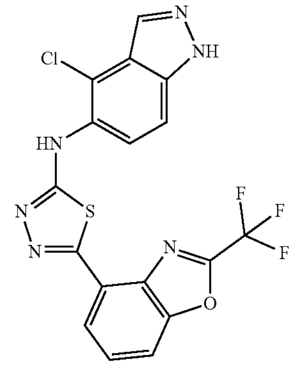 [SMILES: FC(F)(F)c1nc2c(-c3nnc(Nc4ccc5[nH]ncc5c4Cl)s3)cccc2o1] |
| 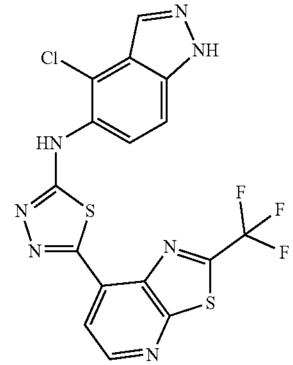 [SMILES: FC(F)(F)c1nc2c(-c3nnc(Nc4ccc5[nH]ncc5c4Cl)s3)ccnc2s1] |
| 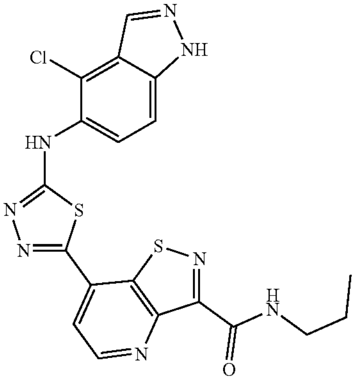 [SMILES: CCCNC(=O)c1nsc2c(-c3nnc(Nc4ccc5[nH]ncc5c4Cl)s3)ccnc12] |
TABLE 2-continued
| Compound |
| --- |
| 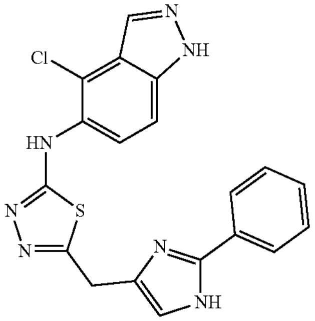 [SMILES: Clc1c(Nc2nnc(Cc3c[nH]c(-c4ccccc4)n3)s2)ccc2[nH]ncc12] |
| 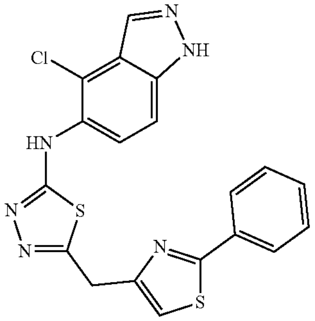 [SMILES: Clc1c(Nc2nnc(Cc3csc(-c4ccccc4)n3)s2)ccc2[nH]ncc12] |
| 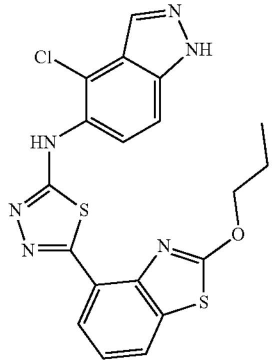 [SMILES: CCCOc1nc2c(-c3nnc(Nc4ccc5[nH]ncc5c4Cl)s3)cccc2s1] |
| 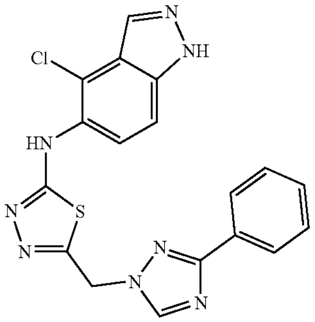 |

TABLE 2-continued

| Compound |
| --- |
| 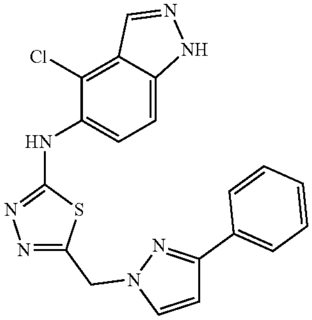 [SMILES: Clc1c(Nc2nnc(Cn3ccc(-c4ccccc4)n3)s2)ccc2[nH]ncc12] |
| 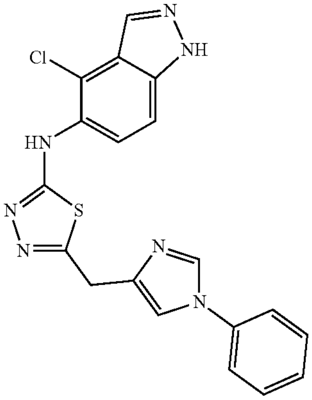 [SMILES: Clc1c(Nc2nnc(Cc3cn(-c4ccccc4)cn3)s2)ccc2[nH]ncc12] |
| 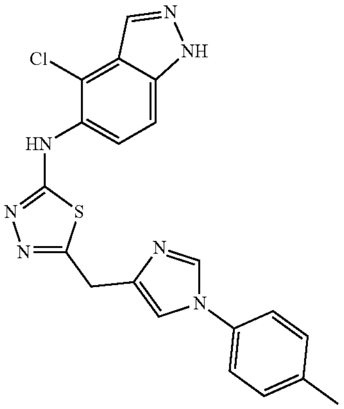 [SMILES: Cc1ccc(-n2cnc(Cc3nnc(Nc4ccc5[nH]ncc5c4Cl)s3)c2)cc1] |

In other embodiments, the compound is a compound in Tables 1-17 herein, or a pharmaceutically acceptable salt thereof. In other embodiments, the compound is a compound in Tables 1-17 herein, a pharmaceutically acceptable salt thereof, or a solvate of the foregoing. In other embodiments, the compound is a compound in any one of Tables 1-17 herein, wherein the compound is in solvated form, non-solvated form, or a pharmaceutically acceptable salt of any of the foregoing. In yet other embodiments, the compound is a compound in Table 1 or 16 herein, or a pharmaceutically acceptable salt thereof. In still other embodiments, the compound is a compound in Table 1 or 16 herein, a pharmaceutically acceptable salt thereof, or a solvate of the foregoing. In embodiments where a compound, such a compound in Table 16, is described as a solvate (e.g., trifluoroacetic acid solvate), the invention includes the free base form of such compounds. Moreover, in embodiments where a compound in any one of Tables 1-17 is described as a solvate (e.g., trifluoroacetic acid solvate), the invention includes the free base form of such compound.

In other embodiments, the compound is propyl (4-(5-((4-chloro-1H-indazol-5-yl)amino)-1,3,4-thiadiazol-2-yl)pyridin-2-yl)carbamate; N-(4-(5-((4-chloro-1H-indazol-5-yl)amino)-1,3,4-thiadiazol-2-yl)pyridin-2-yl)morpholine-4-carboxamide; 1-(4-(5-((4-chloro-1H-indazol-5-yl)amino)-1,3,4-thiadiazol-2-yl)pyridin-2-yl)-3-methylimidazolidin-2-one; (3-(5-((4-chloro-1H-indazol-5-yl)amino)-1,3,4-thiadiazol-2-yl)-5-(4-methyloxazol-2-yl)phenyl)methanol; N-(5-(5-((4-chloro-1H-indazol-5-yl)amino)-1,3,4-thiadiazol-2-yl)-1-methyl-2-oxo-1,2-dihydropyridin-3-yl)acetamide; 5-(2-(4-bromophenyl)imidazo[1,2-a]pyridin-8-yl)-N-(4-chloro-1H-indazol-5-yl)-1,3,4-thiadiazol-2-amine; or N-(4-chloro-1H-indazol-5-yl)-5-(1-(2-(dimethylamino)ethyl)-1H-benzo[d]imidazol-4-yl)-1,3,4-thiadiazol-2-amine. In certain embodiments, the compound is a solvate, a pharmaceutically acceptable salt, or a solvate of a pharmaceutically acceptable salt of the foregoing list of compounds.

Compounds described herein can also be characterized according to their ability to inhibit ROCK1 and/or ROCK2. In certain embodiments, the compound has an $IC_{50}$ towards ROCK1 of less than about 10 μM, 1 μM, 0.1 μM, or 0.01 μM. In certain embodiments, the compound has an $IC_{50}$ towards ROCK2 of less than about 10 μM, 1 μM, 0.1 μM, or 0.01 μM. In certain embodiments, the compounds are characterized according to their ability to selectively inhibit ROCK2 vs. ROCK1. For example, in certain embodiments, the ratio of $IC_{50}$ of ROCK2 to ROCK1 for the compound is at least 5, 10, 25, 50, 100, 250, 500, 750, or 1000. In yet other embodiments, the compound is at least a five-fold more potent inhibitor of Rho-associated protein kinase isoform 2 than Rho-associated protein kinase isoform 1.

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

The synthetic route illustrated in Scheme 1 is a general method for preparing indazolyl thiadiazolamine compounds. Reaction of indazole A having a protecting group (Pg) with carbohydrazide B in a first step provides a hydrazine thiocarbamide C which may be isolated but generally is treated immediately with a strong acid to effect a dehydration to form the product thiadiazole D. Acid-labile protecting groups will be removed upon exposure to the strong acid. Group R on indazole A is any desired substituent on compound D or a functional group that can be converted to a desired substituent on compound D. Group R' on carbohydrazide B is any desired substituent on compound D or a functional group that can be converted to a desired substituent on compound D. See, for example, "Comprehensive Organic Synthesis" (B. M. Trost & I. Fleming, eds., 1991-1992) for a description of standard functional group manipulation procedures. If a functional group that is part of indazole A or carbohydrazide B would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis, 2nd* ed.; Wiley: New York, 1991, for further description of protecting chemistry and strategies. Analagous procedures can be used to prepare N-(1H-pyrazolo[3,4-c]pyridin-5-yl)-1,3,4-thiadiazol-2-amines.

Scheme 1.

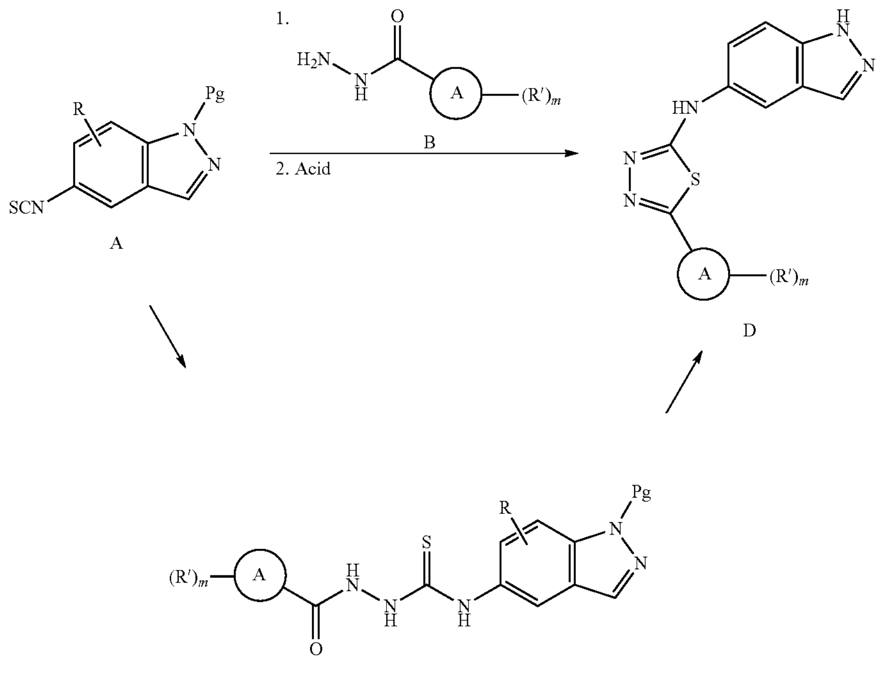

Scheme 2 depicts an alternative approach for preparing indazolyl thiadiazolamine compounds. In this approach, the thiadiazole ring is constructed prior to introduction of the indazolamine moiety, for example, by reacting a carboxylic acid compound with hydrazine carbothioamide in the presence of a reagent to promote their condensation, such as $POCl_3$ (see, for example, *Biomedicinal Chemistry Letters,* 2004, vol. 14, page 5967). Diazotization of the resulting amino-thiadiazole A in the presence of chloride anion provides the corresponding chloro-thiadiazole B. Nucleophilic displacement of the chlorine is promoted by heat and acid catalysis to give indazolyl-thiadiazole C.

Scheme 2.

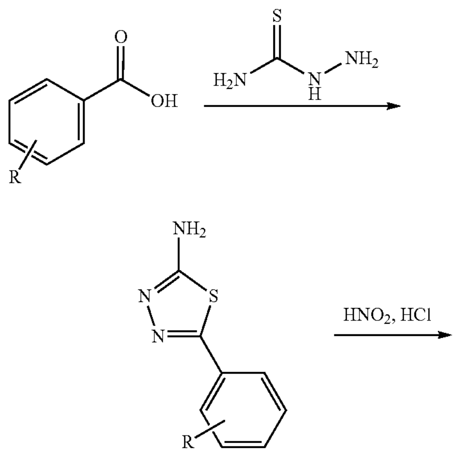

A

-continued

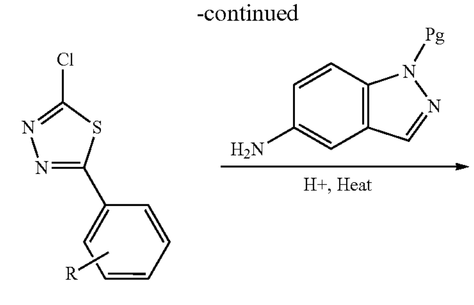

B

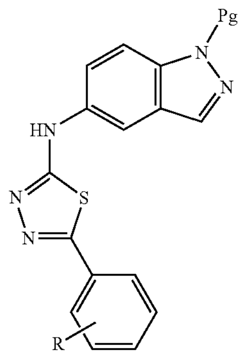

C

The amino-thiadiazole intermediate A from Scheme 2 can itself be used as the nucleophilic coupling partner, which when combined with an appropriate aryl-bromide under transition metal mediated cross-coupling conditions provides indazolyl-thiadiazole B, as shown in Scheme 3.

Scheme 3.

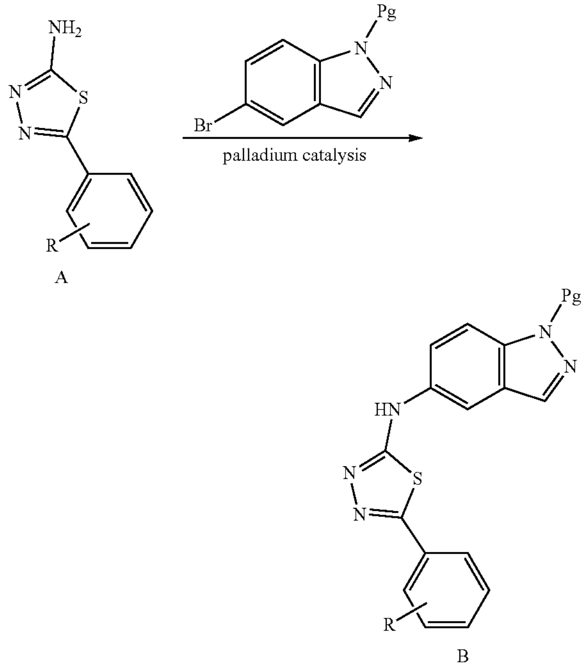

Once the thiadiazole ring is constructed, several routes are available for further elaboration of the molecule. For example, as shown in Scheme 4, bromothiadiazoles, including dibromothiadiazole, undergo cross-coupling with aryl boronic esters and boronic acids under palladium catalysis. For exemplary further description of such cross-coupling reactions, see, for example, Mattmann, M. E. et al. in *Bioorganic and Medicinal Chemistry Letters,* 2012, vol. 22, 5936; International Patent Application Publication WO 2011/130515; Xiao, J et al. in *Journal of Medicinal Chemistry,* 2011, vol. 54, page 6215; International Patent Application Publication WO 2010/146105; International Patent Publication Application WO 2012/129338; and International Patent Application Publication WO 2014/009794.

Scheme 4.

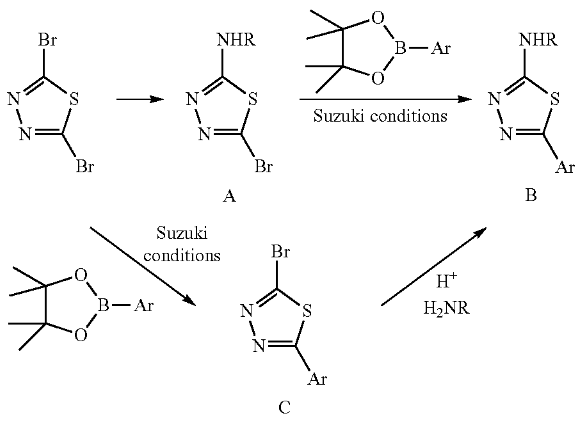

Further elaboration of substituents attached to the thiadiazole ring can be achieved using standard functional group manipulation procedures. For example, as shown in Scheme 5, amine functional groups in compound A can be protected, such as using Boc protecting groups to produce protected compound B. Next, reduction of the nitro group in compound B using hydrogen and a metal catalyst (such as palladium, nickel, platinum or rhodium) produces amine C. Acylation of amine C may be performed using an acid chloride and an organic base (or using a carboxylic acid and a coupling agent such as EDCI) to produce amide D. The final deprotection procedure depends on the choice of protecting group, but may include for example treatment with trifluoroacetic acid to remove Boc groups from compound D to produce final product E.

Scheme 5.

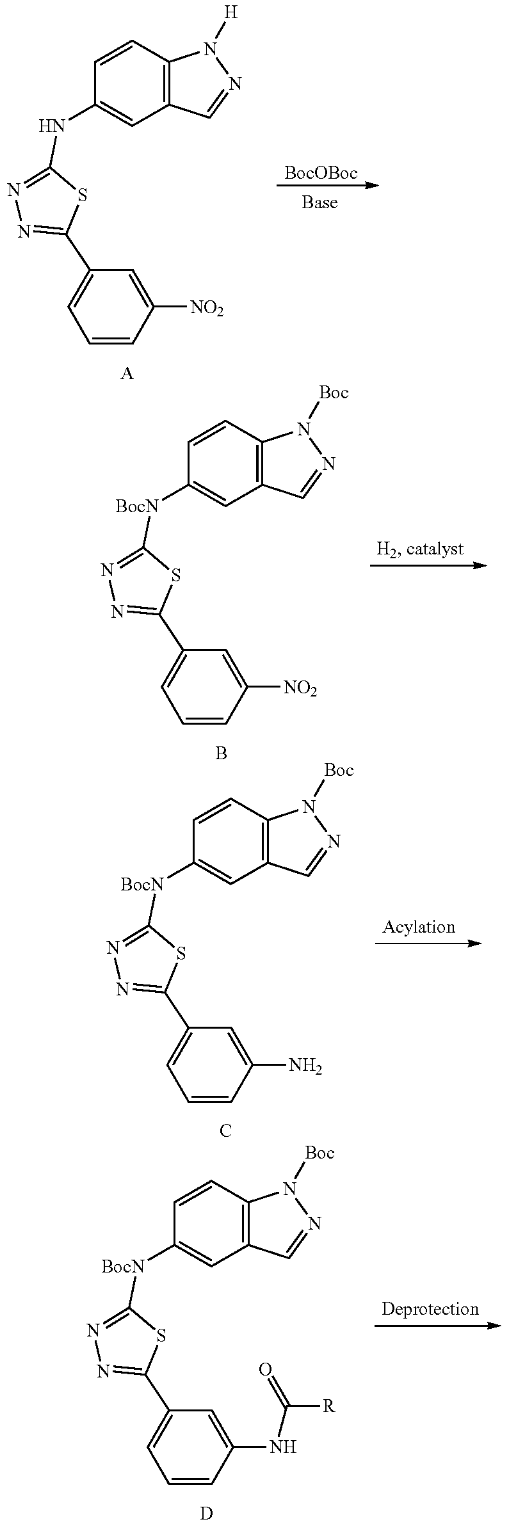

-continued

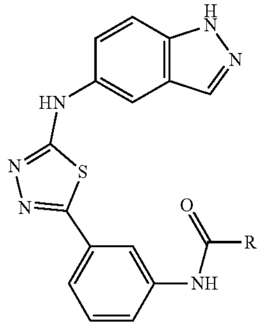

E

Similarly, bromophenyl containing compounds such as compound A in Scheme 6 may be further elaborated using transition metal mediated cross-coupling reactions such as the Suzuki, Stille or Negishi reactions to introduce aryl, heteroaryl, alkenyl, alkynyl, or amino substituents at the position of the bromine.

Scheme 6.

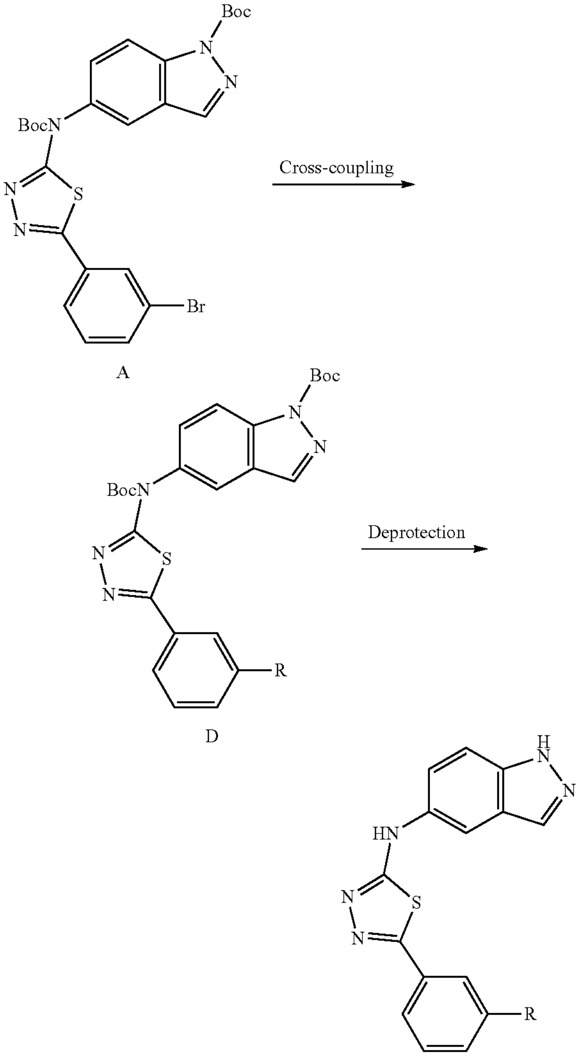

A

D

E

As illustrated in Scheme 7, more than one substituent may be present on the phenyl group of compound E. Exemplary procedures for making such compounds are depicted in Scheme 7.

Scheme 7.

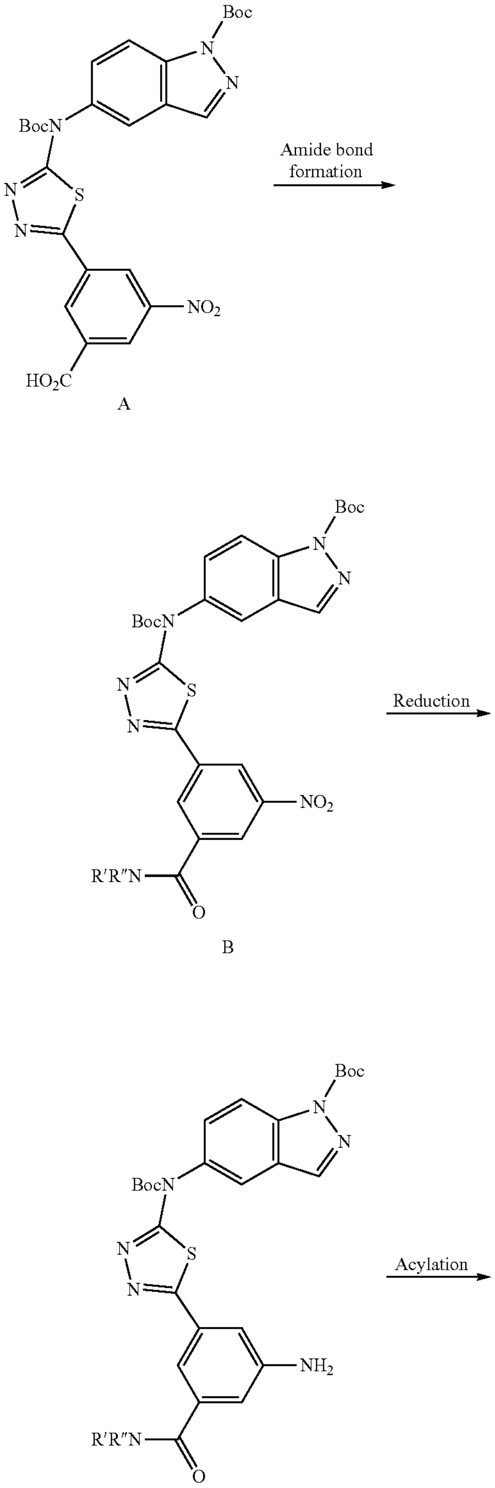

A

B

C

-continued

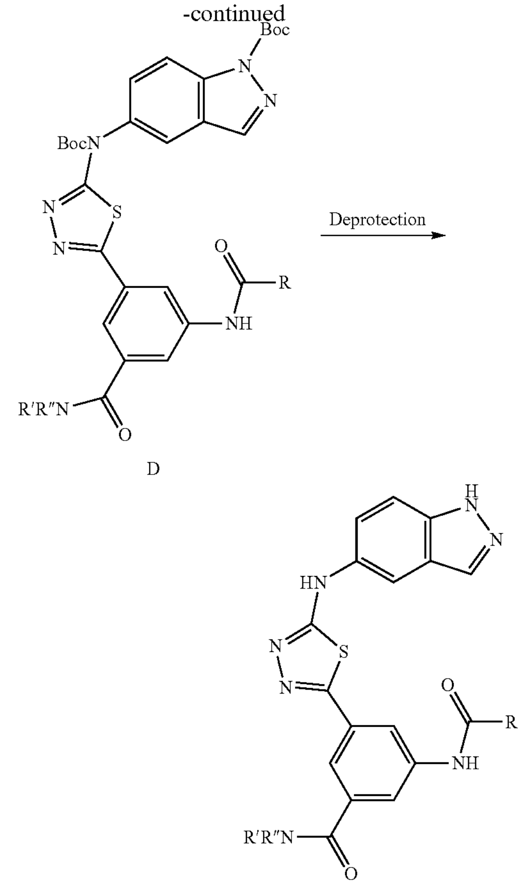

D

E

II. Therapeutic Applications of Indazolyl Thiadiazolamine and Related Compounds

It is contemplated that the indazolyl thiadiazolamine and related compounds described herein, such as a compound of Formula I, I-A, I-1, I-1A, I-1B, II, II-1, II-1A, or II-1B, or other compounds in Section I, provide therapeutic benefits to patients suffering from an inflammatory disorder, immune disorder, fibrotic disorder, or cardiovascular disorder. Accordingly, one aspect of the invention provides a method of treating a disorder selected from the group consisting of an inflammatory disorder, immune disorder, fibrotic disorder, and cardiovascular disorder. The method comprises administering a therapeutically effective amount of a indazolyl thiadiazolamine or related compound described herein, such as a compound of Formula I, I-A, I-1, I-1A, I-1B, II, II-1, II-1A, or II-1B, or other compounds in Section I, to a patient in need thereof to treat the disorder. In certain embodiments, the particular compound of Formula I, I-A, I-1, I-1A, I-1B, II, II-1, II-1A, or II-1B is a compound defined by one of the embodiments described above.

In certain embodiments, the disorder is scleroderma, psoriasis, nonalcoholic steatohepatitis, giant cell arteritis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, ulcerative colitis, asthma, uveitis, rheumatoid arthritis, or epidermal hyperplasia.

In certain embodiments, the disorder is scleroderma or psoriasis.

In certain embodiments, the disorder is nonalcoholic steatohepatitis or giant cell arteritis.

In certain embodiments, the disorder is a fibrotic disorder. In certain embodiments, the fibrotic disorder is liver cirrhosis, renal fibrosis, cardiac fibrosis, pulmonary fibrosis, idiopathic pulmonary fibrosis, hypersensitivity pneumonitis, chronic obstructive pulmonary disease, sarcoidosis, Wegener's granulomatosis, cirrhosis, systemic sclerosis, scleroderma, dermatofibroma, keloids, peyronie's disease, dupuytren's contracture, endomyocardial fibrosis, atrial fibrosis, mediastinal fibrosis, myelofibrosis, retroperitoneal fibrosis, nephrogenic systemic fibrosis, nephrogenic fibrosing dermopathy, mixed connective tissue disease, scleromyxederma, eosinophilic fasciitis, glomerular sclerodis, pancreatitis, or arthrofibrosis. In certain embodiments, the fibrotic disorder is liver cirrhosis, pulmonary fibrosis, systemic sclerosis, endomyocardial fibrosis, atrial fibrosis, mediastinal fibrosis, myelofibrosis, retroperitoneal fibrosis, nephrogenic systemic fibrosis, or arthrofibrosis. In certain embodiments, the fibrotic disorder is cystic fibrosis or idiopathic pulmonary fibrosis. In certain embodiments, the fibrotic disorder is caused by infection, environmental agents, certain medications, chronic inflammatory disease, autoimmune disease or radiation.

In certain embodiments, the disorder is an inflammatory disorder. In certain embodiments, the disorder is an immune disorder. In certain embodiments, the inflammatory disorder is arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costostemal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, fiat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, or yersinial arthritis.

In certain embodiments, the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, or autoimmune hepatitis. In yet other embodiments, the disorder is linear scleroderma.

It has been reported that small molecule inhibitors of Rho kinase are capable of inhibiting MCP-1 mediated chemotaxis in vitro (H. Iijima, *Biorganic and Medicinal Chemistry,* 2007, vol. 15, pages 1022-1033). Due to the dependence of immune cell migration upon the RhoA/ROCK signaling pathway, inhibition of Rho kinase is understood to provide a therapeutic benefit for treating diseases such as rheumatoid arthritis, psoriasis, and inflammatory bowel disease.

In certain embodiments, the disorder is a cardiovascular disorder. In certain embodiments, the cardiovascular disorder is angina, atherosclerosis, stroke, cerebrovascular disease, congestive heart failure, coronary artery disease, myocardial infarction, peripheral vascular disease, stenosis, vasospasm, hypertension, cerebral thrombosis, cerebral embolism, or cerebral hemorrhage. In certain embodiments, the stenosis is coronary artery stenosis, aortic stenosis, restenosis, or pulmonary stenosis.

A link between inhibition of ROCK and treatment of cardiovascular disorders has been described in the literature. For example, the Rho A/ROCK signaling pathway has been reported to have an important role in signal transduction initiated by vasoactive factors such as angiotensin II (T. Yamakawa et al., Hypertension, 2000, 35, 313-318), urotension II (V. Sauzeau et al., Circ. Res., 2001, 88, 1102-1104), endothelin-1 (P. Tangkijvanich et al., Hepatology, 2001, 33, 74-80), serotonin (H. Shimokawa, Jpn. Circ. J., 2000, 64, 1-12), norepinephrine (M. C. Martinez, et al., Am. J. Physiol., 2000, 279, H1228-H1238) and platelet-derived growth factor (PDGF) (H. Kishi et al., J. Biochem., 2000, 128, 719-722). Additional studies in the literature, some using the known ROCK inhibitor fasudil (T. Asano et al., J. Pharmacol. Exp. Ther., 1987, 241, 1033-1040) or Y-27632 (M. Uehata et al., Nature, 1997, 389, 990-994) further illustrate the link between ROCK and cardiovascular disease. For example, ROCK expression and activity have been shown to be elevated in spontaneously hypertensive rats, indicating a link to the development of hypertension in these animals (Y. Mukai et al., FASEB J., 2001, 15, 1062-1064). The ROCK inhibitor Y-27632 (M. Uehata et al., Nature, ibid) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats.

Other studies illustrate a link between ROCK and atherosclerosis. For example, gene transfer of a dominant negative form of ROCK suppressed neointimal formation following balloon injury in porcine femoral arteries (Y. Eto et al., Am. J. Physiol. Heart Circ. Physiol., 2000, 278, H1744-H1750). In a similar model, ROCK inhibitor Y-27632 inhibited neointimal formation in rats (N. Sawada et al., Circulation, 2000, 101, 2030-2033). In a porcine model of IL-1 beta-induced coronary stenosis, treatment with the ROCK inhibitor fasudil was shown to progressively reduce coronary stenosis, as well as promote a regression of coronary constrictive remodeling (H. Shimokawa et al., Cardiovascular Res., 2001, 51, 169-177).

Additional reports indicate that a ROCK inhibitor would be useful in treating other cardiovascular diseases. For example, in a rat stroke model, fasudil was shown to reduce both the infarct size and neurologic deficit (Y. Toshima, Stroke, 2000, 31, 2245-2250). The ROCK inhibitor Y-27632 was shown to improve ventricular hypertrophy, fibrosis and function in a model of congestive heart failure in Dahl salt-sensitive rats (N. Kobayashi et al. Cardiovascular Res., 2002, 55, 757-767).

Other animal or clinical studies have implicated ROCK in additional diseases including coronary vasospasm (H. Shimokawa et al., Cardiovasc. Res., 1999, 43, 1029-1039), cerebral vasospasm (M. Sato et al., Circ. Res., 2000, 87, 195-200), ischemia/reperfusion injury (T. Yada et al., J. Am. Coll. Cardiol., 2505, 45, 599-607), pulmonary hypertension (Y. Fukumoto et al., Heart, 2005, 91, 391-392), angina (H. Shimokawa et al., J. Cardiovasc. Pharmacol., 2002, 39, 319-327), renal disease (S. Satoh et al., Eur. J. Pharmacol., 2002, 455, 169-174) and erectile dysfunction (N. F. Gonzalez-Cadavid and J. Rajifer, Endocrine, 2004, 23, 167-176).

In certain embodiments, the patient is a human.

Another aspect of the invention provides for the use of a compound described herein (such as a compound of Formula I, I-A, I-1, I-1A, I-1B, II, II-1, II-1A, or II-1B, or other compounds in Section I) in the manufacture of a medicament. In certain embodiments, the medicament is for treating a disorder described herein, such as an inflammatory disorder.

Another aspect of the invention provides for the use of a compound described herein (such as a compound of Formula I, I-A, I-1, I-1A, I-1B, II, II-1, II-1A, or II-1B, or other compounds in Section I) for treating a medical disorder, such a medical disorder described herein (e.g., inflammatory disorder).

Another aspect of the invention provides a method of inhibiting a Rho-associated protein kinase. The method comprises exposing a Rho-associated protein kinase to an effective amount of an indazolyl thiadiazolamine or related compound described herein, e.g., a compound of Formula I, I-A, I-1, I-1A, I-1B, II, II-1, II-1A, or II-1B, to inhibit said Rho-associated protein kinase.

In certain embodiments, the Rho-associated protein kinase is the Rho-associated protein kinase isoform 2. In such embodiments, the method is to inhibiting a Rho-associated protein kinase isoform 2, which method comprises exposing a Rho-associated protein kinase isoform 2 to a compound described herein, e.g., a compound of Formula I, I-A, I-1, I-1A, I-1B, II, II-1, II-1A, or II-1B, to inhibit said Rho-associated protein kinase isoform 2.

The description above describes multiple embodiments providing definitions for variables used herein. The application specifically contemplates all combinations of such variables.

III. Combination Therapy

Another aspect of the invention provides for combination therapy. Indazolyl thiadiazolamine and related compounds (e.g., a compound of Formula I, I-A, I-1, I-1A, I-1B, II, II-1, II-1A, or II-1B, or other compounds in Section I) or their pharmaceutically acceptable salts may be used in combination with additional therapeutic agents to treat medical disorders, such as inflammatory disorder, immune disorder, fibrotic disorder, and cardiovascular disorder.

The amount of indazolyl thiadiazolamine or related compound (e.g., a compound of Formula I, I-A, I-1, I-1A, I-1B, II, II-1, II-1A, or II-1B, or other compounds in Section I) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a indazolyl thiadiazolamine or related compound (e.g., a compound of any one of Formula I, I-A, I-1, I-1A, I-1B, II, II-1, II-1A, or II-1B, or other compounds in Section I) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the indazolyl thiadiazolamine or related compound (e.g., a compound of any one of I, I-A, I-1, I-1A, I-1B, II, II-1, II-1A, or II-1B, or other compounds in Section I) and the additional therapeutic agent(s) are administered in doses commonly employed when such agents are used as monotherapy for treating the disorder. In other embodiments, the indazolyl thiadiazolamine or related compound (e.g., a compound of any one of Formula I, I-A, I-1, I-1A, I-1B, II, II-1, II-1A, or II-1B, or other compounds in Section I) and the additional therapeutic agent(s) are administered in doses lower than the doses commonly employed when such agents are used as monotherapy for treating the disorder. In certain embodiments, the indazolyl thiadiazolamine or related compound (e.g., a compound of any one of Formula I, I-A, I-1, I-1A, I-1B, II, II-1, II-1A, or II-1B, or other compounds in Section I) and the additional therapeutic agent(s) are present in the same composition, which is suitable for oral administration.

In certain embodiments, the indazolyl thiadiazolamine or related compound (e.g., a compound of any one of Formula I, I-A, I-1, I-1A, I-1B, II, II-1, II-1A, or II-1B, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the indazolyl thiadiazolamine or related compound (e.g., a compound of any one of Formula I, I-A, I-1, I-1A, I-1B, II, II-1, II-1A, or II-1B, or other compounds in Section I), a pharmaceutically acceptable carrier, vehicle or diluent, and optionally at least one additional therapeutic agent.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases “parenteral administration” and “administered parenterally” as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases “systemic administration,” “administered systemically,” “peripheral administration” and “administered peripherally” as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a indazolyl thiadiazolamine or related compound described herein in a therapeutically effective amount for the treatment of a medical disorder described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art. HPLC Method A was as follows: Agilent Zorbax C-18 column, 4.6x50 mm, 1.8 micron, 28° C., 2.0 mL/min, 5 min gradient of 5% to 95% MeCN (0.05% TFA) in $H_2O$ (0.1% TFA), then 95% MeCN (0.05% TFA) in $H_2O$ (0.1% TFA) for 1.5 min. The phrase "MeCN (0.05% TFA)" is art-recognized and refers to acetonitrile containing 0.05% v/v trifluoroacetic acid. The phrase "$H_2O$ (0.1% TFA)" is art-recognized and refers to water containing 0.1% v/v trifluoroacetic acid.

Example 1—Synthesis of N-(1H-Indazol-5-yl)-5-(3-methoxyphenyl)-1,3,4-thiadiazol-2-amine 2,2,2-trifluoroacetic Acid Solvate

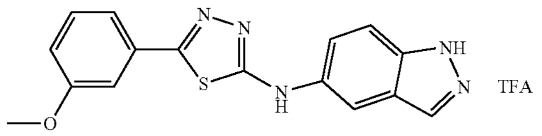 [SMILES: COc1cccc(-c2nnc(Nc3ccc4[nH]ncc4c3)s2)c1]

Part 1—Synthesis of 3-Methoxybenzohydrazide

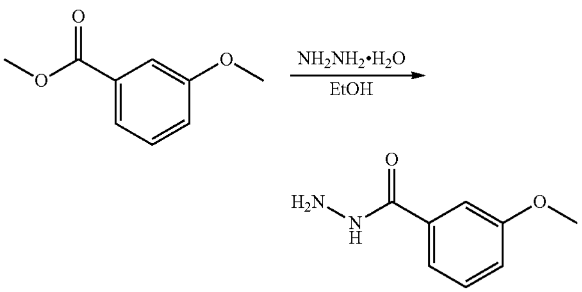

To a solution of methyl 3-methoxybenzoate (5.0 g, 30.1 mmol, 1.00 equiv) in EtOH (50 mL) was added hydrazine hydrate (80%, 9.4 g, 150 mmol, 5.00 equiv). The reaction was refluxed overnight, then concentrated under vacuum. The residue solidified upon standing at rt. The solid was triturated with hexane (100 mL) and the resulting solid separated and dried to yield 4.5 g (90%) of the desired product as a white solid.

Part 2—Synthesis of N-(1H-Indazol-5-yl)-5-(3-methoxyphenyl)-1,3,4-thiadiazol-2-amine 2,2,2-trifluoroacetic Acid Solvate

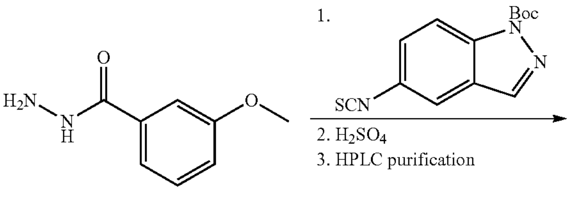

-continued

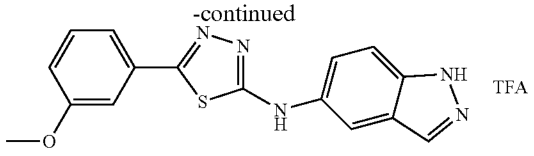

To a 50-mL round bottom flask was added a solution of 3-methoxybenzohydrazide (166 mg, 1.00 mmol, 1.00 equiv) in dichloromethane (DCM) (5 mL). tert-Butyl 5-isothiocyanato-1H-indazole-1-carboxylate (275 mg, 1.00 mmol, 1.00 equiv) was added to the reaction mixture. The reaction mixture was stirred at rt for 4 h, until all the starting material was consumed. Concentrated sulfuric acid (0.3 mL, excess) was added to the reaction mixture, and the reaction mixture was stirred at rt for 1 h. An aqueous solution of $Na_2CO_3$ (10%, 20 mL) was added to the reaction mixture dropwise. A beige solid precipitated out of solution and was collected by filtration to yield 286 mg (88%) of the desired product as a beige solid. A part of this material (25 mg) was further purified by preparative HPLC to yield 7.4 mg of N-(1H-indazol-5-yl)-5-(3-methoxyphenyl)-1,3,4-thiadiazol-2-amine 2,2,2-trifluoroacetic acid solvate as a white solid. (ES-ESI, m/z): 323.95 $[M+H]^+$; $^1H$ NMR (400 MHz, DMSO-$d_6$+$CD_3OD$) δ 8.25-8.33 (m, 1H), 8.08-8.14 (m, 1H), 7.43-7.66 (m, 5H), 8.08-8.14 (m, 1H), 3.90-3.95 (m, 3H).

Example 2—Synthesis of N-[5-[3-(1,3-Oxazol-2-yl)phenyl]-1,3,4-thiadiazol-2-yl]-1H-indazol-5-amine 2,2,2-trifluoroacetic Acid Solvate

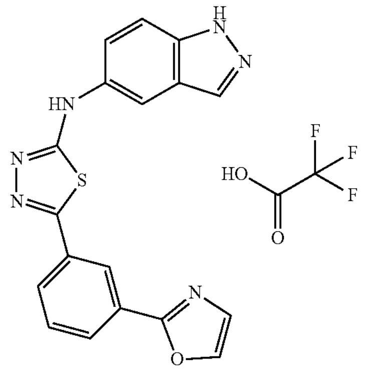 [SMILES: c1cc(-c2ncco2)cc(-c2nnc(Nc3ccc4[nH]ncc4c3)s2)c1 ; O=C(O)C(F)(F)F]

Part 1—Synthesis of 3-Bromobenzohydrazide

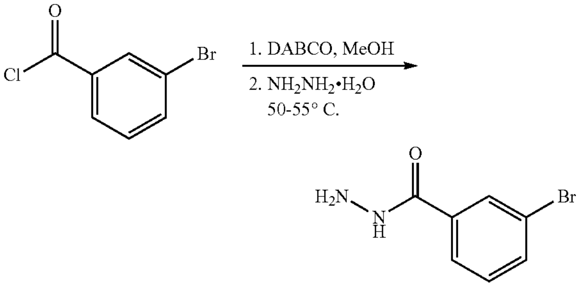

Into a 500-mL round-bottom flask was added a solution of 1,4-diazabicyclo[2.2.2]octane (DABCO) (11.24 g, 100 mmol, 1.10 equiv) in methanol (140 mL). This was followed by the addition of 3-bromobenzoyl chloride (20 g, 91.13 mmol, 1.00 equiv) dropwise with stirring at 20° C. The resulting solution was stirred for 1 h at room temperature. To this was added hydrazine hydrate (36 mL, 0.593 mol, 6.5 equiv) dropwise with stirring. The resulting solution was stirred overnight at 55° C. The resulting solution was diluted with 140 mL of water. The solid formed was collected by filtration to furnish 8 g (41%) of 3-bromobenzohydrazide as a white solid.

Part 2—Synthesis of N-[5-(3-Bromophenyl)-1,3,4-thiadiazol-2-yl]-1H-indazol-5-amine

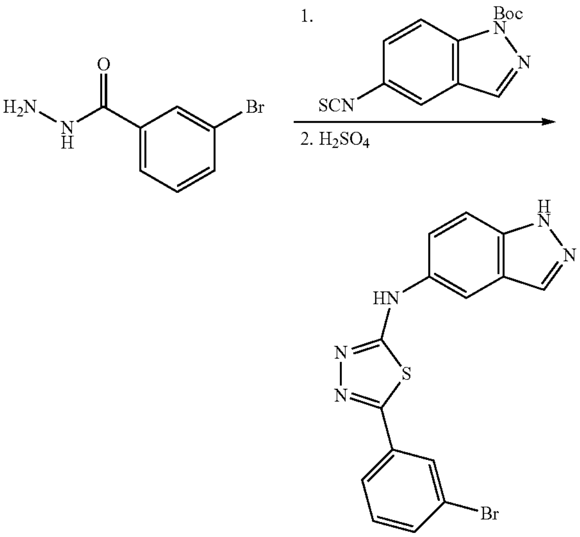

Into a 250-mL round-bottom flask was added a solution of 3-bromobenzohydrazide (3.65 g, 16.97 mmol, 1.00 equiv) in DCM (60 mL). tert-Butyl 5-isothiocyanato-1H-indazole-1-carboxylate (4.67 g, 16.90 mmol, 1.00 equiv) was added to the reaction mixture. The resulting solution was stirred overnight at room temperature. This was followed by the addition of sulfuric acid (98%) (20 mL, excess) dropwise with stirring. The resulting solution was stirred overnight at room temperature and then it was poured into 250 mL of ice water. The pH of the solution was adjusted to pH 8 with saturated aqueous sodium carbonate. The resulting solid precipitate was collected by filtration to yield 5.7 g (90%) of N-[5-(3-bromophenyl)-1,3,4-thiadiazol-2-yl]-1H-indazol-5-amine as a yellow solid.

Part 3—Synthesis of Tert-Butyl 5-((5-(3-bromophenyl)-1,3,4-thiadiazol-2-yl)(tert-butoxycarbonyl)amino)-1H-indazole-1-carboxylate

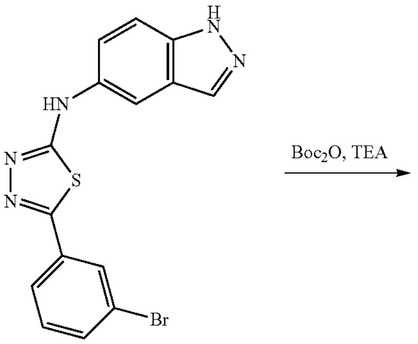

-continued

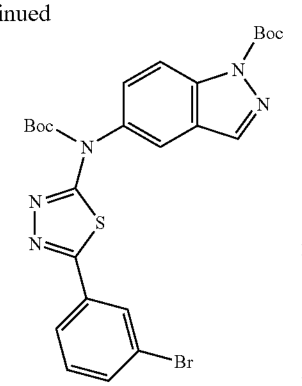

Into a 250-mL round-bottom flask was added a solution of N-[5-(3-bromophenyl)-1,3,4-thiadiazol-2-yl]-1H-indazol-5-amine (5.7 g, 15.31 mmol, 1.00 equiv) in dichloromethane (100 mL). $(Boc)_2O$ (10.01 g, 45.86 mmol, 3.00 equiv) and triethylamine (TEA) (9.28 g, 91.71 mmol, 6.00 equiv) were added to the reaction mixture. The resulting solution was stirred overnight at room temperature. Then, the reaction mixture was concentrated under vacuum to provide a residue that was then purified by silica gel column with ethyl acetate/petroleum ether (1:2) as eluent to furnish 6.7 g (76%) of tert-butyl 5-((5-(3-bromophenyl)-1,3,4-thiadiazol-2-yl)(tert-butoxycarbonyl)amino)-1H-indazole-1-carboxylate as a yellow solid.

Part 4—Synthesis of Tert-Butyl 5-((tert-butoxycarbonyl)(5-(3-(oxazol-2-yl)phenyl)-1,3,4-thiadiazol-2-yl)amino)-1H-indazole-1-carboxylate

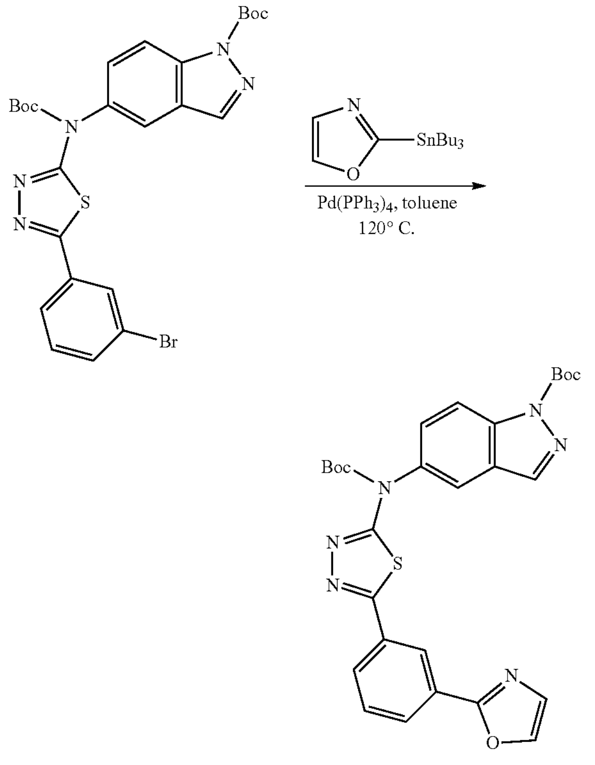

Into a 20-mL vial was added a solution of tert-butyl 5-((5-(3-bromophenyl)-1,3,4-thiadiazol-2-yl)(tert-butoxycarbonyl)amino)-1H-indazole-1-carboxylate (300 mg, 0.52 mmol, 1.00 equiv) in toluene (10 mL). 2-(Tributylstannyl)-1,3-oxazole (225 mg, 0.63 mmol, 1.20 equiv) and tetrakis (triphenylphosphane) palladium (61 mg, 0.05 mmol, 0.10 equiv) were added to the reaction mixture. The reaction mixture was heated under microwave irradiation for 2 h at 120° C. Then, the reaction mixture was concentrated under vacuum to provide a residue that was then purified by silica gel column with ethyl acetate/petroleum ether (2:1) as eluent to furnish 200 mg (68%) of tert-butyl 5-((tert-butoxycarbonyl)(5-(3-(oxazol-2-yl)phenyl)-1,3,4-thiadiazol-2-yl) amino)-1H-indazole-1-carboxylate as a yellow solid.

Part 5—Synthesis of N-[5-[3-(1,3-Oxazol-2-yl)phenyl]-1,3,4-thiadiazol-2-yl]-1H-indazol-5-amine 2,2,2-trifluoroacetic Acid Solvate

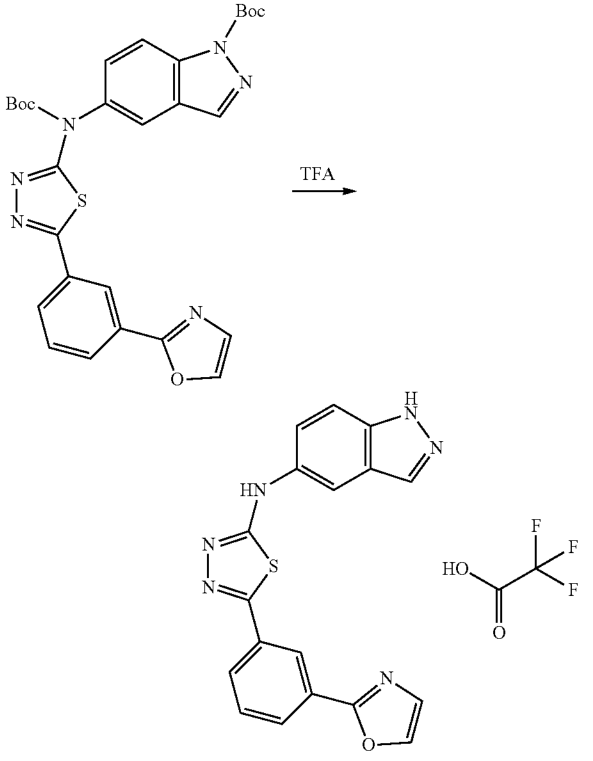

Into a 10-mL round-bottom flask was added a solution of tert-butyl 5-((tert-butoxycarbonyl)(5-(3-(oxazol-2-yl)phenyl)-1,3,4-thiadiazol-2-yl)amino)-1H-indazole-1-carboxylate (200 mg, 0.36 mmol, 1.00 equiv) in a mixture of dichloromethane (4 mL) and trifluoroacetic acid (2 mL). The resulting solution was stirred for 30 min at room temperature. Then, the reaction mixture was concentrated under vacuum. The resulting crude product was purified by preparative HPLC with the following conditions: XBridge C18 OBD preparative column, 5 μm, 19 mm×250 mm; mobile phase, water with 0.05% TFA and ACN (33.0% ACN up to 51.0% in 8 min); detector, 254 nm. This provided 37 mg (22%) of N-[5-[3-(1,3-oxazol-2-yl)phenyl]-1,3,4-thiadiazol-2-yl]-1H-indazol-5-amine 2,2,2-trifluoroacetic solvate as a yellow solid. (ES-ESI, m/z): 361.1 $[M-TFA+H]^+$. $^1H$ NMR (400 MHz, DMSO-$d_6$) δ 10.60 (s, 1H), 8.42-8.43 (m, 1H), 8.26-8.31 (m, 2H), 8.07-8.10 (m, 2H), 7.97-8.00 (m, 1H), 7.67-7.71 (m, 1H), 7.56 (d, J=8.8 Hz, 1H), 7.42-7.48 (m, 2H).

Example 3—Synthesis of N-(3-[5-[(1H-Indazol-5-yl)amino]-1,3,4-thiadiazol-2-yl]phenyl)-3-methyl-1H-pyrazole-5-carboxamide 2,2,2-trifluoroacetic Acid Salt Solvate

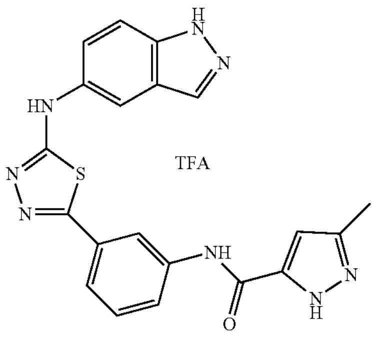 [SMILES: Cc1cc(C(=O)Nc2cccc(-c3nnc(Nc4ccc5[nH]ncc5c4)s3)c2)[nH]n1]

Part 1—Synthesis of 3-Methyl-1H-pyrazole-5-carbonyl Chloride

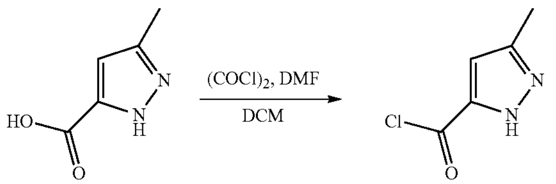

Into a 100-mL round-bottom flask was placed 3-methyl-1H-pyrazole-5-carboxylic acid (200 mg, 1.59 mmol, 1.00 equiv) in dichloromethane (20 mL). DMF (0.2 mL) and $(COCl)_2$ (1 mL) were added to the reaction mixture. The resulting solution was stirred for 3 h at room temperature. Then, the reaction mixture was concentrated under vacuum to yield 180 mg (79%) of 3-methyl-1H-pyrazole-5-carbonyl chloride as a yellow solid.

Part 2—Synthesis of Tert-Butyl 5-[[(tert-butoxy)carbonyl]([5-[3-(3-methyl-1H-pyrazole-5-amido)phenyl]-1,3,4-thiadiazol-2-yl])amino]-1H-indazole-1-carboxylate

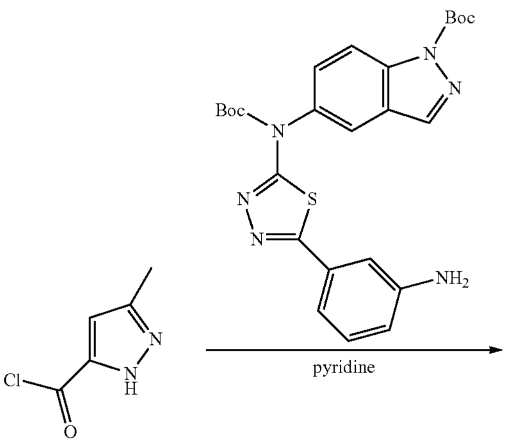

-continued

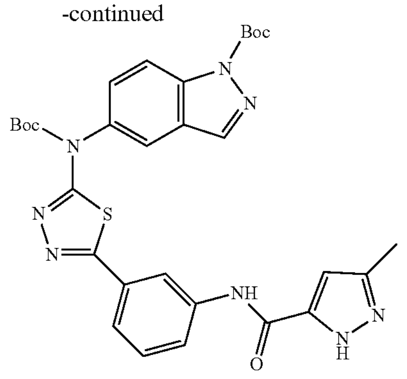

Into a 100-mL round-bottom flask were added tert-butyl 5-[[5-(3-aminophenyl)-1,3,4-thiadiazol-2-yl][(tert-butoxy)carbonyl]amino]-1H-indazole-1-carboxylate (200 mg, 0.39 mmol, 1.00 equiv) and 3-methyl-1H-pyrazole-5-carbonyl chloride (180 mg, 1.25 mmol, 4.00 equiv) in pyridine (20 mL). The resulting solution was stirred for 3 h at room temperature, and then it was concentrated under vacuum to provide a residue, which was then purified by silica gel column with DCM/methanol (10:1) as eluent to furnish 130 mg (54%) of tert-butyl 5-[[(tert-butoxy)carbonyl]([5-[3-(3-methyl-1H-pyrazole-5-amido)phenyl]-1,3,4-thiadiazol-2-yl])amino]-1H-indazole-1-carboxylate as a yellow solid.

Part 3—Synthesis of N-(3-[5-[(1H-Indazol-5-yl)amino]-1,3,4-thiadiazol-2-yl]phenyl)-3-methyl-1H-pyrazole-5-carboxamide 2,2,2-trifluoroacetic Acid Solvate

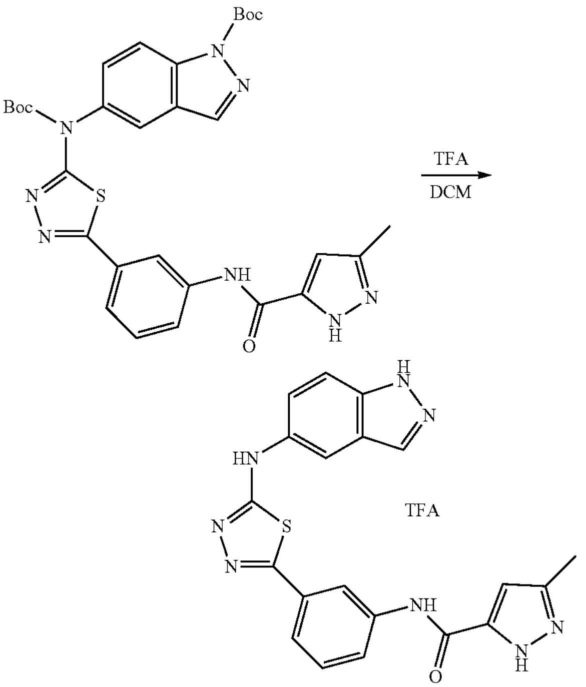

Into a 100-mL round-bottom flask was placed tert-butyl 5-[[(tert-butoxy)carbonyl]([5-[3-(3-methyl-1H-pyrazole-5-amido)phenyl]-1,3,4-thiadiazol-2-yl])amino]-1H-indazole- 1-carboxylate (130 mg, 0.21 mmol, 1.00 equiv) in a mixture of DCM (10 mL) and TFA (3 mL). The resulting solution was stirred for 3 h at room temperature. Then, the reaction mixture was concentrated under vacuum. The resulting crude product was purified by preparative HPLC with the following conditions: Gemini-NX C18 column, 21.2×150 mm×5 μm; mobile phase: water with 0.05% TFA and ACN (30.0% ACN up to 70.0% in 10 min); detector, 254 nm. This provided 50 mg (45%) of N-(3-[5-[(1H-indazol-5-yl)amino]-1,3,4-thiadiazol-2-yl]phenyl)-3-methyl-1H-pyrazole-5-carboxamide TFA solvate as a yellow solid. (ES, m/z): 416.95[M+H$^+$]. $^1$H NMR (DMSO-$d_6$, 300 MHz) δ 8.28 (s, 1H), 8.16-8.17 (m, 1H), 8.05 (s, 1H), 7.73-7.76 (m, 1H), 7.53-7.58 (m, 2H), 7.41-7.48 (m, 2H), 6.57 (s, 1H), 2.26 (s, 3H).

Example 4—Synthesis of N-(3-[5-[(1H-Indazol-5-yl)amino]-1,3,4-thiadiazol-2-yl]phenyl)-5-methyl-1,2-oxazole-3-carboxamide 2,2,2-trifluoroacetic Acid Solvate

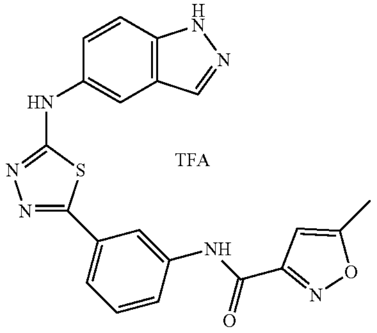 [SMILES: Cc1cc(C(=O)Nc2cccc(-c3nnc(Nc4ccc5[nH]ncc5c4)s3)c2)no1]

Part 1—Synthesis of 5-[[(tert-Butoxy)carbonyl]([5-[3-(5-methyl-1,2-oxazole-3-amido)phenyl]-1,3,4-thiadiazol-2-yl])amino]-1H-indazole-1-carboxylate

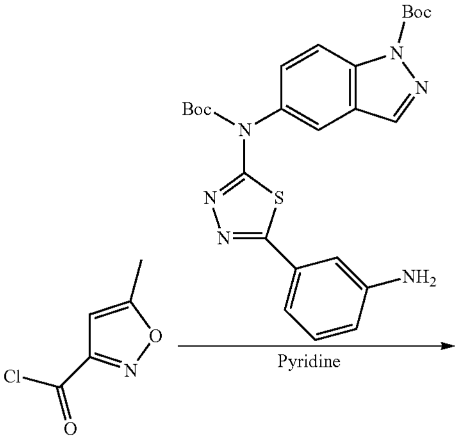

-continued

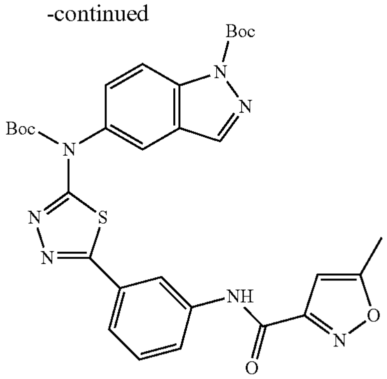

Into a 100-mL round-bottom flask were added tert-butyl 5-[[5-(3-aminophenyl)-1,3,4-thiadiazol-2-yl][(tert-butoxy)carbonyl]amino]-1H-indazole-1-carboxylate (200 mg, 0.39 mmol, 1.00 equiv) and 5-methyl-1,2-oxazole-3-carbonyl chloride (200 mg, 1.37 mmol, 4.00 equiv) in pyridine (20 mL). The resulting solution was stirred for 3 h at room temperature, and then it was concentrated under vacuum to provide a residue, which then purified by silica gel column with DCM/methanol (10:1) as eluent to furnish 180 mg (74%) of tert-butyl 5-[[(tert-butoxy)carbonyl]([5-[3-(5-methyl-1,2-oxazole-3-amido)phenyl]-1,3,4-thiadiazol-2-yl])amino]-1H-indazole-1-carboxylate as a yellow solid.

Part 2—Synthesis of N-(3-[5-[(1H-indazol-5-yl)amino]-1,3,4-thiadiazol-2-yl]phenyl)-5-methyl-1,2-oxazole-3-carboxamide 2,2,2-trifluoroacetic Acid Solvate

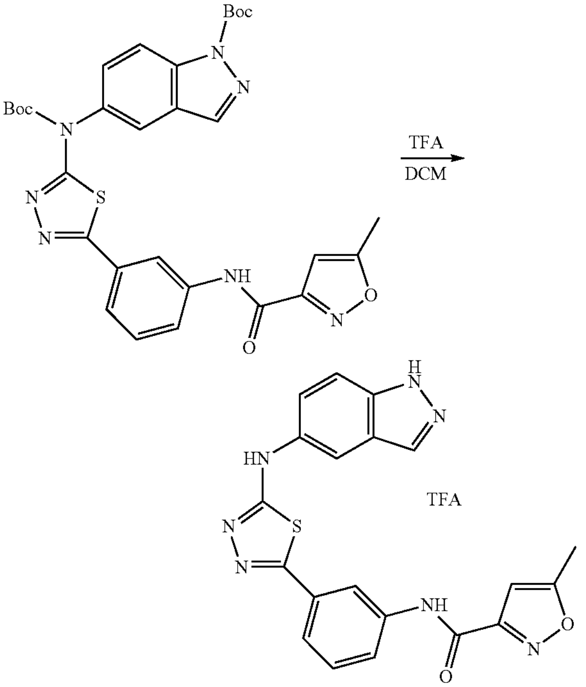

Into a 100-mL round-bottom flask was placed tert-butyl 5-[[(tert-butoxy)carbonyl]([5-[3-(5-methyl-1,2-oxazole-3-amido)phenyl]-1,3,4-thiadiazol-2-yl])amino]-1H-indazole-1-carboxylate (180 mg, 0.29 mmol, 1.00 equiv) in a mixture of DCM (10 mL) and TFA (3 mL). The resulting solution was stirred for 3 h at room temperature. Then, the reaction mixture was concentrated under vacuum. The resulting crude product was purified by preparative HPLC to provide 41 mg (26%) of N-(3-[5-[(1H-indazol-5-yl)amino]-1,3,4-thiadiazol-2-yl]phenyl)-5-methyl-1,2-oxazole-3-carboxamide 2,2,2-trifluoroacetic acid solvate as an off-white solid. (ES, m/z): 417.95[M+H$^+$]; $^1$H NMR (DMSO-$d_6$, 300 MHz) δ 8.23 (s, 1H), 8.15-8.16 (m, 1H), 8.04 (s, 1H), 7.72-7.75 (m, 1H), 7.57-7.60 (m, 2H), 7.48-7.55 (m, 1H), 7.37-7.41 (m, 1H), 6.60 (s, 1H), 2.44 (s, 3H).

Example 5—Preparation of Additional Indazol-5-yl-Amino-1,3,4-thiadiazolyl Compounds The following compounds were prepared using procedures based on those described in Example 4.

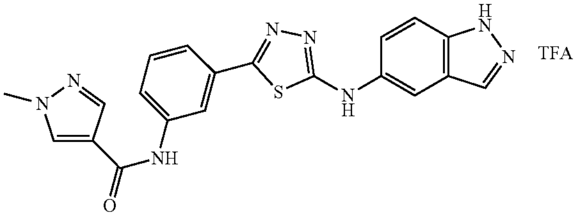 [SMILES: Cn1cc(C(=O)Nc2cccc(-c3nnc(Nc4ccc5[nH]ncc5c4)s3)c2)cn1]

N-(3-(5-((1H-indazol-5-yl)amino)-1,3,4-thiadiazol-2-yl)phenyl)-1-methyl-1H-pyrazole-4-carboxamide 2,2,2-trifluoroacetic Acid Solvate (ES, m/z): 416.95[M+H$^+$]. $^1$H NMR (DMSO-$d_6$, 300 MHz) δ 8.17-8.24 (m, 3H), 8.01-8.05 (m, 2H), 7.71-7.73 (m, 1H), 7.38-7.58 (m, 4H), 3.85 (s, 3H).

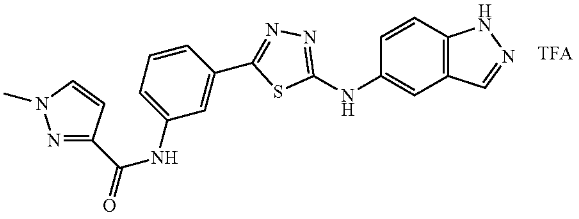 [SMILES: Cn1ccc(C(=O)Nc2cccc(-c3nnc(Nc4ccc5[nH]ncc5c4)s3)c2)n1]

N-(3-[5-[(1H-Indazol-5-yl)amino]-1,3,4-thiadiazol-2-yl]phenyl)-1-methyl-1H-pyrazole-3-carboxamide 2,2,2-trifluoroacetic Acid Solvate (ES, m/z): 417.0[M+H$^+$]. $^1$H NMR (DMSO-$d_6$, 300 MHz) δ 8.28 (s, 1H), 8.17-8.18 (m, 1H), 8.05 (s, 1H), 7.74-7.78 (m, 2H), 7.55-7.58 (m, 2H), 7.38-7.49 (m, 2H), 6.77-6.78 (m, 3H), 3.91 (s, 3H).

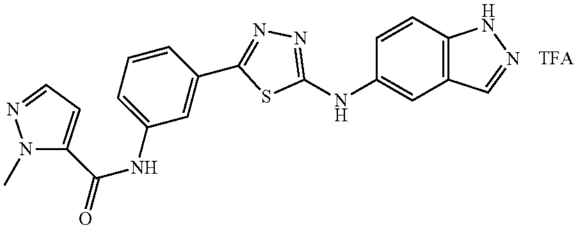 [SMILES: Cn1nccc1C(=O)Nc1cccc(-c2nnc(Nc3ccc4[nH]ncc4c3)s2)c1]

N-(3-[5-[(1H-Indazol-5-yl)amino]-1,3,4-thiadiazol-2-yl]phenyl)-1-methyl-1H-pyrazole-5-carboxamide 2,2,2-trifluoroacetic Acid Solvate (ES, m/z): 417.0[M+H$^+$]. $^1$H NMR (DMSO-$d_6$, 300 MHz) δ 8.17-8.23 (s, 1H), 8.05 (s, 1H), 7.72-7.75 (m, 1H), 7.51-7.58 (m, 4H), 7.38-7.48 (m, 1H), 7.01-7.02 (m, 1H), 4.04 (s, 3H).

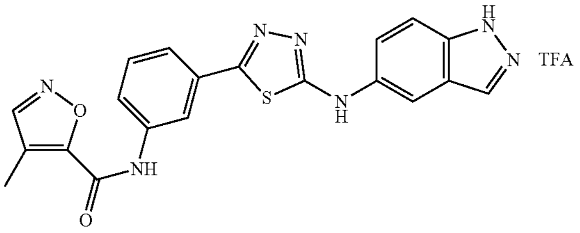 [SMILES: Cc1cnoc1C(=O)Nc1cccc(-c2nnc(Nc3ccc4[nH]ncc4c3)s2)c1]

N-(3-[5-[(1H-Indazol-5-yl)amino]-1,3,4-thiadiazol-2-yl]phenyl)-4-methyl-1,2-oxazole-5-carboxamide 2,2,2-trifluoroacetic Acid Solvate (ES, m/z): 417.95[M+H$^+$]. $^1$H NMR (DMSO-$d_6$, 300 MHz) δ 8.57 (s, 1H), 8.24 (s, 1H), 8.16 (s, 1H), 8.05 (s, 1H), 7.74-7.77 (m, 1H), 7.46-7.59 (m, 3H), 7.38-7.41 (m, 1H), 2.29 (s, 3H).

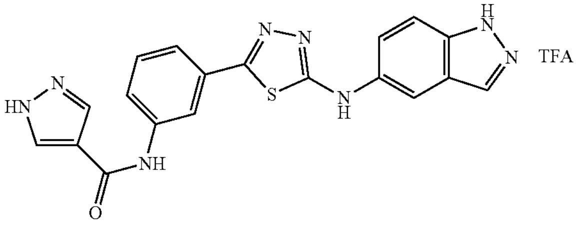 [SMILES: O=C(Nc1cccc(-c2nnc(Nc3ccc4[nH]ncc4c3)s2)c1)c1cn[nH]c1]

N-(3-[5-[(1H-Indazol-5-yl)amino]-1,3,4-thiadiazol-2-yl]phenyl)-1H-pyrazole-4-carboxamide 2,2,2-trifluoroacetic Acid Solvate (ES, m/z): 403.05[M+H$^+$]. $^1$H NMR (DMSO-$d_6$, 300 MHz) δ 13.37 (s, 1H), 13.03 (s, 1H), 10.42 (s, 1H), 10.02 (s, 1H), 8.42 (s, 1H), 8.25 (s, 2H), 8.06 (s, 2H), 7.89-7.91 (m, 1H), 7.42-7.68 (m, 4H).

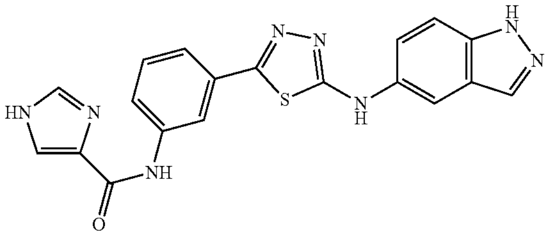 [SMILES: O=C(Nc1cccc(-c2nnc(Nc3ccc4[nH]ncc4c3)s2)c1)c1c[nH]cn1]

N-(3-[5-[(1H-Indazol-5-yl)amino]-1,3,4-thiadiazol-2-yl]phenyl)-1H-imidazole-4-carboxamide (ES-ESI, m/z): 403.2 [M+H]$^+$. $^1$H NMR (400 MHz, $CD_3OD$) δ 8.63-8.72 (m, 1H), 8.32-8.38 (m, 1H), 8.16 (d, J=12.4 Hz, 2H), 8.05 (d, J=9.6 Hz, 1H), 7.83-7.89 (m, 1H), 7.64 (d, J=8 Hz, 1H), 7.59 (d, J=8.8 Hz, 1H), 7.47-7.54 (m, 2H).

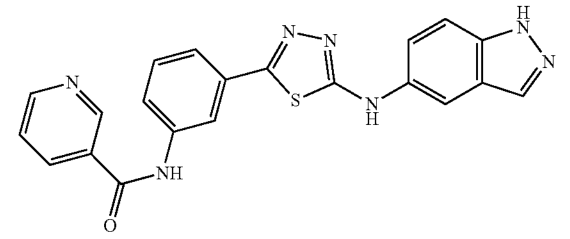 [SMILES: O=C(Nc1cccc(-c2nnc(Nc3ccc4[nH]ncc4c3)s2)c1)c1cccnc1]

N-(3-[5-[(1H-Indazol-5-yl)amino]-1,3,4-thiadiazol-2-yl]phenyl)pyridine-3-carboxamide (ES-ESI, m/z): 414.0 $[M+H]^+$. $^1H$ NMR (400 MHz, $CD_3OD$) δ 9.23 (s, 1H), 8.85 (d, J=4 Hz, 1H), 8.63 (d, J=8 Hz, 1H), 8.33 (s, 1H), 8.18 (d, J=1.2 Hz, 1H), 8.07 (s, 1H), 7.80-7.89 (m, 2H), 7.66-7.71 (m, 1H), 7.47-7.60 (m, 3H).

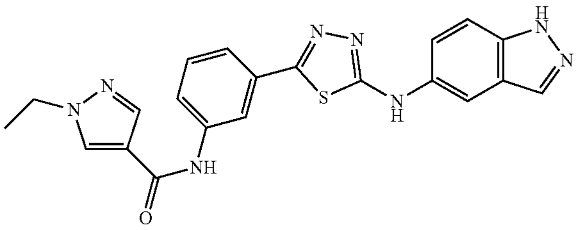 [SMILES: CCn1cc(C(=O)Nc2cccc(-c3nnc(Nc4ccc5[nH]ncc5c4)s3)c2)cn1]

1-Ethyl-N-(3-[5-[(1H-indazol-5-yl)amino]-1,3,4-thiadiazol-2-yl]phenyl)-1H-pyrazole-4-carboxamide (ES, m/z): 431 $[M+H]^+$. $^1H$ NMR (400 MHz, DMSO) δ 13.01 (s, 1H), 10.50 (s, 1H), 9.99 (s, 1H), 8.39 (s, 1H), 8.24 (d, 2H, J=1.6), 8.06 (s, 2H), 7.89-7.87 (m, 1H), 7.56-7.53 (m, 2H), 7.48-7.40 (m, 2H), 4.23-4.19 (m, 2H), 1.43-1.37 (m, 3H).

Example 6—Synthesis of 3-Amino-N-(3-[5-[(1H-indazol-5-yl)amino]-1,3,4-thiadiazol-2-yl]phenyl) pyrrolidine-1-carboxamide 2,2,2-trifluoroacetic Acid Solvate

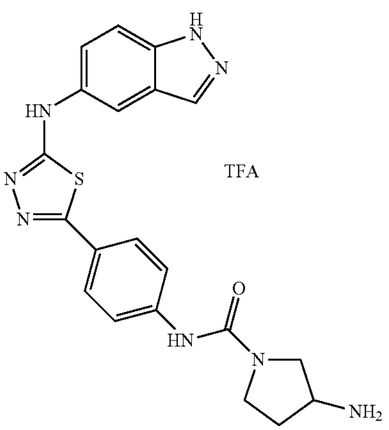 [SMILES: NC1CCN(C(=O)Nc2ccc(-c3nnc(Nc4ccc5[nH]ncc5c4)s3)cc2)C1]

Part 1—Synthesis of Tert-Butyl 5-[[(tert-butoxy) carbonyl](5-[3-[(4-nitrophenoxycarbonyl)amino] phenyl]-1,3,4-thiadiazol-2-yl)amino]-1H-indazole-1-carboxylate

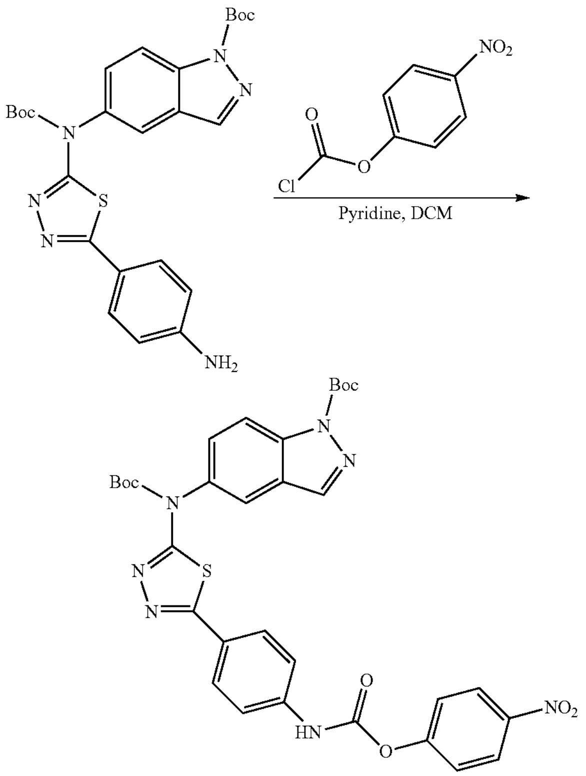

Into a 50-mL round-bottom flask was added a solution of tert-butyl 5-[[5-(3-aminophenyl)-1,3,4-thiadiazol-2-yl] [(tert-butoxy)carbonyl]amino]-1H-indazole-1-carboxylate (160 mg, 0.31 mmol, 1.00 equiv), 4-nitrophenyl chloroformate (94.5 mg, 0.47 mmol, 1.49 equiv) and pyridine (0.3 mL) in DCM (9 mL). The resulting solution was stirred overnight at room temperature. Then, the reaction mixture was concentrated under vacuum to and the resulting residue was purified by silica gel column with ethyl acetate/petroleum ether (1:1) as eluent. This provided 130 mg (61%) of tert-butyl 5-[[(tert-butoxy)carbonyl](5-[3-[(4-nitrophenoxycarbonyl)amino]phenyl]-1,3,4-thiadiazol-2-yl)amino]-1H-indazole-1-carboxylate as a yellow oil.

Part 2—Synthesis of Tert-Butyl 5-[[(tert-butoxy) carbonyl][5-(3-[[(3-[[(tert-butoxy)carbonyl]amino] pyrrolidin-1-yl)carbonyl]amino]phenyl)-1,3,4-thiadiazol-2-yl]amino]-1H-indazole-1-carboxylate

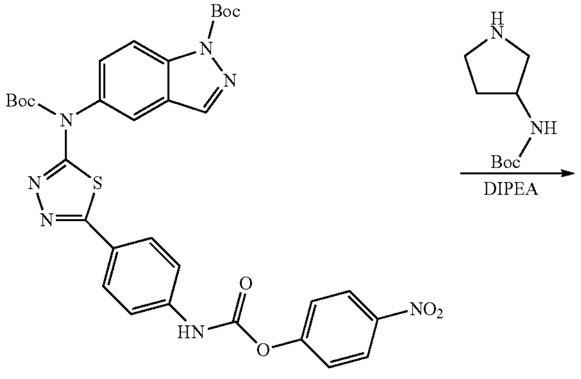

-continued

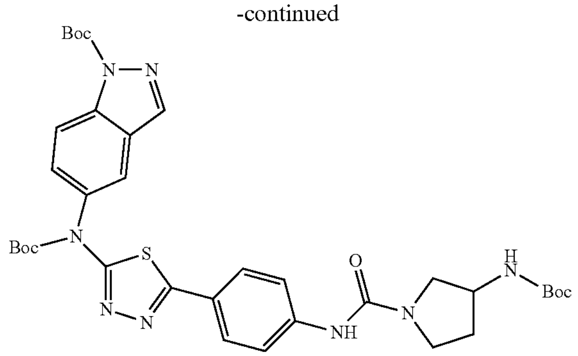

Into a 50-mL round-bottom flask was added a solution of tert-butyl 5-[[(tert-butoxy)carbonyl](5-[3-[(4-nitrophenoxy-carbonyl)amino]phenyl]-1,3,4-thiadiazol-2-yl)amino]-1H-indazole-1-carboxylate (100 mg, 0.15 mmol, 1.00 equiv), tert-butyl N-(pyrrolidin-3-yl)carbamate (98.99 mg, 0.53 mmol, 3.58 equiv) and N,N-diisopropylethylamine (DIPEA) (0.14 mL, 0.846 mmol, 5.64 equiv) in tetrahydrofuran (5.4 mL). The resulting solution was stirred for 2 h at 50° C. in an oil bath, and then it was concentrated under vacuum to provide a residue that was then purified by silica gel column with DCM/methanol (10:1) as eluent to furnish 98 mg (92%) of tert-butyl 5-[[(tert-butoxy)carbonyl][5-(3-[[(3-[[(tert-butoxy)carbonyl]amino]pyrrolidin-1-yl)carbonyl]amino]phenyl)-1,3,4-thiadiazol-2-yl]amino]-1H-indazole-1-carboxylate as a yellow oil.

Part 3—Synthesis of 3-Amino-N-(3-[5-[(1H-indazol-5-yl)amino]-1,3,4-thiadiazol-2-yl]phenyl)pyrrolidine-1-carboxamide 2,2,2-trifluoroacetic Acid Solvate

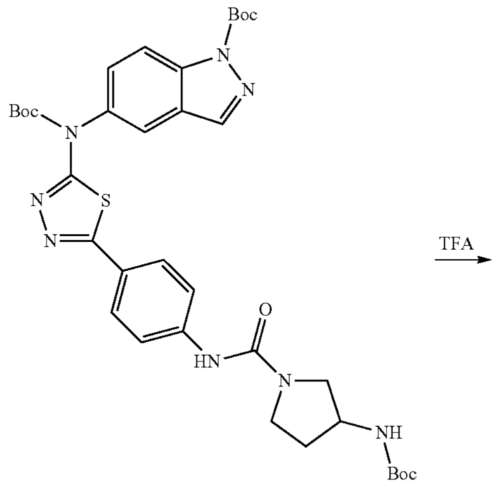

-continued

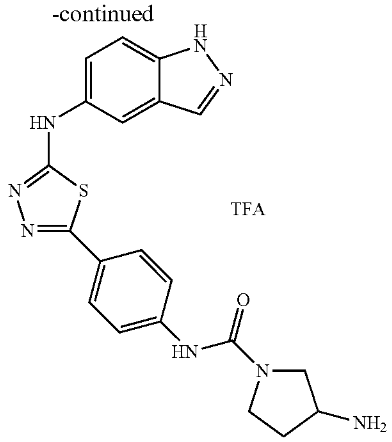

Into a 50-mL round-bottom flask was added a solution of tert-butyl 5-[[(tert-butoxy)carbonyl][5-(3-[[(3-[[(tert-butoxy)carbonyl]amino]pyrrolidin-1-yl)carbonyl]amino]phenyl)-1,3,4-thiadiazol-2-yl]amino]-1H-indazole-1-carboxylate (100 mg, 0.14 mmol, 1.00 equiv) in TFA (2 mL) and DCM (6 mL). The resulting solution was stirred for 2 h at room temperature. The reaction mixture was concentrated under vacuum, and the resulting residue was purified by silica gel column with ethyl acetate/petroleum ether (1:3) as eluent. The product was further purified by preparative HPLC, which provided 30 mg of 3-amino-N-(3-[5-[(1H-indazol-5-yl)amino]-1,3,4-thiadiazol-2-yl]phenyl)pyrrolidine-1-carboxamide TFA solvate as an off-white solid. $^{1}$H NMR ($CDCl_3$, 400 MHz) δ 8.20 (s, 1H), 8.02 (s, 2H), 7.61-7.71 (m, 1H), 7.51-7.61 (m, 1H), 7.31-7.45 (m, 3H), 3.81-3.92 (s, 1H), 3.51-3.53 (m, 4H), 2.21-3.21 (m, 1H), 1.98-2.1 (m, 1H).

Example 7—Synthesis of N-(4-[5-[(1H-Indazol-5-yl)amino]-1,3,4-thiadiazol-2-yl]phenyl)-3-methyl-pyrrolidine-1-carboxamide 2,2,2-trifluoroacetic Acid Solvate

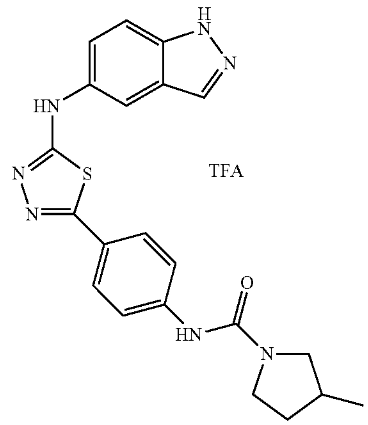 [SMILES: CC1CCN(C(=O)Nc2ccc(-c3nnc(Nc4ccc5[nH]ncc5c4)s3)cc2)C1]

Part 1—Synthesis of Tert-Butyl 5-[[(tert-butoxy) carbonyl][5-(3-[[(3-methylpyrrolidin-1-yl)carbonyl] amino]phenyl)-1,3,4-thiadiazol-2-yl]amino]-1H-indazole-1-carboxylate

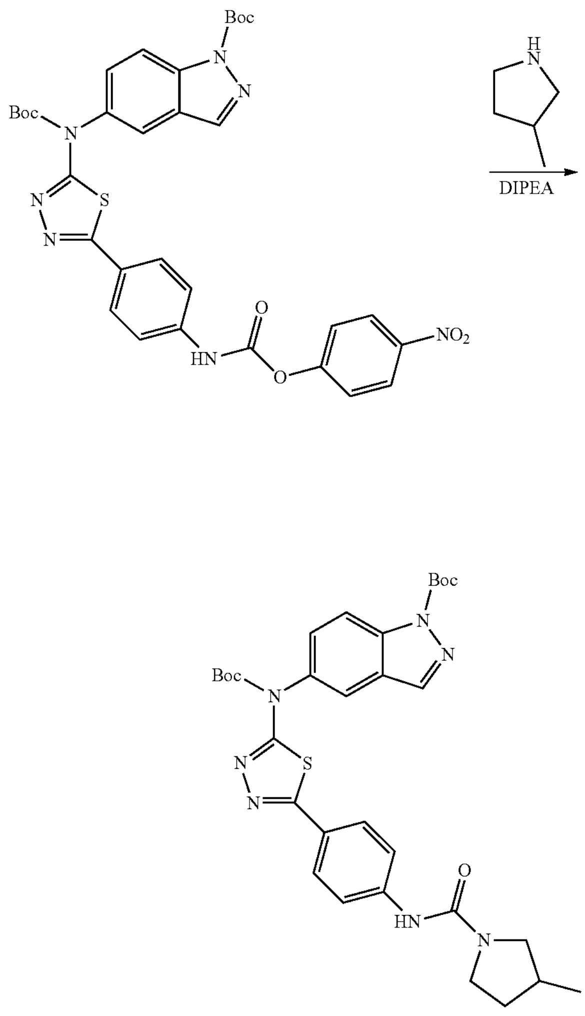

Into a 50-mL round-bottom flask was added a solution of tert-butyl 5-[[(tert-butoxy)carbonyl](5-[3-[(4-nitrophenoxy-carbonyl)amino]phenyl]-1,3,4-thiadiazol-2-yl)amino]-1H-indazole-1-carboxylate (190 mg, 0.28 mmol, 1.00 equiv), 3-methylpyrrolidine (64 mg, 0.75 mmol, 2.67 equiv) and DIPEA (0.224 mL, 1.28 mmol, 4.57 equiv) in tetrahydrofuran (15 mL). The resulting solution was stirred for 2 h at 50° C. in an oil bath and then was concentrated under vacuum. Crude tert-butyl 5-[[(tert-butoxy)carbonyl][5-(3-[[(3-methylpyrrolidin-1-yl)carbonyl]amino]phenyl)-1,3,4-thiadiazol-2-yl]amino]-1H-indazole-1-carboxylate was obtained as yellow oil and used in the next step without purification.

Part 2—Synthesis of N-(4-[5-[(1H-Indazol-5-yl) amino]-1,3,4-thiadiazol-2-yl]phenyl)-3-methylpyrrolidine-1-carboxamide 2,2,2-trifluoroacetic Acid Solvate

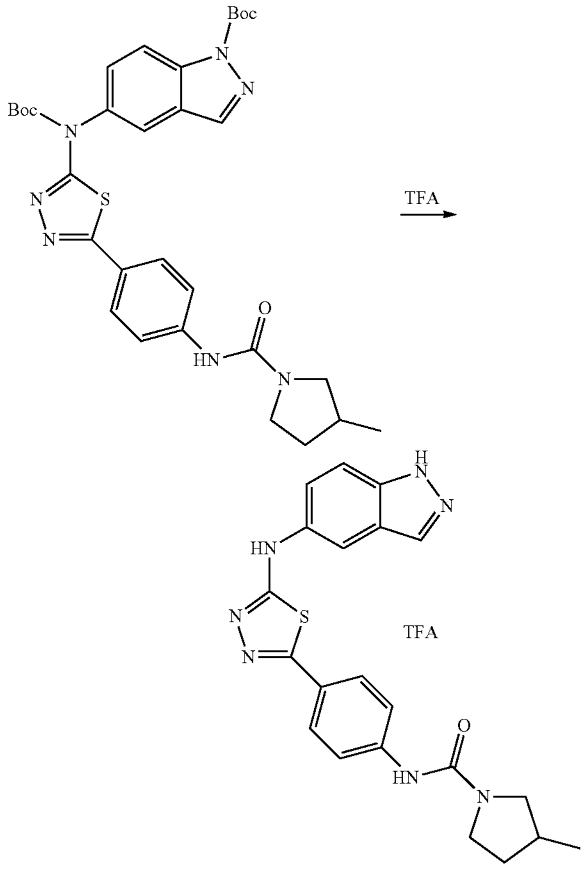

Into a 50-mL round-bottom flask was added a solution of tert-butyl 5-[[(tert-butoxy)carbonyl][5-(4-[[(3-methylpyrrolidin-1-yl)carbonyl]amino]phenyl)-1,3,4-thiadiazol-2-yl]amino]-1H-indazole-1-carboxylate (190 mg, 0.31 mmol, 1.00 equiv) in a mixture of DCM (6 mL) and TFA (2 mL). The resulting solution was stirred for 2 h at room temperature. Then, the reaction mixture was concentrated under vacuum and the resulting residue was purified by silica gel column chromatography with DCM/methanol (2:1) as eluent. The product (80 mg) was further purified by preparative HPLC to provide 41 mg of N-(4-[5-[(1H-indazol-5-yl) amino]-1,3,4-thiadiazol-2-yl]phenyl)-3-methylpyrrolidine-1-carboxamide TFA solvate as an off-white solid. $^1$H NMR ($CDCl_3$, 400 MHz) δ 13.02 (s, 1H), 10.47 (s, 1H), 8.32 (s, 1H), 8.06-8.04 (m, 1H), 7.69-7.67 (m, 2H), 7.56-7.54 (m, 1H), 7.42-7.40 (m, 1H), 7.36-7.34 (m, 2H), 7.33-7.21 (m, 1H), 3.51-3.43 (m, 1H), 3.40 (s, 2H), 2.90-2.93 (m, 1H), 2.33 (s, 1H), 2.01-2.03 (m, 1H), 1.49 (m, 1H), 1.06-1.03 (d, J=12.4 Hz, 3H).

Example 8—Synthesis of 3-[5-[(1H-Indazol-5-yl) amino]-1,3,4-thiadiazol-2-yl]phenol

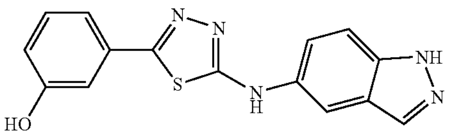 [SMILES: Oc1cccc(-c2nnc(Nc3ccc4[nH]ncc4c3)s2)c1]

Into a 100-mL round-bottom flask was added a solution of N-[5-(3-methoxyphenyl)-1,3,4-thiadiazol-2-yl]-1H-indazol-5-amine (2 g, 6.18 mmol, 1.00 equiv) in DCM (20 mL). This was followed by the addition of boron tribromide (9.3 g, 37.12 mmol, 6.00 equiv) dropwise with stirring at −60° C. The resulting solution was stirred overnight at room temperature. Then, the reaction was then quenched by the addition of 2 mL of MeOH. The pH value of the solution was adjusted to 8 with saturated aqueous $Na_2CO_3$. The solids were collected by filtration to yield 850 mg (44%) of 3-[5-[(1H-indazol-5-yl)amino]-1,3,4-thiadiazol-2-yl]phenol as a yellow solid. (ES-ESI, m/z): 310.1 $[M+H]^+$. $^1H$ NMR (400 MHz, $CD_3OD$) δ 8.15 (s, 1H); 8.03 (s, 1H), 7.50-7.57 (m, 1H), 7.44-7.47 (m, 1H), 7.25-7.31 (m, 3H), 6.88-6.90 (m, 1H).

Example 9—Synthesis of N-(4-[5-[(1H-Indazol-5-yl)amino]-1,3,4-thiadiazol-2-yl]pyridin-2-yl)-1H-imidazole-4-carboxamide 2,2,2-trifluoroacetic Acid Solvate

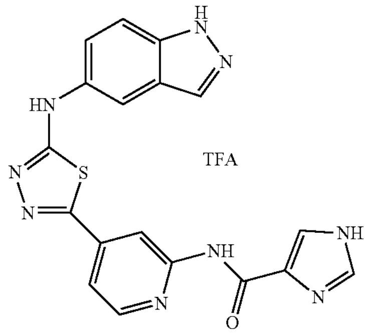 [SMILES: O=C(Nc1cc(-c2nnc(Nc3ccc4[nH]ncc4c3)s2)ccn1)c1c[nH]cn1]

Part 1—Synthesis of Tert-Butyl 2-(2-nitroisonicotinoyl)hydrazine-1-carboxylate

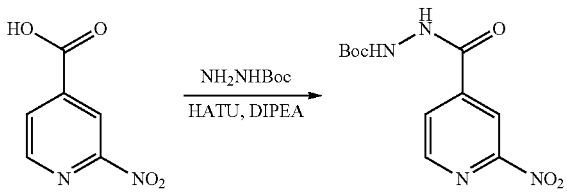 [SMILES: O=C(O)c1ccnc([N+](=O)[O-])c1 ; CC(C)(C)OC(=O)NNC(=O)c1ccnc([N+](=O)[O-])c1 ; "NH2NHBoc"]

Into a 100-mL round-bottom flask was added a solution of 2-nitropyridine-4-carboxylic acid (1 g, 5.95 mmol, 1.00 equiv) in DMF (10 mL), (tert-butoxy)carbohydrazide (1.18 g, 8.93 mmol, 1.50 equiv), 1-[bis(dimethylamino)methylene]-1H-1,2,3-triazolo[4,5-b]pyridinium 3-oxid hexafluorophosphate (HATU) (3.39 g, 8.92 mmol, 1.50 equiv), and DIPEA (2.3 g, 17.80 mmol, 3.00 equiv). The resulting solution was stirred overnight at room temperature, then diluted with 100 mL of ethyl acetate and washed with water (3×50 mL). The mixture was dried over anhydrous sodium sulfate and concentrated under vacuum and the resulting residue was purified by silica gel column with ethyl acetate/petroleum ether (1:1) as eluent to furnish 600 mg (36%) of tert-butyl 2-(2-nitroisonicotinoyl)hydrazine-1-carboxylate as a yellow oil.

Part 2—Synthesis of 2-Nitropyridine-4-carbohydrazide

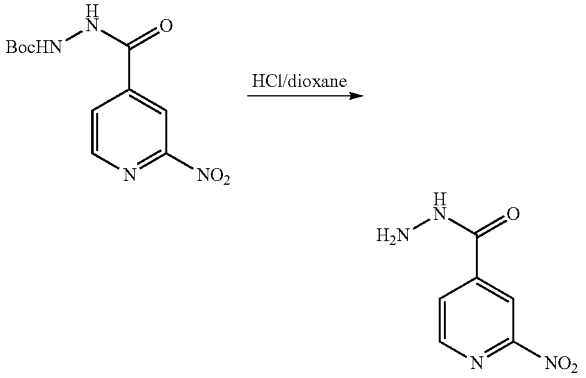

Into a 100-mL round-bottom flask was added a solution of tert-butyl 2-(2-nitroisonicotinoyl)hydrazine-1-carboxylate (600 mg, 2.13 mmol, 1.00 equiv) in hydrogen chloride/dioxane (10 mL). The resulting solution was stirred overnight at room temperature. The solids were collected by filtration to provide 300 mg (77%) of 2-nitropyridine-4-carbohydrazide hydrochloride as a white solid.

Part 3—Synthesis of N-[5-(2-Nitropyridin-4-yl)-1,3,4-thiadiazol-2-yl]-1H-indazol-5-amine

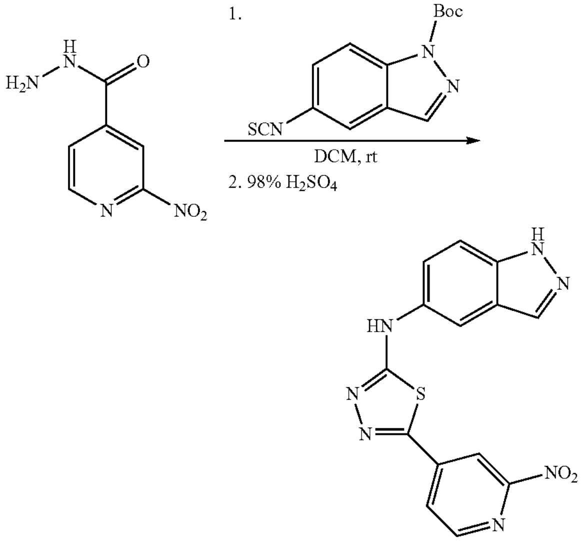

Into a 100-mL round-bottom flask was added a solution of 2-nitropyridine-4-carbohydrazide (500 mg, 2.75 mmol, 1.00 equiv) in DCM (20 mL). tert-Butyl 5-isothiocyanato-1H-indazole-1-carboxylate (756 mg, 2.74 mmol, 1.00 equiv) was added to the reaction mixture. The resulting solution was stirred overnight at room temperature. This was followed by addition of 98% $H_2SO_4$ (2 mL). The resulting solution was stirred overnight at room temperature. Then, the reaction solution was poured into ice water (50 mL). The pH value of the solution was adjusted to pH 9 with sodium hydroxide (1 M). The solids were collected by filtration to furnish 600 mg (64%) of N-[5-(2-nitropyridin-4-yl)-1,3,4-thiadiazol-2-yl]-1H-indazol-5-amine as a yellow solid.

Part 4—Synthesis of Tert-Butyl 5-((tert-butoxycarbonyl)(5-(2-nitropyridin-4-yl)-1,3,4-thiadiazol-2-yl)amino)-1H-indazole-1-carboxylate

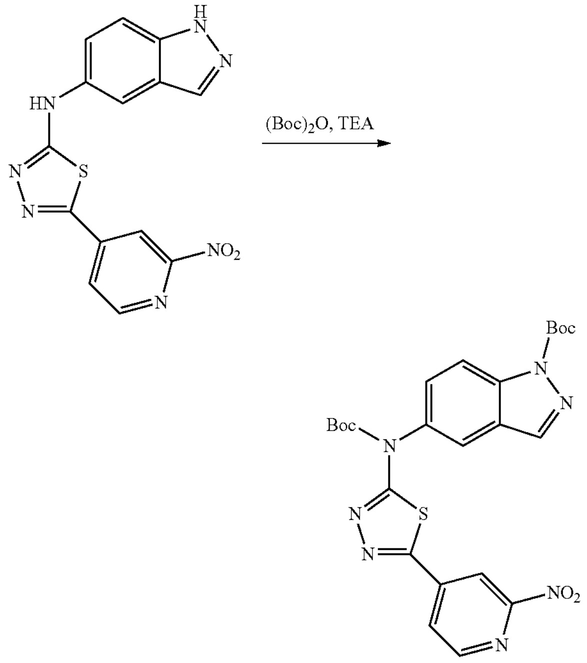

Into a 100-mL round-bottom flask was added a solution of N-[5-(2-nitropyridin-4-yl)-1,3,4-thiadiazol-2-yl]-1H-indazol-5-amine (300 mg, 0.88 mmol, 1.00 equiv) in dichloromethane (10 mL). $(Boc)_2O$ (578 mg, 2.65 mmol, 3.00 equiv) and TEA (536 mg, 5.30 mmol, 6.00 equiv) were added to the reaction mixture. The resulting solution was stirred overnight at room temperature. Then, the reaction mixture was concentrated under vacuum and the resulting residue was purified by silica gel column with ethyl acetate/petroleum ether (1:1) as eluent to furnish 300 mg (63%) of tert-butyl 5-((tert-butoxycarbonyl)(5-(2-nitropyridin-4-yl)-1,3,4-thiadiazol-2-yl)amino)-1H-indazole-1-carboxylate as a yellow solid.

Part 5—Synthesis of Tert-Butyl 5-((5-(2-aminopyridin-4-yl)-1,3,4-thiadiazol-2-yl)(tert-butoxycarbonyl)amino)-1H-indazole-1-carboxylate

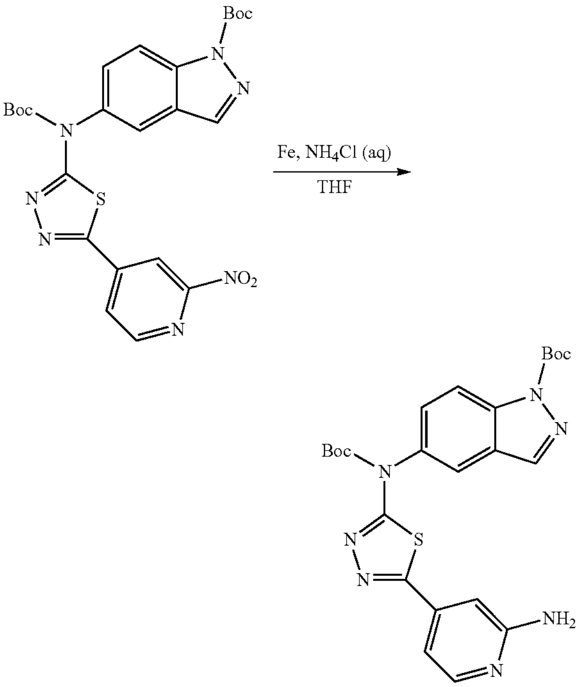

Into a 100-mL round-bottom flask was placed a solution of tert-butyl 5-((tert-butoxycarbonyl)(5-(2-nitropyridin-4-yl)-1,3,4-thiadiazol-2-yl)amino)-1H-indazole-1-carboxylate (300 mg, 0.55 mmol, 1.00 equiv) in tetrahydrofuran (20 mL). Iron powder (623 mg, 11.16 mmol, 20.00 equiv) and saturated aqueous $NH_4Cl$ (20 mL) were added to the reaction. The resulting solution was stirred overnight at 50° C. Then, the solids were filtered out, and the resulting solution was extracted with ethyl acetate (3×20 mL) and the combined organic layers were dried over anhydrous sodium sulfate and concentrated under vacuum. This provided 250 mg (88%) of tert-butyl 5-((5-(2-aminopyridin-4-yl)-1,3,4-thiadiazol-2-yl)(tert-butoxycarbonyl)amino)-1H-indazole-1-carboxylate as a yellow solid.

Part 6—Synthesis of Tert-Butyl 5-((5-(2-(1H-imidazole-4-carboxamido)pyridin-4-yl)-1,3,4-thiadiazol-2-yl)(tert-butoxycarbonyl)amino)-1H-indazole-1-carboxylate

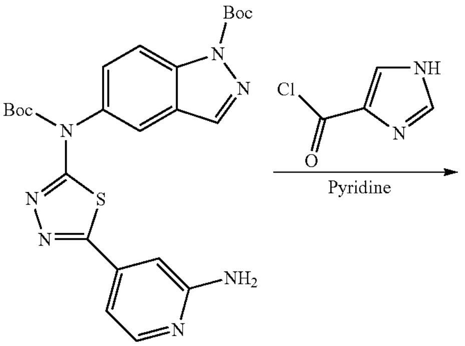

-continued

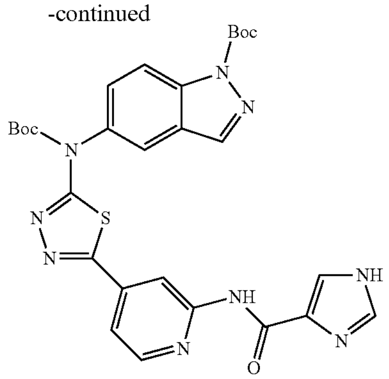

Into a 10-mL round-bottom flask was added a solution of tert-butyl 5-((5-(2-aminopyridin-4-yl)-1,3,4-thiadiazol-2-yl)(tert-butoxycarbonyl)amino)-1H-indazole-1-carboxylate (250 mg, 0.49 mmol, 1.00 equiv) in pyridine (5 mL). 1H-Imidazole-4-carbonyl chloride (96 mg, 0.74 mmol, 1.50 equiv) was added to the reaction mixture. The resulting solution was stirred overnight at room temperature, then concentrated under vacuum to provide a residue, which was then purified by silica gel column chromatograph with DCM/methanol (20:1) as eluent to furnish 150 mg (51%) of tert-butyl 5-((5-(2-(1H-imidazole-4-carboxamido)pyridin-4-yl)-1,3,4-thiadiazol-2-yl)(tert-butoxycarbonyl)amino)-1H-indazole-1-carboxylate as a yellow solid.

Part 7—Synthesis of N-(4-[5-[(1H-Indazol-5-yl)amino]-1,3,4-thiadiazol-2-yl]pyridin-2-yl)-1H-imidazole-4-carboxamide 2,2,2-trifluoroacetic Acid Solvate

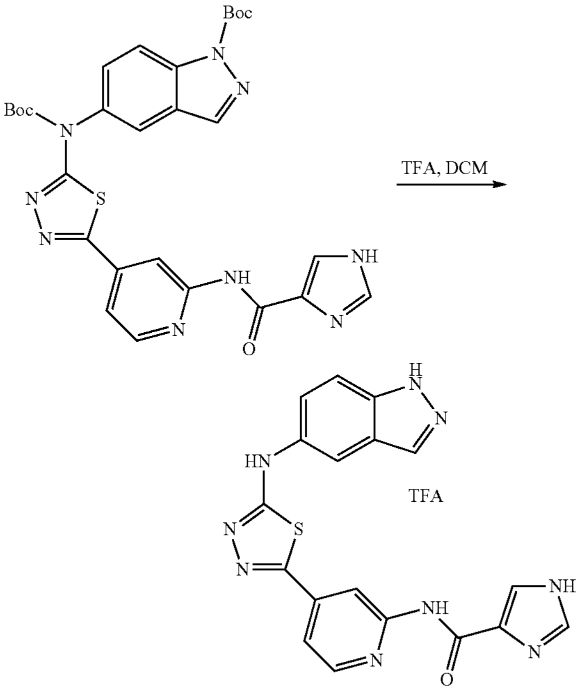

In a 10-mL round-bottom flask was added a solution of tert-butyl 5-((5-(2-(1H-imidazole-4-carboxamido)pyridin-4-yl)-1,3,4-thiadiazol-2-yl)(tert-butoxycarbonyl)amino)-1H-indazole-1-carboxylate (150 mg, 0.25 mmol, 1.00 equiv) in DCM (2 mL) and TFA (1 mL). The resulting solution was stirred for 1 h at room temperature. Then, the reaction mixture was concentrated under vacuum. The crude product was purified by preparative HPLC with the following conditions: X Bridge C18, 19×150 mm, 5 μm column; Mobile Phase A: water/0.05% TFA, Mobile Phase B: ACN; Flow rate: 20 mL/min; Gradient: 30% B to 70% B in 10 min; detector at 254 nm. This provided 14 mg (11%) of N-(4-[5-[(1H-indazol-5-yl)amino]-1,3,4-thiadiazol-2-yl]pyridin-2-yl)-1H-imidazole-4-carboxamide 2,2,2-trifluoroacetic acid solvate as a light yellow solid. (ES-ESI, m/z): 404.00 $[M-TFA+H]^+$. $^1H$ NMR (400 MHz, DMSO-$d_6$) δ 10.80 (s, 1H), 10.53 (s, 1H), 8.68 (s, 1H), 8.46-8.50 (m, 2H), 8.26 (s, 2H), 8.09 (s, 1H), 7.57-7.61 (m, 2H), 7.45 (d, J=8.8 Hz, 1H).

Example 10—Synthesis of N-(6-[5-[(1H-Indazol-5-yl)amino]-1,3,4-thiadiazol-2-yl]pyridin-2-yl)-1H-imidazole-4-carboxamide 2,2,2-trifluoroacetic Acid Solvate

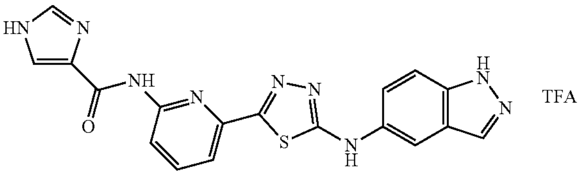 [SMILES: O=C(Nc1cccc(-c2nnc(Nc3ccc4[nH]ncc4c3)s2)n1)c1c[nH]cn1]

The title compound was prepared based on procedures described in Example 9. (ES-ESI, m/z): 404.1 $[M-TFA+H]^+$ $^1H$ NMR (400 MHz, DMSO-$d_6$) δ 13.05 (s, 1H), 10.65 (s, 1H), 9.86 (s, 1H), 8.25 (d, J=10 Hz, 2H), 7.89-7.09 (m, 5H), 7.43-7.58 (m, 2H).

Example 11—Synthesis of N-(2-[5-[(1H-Indazol-5-yl)amino]-1,3,4-thiadiazol-2-yl]pyridin-4-yl)-1H-imidazole-4-carboxamide 2,2,2-trifluoroacetic Acid Solvate

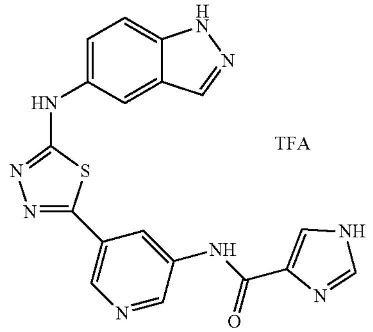 [SMILES: O=C(Nc1cncc(-c2nnc(Nc3ccc4[nH]ncc4c3)s2)c1)c1c[nH]cn1]

Part 1—Synthesis of Tert-Butyl 5-((5-(5-aminopyridin-3-yl)-1,3,4-thiadiazol-2-yl)(tert-butoxycarbonyl)amino)-1H-indazole-1-carboxylate

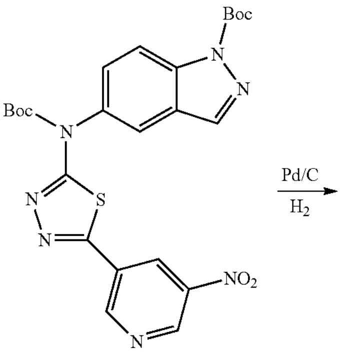

-continued

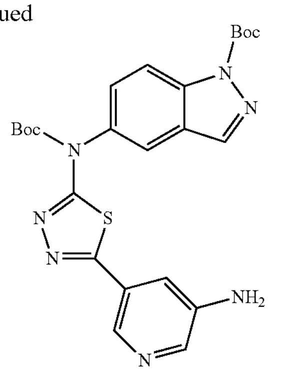

tert-Butyl 5-((tert-butoxycarbonyl)(5-(5-nitropyridin-3-yl)-1,3,4-thiadiazol-2-yl)amino)-1H-indazole-1-carboxylate was prepared similarly to EXAMPLE 9, Part 4 above.

Into a 10-mL round-bottom flask was added a solution of tert-butyl 5-((tert-butoxycarbonyl)(5-(5-nitropyridin-3-yl)-1,3,4-thiadiazol-2-yl)amino)-1H-indazole-1-carboxylate (350 mg, 0.65 mmol, 1.00 equiv) in tetrahydrofuran (5 mL). Palladium on carbon (200 mg) was added to the reaction mixture. The resulting suspension was stirred for 1 h at room temperature under $H_2$ atmosphere. Then, the catalyst was removed by filtration. The resulting mixture was concentrated under vacuum to provide 260 mg (79%) of tert-butyl 5-((5-(5-aminopyridin-3-yl)-1,3,4-thiadiazol-2-yl)(tert-butoxycarbonyl)amino)-1H-indazole-1-carboxylate as a yellow solid.

Part 2—Synthesis of Tert-Butyl 5-((5-(5-(1H-imidazole-4-carboxamido)pyridin-3-yl)-1,3,4-thiadiazol-2-yl)(tert-butoxycarbonyl)amino)-1H-indazole-1-carboxylate

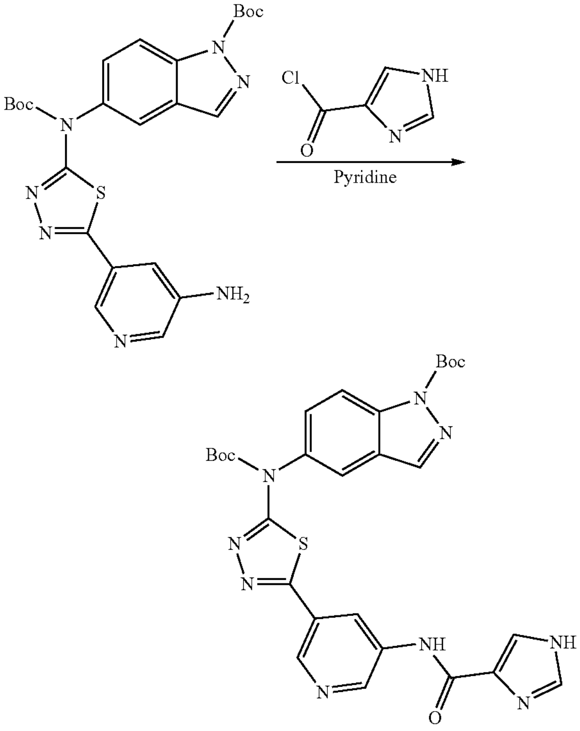

Into a 10-mL round-bottom flask was added a solution of 1H-imidazole-4-carbonyl chloride (100 mg, 0.77 mmol, 1.50 equiv) in pyridine (3 mL). tert-Butyl 5-((5-(5-aminopyridin-3-yl)-1,3,4-thiadiazol-2-yl)(tert-butoxycarbonyl)amino)-1H-indazole-1-carboxylate (260 mg, 0.51 mmol, 1.00 equiv) was added to the reaction mixture and the resulting solution was stirred overnight at room temperature. Next, the solvent was removed and the resulting residue was purified by silica gel column chromatography with DCM/methanol (10:1) as eluent to furnish 120 mg (39%) of tert-butyl 5-((5-(5-(1H-imidazole-4-carboxamido)pyridin-3-yl)-1,3,4-thiadiazol-2-yl)(tert-butoxycarbonyl)amino)-1H-indazole-1-carboxylate as a yellow solid.

Part 3—Synthesis of N-(2-[5-[(1H-Indazol-5-yl)amino]-1,3,4-thiadiazol-2-yl]pyridin-4-yl)-1H-imidazole-4-carboxamide 2,2,2-trifluoroacetic Acid Solvate

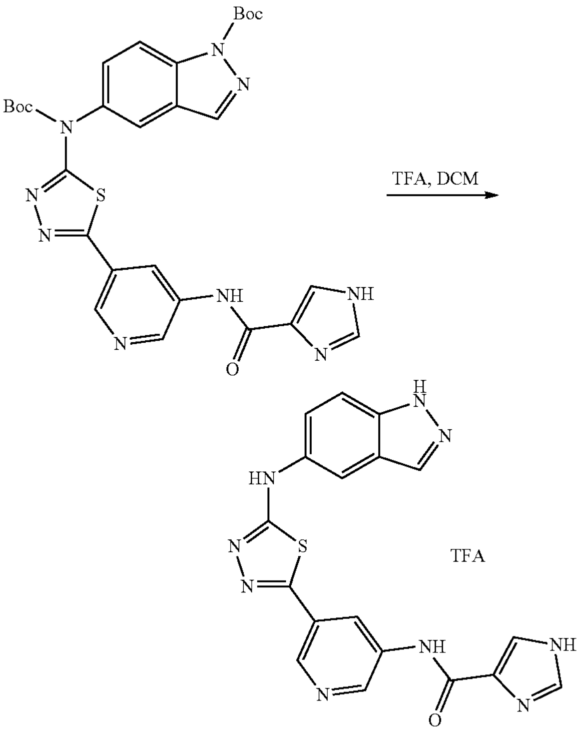

Into a 10-mL round-bottom flask was added a solution of tert-butyl 5-((5-(5-(1H-imidazole-4-carboxamido)pyridin-3-yl)-1,3,4-thiadiazol-2-yl)(tert-butoxycarbonyl)amino)-1H-indazole-1-carboxylate (120 mg, 0.20 mmol, 1.00 equiv) in DCM (2 mL) and TFA (1 mL). The resulting solution was stirred for 1 h at room temperature. Then, the solvent was removed and the crude product was purified by preparative HPLC with the following conditions: Gemini-NX 5μ C18 110A column, AXIA Packed, 150×21.2 mm; mobile phase, water with 0.05% TFA and ACN (5.0% ACN up to 36.0% in 8 min); Detector, 254 nm. This provided 32 mg (40%) of N-(2-[5-[(1H-indazol-5-yl)amino]-1,3,4-thiadiazol-2-yl]pyridin-4-yl)-1H-imidazole-4-carboxamide 2,2,2-trifluoroacetic acid solvate as a yellow solid. (ES-ESI, m/z): 404.2 $[M+H]^+$. $^1H$ NMR 400 MHz, $CD_3OD$) δ 8.99 (d, J=8.4 Hz, 1H), 8.78 (s, 2H), 8.58-8.63 (m, 1H), 8.13-8.18 (m, 2H), 8.06 (d, J=10.8 Hz, 1H), 7.56-7.59 (m, 1H), 7.46-7.48 (m, 1H).

Example 12—Synthesis of N-(1H-Indazol-5-yl)-5-piperazin-1-yl-1,3,4-thiadiazol-2-amine

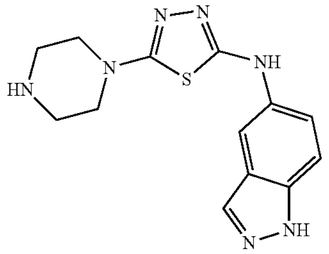 [SMILES: c1cc2[nH]ncc2cc1Nc1nnc(N2CCNCC2)s1]

Part 1—Synthesis of Tert-Butyl 4-methylsulfanylcarbothioylpiperazine-1-carboxylate

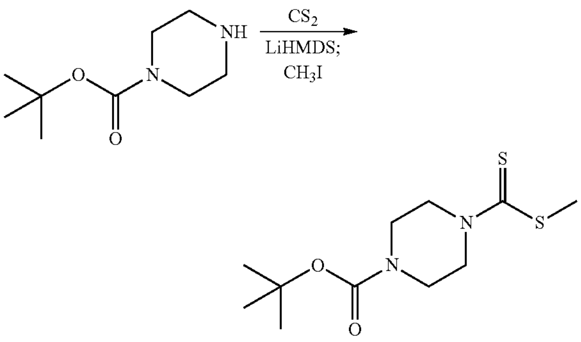

A 100-mL round bottom flask was charged with a solution of tert-butyl piperazine-1-carboxylate (2 g, 10.74 mmol) in THF (40 mL) and the vial was cooled in an ice bath, carbon disulfide (0.981 g, 12.89 mmol) was added drop-wise followed by lithium hexamethyldisilylamide (LiHMDS; 1 M in THF; 12.9 mL, 12.9 mmol) and the reaction mixture stirred for 30 min. Iodomethane (1.829 g, 12.89 mmol) was added and the reaction mixture was allowed to reach room temperature and stirred for 1 h. Then, the mixture was diluted with ethyl acetate (100 mL), washed with saturated $NaHCO_3$ solution and brine, and then dried over $MgSO_4$, filtered, and concentrated to yield tert-butyl 4-methylsulfanylcarbothioylpiperazine-1-carboxylate (2.973 g, 100.16% yield) as a light yellow solid which was used into the next step without further purification.

Part 2—Synthesis of Tert-Butyl 4-(aminocarbamothioyl)piperazine-1-carboxylate

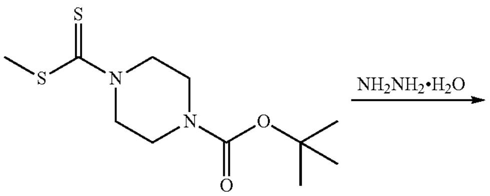

-continued

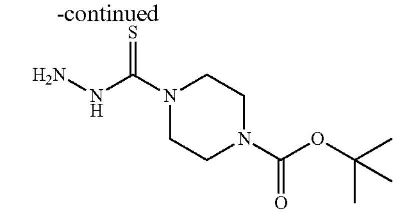

A 40-mL screw cap vial was charged with a solution of tert-butyl 4-methylsulfanylcarbothioylpiperazine-1-carboxylate (1 g, 3.6 mmol) in ethanol (15 mL) with stirring, hydrazine monohydrate (3.622 g, 72.35 mmol) was added dropwise and the reaction mixture was heated to a gentle reflux with stirring for 18 h. After cooling down to room temperature the mixture was adsorbed on silica gel and purified by silica gel chromatography (40 g, 40-63 μm, 60 Å flash cartridge from Silicycle) eluting with 0 to 5% DCM/(methanol containing 10% $NH_4OH$) as eluent to yield tert-butyl 4-(aminocarbamothioyl)piperazine-1-carboxylate (0.554 g, 59% yield) as an off-white solid.

Part 3—Synthesis of tert-Butyl 5-[[5-(4-tert-butoxycarbonylpiperazin-1-yl)-1,3,4-thiadiazol-2-yl]amino]indazole-1-carboxylate

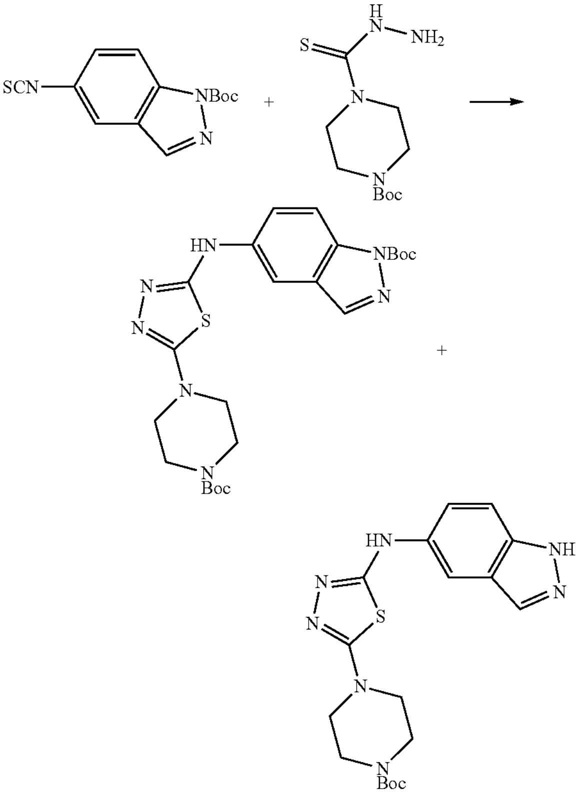

A 20-mL screw cap vial was charged with tert-butyl 4-(aminocarbamothioyl)piperazine-1-carboxylate (0.215 g, 0.826 mmol) and tert-butyl 5-isothiocyanatoindazole-1-carboxylate (0.227 g, 0.826 mmol) in ethanol (6 mL) and the mixture was heated to gentle reflux with stirring for 18 h. After cooling down to room temperature, the mixture was adsorbed on silica gel and purified by silica gel chromatography (40 g, 40-63 μm, 60 Å flash cartridge from Silicycle)

eluting with 0 to 5% DCM/(methanol containing 10% $NH_4OH$) as eluent to yield tert-butyl 5-[[5-(4-tert-butoxycarbonylpiperazin-1-yl)-1,3,4-thiadiazol-2-yl]amino]indazole-1-carboxylate (0.305 g, 74% yield) as a light brown foam. Also obtained was a more polar product that corresponded to the mono-deprotected product tert-butyl 4-[5-(1H-indazol-5-ylamino)-1,3,4-thiadiazol-2-yl]piperazine-1-carboxylate (0.083 g, 25% yield) as an off-white solid.

Part 4—Synthesis of N-(1H-Indazol-5-yl)-5-piperazin-1-yl-1,3,4-thiadiazol-2-amine

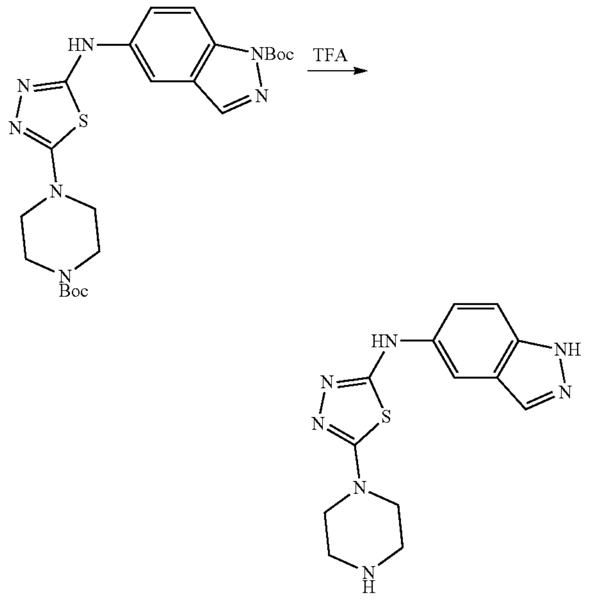

A 25-mL round bottom flask was charged with a solution of tert-butyl 5-[[5-(4-tert-butoxycarbonylpiperazin-1-yl)-1,3,4-thiadiazol-2-yl]amino]indazole-1-carboxylate (0.305 g, 0.608 mmol) in DCM (2 mL) and then TFA (3.467 g, 30.40 mmol) was added and the mixture was stirred for 4 h at room temperature. Then, the solvents were evaporated and the residue purified by silica gel chromatography (40 g, HP 15-40 μm, 60 Å flash cartridge from Silicycle) eluting with 0 to 10% DCM/(methanol containing 10% $NH_4OH$) as eluent. The residue after evaporation was triturated with dichloromethane, the solvent decanted and the solid residue dried in high vacuum to yield N-(1H-indazol-5-yl)-5-piperazin-1-yl-1,3,4-thiadiazol-2-amine (0.15 g, 82% yield) as an off-white solid. (ES, m/z): 302.20 $[M+H]^+$. $^1H$ NMR (DMSO-$d_6$, 400 MHz) δ 12.89 (s, 1H), 9.72 (s, 1H), 8.09 (s, 1H), 7.95 (s, 1H), 7.44 (d, J=9 Hz, 1H), 7.24 (d, J=9 Hz, 1H), 2.87 (m, 4H).

Example 13—Synthesis of 5-[(3R)-3-aminopyrrolidin-1-yl]-N-(1H-indazol-5-yl)-1,3,4-thiadiazol-2-amine

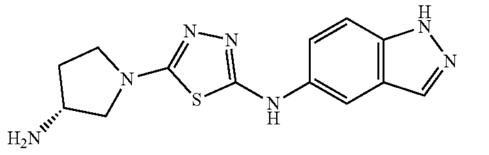 [SMILES: N[C@@H]1CCN(c2nnc(Nc3ccc4[nH]ncc4c3)s2)C1]

The title compound was prepared based on procedures described Example 12. (ES, m/z): 302.37 $[M+H]^+$. $^1H$ NMR ($CD_3OD$, 400 MHz) δ 8.01 (s, 1H), 7.94 (s, 1H), 7.46 (d, J=8.8 Hz, 1H), 7.31 (d, J=8.8 Hz, 1H), 3.71-3.58 (m, 3H), 3.49-3.44 (m, 1H), 3.23-3.21 (m, 1H), 2.38-2.22 (m, 1H), 1.92-1.85 (m, 1H).

Example 14—Synthesis of [4-[5-(1H-Indazol-5-ylamino)-1,3,4-thiadiazol-2-yl]piperazin-1-yl]-pyridazin-4-yl-methanone

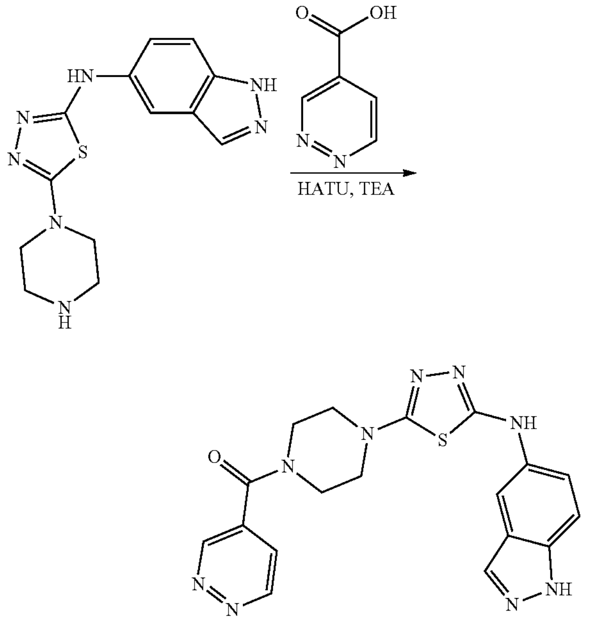

A 10-mL vial was charged with 4-pyridazinecarboxylic acid (0.009 g, 0.073 mmol), HATU (0.030 g, 0.080 mmol), triethylamine (0.013 g, 0.133 mmol) and N-(1H-indazol-5-yl)-5-piperazin-1-yl-1,3,4-thiadiazol-2-amine (0.020 g, 0.066 mmol) in DMF (2 mL) and the mixture stirred at room temperature for 18 h. Then, the volatile components were evaporated and the residue was purified directly by silica gel chromatography (24 g, HP 15-40 μm 60 Å flash cartridge from Silicycle) eluting with 0 to 10% DCM/(methanol containing 10% $NH_4OH$). The solid product obtained was suspended in MeOH, then immersed in an ultrasound bath for few minutes and the solid product was separated by decanting the mother liquor then dried to give [4-[5-(1H-indazol-5-ylamino)-1,3,4-thiadiazol-2-yl]piperazin-1-yl]-pyridazin-4-yl-methanone (0.002 g, 7% yield) as an off-white solid. (ES, m/z): 408.15 $[M+H]^+$. $^1H$ NMR (DMSO-$d_6$, 400 MHz) δ 12.9 (br s, 1H), 9.77 (s, 1H), 9.35 (dd, J=5.2, 1.2 Hz, 1H), 9.30 (m, 1H), 8.09 (d, J=1.2 Hz, 1H), 7.95 (s, 1H), 7.76 (dd, J=5.2, 2.4 Hz, 1H), 7.45 (d, J=8.8 Hz, 1H), 7.25 (dd, J=8.8, 2.0 Hz, 1H), 4.15-4.05 (m, 2H), 3.82-3.75 (m, 2H), 3.50-3.21 (m, 4H).

Example 15—Synthesis of N-(1H-Indazol-5-yl)-5-piperazin-2-yl-1,3,4-thiadiazol-2-amine 2,2,2-trifluoroacetic Acid Solvate

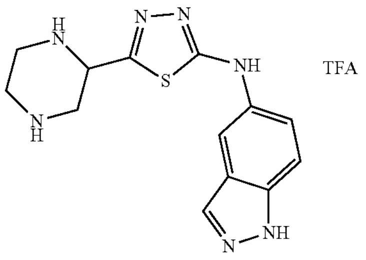 [SMILES: c1cc2[nH]ncc2cc1Nc1nnc(C2CNCCN2)s1]

Part 1—Synthesis of di-tert-Butyl 2-(hydrazinecarbonyl)piperazine-1,4-dicarboxylate

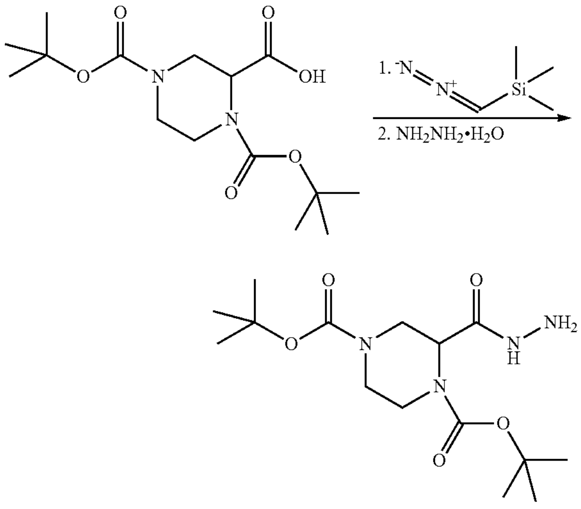

A 100-mL round bottom flask was charged with a solution of 1,4-bis(tert-butoxycarbonyl)piperazine-2-carboxylic acid (1 g, 3 mmol) in 10:1 methanol/water (25 mL) with stirring. A solution of trimethylsilyldiazomethane (2 M in ether) was added drop-wise (about 9 mL) until the yellow color persisted for 1 min. All volatile components were removed under reduced pressure and the residue was co-evaporated with toluene. The obtained methyl ester was dissolved in ethanol (10 mL) and treated with hydrazine monohydrate (0.318 g, 6.36 mmol) and the mixture was heated to 60° C. for 18 h. Next, solvents were removed under reduced pressure and the resulting residue was purified by silica gel chromatography (80 g, 40-63 μm 60 Å flash cartridge from Silicycle) eluting with 0 to 5% DCM/(methanol containing 10% $NH_4OH$) to yield di-tert-butyl 2-(hydrazinecarbonyl) piperazine-1,4-dicarboxylate (0.170 g, 16% yield) as a viscous, light yellow liquid.

Part 2—Synthesis of di-tert-Butyl 2-[[(1-tert-butoxycarbonylindazol-5-yl)carbamothioylamino]carbamoyl]piperazine-1,4-dicarboxylate

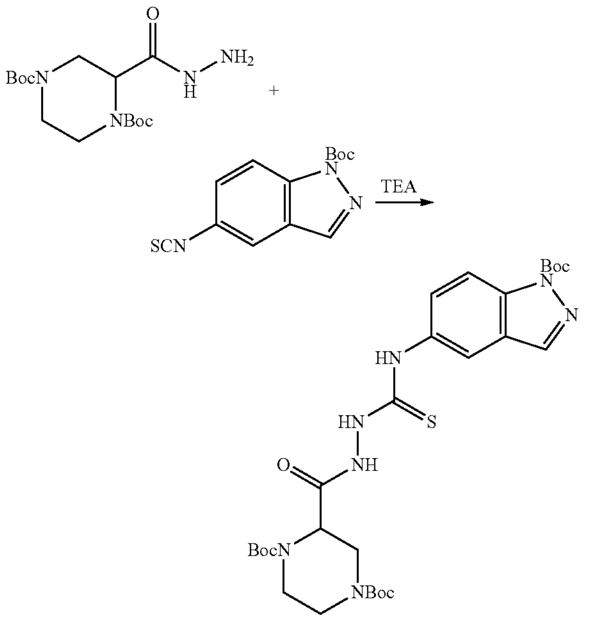

A 40-mL screw cap vial was charged with a solution of di-tert-butyl 2-(hydrazinecarbonyl)piperazine-1,4-dicarboxylate (0.170 g, 0.494 mmol) and tert-butyl 5-isothiocyanatoindazole-1-carboxylate (0.136 g, 0.494 mmol) in THF (8 mL). Triethylamine (0.05 g, 0.49 mmol) was added and the reaction continued at room temperature with stirring for 24 h. Thin layer chromatography (TLC) showed some starting material left, so the mixture was heated to 50° C. for 5 h. The volatile components were removed under reduced pressure and the residue was adsorbed on silica gel and purified by silica gel chromatography (40 g, 40-63 μm, 60 Å flash cartridge from Silicycle) eluting with 0 to 5% DCM/(methanol containing 10% $NH_4OH$) to yield di-tert-butyl 2-[[(1-tert-butoxycarbonylindazol-5-yl)carbamothioylamino]carbamoyl]piperazine-1,4-dicarboxylate (0.128 g, 41% yield) as a beige foam.

Part 3—Synthesis of di-tert-Butyl 2-[5-[(1-tert-butoxycarbonylindazol-5-yl)amino]-1,3,4-thiadiazol-2-yl]piperazine-1,4-dicarboxylate

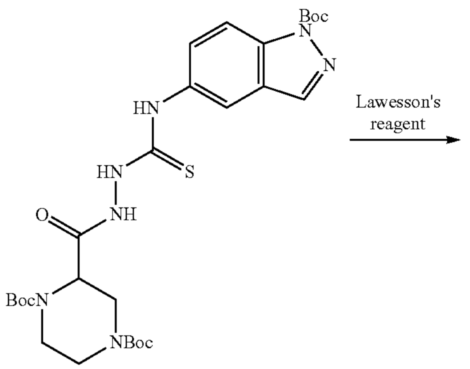

-continued

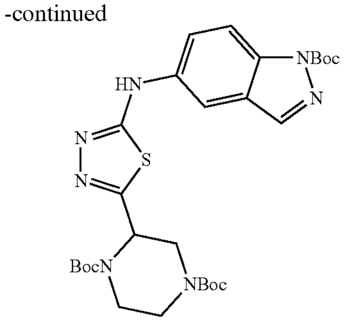

A 50-mL round bottom flask was charged with a mixture of di-tert-butyl 2-[[(1-tert-butoxycarbonylindazol-5-yl)carbamothioylamino]carbamoyl]piperazine-1,4-dicarboxylate (0.128 g, 0.207 mmol) and Lawesson's reagent (0.167 g, 0.413 mmol) in toluene (5 mL) and the mixture was heated with stirring to a gentle reflux for 2 h. After cooling down to room temperature, the crude was directly purified by silica gel chromatography (40 g, 40-63 μm 60 Å flash cartridge from Silicycle) eluting with 0 to 5% DCM/(methanol containing 10% $NH_4OH$) to yield di-tert-butyl 2-[5-[(1-tert-butoxycarbonylindazol-5-yl)amino]-1,3,4-thiadiazol-2-yl]piperazine-1,4-dicarboxylate (0.058 g, 47% yield) as a white solid.

Part 4—Synthesis of N-(1H-Indazol-5-yl)-5-piperazin-2-yl-1,3,4-thiadiazol-2-amine 2,2,2-trifluoroacetic Acid Solvate

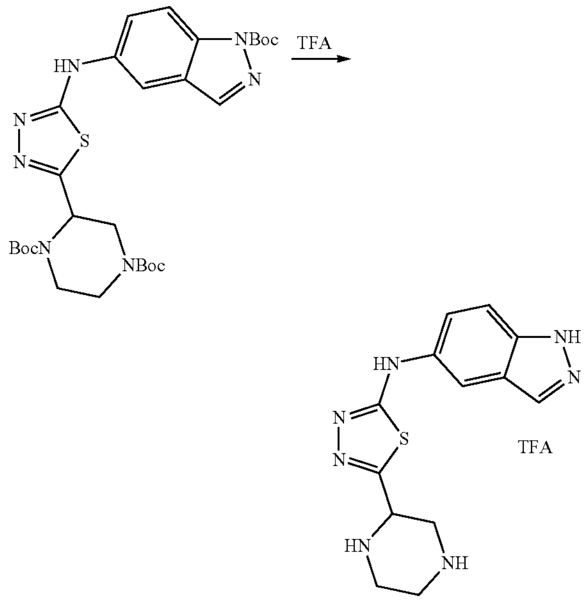

A 50-mL round bottom flask was charged with a mixture of di-tert-butyl 2-[5-[(1-tert-butoxycarbonylindazol-5-yl)amino]-1,3,4-thiadiazol-2-yl]piperazine-1,4-dicarboxylate (0.059 g, 0.098 mmol) and TFA (2.251 g, 19.74 mmol) in DCM (2 mL) and the mixture was stirred at room temperature for 4 h. Next, the solvents were evaporated and the crude mixture was directly purified by preparative reverse phase HPLC (Method A, defined above) to yield the TFA solvate of N-(1H-indazol-5-yl)-5-piperazin-2-yl-1,3,4-thiadiazol-2-amine (0.0430 g, 104.89% yield) as a white solid. (ES, m/z): 302.26 $[M+H]^+$. $^1H$ NMR ($CD_3OD$, 400 MHz) δ 13.02 (br s, 1H), 10.43 (s, 1H), 8.97 (br s, 2H), 8.18 (d, J=1.5 Hz, 1H), 8.02 (s, 1H), 7.52 (d, J=8.8 Hz, 1H), 7.34 (dd, J=8.8, 2.0 Hz, 1H), 4.60 (m, 1H), 3.64 (m, 2H), 3.15 (m, 2H), 3.05 (m, 2H).

Example 16—Preparation of N-(1H-Indazol-5-yl)-5-(3-piperidyl)-1,3,4-thiadiazol-2-amine 2,2,2-trifluoroacetic Acid Solvate

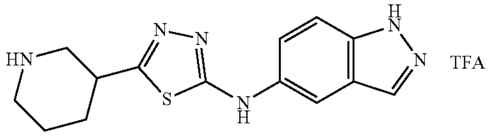 [SMILES: c1cc2[nH]ncc2cc1Nc1nnc(C2CCCNC2)s1]

The title compound was prepared based on procedures described in Example 16. (ES, m/z): 301.29 $[M+H]^+$. $^1H$ NMR ($CD_3OD$, 400 MHz) δ 8.08 (d, J=0.8 Hz, 1H), 8.07 (s, 1H), 7.55 (d, J=9 Hz, 1H), 7.40 (dd, J=9, 2.1 Hz, 1H), 3.7-3.6 (m, 1H), 3.55-3.25 (m, 3H), 3.15-3.05 (m, 1H), 3.3-3.2 (m, 1H), 2.05-1.8 (m, 3H).

Example 17—Preparation of N-[5-[3-(1,3-Oxazol-5-yl)phenyl]-1,3,4-thiadiazol-2-yl]-1H-indazol-5-amine 2,2,2-trifluoroacetic Acid Solvate

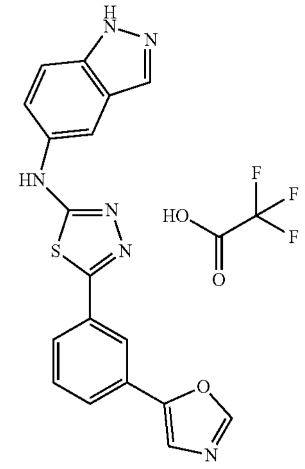 [SMILES: c1cc(-c2cnco2)cc(-c2nnc(Nc3ccc4[nH]ncc4c3)s2)c1 ; O=C(O)C(F)(F)F]

Part 1—Synthesis of Tert-Butyl 5-((tert-butoxycarbonyl)(5-(3-(2-(triisopropylsilyl)oxazol-5-yl)phenyl)-1,3,4-thiadiazol-2-yl)amino)-1H-indazole-1-carboxylate

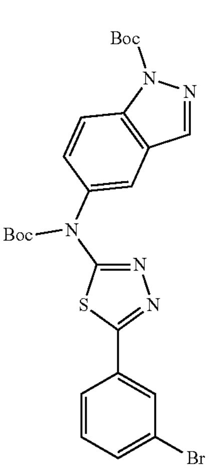

+

-continued

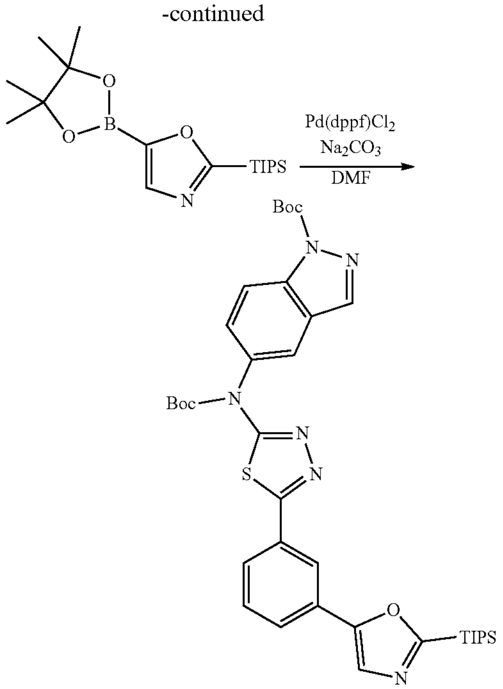

Into a 100-mL round-bottom flask was placed a solution of tert-butyl 5-((5-(3-bromophenyl)-1,3,4-thiadiazol-2-yl)(tert-butoxycarbonyl)amino)-1H-indazole-1-carboxylate (300 mg, 0.52 mmol, 1.00 equiv) in N,N-dimethylformamide (10 mL). 5-(Tetramethyl-1,3,2-dioxaborolan-2-yl)-2-[tris(propan-2-yl)silyl]-1,3-oxazole (276 mg, 0.79 mmol, 1.50 equiv), [1,1'-bis(diphenylphosphino)ferrocene]dichloropalladium(II) ($Pd(dppf)Cl_2$) (38 mg, 0.05 mmol, 0.10 equiv), and sodium carbonate (111 mg, 1.05 mmol, 2.00 equiv) were added to the reaction mixture. The resulting solution was stirred overnight at 80° C. under $N_2$. The resulting solution was diluted with 50 mL of water, then extracted with 3×50 mL of ethyl acetate. The combined organic layers were dried over anhydrous sodium sulfate and concentrated under vacuum to provide a residue, which was purified on a silica gel column with ethyl acetate/petroleum ether (2:1) as eluent to furnish 270 mg (72%) tert-butyl 5-((tert-butoxycarbonyl)(5-(3-(2-(triisopropylsilyl)oxazol-5-yl)phenyl)-1,3,4-thiadiazol-2-yl)amino)-1H-indazole-1-carboxylate as a yellow solid.

Part 2—Synthesis of Tert-Butyl 5-((tert-butoxycarbonyl)(5-(3-(oxazol-5-yl)phenyl)-1,3,4-thiadiazol-2-yl)amino)-1H-indazole-1-carboxylate

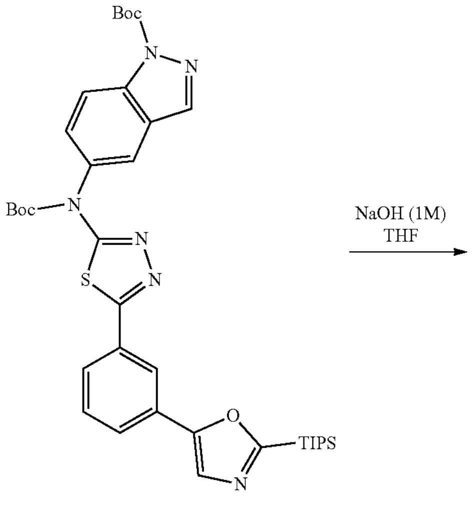

-continued

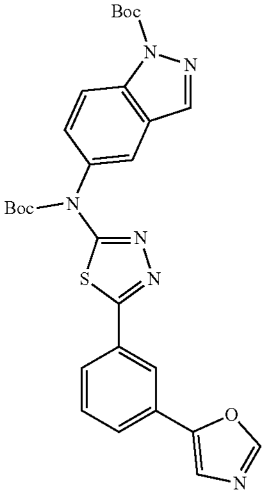

Into a 10-mL round-bottom flask was placed a solution of tert-butyl 5-((tert-butoxycarbonyl)(5-(3-(2-(triisopropylsilyl)oxazol-5-yl)phenyl)-1,3,4-thiadiazol-2-yl)amino)-1H-indazole-1-carboxylate (270 mg, 0.38 mmol, 1.00 equiv) in tetrahydrofuran (2 mL). Sodium hydroxide (1 M, 2 mL) was added to the reaction mixture. The resulting solution was stirred for 3 h at 55° C. then extracted with 3×4 mL of ethyl acetate. The combined organic layers were dried over anhydrous sodium sulfate and concentrated under vacuum to provide 200 mg (95%) of tert-butyl 5-((tert-butoxycarbonyl)(5-(3-(oxazol-5-yl)phenyl)-1,3,4-thiadiazol-2-yl)amino)-1H-indazole-1-carboxylate as a yellow solid, which was used into the next step without further purification.

Part 3—Synthesis of N-[5-[3-(1,3-Oxazol-5-yl)phenyl]-1,3,4-thiadiazol-2-yl]-1H-indazol-5-amine 2,2,2-trifluoroacetic Acid Solvate

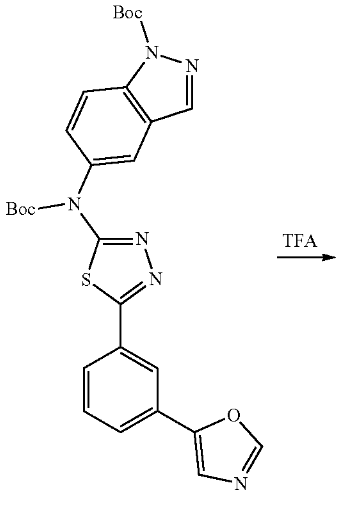

-continued

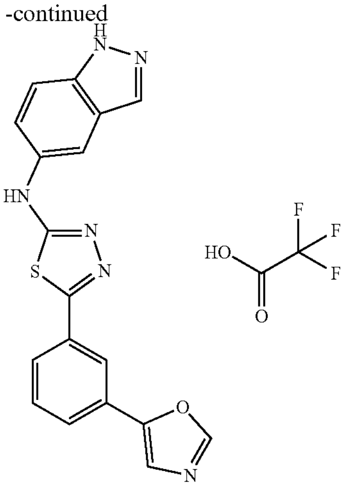

Into a 10-mL round-bottom flask was placed a solution of tert-butyl 5-((tert-butoxycarbonyl)(5-(3-(oxazol-5-yl)phenyl)-1,3,4-thiadiazol-2-yl)amino)-1H-indazole-1-carboxylate (200 mg, 0.36 mmol, 1.00 equiv) in dichloromethane (2 mL) and trifluoroacetic acid (1 mL). The resulting solution was stirred for 30 min at room temperature, then concentrated under vacuum, and the resulting crude product was purified by preparative HPLC with the following conditions: Column, XBridge BEH C18 OBD Prep Column, 5 μm, 19 mm×250 mm; mobile phase, water with 0.05% v/v TFA and ACN (28.0% ACN up to 58.0% in 8 min); Detector, 254 nm. This provided 79.5 mg (47%) of N-[5-[3-(1,3-oxazol-5-yl) phenyl]-1,3,4-thiadiazol-2-yl]-1H-indazol-5-amine 2,2,2-trifluoroacetic acid solvate as a yellow solid. (ES-ESI, m/z): 361.1 $[M+H]^+$. $^1H$ NMR (400 MHz, DMSO-$d_6$) δ 13.03 (s, 1H); 10.58 (s, 1H); 8.53 (s, 1H); 8.25 (s, 1H); 8.18 (s, 1H); 8.08 (s, 1H); 7.84-7.88 (m, 3H); 7.61-7.65 (m, 1H); 7.57 (d, J=8.8 Hz, 1H); 7.43-7.45 (m, 1H).

Example 18—Synthesis of N-(5-[5-[(1H-Indazol-5-yl)amino]-1,3,4-thiadiazol-2-yl]pyridin-3-yl)-2-[(propan-2-yl)amino]acetamide

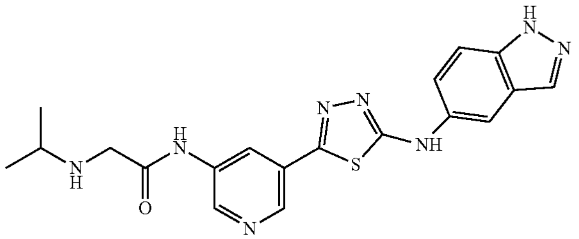 [SMILES: CC(C)NCC(=O)Nc1cncc(-c2nnc(Nc3ccc4[nH]ncc4c3)s2)c1]

Part 1—Synthesis of Tert-Butyl 5-[[(tert-butoxy)carbonyl][5-(5-[2-[(propan-2-yl)amino]acetamido]pyridin-3-yl)-1,3,4-thiadiazol-2-yl]amino]-1H-indazole-1-carboxylate

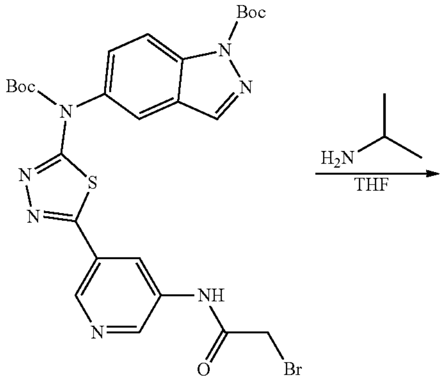

-continued

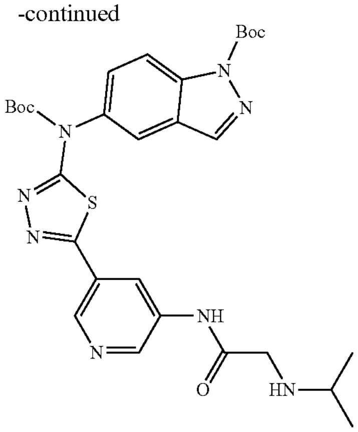

Into a 25-mL round-bottom flask was placed a solution of tert-butyl 5-([5-[5-(2-bromoacetamido)pyridin-3-yl]-1,3,4-thiadiazol-2-yl][(tert-butoxy)carbonyl]amino)-1H-indazole-1-carboxylate (120 mg, 0.19 mmol, 1.00 equiv) in tetrahydrofuran (8 mL) and propan-2-amine (0.1 mL). The resulting solution was stirred for 2 h at 50° C. in an oil bath. Then, the reaction mixture was concentrated under vacuum and the resulting residue purified by column chromatography using EtOAc and petroleum ether (1:1) as eluent. This provided 108 mg (93%) of tert-butyl 5-[[(tert-butoxy)carbonyl][5-(5-[2-[(propan-2-yl)amino]acetamido]pyridin-3-yl)-1,3,4-thiadiazol-2-yl]amino]-1H-indazole-1-carboxylate as an orange solid.

Part 2—Synthesis of N-(5-[5-[(1H-Indazol-5-yl)amino]-1,3,4-thiadiazol-2-yl]pyridin-3-yl)-2-[(propan-2-yl)amino]acetamide

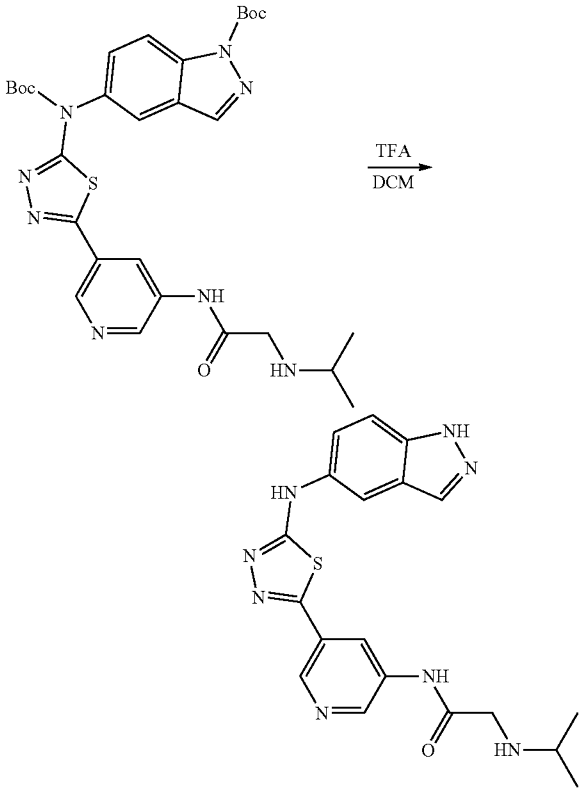

Into a 25-mL round-bottom flask was placed a solution of tert-butyl 5-[[(tert-butoxy)carbonyl][5-(5-[2-[(propan-2-yl)amino]acetamido]pyridin-3-yl)-1,3,4-thiadiazol-2-yl]amino]-1H-indazole-1-carboxylate (108 mg, 0.18 mmol, 1.00 equiv) in dichloromethane (9 mL) and trifluoroacetic acid (2.5 mL). The resulting solution was stirred for 2 h at room temperature. The resulting mixture was concentrated under vacuum. The crude product was purified by preparative HPLC with the following conditions: Column: Gemini-NX 5μ C18, 110A, AXIA Packed 150×21.2 mm; mobile phase: water with 0.05% $NH_4HCO_3$ and ACN (50.0% ACN up to 90.0% in 8 min); Detector: 254 nm. This provided 15.2 mg (21%) of N-(5-[5-[(1H-indazol-5-yl)amino]-1,3,4-thiadiazol-2-yl]pyridin-3-yl)-2-[(propan-2-yl)amino]acetamide as a yellow solid. (ES-ESI, m/z): 408.9 $[M+H]^+$. $^1H$ NMR (400 MHz, DMSO-$d_6$) δ 13.0 (s, 1H), 10.6 (s, 1H), 8.9 (d, J=2.0 Hz, 1H), 8.7 (d, 1H), 8.6 (s, 1H), 8.2 (s, 1H), 8.0 (s, 1H), 7.6 (d, J=8.8 Hz, 1H), 7.4 (d, J=8.8 Hz, 1H), 3.4 (s, 2H), 2.7 (m, 1H), 1.0 (s, 6H).

Example 19—Synthesis of N-[5-(Pyrazin-2-yl)-1,3,4-thiadiazol-2-yl]-1H-indazol-5-amine

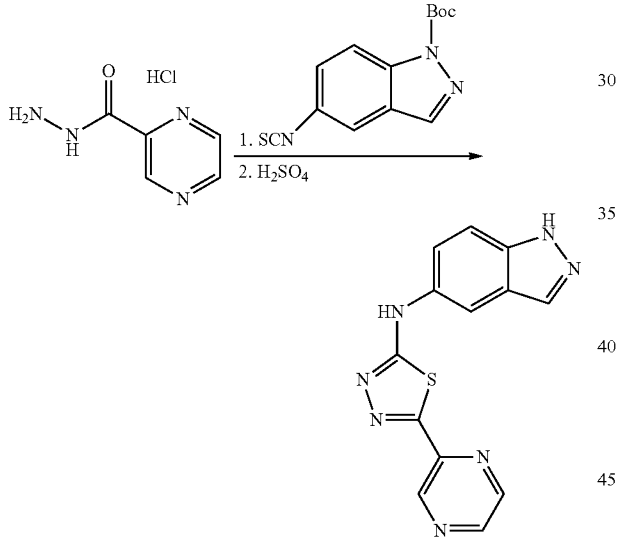

Into a 50-mL round-bottom flask was placed a solution of pyrazine-2-carbohydrazide hydrochloride (1.3 g, 9.41 mmol, 1.00 equiv) in dichloromethane (30 mL). tert-Butyl 5-isothiocyanato-1H-indazole-1-carboxylate (2.05 g, 7.4 mmol, 0.79 equiv) and DIPEA (1.92 g, 14.88 mmol, 1.58 equiv) were added to the reaction mixture. The resulting solution was stirred overnight at room temperature. $H_2SO_4$ (18.46 g, 0.19 mol, 20 equiv) was added dropwise at 0° C. The resulting mixture was stirred at room temperature for 1 h then concentrated under vacuum. Sodium carbonate (2 mol/L) was added to adjust the pH of the mixture to pH 7. Then, solids were collected by filtration. This provided 1 g (36%) of N-[5-(pyrazin-2-yl)-1,3,4-thiadiazol-2-yl]-1H-indazol-5-amine as a yellow solid. This crude product was further purified by preparative HPLC. (ES-ESI, m/z): 269 $[M+H]^+$. $^1H$ NMR (400 MHz, DMSO-$d_6$) δ 13.05 (s, 1H); 10.75 (s, 1H); 9.37 (s, 1H); 8.73 (s, 1H); 8.27 (s, 1H); 8.08 (s, 1H); 7.58-7.56 (m, 1H); 7.46-7.46 (m, 1H).

Example 20—Synthesis of 1-(2-Hydroxyethyl)-N-(3-[5-[(1H-indazol-5-yl)amino]-1,3,4-thiadiazol-2-yl]phenyl)-1H-pyrazole-4-carboxamide 2,2,2-trifluoroacetic Acid Solvate

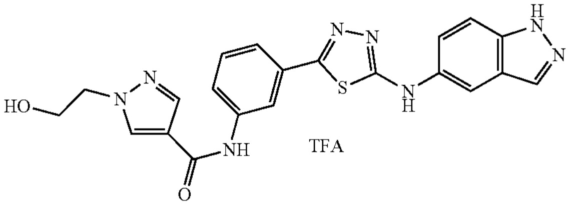 [SMILES: O=C(Nc1cccc(-c2nnc(Nc3ccc4[nH]ncc4c3)s2)c1)c1cnn(CCO)c1]

Part 1—Synthesis of Tert-Butyl 5-[[(tert-butoxy)carbonyl](5-[3-[1-(2-hydroxyethyl)-1H-pyrazole-4-amido]phenyl]-1,3,4-thiadiazol-2-yl)amino]-1H-indazole-1-carboxylate

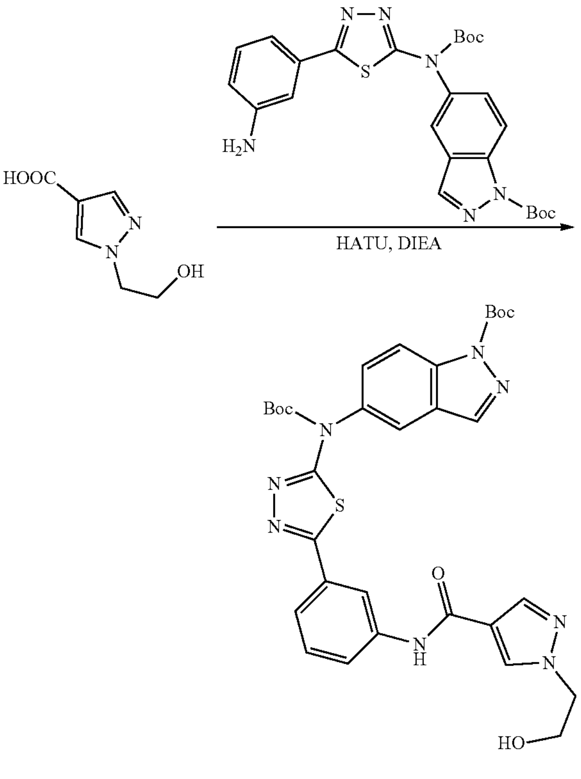

Into a 100-mL round-bottom flask was placed a solution of tert-butyl 5-[[5-(3-aminophenyl)-1,3,4-thiadiazol-2-yl][(tert-butoxy)carbonyl]amino]-1H-indazole-1-carboxylate (300 mg, 0.59 mmol, 1.00 equiv) in N,N-dimethylformamide (12 mL). HATU (336 mg, 0.88 mmol, 1.50 equiv), DIPEA (228 mg, 1.76 mmol, 3.00 equiv), and 1-(2-hydroxyethyl)-1H-pyrazole-4-carboxylic acid (276 mg, 1.77 mmol, 3.00 equiv) were added to the reaction mixture. The resulting solution was stirred 3 days at room temperature. The reaction was then quenched by the addition of 50 mL of water. The resulting solution was extracted with 3×30 mL of dichloromethane, the organic extracts were combined, and the combined extracts were washed with 2×100 mL of water, dried over anhydrous sodium sulfate and concentrated under vacuum to provide a residue, which was applied onto a silica gel column using dichloromethane/methanol (9:1) as eluent to furnish 100 mg (26%) of tert-butyl 5-[[(tert-butoxy) carbonyl](5-[3-[1-(2-hydroxyethyl)-1H-pyrazole-4-amido] phenyl]-1,3,4-thiadiazol-2-yl)amino]-1H-indazole-1-carboxylate as a yellow solid.

Part 2—Synthesis of 1-(2-Hydroxyethyl)-N-(3-[5-[(1H-indazol-5-yl)amino]-1,3,4-thiadiazol-2-yl]phenyl)-1H-pyrazole-4-carboxamide 2,2,2-trifluoroacetic Acid Solvate

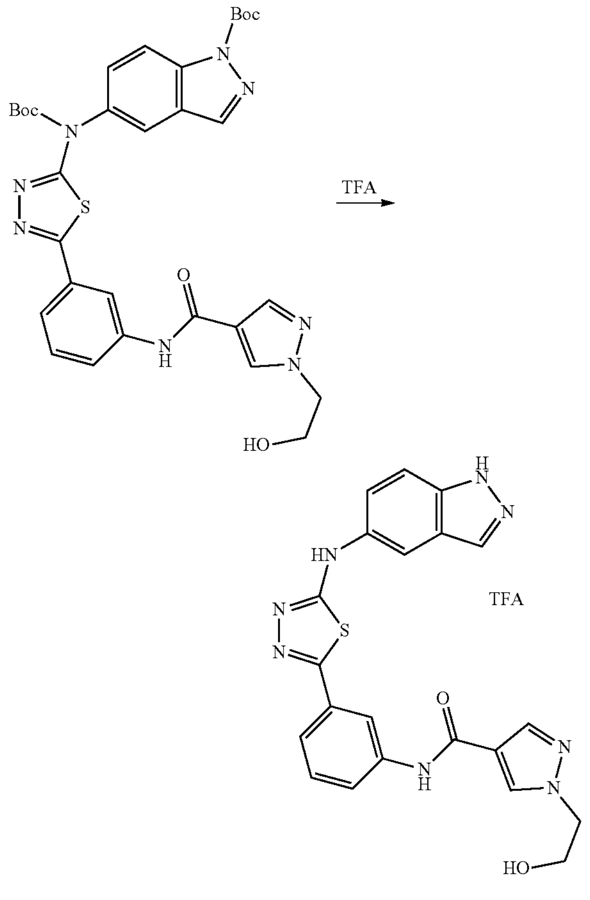

Into a 25-mL round-bottom flask was placed a solution of tert-butyl 5-[[(tert-butoxy)carbonyl](5-[3-[1-(2-hydroxyethyl)-1H-pyrazole-4-amido]phenyl]-1,3,4-thiadiazol-2-yl)amino]-1H-indazole-1-carboxylate (100 mg, 0.15 mmol, 1.00 equiv) in dichloromethane (9 mL). This was followed by the addition of trifluoroacetic acid (2 mL) dropwise with stirring at 0° C. The resulting solution was stirred overnight at room temperature then concentrated under vacuum. The crude product was purified by preparative HPLC using the following conditions: Column, Gemini-NX 5μ, C18 110A, AXIA Packed, 150×21.2 mm; mobile phase, water with 0.05% TFA and ACN (15.0% ACN up to 40.0% in 10 min); Detector, 254 nm. This provided 18.9 mg (22%) of 1-(2-hydroxyethyl)-N-(3-[5-[(1H-indazol-5-yl)amino]-1,3,4-thiadiazol-2-yl]phenyl)-1H-pyrazole-4-carboxamide as the 2,2,2-trifluoroacetic acid solvate as a yellow solid. (ES-ESI, m/z): 447 $[M+H]^+$. $^1H$ NMR (400 MHz, DMSO-$d_6$) δ 13.03 (s, 1H), 10.50 (s, 1H), 10.02 (s, 1H), 8.38 (s, 1H), 8.24 (s, 1H), 8.06 (d, 2H, J=2.4), 7.90-7.88 (m, 1H), 7.56-7.53 (m, 2H), 7.48-7.40 (m, 2H), 4.26-4.19 (m, 2H), 3.77-3.71 (m, 2H).

Example 21—Synthesis of N-(3-[5-[(1H-Indazol-5-yl)amino]-1,3,4-thiadiazol-2-yl]phenyl)methanesulfonamide 2,2,2-trifluoroacetic acid solvate

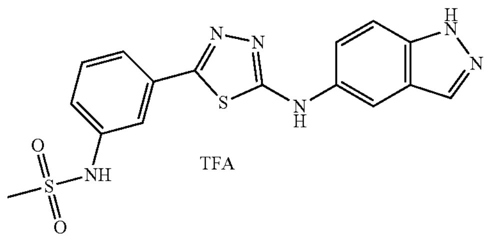 [SMILES: CS(=O)(=O)Nc1cccc(-c2nnc(Nc3ccc4[nH]ncc4c3)s2)c1]

Part 1—Synthesis of Tert-Butyl 5-[[(tert-butoxy) carbonyl][5-(3-methanesulfonamidophenyl)-1,3,4-thiadiazol-2-yl]amino]-1H-indazole-1-carboxylate

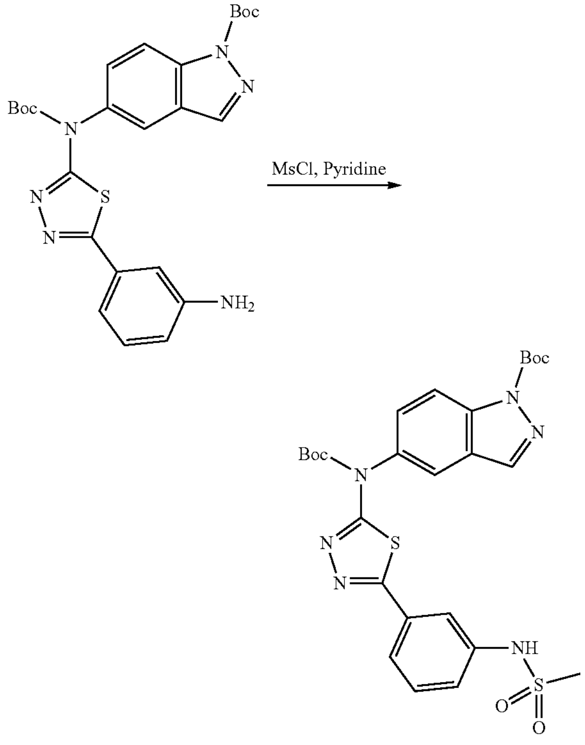

Into a 50-mL round-bottom flask was placed a solution of tert-butyl 5-[[5-(3-aminophenyl)-1,3,4-thiadiazol-2-yl] [(tert-butoxy)carbonyl]amino]-1H-indazole-1-carboxylate (100 mg, 0.20 mmol, 1.00 equiv) in pyridine (6 mL). This was followed by the addition of methanesulfonyl chloride (50 mg, 0.44 mmol, 2.00 equiv) dropwise with stirring at 0° C. The resulting solution was stirred overnight at room temperature. The reaction was then quenched by the addition of 30 mL of water. The resulting solution was extracted with 3×30 mL of dichloromethane. The combined organic layers were dried over anhydrous sodium sulfate and concentrated under vacuum to provide a residue, which was applied onto a silica gel column using ethyl acetate/petroleum ether (9:1) as eluent to furnish 80 mg (69%) of tert-butyl 5-[[(tert-butoxy)carbonyl][5-(3-methanesulfonamidophenyl)-1,3,4-thiadiazol-2-yl]amino]-1H-indazole-1-carboxylate as a yellow solid.

Part 2—Synthesis of N-(3-[5-[(1H-Indazol-5-yl)amino]-1,3,4-thiadiazol-2-yl]phenyl)methanesulfonamide 2,2,2-trifluoroacetic Acid Solvate

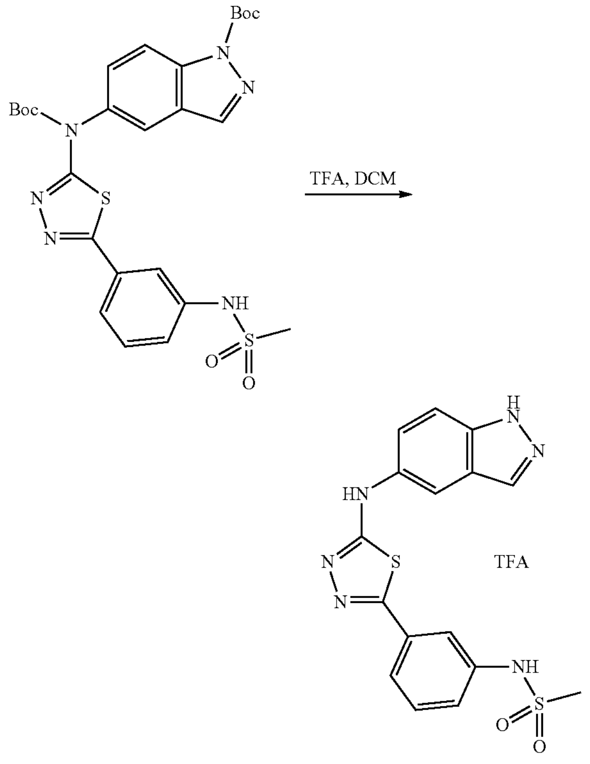

Into a 25-mL round-bottom flask was placed a solution of tert-butyl 5-[[(tert-butoxy)carbonyl][5-(3-methanesulfonamidophenyl)-1,3,4-thiadiazol-2-yl]amino]-1H-indazole-1-carboxylate (80 mg, 0.14 mmol, 1.00 equiv) in dichloromethane (9 mL). This was followed by the addition of trifluoroacetic acid (2 mL) dropwise with stirring at 0° C. The resulting solution was stirred overnight at room temperature. The resulting mixture was concentrated under vacuum. The crude product was purified by preparative HPLC using the following conditions: Column, Gemini-NX 5μ C18 110A, AXIA Packed, 150×21.2 mm; mobile phase, water with 10 mmol TFA and ACN (20.0% ACN up to 46.0% in 8 min); Detector, 254 nm. This provided 25.7 mg (38%) of N-(3-[5-[(1H-indazol-5-yl)amino]-1,3,4-thiadiazol-2-yl]phenyl)methanesulfonamide 2,2,2-trifluoroacetic acid solvate as a yellow solid. (ES-ESI, m/z): 387 $[M+H]^+$. $^1$H NMR (400 MHz, DMSO-$d_6$) δ 13.02 (s, 1H), 10.51 (s, 1H), 9.92 (s, 1H), 8.24 (d, 1H, J=1.2), 8.05 (s, 1H), 7.73-7.72 (m, 1H), 7.56-7.52 (m, 2H), 7.48-7.39 (m, 2H), 7.33-7.31 (m, 1H), 3.05 (s, 3H).

Example 22—Synthesis of N-(5-[5-[(1H-Indazol-5-yl)amino]-1,3,4-thiadiazol-2-yl]pyridin-3-yl)methanesulfonamide 2,2,2-trifluoroacetic Acid Solvate

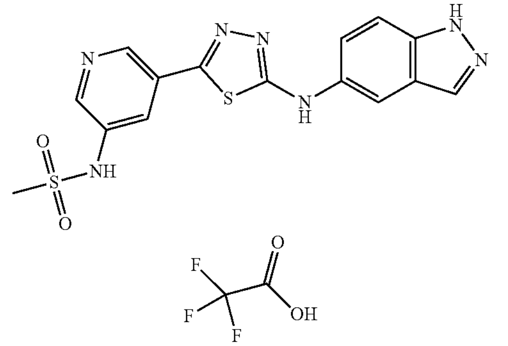

Part 1—Synthesis of N-(6-[5-[(1H-Indazol-5-yl)amino]-1,3,4-thiadiazol-2-yl]pyridin-2-yl)methanesulfonamide

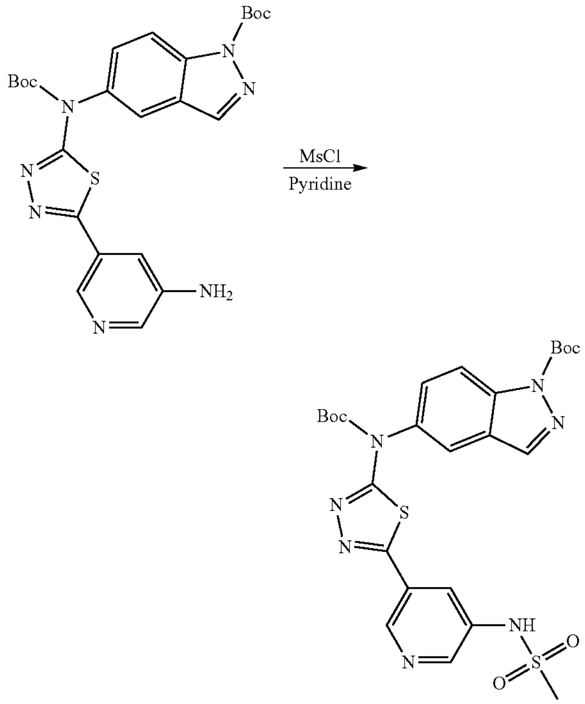

Into a 10-mL round-bottom flask was placed tert-butyl 5-[[5-(5-aminopyridin-3-yl)-1,3,4-thiadiazol-2-yl][(tert-butoxy)carbonyl]amino]-1H-indazole-1-carboxylate (160 mg, 0.32 mmol, 1.00 equiv), pyridine (4 mL) and MsCl (72 mg, 0.64 mmol, 2.00 equiv). The resulting solution was stirred for 2 h at room temperature. The reaction was then quenched by the addition of 1 mL of water. The resulting mixture was concentrated under vacuum and the resulting residue was purified by column chromatography eluting with ethyl acetate:petroleum ether (1:1) to furnish 125 mg (67%) of N-(6-[5-[(1H-indazol-5-yl)amino]-1,3,4-thiadiazol-2-yl]pyridin-2-yl)methanesulfonamide as a brown oil.

Part 2—Synthesis of N-(5-[5-[(1H-Indazol-5-yl)amino]-1,3,4-thiadiazol-2-yl]pyridin-3-yl)methanesulfonamide 2,2,2-trifluoroacetic Acid Solvate

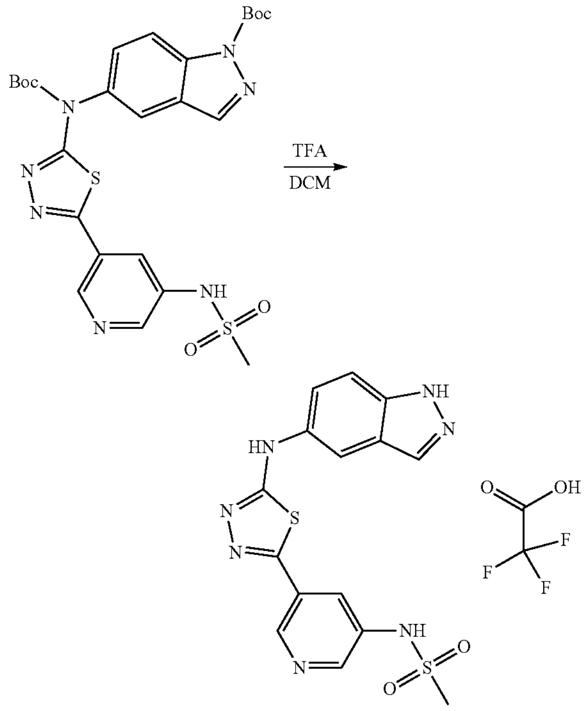

Into a 25-mL round-bottom flask was placed a solution of tert-butyl 5-[[(tert-butoxy)carbonyl][5-(5-methanesulfonamidopyridin-3-yl)-1,3,4-thiadiazol-2-yl]amino]-1H-indazole-1-carboxylate (100 mg, 0.17 mmol, 1.00 equiv) in dichloromethane (6 mL) and trifluoroacetic acid (3 mL). The resulting solution was stirred for 2 h at room temperature. The resulting mixture was concentrated under vacuum. The crude product was purified by preparative HPLC using the following conditions: Column: Gemini-NX 5μ C18 110A, AXIA Packed, 150×21.2 mm; mobile phase: water with 0.05% TFA and ACN (20.0% ACN up to 35.0% in 8 min); Detector: 254 nm. This provided 27.1 mg (32%) of N-(5-[5-[(1H-indazol-5-yl)amino]-1,3,4-thiadiazol-2-yl]pyridin-3-yl)methanesulfonamide trifluoroacetic acid solvate as a light yellow solid. (ES-ESI, m/z): 387.9 $[M+H]^+$. $^1H$ NMR (400 MHz, DMSO-$d_6$) δ 13.0 (br, s, 1H), 10.6 (s, 1H), 10.3 (s, 1H), 8.7 (s, 1H), 8.5 (d, 1H), 8.2 (s, 1H), 8.0 (d, 2H), 7.6 (d, 1H), 7.4 (d, 1H), 3.1 (s, 3H).

The following compound was prepared using similar procedures.

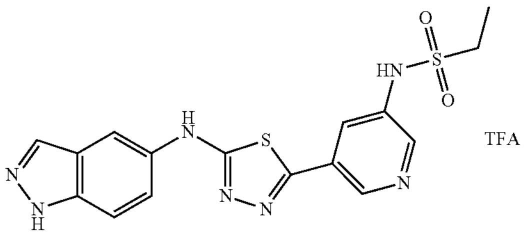 [SMILES: CCS(=O)(=O)Nc1cncc(-c2nnc(Nc3ccc4[nH]ncc4c3)s2)c1]

N-(5-[5-[(1H-Indazol-5-yl)amino]-1,3,4-thiadiazol-2-yl]pyridin-3-yl)ethane-1-sulfonamide 2,2,2-trifluoroacetic Acid Solvate (ES-ESI, m/z): 401.85 $[M+H]^+$. $^1H$ NMR (400 MHz, DMSO-$d_6$) δ 13.0 (br, s, 1H), 10.6 (s, 1H), 10.3 (s, 1H), 8.7 (d, 1H), 8.5 (s, 1H), 8.2 (d, 1H), 8.0 (d, 2H), 7.6 (d, 1H), 7.4 (d, 1H), 3.2 (q, 2H), 1.3 (t, 3H).

Example 23—Synthesis of N-[5-[3-(1H-Pyrazol-4-yl)phenyl]-1,3,4-thiadiazol-2-yl]-1H-indazol-5-amine 2,2,2-trifluoroacetic Acid Solvate

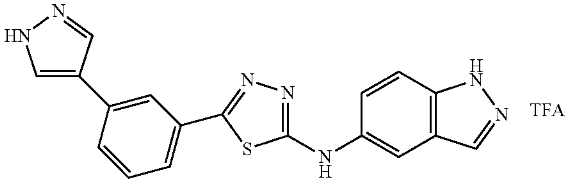 [SMILES: c1cc(-c2cn[nH]c2)cc(-c2nnc(Nc3ccc4[nH]ncc4c3)s2)c1]

Part 1—Synthesis of Tert-Butyl 5-((5-(3-(1H-Pyrazol-4-yl)phenyl)-1,3,4-thiadiazol-2-yl)(tert-butoxycarbonyl)amino)-1H-indazole-1-carboxylate

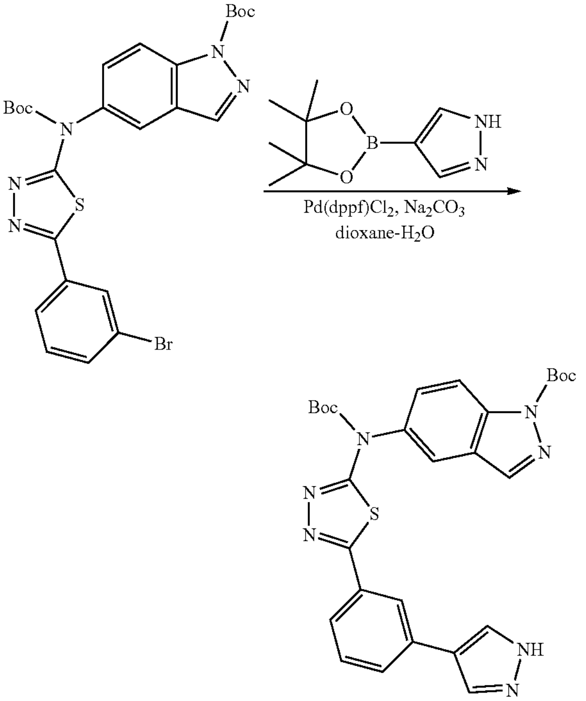

Into a 20-mL round-bottom flask was placed a solution of tert-butyl 5-((5-(3-bromophenyl)-1,3,4-thiadiazol-2-yl)(tert-butoxycarbonyl)amino)-1H-indazole-1-carboxylate (300 mg, 0.52 mmol, 1.00 equiv) and 4-(tetramethyl-1,3,2-dioxaborolan-2-yl)-4H-pyrazole (150 mg, 0.77 mmol, 1.50 equiv) in dioxane (6 mL). Then, Pd(dppf)$Cl_2$ (36 mg, 0.05 mmol, 0.10 equiv), sodium carbonate (114 mg, 1.08 mmol, 2.00 equiv), and water (1.2 mL) were added. The reaction mixture was hated under microwave radiation for 4 h at 120° C. under $N_2$. The resulting solution was diluted with 50 mL of water. The resulting solution was extracted with 3×50 mL of ethyl acetate and the organic layers combined and dried over anhydrous sodium sulfate and concentrated under vacuum to provide a residue, which was then applied onto a silica gel column and the column eluted with ethyl acetate/petroleum ether (1:1) to furnish 200 mg (68%) of tert-butyl 5-((5-(3-(1H-pyrazol-4-yl)phenyl)-1,3,4-thiadiazol-2-yl)(tert-butoxycarbonyl)amino)-1H-indazole-1-carboxylate as a yellow solid.

Part 2—Synthesis of N-[5-[3-(1H-Pyrazol-4-yl)phenyl]-1,3,4-thiadiazol-2-yl]-1H-indazol-5-amine 2,2,2-trifluoroacetic Acid Solvate

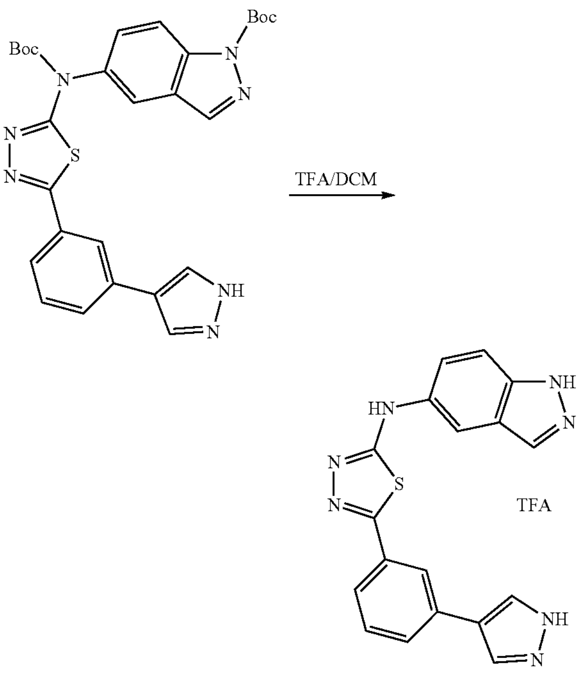

Into a 10-mL round-bottom flask was placed a solution of tert-butyl 5-[[(tert-butoxy)carbonyl]([5-[3-(1H-pyrazol-4-yl)phenyl]-1,3,4-thiadiazol-2-yl])amino]-1H-indazole-1-carboxylate (200 mg, 0.36 mmol, 1.00 equiv) in dichloromethane (2 mL) and trifluoroacetic acid (1 mL). The resulting solution was stirred for 1 h at room temperature. The resulting mixture was concentrated under vacuum. The crude product was purified by preparative HPLC with the following conditions: Column, Gemini-NX C18, 21.2×150 mm, 5 μm; mobile phase, water with 0.05% TFA and ACN (40.0% ACN up to 80.0% in 8 min); Detector, 254 nm. This provided 2.5 mg (2%) of N-[5-[3-(1H-pyrazol-4-yl)phenyl]-1,3,4-thiadiazol-2-yl]-1H-indazol-5-amine 2,2,2-trifluoroacetic acid solvate as an off-white solid. (ES-ESI, m/z): 360.0 $[M+H]^+$. $^1H$ NMR (400 MHz, DMSO-$d_6$) δ 8.17 (s, 1H); 7.99-9.04 (m, 4H); 7.61-7.66 (m, 2H); 7.50 (d, J=9.2 Hz, 1H); 7.42 (d, J=6 Hz, 2H).

Example 24—Synthesis of N-[5-(1-Methyl-1H-1,3-benzodiazol-4-yl)-1,3,4-thiadiazol-2-yl]-1H-indazol-5-amine 2,2,2-trifluoroacetic Acid Solvate

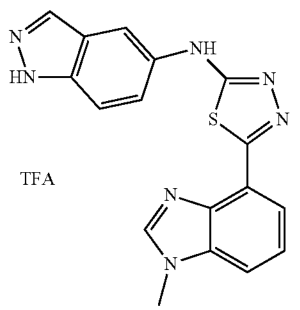 [SMILES: Cn1cnc2c(-c3nnc(Nc4ccc5[nH]ncc5c4)s3)cccc21]

Part 1—Synthesis of Ethyl 1-methyl-1H-1,3-benzodiazole-4-carboxylate

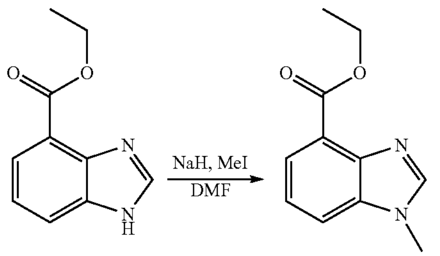

Into a 100-mL round-bottom flask was placed a suspension of sodium hydride (1.24 g, 31.00 mmol, 1.20 equiv) in DMF (10 mL). Ethyl 1H-1,3-benzodiazole-4-carboxylate (4.9 g, 25.76 mmol, 1.00 equiv) was added to the reaction solution at 0° C. The resulting solution was stirred for 1 h at 0° C. Next, iodomethane (3.66 g, 25.79 mmol, 1.00 equiv) was added to the reaction mixture at 0° C. The resulting solution was allowed to react, with stirring, for an additional 2 h while the reaction mixture temperature was maintained 0° C. in an ice bath. Then, the reaction was quenched by the addition of 100 mL of water. The resulting solution was extracted with 3×200 mL of dichloromethane. The combined organic layers were washed with 3×200 mL of $H_2O$. The resulting mixture was concentrated under vacuum and the resulting residue was purified by silica gel column with dichloromethane/methanol (97:3) as eluent to furnish 2.4 g (46%) of ethyl 1-methyl-1H-1,3-benzodiazole-4-carboxylate as a red solid.

Part 2—Synthesis of 1-Methyl-1H-1,3-benzodiazole-4-carbohydrazide

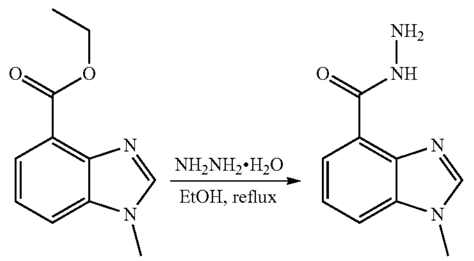

Into a 250-mL round-bottom flask was placed a solution of ethyl 1-methyl-1H-1,3-benzodiazole-4-carboxylate (2.4 g, 11.75 mmol, 1.00 equiv) in ethanol (100 mL). Hydrazine hydrate (8.8 g, 175.79 mmol, 15.00 equiv) was added to the reaction mixture. The resulting solution was hated to reflux overnight. The resulting mixture was concentrated under vacuum to provide 1.7 g (76%) of 1-methyl-1H-1,3-benzodiazole-4-carbohydrazide as a reddish solid.

Part 3—Synthesis of Tert-Butyl 5-([[(1-methyl-1H-1,3-benzodiazol-4-yl)formohydrazido]methanethioyl]amino)-2,3-dihydro-1H-indazole-1-carboxylate

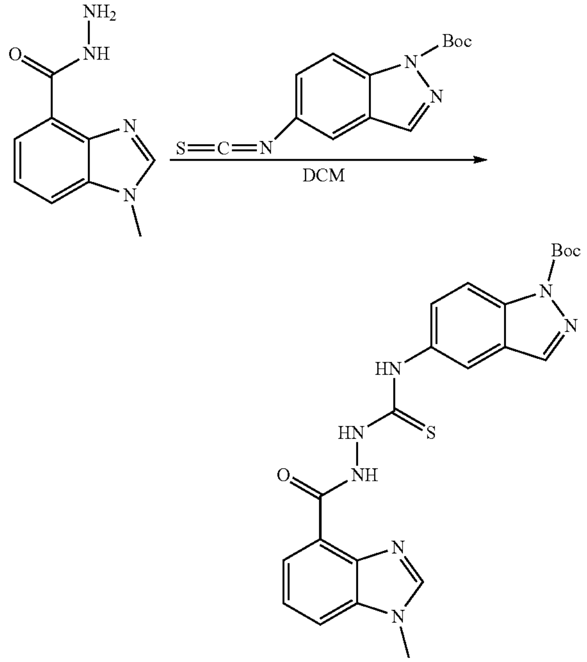

Into a 100-mL round-bottom flask was placed a solution of 1-methyl-1H-1,3-benzodiazole-4-carbohydrazide (500 mg, 2.63 mmol, 1.00 equiv) in dichloromethane (40 mL). tert-Butyl 5-isothiocyanato-1H-indazole-1-carboxylate (720 mg, 2.62 mmol, 1.00 equiv) was added to the reaction. The resulting solution was stirred overnight at room temperature, and then it was concentrated under vacuum. This provided 500 mg (41%) of tert-butyl 5-([[(1-methyl-1H-1,3-benzodiazol-4-yl)formohydrazido]methanethioyl]amino)-2,3-dihydro-1H-indazole-1-carboxylate as a greenish solid solid that was used into the next step without further purification.

Part 4—Synthesis of N-[5-(1-Methyl-1H-1,3-benzodiazol-4-yl)-1,3,4-thiadiazol-2-yl]-1H-indazol-5-amine 2,2,2-trifluoroacetic Acid Solvate

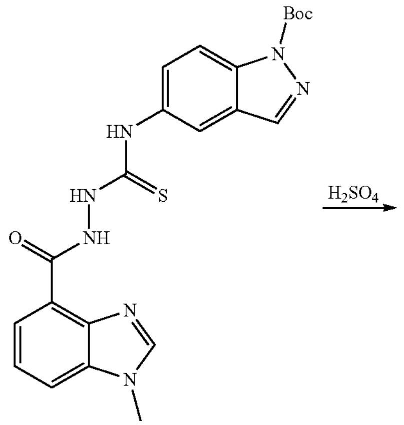

-continued

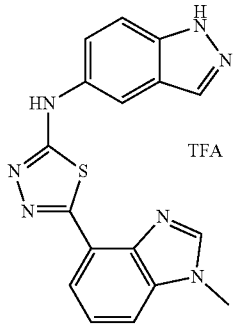

Into a 250-mL round-bottom flask was placed a solution of tert-butyl 5-([[(1-methyl-1H-1,3-benzodiazol-4-yl)formohydrazido]methanethioyl]amino)-1H-indazole-1-carboxylate (500 mg, 1.07 mmol, 1.00 equiv) in dichloromethane (30 mL). Sulfuric acid (5 g, 50.98 mmol, 20.00 equiv) was added dropwise. The resulting solution was stirred for 2 h at room temperature. The resulting mixture was concentrated under vacuum. The pH value of the solution was adjusted to pH 8 with sodium carbonate (2M), and the solids were collected by filtration. The compound was further purified by preparative HPLC (Column: Gemini-NX 5u C18 110A, AXIA Packed 150×21.2 mm; Mobile Phase A: water with 0.05% TFA, Mobile Phase B: ACN; Flow rate: mL/min; Gradient: 10% B to 35% B in 8 min; 254 nm) to yield 40 mg of N-[5-(1-methyl-1H-1,3-benzodiazol-4-yl)-1,3,4-thiadiazol-2-yl]-1H-indazol-5-amine 2,2,2-trifluoroacetic acid solvate. (ES-ESI, m/z): 347.4 $[M+H]^+$. $^1H$ NMR (300 MHz, DMSO-$d_6$) δ 12.87-13.00 (m, 1H); 10.41 (s, 1H); 8.51 (s, 1H); 8.26 (s, 1H); 8.08 (d, J=8.1, 2H); 7.75 (d, J=7.8, 1H); 7.56 (d, J=8.7, 1H); 7.43-7.49 (m, 2H); 3.93 (s, 3H).

Example 25—Synthesis of N-(3-[5-[(4-Chloro-1H-indazol-5-yl)amino]-1,3,4-thiadiazol-2-yl]phenyl)-1-methyl-1H-pyrazole-4-carboxamide 2,2,2-trifluoroacetic Acid Solvate

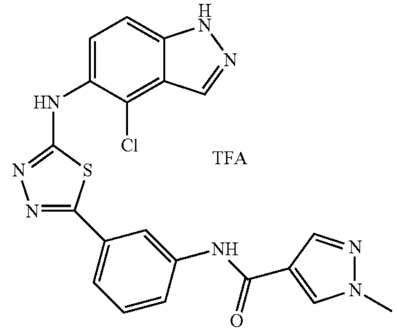 [SMILES: Cn1cc(C(=O)Nc2cccc(-c3nnc(Nc4ccc5[nH]ncc5c4Cl)s3)c2)cn1]

Part 1—Synthesis of 4-Chloro-5-isothiocyanato-1H-indazole

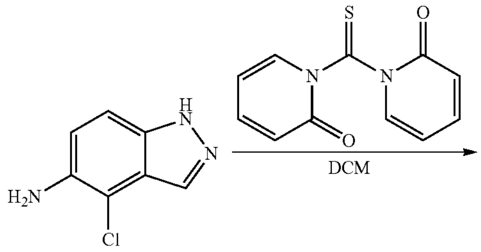

-continued

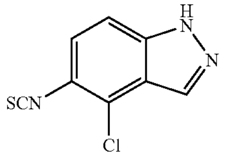

Into a 100-mL round-bottom flask was placed a solution of 4-chloro-1H-indazol-5-amine (580 mg, 3.46 mmol, 1.00 equiv) in dichloromethane (12 mL). 1-[(2-Oxo-1,2-dihydropyridin-1-yl)carbothioyl]-1,2-dihydropyridin-2-one (750 mg, 3.23 mmol, 1.00 equiv) was added to the reaction mixture. The resulting solution was stirred for 4 h at room temperature, and then it was quenched by the addition of 50 mL of saturated sodium bicarbonate (aqueous). The resulting solution was extracted with 2×50 mL of ethyl acetate and the organic layers combined and dried over anhydrous sodium sulfate and concentrated under vacuum. This provided 600 mg (83%) of 4-chloro-5-isothiocyanato-1H-indazole as a yellow solid that was used into the next step without further purification.

Part 2—Synthesis of 4-Chloro-N-[5-(3-nitrophenyl)-1,3,4-thiadiazol-2-yl]-1H-indazol-5-amine

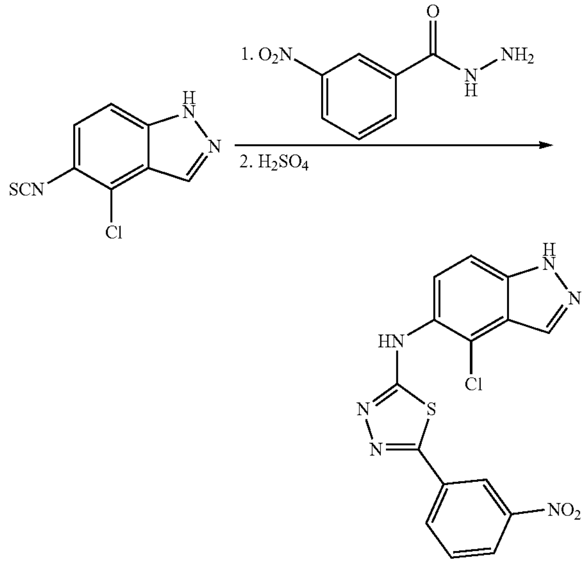

Into a 250-mL round-bottom flask was placed a solution of 4-chloro-5-isothiocyanato-1H-indazole (580 mg, 2.77 mmol, 1.00 equiv) in dichloromethane (20 mL). 3-Nitrobenzohydrazide (510 mg, 2.82 mmol, 1.00 equiv) was added to the reaction mixture. The resulting solution was stirred overnight at room temperature. This was followed by the addition of sulfuric acid (5.5 g, 56.08 mmol, 20.00 equiv) dropwise with stirring at 0° C. The resulting solution was allowed to react, with stirring, for an additional 3 h at room temperature. The resulting mixture was concentrated under vacuum and the reaction was then quenched by the addition of 50 mL of water. The pH value of the solution was adjusted to pH 7 with 10% sodium bicarbonate (aqueous). The solids were collected by filtration. This resulted in 1 g (97%) of 4-chloro-N-[5-(3-nitrophenyl)-1,3,4-thiadiazol-2-yl]-1H-indazol-5-amine as a brown solid.

Part 3—Synthesis of Tert-Butyl 5-[[(tert-butoxy)carbonyl][5-(3-nitrophenyl)-1,3,4-thiadiazol-2-yl]amino]-4-chloro-1H-indazole-1-carboxylate

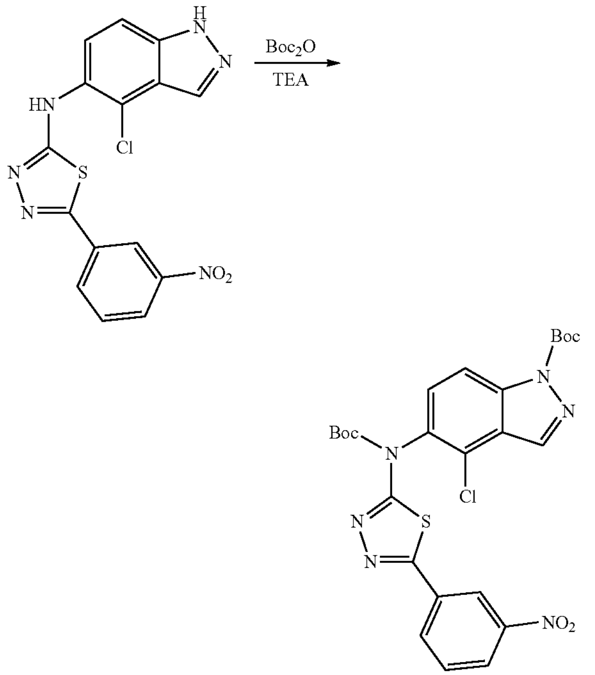

Into a 100-mL round-bottom flask was placed a solution of 4-chloro-N-[5-(3-nitrophenyl)-1,3,4-thiadiazol-2-yl]-1H-indazol-5-amine (1 g, 2.68 mmol, 1.00 equiv) in dichloromethane (20 mL). TEA (1.5 mL, 3.00 equiv), 4-dimethylaminopyridine (150 mg, 1.23 mmol, 0.20 equiv), and di-tert-butyl dicarbonate (3.5 g, 16.04 mmol, 5.00 equiv) were added to the reaction mixture. The resulting solution was stirred overnight at room temperature. The resulting mixture was concentrated under vacuum and the resulting residue was applied onto a silica gel column with ethyl acetate/petroleum ether (3:1) as eluent to furnish 800 mg (52%) of tert-butyl 5-[[(tert-butoxy)carbonyl][5-(3-nitrophenyl)-1,3,4-thiadiazol-2-yl]amino]-4-chloro-1H-indazole-1-carboxylate as a yellow solid.

Part 4—Synthesis of Tert-Butyl 5-[[5-(3-aminophenyl)-1,3,4-thiadiazol-2-yl][(tert-butoxy)carbonyl]amino]-4-chloro-1H-indazole-1-carboxylate

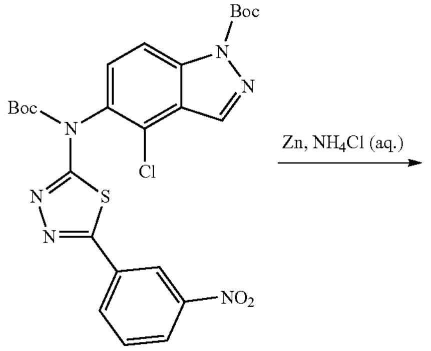

-continued

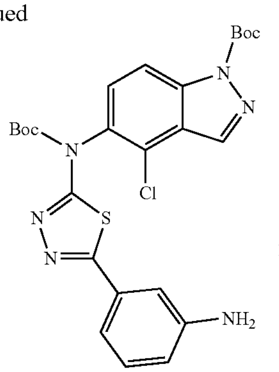

Into a 100-mL round-bottom flask, was placed a solution of tert-butyl 5-[[(tert-butoxy)carbonyl][5-(3-nitrophenyl)-1,3,4-thiadiazol-2-yl]amino]-4-chloro-1H-indazole-1-carboxylate (800 mg, 1.40 mmol, 1.00 equiv) in methanol (15 mL). Zn (0.91 g, 14 mmol, 10.00 equiv) and $NH_4Cl$ (saturated aqueous, 15 mL) were added to the reaction. The resulting solution was stirred overnight at room temperature. The reaction was then quenched by the addition of 80 mL of water. The resulting solution was extracted with 3×50 mL of ethyl acetate and the organic layers combined and dried over anhydrous sodium sulfate and concentrated under vacuum to provide a residue, which was then purified using silica gel column chromatograph with ethyl acetate/petroleum ether (3:1) as eluent to furnish 500 mg (66%) of tert-butyl 5-[[5-(3-aminophenyl)-1,3,4-thiadiazol-2-yl][(tert-butoxy)carbonyl]amino]-4-chloro-1H-indazole-1-carboxylate as a yellow solid.

Part 5—Synthesis of Tert-Butyl 5-[[(tert-butoxy)carbonyl]([5-[3-(1-methyl-1H-pyrazole-4-amido)phenyl]-1,3,4-thiadiazol-2-yl])amino]-4-chloro-1H-indazole-1-carboxylate

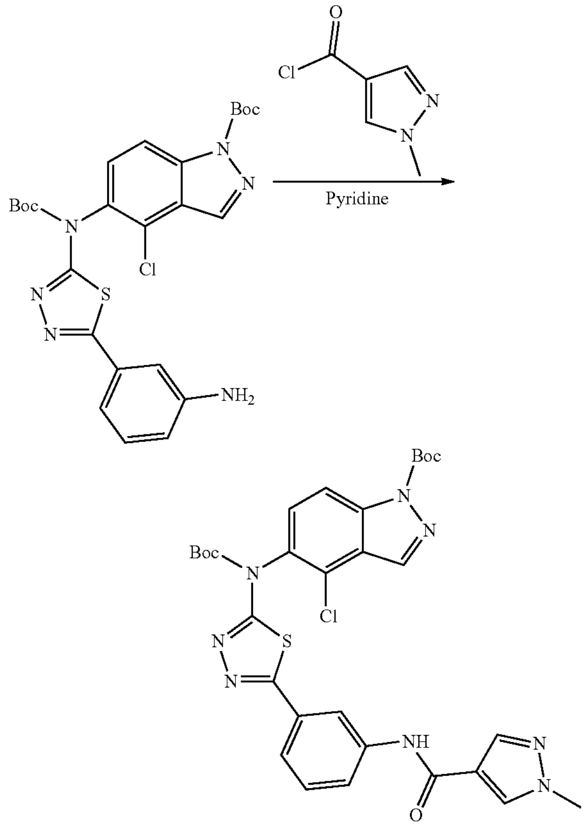

Into a 100-mL round-bottom flask was placed a solution of tert-butyl 5-[[5-(3-aminophenyl)-1,3,4-thiadiazol-2-yl][(tert-butoxy)carbonyl]amino]-4-chloro-1H-indazole-1-carboxylate (180 mg, 0.33 mmol, 1.00 equiv) in pyridine (30 mL). This was followed by the addition of 1-methyl-1H-pyrazole-4-carbonyl chloride (145 mg, 1.00 mmol, 3.00 equiv), in portions at 0° C. The resulting solution was stirred overnight at room temperature. The reaction was then quenched by the addition of 100 mL of water. The resulting solution was extracted with 3×50 mL of ethyl acetate, and the organic layers combined and dried over anhydrous sodium sulfate and concentrated under vacuum to provide a residue, which was applied onto a silica gel column using dichloromethane/methanol (95:5) as eluent to furnish 150 mg (69%) of tert-butyl 5-[[(tert-butoxy)carbonyl]([5-[3-(1-methyl-1H-pyrazole-4-amido)phenyl]-1,3,4-thiadiazol-2-yl])amino]-4-chloro-1H-indazole-1-carboxylate as a solid.

Part 6—Synthesis of N-(3-[5-[(4-Chloro-1H-indazol-5-yl)amino]-1,3,4-thiadiazol-2-yl]phenyl)-1-methyl-1H-pyrazole-4-carboxamide 2,2,2-trifluoroacetic Acid Solvate

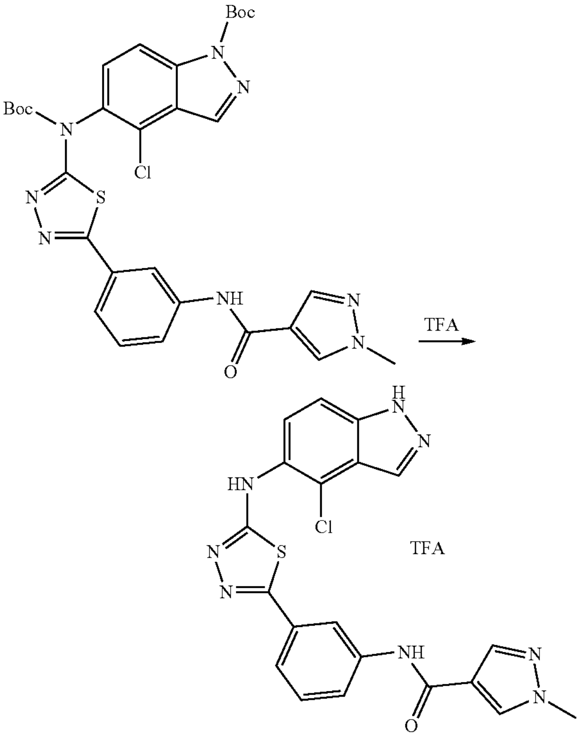

Into a 25-mL round-bottom flask was placed a solution of tert-butyl 5-[[(tert-butoxy)carbonyl]([5-[3-(1-methyl-1H-pyrazole-4-amido)phenyl]-1,3,4-thiadiazol-2-yl])amino]-4-chloro-1H-indazole-1-carboxylate (150 mg, 0.23 mmol, 1.00 equiv) in dichloromethane (9 mL). This was followed by the addition of trifluoroacetic acid (2 mL) dropwise with stirring at 0° C. The resulting solution was stirred overnight at room temperature. The resulting mixture was concentrated under vacuum. The crude product was purified by preparative HPLC with the following conditions: Column, Gemini-NX 5μ C18 110A, AXIA Packed, 150×21.2 mm; mobile phase, water with 0.05% TFA and ACN (22.0% ACN up to 50.0% in 8 min); Detector, 254 nm. This provided 36.4 mg (28%) of N-(3-[5-[(4-chloro-1H-indazol-5-yl)amino]-1, 3,4-thiadiazol-2-yl]phenyl)-1-methyl-1H-pyrazole-4-carboxamide 2,2,2-trifluoroacetic acid solvate as a yellow solid. (ES-ESI, m/z): 451 $[M+H]^+$. $^1H$ NMR (400 MHz, DMSO-$d_6$) δ 13.49 (s, 1H), 10.50-9.97 (m, 2H), 8.33 (s, 1H), 8.20 (s, 1H), 8.15 (s, 1H), 8.03 (s, 1H), 7.88-7.85 (m, 2H), 7.60 (d, 1H, J=9.2), 7.50-7.41 (m, 2H), 3.90 (s, 3H).

Example 26—Synthesis of N-(2,3-Dihydroxypropyl)-3-[5-[(1H-indazol-5-yl)amino]-1,3,4-thiadiazol-2-yl]-N-methylbenzamide

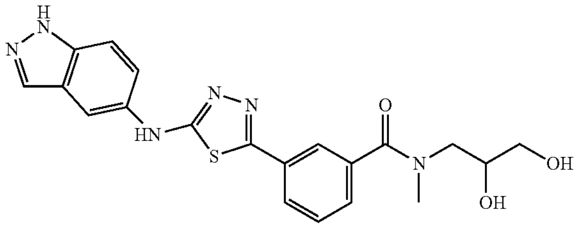 [SMILES: CN(CC(O)CO)C(=O)c1cccc(-c2nnc(Nc3ccc4[nH]ncc4c3)s2)c1]

Part 1—Synthesis of 3-[5-[(1H-Indazol-5-yl)amino]-1,3,4-thiadiazol-2-yl]benzoic Acid

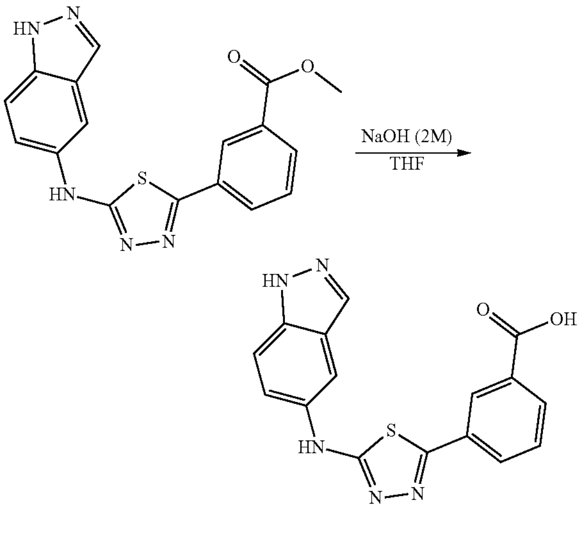

Into a 100-mL round-bottom flask was placed a solution of methyl 3-[5-[(1H-indazol-5-yl)amino]-1,3,4-thiadiazol-2-yl]benzoate (3.5 g, 9.96 mmol, 1.00 equiv) in tetrahydrofuran (20 mL) and sodium hydroxide (2 M, aqueous, 20 mL). The resulting solution was stirred overnight at 50° C. Then, the resulting mixture was concentrated under vacuum. The pH value of the solution was adjusted to pH 5 with aqueous HCl (1M). The solids were collected by filtration. This provided 2.5 g (74%) of 3-[5-[(1H-indazol-5-yl)amino]-1,3,4-thiadiazol-2-yl]benzoic acid as a brown solid. (ES-ESI, m/z): 335.9 $[M+H]^+$. $^1H$ NMR (400 MHz, DMSO-$d_6$) δ 13.03 (s, 1H); 8.32 (d, J=6 Hz, 2H); 8.10 (s, 1H); 7.99-8.01 (m, 2H); 7.49-7.57 (m, 3H).

Part 2—Synthesis of N-(2,3-Dihydroxypropyl)-3-[5-[(1H-indazol-5-yl)amino]-1,3,4-thiadiazol-2-yl]-N-methylbenzamide

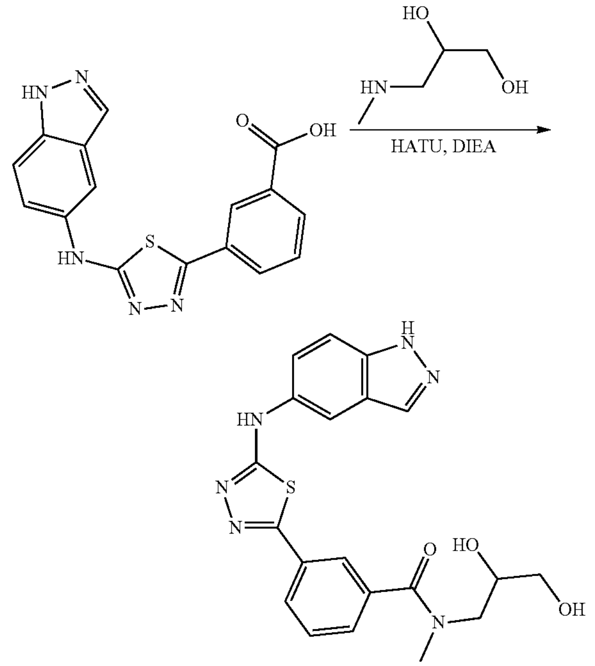

Into a 10-mL round-bottom flask was placed a solution of 3-[5-[(1H-indazol-5-yl)amino]-1,3,4-thiadiazol-2-yl]benzoic acid (100 mg, 0.30 mmol, 1.00 equiv) in N,N-dimethylformamide (5 mL). 3-(Methylamino)propane-1,2-diol (47 mg, 0.45 mmol, 1.50 equiv), HATU (169 mg, 0.44 mmol, 1.50 equiv), and DIPEA (115 mg, 0.89 mmol, 3.00 equiv) were added to the reaction mixture. The resulting solution was stirred overnight at room temperature. The crude product was purified by preparative HPLC with the following conditions: Column, Gemini-NX 5μ C18 110A, AXIA Packed, 150×21.2 mm; mobile phase, water with 10 mmol $NH_4HCO_3$ and ACN (10.0% ACN up to 32.0% in 10 min); Detector, 254 nm. This provided 32 mg (25%) of N-(2,3-dihydroxypropyl)-3-[5-[(1H-indazol-5-yl)amino]-1,3,4-thiadiazol-2-yl]-N-methylbenzamide as a white solid. (ES-ESI, m/z): 425.1 $[M+H]^+$. $^1H$ NMR (400 MHz, DMSO-$d_6$) δ 13.04 (s, 1H); 10.55 (s, 1H); 8.26 (s, 1H); 8.06 (s, 1H); 7.86-7.91 (m, 2H); 7.50-7.60 (m, 3H); 7.40-7.43 (m, 1H); 4.92-5.02 (m, 1H); 4.53-4.63 (m, 1H); 3.59-3.84 (m, 1.5H); 3.37-3.40 (m, 1.5H); 3.13-3.27 (m, 2H); 3.01 (d, J=14.4 Hz, 3H).

Example 27—Synthesis of N-(2,3-Dihydroxypropyl)-3-[5-[(1H-indazol-5-yl)amino]-1,3,4-thiadiazol-2-yl]benzamide

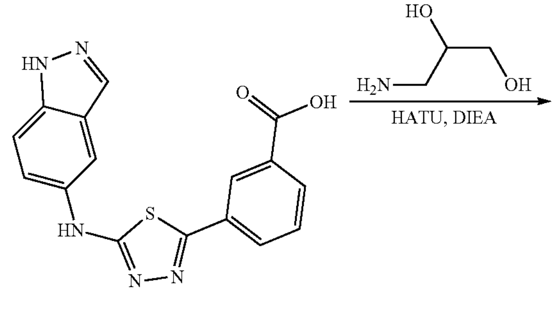

-continued

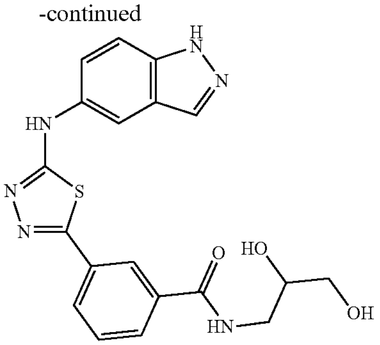

Into a 10-mL round-bottom flask was placed a solution of 3-[5-[(1H-indazol-5-yl)amino]-1,3,4-thiadiazol-2-yl]benzoic acid (200 mg, 0.59 mmol, 1.00 equiv) in N,N-dimethylformamide (5 mL). HATU (338 mg, 0.89 mmol, 1.50 equiv), DIPEA (230 mg, 1.78 mmol, 3.00 equiv) and 3-aminopropane-1,2-diol (81 mg, 0.89 mmol, 1.50 equiv) were added to the reaction mixture. The reaction mixture was heated under microwave radiation overnight at 140° C. The crude product was purified by preparative HPLC with the following conditions: Column, Gemini-NX 5μ C18 110A, AXIA Packed, 150×21.2 mm; mobile phase, water with 10 mmol $NH_4HCO_3$ and ACN (10.0% ACN up to 32.0% in 10 min); Detector, 254 nm. This provided 45 mg (18%) of N-(2,3-dihydroxypropyl)-3-[5-[(1H-indazol-5-yl)amino]-1,3,4-thiadiazol-2-yl]benzamide as a brown solid. (ES-ESI, m/z): 411.2 $[M+H]^+$. $^1H$ NMR (400 MHz, DMSO-$d_6$) δ 13.03 (s, 1H); 10.56 (s, 1H); 8.64-8.67 (m, 1H); 8.24-8.29 (m, 2H); 7.95-8.07 (m, 3H); 7.55-7.63 (m, 2H); 7.41-7.44 (m, 1H); 4.85 (d, J=4.8 Hz, 1H); 4.58-4.61 (m, 1H); 3.64-3.71 (m, 1H); 3.40-3.61 (m, 1H); 3.23-3.38 (m, 2H); 3.19-3.25 (m, 1H).

Example 28—Synthesis of N-(3-[5-[(1H-Indazol-5-yl)amino]-1,3,4-thiadiazol-2-yl]phenyl)ethane-1-sulfonamide 2,2,2-trifluoroacetic Acid Solvate

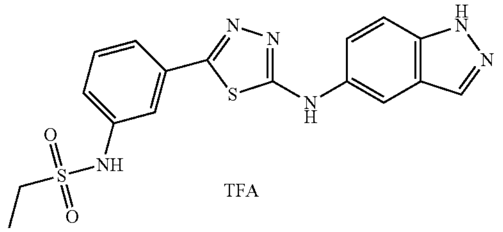 [SMILES: CCS(=O)(=O)Nc1cccc(-c2nnc(Nc3ccc4[nH]ncc4c3)s2)c1]

TFA

Part 1—Synthesis of Tert-Butyl 5-[[(tert-butoxy)carbonyl][5-(3-ethanesulfonamidophenyl)-1,3,4-thiadiazol-2-yl]amino]-1H-indazole-1-carboxylate

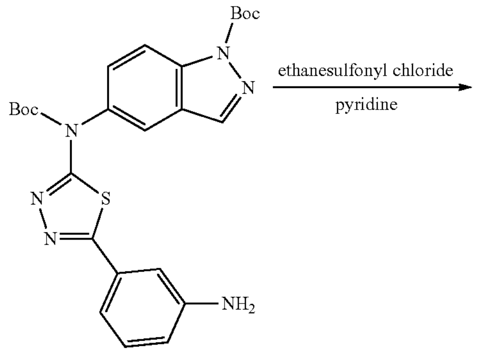

-continued

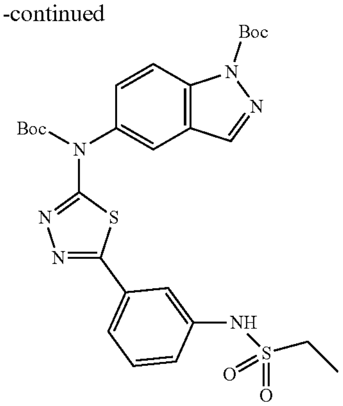

Into a 50-mL round-bottom flask was placed a solution of tert-butyl 5-[[5-(3-aminophenyl)-1,3,4-thiadiazol-2-yl][(tert-butoxy)carbonyl]amino]-1H-indazole-1-carboxylate (150 mg, 0.29 mmol, 1.00 equiv) in pyridine (6 mL). This was followed by the addition of ethanesulfonyl chloride (110 mg, 0.86 mmol, 3.00 equiv), in portions at 0° C. The resulting solution was stirred overnight at room temperature. The reaction was then quenched by the addition of 100 mL of water. The resulting solution was extracted with 3×50 mL of dichloromethane. The combined organic layers were dried over anhydrous sodium sulfate and concentrated under vacuum to provide a residue, which was then applied onto a silica gel column with ethyl acetate/petroleum ether (3:1) as eluent to furnish 130 mg (73%) of tert-butyl 5-[[(tert-butoxy)carbonyl][5-(3-ethanesulfonamidophenyl)-1,3,4-thiadiazol-2-yl]amino]-1H-indazole-1-carboxylate as a yellow solid.

Part 2—Synthesis of N-(3-[5-[(1H-Indazol-5-yl)amino]-1,3,4-thiadiazol-2-yl]phenyl)ethane-1-sulfonamide 2,2,2-trifluoroacetic Acid Solvate

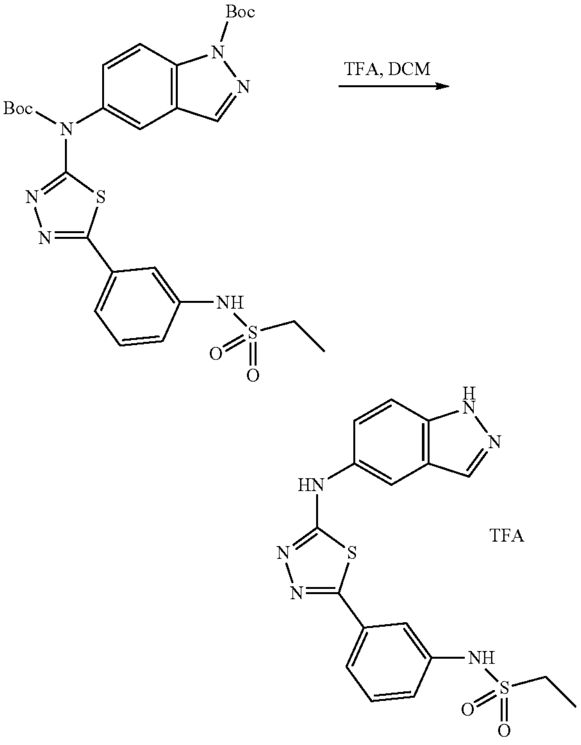

TFA

Into a 25-mL round-bottom flask was placed a solution of tert-butyl 5-[[(tert-butoxy)carbonyl][5-(3-ethanesulfonamidophenyl)-1,3,4-thiadiazol-2-yl]amino]-1H-indazole-1-carboxylate (130 mg, 0.22 mmol, 1.00 equiv) in dichloromethane (8 mL). This was followed by the addition of trifluoroacetic acid (2 mL) dropwise with stirring at 0° C. The resulting solution was stirred overnight at room temperature. The resulting mixture was concentrated under vacuum. The crude product was purified by preparative HPLC with the following conditions: Column, Gemini-NX 5μ C18 110A, AXIA Packed, 150×21.2 mm; mobile phase, water with 0.05% TFA and ACN (23.0% ACN up to 50.0% in 8 min); Detector, 254 nm. This provided 34.5 mg (31%) of N-(3-[5-[(1H-indazol-5-yl)amino]-1,3,4-thiadiazol-2-yl]phenyl)ethane-1-sulfonamide 2,2,2-trifluoroacetic acid solvate as an off-white solid. (ES-ESI, m/z): 401 $[M+H]^+$. $^1H$ NMR (400 MHz, DMSO-$d_6$) δ 13.05 (s, 1H), 10.50 (s, 1H), 10.03 (s, 1H), 8.24 (d, 1H, J=1.6), 8.05 (s, 1H), 7.75 (t, 1H, J=3.2), 7.56-7.50 (m, 2H), 7.47-7.39 (m, 2H), 7.34-7.31 (m, 1H), 3.18-3.12 (m, 2H), 1.23-1.19 (m, 2H).

Example 29—Synthesis of 2-Amino-N-(3-[5-[(1H-indazol-5-yl)amino]-1,3,4-thiadiazol-2-yl]phenyl)ethane-1-sulfonamide 2,2,2-trifluoroacetic Acid Solvate

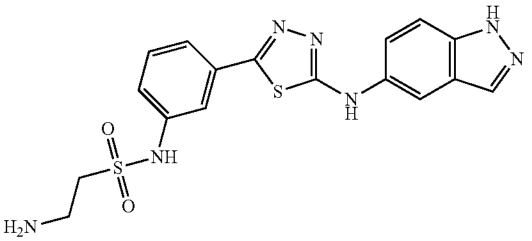

TFA

Part 1—Synthesis of Tert-Butyl 5-[[(tert-butoxy)carbonyl][5-(3-[[2-(1,3-dioxo-2,3-dihydro-1H-isoindol-2-yl)ethane]sulfonamido]phenyl)-1,3,4-thiadiazol-2-yl]amino]-1H-indazole-1-carboxylate

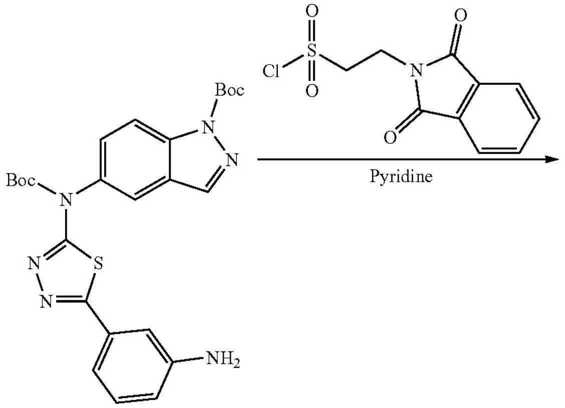

-continued

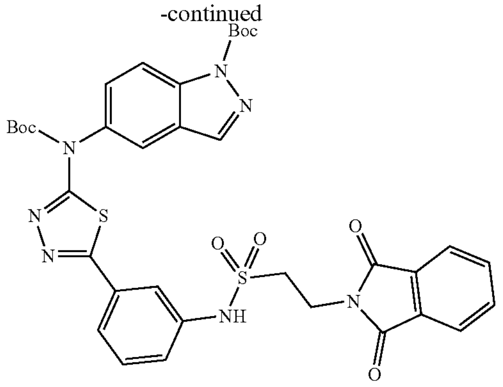

Into a 50-mL round-bottom flask was placed a solution of tert-butyl 5-[[5-(3-aminophenyl)-1,3,4-thiadiazol-2-yl][(tert-butoxy)carbonyl]amino]-1H-indazole-1-carboxylate (300 mg, 0.59 mmol, 1.00 equiv) in pyridine (10 mL). 2-(1,3-Dioxo-2,3-dihydro-1H-isoindol-2-yl)ethane-1-sulfonyl chloride (484 mg, 1.77 mmol, 3.00 equiv) was added to the reaction mixture. The resulting solution was stirred overnight at room temperature, and then it was concentrated under vacuum to provide a residue, which was then applied onto a silica gel column with ethyl acetate/petroleum ether (1:1) as eluent to furnish 310 mg (70%) of tert-butyl 5-[[(tert-butoxy)carbonyl][5-(3-[[2-(1,3-dioxo-2,3-dihydro-1H-isoindol-2-yl)ethane]sulfonamido]phenyl)-1,3,4-thiadiazol-2-yl]amino]-1H-indazole-1-carboxylate as a yellow solid.

Part 2—Synthesis of Tert-Butyl 5-[(5-[3-[(2-aminoethane)sulfonamido]phenyl]-1,3,4-thiadiazol-2-yl)[(tert-butoxy)carbonyl]amino]-1H-indazole-1-carboxylate

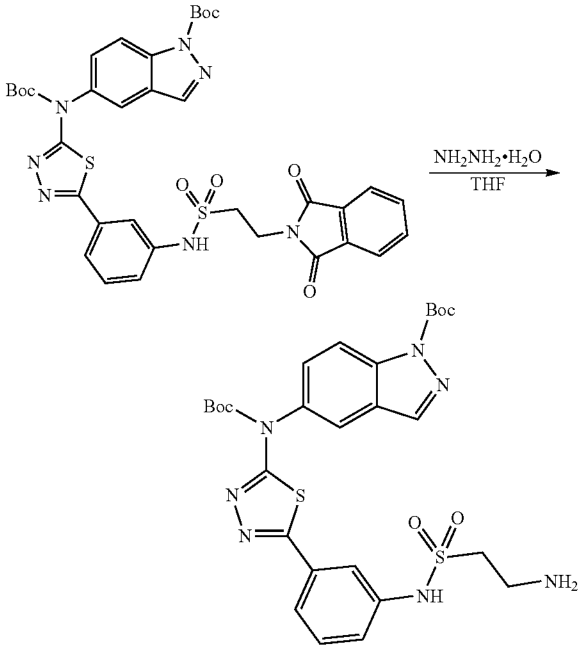

Into a 50-mL round-bottom flask was placed a solution of tert-butyl 5-[[(tert-butoxy)carbonyl][5-(3-[[2-(1,3-dioxo-2, 3-dihydro-1H-isoindol-2-yl)ethane]sulfonamido]phenyl)-1,3,4-thiadiazol-2-yl]amino]-1H-indazole-1-carboxylate (160 mg, 0.21 mmol, 1.00 equiv) in tetrahydrofuran (15 mL). Hydrazine hydrate (215 mg, 4.29 mmol, 20.00 equiv) was added to the reaction mixture. The resulting solution was stirred for overnight at 60° C. in an oil bath. The resulting mixture was concentrated under vacuum and the resulting residue was purified by silica gel column chromatography with EtOAc and petroleum ether (1:1) as eluent. This provided 180 mg (76%) of tert-butyl5-[(5-[3-[(2-aminoethane)sulfonamido]phenyl]-1,3,4-thiadiazol-2-yl)[(tert-butoxy)carbonyl]amino]-1H-indazole-1-carboxylate as an off-white solid.

Part 3—Synthesis of 2-Amino-N-(3-[5-[(1H-indazol-5-yl)amino]-1,3,4-thiadiazol-2-yl]phenyl)ethane-1-sulfonamide 2,2,2-trifluoroacetic Acid Solvate

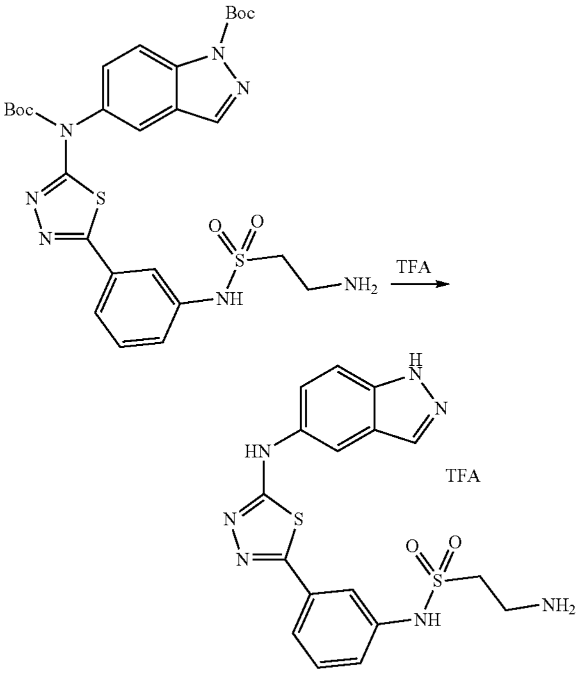

Into a 100-mL round-bottom flask was placed a solution of tert-butyl 5-[(5-[3-[(2-aminoethane)sulfonamido]phenyl]-1,3,4-thiadiazol-2-yl)[(tert-butoxy)carbonyl]amino]-1H-indazole-1-carboxylate (180 mg, 0.29 mmol, 1.00 equiv) in dichloromethane (9 mL). Trifluoroacetic acid (3 mL) was added dropwise to the reaction mixture. The resulting solution was stirred for 3 h at room temperature. The resulting mixture was concentrated under vacuum. The crude product was purified by preparative HPLC (Column: Gemini-NX 5µ C18 110A, AXIA Packed 150×21.2 mm; Mobile Phase A: water with 0.05% TFA, Mobile Phase B: ACN; Flow rate: mL/min; Gradient: 50% B to 80% B in 8 min; 254 nm) to furnish 50 mg (41%) of 2-amino-N-(3-[5-[(1H-indazol-5-yl)amino]-1,3,4-thiadiazol-2-yl]phenyl)ethane-1-sulfonamide 2,2,2-trifluoroacetic acid solvate as a white solid. (ES-ESI, m/z): 415.5 $[M+H]^+$. $^1$H NMR (300 MHz, DMSO-$d_6$) δ 13.03 (s, 1H); 10.53 (s, 1H); 8.24 (s, 1H); 8.05 (s, 1H); 7.80 (s, 3H); 7.47-7.58 (m, 3H); 7.33-7.42 (m, 2H); 3.43-3.48 (m, 2H); 3.14-3.19 (m, 2H).

Example 30—Synthesis of 5-(3-(1,3,4-oxadiazol-2-yl)phenyl)-N-(1H-indazol-5-yl)-1,3,4-thiadiazol-2-amine

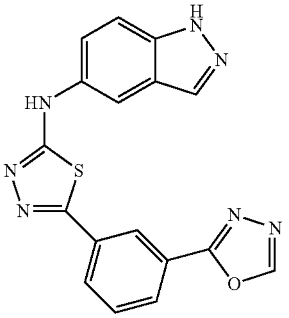 [SMILES: c1cc(-c2nnco2)cc(-c2nnc(Nc3ccc4[nH]ncc4c3)s2)c1]

Part 1—Synthesis of Tert-Butyl 2-(3-(methoxycarbonyl)benzoyl)hydrazine-1-carboxylate

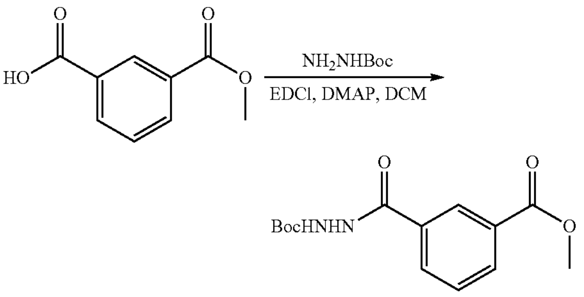

Into a 100-mL round-bottom flask was placed a solution of 3-(methoxycarbonyl)benzoic acid (4 g, 22.20 mmol, 1.00 equiv) in dichloromethane (50 mL). 1-Ethyl-3-(3-dimethylaminopropyl)carbodiimide (EDCI) (5.11 g, 26.66 mmol, 1.20 equiv), 4-dimethylaminopyridine (3.25 g, 26.60 mmol, 1.20 equiv), and (tert-butoxy)carbohydrazide (3.52 g, 26.63 mmol, 1.20 equiv) were added to the reaction mixture. The resulting solution was stirred overnight at room temperature. The resulting mixture was washed with 3×50 mL of water, dried over anhydrous sodium sulfate and concentrated under vacuum to provide a residue, which was then purified by a silica gel column with ethyl acetate/petroleum ether (1:1) as eluent to furnish 6 g (92%) of tert-butyl 2-(3-(methoxycarbonyl)benzoyl)hydrazine-1-carboxylate as a white solid.

Part 2—Synthesis of Methyl 3-(hydrazinecarbonyl)benzoate Hydrochloride

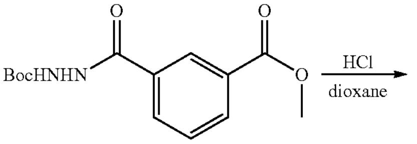

-continued

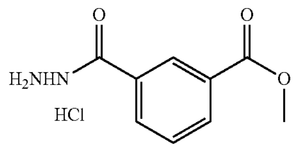

Into a 10-mL round-bottom flask was placed a solution of methyl 3-[([[(tert-butoxy)carbonyl]amino]amino)carbonyl] benzoate (1 g, 3.40 mmol, 1.00 equiv) in hydrogen chloride/ dioxane (4 M, 10 mL). The resulting solution was stirred for 1 h at room temperature. The solids were collected by filtration. This provided 550 mg (70%) of methyl 3-(hydrazinecarbonyl)benzoate hydrochloride as a white solid.

Part 3—Synthesis of Methyl 3-[5-[(1H-indazol-5-yl)amino]-1,3,4-thiadiazol-2-yl]benzoate

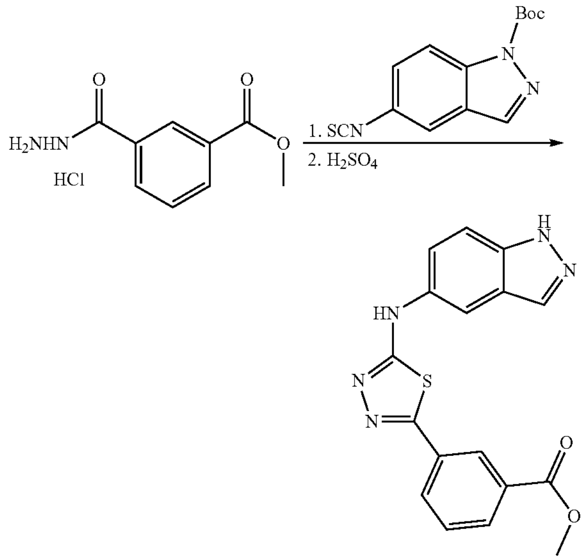

Into a 50-mL round-bottom flask was placed a solution of methyl 3-(hydrazinecarbonyl)benzoate hydrochloride (500 mg, 2.17 mmol, 1.00 equiv) in dichloromethane (10 mL). tert-Butyl 5-isothiocyanato-1H-indazole-1-carboxylate (600 mg, 2.18 mmol, 1.00 equiv) and DIPEA (280 mg, 2.17 mmol, 1.00 equiv) were added to the reaction solution. The resulting solution was stirred overnight at room temperature. This was followed by the addition of sulfuric acid (98%) (3 mL) dropwise with stirring. The resulting solution was stirred overnight at room temperature, and then it was poured into 50 mL of ice water. The pH value of the solution was adjusted to pH 9 with sodium carbonate (sat. aqueous). The solids were collected by filtration. This provided 500 mg (66%) of methyl 3-[5-[(1H-indazol-5-yl)amino]-1,3,4-thiadiazol-2-yl]benzoate as a yellow solid that was used into the next step without further purification.

Part 4—Synthesis of Tert-Butyl 5-[[(tert-butoxy) carbonyl]([5-[3-(methoxycarbonyl)phenyl]-1,3,4-thiadiazol-2-yl])amino]-1H-indazole-1-carboxylate

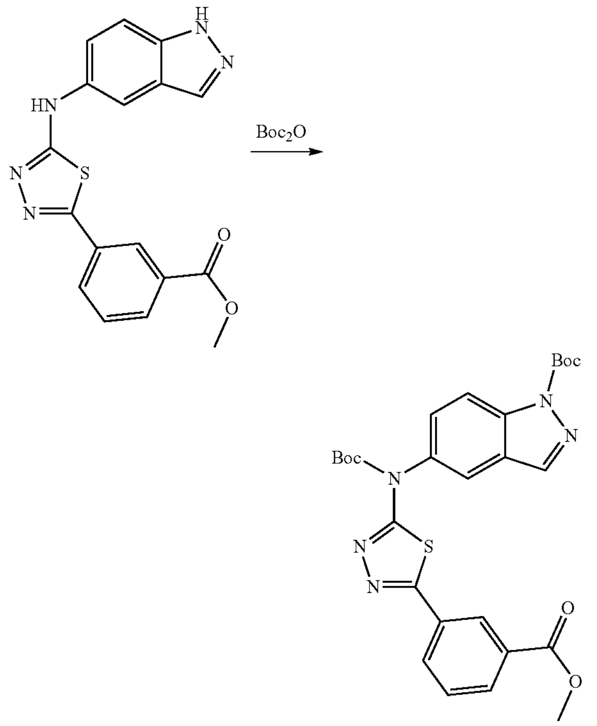

Into a 100-mL round-bottom flask was placed a solution of methyl 3-[5-[(1H-indazol-5-yl)amino]-1,3,4-thiadiazol-2-yl]benzoate (500 mg, 1.42 mmol, 1.00 equiv) in dichloromethane (20 mL). $(Boc)_2O$ (931 mg, 4.27 mmol, 3.00 equiv) and TEA (862 mg, 8.52 mmol, 6.00 equiv) were added to the reaction solution. The resulting solution was stirred overnight at room temperature. The resulting mixture was concentrated under vacuum and the resulting residue was applied onto a silica gel column with ethyl acetate/ petroleum ether (1:2) as eluent to furnish 360 mg (46%) of tert-butyl 5-[[(tert-butoxy)carbonyl]([5-[3-(methoxycarbonyl)phenyl]-1,3,4-thiadiazol-2-yl])amino]-1H-indazole-1-carboxylate as a yellow solid.

Part 5—Synthesis of 3-[5-[(1H-Indazol-5-yl) amino]-1,3,4-thiadiazol-2-yl]benzohydrazide

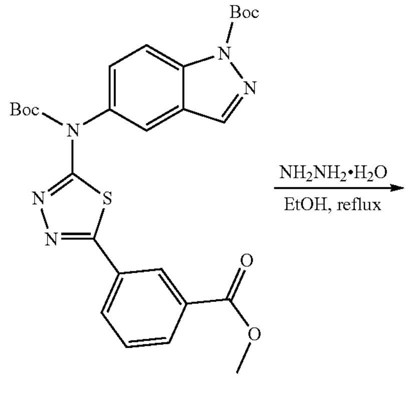

-continued

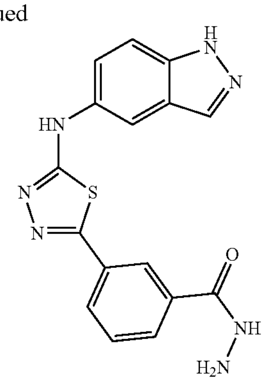

Into a 100-mL round-bottom flask was placed a solution of tert-butyl 5-[[(tert-butoxy)carbonyl]([5-[3-(methoxycarbonyl)phenyl]-1,3,4-thiadiazol-2-yl])amino]-1H-indazole-1-carboxylate (300 mg, 0.54 mmol, 1.00 equiv) in ethanol. Hydrazine hydrate (3 mL) were added to the reaction mixture. The resulting solution was stirred overnight at 80° C. The resulting mixture was concentrated under vacuum. This resulted in 180 mg (94%) of 3-[5-[(1H-indazol-5-yl)amino]-1,3,4-thiadiazol-2-yl]benzohydrazide as a yellow solid that was used into the next step without further purification.

Part 6—Synthesis of 5-(3-(1,3,4-oxadiazol-2-yl)phenyl)-N-(1H-indazol-5-yl)-1,3,4-thiadiazol-2-amine

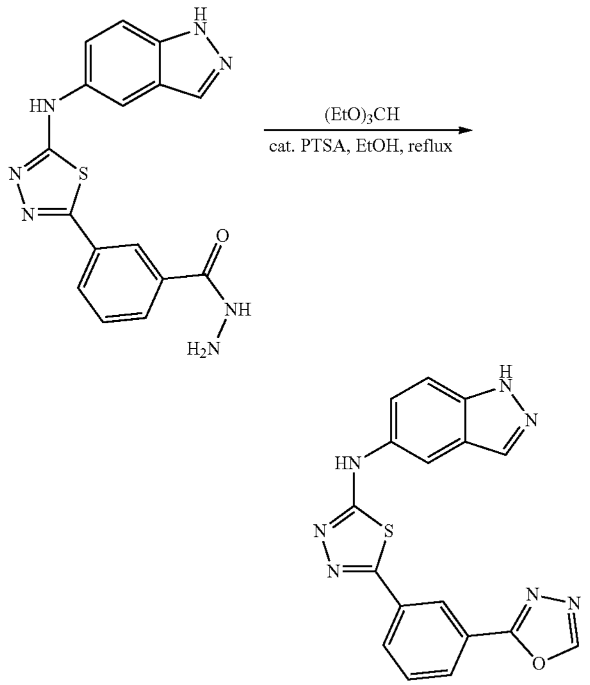

Into a 100-mL round-bottom flask was placed a solution of 3-[5-[(1H-indazol-5-yl)amino]-1,3,4-thiadiazol-2-yl]benzohydrazide (180 mg, 0.51 mmol, 1.00 equiv) in ethanol (10 mL). $HC(OEt)_3$ (5 mL) and a catalytic amount of para-toluenesulfonic acid (PTSA) were added to the reaction mixture. The resulting solution was stirred overnight at 95° C. The reaction mixture was cooled to room temperature. The solids were collected by filtration, and then it was washed with EtOH and dried. This provided 120 mg (65%) of 5-(3-(1,3,4-oxadiazol-2-yl)phenyl)-N-(1H-indazol-5-yl)-1,3,4-thiadiazol-2-amine as an off-white solid. (ES-ESI, m/z): 362.0 $[M+H]^+$. $^1H$ NMR (400 MHz, DMSO-$d_6$) δ 13.03 (s, 1H); 10.71 (s, 1H); 9.46 (s, 1H); 8.46 (s, 1H); 8.27 (s, 1H); 8.08-8.14 (m, 3H); 7.74-7.78 (m, 1H); 7.56 (d, J=8.8 Hz, 1H); 7.44 (d, J=8.4 Hz, 1H).

Example 31—Synthesis of 2-(3-[5-[(1H-Indazol-5-yl)amino]-1,3,4-thiadiazol-2-yl]phenoxy)-N-(propan-2-yl)acetamide 2,2,2-trifluoroacetic Acid Solvate

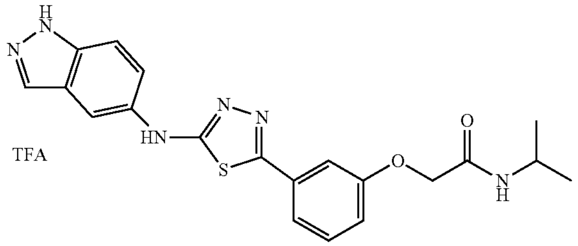 [SMILES: CC(C)NC(=O)COc1cccc(-c2nnc(Nc3ccc4[nH]ncc4c3)s2)c1]

Part 1—Synthesis of Methyl 3-[2-(tert-butoxy)-2-oxoethoxy]benzoate

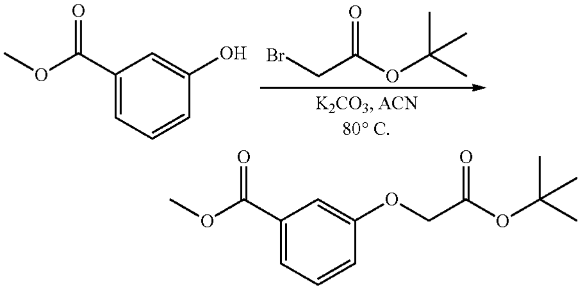

Into a 50-mL round-bottom flask was placed a solution of methyl 3-hydroxybenzoate (1 g, 6.57 mmol, 1.00 equiv) in ACN (20 mL). tert-Butyl 2-bromoacetate (1.28 g, 6.56 mmol, 1.00 equiv) and potassium carbonate (1.81 g, 13.00 mmol, 2.00 equiv) were added to the reaction mixture. The resulting solution was stirred overnight at 80° C. Then, the solids were filtered out. The filtrate was concentrated under vacuum to provide a residue, which was then triturated with hexane. This provided 1.7 g (97%) of methyl 3-[2-(tert-butoxy)-2-oxoethoxy]benzoate as a white solid.

Part 2—Synthesis of Tert-Butyl 2-[3-(hydrazinecarbonyl)phenoxy]acetate

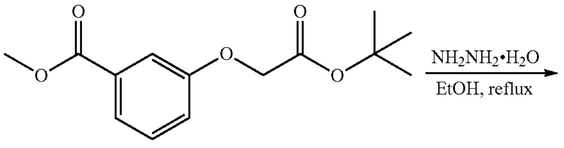

-continued

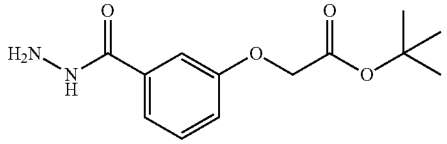

Into a 50-mL round-bottom flask was placed a solution of methyl 3-[2-(tert-butoxy)-2-oxoethoxy]benzoate (1.5 g, 5.63 mmol, 1.00 equiv) in ethanol (15 mL), and hydrazine hydrate (80%, 0.35 g, 5.63 mmol, 1.00 equiv). The resulting solution was stirred 3 h at 80° C. The resulting mixture was concentrated under vacuum. This resulted in 750 mg (50%) of tert-butyl 2-[3-(hydrazinecarbonyl)phenoxy]acetate as a yellow solid that was used into the next step without further purification.

Part 3—Synthesis of 2-(3-[5-[(1H-Indazol-5-yl) amino]-1,3,4-thiadiazol-2-yl]phenoxy)acetic Acid

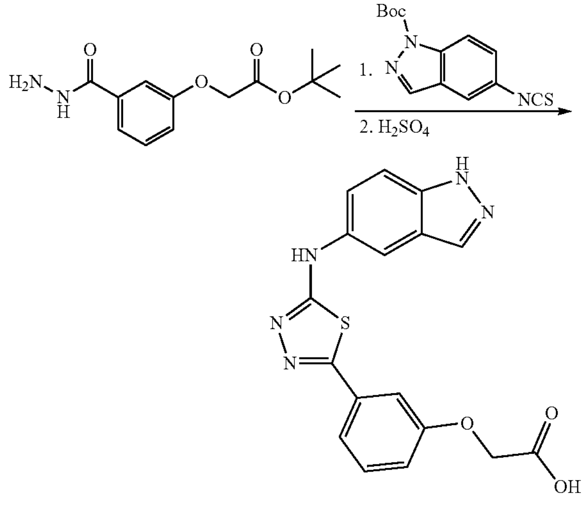

Into a 100-mL round-bottom flask was placed a solution of tert-butyl 2-[3-(hydrazinecarbonyl)phenoxy]acetate (750 mg, 2.82 mmol, 1.00 equiv) in dichloromethane (10 mL). tert-Butyl 5-isothiocyanato-1H-indazole-1-carboxylate (775 mg, 2.80 mmol, 1.00 equiv) was added to the reaction mixture. The resulting solution was stirred for 6 hrs at room temperature. This was followed by the addition of sulfuric acid (98%) (3 mL) dropwise with stirring. The resulting solution was stirred overnight at room temperature. The pH value of the solution was adjusted to pH 9 with sodium carbonate (aqueous). The solids were collected by filtration. This provided 500 mg (48%) of 2-(3-[5-[(1H-indazol-5-yl) amino]-1,3,4-thiadiazol-2-yl]phenoxy)acetic acid as a yellow solid that was used into the next step without further purification. (ES-ESI, m/z): 368.0 $[M+H]^+$. $^1H$ NMR (400 MHz, $CD_3OD+DMSO-d_6$) δ 8.27 (s, 1H); 8.05 (s, 1H); 7.55 (d, J=8.8 Hz, 1H); 7.39-7.44 (m, 3H); 7.34 (s, 1H); 6.97-7.00 (m, 1H); 4.56 (s, 2H).

Part 4—Synthesis of 2-(3-[5-[(1H-Indazol-5-yl) amino]-1,3,4-thiadiazol-2-yl]phenoxy)-N-(propan-2-yl)acetamide 2,2,2-trifluoroacetic Acid Solvate

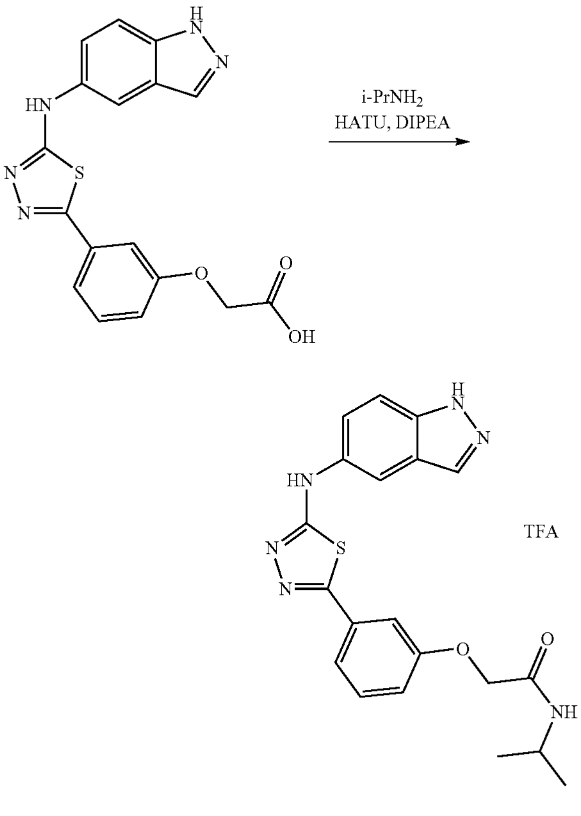

Into a 10-mL round-bottom flask was placed a solution of 2-(3-[5-[(1H-indazol-5-yl)amino]-1,3,4-thiadiazol-2-yl] phenoxy)acetic acid (500 mg, 1.36 mmol, 1.00 equiv) in N,N-dimethylformamide (5 mL). Isopropylamine (80 mg, 1.36 mmol, 1.00 equiv), HATU (775 mg, 2.04 mmol, 1.50 equiv), and DIPEA (527 mg, 4.08 mmol, 3.00 equiv) were added to the reaction mixture. The resulting solution was stirred overnight at room temperature, and then it was concentrated under vacuum. The crude product was purified by preparative HPLC using the following conditions (Column: Gemini NX, 19×150 mm, 5 μm; Mobile Phase A: Water/0.05% TFA, Mobile Phase B: ACN; Flow rate: 20 mL/min; Gradient: 17% B to 48% B in 8 min; 254 nm): This provided 50 mg (9%) of 2-(3-[5-[(1H-indazol-5-yl)amino]-1,3,4-thiadiazol-2-yl]phenoxy)-N-(propan-2-yl)acetamide 2,2,2-trifluoroacetic acid solvate as a white solid. (ES-ESI, m/z): 409.1 $[M+H]^+$. $^1H$ NMR (400 MHz, $DMSO-d_6$) δ 10.52 (s, 1H); 8.24 (s, 1H); 8.06 (s, 1H); 7.98 (d, J=8 Hz, 1H); 7.55 (d, J=9.2 Hz, 1H); 7.40-7.45 (m, 4H); 7.06-7.10 (m, 1H); 4.53 (s, 2H); 3.94-4.01 (m, 1H); 1.10 (d, J=6.4 Hz, 6H).

The following compound was prepared using similar procedures.

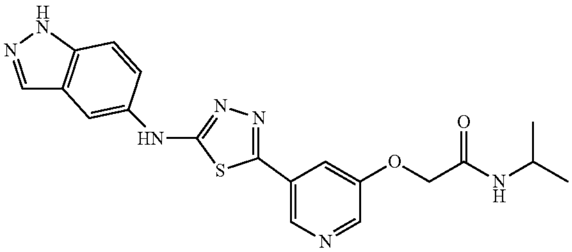 [SMILES: CC(C)NC(=O)COc1cncc(-c2nnc(Nc3ccc4[nH]ncc4c3)s2)c1]

2-[(5-[5-[(1H-Indazol-5-yl)amino]-1,3,4-thiadiazol-2-yl]pyridin-3-yl)oxy]-N-(propan-2-yl)acetamide (ES-ESI, m/z): 410 $[M+H]^+$. $^1H$ NMR (400 MHz, DMSO-$d_6$) δ 10.62 (s, 1H), 8.65 (d, 1H, J=1.6 Hz), 8.41 (d, 1H, J=2.6 Hz), 8.24 (d, 1H, J=1.6 Hz), 8.04-8.00 (m, 2H), 7.78-7.77 (m, 1H), 7.57-7.55 (m, 1H), 7.43-7.40 (m, 1H), 4.65 (s, 1H), 4.00-3.91 (m, 1H), 1.14 (s, 6H).

Example 32—Synthesis of 4-[5-[(1H-Indazol-5-yl)amino]-1,3,4-thiadiazol-2-yl]-2-(1-methyl-1H-pyrazole-4-amido)benzoic Acid

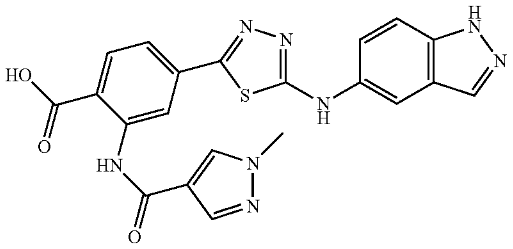 [SMILES: Cn1cc(C(=O)Nc2cc(-c3nnc(Nc4ccc5[nH]ncc5c4)s3)ccc2C(=O)O)cn1]

Part 1—Synthesis of Tert-Butyl 5-[[(tert-butoxy)carbonyl]([5-[4-(methoxycarbonyl)-3-(1-methyl-1H-pyrazole-4-amido)phenyl]-1,3,4-thiadiazol-2-yl])amino]-1H-indazole-1-carboxylate

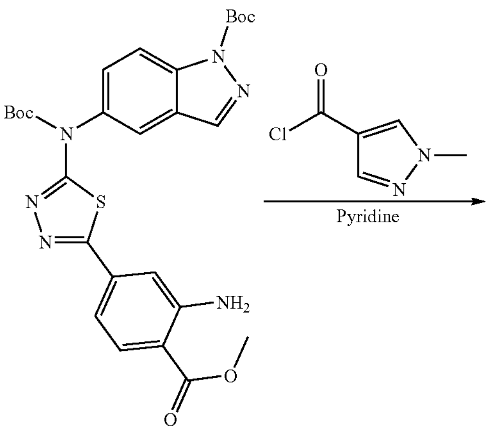

-continued

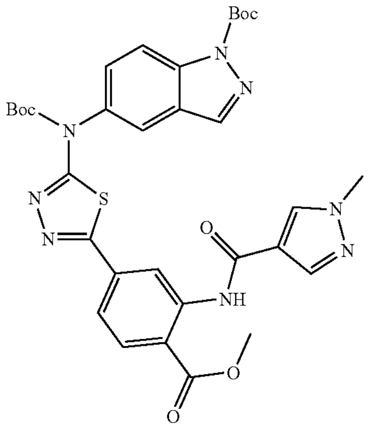

Into a 50-mL round-bottom flask was placed a solution of tert-butyl 5-([5-[3-amino-4-(methoxycarbonyl)phenyl]-1,3,4-thiadiazol-2-yl][(tert-butoxy)carbonyl]amino)-1H-indazole-1-carboxylate (200 mg, 0.35 mmol, 1.00 equiv) in pyridine (10 mL). 1-Methyl-1H-pyrazole-4-carbonyl chloride (438 mg, 3.03 mmol, 10.00 equiv) was added to the reaction mixture. The resulting solution was stirred overnight at room temperature. The reaction was then quenched by the addition of 20 mL of water. The resulting solution was extracted with 3×30 mL of dichloromethane and the organic layers combined and dried over anhydrous sodium sulfate and concentrated under vacuum to provide a residue, which was then applied onto a silica gel column with ethyl acetate/petroleum ether (1:1) as eluent to furnish 100 mg (42%) of tert-butyl 5-[[(tert-butoxy)carbonyl]([5-[4-(methoxycarbonyl)-3-(1-methyl-1H-pyrazole-4-amido)phenyl]-1,3,4-thiadiazol-2-yl])amino]-1H-indazole-1-carboxylate as a light yellow solid.

Part 2—Synthesis of 4-[5-[(1H-Indazol-5-yl)amino]-1,3,4-thiadiazol-2-yl]-2-(1-methyl-1H-pyrazole-4-amido)benzoic Acid

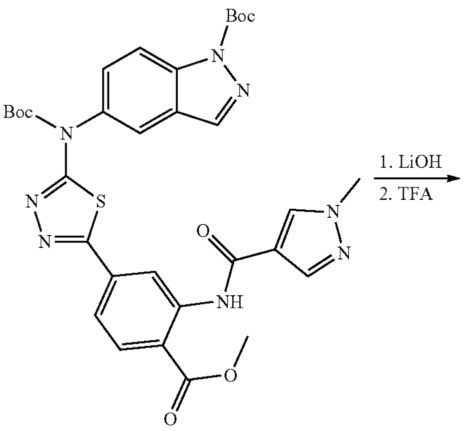

-continued

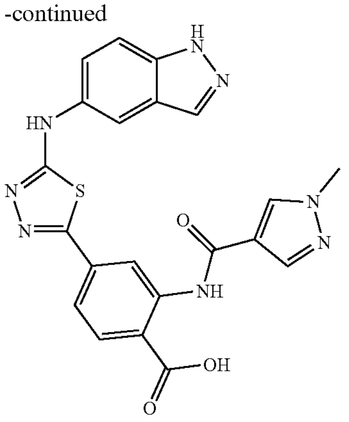

Into a 50-mL round-bottom flask was placed a solution of tert-butyl 5-[[(tert-butoxy)carbonyl]([5-[4-(methoxycarbonyl)-3-(1-methyl-1H-pyrazole-4-amido)phenyl]-1,3,4-thiadiazol-2-yl])amino]-1H-indazole-1-carboxylate (90 mg, 0.13 mmol, 1.00 equiv) in tetrahydrofuran (5 mL) and a solution of LiOH (32 mg, 1.34 mmol, 10.00 equiv) in water (5 mL). The resulting solution was stirred overnight at room temperature. The pH value of the solution was adjusted to pH 5 with HCl (1M). The resulting solution was extracted with 3×50 mL of dichloromethane and the organic layers combined, dried with sodium sulfate, and concentrated under vacuum to provide a residue, which was subsequently dissolved in DCM (5 mL). Trifluoroacetic acid (5 mL) was added to the reaction solution. The resulting solution was stirred for 2 hours at room temperature. Then, the resulting mixture was concentrated under vacuum. The crude product was purified by preparative HPLC (Column: Gemini-NX C18 110A, AXIA Packed 150×21.2 mm; Mobile Phase A: water with 10 mM $NH_4HCO_3$, Mobile Phase B: ACN; Gradient: 10% B to 32% B in 8 min; 254 nm). This resulted in 6 mg (10%) of 4-[5-[(1H-indazol-5-yl)amino]-1,3,4-thiadiazol-2-yl]-2-(1-methyl-1H-pyrazole-4-amido)benzoic acid as a yellow solid. (ES-ESI, m/z): 460.5 $[M+H]^+$. $^1H$ NMR (300 MHz, DMSO-$d_6$) δ 13.53 (s, 1H); 13.28 (s, 1H); 10.58 (s, 1H); 9.09 (s, 1H); 8.46 (s, 2H); 8.06 (s, 2H); 7.89 (s, 1H); 7.33-7.66 (m, 3H); 6.92 (s, 1H); 3.91 (s, 3H).

Example 33—Synthesis of 2-(Dimethylamino)-N-(5-[5-[(1H-indazol-5-yl)amino]-1,3,4-thiadiazol-2-yl]pyridin-3-yl)acetamide

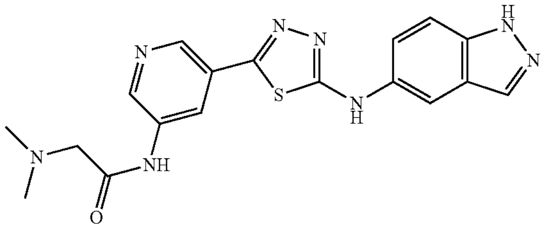 [SMILES: CN(C)CC(=O)Nc1cncc(-c2nnc(Nc3ccc4[nH]ncc4c3)s2)c1]

Part 1—Synthesis of Tert-Butyl 5-([5-[5-(2-bromoacetamido)pyridin-3-yl]-1,3,4-thiadiazol-2-yl][(tert-butoxy)carbonyl]amino)-1H-indazole-1-carboxylate

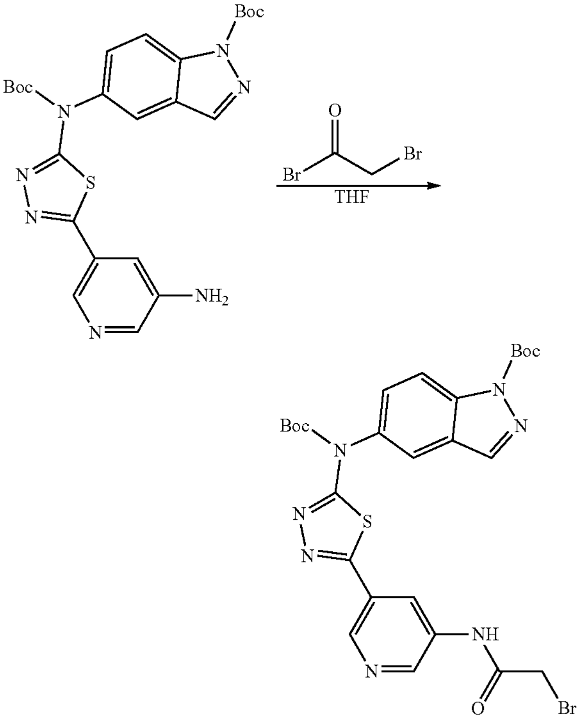

Into a 25-mL round-bottom flask was placed a solution of tert-butyl 5-[[5-(5-aminopyridin-3-yl)-1,3,4-thiadiazol-2-yl][(tert-butoxy)carbonyl]amino]-1H-indazole-1-carboxylate (100 mg, 0.20 mmol, 1.00 equiv) in tetrahydrofuran (5 mL). This was followed by the addition of a solution of 2-bromoacetyl bromide (47.4 mg, 0.23 mmol, 1.20 equiv) in tetrahydrofuran (0.5 mL) dropwise with stirring. The resulting solution was stirred for 2 h at room temperature. The resulting mixture was concentrated under vacuum and then purified by column chromatography (1:1 ethyl acetate/petroleum ether). This provided 107 mg (86%) of tert-butyl 5-([5-[5-(2-bromoacetamido)pyridin-3-yl]-1,3,4-thiadiazol-2-yl][(tert-butoxy)carbonyl]amino)-1H-indazole-1-carboxylate as an orange solid.

Part 2—Synthesis of Tert-Butyl 5-[[(tert-butoxy)carbonyl](5-[5-[2-(dimethylamino)acetamido]pyridin-3-yl]-1,3,4-thiadiazol-2-yl)amino]-1H-indazole-1-carboxylate

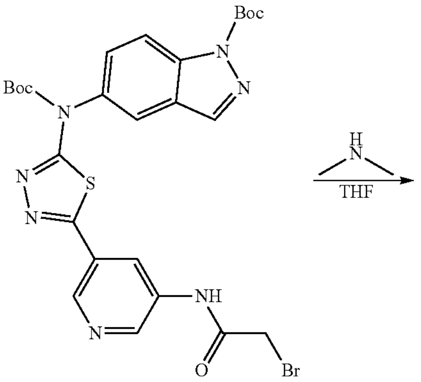

-continued

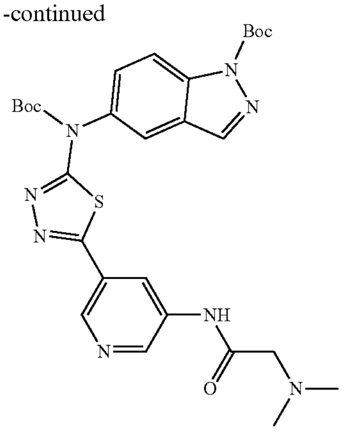

Into a 25-mL round-bottom flask was placed a solution of tert-butyl 5-([5-[5-(2-bromoacetamido)pyridin-3-yl]-1,3,4-thiadiazol-2-yl][(tert-butoxy)carbonyl]amino)-1H-indazole-1-carboxylate (100 mg, 0.16 mmol, 1.00 equiv) in tetrahydrofuran (10 mL) and a solution of dimethylamine in THF (2M, 0.4 mL, 5.00 equiv). The resulting solution was stirred for 2 h at 50° C. in an oil bath. The resulting mixture was concentrated under vacuum. The crude product was purified by column chromatography (1:1 ethyl acetate/petroleum ether). This provided 90 mg (95%) of tert-butyl 5-[[(tert-butoxy)carbonyl](5-[5-[2-(dimethylamino)acetamido]pyridin-3-yl]-1,3,4-thiadiazol-2-yl)amino]-1H-indazole-1-carboxylate as an orange solid.

Part 3—Synthesis of 2-(Dimethylamino)-N-(5-[5-[(1H-indazol-5-yl)amino]-1,3,4-thiadiazol-2-yl]pyridin-3-yl)acetamide

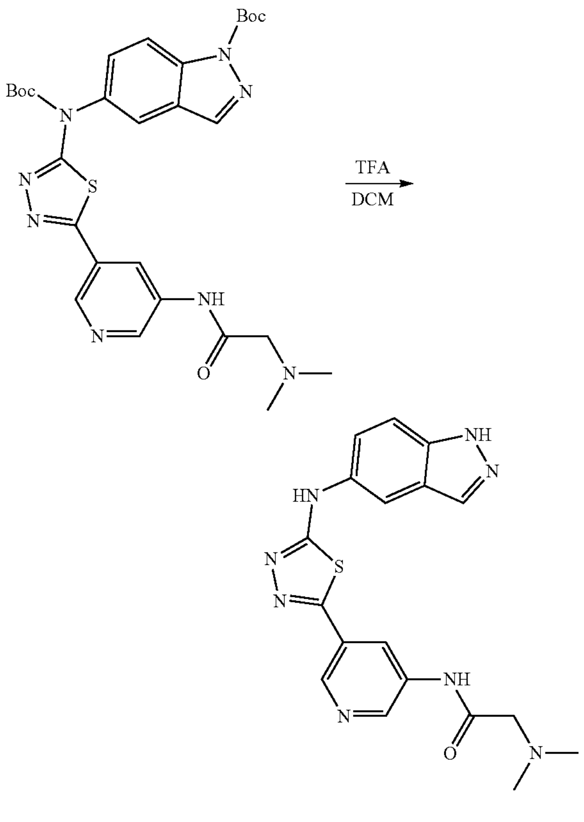

Into a 25-mL round-bottom flask was placed a solution of tert-butyl 5-[[(tert-butoxy)carbonyl](5-[5-[2-(dimethylamino)acetamido]pyridin-3-yl]-1,3,4-thiadiazol-2-yl)amino]-1H-indazole-1-carboxylate (100 mg, 0.17 mmol, 1.00 equiv) in dichloromethane (9 mL) and trifluoroacetic acid (3 mL). The resulting solution was stirred for 2 h at room temperature. The resulting mixture was concentrated under vacuum. The crude product was purified by preparative HPLC with the following conditions: Column: Gemini-NX 5μ C18 110A, AXIA Packed, 150×21.2 mm; mobile phase: water with 0.05% $NH_4HCO_3$ and ACN (15.0% ACN up to 42.0% in 8 min); Detector; 254 nm. This provided 8.9 mg (13%) of 2-(dimethylamino)-N-(5-[5-[(1H-indazol-5-yl)amino]-1,3,4-thiadiazol-2-yl]pyridin-3-yl)acetamide as a light yellow solid. (ES-ESI, m/z): 395.0 $[M+H]^+$. $^1H$ NMR (400 MHz, DMSO-$d_6$) δ 13.0 (s, 1H), 10.6 (s, 1H), 10.2 (s, 1H), 8.9 (s, 1H), 8.7 (s, 1H), 8.6 (s, 1H), 8.2 (s, 1H), 8.0 (s, 1H), 7.5 (d, 1H), 7.4 (d, 1H), 3.1 (s, 2H), 2.2 (s, 6H).

Example 34—Synthesis of N-(4-(5-((4-Chloro-1H-indazol-5-yl)amino)-1,3,4-thiadiazol-2-yl)pyridin-2-yl)-2-(4-fluorophenyl)propanamide

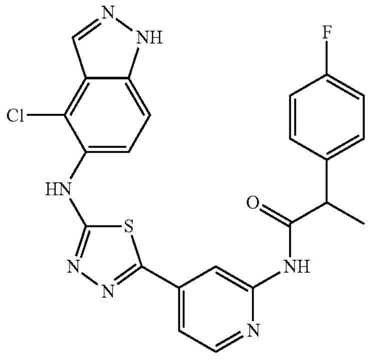 [SMILES: CC(C(=O)Nc1cc(-c2nnc(Nc3ccc4[nH]ncc4c3Cl)s2)ccn1)c1ccc(F)cc1]

Part 1—Synthesis of 2-(4-fluorophenyl)propanoyl Chloride

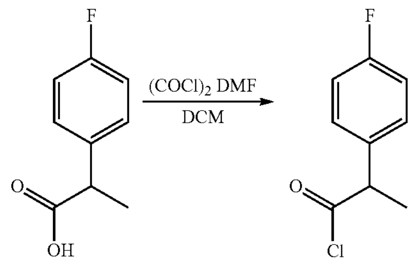

Into a 25-mL round-bottom flask, was placed 2-(4-fluorophenyl)propanoic acid (500 mg, 2.97 mmol, 1.00 equiv), dichloromethane (10 mL), oxalyl chloride (3024 mg, 23.82 mmol, 8.00 equiv), and N,N-dimethylformamide (26 mg, 0.36 mmol, 0.10 equiv). The resulting solution was stirred for 3 h at room temperature. The resulting mixture was concentrated under vacuum. This resulted in 512 mg (92%) of 2-(4-fluorophenyl)propanoyl chloride as a yellow oil.

Part 2—Synthesis of 2-(4-fluorophenyl)propanamide

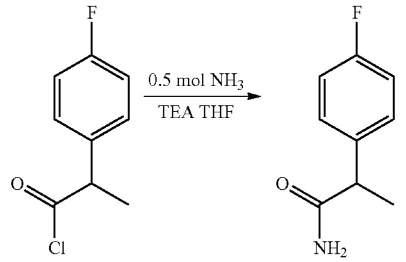

Into a 50-mL round-bottom flask, was placed 2-(4-fluorophenyl)propanoyl chloride (512 mg, 2.74 mmol, 1.00 equiv), tetrahydrofuran (20 mL), TEA (0.2 mL), ammonia (15 mL). The resulting solution was stirred for 1 h at room temperature. The resulting mixture was concentrated under vacuum. This resulted in 356.6 mg (78%) of 2-(4-fluorophenyl)propanamide as a light yellow oil.

Part 3—Synthesis of Methyl 2-(2-(4-fluorophenyl)propanamido)isonicotinate

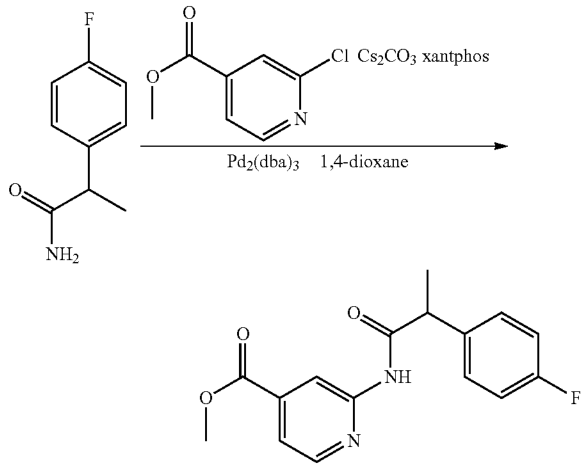

Into a 50-mL round-bottom flask purged and maintained with an inert atmosphere of nitrogen, was placed 2-(4-fluorophenyl)propanamide (317.6 mg, 1.90 mmol, 1.00 equiv), dioxane (20 mL), $Cs_2CO_3$ (930 mg, 2.85 mmol, 1.50 equiv), Xantphos (55 mg, 0.10 mmol, 0.05 equiv). This was followed by the addition of methyl 2-chloropyridine-4-carboxylate (650 mg, 3.79 mmol, 2.00 equiv). After 5 minutes, $Pd_2(dba)_3$ (30 mg, 0.03 mmol, 0.01 equiv) was added. The resulting solution was stirred overnight at 100° C. then concentrated under vacuum. The resulting solution was extracted with 500 mL of ethyl acetate and the extracts were washed with 3×100 mL of aqueous sodium chloride. After concentrating under vacuum, the residue was applied onto a silica gel column with ethyl acetate/petroleum ether (2:1) and chromatographed to provide 314 mg (55%) of methyl 2-[2-(4-fluorophenyl)propanamido]pyridine-4-carboxylate as a white solid Part 4—Synthesis of 2-(4-fluorophenyl)-N-(4-(hydrazinecarbonyl)pyridin-2-yl)propanamide

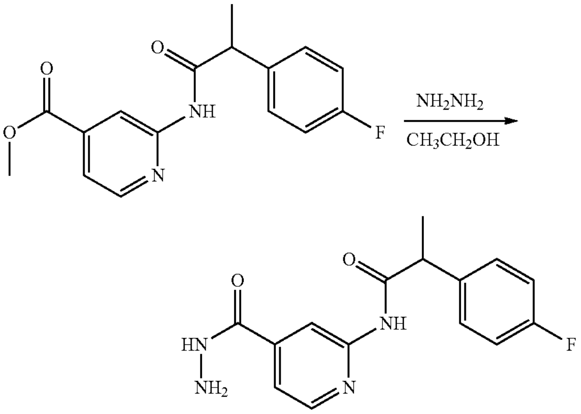

Into a 25-mL round-bottom flask, was placed methyl 2-[2-(4-fluorophenyl)propanamido]pyridine-4-carboxylate (294 mg, 0.97 mmol, 1.00 equiv), ethanol (2 mL), hydrazine (2 mL). The resulting solution was stirred for 6 h at room temperature. The resulting mixture was concentrated under vacuum. This resulted in 215 mg (73%) of 2-(4-fluorophenyl)-N-[4-(hydrazinecarbonyl)pyridin-2-yl]propanamide as a light yellow solid.

Part 5—Synthesis of N-(4-(2-((4-chloro-1H-indazol-5-yl)carbamothioyl)hydrazine-1-carbonyl)pyridin-2-yl)-2-(4-fluorophenyl)propanamide

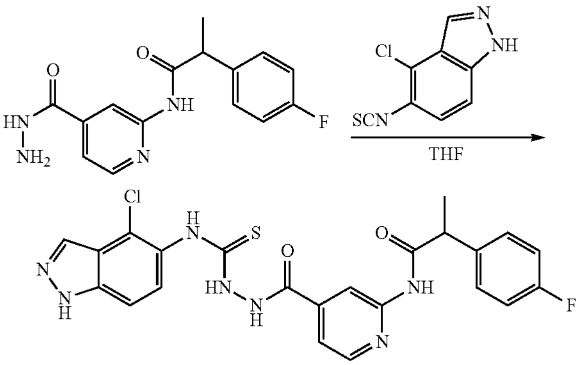

Into a 25-mL round-bottom flask, was placed 2-(4-fluorophenyl)-N-[4-(hydrazinecarbonyl)pyridin-2-yl]propanamide (195 mg, 0.65 mmol, 1.00 equiv), tetrahydrofuran (5 mL), 4-chloro-5-isothiocyanato-1H-indazole (135.6 mg, 0.65 mmol, 1.00 equiv). The resulting solution was stirred for 1 overnight at room temperature. The resulting mixture was concentrated under vacuum. The residue was applied onto a silica gel column with dichloromethane/methanol (10:1). This resulted in 156 mg (47%) of N-[[(4-chloro-1H-indazol-5-yl)carbamothioyl]amino]-2-[2-(4-fluorophenyl)propanamido]pyridine-4-carboxamide as a light yellow solid.

Part 6—Synthesis of N-(4-(5-((4-chloro-1H-indazol-5-yl)amino)-1,3,4-thiadiazol-2-yl)pyridin-2-yl)-2-(4-fluorophenyl)propanamide

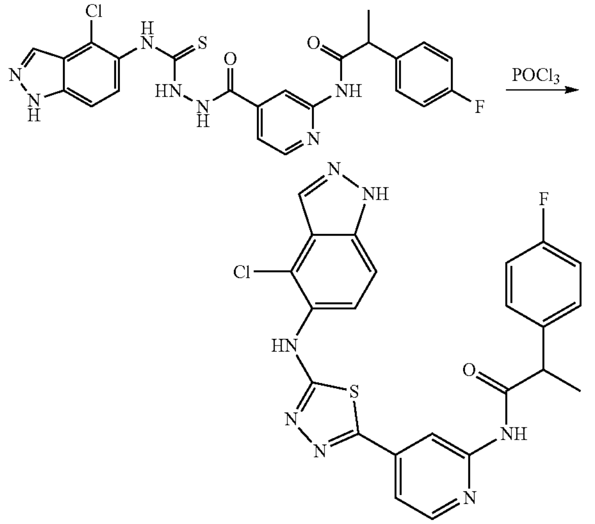

Into a 25-mL round-bottom flask, was placed N-[[(4-chloro-1H-indazol-5-yl)carbamothioyl]amino]-2-[2-(4-fluorophenyl)propanamido]pyridine-4-carboxamide (170 mg, 0.33 mmol, 1.00 equiv), and phosphoroyl trichloride (3 mL). The resulting solution was stirred for 4 h at 50° C. then concentrated under vacuum. The crude product was purified by Prep-HPLC with the following conditions: Column, XBridge Shield RP18 OBD Column, 5um, 19×150 mm; mobile phase, Water (0.05% $NH_3$) and ACN (hold at 44% ACN for 8 min); Detector, UV 254 nm. This resulted in 6.5 mg (4%) of N-(4-[5-[(4-chloro-1H-indazol-5-yl)amino]-1,3,4-thiadiazol-2-yl]pyridin-2-yl)-2-(4-fluorophenyl)propanamide as a light yellow solid. (ES, m/z): $[M+H]^+$494; $^1H$ NMR (300 MHz, DMSO-$d_6$, ppm): δ 13.46 (s, 1H), 10.84 (s, 1H), 10.25 (s, 1H), 8.43 (s, 1H), 8.34 (s, 1H), 8.11 (d, J=1.4 Hz, 1H), 7.77 (d, J=9.1 Hz, 1H), 7.57 (d, J=8.9 Hz, 1H), 7.42 (ddd, J=14.5, 5.6, 1.8 Hz, 3H), 7.11 (t, J=8.8 Hz, 2H), 4.00 (t, J=7.2 Hz, 1H), 1.37 (d, J=6.9 Hz, 3H).

Example 35—Preparation of Additional N-(1H-indazol-5-yl)-1,3,4-thiadiazol-2-amine Compounds The compounds in Table 3 were prepared based on procedures described in Examples 32 and 34 above.

TABLE 3

| Example No. | Chemical Structure | Physical Characterization Data |
|---|---|---|
| 35A | 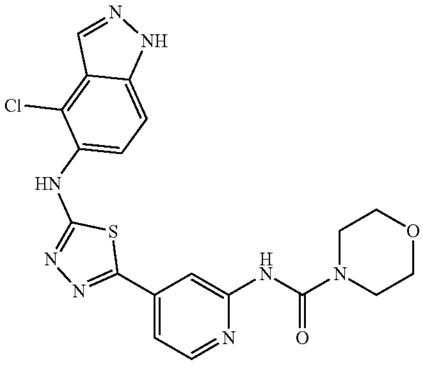 [SMILES: O=C(Nc1cc(-c2nnc(Nc3ccc4[nH]ncc4c3Cl)s2)ccn1)N1CCOCC1] | (ES, m/z): $[M + H]^+$ 457. $^1H$ NMR (400 MHz, DMSO-$d_6$ ppm): δ 13.44 (s, 1H), 10.20 (s, 1H), 9.39 (s, 1H), 8.27 (d, J = 5.2 Hz, 1H), 8.12 (d, J = 9.2 Hz, 2H), 7.75 (s, 1H), 7.56 (d, J = 8.4 Hz, 1H), 7.34 (d, J = 4.4 Hz, 1H), 3.57 (t, J = 9.2 Hz, 4H), 3.44 (t, J = 9.2 Hz, 4H). |
| 35B | 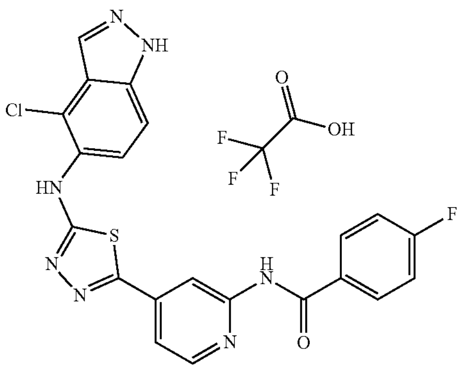 [SMILES: O=C(Nc1cc(-c2nnc(Nc3ccc4[nH]ncc4c3Cl)s2)ccn1)c1ccc(F)cc1 ; O=C(O)C(F)(F)F] | (ES, m/z): $[M + H]^+$ 466. $^1H$ NMR (400 MHz, DMSO-$d_6$ ppm): δ 13.44 (s, 1H), 11.01 (s, 1H), 10.02 (s, 1H), 8.56 (s, 1H), 8.44 (d, J = 4.8 Hz, 1H), 8.10 (m, 3H), 7.78 (d, J = 8.8 Hz, 1H), 7.59-7.51 (m, 2H), 7.34 (t, J = 17.6 Hz, 2H). |

TABLE 3-continued

| Example No. | Chemical Structure | Physical Characterization Data |
| --- | --- | --- |
| 35C | 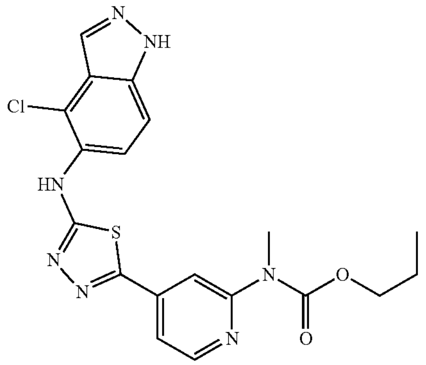 [SMILES: CCCOC(=O)N(C)c1cc(-c2nnc(Nc3ccc4[nH]ncc4c3Cl)s2)ccn1] | (ES, m/z): $[M+H]^+$ 444. $^1H$ NMR (400 MHz, DMSO-$d_6$) δ 13.48 (s, 1H), 10.26 (s, 1H), 8.45 (d, J = 5.2 Hz, 1H), 8.14 (s, 1H), 8.07 (s, 1H), 7.80 (d, J = 9.2 Hz, 1H), 7.59 (d, J = 8.8 Hz, 1H), 7.52 (d, J = 5.2 Hz, 1H), 3.32 (s, 3H), 4.08 (d, J = 13.2 Hz, 2H), 1.67-1.58 (m, 2H), 0.92 (t, J = 7.2 Hz, 3H). |
| 35D | 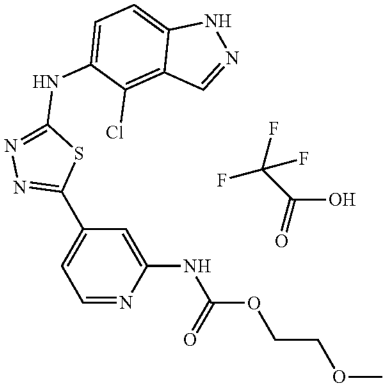 [SMILES: COCCOC(=O)Nc1cc(-c2nnc(Nc3ccc4[nH]ncc4c3Cl)s2)ccn1 ; O=C(O)C(F)(F)F] | (ES, m/z): $[M+H]^+$ 456. $^1H$ NMR (400 MHz, DMSO-$d_6$) δ 13.48 (s, 1H), 10.40 (s, 1H), 10.26 (s, 1H), 8.33 (d, J = 5.2 Hz, 1H), 8.20 (s, 1H), 8.13 (s, 1H), 7.80 (s, 1H), 7.59 (d, J = 8.4 Hz, 1H), 7.41 (d, J = 5.2 Hz, 1H), 4.22 (t, J = 9.2 Hz, 2H), 3.55 (t, J = 9.2 Hz, 2H), 3.26 (s, 3H). |
| 35E | 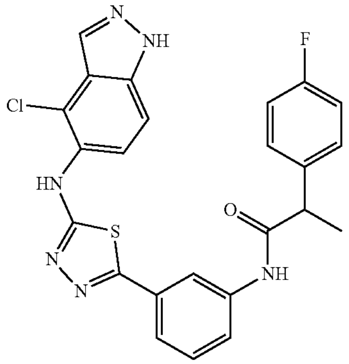 [SMILES: CC(C(=O)Nc1cccc(-c2nnc(Nc3ccc4[nH]ncc4c3Cl)s2)c1)c1ccc(F)cc1] | (ES, m/z): $[M+H]^+$ 493. $^1H$ NMR (400 MHz, DMSO-$d_6$ ppm): δ 13.45 (s, 1H), 10.24 (s, 1H), 10.02 (s, 1H), 8.16-8.06 (m, 2H), 7.82 (d, J = 8.9 Hz, 1H), 7.66 (dt, J = 8.1, 1.6 Hz, 1H), 7.58 (d, J = 8.9 Hz, 1H), 7.51-7.28 (m, 4H), 7.19-7.08 (m, 2H), 3.83 (q, J = 7.0 Hz, 1H), 1.40 (d, J = 7.0 Hz, 3H). |
| 35F | 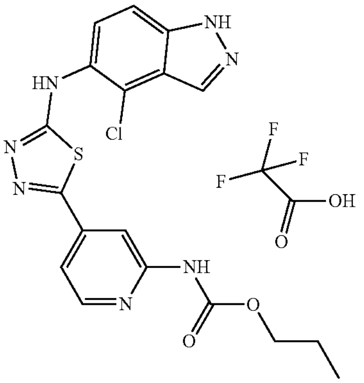 [SMILES: CCCOC(=O)Nc1cc(-c2nnc(Nc3ccc4[nH]ncc4c3Cl)s2)ccn1 ; O=C(O)C(F)(F)F] | (ES, m/z): $[M+H]^+$ 430. $^1H$ NMR (DMSO-$d_6$, 400 MHz, ppm): δ 13.48 (s, 1H), 10.32 (s, 1H), 10.26 (s, 1H), 8.33 (d, J = 5.2 Hz, 1H), 8.21 (s, 1H), 8.14 (s, 1H), 7.81 (d, J = 9.2 Hz, 1H), 7.60 (d, J = 8.8 Hz, 1H), 7.40 (d, J = 4.8 Hz, 1H), 4.07-4.03 (m, 2H), 1.67-1.60 (m, 2H), 1.21 (s, 2H), 0.93 (s, 3H). |

TABLE 3-continued

| Example No. | Chemical Structure | Physical Characterization Data |
|---|---|---|
| 35G | 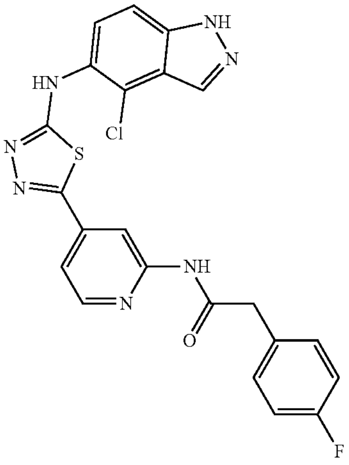 | (ES, m/z): $[M + H]^+$ 480. $^1H$ NMR (400 MHz, DMSO-$d_6$) δ 13.47 (s, 1H), 10.92 (s, 1H), 10.26 (s, 1H), 8.44 (s, 1H), 8.39 (d, J = 5.2 Hz, 1H), 8.13 (s, 1H), 7.78 (d, J = 8.8 Hz, 1H), 7.48 (t, J = 8.0 Hz, 1H), 7.46 (d, J = 1.6 Hz, 1H), 7.37-7.34 (m, 2H), 7.13 (d, J = 8.8 Hz, 2H), 3.72 (s, 2H). |
| 35H | 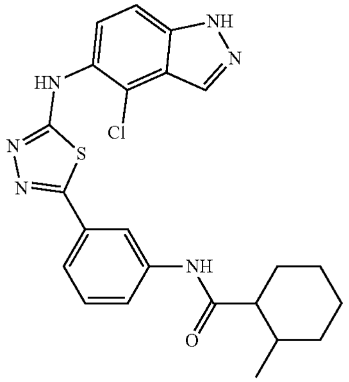 [SMILES: CC1CCCCC1C(=O)Nc1cccc(-c2nnc(Nc3ccc4[nH]ncc4c3Cl)s2)c1] | (ES, m/z): $[M + H]^+$ 467. $^1H$ NMR (400 MHz, DMSO-$d_6$) δ 13.44 (s, 1H), 9.90 (s, 2H), 8.11 (t, J = 5.2 Hz, 2H), 7.83 (d, J = 8.4 Hz, 1H), 7.66-7.57 (m, 2H), 7.43-7.34 (m, 2H), 2.47 (s, 1H), 2.11 (s, 1H), 1.72-1.61 (m, 2H), 1.48 (d, J = 7.6 Hz, 2H), 1.35-1.17 (m, 2H), 0.85 (s, 3H). |
| 35I | 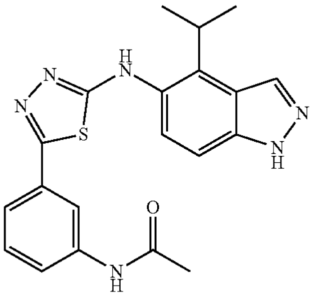 [SMILES: CC(=O)Nc1cccc(-c2nnc(Nc3ccc4[nH]ncc4c3C(C)C)s2)c1] | (ES, m/z): $[M + H]^+$ 393.05. $^1H$ NMR (DMSO-$d_6$, 400 MHz, ppm): δ 13.19 (s, 1H), 10.09 (s, 1H), 8.34 (s, 1H), 8.08 (s, 1H), 7.60 (dd, J = 7.4, 2.3 Hz, 1H), 7.48-7.29 (m, 4H), 3.34-3.24 (m, 1H), 2.05 (s, 3H), 1.41 (d, J = 7.0 Hz, 6H). |
| 35J | 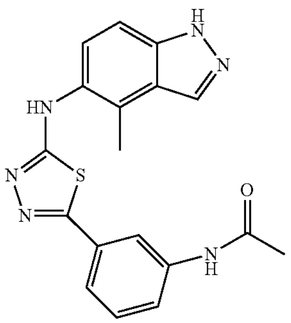 [SMILES: CC(=O)Nc1cccc(-c2nnc(Nc3ccc4[nH]ncc4c3C)s2)c1] | (ES, m/z): $[M + H]^+$ 365. $^1H$ NMR (DMSO-$d_6$, 400 MHz, ppm): δ 13.08 (s, 1H), 10.06 (s, 1H), 9.74 (s, 1H), 8.15 (s, 1H), 8.07 (s, 1H), 7.59 (d, J = 7.6 Hz, 1H), 7.46-7.34 (m, 4H), 2.49-2.48 (m, 3H), 2.03 (s, 3H). |

TABLE 3-continued

| Example No. | Chemical Structure | Physical Characterization Data |
|---|---|---|
| 35K | 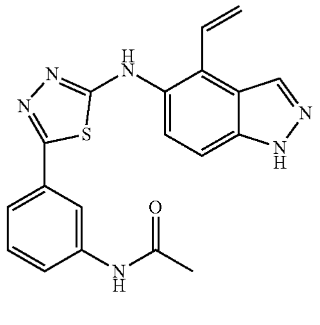 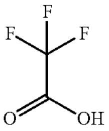 | (ES, m/z): [M + H]$^+$ [M − TFA + H]$^+$ 377.00. $^1$H NMR (DMSO-$d_6$, 400 MHz, ppm): δ 13.33 (s, 1H), 10.10 (s, 1H), 9.94 (s, 1H), 8.38 (s, 1H), 8.08 (s, 1H), 7.67-7.48 (m, 3H), 7.45-7.33 (m, 2H), 7.13 (dd, J = 17.8, 11.5 Hz, 1H), 6.10 (d, J = 17.6 Hz, 1H), 5.64 (d, J = 11.7 Hz, 1H), 2.06 (s, 3H). |
| 35L | 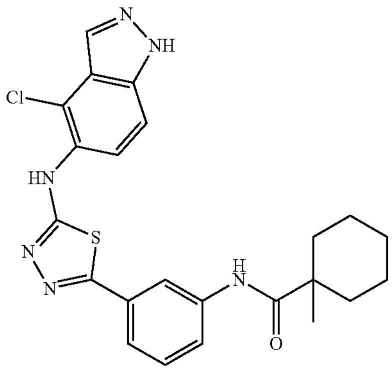 [SMILES: CC1(C(=O)Nc2cccc(-c3nnc(Nc4ccc5[nH]ncc5c4Cl)s3)c2)CCCCC1] | (ES, m/z): [M + H]$^+$ 466.13. $^1$H NMR (DMSO-$d_6$, 400 MHz, ppm): δ 13.49 (s, 1H), 10.06 (s, 1H), 9.36 (s, 1H), 8.15 (d, J = 2.1 Hz, 2H), 7.89-7.79 (m, 2H), 7.61 (d, J = 8.8 Hz, 1H), 7.52-7.37 (m, 2H), 2.08 (d, J = 11.0, 7.3 Hz, 2H), 1.59-1.23 (m, 9H), 1.20 (s, 3H). |
| 35M | 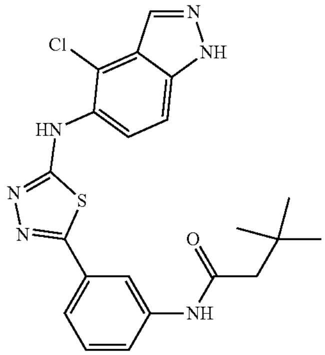 [SMILES: CC(C)(C)CC(=O)Nc1cccc(-c2nnc(Nc3ccc4[nH]ncc4c3Cl)s2)c1] | (ES, m/z): [M + H]$^+$ 441. $^1$H NMR (DMSO-$d_6$, 400 MHz, ppm): δ 13.48 (s, 1H), 10.05 (s, 1H), 10.00 (s, 1H), 8.18-8.13 (m, 2H), 7.87 (d, J = 8.8 Hz, 1H), 7.69 (dt, J = 8.1, 1.5 Hz, 1H), 7.64-7.58 (m, 1H), 7.46 (d, J = 7.7 Hz, 1H), 7.40 (t, J = 7.8 Hz, 1H), 2.21 (s, 2H), 1.04 (s, 9H). |
| 35N | 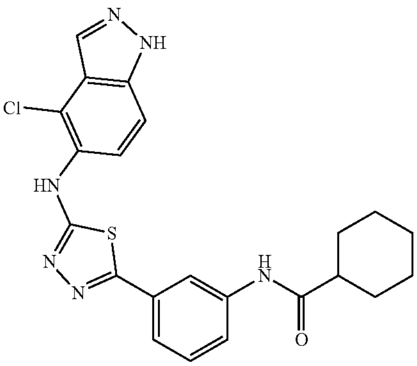 [SMILES: O=C(Nc1cccc(-c2nnc(Nc3ccc4[nH]ncc4c3Cl)s2)c1)C1CCCCC1] | (ES, m/z): [M + H]$^+$ 452.12. $^1$H NMR (DMSO-$d_6$, 400 MHz, ppm): δ 13.45 (s, 1H), 9.99 (d, J = 18.3 Hz, 2H), 8.13 (d, J = 1.5 Hz, 2H), 7.91-7.62 (m, 2H), 7.61-7.34 (m, 3H), 2.37-2.25 (m, 1H), 1.89-1.53 (m, 5H), 1.46-1.12 (m, 6H). |

TABLE 3-continued

| Example No. | Chemical Structure | Physical Characterization Data |
|---|---|---|
| 35O | 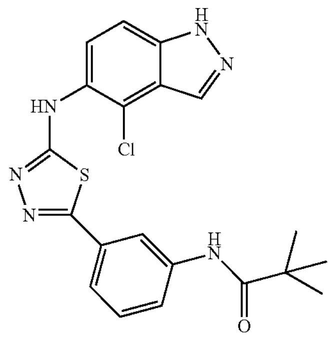 [SMILES: CC(C)(C)C(=O)Nc1cccc(-c2nnc(Nc3ccc4[nH]ncc4c3Cl)s2)c1] | (ES, m/z): $[M + H]^+$ 427. $^1H$ NMR (DMSO-$d_6$, 400 MHz, ppm): δ 13.49 (s, 1H), 10.05 (s, 1H), 9.39 (s, 1H), 8.15 (dd, J = 4.7, 2.9 Hz, 2H), 7.90-7.76 (m, 2H), 7.62 (d, J = 8.8 Hz, 1H), 7.49 (d, J = 7.8 Hz, 1H), 7.40 (t, J = 7.9 Hz, 1H), 1.24 (s, 9H). |
| 35P | 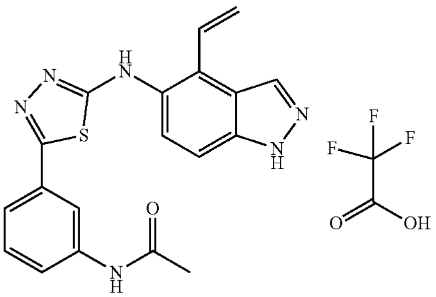 | (ES, m/z): $[M + H]^+$ 377.00. $^1H$ NMR (DMSO-$d_6$, 400 MHz, ppm): δ 13.33 (s, 1H), 10.10 (s, 1H), 9.94 (s, 1H), 8.38 (s, 1H), 8.08 (s, 1H), 7.67-7.48 (m, 3H), 7.45-7.33 (m, 2H), 7.13 (dd, J = 17.8, 11.5 Hz, 1H), 6.10 (d, J = 17.6 Hz, 1H), 5.64 (d, J = 11.7 Hz, 1H), 2.06 (s, 3H). |
| 35Q | 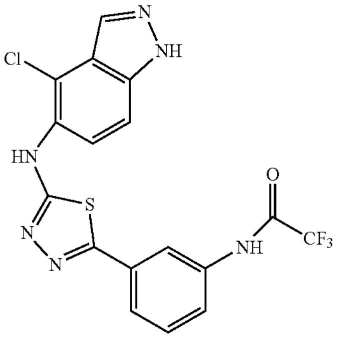 [SMILES: O=C(Nc1cccc(-c2nnc(Nc3ccc4[nH]ncc4c3Cl)s2)c1)C(F)(F)F] | (ES, m/z): $[M + H]^+$ 438.03. $^1H$ NMR (DMSO-$d_6$, 400 MHz, ppm): δ 13.45 (s, 1H), 11.39 (s, 1H), 10.07 (s, 1H), 8.20-8.10 (m, 2H), 7.85 (d, J = 8.9 Hz, 1H), 7.81-7.73 (m, 1H), 7.67-7.55 (m, 2H), 7.51 (m, J = 8.0 Hz, 1H), 1.22 (s, 1H), 1.04 (m, J = 7.0 Hz, 1H). |
| 35R | 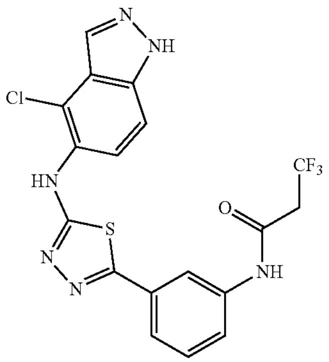 [SMILES: O=C(CC(F)(F)F)Nc1cccc(-c2nnc(Nc3ccc4[nH]ncc4c3Cl)s2)c1] | (ES, m/z): $[M + H]^+$ 452.04. $^1H$ NMR (DMSO-$d_6$, 400 MHz, ppm): δ 13.45 (s, 1H), 10.48 (s, 1H), 10.04 (s, 1H), 8.15-8.06 (m, 2H), 7.85 (d, J = 8.8 Hz, 1H), 7.69-7.55 (m, 2H), 7.54-7.39 (m, 2H), 3.52 (m, J = 11.1 Hz, 2H). |

TABLE 3-continued

| Example No. | Chemical Structure | Physical Characterization Data |
|---|---|---|
| 35S | 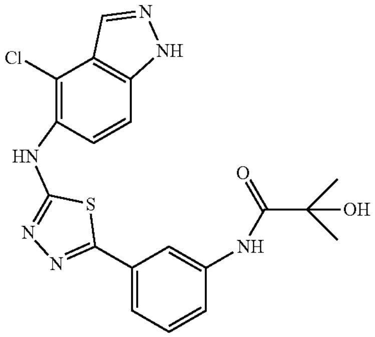 [SMILES: CC(C)(O)C(=O)Nc1cccc(-c2nnc(Nc3ccc4[nH]ncc4c3Cl)s2)c1] | (ES, m/z): [M + H]$^+$ 428.08. $^1$H NMR (DMSO-$d_6$, 400 MHz, ppm): δ 13.45 (s, 1H), 10.02 (s, 1H), 9.76 (s, 1H), 8.26 (s, 1H), 8.13 (s, 1H), 7.87-7.77 (m, 2H), 7.59 (d, J = 8.8 Hz, 1H), 7.50 (d, J = 7.8 Hz, 1H), 7.38 (t, J = 8.0 Hz, 1H), 3.42 (q, J = 7.0 Hz, 1H), 1.34 (s, 6H). |
| 35T | 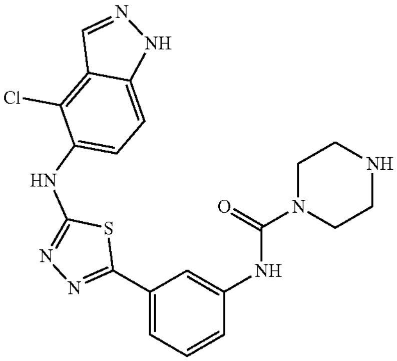 [SMILES: O=C(Nc1cccc(-c2nnc(Nc3ccc4[nH]ncc4c3Cl)s2)c1)N1CCNCC1] | (ES, m/z): [M + H]$^+$ 455. $^1$H NMR (DMSO-$d_6$, 400 MHz, ppm): δ 13.46 (s, 1H), 8.61 (s, 1H), 8.13 (d, J = 1.0 Hz, 1H), 7.94 (t, J = 1.9 Hz, 1H), 7.82 (d, J = 8.9 Hz, 1H), 7.58 (dt, J = 8.9 , 2.1 Hz, 2H), 7.38-7.27 (m, 2H), 3.42 (dt, J = 11.8, 7.0 Hz, 1H), 3.39-3.33 (m, 4H), 2.75-2.62 (m, 4H), 1.04 (s, 1H). |
| 35U | 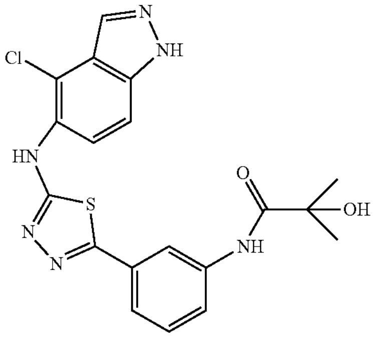 [SMILES: CC(C)(O)C(=O)Nc1cccc(-c2nnc(Nc3ccc4[nH]ncc4c3Cl)s2)c1] | (ES, m/z): [M + H]$^+$ 428.08. $^1$H NMR (DMSO-$d_6$, 400 MHz, ppm): δ 13.45 (s, 1H), 10.02 (s, 1H), 9.76 (s, 1H), 8.26 (s, 1H), 8.13 (s, 1H), 7.87-7.77 (m, 2H), 7.59 (d, J = 8.8 Hz, 1H), 7.50 (d, J = 7.8 Hz, 1H), 7.38 (t, J = 8.0 Hz, 1H), 3.42 (q, J = 7.0 Hz, 1H), 1.34 (s, 6H). |
| 35V | 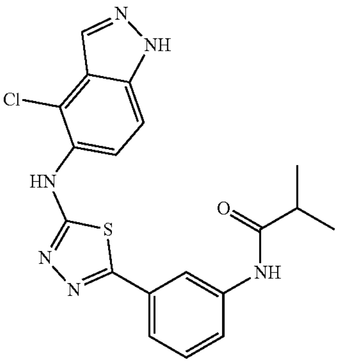 [SMILES: CC(C)C(=O)Nc1cccc(-c2nnc(Nc3ccc4[nH]ncc4c3Cl)s2)c1] | (ES, m/z): [M + H]$^+$ 413. $^1$H NMR (DMSO-$d_6$, 400 MHz, ppm): δ 13.47 (s, 1H), 9.99 (s, 2H), 8.13 (s, 2H), 7.84-7.82 (d, J = 8.8 Hz, 1H), 7.69-7.58 (m, 2H), 7.45-7.36 (m, 2H), 2.62-2.55 (m, 1H), 1.10-1.08 (s, 6H). |

TABLE 3-continued

| Example No. | Chemical Structure | Physical Characterization Data |
|---|---|---|
| 35W | 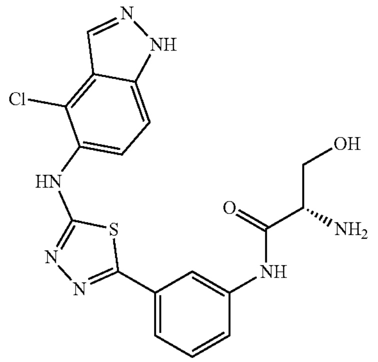 [SMILES: N[C@@H](CO)C(=O)Nc1cccc(-c2nnc(Nc3ccc4[nH]ncc4c3Cl)s2)c1] | (ES, m/z): $[M + H]^+$ 413. $^1H$ NMR ($DMSO-d_6$, 400 MHz, ppm): δ 13.48 (s, 1H), 8.21 (t, J = 1.9 Hz, 1H), 8.14 (d, J = 1.0 Hz, 1H), 7.84 (d, J = 8.9 Hz, 1H), 7.73 (ddd, J = 8.1, 2.1, 1.1 Hz, 1H), 7.60 (dd, J = 8.9, 1.1 Hz, 1H), 7.49 (dt, J = 7.9, 1.3 Hz, 1H), 7.41 (t, J = 7.9 Hz, 1H), 4.85 (s, 1H), 3.56 (q, J = 4.4 Hz, 2H), 3.39 (t, J = 5.4 Hz, 1H). |
| 35X | 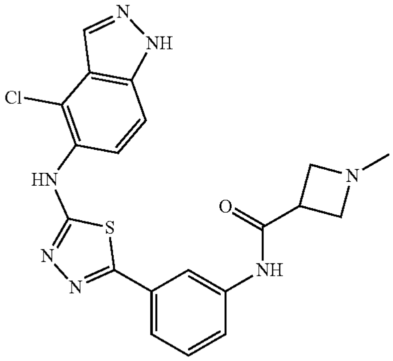 [SMILES: CN1CC(C(=O)Nc2cccc(-c3nnc(Nc4ccc5[nH]ncc5c4Cl)s3)c2)C1] | (ES, m/z): $[M + H]^+$ 439.1. $^1H$ NMR ($DMSO-d_6$, 400 MHz, ppm): δ 13.46 (s, 1H), 10.05 (d, J = 16.2 Hz, 2H), 8.12 (dd, J = 4.2, 2.3 Hz, 2H), 7.83 (d, J = 8.8 Hz, 1H), 7.66 (dt, J = 8.1, 1.6 Hz, 1H), 7.58 (dd, J = 8.9, 1.0 Hz, 1H), 7.45 (dt, J = 7.7, 1.3 Hz, 1H), 7.43-7.30 (m, 1H), 3.43 (t, J = 6.9 Hz, 2H), 3.34 (d, J = 7.2 Hz, 1H), 3.17 (t, J = 6.7 Hz, 2H), 2.20 (s, 3H). |
| 35Y | 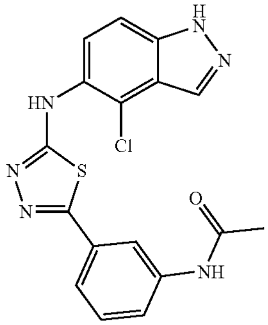 [SMILES: CC(=O)Nc1cccc(-c2nnc(Nc3ccc4[nH]ncc4c3Cl)s2)c1] | (ES, m/z): $[M + H]^+$ 385. $^1H$ NMR ($DMSO-d_6$, 400 MHz, ppm): δ 13.44 (s, 1H), 10.10 (s, 1H), 10.01 (s, 1H), 8.11 (d, J = 7.6 Hz, 2H), 7.85 (d, J = 8.0 Hz, 1H), 7.64-7.56 (m, 2H), 7.44-7.35 (m, 2H), 2.04 (s, 3H). |
| 35Z | 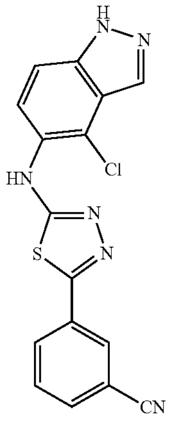 [SMILES: N#Cc1cccc(-c2nnc(Nc3ccc4[nH]ncc4c3Cl)s2)c1] | (ES, m/z): $[M + H]^+$ 352.90. $^1H$ NMR ($DMSO-d_6$, 400 MHz, ppm): δ 8.23 (s, 1H), 8.14 (d, J = 6.8 Hz, 2H), 7.91 (d, J = 8 Hz, 1H), 7.82 (d, J = 8.8 Hz, 1H), 7.66-7.70 (m, 1H), 7.59 (d, J = 9.2 Hz, 1H). |

TABLE 3-continued

| Example No. | Chemical Structure | Physical Characterization Data |
| --- | --- | --- |
| 35AA | 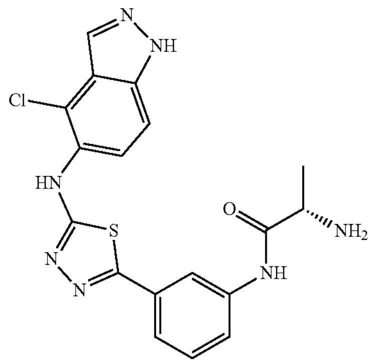 [SMILES: C[C@H](N)C(=O)Nc1cccc(-c2nnc(Nc3ccc4[nH]ncc4c3Cl)s2)c1] | (ES, m/z): $[M + H]^+$ 414. $^1H$ NMR (DMSO-$d_6$, 400 MHz, ppm): δ 13.50 (s, 1H), 8.17-8.13 (m, 2H), 7.84-7.82 (d, 1H), 7.72-7.69 (m, 1H), 7.60-7.57 (m, 1H), 7.48-7.44 (m, 2H), 3.48-3.43 (m, 1H), 1.23-1.21 (d, 3H). |
| 35AB | 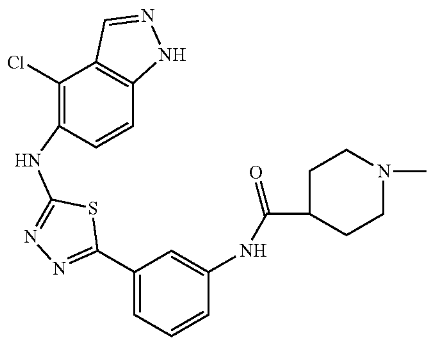 [SMILES: CN1CCC(C(=O)Nc2cccc(-c3nnc(Nc4ccc5[nH]ncc5c4Cl)s3)c2)CC1] | (ES, m/z): $[M + H]^+$ 467.13. $^1H$ NMR (DMSO-$d_6$, 400 MHz, ppm): δ 13.46 (s, 1H), 10.02 (s, 1H), 8.13 (d, J = 1.7 Hz, 1H), 7.83 (d, J = 8.8 Hz, 1H), 7.66 (d, J = 8.1 Hz, 1H), 7.62-7.55 (m, 1H), 7.47-7.41 (m, 1H), 7.37 (t, J = 7.9 Hz, 1H), 2.80 (d, J = 11.1 Hz, 2H), 2.14 (s, 3H), 1.85 (t, J = 11.5 Hz, 2H), 1.74 (d, J = 12.5 Hz, 2H), 1.70-1.57 (m, 2H). |
| 35AC | 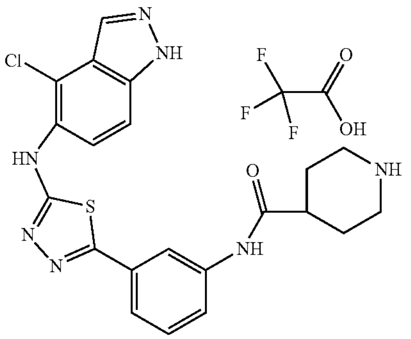 | (ES, m/z): $[M + H]^+$ 453.11. $^1H$ NMR (DMSO-$d_6$, 400 MHz, ppm): δ 10.31 (s, 1H), 10.22 (d, J = 2.2 Hz, 1H), 8.57 (d, J = 11.3 Hz, 1H), 8.33 (d, J = 12.1 Hz, 1H), 8.13 (d, J = 1.7 Hz, 2H), 7.80 (d, J = 8.8 Hz, 1H), 7.67-7.55 (m, 2H), 7.49-7.35 (m, 2H), 3.37-3.28 (m, 2H), 2.98-2.85 (m, 2H), 2.69-2.56 (m, 1H), 1.96 (dd, J = 14.4, 3.7 Hz, 2H), 1.79 (qd, J = 14.6, 13.1, 4.0 Hz, 2H). |
| 35AD | 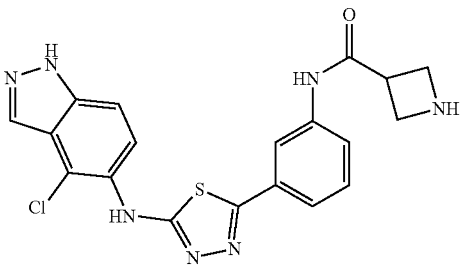 [SMILES: O=C(Nc1cccc(-c2nnc(Nc3ccc4[nH]ncc4c3Cl)s2)c1)C1CNC1] | (ES, m/z): $[M + H]^+$ 426. $^1H$ NMR (DMSO-$d_6$, 400 MHz, ppm): δ 13.46 (s, 1H), 10.19-10.00 (d, 1H), 8.13-8.13 (d, 2H), 7.88-7.82 (m, 1H), 7.68-7.53 (m, 2H), 7.46-7.37 (m, 2H), 3.94-3.49 (m, 6H). |

TABLE 3-continued

| Example No. | Chemical Structure | Physical Characterization Data |
| --- | --- | --- |
| 35AE | 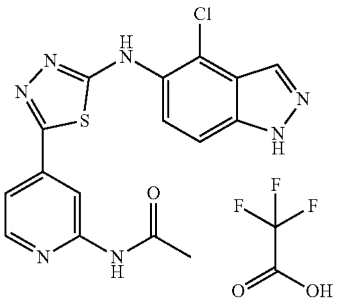 | (ES, m/z): [M − TFA + H]+ 385.95. $^1$H NMR (DMSO-$d_6$, 400 MHz, ppm): δ 13.53 (s, 1H), 10.70 (s, 1H), 10.29 (s, 1H), 8.51 (s, 1H), 8.39 (d, J = 5.2 Hz, 1H), 8.16 (d, J = 1.0 Hz, 1H), 7.84 (d, J = 8.9 Hz, 1H), 7.61 (dd, J = 8.9, 1.0 Hz, 1H), 7.47 (dd, J = 5.3, 1.6 Hz, 1H), 2.12 (s, 3H). |
| 35AF | 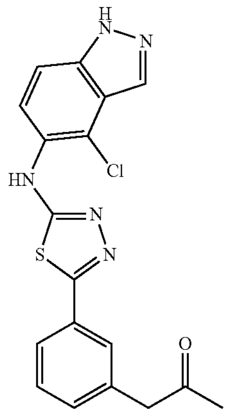 [SMILES: CC(=O)Cc1cccc(-c2nnc(Nc3ccc4[nH]ncc4c3Cl)s2)c1] | (ES, m/z): [M + H]$^+$ 384.05. $^1$H NMR (DMSO-$d_6$, 400 MHz, ppm): δ 13.44 (s, 1H), 10.01 (s, 1H), 8.12 (s, 1H), 7.82 (d, J = 8.4 Hz, 1H), 7.57-7.67 (m, 3H), 7.39-7.43 (m, 1H), 7.25 (d, J = 7.6 Hz, 1H), 3.85 (s, 2H), 2.15 (s, 3H). |
| 35AG | 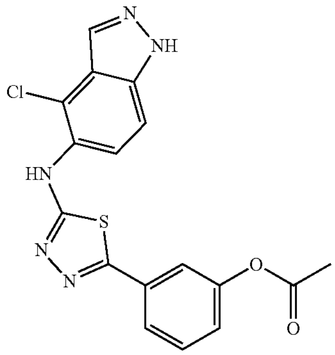 [SMILES: CC(=O)Oc1cccc(-c2nnc(Nc3ccc4[nH]ncc4c3Cl)s2)c1] | (ES, m/z): [M + H]$^+$ 386. $^1$H NMR (DMSO-$d_6$, 400 MHz, ppm): δ 13.45 (s, 1H), 10.08 (s, 1H), 8.12 (s, 1H), 7.84-7.82 (d, 1H), 7.68-7.66 (d, 1H), 7.59-7.57 (m, 2H), 7.53-7.49 (m, 1H), 7.23-7.20 (m, 1H), 2.31 (s, 3H). |
| 35AH | 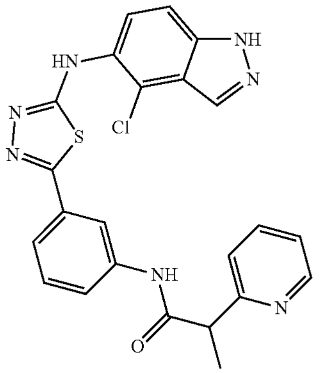 [SMILES: CC(C(=O)Nc1cccc(-c2nnc(Nc3ccc4[nH]ncc4c3Cl)s2)c1)c1ccccn1] | (ES, m/z): [M + H]$^+$ 476. $^1$H NMR (DMSO-$d_6$, 400 MHz, ppm): δ 13.44 (s, 1H), 10.30 (s, 1H), 10.00 (s, 1H), 8.50 (d, J = 4.4 Hz, 1H), 8.12 (d, J = 5.2 Hz, 2H), 7.83-7.74 (m, 2H), 7.67 (d, J = 8.4 Hz, 1H), 7.57 (d, J = 9.2 Hz, 1H), 7.46-7.36 (m, 3H), 7.27-7.24 (m, 1H), 4.01 (d, J = 7.2 Hz, 1H), 1.47 (d, J = 7.2 Hz, 3H). |

TABLE 3-continued
| Example No. | Chemical Structure | Physical Characterization Data |
| --- | --- | --- |
| 35AI | 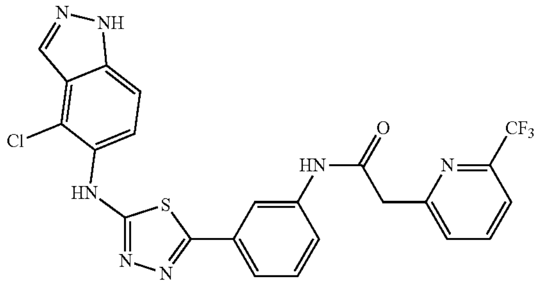 [SMILES: O=C(Cc1cccc(C(F)(F)F)n1)Nc1cccc(-c2nnc(Nc3ccc4[nH]ncc4c3Cl)s2)c1] | (ES, m/z): $[M + H]^+$ 530. $^1H$ NMR (DMSO-$d_6$, 400 MHz, ppm): δ 10.51 (1H, s), 10.03 (1H, s), 8.1-8.06 (3H, m), 7.86-7.75 (3H, m), 7.68-7.58 (2H, m), 7.50-7.40 (2H, m), 4.01 (2H, s). |
| 35AJ | 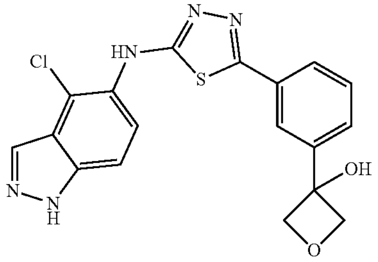 [SMILES: OC1(c2cccc(-c3nnc(Nc4ccc5[nH]ncc5c4Cl)s3)c2)COC1] | (ES, m/z): $[M + H]^+$ 400.05. $^1H$ NMR (DMSO-$d_6$, 400 MHz, ppm): δ 13.45 (s, 1H), 10.03 (s, 1H), 8.13 (s, 1H), 7.99 (s, 1H), 7.83 (d, J = 8.4 Hz, 1H), 7.70-7.73 (m, 2H), 7.59 (d, J = 8.8 Hz, 1H), 7.49-7.53 (m, 1H), 6.49 (s, 1H), 4.78 (d, J = 6.8 Hz, 2H), 4.69 (d, J = 6.8 Hz, 1H). |
| 35AK | 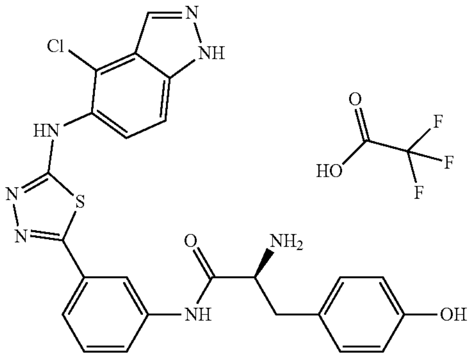 [SMILES: N[C@@H](Cc1ccc(O)cc1)C(=O)Nc1cccc(-c2nnc(Nc3ccc4[nH]ncc4c3Cl)s2)c1 ; O=C(O)C(F)(F)F] | (ES, m/z): $[M + H]^+$ 506. $^1H$ NMR (DMSO-$d_6$, 400 MHz, ppm): δ 13.47-13.43 (s, 1H), 10.53 (s, 1H), 10.05 (s, 1H), 9.35 (s, 1H), 8.25-8.06 (m, 5H), 7.84-7.82 (d, 1H), 7.68-7.43 (m, 4H), 7.09-7.03 (m, 2H), 6.73-6.68 (m, 2H), 4.05-4.04 (s, 1H), 3.09-2.93 (m, 2H). |
| 35AL | 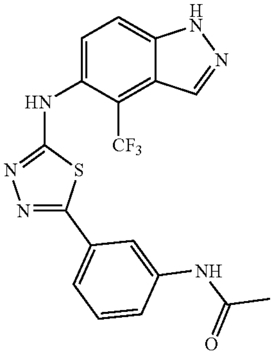 [SMILES: CC(=O)Nc1cccc(-c2nnc(Nc3ccc4[nH]ncc4c3C(F)(F)F)s2)c1] | (ES, m/z): $[M + H]^+$ 419. $^1H$ NMR (DMSO-$d_6$, 400 MHz, ppm): δ 13.64 (s, 1H), 10.10-9.90 (m, 2H), 8.16-8.09 (m, 2H), 7.91-7.89 (m, 1H), 7.67-7.61 (m, 2H), 7.39-7.35 (m, 2H), 2.06 (s, 3H). |

TABLE 3-continued

| Example No. | Chemical Structure | Physical Characterization Data |
| --- | --- | --- |
| 35AM | 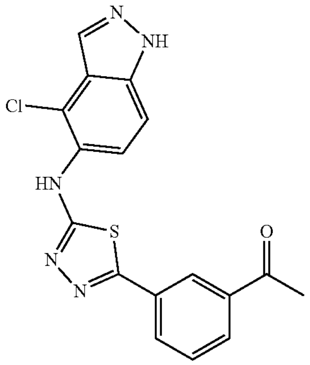 [SMILES: CC(=O)c1cccc(-c2nnc(Nc3ccc4[nH]ncc4c3Cl)s2)c1] | (ES, m/z): $[M + H]^+$ 370. $^1H$ NMR (DMSO-$d_6$, 400 MHz, ppm): δ 13.46 (s, 1H), 10.12 (s, 1H), 8.26 (s, 1H), 8.13 (s, 1H), 8.04-8.01 (m, 2H), 7.84-7.82 (d, 1H), 7.65-7.58 (m, 2H), 2.62 (s, 3H). |
| 35AN | 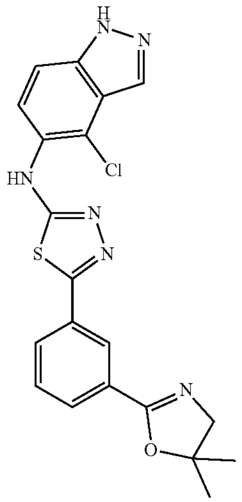 [SMILES: CC1(C)CN=C(c2cccc(-c3nnc(Nc4ccc5[nH]ncc5c4Cl)s3)c2)O1] | (ES, m/z): $[M + H]^+$ 425.00. $^1H$ NMR (DMSO-$d_6$, 400 MHz, ppm): δ 13.47 (s, 1H), 10.10 (s, 1H), 8.20 (s, 1H), 8.12 (s, 1H), 7.87-7.92 (m, 2H), 7.82 (d, J = 8.8 Hz, 1H), 7.54-7.59 (m, 2H), 3.71 (s, 2H), 1.43 (s, 6H). |
| 35AO | 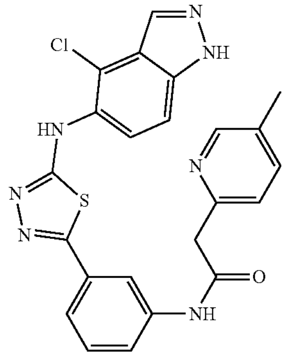 [SMILES: Cc1ccc(CC(=O)Nc2cccc(-c3nnc(Nc4ccc5[nH]ncc5c4Cl)s3)c2)nc1] | (ES, m/z): $[M + H]^+$ 476. $^1H$ NMR (DMSO-$d_6$, 400 MHz, ppm): δ 13.44 (s, 1H), 10.39 (s, 1H), 10.01 (s, 1H), 8.32 (s, 1H), 8.12 (d, J = 5.2 Hz, 2H), 7.84 (d, J = 8.4 Hz, 1H), 7.65 (d, J = 8.0 Hz, 1H), 7.58-7.54 (m, 2H), 7.46-7.37 (m, 2H), 7.28 (d, J = 8.0 Hz, 1H), 3.79 (s, 2H), 2.25 (m, 3H). |
| 35AP | 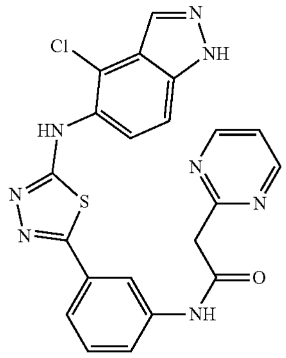 [SMILES: O=C(Cc1ncccn1)Nc1cccc(-c2nnc(Nc3ccc4[nH]ncc4c3Cl)s2)c1] | (ES, m/z): $[M + H]^+$ 463. $^1H$ NMR (DMSO-$d_6$, 400 MHz, ppm): δ 13.44 (s, 1H), 10.45 (s, 1H), 9.99 (s, 1H), 8.76 (d, J = 5.2 Hz, 2H), 8.13 (d, J = 8.4 Hz, 2H), 7.83 (d, J = 8.8 Hz, 1H), 7.66-7.56 (m, 2H), 7.47-7.38 (m, 3H), 3.99 (s, 2H). |

TABLE 3-continued
| Example No. | Chemical Structure | Physical Characterization Data |
|---|---|---|
| 35AQ | 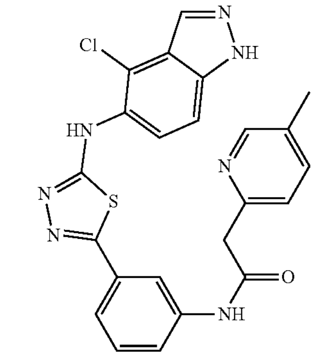 [SMILES: Cc1ccc(CC(=O)Nc2cccc(-c3nnc(Nc4ccc5[nH]ncc5c4Cl)s3)c2)nc1] | (ES, m/z): [M + H]$^+$ 476. $^1$H NMR (DMSO-$d_6$, 400 MHz, ppm): δ 13.44 (s, 1H), 10.39 (s, 1H), 10.01 (s, 1H), 8.32 (s, 1H), 8.12 (d, J = 5.2 Hz, 2H), 7.84 (d, J = 8.4 Hz, 1H), 7.65 (d, J = 8.0 Hz, 1H), 7.58-7.54 (m, 2H), 7.46-7.37 (m, 2H), 7.28 (d, J = 8.0 Hz, 1H), 3.79 (s, 2H), 2.25 (m, 3H). |
| 35AR | 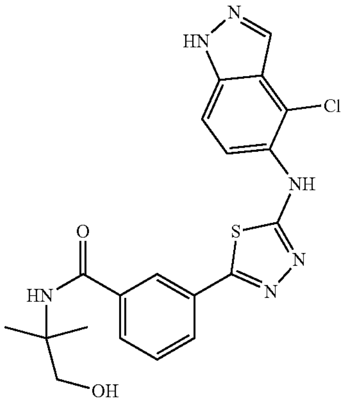 [SMILES: CC(C)(CO)NC(=O)c1cccc(-c2nnc(Nc3ccc4[nH]ncc4c3Cl)s2)c1] | (ES, m/z): [M + H]$^+$ 443.2. $^1$H NMR (DMSO-$d_6$, 400 MHz, ppm): δ 13.39 (s, 1H), 8.11 (s, 2H), 7.89 (d, J = 6.8 Hz, 1H), 7.80 (d, J = 9.2 Hz, 1H), 7.51-7.58 (m, 2H), 4.87-4.90 (m, 1H), 3.53 (d, J = 6 Hz, 2H), 1.32 (m, 6H). |
| 35AS | 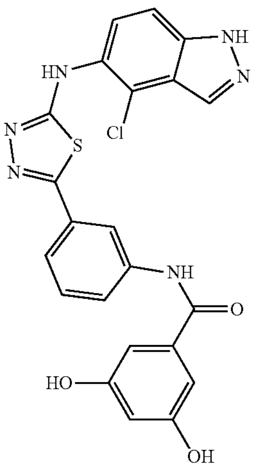 [SMILES: O=C(Nc1cccc(-c2nnc(Nc3ccc4[nH]ncc4c3Cl)s2)c1)c1cc(O)cc(O)c1] | (ES, m/z): [M + H]$^+$ 479. $^1$H NMR (DMSO-$d_6$, 400 MHz, ppm): δ 13.45 (s, 1H), 10.31 (s, 1H), 9.67 (s, 2H), 8.26 (d, J = 1.6 Hz, 1H), 8.13 (s, 1H), 7.90-7.82 (m, 2H), 7.60-7.43 (m, 3H), 6.71 (s, 1H), 6.53 (s, 1H). |

TABLE 3-continued
| Example No. | Chemical Structure | Physical Characterization Data |
| --- | --- | --- |
| 35AU | 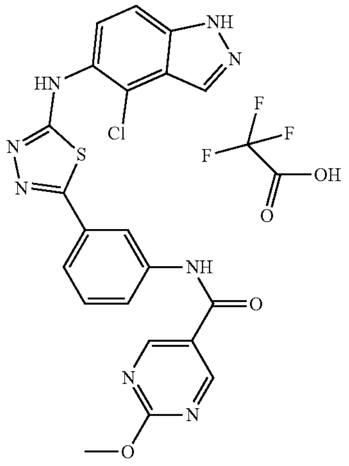 | (ES, m/z): $[M + H]^+$ 479. $^1H$ NMR ($DMSO-d_6$, 400 MHz, ppm): δ 10.53 (s, 1H), 10.04 (s, 1H), 9.11 (s, 2H), 8.24 (s, 1H), 8.13 (s, 1H), 7.85 (d, J = 18.8 Hz, 1H), 7.60-7.45 (m, 3H), 4.00 (s, 3H). |
| 35AV | 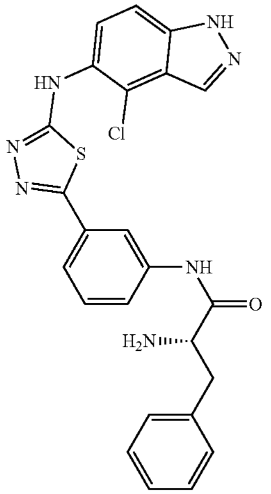 [SMILES: N[C@@H](Cc1ccccc1)C(=O)Nc1cccc(-c2nnc(Nc3ccc4[nH]ncc4c3Cl)s2)c1] | (ES, m/z): $[M + H]^+$ 490. $^1H$ NMR ($DMSO-d_6$, 400 MHz, ppm): δ 13.44 (s, 1H), 10.48 (s, 1H), 10.02 (s, 1H), 8.12 (d, J = 7.2 Hz, 2H), 7.83 (d, J = 8.8 Hz, 1H), 7.67 (d, J = 8.0 Hz, 1H), 7.58 (d, J = 8.8 Hz, 1H), 7.47-7.41 (m, 1H), 7.38 (d, J = 8.0 Hz, 1H), 7.27-7.22 (m, 4H), 7.19-7.14 (m, 1H), 3.58-3.55 (m, 1H), 3.01-2.96 (m, 1H), 2.74-2.69 (m, 1H). |
| 35AW | 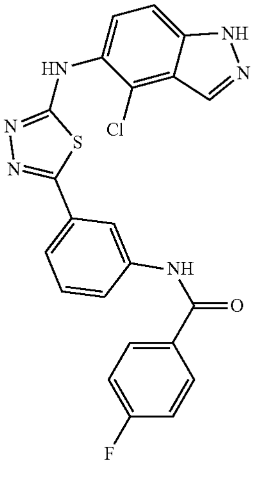 [SMILES: O=C(Nc1cccc(-c2nnc(Nc3ccc4[nH]ncc4c3Cl)s2)c1)c1ccc(F)cc1] | (ES, m/z): $[M + H]^+$ 465. $^1H$ NMR ($DMSO-d_6$, 400 MHz, ppm): δ 13.45 (s, 1H), 10.41 (s, 1H), 10.03 (s, 1H), 8.26 (s, 1H), 8.12-8.02 (m, 3H), 7.90-7.83 (m, 2H), 7.60-7.34 (m, 5H). |

TABLE 3-continued
| Example No. | Chemical Structure | Physical Characterization Data |
| --- | --- | --- |
| 35AX | 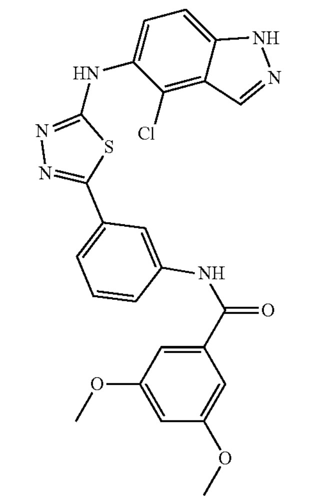 | (ES, m/z): [M + H]+ 477. $^1$H NMR (DMSO-$d_6$, 400 MHz, ppm): δ 13.45 (s, 1H), 10.31 (s, 1H), 10.02 (s, 1H), 8.26 (d, J = 1.6 Hz, 1H), 8.13 (s, 1H), 7.90-7.82 (m, 2H), 7.60-7.43 (m, 3H), 7.11 (d, J = 2 Hz, 2H), 6.71 (t, J = 4.4 Hz, 1H), 3.81 (s, 6H). |
| 35AY | 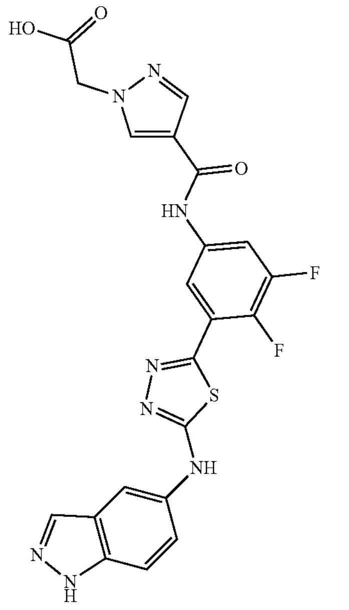 [SMILES: O=C(O)Cn1cc(C(=O)Nc2cc(F)c(F)c(-c3nnc(Nc4ccc5[nH]ncc5c4)s3)c2)cn1] | (ES, m/z): [M + H]+ 497.10. $^1$H NMR (DMSO-$d_6$, 400 MHz, ppm): δ 10.65 (s, 1H), 10.22 (s, 1H), 8.35 (s, 1H), 8.23 (d, J = 1.2 Hz, 2H), 8.06-8.13 (m, 2H), 7.91 (s, 1H), 7.55 (d, J = 8.8 Hz, 1H), 7.42-7.44 (m, 1H), 4.54 (s, 2H). |
| 35AZ | 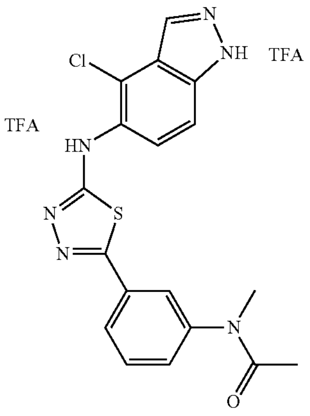 [SMILES: CC(=O)N(C)c1cccc(-c2nnc(Nc3ccc4[nH]ncc4c3Cl)s2)c1] | (ES, m/z): [M + H]+ 399. $^1$H NMR (DMSO-$d_6$, 400 MHz, ppm): δ 13.60 (s, 1H), 11.00 (s, 1H), 10.37 (s, 1H), 8.23-8.13 (m, 2H), 7.77 (d, J = 8.6 Hz, 2H), 7.71-7.57 (m, 2H), 7.50 (d, J = 7.9 Hz, 1H), 7.08 (s, 1H), 4.00 (s, 3H), 2.08 (s, 3H). |

TABLE 3-continued

| Example No. | Chemical Structure | Physical Characterization Data |
|---|---|---|
| 35BA | 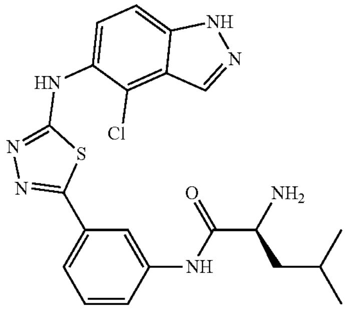 [SMILES: CC(C)C[C@H](N)C(=O)Nc1cccc(-c2nnc(Nc3ccc4[nH]ncc4c3Cl)s2)c1] | (ES, m/z): $[M + H]^+$ 456. $^1$H NMR ($DMSO-d_6$, 400 MHz, ppm): δ 13.47 (s, 1H), 8.16 (t, J = 1.9 Hz, 1H), 8.13 (d, J = 1.0 Hz, 1H), 7.83 (d, J = 8.9 Hz, 1H), 7.74-7.69 (m, 1H), 7.58 (dd, J = 8.8, 1.0 Hz, 1H), 7.46 (dt, J = 7.8, 1.3 Hz, 1H), 7.39 (t, J = 7.9 Hz, 1H), 3.34-3.30 (m, 1H), 1.74 (ddt, J = 14.7, 12.9, 6.4 Hz, 1H), 1.46 (ddd, J = 13.6, 8.2, 5.5 Hz, 1H), 1.32 (ddd, J = 13.3, 8.8, 5.8 Hz, 1H), 0.88 (dd, J = 10.3, 6.6 Hz, 6H). |
| 35BB | 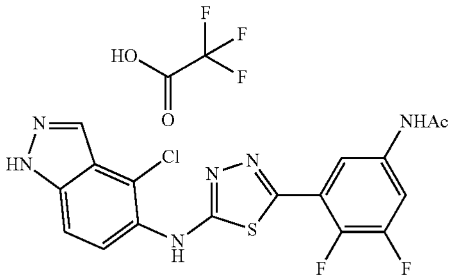 | (ES, m/z): $[M + H]^+$ 421.2. $^1$H NMR ($DMSO-d_6$, 400 MHz, ppm): δ 13.47 (s, 1H), 10.33 (s, 1H), 10.16 (s, 1H), 8.14 (s, 1H), 8.00-8.02 (m, 1H), 7.84-7.90 (m, 2H), 7.59 (d, J = 9.2 Hz, H), 2.06 (s, 3H). |
| 35BC | 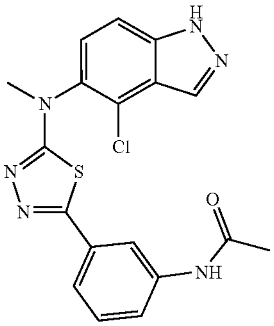 [SMILES: CC(=O)Nc1cccc(-c2nnc(N(C)c3ccc4[nH]ncc4c3Cl)s2)c1] | (ES, m/z): $[M + H]^+$ 399. $^1$H NMR ($DMSO-d_6$, 400 MHz, ppm): δ 13.68 (s, 1H), 10.05 (s, 1H), 8.25 (d, J = 1.0 Hz, 1H), 8.03 (q, J = 1.4 Hz, 1H), 7.69 (dd, J = 8.6, 1.0 Hz, 1H), 7.63-7.55 (m, 2H), 7.35-7.28 (m, 2H), 3.50 (s, 3H), 2.01 (s, 3H). |
| 35BD | 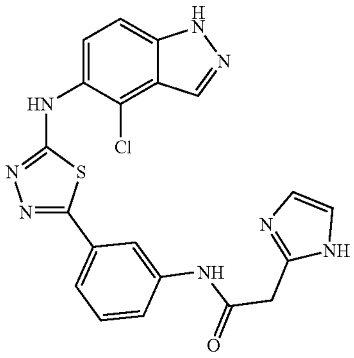 [SMILES: O=C(Cc1ncc[nH]1)Nc1cccc(-c2nnc(Nc3ccc4[nH]ncc4c3Cl)s2)c1] | (ES, m/z): $[M + H]^+$ 451. $^1$H NMR ($DMSO-d_6$, 400 MHz, pm): δ 11.86 (s, 1H), 10.46 (s, 1H), 8.12 (d, J = 6.8 Hz, 2H), 7.82 (d, J = 8.8 Hz, 1H), 7.67-7.61 (m, 1H), 7.56 (d, J = 8.9 Hz, 1H), 7.49-7.43 (m, 1H), 7.40 (t, J = 7.9 Hz, 1H), 7.02 (s, 1H), 6.80 (s, 1H), 3.74 (s, 2H). |

TABLE 3-continued

| Example No. | Chemical Structure | Physical Characterization Data |
|---|---|---|
| 35BE | 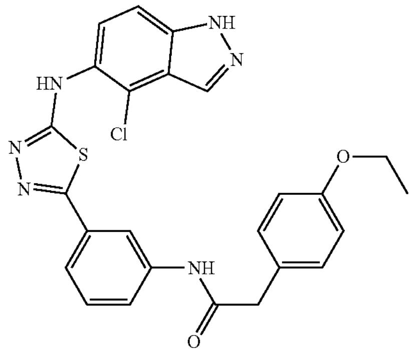 [SMILES: CCOc1ccc(CC(=O)Nc2cccc(-c3nnc(Nc4ccc5[nH]ncc5c4Cl)s3)c2)cc1] | (ES, m/z): $[M + H]^+$ 505. $^1H$ NMR ($DMSO-d_6$, 400 MHz, ppm): δ 13.46 (s, 1H), 10.28 (s, 1H), 9.98 (s, 1H), 8.15-8.08 (m, 2H), 7.83 (d, J = 8.8 Hz, 1H), 7.66 (dt, J = 7.9, 1.5 Hz, 1H), 7.58 (dd, J = 8.9, 1.0 Hz, 1H), 7.44 (dt, J = 8.0, 1.4 Hz, 1H), 7.38 (t, J = 7.9 Hz, 1H), 7.26-7.19 (m, 2H), 6.89-6.82 (m, 2H), 3.97 (q, J = 7.0 Hz, 2H), 3.55 (s, 2H), 1.29 (t, J = 7.0 Hz, 3H). |
| 35BF | 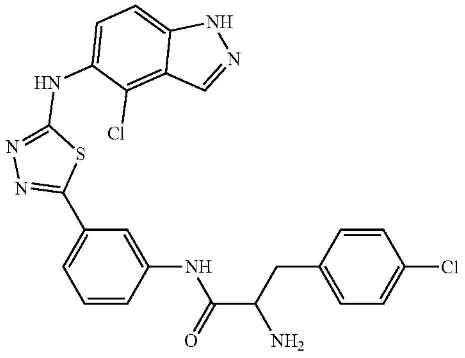 [SMILES: NC(Cc1ccc(Cl)cc1)C(=O)Nc1cccc(-c2nnc(Nc3ccc4[nH]ncc4c3Cl)s2)c1] | (ES, m/z): $[M + H]^+$ 524. $^1H$ NMR ($DMSO-d_6$, 400 MHz, ppm): δ 13.47 (s, 1H), 8.16-8.09 (m, 2H), 7.83 (d, J = 8.9 Hz, 1H), 7.71-7.64 (m, 1H), 7.59 (dd, J = 8.8, 1.0 Hz, 1H), 7.46 (dt, J = 7.8, 1.3 Hz, 1H), 7.39 (t, J = 7.9 Hz, 1H), 7.33-7.29 (m, 2H), 7.25 (d, J = 8.5 Hz, 2H), 3.54 (dd, J = 8.0, 5.5 Hz, 1H), 2.97 (dd, J = 13.5, 5.4 Hz, 1H), 2.72 (dd, J = 13.4, 8.0 Hz, 1H). |
| 35BG | 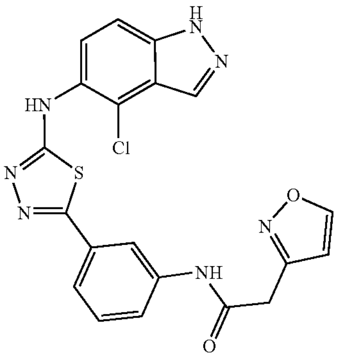 [SMILES: O=C(Cc1ccon1)Nc1cccc(-c2nnc(Nc3ccc4[nH]ncc4c3Cl)s2)c1] | (ES, m/z): $[M + H]^+$ 452. $^1H$ NMR ($DMSO-d_6$, 400 MHz, ppm): δ 13.43 (s, 1H), 10.48 (s, 1H), 10.01 (s, 1H), 8.85 (d, J = 1.6 Hz, 1H), 8.12 (d, J = 1.9 Hz, 2H), 7.83 (d, J = 8.8 Hz, 1H), 7.64 (dt, J = 8.0, 1.5 Hz, 1H), 7.57 (dd, J = 8.8, 1.0 Hz, 1H), 7.47 (dt, J = 7.8, 1.4 Hz, 1H), 7.41 (t, J = 7.9 Hz, 1H), 6.59 (d, J = 1.7 Hz, 1H), 3.82 (s, 2H). |
| 35BH | 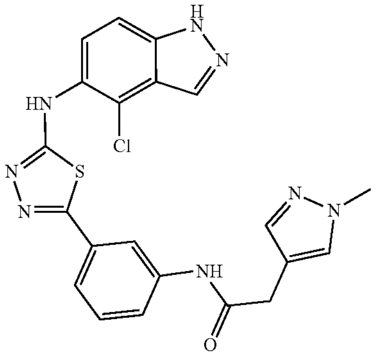 [SMILES: Cn1cc(CC(=O)Nc2cccc(-c3nnc(Nc4ccc5[nH]ncc5c4Cl)s3)c2)cn1] | (ES, m/z): $[M + H]^+$ 465. $^1H$ NMR ($DMSO-d_6$, 400 MHz, ppm): δ 13.47 (s, 1H), 10.22 (s, 1H), 10.02 (s, 1H), 8.18-8.07 (m, 2H), 7.83 (d, J = 8.9 Hz, 1H), 7.65 (dt, J = 8.1, 1.5 Hz, 1H), 7.61-7.56 (m, 2H), 7.48-7.35 (m, 2H), 7.32 (s, 1H), 3.77 (s, 3H), 3.45 (s, 2H). |

TABLE 3-continued

| Example No. | Chemical Structure | Physical Characterization Data |
|---|---|---|
| 35BI | 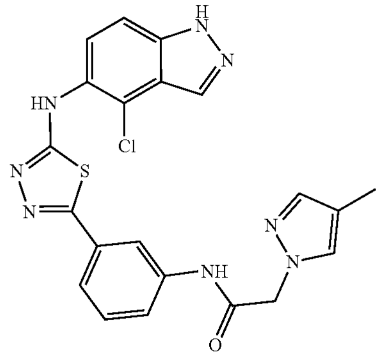 [SMILES: Cc1cnn(CC(=O)Nc2cccc(-c3nnc(Nc4ccc5[nH]ncc5c4Cl)s3)c2)c1] | (ES, m/z): [M + H]$^+$ 465. $^1$H NMR (DMSO-$d_6$, 400 MHz, ppm): δ 13.46 (s, 1H), 10.45 (s, 1H), 8.16-8.07 (m, 2H), 7.83 (d, J = 8.9 Hz, 1H), 7.64 (dt, J = 8.0, 1.5 Hz, 1H), 7.58 (dd, J = 8.9, 1.0 Hz, 1H), 7.51 (s, 1H), 7.48 (dt, J = 7.9, 1.3 Hz, 1H), 7.42 (t, J = 7.9 Hz, 1H), 7.24 (s, 1H), 4.93 (s, 2H), 2.01 (s, 3H). |
| 35BJ | 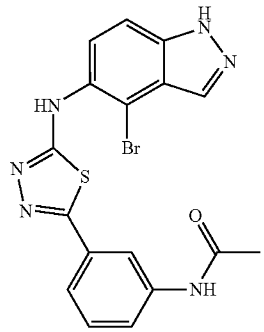 [SMILES: CC(=O)Nc1cccc(-c2nnc(Nc3ccc4[nH]ncc4c3Br)s2)c1] | (ES, m/z): [M + H]$^+$ 428.01. $^1$H NMR (DMSO-$d_6$, 400 MHz, ppm): δ 13.48 (s, 1H), 10.10 (s, 1H), 9.95 (s, 1H), 8.12-8.02 (m, 2H), 7.71 (d, J = 8.8 Hz, 1H), 7.62 (td, J = 5.8, 2.8 Hz, 2H), 7.39 (dt, J = 15.6, 7.8 Hz, 2H), 2.04 (s, 3H). |
| 35BK | 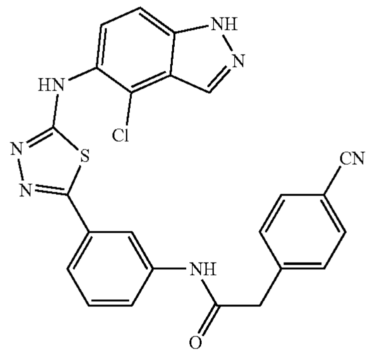 [SMILES: N#Cc1ccc(CC(=O)Nc2cccc(-c3nnc(Nc4ccc5[nH]ncc5c4Cl)s3)c2)cc1] | ES, m/z): [M + H]$^+$ 486. $^1$H NMR (DMSO-$d_6$, 400 MHz, ppm): δ 13.50 (s, 1H), 10.47 (s, 1H), 10.08 (s, 1H), 8.11 (d, J = 7.0 Hz, 2H), 7.85-7.79 (m, 2H), 7.78 (s, 1H), 7.65 (d, J = 8.0 Hz, 1H), 7.58 (d, J = 8.9 Hz, 1H), 7.53 (d, J = 7.9 Hz, 2H), 7.46 (d, J = 7.7 Hz, 1H), 7.39 (t, J = 7.9 Hz, 1H), 3.79 (s, 2H). |
| 35BL | 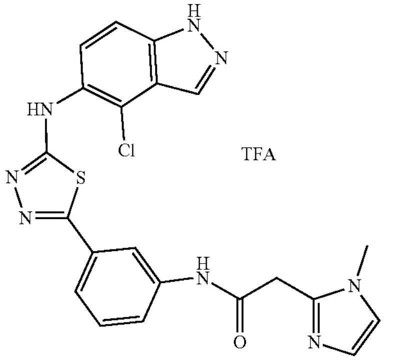 [SMILES: Cn1ccnc1CC(=O)Nc1cccc(-c2nnc(Nc3ccc4[nH]ncc4c3Cl)s2)c1] | (ES, m/z): [M + H]$^+$ 465. $^1$H NMR (DMSO-$d_6$, 400 MHz, ppm): δ 10.50 (s, 1H), 8.12 (s, 2H), 7.83 (d, J = 8.8 Hz, 1H), 7.64-7.56 (m, 2H), 7.47-7.38 (m, 2H), 7.06 (s, 1H), 6.76 (s, 1H), 3.83 (s, 2H), 3.61 (s, 3H). |

TABLE 3-continued
| Example No. | Chemical Structure | Physical Characterization Data |
|---|---|---|
| 35BM | 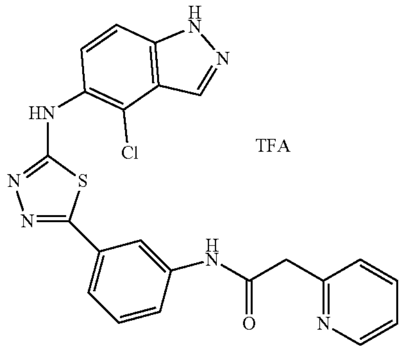 TFA | (ES, m/z): $[M + H]^+$ 462. $^1H$ NMR (DMSO-$d_6$, 400 MHz, ppm): δ 13.44 (s, 1H), 10.42 (s, 1H), 10.01 (s, 1H), 8.48 (d, J = 4 Hz, 1H), 8.14-8.12 (m, 2H), 7.85-7.83 (m, 1H), 7.77-7.72 (m, 1H), 7.67-7.65 (m, 1H), 7.59-7.56 (m, 1H), 7.47-7.38 (m, 3H), 7.27-7.24 (m, 1H), 3.85 (s, 2H). |
| 35BN | 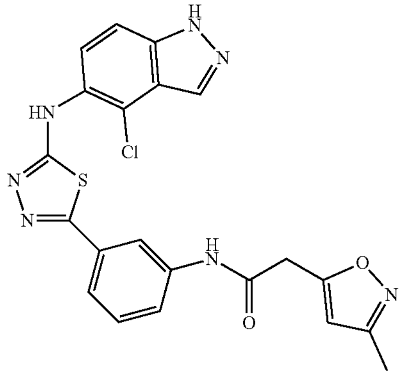 | (ES, m/z): $[M + H]^+$ 466. $^1H$ NMR (DMSO-$d_6$, 400 MHz, ppm): δ 13.44 (s, 1H), 10.47 (s, 1H), 10.02 (s, 1H), 8.11 (d, J = 6.4 Hz, 2H), 7.85-7.83 (m, 1H), 7.65-7.57 (m, 2H), 7.49-7.39 (m, 2H), 6.27 (s, 1H), 3.89 (s, 2H), 2.19 (s, 3H). |
| 35BO | 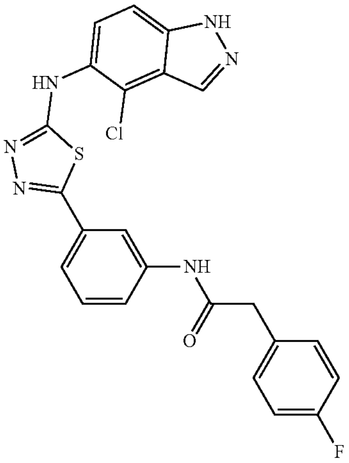 | (ES, m/z): $[M + H]^+$ 479. $^1H$ NMR (DMSO-$d_6$, 400 MHz, ppm): δ 13.45 (s, 1H), 10.34 (s, 1H), 10.02 (s, 1H), 8.11 (d, J = 4.8 Hz, 2H), 7.82 (d, J = 8.4 Hz, 1H), 7.65 (d, J = 8.0 Hz, 1H), 7.57 (d, J = 9.2 Hz, 1H), 7.46-7.33 (m, 4H), 6.52 (s, 2H), 3.64 (s, 2H). |

TABLE 3-continued
| Example No. | Chemical Structure | Physical Characterization Data |
|---|---|---|
| 35BP | 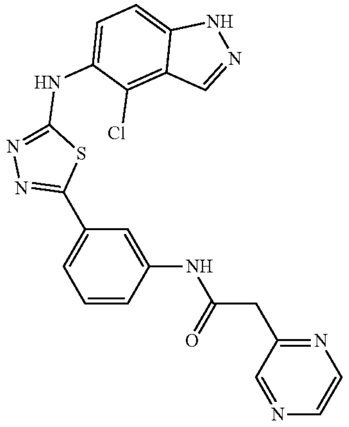 [SMILES: O=C(Cc1cnccn1)Nc1cccc(-c2nnc(Nc3ccc4[nH]ncc4c3Cl)s2)c1] | (ES, m/z): $[M+H]^+$ 465. $^1H$ NMR ($DMSO-d_6$, 400 MHz, ppm): δ 13.44 (s, 1H), 10.48 (s, 1H), 10.02 (s, 1H), 8.66 (s, 1H), 8.53 (t, J = 18.8 Hz, 1H), 8.12 (d, J = 7.2 Hz, 2H), 7.83 (d, J = 8.4 Hz, 1H), 7.65 (d, J = 8.0 Hz, 1H), 7.57 (d, J = 8.8 Hz, 1H), 7.47-7.38 (m, 2H), 3.95 (s, 2H). |
| 35BQ | 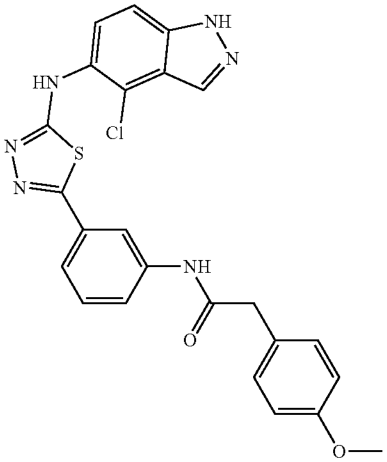 [SMILES: COc1ccc(CC(=O)Nc2cccc(-c3nnc(Nc4ccc5[nH]ncc5c4Cl)s3)c2)cc1] | (ES, m/z): $[M+H]^+$ 491. $^1H$ NMR ($DMSO-d_6$, 400 MHz, ppm): δ 13.46 (s, 1H), 10.28 (s, 1H), 9.91 (s, 1H), 8.11 (d, J = 7.6 Hz, 2H), 7.82 (t, J = 8.8 Hz, 1H), 7.66-7.56 (m, 2H), 7.45-7.36 (m, 2H), 7.23 (d, J = 8.4 Hz, 2H), 6.87 (d, J = 8.4 Hz, 2H), 3.71 (s, 3H), 3.54 (d, J = 12.8 Hz, 2H). |
| 35BR | 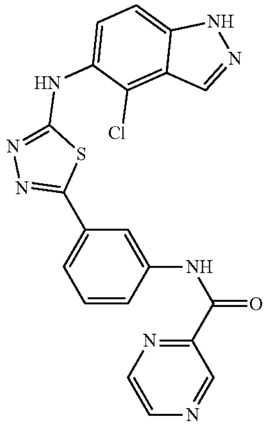 [SMILES: O=C(Nc1cccc(-c2nnc(Nc3ccc4[nH]ncc4c3Cl)s2)c1)c1cnccn1] | (ES, m/z): $[M+H]^+$ 449. $^1H$ NMR ($DMSO-d_6$, 400 MHz, ppm): δ 13.47 (s, 1H), 10.89 (s, 1H), 10.05 (d, J = 10 Hz, 1H), 9.30 (s, 1H), 8.88 (s, 1H), 8.87 (s, 1H), 8.42 (s, 1H), 8.13 (s, 1H), 8.00 (s, 1H), 7.79-7.98 (m, 1H), 7.60-7.77 (m, 2H), 7.37-7.49 (m, 1H). |

TABLE 3-continued
| Example No. | Chemical Structure | Physical Characterization Data |
|---|---|---|
| 35BS | 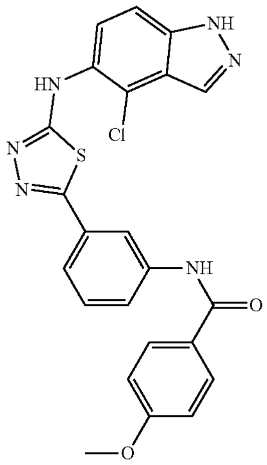 [SMILES: COc1ccc(C(=O)Nc2cccc(-c3nnc(Nc4ccc5[nH]ncc5c4Cl)s3)c2)cc1] | (ES, m/z): $[M + H]^+$ 477. $^1H$ NMR (DMSO-$d_6$, 400 MHz, ppm): δ 13.45 (s, 1H), 10.23 (s, 1H), 10.02 (s, 1H), 8.26 (s, 1H), 8.12 (s, 1H), 7.96 (t, J = 28 Hz, 2H), 7.89-7.84 (m, 2H), 7.60-7.41 (m, 3H), 7.06 (d, J = 8.8 Hz, 2H), 3.83 (s, 3H). |
| 35BT | 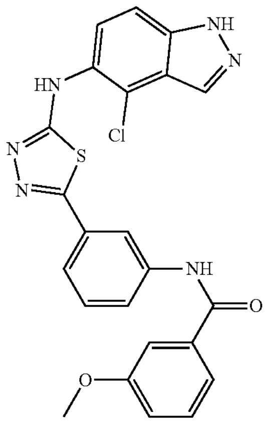 [SMILES: COc1cccc(C(=O)Nc2cccc(-c3nnc(Nc4ccc5[nH]ncc5c4Cl)s3)c2)c1] | (ES, m/z): $[M + H]^+$ 477. $^1H$ NMR (DMSO-$d_6$, 400 MHz, ppm): δ 13.46 (s, 1H), 10.36 (s, 1H), 9.98 (d, J = 10.4 Hz, 1H), 8.27 (d, J = 2 Hz, 1H), 8.13 (s, 1H), 7.91-7.83 (m, 2H), 7.60-7.42 (m, 6H), 7.17-7.14 (s, 1H), 3.83 (s, 3H). |
| 35BU | 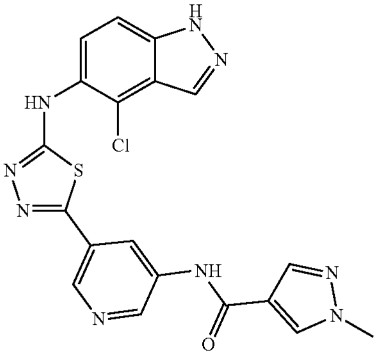 [SMILES: Cn1cc(C(=O)Nc2cncc(-c3nnc(Nc4ccc5[nH]ncc5c4Cl)s3)c2)cn1] | (ES, m/z): $[M + H]^+$ 452. $^1$HNMR (DMSO-$d_6$, 400 MHz, ppm): δ 13.46 (s, 1H), 10.17 (s, 1H), 8.97 (d, J = 2.4 Hz, 1H), 8.64 (d, J = 2.0 Hz, 1H), 8.56 (s, 1H), 8.35 (s, 1H), 8.12 (s, 1H), 8.04 (s, 1H), 7.83 (d, J = 8.8 Hz, 1H), 7.58 (d, J = 8.9 Hz, 1H), 3.90 (s, 3H). |

TABLE 3-continued

| Example No. | Chemical Structure | Physical Characterization Data |
|---|---|---|
| 35BV | 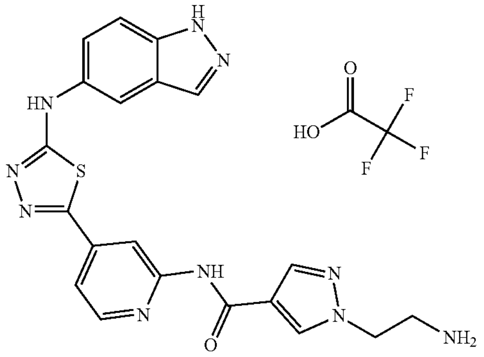 [SMILES: NCCn1cc(C(=O)Nc2cc(-c3nnc(Nc4ccc5[nH]ncc5c4)s3)ccn2)cn1 ; O=C(O)C(F)(F)F] | (ES, m/z): $[M + H]^+$ 447. $^1H$ NMR (DMSO-$d_6$, 400 MHz, ppm): δ 13.07 (s, 1H), 10.81 (s, 1H), 10.73 (s, 1H), 8.71-8.65 (m, 1H), 8.56 (s, 1H), 8.49 (d, J = 5.2 Hz, 1H), 8.33 (s, 1H), 8.25 (d, J = 2.0 Hz, 1H), 8.09 (d, J = 1.1 Hz, 1H), 7.90 (s, 2H), 7.62-7.54 (m, 2H), 7.44 (dd, J = 8.9, 2.1 Hz, 1H), 4.42 (t, J = 6.0 Hz, 2H), 3.32 (q, J = 5.9 Hz, 2H). |
| 35BW | 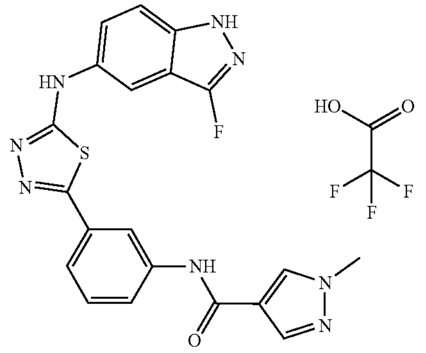 | (ES, m/z): $[M + H]^+$ 435.2. $^1H$ NMR (DMSO-$d_6$, 400 MHz, ppm): δ 12.52 (s, 1H), 10.65 (s, 1H), 10.02 (s, 1H), 8.36 (s, 1H), 8.27 (s, 2H), 8.06 (s, 1H), 7.89 (d, J = 8.8, 1), 7.45-7.57 (m, 4H), 3.92 (s, 3H). |
| 35BX | 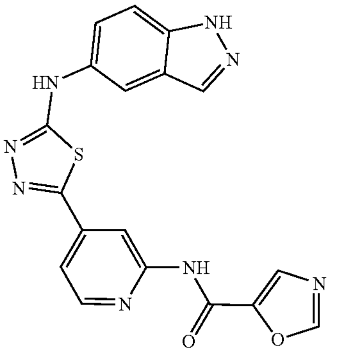 [SMILES: O=C(Nc1cc(-c2nnc(Nc3ccc4[nH]ncc4c3)s2)ccn1)c1cnco1] | (ES, m/z): $[M + H]^+$ 405. $^1H$ NMR (DMSO-$d_6$, 400 MHz, ppm): δ 13.05 (s, 1H), 11.27 (s, 1H), 10.74 (s, 1H), 8.67 (s, 1H), 8.61-8.56 (m, 1H), 8.53-8.47 (m, 1H), 8.27 (s, 1H), 8.23 (d, J = 1.9 Hz, 1H), 8.07 (d, J = 1.0 Hz, 1H), 7.61 (dd, J = 5.2, 1.6 Hz, 1H), 7.56 (d, J = 8.9 Hz, 1H), 7.43 (dd, J = 8.9, 2.1 Hz, 1H) |
| 35BY | 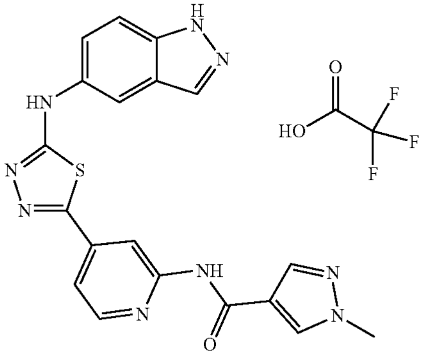 [SMILES: Cn1cc(C(=O)Nc2cc(-c3nnc(Nc4ccc5[nH]ncc5c4)s3)ccn2)cn1 ; O=C(O)C(F)(F)F] | (ES, m/z): $[M + H]^+$ 418. $^1H$ NMR (DMSO-$d_6$, 400 MHz, ppm): δ 13.04 (s, 1H), 10.71 (d, J = 2.0 Hz, 2H), 8.66-8.60 (m, 1H), 8.49-8.42 (m, 2H), 8.22 (d, J = 1.9 Hz, 1H), 8.15 (d, J = 0.8 Hz, 1H), 8.07 (t, J = 1.2 Hz, 1H), 7.60-7.52 (m, 2H), 7.43 (dd, J = 8.9, 2.1 Hz, 1H), 3.88 (s, 3H). |

TABLE 3-continued

| Example No. | Chemical Structure | Physical Characterization Data |
|---|---|---|
| 35BZ | 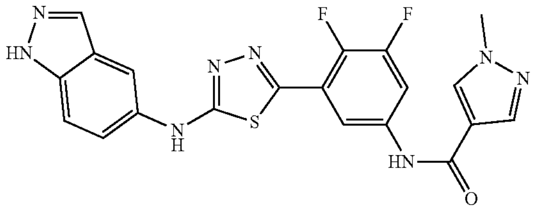 [SMILES: Cn1cc(C(=O)Nc2cc(F)c(F)c(-c3nnc(Nc4ccc5[nH]ncc5c4)s3)c2)cn1] | (ES, m/z): $[M + H]^+$ 453.2. $^1$H NMR (DMSO-$d_6$, 400 MHz, ppm): δ 13.06 (s, 1H), 10.44 (s, 1H), 10.22 (s, 1H), 8.36 (s, 1H), 8.23-8.25 (m, 2H), 8.05-8.13 (m, 3H), 7.57 (d, J = 9.2 Hz, 1H), 7.42-7.45 (m, 1H), 3.91 (s, 3H). |
| 35CA | 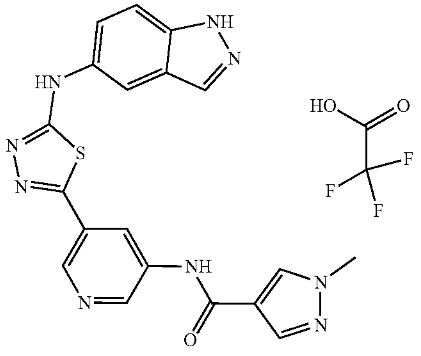 | (ES, m/z): $[M + H]^+$ 418.2. $^1$H NMR (DMSO-$d_6$, 400 MHz, ppm): δ 13.05 (s, 1H), 10.69 (s, 1H), 10.23 (s, 1H), 9.01 (s, 1H), 8.73 (s, 1H), 8.64 (s, 1H), 8.38 (s, 1H), 8.26 (s, 1H), 8.08 (s, 2H), 7.56 (d, J = 8.8, 1H), 7.42 (d, J = 2, 1H), 3.92 (s, 3H). |
| 35CB | 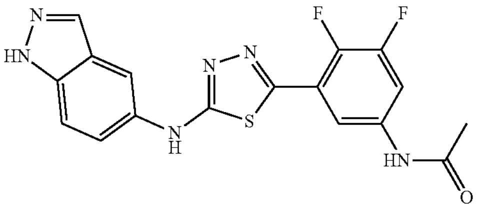 [SMILES: CC(=O)Nc1cc(F)c(F)c(-c2nnc(Nc3ccc4[nH]ncc4c3)s2)c1] | (ES, m/z): $[M + H]^+$ 387.2. $^1$H NMR (DMSO-$d_6$, 400 MHz, ppm): δ 13.05 (s, 1H), 10.63 (s, 1H), 10.38 (s, 1H), 8.26 (d, J = 1.6 Hz, 1H), 8.08 (s, 2H), 7.87-7.93 (m, 1H), 7.57 (d, J = 8.8 Hz, 1H), 7.42-7.45 (m, 1H), 2.09 (s, 3H). |
| 35CC | 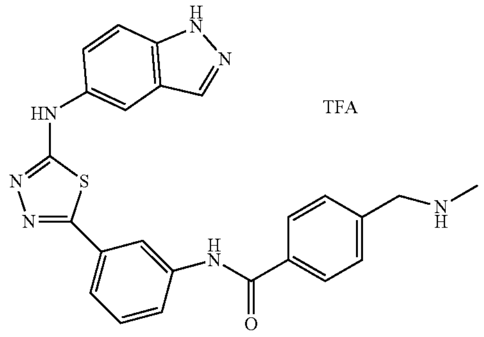 [SMILES: CNCc1ccc(C(=O)Nc2cccc(-c3nnc(Nc4ccc5[nH]ncc5c4)s3)c2)cc1] TFA | (ES, m/z): $[M + H]^+$457. $^1$H NMR (DMSO-$d_6$, 400 MHz, ppm): δ 13.03 (s, 1H), 10.70 (s, 1H), 10.53 (s, 1H), 9.19 (d, J = 1.8 Hz, 1H), 9.08 (s, 2H), 8.45-8.43 (m, 1H), 8.33 (s, 1H), 8.25 (d, J = 1.6 Hz, 1H), 8.06 (s, 1H), 7.94 (d, J = 8 Hz, 1H), 7.69-7.61 (m, 2H), 7.57-7.50 (m, 2H), 7.43-7.40 (m, 1H), 4.45-4.42 (m, 2H), 2.69-2.67 (m, 3H). |
| 35CD | 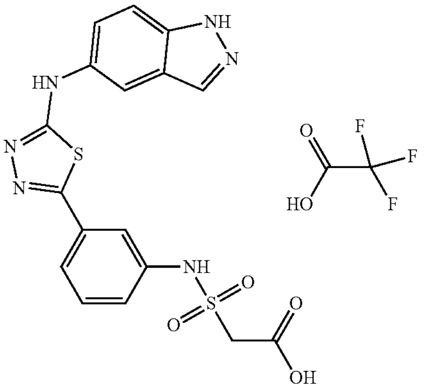 [SMILES: O=C(O)CS(=O)(=O)Nc1cccc(-c2nnc(Nc3ccc4[nH]ncc4c3)s2)c1 ; O=C(O)C(F)(F)F] | (ES, m/z): $[M + H]^+$ 431. $^1$H NMR (DMSO-$d_6$, 400 MHz, ppm): δ 13.07 (s, 2H), 10.50 (s, 1H), 10.31 (s, 1H), 8.23 (d, J = 2.0 Hz, 1H), 8.04 (d, J = 1.0 Hz, 1H), 7.74 (t, J = 1.9 Hz, 1H), 7.53-7.56 (m, 2H), 7.46 (t, J = 7.9 Hz, 1H), 7.38-7.41 (m, 1H), 7.31-7.34 (m, 1H), 4.16 (s, 2H). |

TABLE 3-continued

| Example No. | Chemical Structure | Physical Characterization Data |
|---|---|---|
| 35CE | 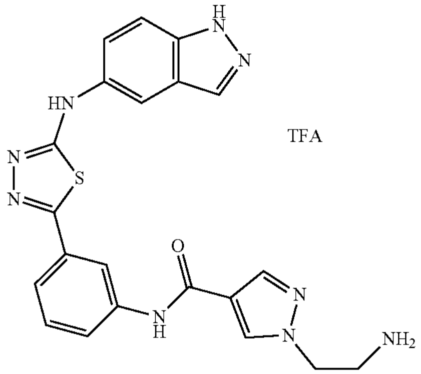 TFA | (ES, m/z): [M + H]$^+$ 446. $^1$H NMR (DMSO-$d_6$, 400 MHz, ppm): δ 13.03 (s, 1H), 10.52 (s, 1H), 10.08 (s, 1H), 8.45 (s, 1H), 8.25 (t, J = 8.4 Hz, 2H), 8.19 (s, 1H), 8.06 (s, 1H), 7.90-7.88 (m, 3H), 7.54-7.47 (m, 4H), 4.45-4.42 (m, 2H), 3.32-3.31 (m, 2H). |
| 35CF | 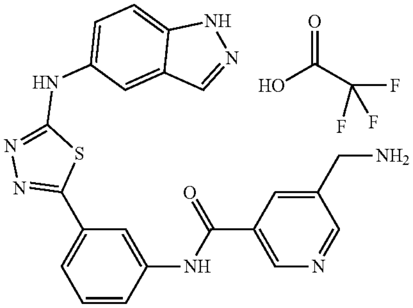 | (ES, m/z): [M + H]$^+$ 443. $^1$H NMR ($D_2O$/DMSO-$d_6$, 400 MHz, ppm): δ 9.12 (d, J = 2.1 Hz, 1H), 8.80 (d, J = 2.1 Hz, 1H), 8.38 (t, J = 2.1 Hz, 1H), 8.30 (t, J = 1.9 Hz, 1H), 8.21 (d, J = 1.6 Hz, 1H), 8.05 (d, J = 1.0 Hz, 1H), 7.87-7.79 (m, 1H), 7.62-7.47 (m, 3H), 7.40-7.46 (m, 1H), 4.16 (s, 2H). |
| 35CG | 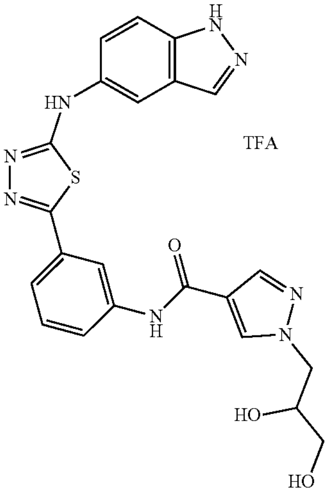 TFA | (ES, m/z): [M + H]$^+$ 477. $^1$H NMR ($D_2O$/DMSO-$d_6$, 400 MHz, ppm): δ 8.33 (s, 1H), 8.26-8.24 (m, 2H), 8.10 (d, J = 6 Hz, 2H), 7.79 (d, J = 8.8 Hz, 1H), 7.63-7.58 (m, 2H), 7.54-7.52 (m, 1H), 7.47-7.44 (m, 1H), 4.31-4.28 (m, 1H), 4.12 (s, 1H), 3.87 (s, 1H), 3.42-3.39 (m, 2H). |
| 35CH | 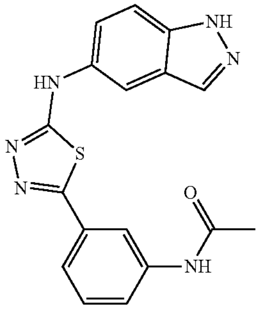 | (ES, m/z): [M + H]$^+$ 350.1. $^1$H NMR (DMSO-$d_6$, 400 MHz, ppm): δ 13.01 (s, 1H), 10.48 (s, 1H), 10.13 (s, 1H), 8.23 (d, J = 1.9 Hz, 1H), 8.14 (t, J = 1.9 Hz, 1H), 8.05 (d, J = 1.0 Hz, 1H), 7.65 (dt, J = 7.9, 1.5 Hz, 1H), 7.61-7.36 (m, 4H), 2.06 (s, 3H). |

TABLE 3-continued
| Example No. | Chemical Structure | Physical Characterization Data |
|---|---|---|
| 35CI | 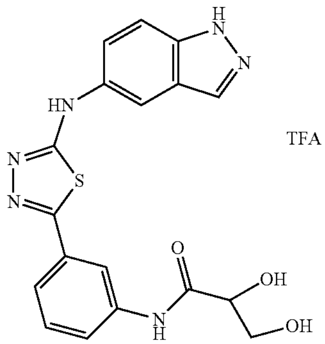 TFA | (ES, m/z): [M + H]+ 397. $^1$H NMR ($D_2O$/DMSO-$d_6$, 400 MHz, ppm): δ 8.25 (t, J = 1.8 Hz, 1H), 8.23-8.20 (m, 1H), 8.05 (d, J = 1.0 Hz, 1H), 7.74-7.67 (m, 1H), 7.59-7.50 (m, 2H), 7.48-7.37 (m, 2H), 4.10-4.08 (m, 1H), 3.65-3.62 (m, 2H). |
| 35CJ | 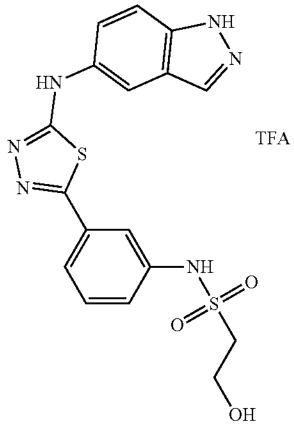 TFA | (ES, m/z): [M + H]+ 416. $^1$H NMR (DMSO-$d_6$, 400 MHz, ppm): δ 13.02 (s, 1H), 10.51 (s, 1H), 9.98 (s, 1H), 8.24 (s, 1H), 8.05 (s, 1H), 7.74 (t, J = 3.6 Hz, 1H), 7.56-7.51 (m, 2H), 7.48-7.41 (m, 2H), 7.34-7.33 (m, 1H), 4.97-4.95 (m, 1H), 3.77-3.75 (m, 2H), 3.32-3.27 (m, 2H). |
| 35CK | 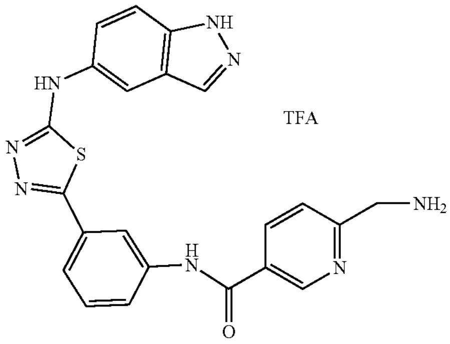 TFA | (ES, m/z): [M + H]+ 442. $^1$H NMR (DMSO-$d_6$, 400 MHz, ppm): δ 10.68 (s, 1H), 10.53 (s, 1H), 9.18 (d, J = 2 Hz, 1H), 8.44-8.33 (m, 5H), 8.25 (d, J = 1.2 Hz, 1H), 8.06-7.90 (m, 1H), 7.67-7.60 (m, 2H), 7.57-7.52 (m, 2H), 7.46-7.43 (m, 1H), 4.34-4.32 (m, 2H). |
| 35CL | 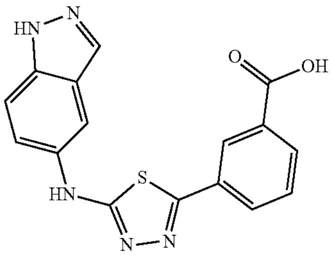 | (ES, m/z): [M + H]+ 335.9. $^1$H NMR (DMSO-$d_6$, 400 MHz, ppm): δ 13.03 (s, 1H), 8.32 (d, J = 6 Hz, 2H), 8.10 (s, 1H), 7.99-8.01 (m, 2H), 7.49-7.57 (m, 3H). |

TABLE 3-continued

| Example No. | Chemical Structure | Physical Characterization Data |
|---|---|---|
| 35CM | 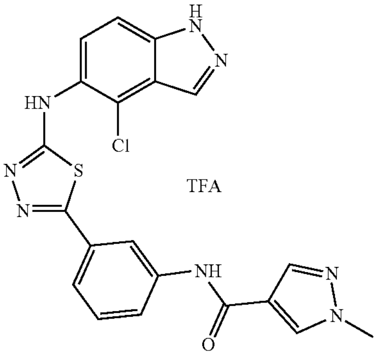 TFA | (ES, mz): [M + H]$^+$ 451. $^1$H NMR (DMSO-$d_6$, 400 MHz, ppm): δ 13.49 (s, 1H), 10.50-9.97 (m, 2H), 8.33 (s, 1H), 8.20 (s, 1H), 8.15 (s, 1H), 8.03 (s, 1H), 7.88-7.85 (m, 2H), 7.60 (d, J = 9.2 Hz, 1H), 7.50-7.41 (m, 2H), 3.90 (s, 3H). |
| 35CN | 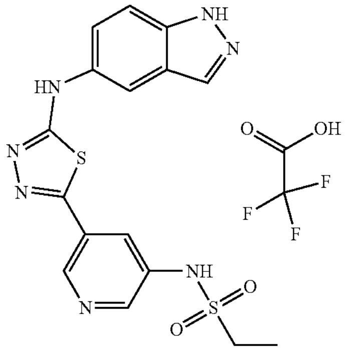 | (ES, m/z): [M + H]$^+$ 401.85. $^1$H NMR (DMSO-$d_6$, 400 MHz, ppm): δ 13.0 (br, s, 1H), 10.6 (s, 1H), 10.3 (s, 1H), 8.7 (d, 1H), 8.5 (s, 1H), 8.2 (d, 1H), 8.0 (d, 2H), 7.6 (d, 1H), 7.4 (d, 1H), 3.2 (q, 2H), 1.3 (t, 3H). |
| 35CO | 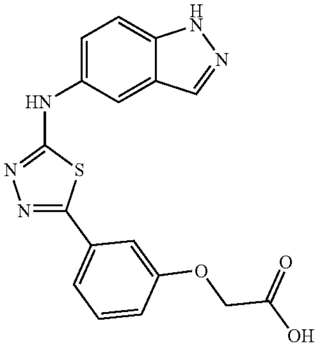 | (ES, m/z): [M + H]$^+$ 368.0. $^1$H NMR (DMSO-$d_6$ + $CD_3OD$, 400 MHz, ppm): δ 8.27 (s, 1H), 8.05 (s, 1H), 7.55 (d, J = 8.8 Hz, 1H), 7.39-7.44 (m, 3H), 7.34 (s, 1H), 6.97-7.00 (m, 1H), 4.56 (s, 2H). |
| 35CP | 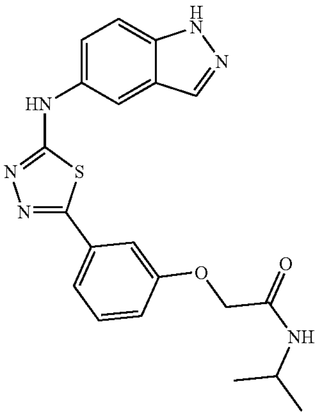 | (ES, m/z): [M + H]$^+$ 409.1. $^1$H NMR (DMSO-$d_6$, 400 MHz, ppm): δ 10.52 (s, 1H), 8.24 (s, 1H), 8.06 (s, 1H), 7.98 (d, J = 8 Hz, 1H), 7.55 (d, J = 9.2 Hz, 1H), 7.40-7.45 (m, 4H), 7.06-7.10 (m, 1H), 4.53 (s, 2H), 3.94-4.01 (m, 1H), 1.10 (d, J = 6.4 Hz, 6H). |

TABLE 3-continued
| Example No. | Chemical Structure | Physical Characterization Data |
|---|---|---|
| 35CQ | 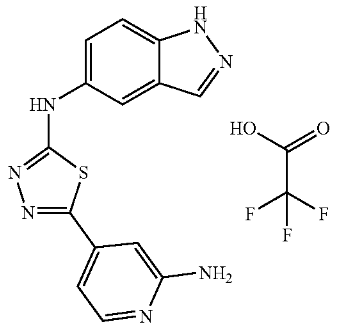 | (ES, m/z): $[M + H]^+$ 309.95. $^1H$ NMR (DMSO-$d_6$, 400 MHz, ppm): δ 8.22 (s, 1H), 8.18 (s, 1H), 7.96 (d, J = 4.4 Hz, 1H), 7.60 (d, J = 8.8 Hz, 1H), 7.40-7.54 (m, 2H), 7.35 (s, 1H). |
| 35CR | 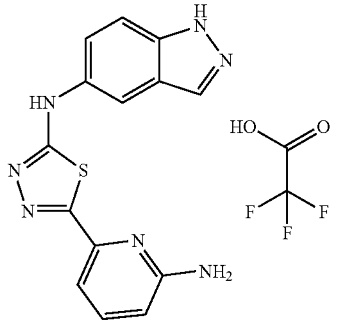 | (ES, m/z): $[M + H]^+$ 310.2. $^1H$ NMR (DMSO-$d_6$, 400 MHz, ppm): δ 8.94 (s, 1H), 8.18 (s, 1H), 7.79 (m, 1H), 7.61 (m, 1H), 7.49 (m, 1H), 7.26 (m, 1H), 6.86 (m, 1H). |
| 35CS | 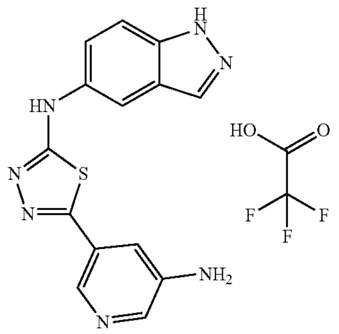 | (ES, m/z): $[M + H]^+$ 309.85. $^1H$ NMR (DMSO-$d_6$, 400 MHz, ppm): δ 8.40 (s, 1H), 8.37 (s, 1H), 8.03-8.18 (m, 2H), 7.88 (s, 1H), 7.38-7.52 (m, 2H). |

TABLE 3-continued

| Example No. | Chemical Structure | Physical Characterization Data |
| --- | --- | --- |
| 35CT | 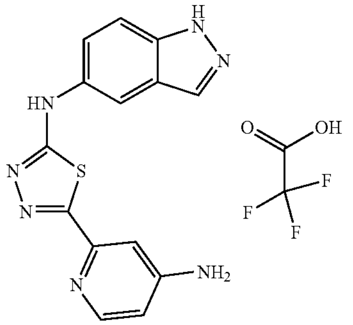 | (ES, m/z): [M + H]$^+$ 309.95. $^1$H NMR ($CD_3OD$, 400 MHz, ppm): δ 8.2 (s, 1H), 8.0-8.1 (m, 2H), 7.6 (d, 1H), 7.5 (d, 1H), 7.1 (s, 1H), 6.8 (d, 1H). |
| 35CU | 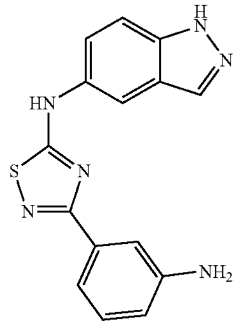 [SMILES: Nc1cccc(-c2nsc(Nc3ccc4[nH]ncc4c3)n2)c1] | (ES, m/z): [M + H]$^+$ 308.95. $^1$H NMR (DMSO-$d_6$, 400 MHz, ppm): δ 13.01 (s, 1H), 10.42 (s, 1H), 8.24 (s, 1H), 8.05 (s, 1H), 7.53-7.56 (m, 1H), 7.39-7.42 (m, 1H), 7.17-7.22 (m, 2H), 7.06-7.09 (m, 1H), 6.75-6.78 (m, 1H). |
| 35CV | 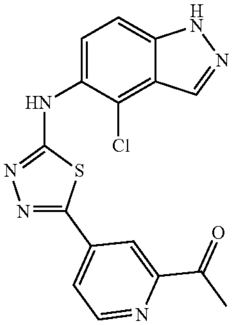 [SMILES: CC(=O)c1cc(-c2nnc(Nc3ccc4[nH]ncc4c3Cl)s2)ccn1] | (ES, m/z): [M + H]$^+$ 371. $^1$H NMR (DMSO-$d_6$, 400 MHz, ppm): δ 13.49 (s, 1H), 8.80 (d, J = 5.2 Hz, 1H), 8.21 (d, J = 8.0 Hz, 1H), 8.14 (s, 1H), 8.00-7.99 (m, 1H), 7.81 (d, J = 9.2 Hz, 1H), 7.60 (d, J = 8.8 Hz, 1H), 2.65 (s, 3H). |

Example 36—Synthesis of N-(4-(5-((4-Chloro-1H-indazol-5-yl)amino)-1,3,4-thiadiazol-2-yl)pyridin-2-yl)-2-(1-methyl-1H-pyrazol-4-yl)acetamide

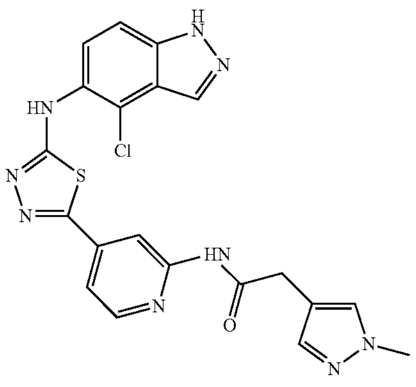 [SMILES: Cn1cc(CC(=O)Nc2cc(-c3nnc(Nc4ccc5[nH]ncc5c4Cl)s3)ccn2)cn1]

Part 1—Synthesis of Tert-Butyl 5-((tert-butoxycarbonyl)(5-(2-(2-(1-methyl-1H-pyrazol-4-yl)acetamido)pyridin-4-yl)-1,3,4-thiadiazol-2-yl)amino)-4-chloro-1H-indazole-1-carboxylate

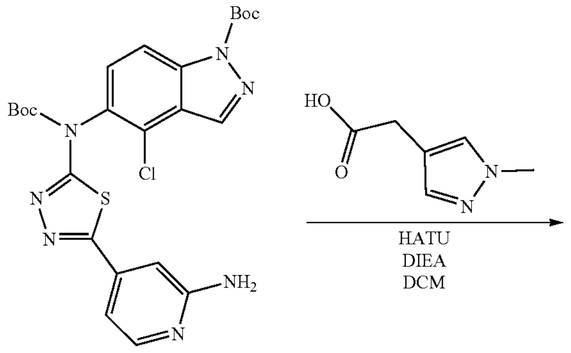

-continued

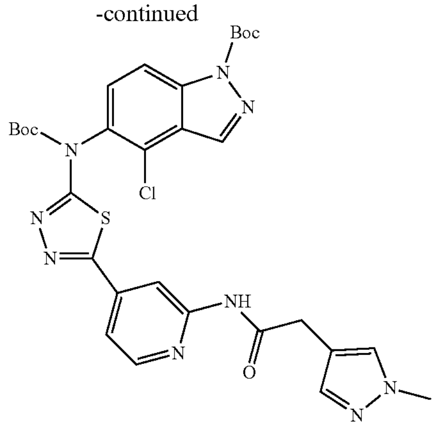

Into a 100-mL round-bottom flask, was placed tert-butyl 5-[[5-(2-aminopyridin-4-yl)-1,3,4-thiadiazol-2-yl][(tert-butoxy)carbonyl]amino]-4-chloro-1H-indazole-1-carboxylate (120 mg, 0.22 mmol, 1.00 equiv), dichloromethane (10 mL), 2-(1-methyl-1H-pyrazol-4-yl)acetic acid (34 mg, 0.24 mmol, 1.10 equiv), HATU (109 mg, 0.29 mmol, 1.30 equiv), and DIEA (114 mg, 0.88 mmol, 4.00 equiv). The resulting solution was stirred overnight at room temperature. The resulting mixture was washed with 20 mL of $H_2O$ then concentrated under vacuum. The residue was applied onto a silica gel column with ethyl acetate/petroleum ether (1:1) and chromatographed to give 60 mg (41%) of tert-butyl 5-[[(tert-butoxy)carbonyl](5-[2-[2-(1-methyl-1H-pyrazol-4-yl)acetamido]pyridin-4-yl]-1,3,4-thiadiazol-2-yl)amino]-4-chloro-1H-indazole-1-carboxylate as a solid.

Part 2—Synthesis of N-(4-(5-((4-chloro-1H-indazol-5-yl)amino)-1,3,4-thiadiazol-2-yl)pyridin-2-yl)-2-(1-methyl-1H-pyrazol-4-yl)acetamide

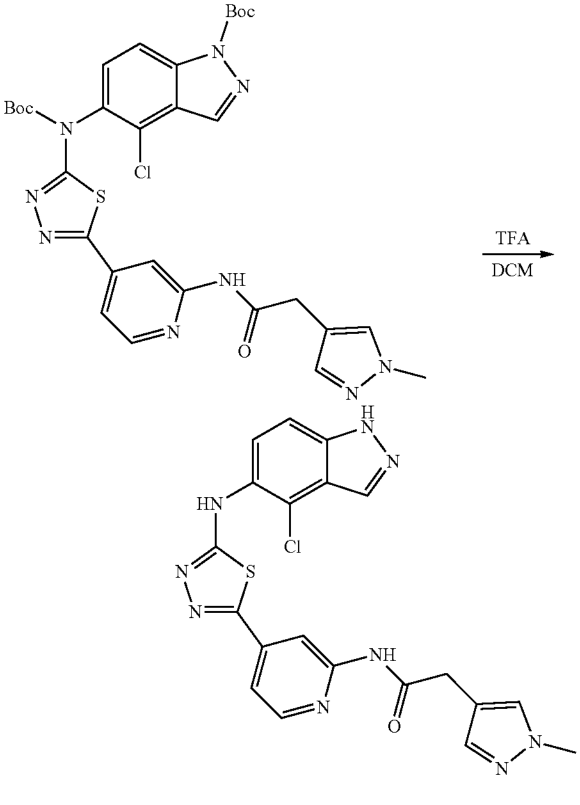

Into a 50-mL round-bottom flask, was placed tert-butyl 5-[[(tert-butoxy)carbonyl](5-[2-[2-(1-methyl-1H-pyrazol-4-yl)acetamido]pyridin-4-yl]-1,3,4-thiadiazol-2-yl)amino]-4-chloro-1H-indazole-1-carboxylate (60 mg, 0.09 mmol, 1.00 equiv), trifluoroacetic acid (9 g, 105.97 mmol, 1176.53 equiv), and dichloromethane (3 mL). The resulting solution was stirred for 2 h at room temperature. The resulting mixture was concentrated under vacuum. The crude product was purified by Prep-HPLC to give 26.6 mg (63%) of N-(4-[5-[(4-chloro-1H-indazol-5-yl)amino]-1,3,4-thiadiazol-2-yl]pyridin-2-yl)-2-(1-methyl-1H-pyrazol-4-yl)acetamide as a light yellow solid. (ES, m/z): $[M+H]^+$466. $^1H$ NMR (400 MHz, DMSO-$d_6$): δ 13.47 (s, 1H), 10.76 (s, 1H), 10.26 (s, 1H), 8.45 (s, 1H), 8.37 (d, J=5.2 Hz, 1H), 8.13 (s, 1H), 7.80 (d, J=8.0 Hz, 1H), 7.59 (d, J=10.0 Hz, 2H), 7.47-7.46 (m, 1H), 3.88 (s, 3H), 3.54 (s, 2H).

Example 37—Synthesis of N-(4-Chloro-1H-indazol-5-yl)-5-(3-(1-(oxetan-3-yl)-1H-imidazol-2-yl)phenyl)-1,3,4-thiadiazol-2-amine

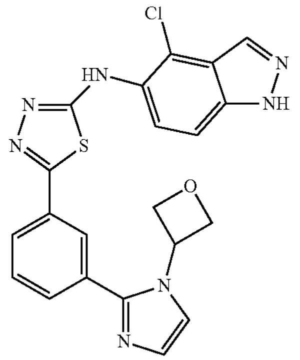 [SMILES: Clc1c(Nc2nnc(-c3cccc(-c4nccn4C4COC4)c3)s2)ccc2[nH]ncc12]

Part 1—Synthesis of 1-(oxetan-3-yl)-1H-imidazole

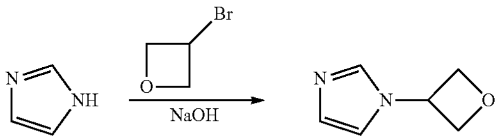

Into a 100-mL round-bottom flask, was placed 1H-imidazole (3 g, 44.07 mmol, 1.00 equiv), ACN (50 mL), sodium hydroxide (3.5 g, 87.50 mmol, 2.00 equiv), and 3-bromooxetane (7.24 g, 52.86 mmol, 1.20 equiv). The resulting solution was stirred overnight at 90° C., then diluted with 200 mL of $H_2O$ and extracted with 3×50 mL of dichloromethane. The organic layers were combined and dried over anhydrous sodium sulfate. After filtration and concentration, the residue was applied onto a silica gel column with dichloromethane/methanol (100/1). The collected fractions were combined and concentrated under vacuum. This resulted in 1 g (18%) of 1-(oxetan-3-yl)-1H-imidazole as a colorless oil.

Part 2—Synthesis of 1-(oxetan-3-yl)-2-(tributylstannyl)-1H-imidazole

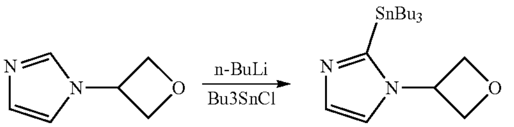

Into a 50-mL, 3-necked, round-bottom flask purged and maintained with an inert atmosphere of nitrogen, was placed 1-(oxetan-3-yl)-1H-imidazole (900 mg, 7.37 mmol, 1.00 equiv), and tetrahydrofuran (20 mL). n-BuLi (2.5M) (4.35 mL, 1.50 equiv) was added dropwise with stirring at −78° C. The resulting solution was stirred for 1 h at −78° C. To this mixture was added $Bu_3SnCl$ (2.07 mL) dropwise with stirring at −78° C. The resulting solution was stirred overnight at room temperature then concentrated under vacuum and washed with 30 mL of hexane. The resulting solids were filtered out and the filtrate was concentrated under vacuum. This resulted in 1 g (crude) of 1-(oxetan-3-yl)-2-(tributylstannyl)-1H-imidazole as a white solid.

Part 3—Synthesis of Tert-Butyl 5-((tert-butoxycarbonyl)(5-(3-(1-(oxetan-3-yl)-1H-imidazol-2-yl)phenyl)-1,3,4-thiadiazol-2-yl)amino)-4-chloro-1H-indazole-1-carboxylate

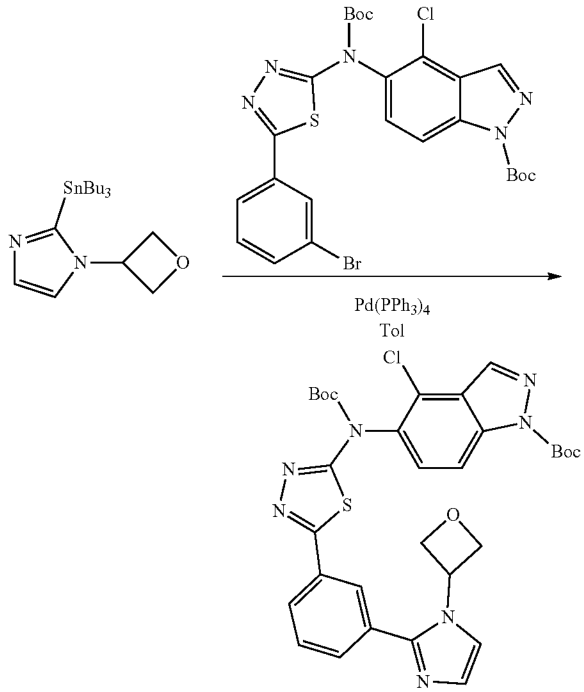

Into a 10-mL microwave tube purged and maintained with an inert atmosphere of nitrogen, was placed tert-butyl 5-[[5-(3-bromophenyl)-1,3,4-thiadiazol-2-yl][(tert-butoxy)carbonyl]amino]-4-chloro-1H-indazole-1-carboxylate (150 mg, 0.25 mmol, 1.00 equiv), 1-(oxetan-3-yl)-2-(tributylstannyl)-1H-imidazole (1 g, 2.43 mmol, 9.84 equiv), toluene (6 mL), and $Pd(PPh_3)_4$ (28 mg, 0.02 mmol, 0.10 equiv). The final reaction mixture was heated under microwave irradiation for 2 h at 120° C. The resulting mixture was concentrated under vacuum. The residue was applied onto a silica gel column and eluted with ethyl acetate/petroleum ether (40%-50%) to give 60 mg (37%) of tert-butyl tert-butyl 5-(tert-butoxycarbonyl(5-(3-(1-(oxetan-3-yl)-1H-imidazol-2-yl)phenyl)-1,3,4-thiadiazol-2-yl)amino)-4-chloro-1H-indazole-1-carboxylate as a light yellow solid.

Part 4—Synthesis of N-(4-chloro-1H-indazol-5-yl)-5-(3-(1-(oxetan-3-yl)-1H-imidazol-2-yl)phenyl)-1,3,4-thiadiazol-2-amine

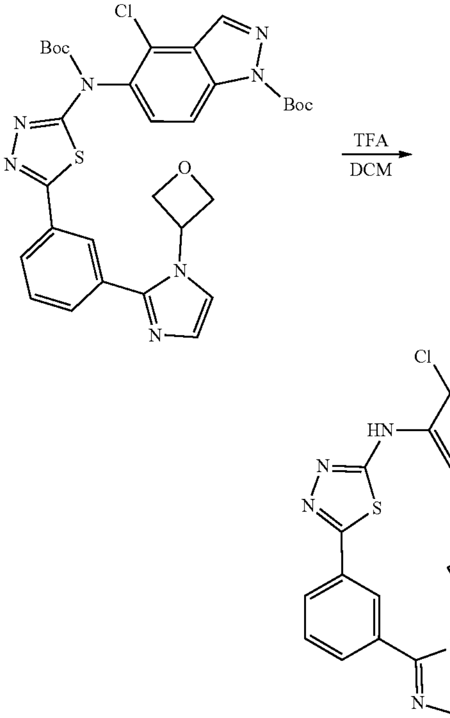

Into a 50-mL round-bottom flask purged and maintained with an inert atmosphere of nitrogen, was placed tert-butyl 5-[[(tert-butoxy)carbonyl](5-[3-[1-(oxetan-3-yl)-1H-imidazol-2-yl]phenyl]-1,3,4-thiadiazol-2-yl)amino]-4-chloro-1H-indazole-1-carboxylate (60 mg, 0.09 mmol, 1.00 equiv), dichloromethane (2 mL), and trifluoroacetic acid (1 mL). The resulting solution was stirred for 2 h at room temperature then concentrated under vacuum. The crude product was purified by Prep-HPLC with the following conditions (2#-AnalyseHPLC-SHIMADZU (HPLC-10)): Column, XBridge Prep C18 OBD Column, Sum; mobile phase, 10 mM aqueous $NH_4HCO_3$ and ACN (15.0% ACN to 45.0% over 8 min); Detector, UV 254 nm. This resulted in 12 mg (29%) of 4-chloro-N-(5-[3-[1-(oxetan-3-yl)-1H-imidazol-2-yl]phenyl]-1,3,4-thiadiazol-2-yl)-1H-indazol-5-amine as a light yellow solid. (ES, m/z): $[M+H]^+$450.00. $^1$H NMR (400 MHz, DMSO-$d_6$, ppm) δ 13.52 (s, 1H), 9.90 (s, 1H), 8.29 (s, 1H), 8.16 (s, 1H), 7.85 (dd, J=15.6, 8.4 Hz, 2H), 7.71 (t, J=1.7 Hz, 1H), 7.65-7.54 (m, 2H), 7.48-7.40 (m, 1H), 7.18 (d, J=1.1 Hz, 1H), 5.47 (p, J=7.0 Hz, 1H), 4.87 (p, J=6.9 Hz, 4H).

Example 38—Synthesis of 1-(4-(5-((4-Chloro-1H-indazol-5-yl)amino)-1,3,4-thiadiazol-2-yl)pyridin-2-yl)-3-methylimidazolidin-2-one

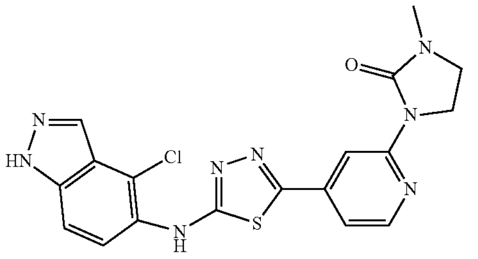 [SMILES: CN1CCN(c2cc(-c3nnc(Nc4ccc5[nH]ncc5c4Cl)s3)ccn2)C1=O]

Part 1—Synthesis of Methyl 2-bromoisonicotinate

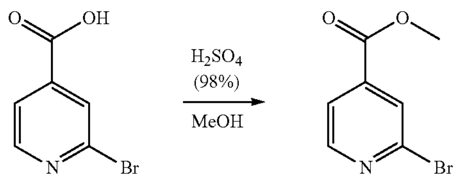

Into a 250-mL round-bottom flask, was placed a solution of 2-bromopyridine-4-carboxylic acid (10 g, 49.50 mmol, 1.00 equiv) in methanol (100 mL), and sulfuric acid (98%, 5 mL). The resulting solution was stirred overnight at 70° C. then concentrated under vacuum. The residue was dissolved in 200 mL of EtOAc and washed with 3×150 mL of saturated sodium bicarbonate. The organic layer was dried over anhydrous sodium sulfate and concentrated under vacuum. This resulted in 10 g (94%) of methyl 2-bromopyridine-4-carboxylate as colorless oil.

Part 2—Synthesis of Methyl 2-(3-methyl-2-oxoimidazolidin-1-yl)isonicotinate

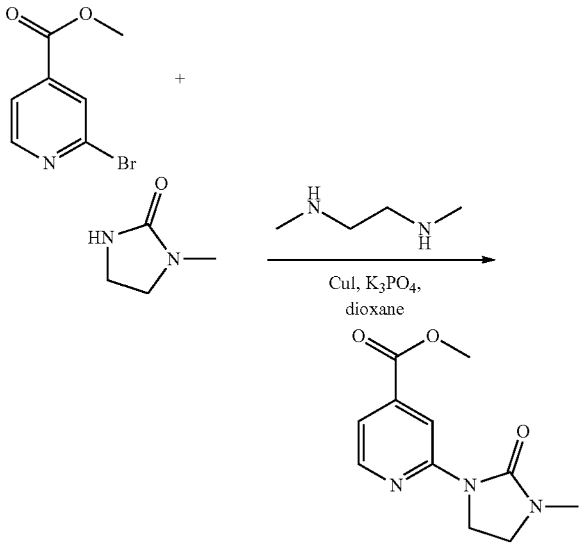

Into a 100-mL round-bottom flask, was placed a solution of methyl 2-bromopyridine-4-carboxylate (1 g, 4.63 mmol, 1.00 equiv) in dioxane (20 mL), 1-methylimidazolidin-2-one (930 mg, 9.29 mmol, 2.00 equiv), methyl[2-(methylamino)ethyl]amine (80 mg, 0.91 mmol, 0.20 equiv), potassium phosphaste (2.95 g, 13.90 mmol, 3.00 equiv), and copper iodide (180 mg, 0.95 mmol, 0.20 equiv). The resulting solution was stirred overnight at 80° C. under $N_2$. The solids were removed by filtration and the filtrated was concentrated under vacuum. The residue was applied onto a silica gel column and eluted with ethyl acetate/petroleum ether (1:1). This resulted in 50 mg (5%) of methyl 2-(3-methyl-2-oxoimidazolidin-1-yl)pyridine-4-carboxylate as a white solid.

Part 3—Synthesis of 2-(3-methyl-2-oxoimidazolidin-1-yl)isonicotinohydrazide

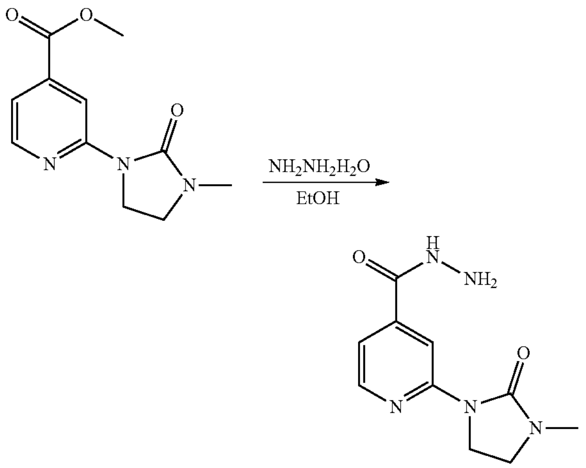

Into a 10-mL round-bottom flask, was placed a solution of methyl 2-(3-methyl-2-oxoimidazolidin-1-yl)pyridine-4-carboxylate (50 mg, 0.21 mmol, 1.00 equiv) in ethanol (1 mL), and hydrazine hydrate (1 mL). The resulting solution was stirred overnight at 80° C. then concentrated under vacuum. This resulted in 50 mg (100%) of 2-(3-methyl-2-oxoimidazolidin-1-yl)pyridine-4-carbohydrazide as a white solid.

Part 4—Synthesis of 1-(4-(5-((4-chloro-1H-indazol-5-yl)amino)-1,3,4-thiadiazol-2-yl)pyridin-2-yl)-3-methylimidazolidin-2-one

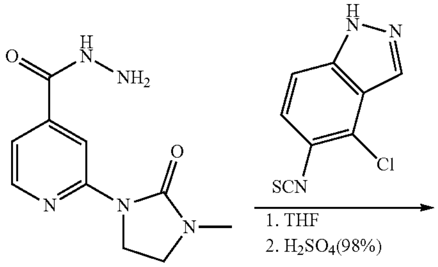

-continued

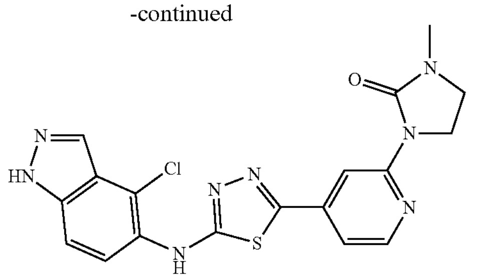

Into a 10-mL round-bottom flask, was placed a solution of 2-(3-methyl-2-oxoimidazolidin-1-yl)pyridine-4-carbohydrazide (50 mg, 0.21 mmol, 1.00 equiv) in tetrahydrofuran (1 mL), and 4-chloro-5-isothiocyanato-1H-indazole (44 mg, 0.21 mmol, 1.00 equiv). The resulting solution was stirred overnight at room temperature then concentrated under vacuum. The residue was dissolved in 1 mL of sulfuric acid (98%). The resulting solution was stirred overnight at room temperature and poured into ice-water (10 mL). The pH value of the solution was adjusted to 8 with sodium carbonate (aq). The solids were collected by filtration. The crude product was purified by Prep-HPLC with the following conditions: Column, XBridge C18 OBD Prep Column, 10 μm, 19 mm×250 mm; mobile phase, Water (0.05% $NH_3$) and ACN (28.0% ACN up to 48.0% in 6 min); Detector, UV 254 nm. This resulted in 36.2 mg (40%) of 1-(4-[5-[(4-chloro-1H-indazol-5-yl)amino]-1,3,4-thiadiazol-2-yl]pyridin-2-yl)-3-methylimidazolidin-2-one as a yellow solid. (ES, m/z): $[M+H]^+$427.2. $^1H$ NMR (400 MHz, DMSO-$d_6$, ppm) δ 13.49 (s, 1H); 10.25 (s, 1H); 8.57 (s, 1H); 8.34 (d, J=5.2 Hz, 1H); 8.14 (s, 1H); 7.81 (d, J=8.8 Hz, 1H); 7.59 (d, J=8.8 Hz, 1H); 7.35-7.36 (m, 1H); 3.91-3.95 (m, 2H); 3.43-3.47 (m, 2H); 2.79 (s, 3H).

Example 39—Synthesis of Additional N-(1H-Indazol-5-yl)-1,3,4-thiadiazol-2-amine Compounds The compounds in Table 4 were prepared based on procedures described in Examples 17 and 37.

TABLE 4

| Example No. | Chemical Structure | Physical Characterization Data |
|---|---|---|
| 39A | 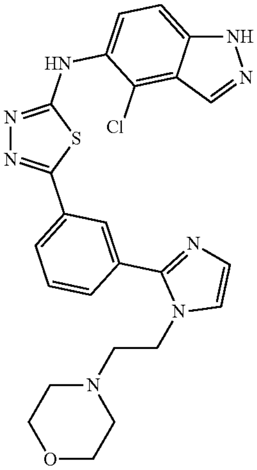 [SMILES: Clc1c(Nc2nnc(-c3cccc(-c4nccn4CCN4CCOCC4)c3)s2)ccc2[nH]ncc12] | (ES, m/z): $[M + H]^+$ 508. $^1H$-NMR (400 MHz, DMSO-$d_6$, ppm): δ 13.45 (s, 1H), 10.08 (s, 1H), 8.12 (s, 1H), 7.99 (s, 1H), 7.85 (d, J = 8.4 Hz, 2H), 7.72 (d, J = 8.0 Hz, 1H), 7.59 (t, J = 7.6 Hz, 2H), 7.39 (d, J = 1.2 Hz, 1H), 7.00 (s, 1H), 4.15 (t, J = 12.8 Hz, 2H), 3.41 (t, J = 8.8 Hz, 4H), 2.59 (s, 2H), 2.25 (t, J = 8.4 Hz, 4H). |
| 39B | 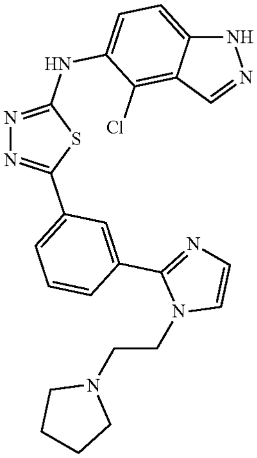 [SMILES: Clc1c(Nc2nnc(-c3cccc(-c4nccn4CCN4CCCC4)c3)s2)ccc2[nH]ncc12] | (ES, m/z): $[M + H]^+$ 492. $^1H$ NMR (400 MHz, DMSO-$d_6$) δ 13.46 (s, 1H), 10.05 (s, 1H), 8.12 (s, 1H), 8.01 (s, 1H), 7.87-7.80 (m, 2H), 7.70 (d, J = 7.6 Hz, 2H), 7.39 (t, J = 7.6 Hz, 2H), 7.38 (d, J = 0.8 Hz, 1H), 7.00 (s, 1H), 4.12 (t, J = 13.2 Hz, 2H), 2.65 (s, 2H), 2.30 (t, J = 14.8 Hz, 4H), 1.53 (s, 4H). |

TABLE 4-continued
| Example No. | Chemical Structure | Physical Characterization Data |
|---|---|---|
| 39C | 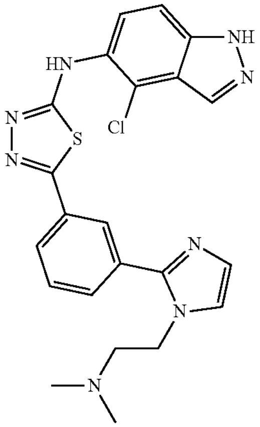 | (ES, m/z): $[M + H]^+$ 479. $^1H$ NMR (400 MHz, DMSO-$d_6$) δ 13.44 (s, 1H), 10.09 (s, 1H), 8.12 (s, 1H), 7.99 (s, 1H), 7.85 (t, J = 15.2 Hz, 2H), 7.70 (d, J = 7.6 Hz, 1H), 7.59 (t, J = 7.6 Hz, 2H), 7.38 (d, J = 1.2 Hz, 1H), 7.00 (s, 1H), 4.12 (t, J = 12.0 Hz, 2H), 2.65 (s, 2H), 2.06 (s, 6H). |
| 39D | 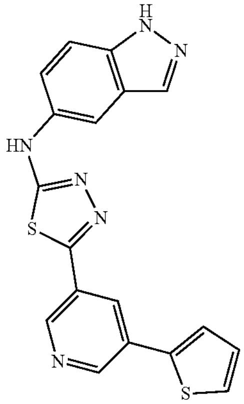 [SMILES: c1csc(-c2cncc(-c3nnc(Nc4ccc5[nH]ncc5c4)s3)c2)c1] | (ES-ESI, m/z): 377.4 $[M + H]^+$. $^1H$ NMR (400 MHz, DMSO-$d_6$, ppm): δ 13.3 (s, 1H), 10.7 (s, 1H), 8.95 (d, J = 7 Hz, 2H), 8.35 (s, 1H), 8.25 (s, 1H), 8.03 (s, 1H), 7.50-7.60 (m, 2H), 7.40 (d, J = 7 Hz, 1H), 7.19 (s, 1H). |
| 39E | 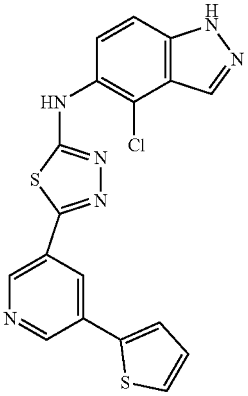 [SMILES: Clc1c(Nc2nnc(-c3cncc(-c4cccs4)c3)s2)ccc2[nH]ncc12] | (ES-ESI, m/z): 489 $[M + H]^+$. $^1H$ NMR (400 MHz, DMSO-$d_6$, ppm): δ 8.61 (s, 1H), 8.23 (s, 1H), 8.04 (s, 1H), 7.97 (d, J = 7 Hz, 1H), 7.55 (d, J = 7 Hz, 1H), 7.38 (d, J = 7 Hz, 1H), 7.26 (t, J = 7 Hz, 2H), 7.15 (t, J = 7 Hz, 2H), 6.95 (d, J = 7 Hz, 1H). |

Example 40—Synthesis of N-(4-Chloro-1H-indazol-5-yl)-5-(2-(4-methyloxazol-2-yl)pyridin-4-yl)-1,3,4-thiadiazol-2-amine

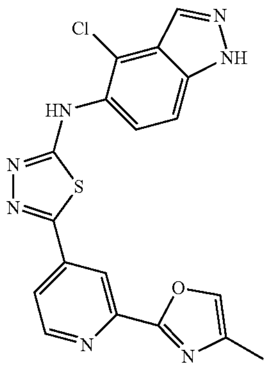 [SMILES: Cc1coc(-c2cc(-c3nnc(Nc4ccc5[nH]ncc5c4Cl)s3)ccn2)n1]

Part 1—Synthesis of Methyl 2-bromoisonicotinate

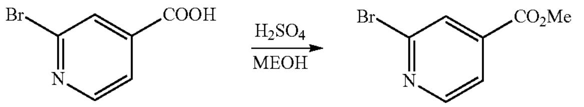 [SMILES: O=C(O)c1ccnc(Br)c1 ; "H2SO4" ; "MEOH" ; COC(=O)c1ccnc(Br)c1]

Into a 100-mL round-bottom flask, was placed 2-bromopyridine-4-carboxylic acid (2 g, 9.90 mmol, 1.00 equiv), MeOH (50 mL), and sulfuric acid (0.5 mL). The resulting solution was stirred overnight at 70° C. then concentrated under vacuum. The residue was dissolved in 500 mL of ethyl acetate then washed with 3×50 mL of aqueous sodium carbonate and 3×50 mL of brine. The organic layer was dried over anhydrous sodium sulfate and concentrated under vacuum. This resulted in 1.8 g (84%) of methyl 2-bromopyridine-4-carboxylate as light yellow oil.

Part 2—Synthesis of Methyl 2-(4-methyloxazol-2-yl)isonicotinate

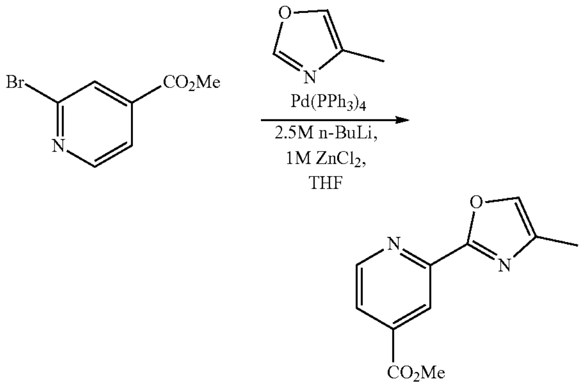

Butyl lithium (0.88 mL, 2.40 equiv, 2.5 M) was added drop-wise to a stirred solution of 4-methyl-1,3-oxazole (154 mg, 1.85 mmol, 2.00 equiv) in THF (2 mL) at −78° C. The solution was stirred at this temperature for 10 minutes then a solution of zinc chloride (5.6 mL, 6.00 equiv, 1 M) was added drop-wise. Solution was stirred for 15 minutes at −78° C. then cooling bath removed and reaction mixture allowed to warm to RT. The zinc oxazole solution was added via a syringe to a pre-sealed and nitrogen purged microwave vial (Biotage) containing the methyl 2-bromopyridine-4-carboxylate (200 mg, 0.93 mmol, 1.00 equiv) and $Pd(PPh_3)_4$ (100 mg, 0.09 mmol, 0.10 equiv). The vial was heated under microwave irradiation (Biotage) for 30 minutes at 60° C. The resulting solution was diluted with 200 mL of ethyl acetate and washed with 3×50 mL of brine. The organic layer was dried over sodium sulfate and concentrated under vacuum. The residue was applied onto a silica gel column and eluted with PE:EA (3:1) to give 90 mg (45%) of methyl 2-(4-methyl-1,3-oxazol-2-yl)pyridine-4-carboxylate as an off-white solid.

Part 3—Synthesis of 2-(4-methyloxazol-2-yl)isonicotinohydrazide

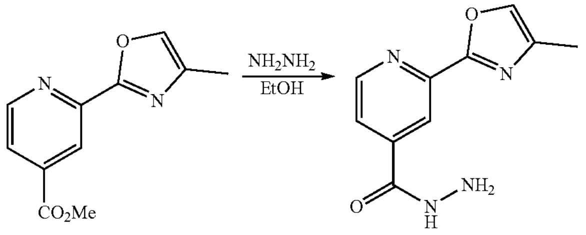

Into a 50-mL round-bottom flask, was placed methyl 2-(4-methyl-1,3-oxazol-2-yl)pyridine-4-carboxylate (190 mg, 0.87 mmol, 1.00 equiv), ethanol (3 mL), and hydrazine (3 mL, 80%). The resulting solution was stirred for 4 h at 80° C. in an oil bath then concentrated under vacuum. This resulted in 190 mg (100%) of 2-(4-methyl-1,3-oxazol-2-yl)pyridine-4-carbohydrazide as a gray solid.

Part 4—Synthesis of N-(4-chloro-1H-indazol-5-yl)-2-(2-(4-methyloxazol-2-yl)isonicotinoyl)hydrazine-1-carbothioamide

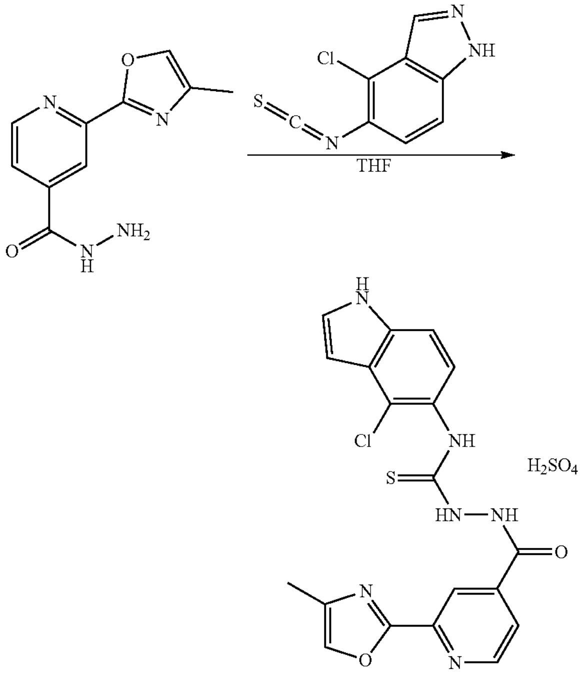

Into a 25-mL round-bottom flask, was placed 2-(4-methyl-1,3-oxazol-2-yl)pyridine-4-carbohydrazide (200 mg, 0.92 mmol, 1.00 equiv), tetrahydrofuran (10 mL), and 4-chloro-5-isothiocyanato-1H-indazole (192 mg, 0.92 mmol, 1.00 equiv). The resulting solution was stirred overnight at room temperature then concentrated under vacuum. This resulted in 390 mg (crude) of N-[[(4-chloro-1H-indazol-5-yl)carbamothioyl]amino]-2-(4-methyl-1,3-oxazol-2-yl)pyridine-4-carboxamide as a light yellow solid.

Part 5—Synthesis of N-(4-chloro-1H-indazol-5-yl)-5-(2-(4-methyloxazol-2-yl)pyridin-4-yl)-1,3,4-thiadiazol-2-amine

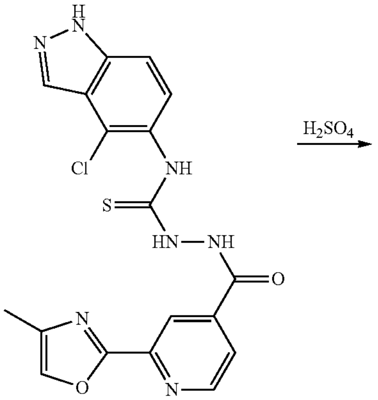

-continued

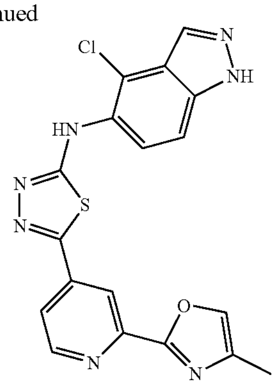

Into a 25-mL round-bottom flask, was placed N-[[(4-chloro-1H-indazol-5-yl)carbamothioyl]amino]-2-(4-methyl-1,3-oxazol-2-yl)pyridine-4-carboxamide (400 mg, 0.93 mmol, 1.00 equiv), and sulfuric acid (5 mL). The resulting solution was stirred for 1 h at room temperature. The reaction was then quenched by the addition of 100 mL of water/ice. The pH value of the solution was adjusted to 8 with sodium bicarbonate. The solids were collected by filtration. The solid was dried in an oven under reduced pressure. The residue was dissolved in 5 mL of DMF. The crude product was purified by Prep-HPLC with the following conditions (2#-AnalyseHPLC-SHIMADZU(HPLC-10)): Column, XBridge Shield RP18 OBD Column, 5 um, 19*150 mm; mobile phase, 10 mMOL/L $NH_4HCO_3$ and CAN (30.0% ACN up to 45.0% in 8 min); Detector, UV 254 nm. This resulted in 29.1 mg (8%) of 4-chloro-N-[5-[2-(4-methyl-1,3-oxazol-2-yl)pyridin-4-yl]-1,3,4-thiadiazol-2-yl]-1H-indazol-5-amine as a yellow solid. (ES, m/z): $[M+H]^+$410. $^1H$ NMR (300 MHz, DMSO-$d_6$, ppm) δ 8.77 (d, J=5.1 Hz, 1H), 8.38-8.31 (s, 1H), 8.16 (s, 1H), 8.04 (s, 1H), 7.92-7.78 (m, 2H), 7.62 (d, J=8.9 Hz, 1H), 2.21 (s, 3H).

Example 41—Synthesis of Additional Compounds

The compounds in Table 5 were prepared based on procedures described in Example 40.

TABLE 5

| Example No. | Chemical Structure | Physical Characterization Data |
| --- | --- | --- |
| 41A | 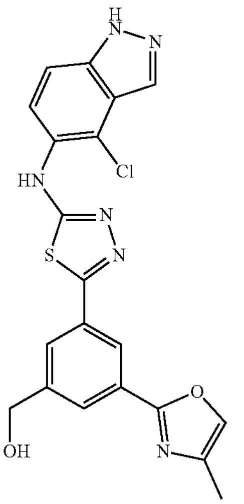 [SMILES: Cc1coc(-c2cc(CO)cc(-c3nnc(Nc4ccc5[nH]ncc5c4Cl)s3)c2)n1] | (ES-ESI, m/z): $[M + H]^+$ 438.90. 1H-NMR (400 MHz, DMSO-$d_6$, ppm): δ 13.45 (s, 1H), 10.07 (s, 1H), 8.17 (s, 1H), 8.12 (s, 1H), 7.94-7.96 (m, 2H), 7.82 (d, J = 9.2 Hz, 2H), 7.58 (d, J = 8.8 Hz, 1H), 5.46 (s, 1H), 4.61 (s, 2H), 2.17 (s, 3H). |

TABLE 5-continued
| Example No. | Chemical Structure | Physical Characterization Data |
|---|---|---|
| 41B | 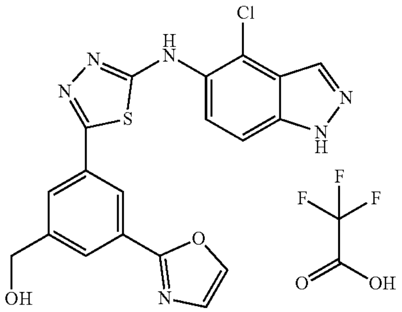 | (ES, m/z): [M-TFA + H]+ 425.00 $^1$H NMR (DMSO-$d_6$, 400 MHz, ppm): δ 13.50 (s, 1H), 10.16 (s, 1H), 8.28 (d, J = 11.1 Hz, 2H), 8.16 (s, 1H), 8.04 (s, 1H), 7.87 (d, J = 11.7 Hz, 2H), 7.62 (d, J = 8.9 Hz, 1H), 7.45 (s, 1H), 5.51 (t, J = 5.8 Hz, 1H), 4.66 (d, J = 5.7 Hz, 2H). |
| 41C | 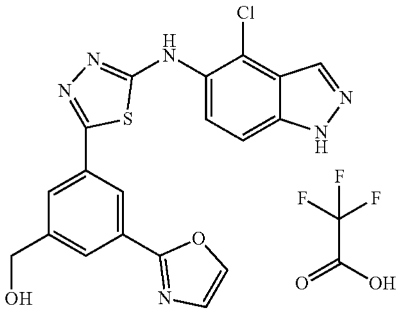 | (ES, m/z) [M-TFA + H]+ 425.00. $^1$H NMR (DMSO-$d_6$, 400 MHz, ppm): δ 13.50 (s, 1H), 10.16 (s, 1H), 8.28 (d, J = 11.1 Hz, 2H), 8.16 (s, 1H), 8.04 (s, 1H), 7.87 (d, J = 11.7 Hz, 2H), 7.62 (d, J = 8.9 Hz, 1H), 7.45 (s, 1H), 5.51 (t, J = 5.8 Hz, 1H), 4.66 (d, J = 5.7 Hz, 2H). |
| 41D | 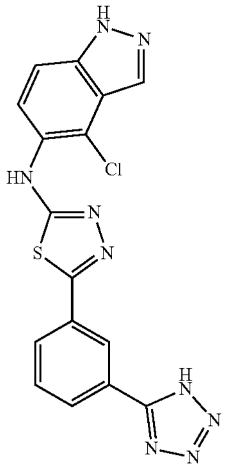 [SMILES: Clc1c(Nc2nnc(-c3cccc(-c4nnn[nH]4)c3)s2)ccc2[nH]ncc12] | (ES, m/z): [M + H]+ 396.00. $^1$H NMR (DMSO-$d_6$, 400 MHz, ppm): δ 13.40 (s, 1H), 10.13 (s, 1H), 8.50 (s, 1H), 8.10-8.14 (m, 2H), 7.95 (d, J = 8 Hz, 1H), 7.85 (d, J = 8.4 Hz, 1H), 7.66-7.75 (m, 1H), 7.60 (d, J = 8.8 Hz, 1H). |

Example 42—Synthesis of 1-(3-(5-((4-Chloro-1H-indazol-5-yl)amino)-1,3,4-thiadiazol-2-yl)phenyl)-4-methylpiperazin-2-one

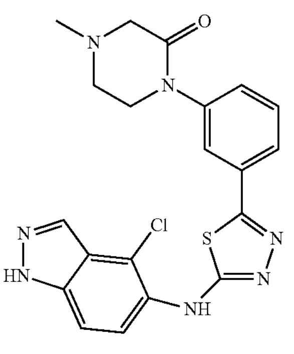 [SMILES: CN1CCN(c2cccc(-c3nnc(Nc4ccc5[nH]ncc5c4Cl)s3)c2)C(=O)C1]

Part 1—Synthesis of Methyl 3-(2-((2-hydroxyethyl)(methyl)amino)acetamido)benzoate

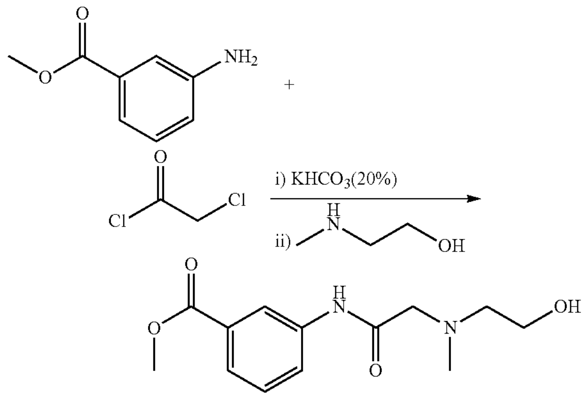

Into a 100-mL round-bottom flask, was placed a solution of methyl 3-aminobenzoate (1.51 g, 9.99 mmol, 1.00 equiv) in ethyl acetate (30 mL), and 20% aqueous $KHCO_3$ (20 mL, 5.00 equiv). This was followed by the addition of 2-chloroacetyl chloride (1.24 g, 10.98 mmol, 1.10 equiv) dropwise with stirring at 0° C. The resulting solution was stirred for 30 min at room temperature. To this was added 2-(methylamino)ethan-1-ol (2.63 g, 35.02 mmol, 33.50 equiv). The resulting solution was stirred for 3 hours at 60° C. then washed with 3×20 mL of brine. The mixture was dried over anhydrous sodium sulfate and concentrated under vacuum. This resulted in 1.5 g (56%) of methyl 3-[2-[(2-hydroxyethyl)(methyl)amino]acetamido]benzoate as colorless oil.

Part 2—Synthesis of Methyl 3-(4-methyl-2-oxopiperazin-1-yl)benzoate

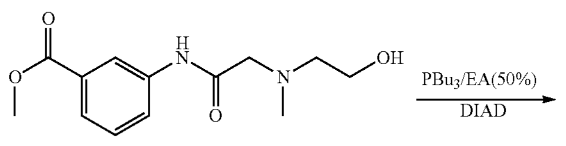

-continued

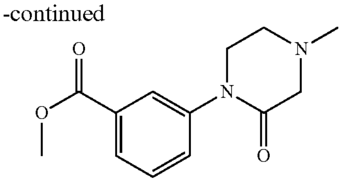

Into a 100-mL round-bottom flask, was placed a solution of methyl 3-[2-[(2-hydroxyethyl)(methyl)amino]acetamido]benzoate (1 g, 3.76 mmol, 1.00 equiv) in ethyl acetate (20 mL), $PBu_3$ in ethyl acetate (50%) (4 g, 2.60 equiv). This was followed by the addition of DIAD (2 g, 9.89 mmol, 2.60 equiv) dropwise with stirring at 0° C. under $N_2$. The resulting solution was stirred overnight at room temperature then concentrated under vacuum. The residue was applied onto a silica gel column and eluted with dichloromethane/methanol (20:1). This resulted in 900 mg (97%) of methyl 3-(4-methyl-2-oxopiperazin-1-yl)benzoate as colorless oil.

Part 3—Synthesis of 3-(4-methyl-2-oxopiperazin-1-yl)benzohydrazide

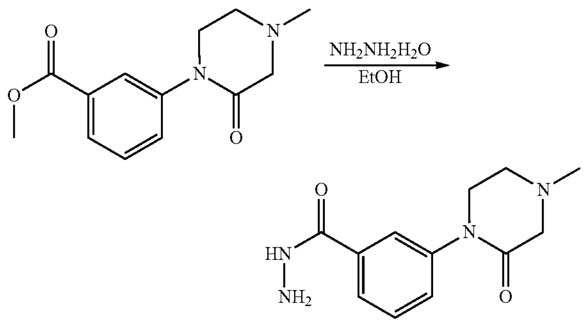

Into a 100-mL round-bottom flask, was placed a solution of methyl 3-(4-methyl-2-oxopiperazin-1-yl)benzoate (800 mg, 3.22 mmol, 1.00 equiv) in ethanol (10 mL), hydrazine hydrate (5 mL). The resulting solution was stirred overnight at room temperature then concentrated under vacuum. The crude product (30 mL) was purified by Flash-Prep-HPLC with the following conditions (CombiFlash-1): Column, C18 (40 g, 20~45 um); mobile phase, methanol/$H_2O$ (1:10) increasing to methanol/$H_2O$ (1:1) within 30 min; Detector, UV 254 nm. This resulted in 200 mg (25%) of 3-(4-methyl-2-oxopiperazin-1-yl)benzohydrazide as a yellow solid.

Part 4—Synthesis of 1-(3-(5-((4-chloro-1H-indazol-5-yl)amino)-1,3,4-thiadiazol-2-yl)phenyl)-4-methylpiperazin-2-one

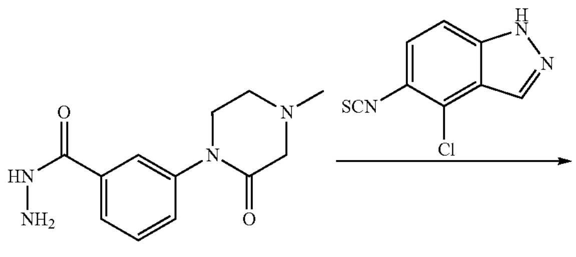

-continued

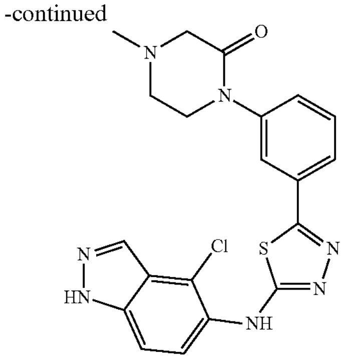

Into a 100-mL round-bottom flask, was placed a solution of 3-(4-methyl-2-oxopiperazin-1-yl)benzohydrazide (200 mg, 0.81 mmol, 1.00 equiv) in dichloromethane (10 mL), and 4-chloro-5-isothiocyanato-1H-indazole (169 mg, 0.81 mmol, 1.00 equiv). The resulting solution was stirred overnight at room temperature then concentrated under vacuum. The residue was dissolved in 5 mL of sulfuric acid (98%). The resulting solution was stirred overnight at room temperature and poured into ice-water (50 mL). The pH value of the solution was adjusted to 8 with sodium carbonate (aq). The solids were collected by filtration. The crude product was purified by Prep-HPLC with the following conditions (2#-AnalyseHPLC-SHIMADZU(HPLC-10)): Column, XBridge Shield RP18 OBD Column, 5 um, 19*150 mm; mobile phase, Waters (10 mM $NH_4HCO_3$) and ACN (18.0% ACN up to 38.0% in 6 min); Detector, UV 220 nm. This resulted in 75.8 mg (21%) of 1-(3-[5-[(4-chloro-1H-indazol-5-yl)amino]-1,3,4-thiadiazol-2-yl]phenyl)-4-methylpiperazin-2-one as an off-white solid. (ES, m/z): $[M+H]^+$439.9. $^1H$ NMR (DMSO-$d_6$, 400 MHz, ppm): δ 13.49 (s, 1H), 10.11 (s, 1H), 8.15 (s, 1H), 7.84 (d, J=8.8 Hz, 1H), 7.77-7.78 (m, 1H), 7.68-7.71 (m, 1H), 7.61 (d, J=8.8 Hz, 1H), 7.49-7.54 (m, 1H), 7.42-7.45 (m, 1H), 3.69-3.72 (m, 2H), 3.13 (s, 2H), 2.73-2.75 (m, 2H), 2.29 (s, 3H).

Example 43—Synthesis of 4-(5-((4-Chloro-1H-indazol-5-yl)amino)-1,3,4-thiadiazol-2-yl)-1-methylindolin-2-one 2,2,2-trifluoroacetic Acid Solvate

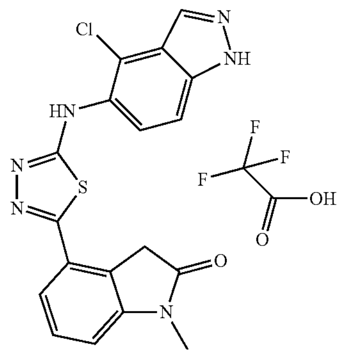

Part 1—Synthesis of 4-bromo-1-methylindoline-2,3-dione

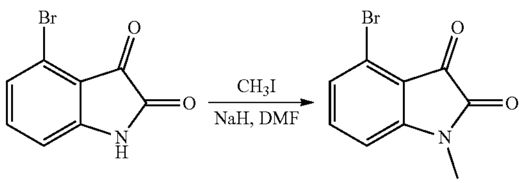

Into a 250-mL round-bottom flask, was placed 4-bromo-2,3-dihydro-1H-indole-2,3-dione (2.25 g, 9.95 mmol, 1.00 equiv), N,N-dimethylformamide (50 mL), sodium hydride (480 mg, 12.00 mmol, 2.00 equiv), and iodomethane (1.7 g, 11.98 mmol, 1.20 equiv). The resulting solution was stirred for 1 h at room temperature in a water/ice bath. The resulting solution was diluted with 800 mL of EA then washed with 4×50 mL of brine. The organic layer was dried over anhydrous sodium sulfate and concentrated under vacuum. This resulted in 2 g (84%) of 4-bromo-1-methyl-2,3-dihydro-1H-indole-2,3-dione as a red solid.

Part 2—Synthesis of 4-bromo-1-methylindolin-2-one

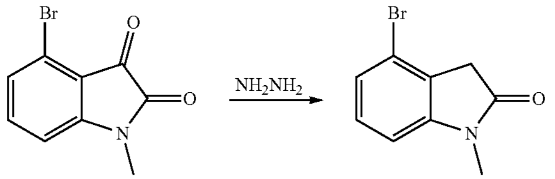

Into a 100-mL round-bottom flask, was placed 4-bromo-1-methyl-2,3-dihydro-1H-indole-2,3-dione (1 g, 4.17 mmol, 1.00 equiv), and hydrazine (20 mL). The resulting solution was stirred overnight at 125° C. then concentrated under vacuum. This resulted in 750 mg (80%) of 4-bromo-1-methyl-2,3-dihydro-1H-indol-2-one as a red solid.

Part 3—Synthesis of Methyl 1-methyl-2-oxoindoline-4-carboxylate

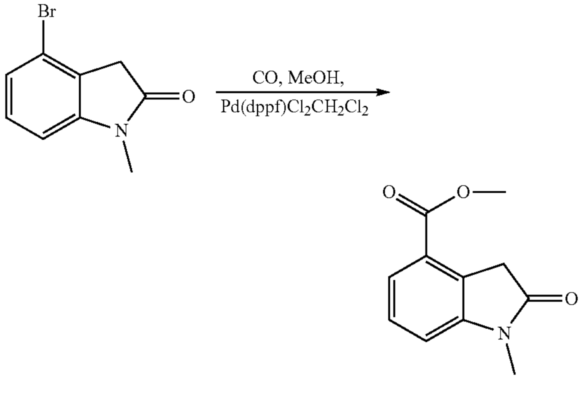

Into a 30-mL pressure tank reactor (5 atm), was placed 4-bromo-1-methyl-2,3-dihydro-1H-indol-2-one (190 mg, 0.84 mmol, 1.00 equiv), methanol (12 g, 374.53 mmol, 445.63 equiv), $Pd(dppf)Cl_2.CH_2Cl_2$ (68.6 mg, 0.10 equiv), triethylamine (170 mg, 1.68 mmol, 2.00 equiv), and CO gas. The reaction mixture was stirred overnight at 100° C. The resulting mixture was concentrated under vacuum. The residue was applied onto a silica gel column and eluted with ethyl acetate/petroleum ether (1:4). This resulted in 120 mg (70%) of methyl 1-methyl-2-oxo-2,3-dihydro-1H-indole-4-carboxylate as a light yellow solid.

Part 4—Synthesis of 1-methyl-2-oxoindoline-4-carbohydrazide

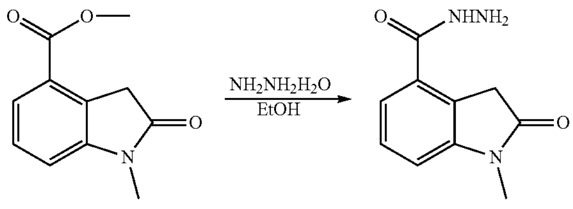

Into a 100-mL round-bottom flask, was placed methyl 1-methyl-2-oxo-2,3-dihydro-1H-indole-4-carboxylate (120 mg, 0.58 mmol, 1.00 equiv), ethanol (30 mL), and $NH_2NH_2.H_2O$ (585.5 mg, 20.00 equiv). The resulting solution was stirred overnight at 90° C. then concentrated under vacuum. This resulted in 110 mg (92%) of 1-methyl-2-oxo-2,3-dihydro-1H-indole-4-carbohydrazide as a yellow solid.

Part 5—Synthesis of 4-(5-((4-chloro-1H-indazol-5-yl)amino)-1,3,4-thiadiazol-2-yl)-1-methylindolin-2-one 2,2,2-trifluoroacetic Acid Solvate

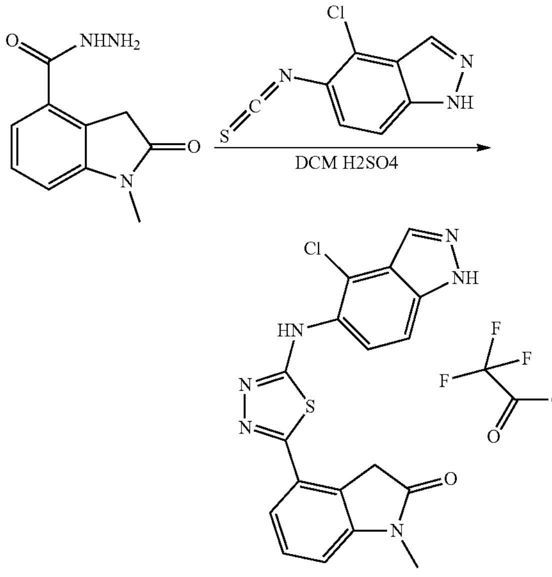

Into a 100-mL round-bottom flask, was placed 1-methyl-2-oxo-2,3-dihydro-1H-indole-4-carbohydrazide (294 mg, 1.43 mmol, 1.00 equiv), dichloromethane (20 mL), and 4-chloro-5-isothiocyanato-1H-indazole (300 mg, 1.43 mmol, 1.00 equiv). The resulting solution was stirred overnight at room temperature then concentrated under vacuum. Sulfuric acid (1 g, 10.20 mmol, 7.12 equiv) was added dropwise with stirring at 0° C. The resulting solution was allowed to react, with stirring, for an additional 3 h at room temperature. The reaction was then quenched by the addition of 50 mL of water/ice. The solids were collected by filtration and dried in an oven under reduced pressure. The crude product was purified by prep-HPLC. This resulted in 9.3 mg (1%) of 4-[5-[(4-chloro-1H-indazol-5-yl)amino]-1,3,4-thiadiazol-2-yl]-1-methyl-2,3-dihydro-1H-indol-2-one; trifluoroacetic acid solvate as a pink solid. (ES, m/z): $[M+H]^+397$.

$^1H$ NMR (DMSO-$d_6$, 400 MHz, ppm): δ 13.44 (s, 1H), 10.07 (s, 1H), 8.12 (s, 1H), 7.86 (d, J=8.8 Hz, 1H), 7.58 (d, J=8.8 Hz, 1H), 7.37 (t, J=13.6 Hz, 2H), 7.08-6.94 (m, 2H), 3.75 (s, 2H), 3.14 (s, 3H).

Example 44—Synthesis of N-(4-Chloro-1H-indazol-5-yl)-5-(3-(1-(2-methoxyethyl)-1H-imidazol-2-yl)phenyl)-1,3,4-thiadiazol-2-amine 2,2,2-trifluoroacetic Acid Solvate

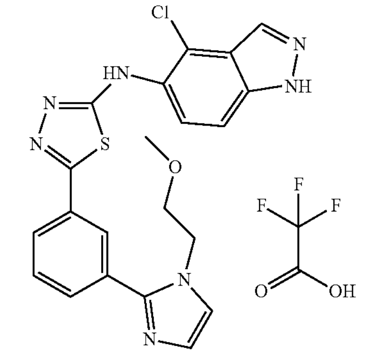

Part 1—Synthesis of 1-(2-methoxyethyl)-1H-imidazole

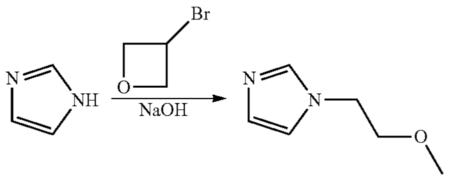

Into a 250-mL round-bottom flask purged and maintained with an inert atmosphere of nitrogen, was placed 1H-imidazole (5 g, 73.45 mmol, 1.00 equiv), ACN (100 mL), sodium hydroxide (5.9 g, 147.50 mmol, 2.01 equiv), and 1-chloro-2-methoxyethane (10.1 mL, 1.50 equiv). The resulting solution was heated to reflux overnight. The resulting solution was diluted with 300 mL of $H_2O$ and extracted with 3×100 mL of dichloromethane. The organic layers were combined, washed with 100 mL of brine then dried over anhydrous sodium. After filtration and evaporation the residue was applied onto a silica gel column and eluted with dichloromethane/methanol (0-2%). This resulted in 5 g (54%) of 1-(2-methoxyethyl)-1H-imidazole as a light red solid.

Part 2—Synthesis of 1-(2-methoxyethyl)-2-(tributylstannyl)-1H-imidazole

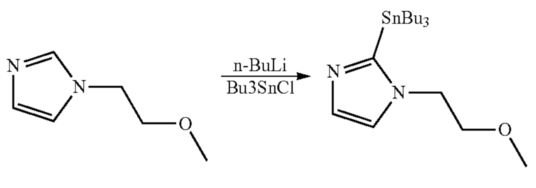

Into a 100-mL 3-necked round-bottom flask purged and maintained with an inert atmosphere of nitrogen, was placed 1-(2-methoxyethyl)-1H-imidazole (2 g, 15.85 mmol, 1.00 equiv), and tetrahydrofuran (30 mL). n-BuLi (9.5 mL) was dropwise with stirring at −78° C. The resulting solution was stirred for 1 h at −78° C. To this mixture was added $Bu_3SnCl$ (4.52 mL) dropwise with stirring at −78° C. The resulting solution was stirred for overnight at RT then concentrated under vacuum. The residue was diluted with 50 mL of hexane and the solids were filtered out. The filtrate was concentrated under vacuum. This resulted in 6 g (crude) of 1-(2-methoxyethyl)-2-(tributylstannyl)-1H-imidazole as a colorless liquid.

Part 3—Synthesis of Tert-Butyl 5-((tert-butoxycarbonyl)(5-(3-(1-(2-methoxyethyl)-1H-imidazol-2-yl) phenyl)-1,3,4-thiadiazol-2-yl)amino)-4-chloro-1H-indazole-1-carboxylate

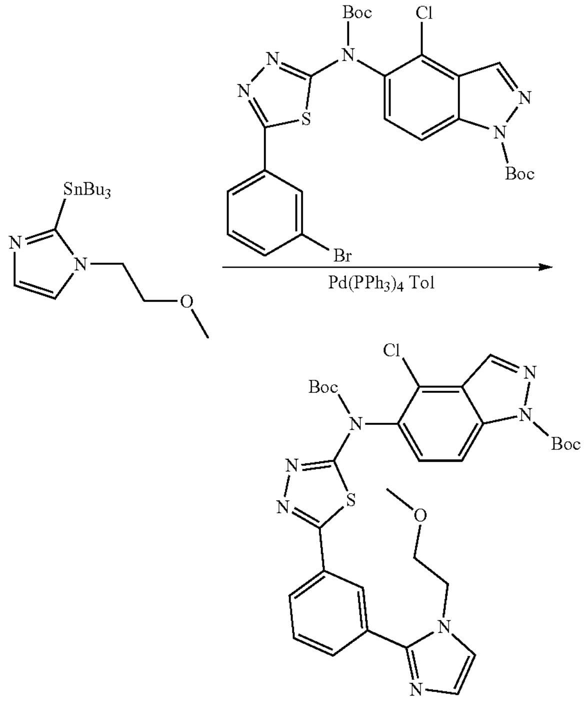

Into a 20-mL microwave tube purged and maintained with an inert atmosphere of nitrogen, was placed tert-butyl 5-[[5-(3-bromophenyl)-1,3,4-thiadiazol-2-yl][(tert-butoxy)carbonyl]amino]-4-chloro-1H-indazole-1-carboxylate (300 mg, 0.49 mmol, 1.00 equiv), Toluene (10 mL), 1-(2-methoxyethyl)-2-(tributylstannyl)-1H-imidazole (4 g, 9.63 mmol, 19.49 equiv), and $Pd(PPh_3)_4$ (57 mg, 0.05 mmol, 0.10 equiv). The resulting solution was stirred for 2 h at 120° C. then concentrated under vacuum. The residue was applied onto a silica gel column and eluted with ethyl acetate/petroleum ether (30%-40%). This resulted in 150 mg (47%) of tert-butyl 5-[[(tert-butoxy)carbonyl](5-[3-[1-(2-methoxyethyl)-1H-imidazol-2-yl]phenyl]-1,3,4-thiadiazol-2-yl) amino]-4-chloro-1H-indazole-1-carboxylate as a light yellow solid.

Part 4—Synthesis of N-(4-chloro-1H-indazol-5-yl)-5-(3-(1-(2-methoxyethyl)-1H-imidazol-2-yl)phenyl)-1,3,4-thiadiazol-2-amine 2,2,2-trifluoroacetic Acid Solvate

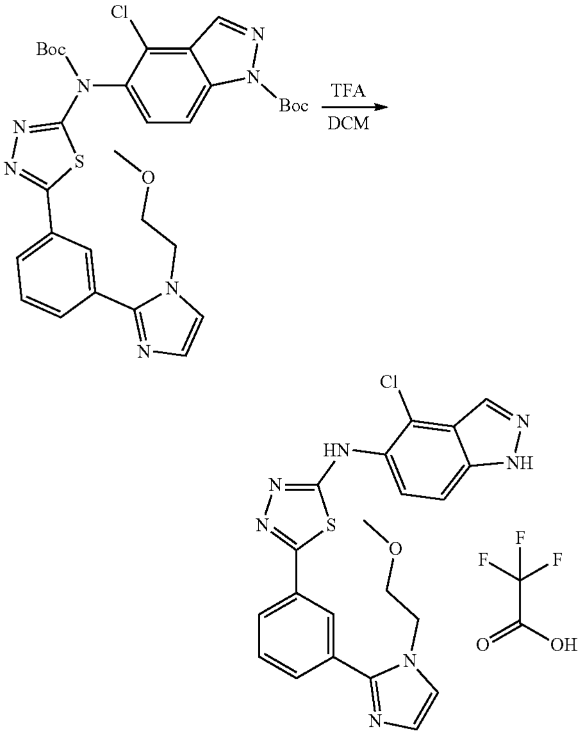

Into a 50-mL round-bottom flask, was placed tert-butyl 5-[[(tert-butoxy)carbonyl](5-[3-[1-(2-methoxyethyl)-1H-imidazol-2-yl]phenyl]-1,3,4-thiadiazol-2-yl)amino]-4-chloro-1H-indazole-1-carboxylate (100 mg, 0.15 mmol, 1.00 equiv), dichloromethane (3 mL), and trifluoroacetic acid (1 mL). The resulting solution was stirred for 2 h at room temperature then concentrated under vacuum. The crude product was purified by Prep-HPLC with the following conditions: Column: XBridge Shield RP18 OBD Column, 5 um, 19*150 mm; Mobile Phase A: Water (0.05% TFA), Mobile Phase B: ACN; Flow rate: 30 mL/min; Gradient: 15% B to 32% B in 8 min; Detection by UV at 220 nm. This resulted in 40 mg (46%) of 4-chloro-N-(5-[3-[1-(2-methoxyethyl)-1H-imidazol-2-yl]phenyl]-1,3,4-thiadiazol-2-yl)-1H-indazol-5-amine trifluoroacetic acid solvate as a yellow solid. (ES, m/z): $[M-TFA+H]^+$452.00. $^1H$ NMR ($DMSO-d_6$, 400 MHz, ppm): δ 13.49 (s, 1H), 10.18 (s, 1H), 8.21 (s, 1H), 8.16-8.09 (m, 2H), 7.92 (s, 1H), 7.88-7.72 (m, 4H), 7.60 (d, J=8.9 Hz, 1H), 4.31 (t, J=5.0 Hz, 2H), 3.70 (t, J=4.9 Hz, 2H), 3.19 (s, 3H).

Example 45—Synthesis 2-(2-(3-(5-((4-Chloro-1H-indazol-5-yl)amino)-1,3,4-thiadiazol-2-yl)phenyl)-1H-imidazol-1-yl)ethan-1-ol 2,2,2-trifluoroacetic Acid Solvate The compound in Table 6 was prepared based on procedures described in Example 44.

TABLE 6

| Example No. | Chemical Structure | Physical Characterization Data |
|---|---|---|
| 45A | 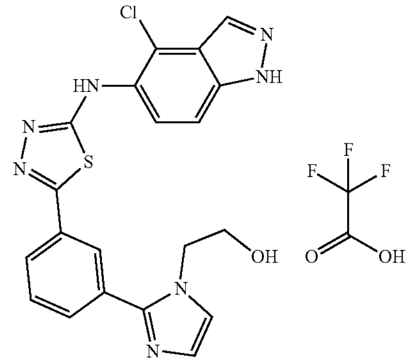 | (ES, m/z): [M-TFA + H]$^+$ 438.00. $^1$H NMR (DMSO-$d_6$, 400 MHz, ppm): δ 13.49 (s, 1H), 10.17 (s, 1H), 8.26-8.05 (m, 2H), 7.95-7.70 (m, 5H), 7.61 (dd, J = 8.7, 1.0 Hz, 1H), 5.20 (s, 1H), 4.20 (t, J = 4.7 Hz, 2H), 3.77 (t, J = 5.0 Hz, 2H). |

Example 46—Synthesis of Additional N-(1H-Indazol-5-yl)-1,3,4-thiadiazol-2-amine Compounds The compounds in Table 7 were prepared based on procedures described above.

TABLE 7

| Example No. | Chemical Structure | Physical Characterization Data |
|---|---|---|
| 46A | 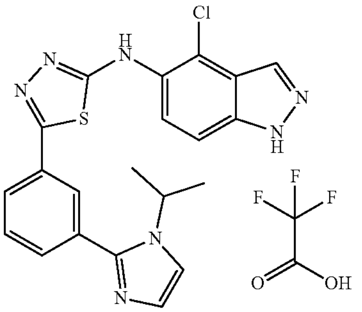 | (ES, m/z): [M + H]$^+$ 436.05. $^1$H NMR (DMSO-$d_6$, 400 MHz, ppm): δ 13.51 (s, 1H), 10.19 (s, 1H), 8.18-8.08 (m, 4H), 7.92-7.73 (m, 4H), 7.61 (dd, J = 8.8, 1.0 Hz, 1H), 4.57 (p, J = 6.6 Hz, 1H), 1.48 (d, J = 6.6 Hz, 6H). |
| 46B | 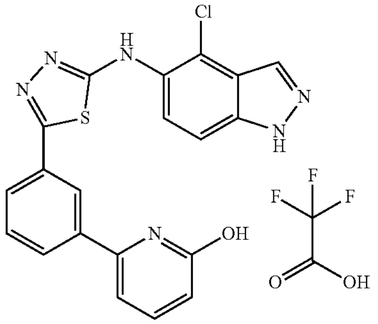 | (ES, m/z): [M + H]$^+$ 420.95. $^1$H NMR (DMSO-$d_6$, 400 MHz, ppm): δ 13.50 (s, 1H), 10.15 (s, 1H), 8.24 (s, 2H), 7.93-7.81 (m, 4H), 7.68-7.56 (m, 4H), 6.46-6.43 (d, J = 9.0 Hz, 1H). |

TABLE 7-continued
| Example No. | Chemical Structure | Physical Characterization Data |
|---|---|---|
| 46C | 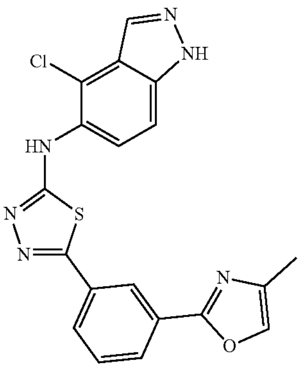 [SMILES: Cc1coc(-c2cccc(-c3nnc(Nc4ccc5[nH]ncc5c4Cl)s3)c2)n1] | (ES, m/z): $[M + H]^+$ 409. $^1H$ NMR (DMSO-$d_6$, 400 MHz, ppm): δ 13.47 (s, 1H), 10.21 (s, 1H), 8.32-8.32 (d, 1H), 8.14-8.14 (d, 1H), 8.02-7.83 (m, 4H), 7.64-7.59 (m, 2H), 2.17-2.17 (s, 3H). |
| 46D | 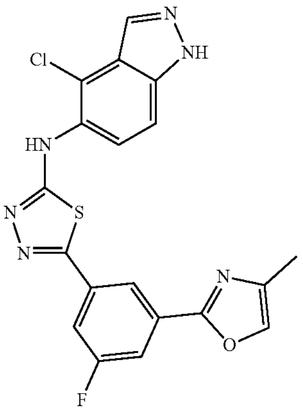 [SMILES: Cc1coc(-c2cc(F)cc(-c3nnc(Nc4ccc5[nH]ncc5c4Cl)s3)c2)n1] | (ES, m/z): $[M + H]^+$ 427. $^1H$ NMR (DMSO-$d_6$, 400 MHz, ppm): δ 13.47 (s, 1H), 10.21 (s, 1H), 8.15-8.14 (d, 2H), 8.0-7.99 (d, 1H), 7.84-7.76 (m, 3H), 7.61-7.59 (m, 1H), 2.18-2.71 (d, 3H). |
| 46E | 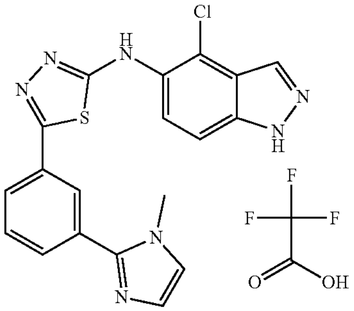 | (ES, m/z): $[M + H]^+$ 407.95. $^1H$ NMR (DMSO-$d_6$, 400 MHz, ppm): δ 13.53 (s, 1H), 10.21 (s, 1H), 8.24 - 8.08 (m, 3H), 7.93 - 7.74 (m, 4H), 7.63 (dd, J = 8.8, 1.0 Hz, 1H), 3.89 (s, 3H). |
| 46F | 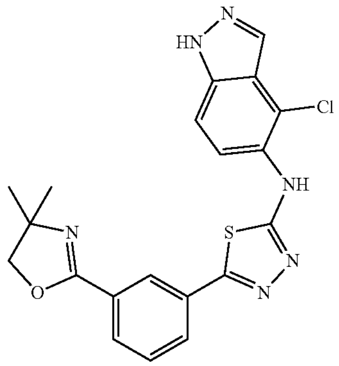 [SMILES: CC1(C)COC(c2cccc(-c3nnc(Nc4ccc5[nH]ncc5c4Cl)s3)c2)=N1] | (ES, m/z): $[M + H]^+$ 425.05. $^1H$ NMR (DMSO-$d_6$, 400 MHz, ppm): δ 10.11 (s, 1H), 8.21 (s, 1H), 8.13 (s, 1H), 7.88-7.94 (m, 2H), 7.83 (d, J = 8.8 Hz, 1H), 7.55-7.60 (m, 2H), 4.13 (s, 2H), 1.29 (s, 6H). |

TABLE 7-continued

| Example No. | Chemical Structure | Physical Characterization Data |
|---|---|---|
| 46G | 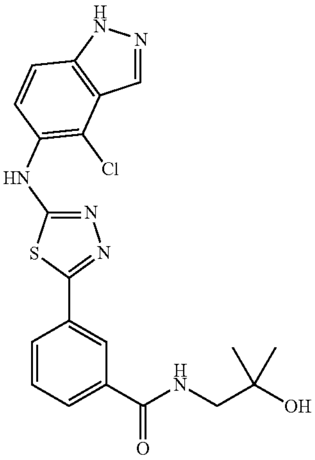 [SMILES: CC(C)(O)CNC(=O)c1cccc(-c2nnc(Nc3ccc4[nH]ncc4c3Cl)s2)c1] | (ES, m/z): $[M + H]^+$ 443.05. $^1H$ NMR ($DMSO-d_6$, 400 MHz, ppm): δ 8.47 (s, 1H); 8.22 (s, 1H), 8.13 (d, J = 0.8 Hz, 1H), 7.91-7.95 (m, 2H), 7.81 (d, J = 8.8 Hz, 1H), 7.54-7.60 (m, 2H), 4.54 (s, 1H), 3.25 (d, J = 6 Hz, 2H), 1.09 (s, 6H). |
| 46H | 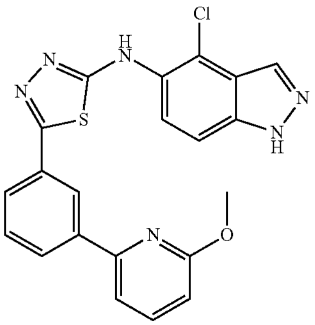 [SMILES: COc1cccc(-c2cccc(-c3nnc(Nc4ccc5[nH]ncc5c4Cl)s3)c2)n1] | (ES, m/z): $[M + H]^+$ 435.0. $^1H$ NMR ($DMSO-d_6$, 400 MHz, ppm): δ 8.49 (s, 1H), 8.19-8.17 (d, J = 8.0 Hz, 1H), 8.14 (s, 1H), 7.89-7.80 (m 3H), 7.67-7.65 (d, J = 7.6 Hz, 1H), 7.63-7.59 (t, J = 7.6 Hz, 2H), 6.85-6.83 (d, J = 8.0 Hz, 1H), 3.98 (s, 3H). |
| 46I | 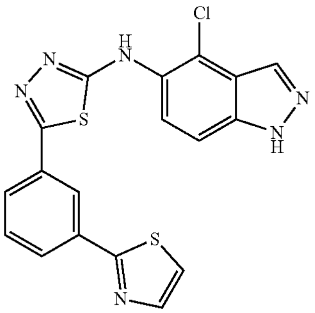 [SMILES: Clc1c(Nc2nnc(-c3cccc(-c4nccs4)c3)s2)ccc2[nH]ncc12] | (ES, m/z): $[M + H]^+$ 410.9. $^1H$ NMR ($DMSO-d_6$, 400 MHz, ppm): δ 8.36 (s, 1H), 8.15 (s, 1H), 8.04-8.02 (d, J = 8.0 Hz, 1H), 7.99-7.98 (d, J = 3.2 Hz, 1H), 7.89-7.85 (m, 3H), 7.64-7.60 (m, 2H). |
| 46J | 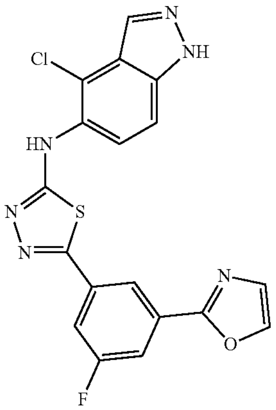 [SMILES: Fc1cc(-c2ncco2)cc(-c2nnc(Nc3ccc4[nH]ncc4c3Cl)s2)c1] | (ES, m/z): $[M + H]^+$ 413. $^1H$ NMR ($DMSO-d_6$, 400 MHz, ppm): δ 13.49 (s, 1H), 10.21 (s, 1H), 8.33 (s, 1H), 8.22-8.16 (d, 2H), 7.86-7.80 (m, 3H), 7.63-7.601 (d, 1H), 7.48 (s, 1H). |

TABLE 7-continued

| Example No. | Chemical Structure | Physical Characterization Data |
|---|---|---|
| 46K | 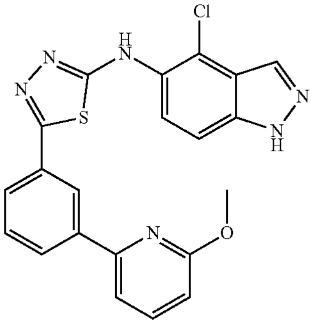 | (ES, m/z): $[M+H]^+$ 418.95. $^1H$ NMR ($DMSO-d_6$, 400 MHz, ppm): δ 8.49 (s, 1H), 8.15-8.14 (d, 6.4 Hz, 2H), 7.87-7.78 (m, 4H), 7.62-7.58 (t, J = 8.4 Hz, 2H), 7.28-7.26 (d, J = 6.8 Hz, 1H), 2.57 (s, 3H). |
| 46L | 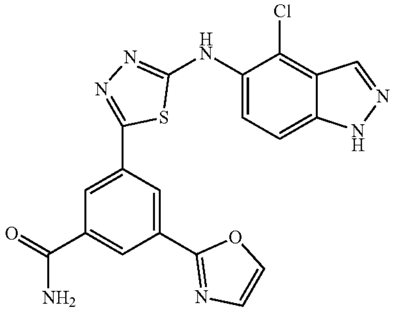 [SMILES: NC(=O)c1cc(-c2ncco2)cc(-c2nnc(Nc3ccc4[nH]ncc4c3Cl)s2)c1] | (ES, m/z): $[M+H]^+$ 438.05. $^1H$ NMR ($DMSO-d_6$, 400 MHz, ppm): δ 13.50 (s, 1H), 10.10 (s, 1H), 8.51 (s, 2H), 8.38 (s, 1H), 8.33 (s, 1H), 8.31 (s, 1H), 8.14 (s, 1H), 7.85-7.80 (m, 1H), 7.64-7.59 (m, 2H), 7.48 (s, 1H). |
| 46M | 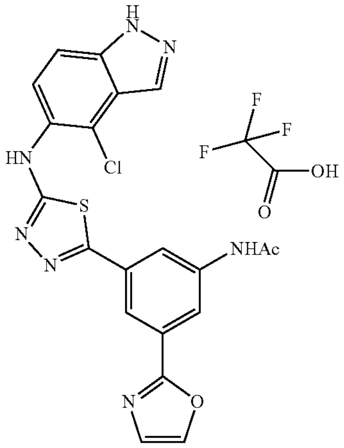 | (ES, m/z): $[M+H]^+$ 452. $^1H$ NMR ($DMSO-d_6$, 400 MHz, ppm): δ 13.46 (s, 1H), 10.33 (s, 1H), 10.11 (s, 1H), 8.38 (s, 1H), 8.26 (s, 1H), 8.14 (d, J = 13.6 Hz, 2H), 7.99 (s, 1H), 7.86 (d, J = 8.4 Hz, 1H), 7.59 (d, J = 8.8 Hz, 1H), 7.41 (s, 1H), 2.08 (s, 3H). |
| 46N | 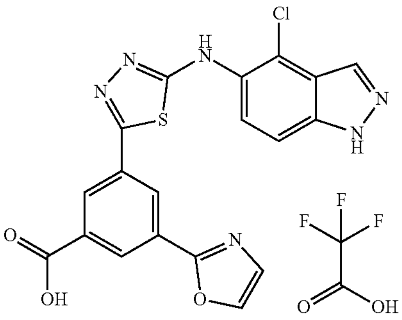 | (ES, m/z): $[M-TFA+H]^+$ 438.95. $^1H$ NMR ($DMSO-d_6$, 400 MHz, ppm): δ 13.78 (s, 1H), 13.56 (s, 1H), 10.24 (s, 1H), 8.54 (s, 2H), 8.37 (s, 1H), 8.34 (s, 1H), 8.16 (s, 1H), 7.64 - 7.61 (d, J = 8.8 Hz, 2H), 7.49 (s, 1H). |

TABLE 7-continued

| Example No. | Chemical Structure | Physical Characterization Data |
|---|---|---|
| 46O | 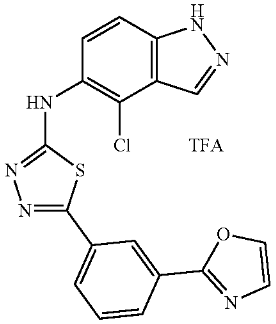 [SMILES: Clc1c(Nc2nnc(-c3cccc(-c4ncco4)c3)s2)ccc2[nH]ncc12 ; "TFA"] | (ES, m/z): $[M + H]^+$ 395. $^1H$ NMR ($DMSO-d_6$, 400 MHz, ppm): δ 13.46 (s, 1H), 10.13 (s, 1H), 8.37 (s, 1H), 8.27 (d, J = 0.4 Hz, 1H), 8.13 (s, 1H), 8.06-8.03 (m, 1H), 7.92-7.84 (m, 2H), 7.66-7.58 (m, 2H), 7.42 (d, J = 0.4 Hz, 1H). |
| 46P | 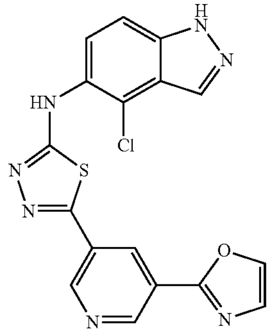 [SMILES: Clc1c(Nc2nnc(-c3cncc(-c4ncco4)c3)s2)ccc2[nH]ncc12] | (ES, m/z): $[M + H]^+$ 396. $^1H$ NMR ($DMSO-d_6$, 400 MHz, ppm): δ 9.21 (d, J = 2.1 Hz, 1H), 9.10 (d, J = 2.2 Hz, 1H), 8.64 (t, J = 2.1 Hz, 1H), 8.38 (s, 1H), 8.16 (s, 1H), 7.85 (d, J = 8.9 Hz, 1H), 7.62 (d, J = 8.8 Hz, 1H), 7.52 (s, 1H). |

Example 47—Synthesis of (S)-(3-Acetamido-5-(5-((4-chloro-1H-indazol-5-yl)amino)-1,3,4-thiadiazol-2-yl)benzyl)ethanethioate

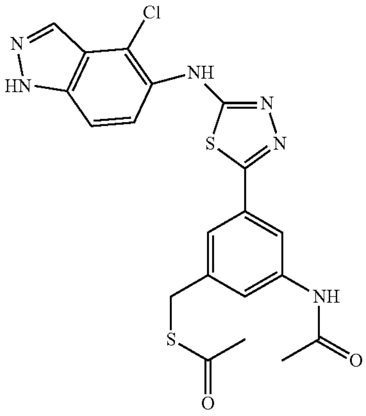 [SMILES: CC(=O)Nc1cc(CSC(C)=O)cc(-c2nnc(Nc3ccc4[nH]ncc4c3Cl)s2)c1]

Part 1—Synthesis of Tert-Butyl 5-((5-(3-acetamido-5-(bromomethyl)phenyl)-1,3,4-thiadiazol-2-yl) amino)-4-chloro-1H-indazole-1-carboxylate

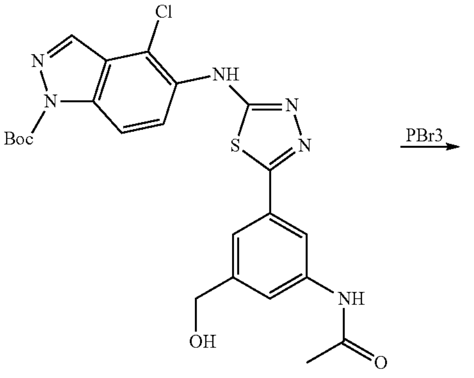

-continued

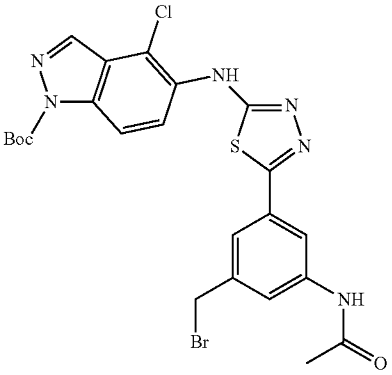

Into a 100-mL round-bottom flask, was placed a solution of tert-butyl 4-chloro-5-([5-[3-acetamido-5-(hydroxymethyl)phenyl]-1,3,4-thiadiazol-2-yl]amino)-1H-indazole-1-carboxylate (800 mg, 1.55 mmol, 1.00 equiv) in dichloromethane (15 mL), and phosphorous tribromide (631 mg, 2.33 mmol, 1.50 equiv). The resulting solution was stirred overnight at room temperature then quenched by the addition of 2 mL of methanol. The resulting mixture was concentrated under vacuum. The residue was applied onto a silica gel column and eluted with dichloromethane/methanol (10:1). This resulted in 400 mg (45%) of tert-butyl 5-([5-[3-(bromomethyl)-5-acetamidophenyl]-1,3,4-thiadiazol-2-yl]amino)-4-chloro-1H-indazole-1-carboxylate as a yellow solid.

Part 2—Synthesis of Tert-Butyl 5-((5-(3-acetamido-5-((acetylthio)methyl)phenyl)-1,3,4-thiadiazol-2-yl)amino)-4-chloro-1H-indazole-1-carboxylate

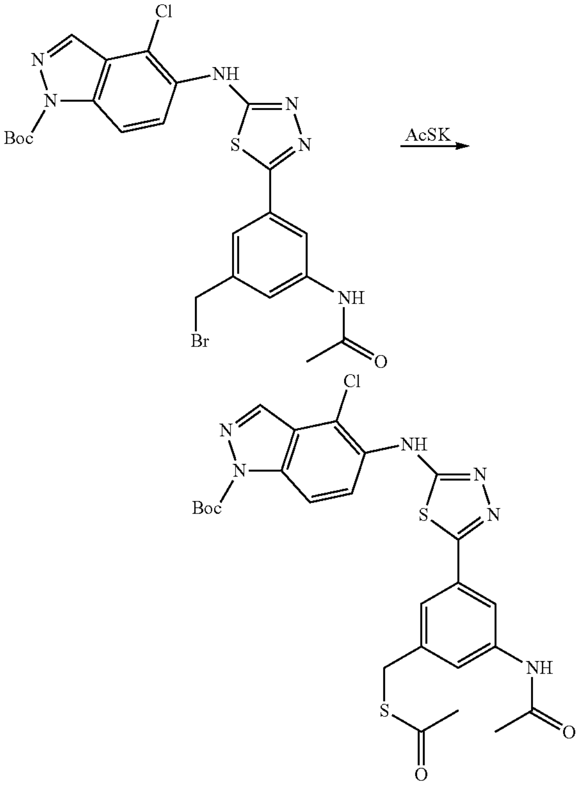

Into a 100-mL round-bottom flask, was placed a solution of tert-butyl 5-([5-[3-(bromomethyl)-5-acetamidophenyl]-1,3,4-thiadiazol-2-yl]amino)-4-chloro-1H-indazole-1-carboxylate (250 mg, 0.43 mmol, 1.00 equiv) in acetone (10 mL), and potassium thioacetate (99 mg, 0.87 mmol, 2.00 equiv). The resulting solution was stirred overnight at room temperature. The solids were filtered out. The filtrate was purified by preparative-TLC eluting with ethyl acetate to give 150 mg (61%) of tert-butyl 5-[(5-[3-[(acetylsulfanyl)methyl]-5-acetamidophenyl]-1,3,4-thiadiazol-2-yl)amino]-4-chloro-1H-indazole-1-carboxylate as a yellow solid.

Part 3—Synthesis of S-(3-acetamido-5-(5-((4-chloro-1H-indazol-5-yl)amino)-1,3,4-thiadiazol-2-yl)benzyl) Ethanethioate

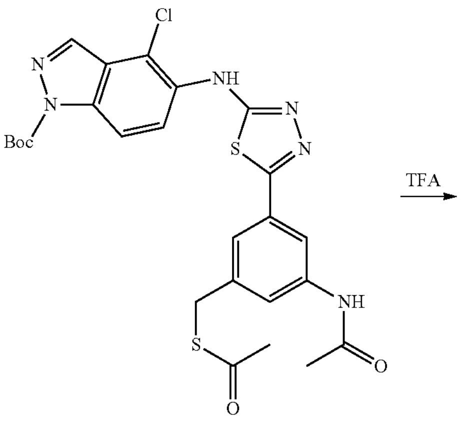

-continued

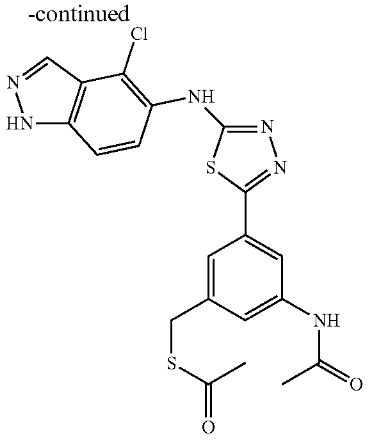

Into a 10-mL round-bottom flask, was placed a solution of tert-butyl 5-[(5-[3-[(acetylsulfanyl)methyl]-5-acetamidophenyl]-1,3,4-thiadiazol-2-yl)amino]-4-chloro-1H-indazole-1-carboxylate (150 mg, 0.26 mmol, 1.00 equiv) in dichloromethane (2 mL), and trifluoroacetic acid (1 mL). The resulting solution was stirred overnight at room temperature. The resulting mixture was concentrated under vacuum. The crude product was purified by Prep-HPLC with the following conditions (2#-AnalyseHPLC-SHIMADZU (HPLC-10)): Column, XBridge Shield RP18 OBD Column, 5 um, 19*150 mm; mobile phase, Water (0.05% TFA) and ACN (30.0% ACN up to 50.0% in 8 min); Detector, UV 220 nm. This resulted in 80 mg (65%) of N-[3-[(acetylsulfanyl)methyl]-5-[5-[(4-chloro-1H-indazol-5-yl)amino]-1,3,4-thiadiazol-2-yl]phenyl]acetamide; trifluoroacetic acid solvate as an off-white solid. (ES-ESI, m/z): 472.9 $[M+H]^+$. $^1H$ NMR (400 MHz, DMSO-$d_6$, ppm): δ 13.45 (s, 1H), 10.11 (s, 1H), 10.03 (s, 1H), 8.12 (s, 1H), 7.99 (s, 1H), 7.84 (d, J=8.8 Hz, 1H), 7.55-7.59 (m, 2H), 7.39 (s, 1H), 4.12 (s, 2H), 2.35 (s, 3H), 2.03 (s, 3H).

Example 48—Synthesis of Additional N-(1H-Indazol-5-yl)-1,3,4-thiadiazol-2-amine Compounds The compounds in Table 8 were prepared based on procedures described in Example 32.

TABLE 8
| Example No. | Chemical Structure | Physical Characterization Data |
|---|---|---|
| 48A | 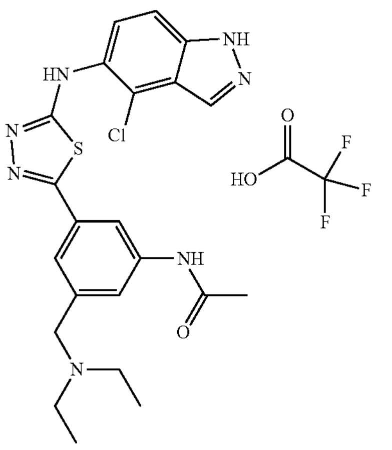 | (ES, m/z): [M − TFA + H]$^+$. 470. $^1$H NMR (400 MHz, DMSO-$d_6$, ppm) δ 13.52 (s, 1H), 10.29 (s, 1H), 10.14 (s, 1H), 9.41 (s, 1H), 8.17 (s, 1H), 8.04 (t, J = 1.6 Hz, 1H), 7.94 (s, 1H), 7.81 (d, J = 8.9 Hz, 1H), 7.67 (s, 1H), 7.63 (d, J = 8.8 Hz, 1H), 7.34 − 6.89 (m, 2H), 7.23 (s, 1H), 6.97 (s, 1H), 4.36 (d, J = 5.5 Hz, 2H), 2.10 (s, 3H), 1.23 (t, J = 7.2 Hz, 6H). |
| 48B | 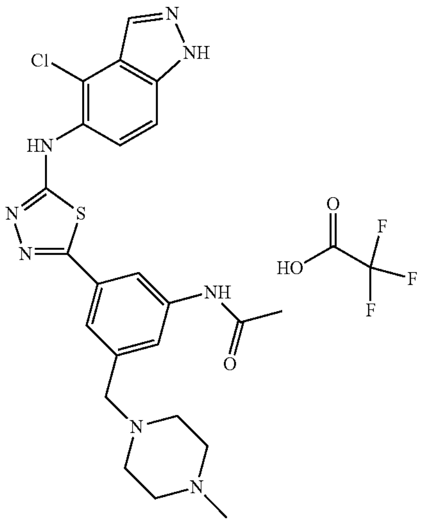 | (ES, m/z): 497.10 [M + H]$^+$. $^1$H NMR ($CD_3OD$, ppm): δ 8.12 (s, 1H), 7.89 (s, 1H), 7.74 − 7.79 (m, 2H), 7.55 − 7.57 (m, 2H), 3.74 (m, 2H), 3.29 − 3.33 (m, 4H), 2.60 − 2.90 (m, 7H), 2.14 (s, 3H). |
| 48C | 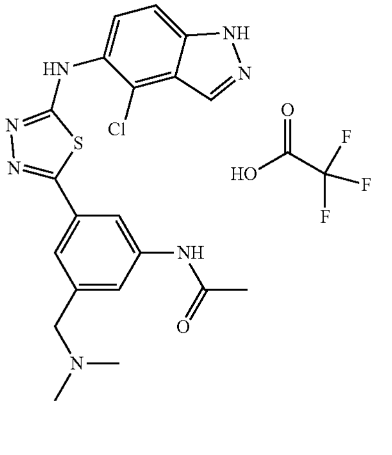 | (ES, m/z): [M − TFA + H]$^+$ 442. $^1$H NMR (DMSO-$d_6$, 400 MHz, ppm) δ 13.51 (s, 1H), 10.29 (s, 1H), 10.13 (s, 1H), 9.67 (d, J = 9.2 Hz, 1H), 8.16 (s, 1H), 8.02 (t, J = 1.7 Hz, 1H), 7.92 (s, 1H), 7.81 (d, J = 8.9 Hz, 1H), 7.62 (d, J = 9.1 Hz, 2H), 4.32 (d, J = 5.2 Hz, 2H), 2.75 (d, J = 4.4 Hz, 6H), 2.09 (s, 3H). |

TABLE 8-continued

| Example No. | Chemical Structure | Physical Characterization Data |
|---|---|---|
| 48D | 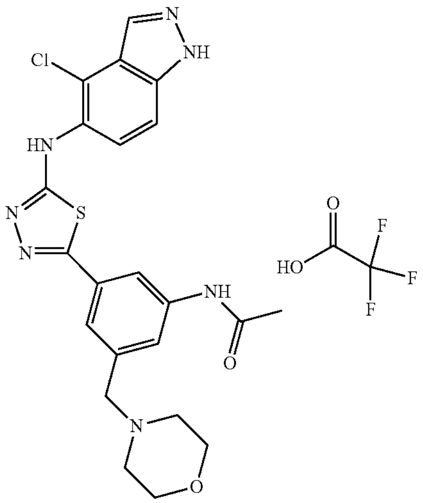 | (ES, m/z): $[M + H]^+$ 484.1. $^1H$ NMR ($DMSO-d_6$, 400 MHz, ppm): δ 13.48 (s, 1H), 10.27 (s, 1H), 10.10 (s, 1H), 8.14 (s, 1H), 7.99 (s, 1H), 7.92 (s, 1H), 7.78 (d, J = 8.8 Hz, 1H), 7.65 – 7.57 (m, 2H), 4.35 (s, 2H), 3.93 (s, 2H), 3.60 (s, 3H), 3.12 (s, 3H), 2.07 (s, 3H). |
| 48E | 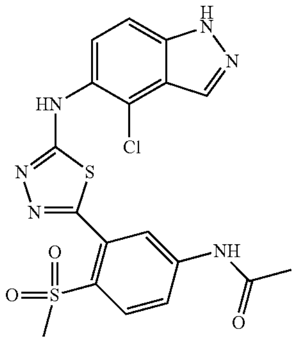 [SMILES: CC(=O)Nc1ccc(S(C)(=O)=O)c(-c2nnc(Nc3ccc4[nH]ncc4c3Cl)s2)c1] | (ES, m/z): $[M + H]^+$ 463. $^1H$ NMR ($DMSO-d_6$, 400 MHz, ppm): δ 13.46 (s, 1H), 10.56 (s, 1H), 10.06 (s, 1H), 8.14 (s, 1H), 8.06 (d, J = 8.8, 1H), 7.99 – 7.95 (m, 2H), 7.90 – 7.87 (m, 1H), 7.62 (d, J = 8.8, 1H), 3.33 (s, 3H), 2.11 (s, 3H). |
| 48F | 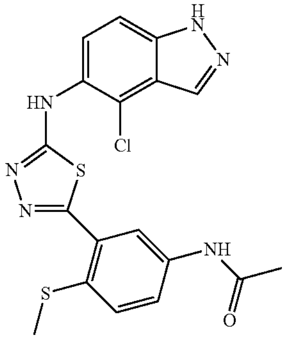 [SMILES: CSc1ccc(NC(C)=O)cc1-c1nnc(Nc2ccc3[nH]ncc3c2Cl)s1] | (ES, m/z): $[M + H]^+$ 431. $^1H$ NMR ($DMSO-d_6$, 400 MHz, ppm): δ 13.47 (s, 1H), 10.10 (s, 1H), 9.84 (s, 1H), 8.12 – 8.10 (m, 2H), 7.87 – 7.85 (m, 1H), 7.68 – 7.66 (m, 1H), 7.59 – 7.56 (m, 1H), 7.45 – 7.42 (m, 1H), 2.41 (s, 3H), 2.03 (s, 3H). |
| 48G | 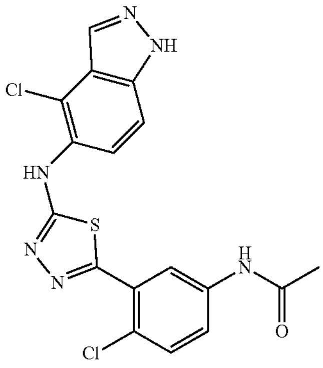 [SMILES: CC(=O)Nc1ccc(Cl)c(-c2nnc(Nc3ccc4[nH]ncc4c3Cl)s2)c1] | (ES, m/z): $[M + H]^+$ 418.02. $^1H$ NMR ($DMSO-d_6$, 400 MHz, ppm): δ 13.49 (s, 1H), 10.27 (s, 1H), 10.10 (s, 1H), 8.34 (d, J = 2.6 Hz, 1H), 8.16 (s, 1H), 7.89 (d, J = 8.9 Hz, 1H), 7.75 (m, J = 8.9, 2.6 Hz, 1H), 7.59 (m, J = 24.1, 8.8 Hz, 2H), 2.08 (s, 3H). |

TABLE 8-continued

| Example No. | Chemical Structure | Physical Characterization Data |
|---|---|---|
| 48H | 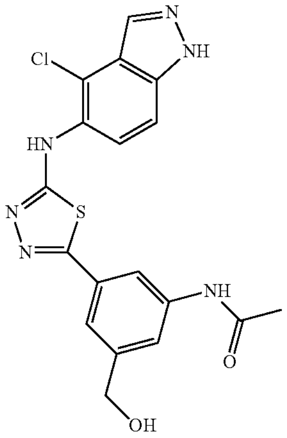 [SMILES: CC(=O)Nc1cc(CO)cc(-c2nnc(Nc3ccc4[nH]ncc4c3Cl)s2)c1] | (ES, m/z): $[M+H]^+$ 414.95. $^1H$ NMR ($DMSO-d_6$, 400 MHz, ppm): δ 13.45 (s, 1H), 10.08 (s, 2H), 8.12 (s, 1H), 8.02 - 7.96 (m, 1H), 7.84 (d, J = 8.8 Hz, 1H), 7.63 - 7.55 (m, 2H), 7.37 (s, 1H), 5.31 (t, J = 5.8 Hz, 1H), 4.49 (d, J = 5.0 Hz, 2H), 2.04 (s, 3H). |
| 48I | 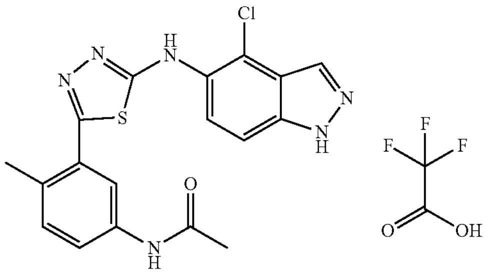 [SMILES: CC(=O)Nc1ccc(C)c(-c2nnc(Nc3ccc4[nH]ncc4c3Cl)s2)c1 ; O=C(O)C(F)(F)F] | (ES, m/z): $[M+H]^+$ 399.00. $^1H$ NMR ($DMSO-d_6$, 400 MHz, ppm): δ 13.46 (s, 1H), 10.03 (d, J = 13.9 Hz, 2H), 8.14 (s, 1H), 7.92 - 7.90 (m, 2H), 7.57 (ddd, J = 19.1, 8.6, 1.6 Hz, 2H), 7.28 (d, J = 8.3 Hz, 1H), 2.44 (s, 3H), 2.04 (s, 3H). |
| 48J | 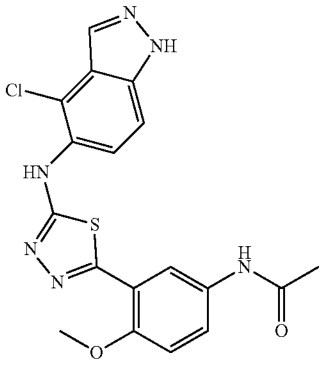 [SMILES: COc1ccc(NC(C)=O)cc1-c1nnc(Nc2ccc3[nH]ncc3c2Cl)s1] | (ES, m/z): $[M+H]^+$ 415. $^1H$ NMR ($DMSO-d_6$, 400 MHz, ppm): δ 13.43 (s, 1H), 9.96 (s, 1H), 8.34 (d, J = 2.7 Hz, 1H), 8.11 (s, 1H), 7.86 (d, J = 8.9 Hz, 1H), 7.70 (dd, J = 9.0, 2.7 Hz, 1H), 7.57 (dd, J = 8.8, 1.0 Hz, 1H), 7.15 (d, J = 9.0 Hz, 1H), 3.87 (s, 3H), 2.02 (s, 3H). |
| 48K | 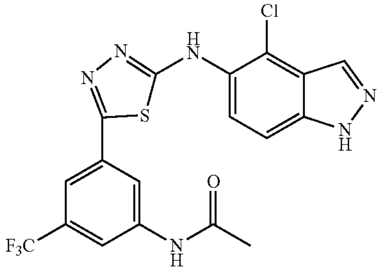 [SMILES: CC(=O)Nc1cc(-c2nnc(Nc3ccc4[nH]ncc4c3Cl)s2)cc(C(F)(F)F)c1] | (ES, m/z): $[M+H]^+$ 452.95. $^1H$ NMR ($DMSO-d_6$, 400 MHz, ppm): δ 13.51 (s, 1H), 10.48 (s, 1H), 10.21 (s, 1H), 8.27 (s, 1H), 8.15 (d, J = 11.8 Hz, 2H), 7.86 (d, J = 8.8 Hz, 1H), 7.74 (s, 1H), 7.62 (d, J = 8.9 Hz, 1H), 2.11 (s,3H). |

TABLE 8-continued

| Example No. | Chemical Structure | Physical Characterization Data |
|---|---|---|
| 48L | 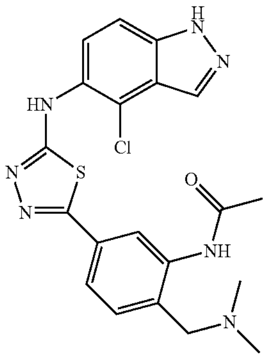 [SMILES: CC(=O)Nc1cc(-c2nnc(Nc3ccc4[nH]ncc4c3Cl)s2)ccc1CN(C)C] | (ES, m/z): [M + H]$^+$ 442. $^1$H NMR (DMSO-$d_6$, 400 MHz, ppm): δ 13.44 (s, 1H), 10.51 (s, 1H), 10.01 (s, 1H), 8.43 (s, 1H), 8.11 (s, 1H), 7.85 - 7.83 (m, 1H), 7.58 - 7.56 (m, 1H), 7.45 - 7.43 (m, 1H), 7.31 - 7.29 (m, 1H), 3.51 (s, 2H), 2.19 (s, 6H), 2.06 (s, 3H). |
| 48M | 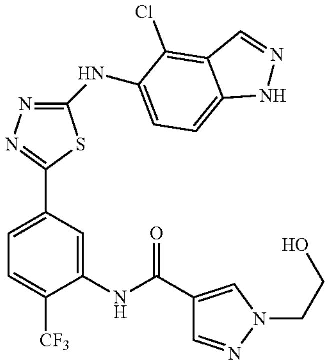 [SMILES: O=C(Nc1cc(-c2nnc(Nc3ccc4[nH]ncc4c3Cl)s2)ccc1C(F)(F)F)c1cnn(CCO)c1] | (ES, m/z): [M + H]$^+$ 549.05. $^1$H NMR (DMSO-$d_6$, 400 MHz, ppm): δ 13.49 (s, 1H), 10.24 (s, 1H), 9.83 (s, 1H), 8.31 (s, 1H), 8.14 (s, 1H), 7.99 (s, 1H), 7.95 - 7.80 (m, 4H), 7.60 (d, J = 9.0 Hz, 1H), 4.98 (t, J = 5.2 Hz, 1H), 4.19 (t, J = 5.4 Hz, 2H), 3.75 (q, J = 5.4 Hz, 2H). |
| 48N | 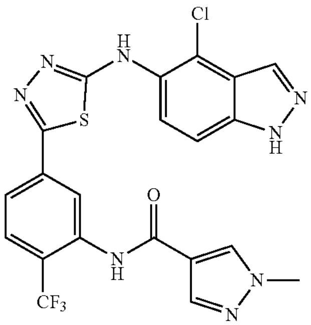 [SMILES: Cn1cc(C(=O)Nc2cc(-c3nnc(Nc4ccc5[nH]ncc5c4Cl)s3)ccc2C(F)(F)F)cn1] | (ES, m/z): [M + H]$^+$ 519.00. $^1$H NMR (DMSO-$d_6$, 400 MHz, ppm): δ 13.49 (s, 1H), 10.23 (s, 1H), 9.80 (s, 1H), 8.30 (s, 1H), 8.16 (s, 1H), 7.99 (s, 1H), 7.88 (dd, J = 21.0, 12.0 Hz, 4H), 7.62 (d, J = 9.0 Hz, 1H), 3.91 (s, 3H). |
| 48O | 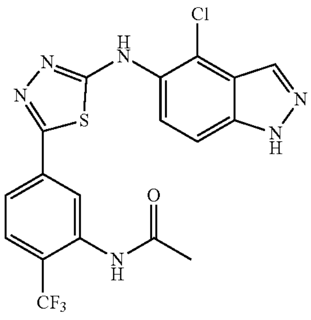 [SMILES: CC(=O)Nc1cc(-c2nnc(Nc3ccc4[nH]ncc4c3Cl)s2)ccc1C(F)(F)F] | (ES, m/z): [M + H]$^+$ 452.95. $^1$H NMR (DMSO-$d_6$, 400 MHz, ppm): δ 13.51 (s, 1H), 10.18 (s, 1H), 9.70 (s, 1H), 8.17 (s, 1H), 7.94 (s, 1H), 7.86 - 7.83 (m, 3H), 7.62 (d, J = 8.8 Hz, 1H), 2.09 (s, 3H). |

TABLE 8-continued
| Example No. | Chemical Structure | Physical Characterization Data |
| --- | --- | --- |
| 48P | 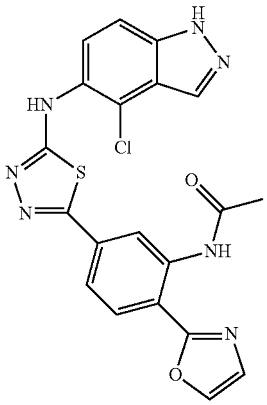 [SMILES: CC(=O)Nc1cc(-c2nnc(Nc3ccc4[nH]ncc4c3Cl)s2)ccc1-c1ncco1] | (ES, m/z): $[M + H]^+$ 451.95. $^1H$ NMR (DMSO-$d_6$, 400 MHz, ppm): δ 13.34 (s, 1H), 11.54 (s, 1H), 9.02 (s, 1H), 8.34 (s, 1H), 8.17 – 8.00 (m, 2H), 7.79 (d, J = 8.7 Hz, 1H), 7.66 – 7.50 (m, 3H), 2.20 (s, 3H). |
| 48Q | 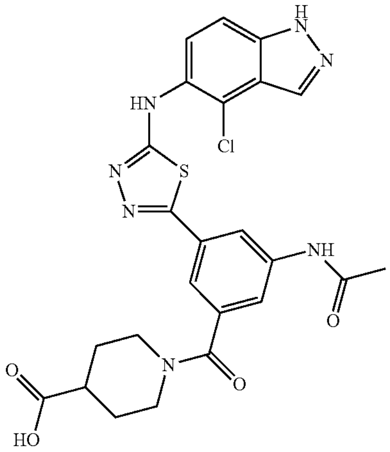 [SMILES: CC(=O)Nc1cc(C(=O)N2CCC(C(=O)O)CC2)cc(-c2nnc(Nc3ccc4[nH]ncc4c3Cl)s2)c1] | (ES, m/z): $[M + H]^+$ 540. $^1H$ NMR (DMSO-$d_6$, 400 MHz, ppm): δ 13.46 (s, 1H), 10.25 (s, 1H), 8.12 (dd, J = 4.1, 1.5 Hz, 2H), 7.85 (d, J = 8.8 Hz, 1H), 7.68 (t, J = 1.7 Hz, 1H), 7.58 (dd, J = 8.8, 1.0 Hz, 1H), 7.39 (t, J = 1.6 Hz, 1H), 4.29 (s, 1H), 3.55 – 2.93 (m, 5H), 2.06 – 1.13 (m, 8H). |
| 48R | 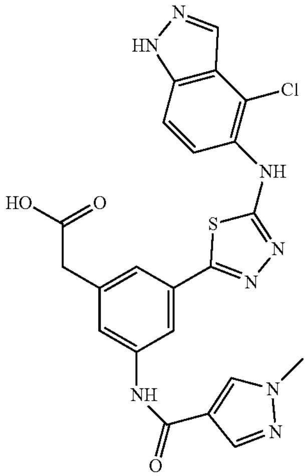 [SMILES: Cn1cc(C(=O)Nc2cc(CC(=O)O)cc(-c3nnc(Nc4ccc5[nH]ncc5c4Cl)s3)c2)cn1] | (ES, m/z): $[M + H]^+$ 509.0. $^1H$ NMR (DMSO-$d_6$, 400 MHz, ppm): δ 9.95 (s, 1H), 8.32 (d, J = 8.4 Hz, 1H), 8.13 (s, 2H); 8.01 (s, 1H), 7.83 (d, J = 8.8 Hz, 1H), 7.58 – 7.60 (m, 1H), 7.37 (s, 1H), 3.88 (s, 3H), 3.62 (s, 2H). |

TABLE 8-continued

| Example No. | Chemical Structure | Physical Characterization Data |
| --- | --- | --- |
| 48S | 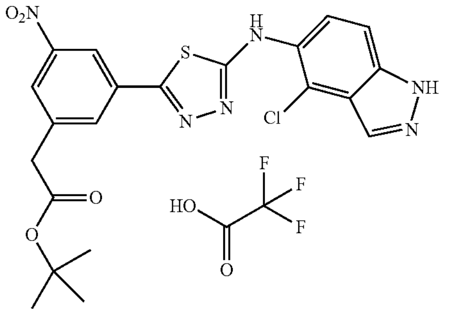 | (ES, m/z): $[M + H]^+$ 487.05. $^1H$ NMR ($DMSO-d_6$, 400 MHz, ppm): δ 13.49 (s, 1H), 10.26 (s, 1H), 8.44 (s, 1H), 8.22 (s, 1H), 8.13 (d, J = 7.6 Hz, 2H), 7.82 (d, J = 8.8 Hz, 1H), 7.60 (d, J = 8.8 Hz, 1H), 3.86 (s, 2H), 1.41 (s, 9H). |
| 48T | 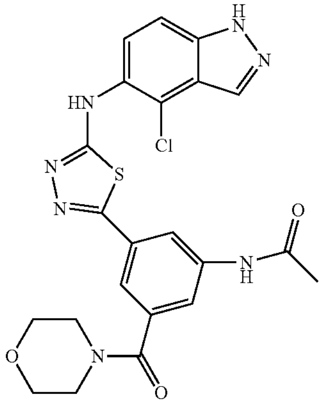 [SMILES: CC(=O)Nc1cc(C(=O)N2CCOCC2)cc(-c2nnc(Nc3ccc4[nH]ncc4c3Cl)s2)c1] | (ES, m z): $[M + H]^+$ 497.1. $^1H$ NMR ($DMSO-d_6$, 400 MHz, ppm): δ 13.46 (s, 1H), 10.24 (s, 1H), 10.07 (s, 1H), 8.33 - 7.97 (m, 2H), 7.99 - 7.79 (m, 1H), 7.80 - 7.65 (m, 1H), 7.58 (dd, J = 8.8, 1.0 Hz, 1H), 7.42 (t, J = 1.5 Hz, 1H), 3.31 (s, 8H), 2.06 (s, 3H). |
| 48U | 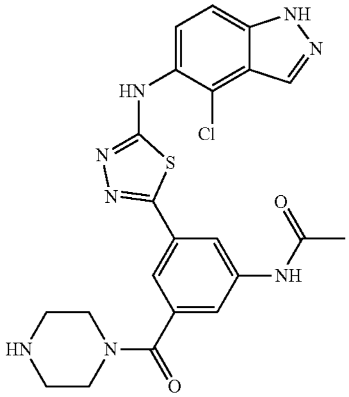 [SMILES: CC(=O)Nc1cc(C(=O)N2CCNCC2)cc(-c2nnc(Nc3ccc4[nH]ncc4c3Cl)s2)c1] | (ES, m z): $[M + H]^+$ 496.12. $^1H$ NMR ($DMSO-d_6$, 400 MHz, ppm): δ 13.47 (s, 1H), 10.23 (s, 1H), 8.15 - 8.05 (m, 2H), 7.84 (d, J = 8.9 Hz, 1H), 7.69 (t, J = 1.7 Hz, 1H), 7.58 (dd, J = 8.8, 1.0 Hz, 1H), 7.38 (t, J = 1.6 Hz, 1H), 3.52 (s, 2H), 3.24 (s, 3H), 2.72 (s, 2H), 2.63 (s, 2H), 2.06 (s, 3H). |
| 48V | 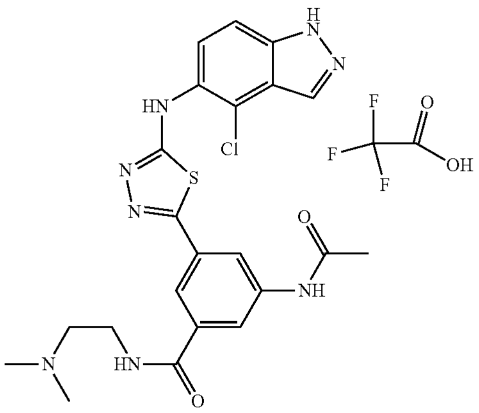 | (ES, m/z): $[M + H]^+$ 498.14. $^1H$ NMR ($DMSO-d_6$, 400 MHz, ppm): δ 13.49 (d, J = 5.0 Hz, 1H), 10.31 (s, 1H), 10.26 (s, 1H), 8.60 (t, J = 5.7 Hz, 1H), 8.38 (s, 1H), 8.14 (d, J = 2.6 Hz, 2H), 7.87 - 7.76 (m, 2H), 7.60 (d, J = 8.8 Hz, 1H), 3.37 (s, 2H), 2.54 (t, J = 5.7 Hz, 2H), 2.28 (s, 6H), 2.06 (s, 3H). |

TABLE 8-continued

| Example No. | Chemical Structure | Physical Characterization Data |
|---|---|---|
| 48W | 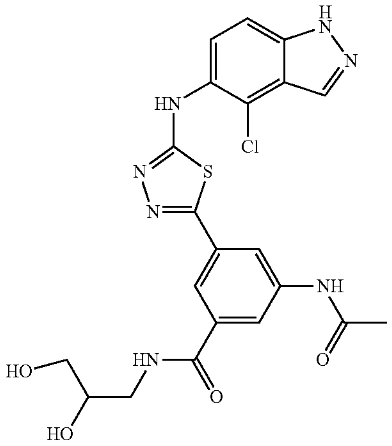 [SMILES: CC(=O)Nc1cc(C(=O)NCC(O)CO)cc(-c2nnc(Nc3ccc4[nH]ncc4c3Cl)s2)c1] | (ES, m/z): $[M + H]^+$ 502. $^1H$ NMR (DMSO-$d_6$, 400 MHz, ppm): δ 13.46 (s, 1H), 10.23 (s, 1H), 10.11 (s, 1H), 8.56 (t, J = 5.8 Hz, 1H), 8.36 – 8.23 (m, 1H), 8.11 (s, 1H), 8.04 (d, J = 2.2 Hz, 1H), 7.85 (s, 1H), 7.78 (d, J = 8.7 Hz, 1H), 7.57 (d, J = 8.8 Hz, 1H), 4.80 (d, J = 4.9 Hz, 1H), 4.55 (t, J = 5.8 Hz, 1H), 3.61 (p, J = 5.7 Hz, 1H), 3.41 – 3.32 (m, 3H), 3.16 (dt, J = 13.1, 6.2 Hz, 1H), 2.06 (s, 3H). |
| 48X | 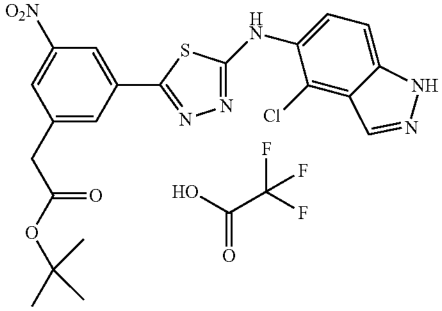 | (ES, m/z): $[M + H]^+$ 442.92. $^1H$ NMR (DMSO-$d_6$, 400 MHz, ppm): δ 13.49 (s, 1H), 10.21 (s, 1H), 8.44 (s, 1H), 8.22 (s, 1H), 8.14 (s, 2H), 7.82 (d, J = 8.8 Hz, 1H), 7.60 (d, J = 7.6 Hz, 1H), 7.21 (bs, 1H), 3.86 (s, 2H), 1.40 (s, 9H). |
| 48Y | 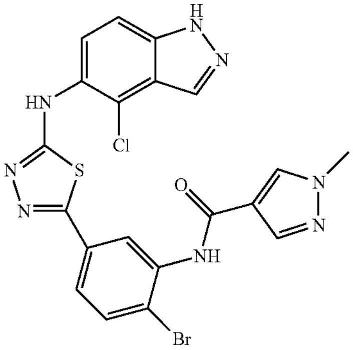 [SMILES: Cn1cc(C(=O)Nc2cc(-c3nnc(Nc4ccc5[nH]ncc5c4Cl)s3)ccc2Br)cn1] | (ES, m/z): $[M + H]^+$ 530.75. $^1H$ NMR (DMSO-$d_6$, 400 MHz, ppm): δ 13.40 (s, 1H), 9.71 (s, 1H), 8.36 (s, 1H), 8.12 (s, 1H), 8.02 (s, 1H), 7.95 (s, 1H), 7.78 – 7.83 (m, 2H), 7.57 – 7.60 (m, 2H), 3.91 (s, 3H). |
| 48Z | 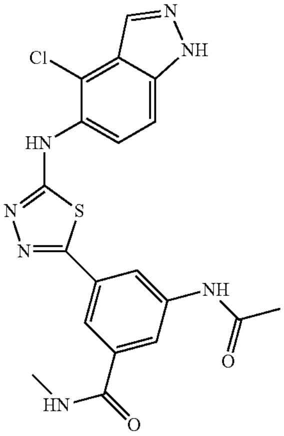 [SMILES: CNC(=O)c1cc(NC(C)=O)cc(-c2nnc(Nc3ccc4[nH]ncc4c3Cl)s2)c1] | (ES, m/z): $[M + H]^+$ 441.08. $^1H$ NMR (DMSO-$d_6$, 400 MHz, ppm): δ 13.46 (s, 1H), 10.23 (s, 1H), 8.58 (d, J = 4.9 Hz, 1H), 8.28 (s, 1H), 8.13 (s, 1H), 8.06 (s, 1H), 7.80 (d, J = 10.0 Hz, 2H), 7.58 (d, J = 8.9 Hz, 1H), 2.76 (d, J = 4.5 Hz, 3H), 2.06 (s, 3H). |

TABLE 8-continued
| Example No. | Chemical Structure | Physical Characterization Data |
|---|---|---|
| 48AA | 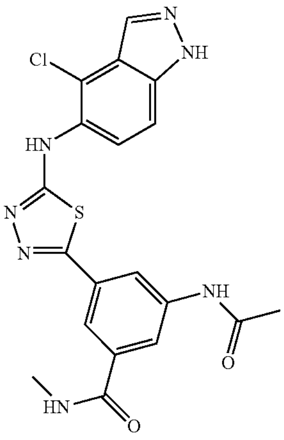 [SMILES: CNC(=O)c1cc(NC(C)=O)cc(-c2nnc(Nc3ccc4[nH]ncc4c3Cl)s2)c1] | (ES, m/z): $[M + H]^+$ 441.08. $^1H$ NMR ($DMSO-d_6$, 400 MHz, ppm): δ 13.46 (s, 1H), 10.23 (s, 1H), 8.58 (d, J = 4.9 Hz, 1H), 8.28 (s, 1H), 8.13 (s, 1H), 8.06 (s, 1H), 7.80 (d, J = 10.0 Hz, 2H), 7.58 (d, J = 8.9 Hz, 1H), 2.76 (d, J = 4.5 Hz, 3H), 2.06 (s, 3H). |
| 48AB | 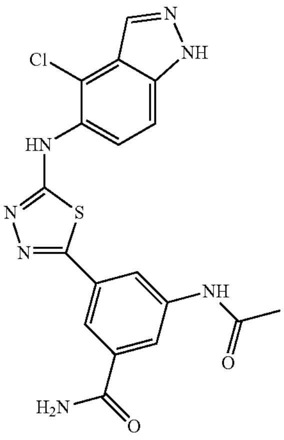 [SMILES: CC(=O)Nc1cc(C(N)=O)cc(-c2nnc(Nc3ccc4[nH]ncc4c3Cl)s2)c1] | (ES, m/z): $[M + H]^+$ 427.06. $^1H$ NMR ($DMSO-d_6$, 400 MHz, ppm): δ 10.18 (s, 1H), 8.19 (s, 1H), 8.11 - 8.00 (m, 3H), 7.80 (s, 1H), 7.70 (d, J = 8.9 Hz, 1H), 7.50 (d, J = 9.0 Hz, 1H), 7.37 (s, 1H), 2.04 (s, 3H), 1.22 (s, 2H). |
| 48AC | 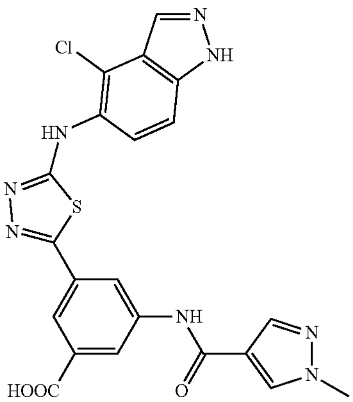 [SMILES: Cn1cc(C(=O)Nc2cc(C(=O)O)cc(-c3nnc(Nc4ccc5[nH]ncc5c4Cl)s3)c2)cn1] | (ES, m/z): $[M + H]^+$ 495. $^1H$ NMR ($DMSO-d_6$, 400 MHz, ppm): δ 13.49 (s, 1H), 10.11 (s, 1H), 8.46 (t, J = 1.9 Hz, 1H), 8.37 (d, J = 5.2 Hz, 2H), 8.13 (d, J = 1.0 Hz, 1H), 8.04 (s, 1H), 7.94 (t, J = 1.5 Hz, 1H), 7.86 (d, J = 8.8 Hz, 1H), 7.60 (dd, J = 8.8, 1.0 Hz, 1H), 3.89 (s, 3H). |

TABLE 8-continued

| Example No. | Chemical Structure | Physical Characterization Data |
|---|---|---|
| 48AD | 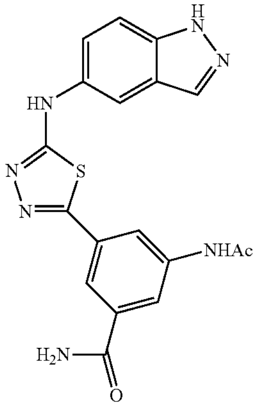 [SMILES: CC(=O)Nc1cc(C(N)=O)cc(-c2nnc(Nc3ccc4[nH]ncc4c3)s2)c1] | (ES, m/z): $[M + H]^+$ 393.1. $^1H$ NMR (DMSO-$d_6$, 400 MHz, ppm): δ 13.02 (s, 1H), 10.52 (s, 1H), 10.25 (s, 1H), 8.34 (t, J = 1.8 Hz, 1H), 8.22 (d, J = 1.9 Hz, 1H), 8.16 (s, 1H), 8.12 - 8.03 (m, 2H), 7.91 (t, J = 1.5 Hz, 1H), 7.55 (d, J = 8.9 Hz, 1H), 7.49 - 7.37 (m, 2H), 2.08 (s, 3H). |
| 48AE | 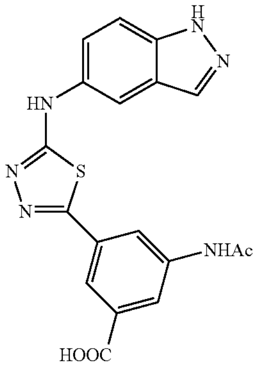 [SMILES: CC(=O)Nc1cc(C(=O)O)cc(-c2nnc(Nc3ccc4[nH]ncc4c3)s2)c1] | (ES, m/z): $[M + H]^+$ 394.1. $^1H$ NMR (DMSO-$d_6$, 400 MHz, ppm): δ 13.02 (s, 1H), 10.62 (s, 1H), 10.26 (s, 1H), 8.35 (t, J = 1.8 Hz, 1H), 8.23 (d, J = 17.1, 2.1 Hz, 2H), 8.06 (s, 1H), 7.96 (t, J = 1.5 Hz, 1H), 7.54 (d, J = 8.9 Hz, 1H), 7.43 (d, J = 8.9, 2.1 Hz, 1H), 2.08 (s, 3H). |
| 48AF | 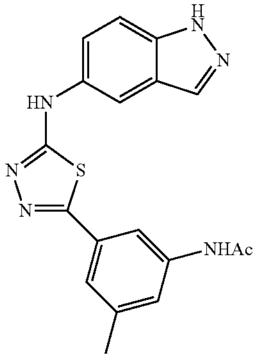 [SMILES: CC(=O)Nc1cc(C)cc(-c2nnc(Nc3ccc4[nH]ncc4c3)s2)c1] | (ES, m/z): $[M + H]^+$ 364.1. $^1H$ NMR (DMSO-$d_6$, 400 MHz, ppm): δ 13.01 (s, 1H), 10.47 (s, 1H), 10.05 (s, 1H), 8.23 (d, J = 1.9 Hz, 1H), 8.05 (s, 1H), 7.93 (t, J = 1.7 Hz, 1H), 7.57 - 7.48 (m, 2H), 7.40 (dd, J = 9.1, 2.1 Hz, 1H), 7.31 (s, 1H), 2.33 (s, 3H), 2.05 (s, 3H). |
| 48AG | 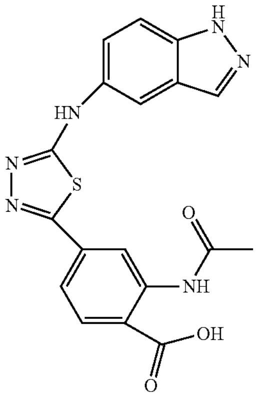 [SMILES: CC(=O)Nc1cc(-c2nnc(Nc3ccc4[nH]ncc4c3)s2)ccc1C(=O)O] | (ES, m/z): $[M + H]^+$ 394. $^1H$ NMR (DMSO-$d_6$, 400 MHz, ppm): δ 13.02 (s, 1H), 10.52 (s, 1H), 8.97 (d, J = 1.9 Hz, 1H), 8.23 (d, J = 1.9 Hz, 1H), 8.08 - 8.00 (m, 2H), 7.58 - 7.37 (m, 3H), 7.08 (s, 2H), 2.10 (s, 3H). |

Example 49—Synthesis of 5-Imidazo[1,2-a]pyridin-8-yl-N-(1H-indazol-5-yl)-1,3,4-thiadiazol-2-amine 2,2,2-trifluoroacetic Acid Solvate

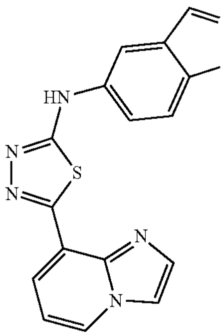

TFA

Part 1—Synthesis of imidazo[1,2-a]pyridine-8-carbohydrazide

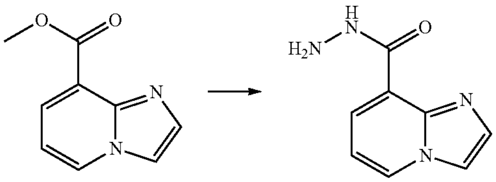

A 100 mL round bottom flask was charged with a solution of methyl imidazo[1,2-a]pyridine-8-carboxylate (1.168 g, 6.63 mmol) in methanol (50 mL), and hydrazine (2.125 g, 66.3 mmol) was added drop-wise with stirring then the reaction mixture was heated to a gentle reflux for 18 h. After cooling down to room temperature the solid formed was separated by filtration and dried in high vacuum, a second crop was obtained and combined with the first to give imidazo[1,2-a]pyridine-8-carbohydrazide (0.875 g, 75% yield) as a beige solid.

Part 2—Synthesis of 5-imidazo[1,2-a]pyridin-8-yl-N-(1H-indazol-5-yl)-1,3,4-thiadiazol-2-amine 2,2,2-trifluoroacetic Acid Solvate

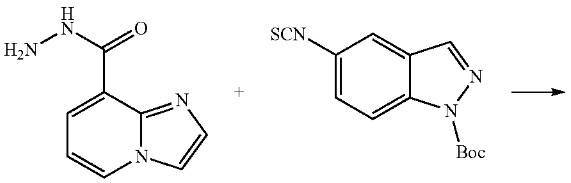

-continued

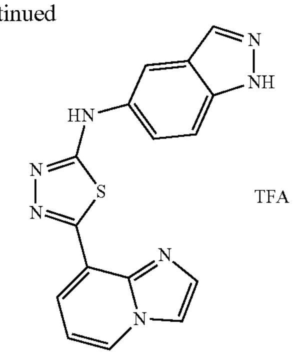

TFA

A 100 mL round bottom flask was charged with a solution of tert-butyl 5-isothiocyanatoindazole-1-carboxylate (0.547 g, 1.987 mmol) in dichloromethane (30 mL) then imidazo[1,2-a]pyridine-8-carbohydrazide (0.350 g, 1.987 mmol) was added and the resulting white suspension was stirred at room temperature overnight. Sulfuric acid (3.89 g, 39.7 mmol) was added and the reaction continued at room temperature for 2 h. The reaction was quenched with a saturated aqueous solution of $NaHCO_3$ to pH about 9 and the resulting yellow solid was separated by filtration, rinsed with water and dried. The dried solid was suspended in methanol and adsorbed onto silica gel and purified by silica gel chromatography (40 g, HP 15-40 uM 60 A flash cartridge from Silicycle) eluting with 0 to 10% dichloromethane/(methanol containing 10% $NH_4OH$) to give crude 5-imidazo[1,2-a]pyridin-8-yl-N-(1H-indazol-5-yl)-1,3,4-thiadiazol-2-amine (0.21 g, 32% yield). 80 mg of the crude product was further purified by preparative HPLC to give 51.3 mg of 5-imidazo[1,2-a]pyridin-8-yl-N-(1H-indazol-5-yl)-1,3,4-thiadiazol-2-amine 2,2,2-trifluoroacetic acid solvate as an orange solid. (ES, m/z): 334.21 $[M+H]^+$. $^1H$ NMR (400 MHz, DMSO-$d_6$) δ 13.03 (br s, 1H), 10.69 (br s, 1H), 8.83 (d, J=6.33 Hz, 1H), 8.31-8.24 (m, 3H), 8.07 (s, 1H), 7.93 (br s, 1H), 7.56 ((d, J=8.89 Hz, 1H), 7.44-7.41 (m, 2H).

Example 50—Synthesis of Additional Compounds

The compounds in Table 9 were prepared based on procedures described in Example 48.

TABLE 9

| Example No. | Chemical Structure | Physical Characterization Data |
|---|---|---|
| 50A | 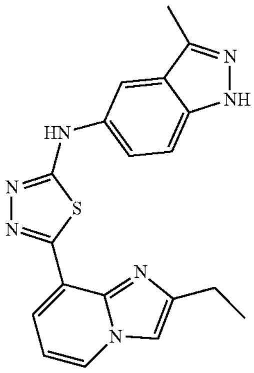 [SMILES: CCc1cn2cccc(-c3nnc(Nc4ccc5[nH]nc(C)c5c4)s3)c2n1] | (ES, m/z): 376.22 $[M+H]^+$. $^1H$ NMR (400 MHz, DMSO-$d_6$) δ 12.66 (br s, 1H), 10.72 (br s, 1H), 8.80 (br s, 1H), 8.31 - 8.08 (m, 3H), 7.53 - 7.33 (m, 3H), 2.91 (q, J = 7.20 Hz, 2H), 2.47 (s, 3H), 1.31 (t, J = 7.51 Hz, 3H) |
| 50B* | 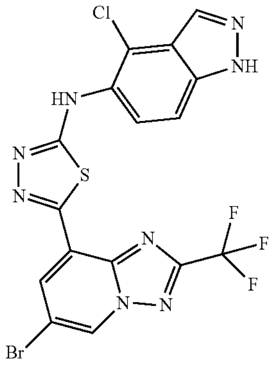 [SMILES: FC(F)(F)c1nc2c(-c3nnc(Nc4ccc5[nH]ncc5c4Cl)s3)cc(Br)cn2n1] | (ES, m/z): 515.01, 517.02 $[M+H]^+$. $^1H$ NMR (400 MHz, DMSO-$d_6$) δ 13.46 (br s, 1H), 10.24 (br s, 1H), 9.69 (d, J = 1.70 Hz, 1H), 8.59 (d, J = 1.66 Hz, 1H), 8.13 (s, 1H), 7.93 (d, J = 8.87 Hz, 1H), 7.61 (d, J = 8.82 Hz, 1 H) |
| 50C | 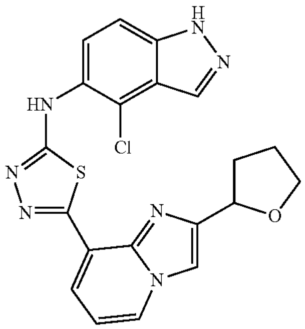 [SMILES: Clc1c(Nc2nnc(-c3cccn4cc(C5CCCO5)nc34)s2)ccc2[nH]ncc12] | (ES, m/z): $[M+H]^+$ 438. $^1H$ NMR (400 MHz, DMSO-$d_6$, ppm): 13.43 (s, 1H), 9.94 (s, 1H), 8.61 - 8.59 (m, 1H), 8.11 - 8.06 (m, 2H), 7.96 (s, 2H), 7.59 - 7.57 (m, 1H), 7.06 - 7.02 (m, 1H), 5.05 - 5.01 (m, 1H), 3.96 - 3.91 (m, 1H), 3.80 - 3.75 (m, 1H), 2.23 - 2.21 (m, 1H), 2.08 - 2.01 (m, 3H) |
| 50D | 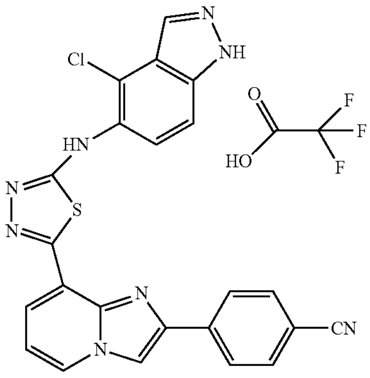 | (ES, m/z): $[M+H]^+$ 468.07. $^1H$ NMR (400 MHz, DMSO-$d_6$,) δ 13.46 (s, 1H), 10.05 (s, 1H), 8.79 (s, 1H), 8.73 (dd, J = 6.7, 1.1 Hz, 1H), 8.24 (d, J = 8.3 Hz, 2H), 8.22 - 8.13 (m, 2H), 8.06 (d, J = 8.8 Hz, 1H), 8.03 - 7.95 (m, 2H), 7.66 - 7.59 (m, 1H) |

TABLE 9-continued

| Example No. | Chemical Structure | Physical Characterization Data |
|---|---|---|
| 50E | 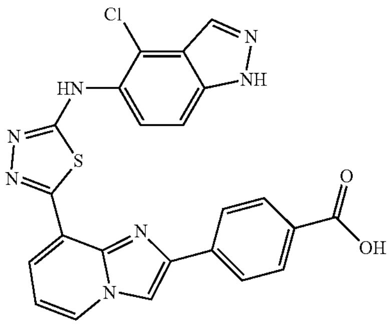 [SMILES: O=C(O)c1ccc(-c2cn3cccc(-c4nnc(Nc5ccc6[nH]ncc6c5Cl)s4)c3n2)cc1] | (ES, m/z): [M + H]$^+$ 488. $^1$H NMR (300 MHz, DMSO-$d_6$, ppm): δ 13.48 (s, 1H), 9.83 (s, 1H), 8.72 - 8.55 (m, 2H), 8.21 - 7.89 (m, 7H), 7.58 (d, J = 8.9 Hz, 1H), 7.07 (t, J = 7.0 Hz, 1H) |
| 50F | 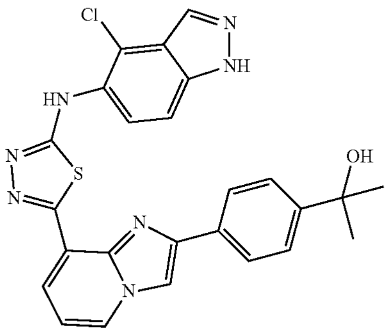 [SMILES: CC(C)(O)c1ccc(-c2cn3cccc(-c4nnc(Nc5ccc6[nH]ncc6c5Cl)s4)c3n2)cc1] | (ES, m/z): [M + H]$^+$ 502. $^1$H NMR (400 MHz, DMSO-$d_6$, ppm): δ 8.65 (dd, J = 6.7, 1.2 Hz, 1H), 8.51 (s, 1H), 8.15 - 8.08 (m, 2H), 8.01 (d, J = 8.8 Hz, 1H), 7.96 - 7.91 (m, 2H), 7.61 - 7.51 (m, 3H), 7.08 (t, J = 7.0 Hz, 1H), 5.04 (s, 1H), 1.45 (s, 6H). |
| 50G | 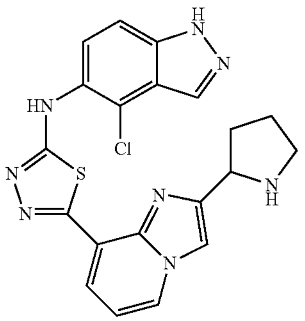 [SMILES: Clc1c(Nc2nnc(-c3cccn4cc(C5CCCN5)nc34)s2)ccc2[nH]ncc12] | (ES, m/z): [M + H]$^+$ 437. $^1$H NMR (400 MHz, DMSO-$d_6$): δ 13.53 (s, 1H), 9.91 (s, 1H), 8.60 (d, J = 6.4, 1H), 8.11 (s, 1H), 8.04 - 8.03 (m, 1H), 7.96 - 7.90 (m, 2H), 7.59 - 7.57 (m. 1H), 7.02 - 6.99 (m, 1H), 4.25 - 4.21 (m, 1H), 2.99 - 2.96 (m, 1H), 2.87 - 2.83 (m, 1H), 2.07 - 1.99 (m, 2H), 1.85 - 1.83 (m, 1H), 1.81 - 1.80 (m, 1H) |
| 50H | 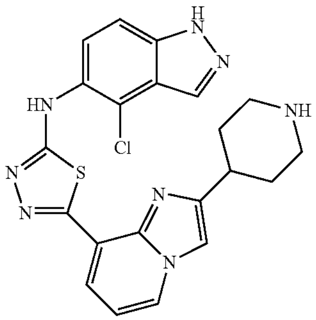 [SMILES: Clc1c(Nc2nnc(-c3cccn4cc(C5CCNCC5)nc34)s2)ccc2[nH]ncc12] | (ES, m/z): [M + H]$^+$ 451. $^1$H NMR (400 MHz, DMSO-$d_6$, ppm): δ 13.47 (s, 1H), 8.59 - 8.57 (m, 1H), 8.11 (d, J = 0.8, 1H), 8.05 - 7.98 (m, 2H), 7.82 (s, 1H), 7.59 - 7.56 (m, 1H), 7.02 - 6.99 (m, 1H), 3.01 - 2.98 (m, 2H), 2.80 - 2.74 (m, 1H), 2.65 - 2.57 (m, 2H), 1.95 - 1.93 (m, 2H), 1.60 - 1.57 (m, 2H) |

*The starting material for preparing this compound, 2-trifluoromethyl-[1,2,4]triazolo[1,5-a] pyridine-8-carboxylic acid ethyl ester, was prepared following the procedure described by Ochiai, Koji et al; *Bioorganic & Medicinal Chemistry*, 20(5), 1644 (2012).

Example 51—Synthesis of 1-(4-(8-(5-((4-Chloro-1H-indazol-5-yl)amino)-1,3,4-thiadiazol-2-yl)imidazo[1,2-a]pyridin-2-yl)phenyl)ethan-1-one

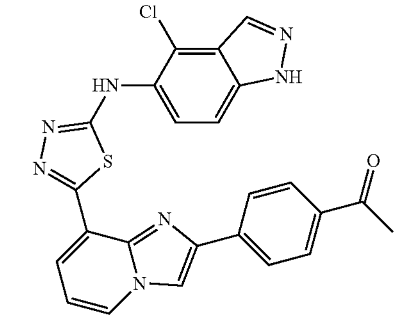 [SMILES: CC(=O)c1ccc(-c2cn3cccc(-c4nnc(Nc5ccc6[nH]ncc6c5Cl)s4)c3n2)cc1]

Part 1—Synthesis of 2-(4-bromophenyl)imidazo[1,2-a]pyridine-8-carboxylic Acid

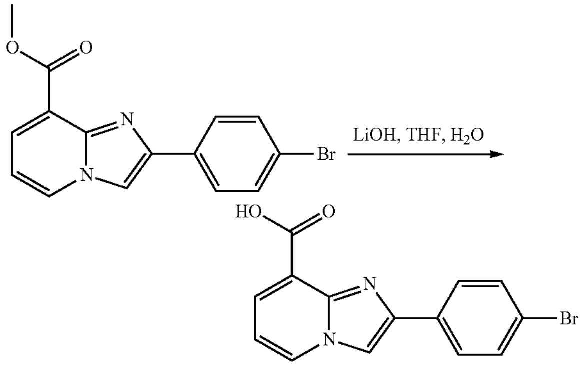

Into a 50-mL round-bottom flask, was placed methyl 2-(4-bromophenyl)imidazo[1,2-a]pyridine-8-carboxylate (1 g, 3.02 mmol, 1.00 equiv), tetrahydrofuran (20 mL), LiOH (747 mg, 31.19 mmol, 10.00 equiv), and water (3 mL). The resulting solution was stirred overnight at room temperature. The pH value of the solution was adjusted to 5 with dilute hydrochloric acid (1 M). The resulting solution was extracted with 4×200 mL of ethyl acetate and the organic layers combined and dried over anhydrous sodium sulfate and concentrated under vacuum. This resulted in 950 mg (99%) of 2-(4-bromophenyl)imidazo[1,2-a]pyridine-8-carboxylic acid as a light brown solid.

Part 2—Synthesis of Tert-Butyl 2-(2-(4-bromophenyl)imidazo[1,2-a]pyridine-8-carbonyl)hydrazine-1-carboxylate

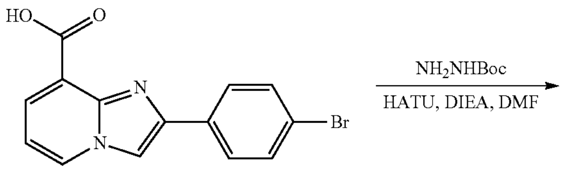

-continued

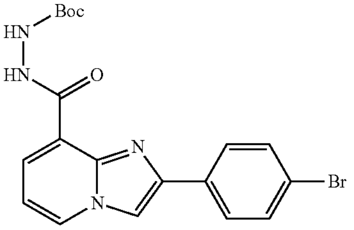

Into a 100-mL round-bottom flask, was placed 2-(4-bromophenyl)imidazo[1,2-a]pyridine-8-carboxylic acid (954 mg, 3.01 mmol, 1.00 equiv), N,N-dimethylformamide (50 mL), DIEA (2 mL, 4.00 equiv), (tert-butoxy)carbohydrazide (795 mg, 6.02 mmol, 2.00 equiv), and HATU (2.3 g, 6.05 mmol, 2.00 equiv). The resulting solution was stirred overnight at room temperature. The resulting solution was diluted with 500 mL of EA and washed with 3×50 mL of brine. After filtration and evaporation, the solid was dried in an oven under reduced pressure. The residue was applied onto a silica gel column and eluted with ethyl acetate/petroleum ether (0:100-70:30). This resulted in 1.8 g (75%) of [2-(4-bromophenyl)imidazo[1,2-a]pyridin-8-yl]([[(tert-butoxy)carbonyl]amino]amino)methanone as a light yellow solid.

Part 3—Synthesis of 2-(4-bromophenyl)imidazo[1,2-a]pyridine-8-carbohydrazide

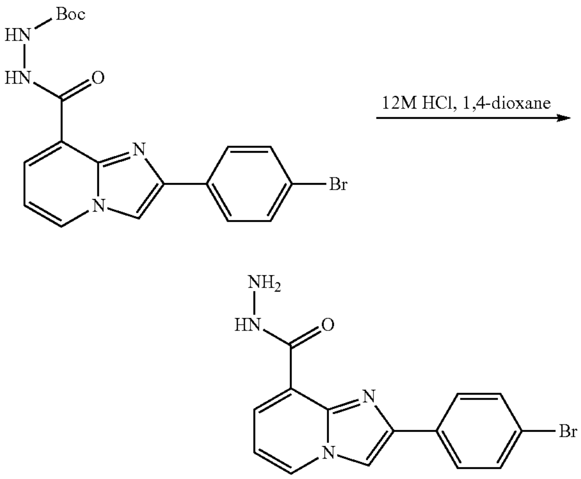

Into a 50-mL round-bottom flask, was placed [2-(4-bromophenyl)imidazo[1,2-a]pyridin-8-yl]([[(tert-butoxy)carbonyl]amino]amino)methanone (1.8 g, 2.25 mmol, 1.00 equiv, 54%), 1,4-dioxane (4 mL), and concentrated hydrochloric acid (5 mL). The resulting solution was stirred for 3 h at room temperature. The solids were collected by filtration then dried in an oven under reduced pressure. This resulted in 0.9 g (crude) of 2-(4-bromophenyl)imidazo[1,2-a]pyridine-8-carbohydrazide hydrochloride as a light brown crude solid.

Part 4—Synthesis of 2-(2-(4-bromophenyl)imidazo[1,2-a]pyridine-8-carbonyl)-N-(4-chloro-1H-indazol-5-yl)hydrazine-1-carbothioamide

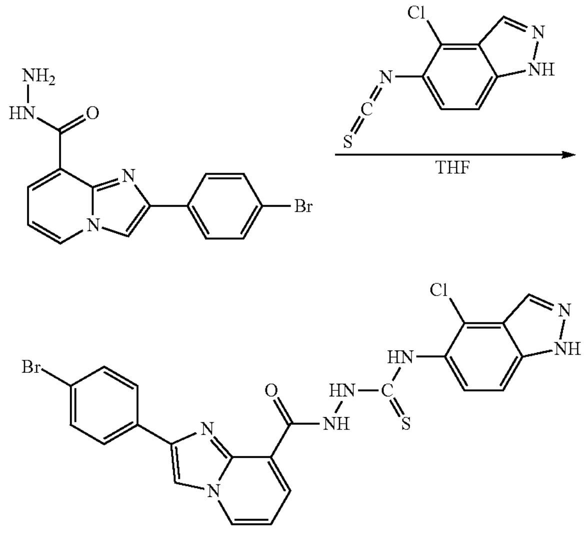

Into a 50-mL round-bottom flask, was placed 2-(4-bromophenyl)imidazo[1,2-a]pyridine-8-carbohydrazide hydrochloride (787 mg, 2.14 mmol, 1.00 equiv), tetrahydrofuran (20 mL), TEA (2 ml, 2.00 equiv), and 4-chloro-5-isothiocyanato-1H-indazole (600 mg, 2.86 mmol, 1.20 equiv). The resulting solution was stirred overnight at room temperature. The resulting mixture was concentrated under vacuum. This resulted in 1.37 g (crude) of 2-(4-bromophenyl)-N-[[(4-chloro-1H-indazol-5-yl)carbamothioyl]amino]imidazo[1,2-a]pyridine-8-carboxamide as a light yellow crude solid.

Part 5—Synthesis of 1-(5-((5-(2-(4-bromophenyl)imidazo[1,2-a]pyridin-8-yl)-1,3,4-thiadiazol-2-yl)amino)-4-chloro-1H-indazol-1-yl)ethan-1-one

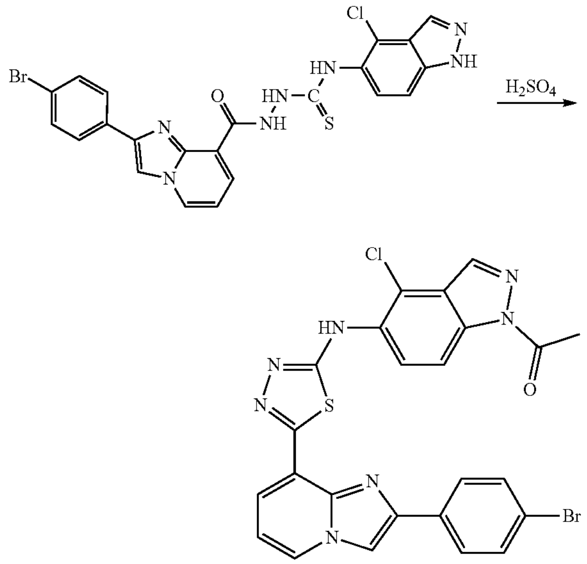

Into a 100-mL round-bottom flask, was placed 2-(4-bromophenyl)-N-[[(4-chloro-1H-indazol-5-yl)carbamothioyl]amino]imidazo[1,2-a]pyridine-8-carboxamide (1.37 g, 2.53 mmol, 1.00 equiv), and sulfuric acid (20 mL). The resulting solution was stirred overnight at room temperature. The reaction was then quenched by the addition of 150 ml of water/ice. The solids were collected by filtration then dried in an oven under reduced pressure. This resulted in 0.9 g (68%) of N-[5-[2-(4-bromophenyl)imidazo[1,2-a]pyridin-8-yl]-1,3,4-thiadiazol-2-yl]-4-chloro-1H-indazol-5-amine as a light brown crude solid.

Part 6—Synthesis of Tert-Butyl 5-((5-(2-(4-bromophenyl)imidazo[1,2-a]pyridin-8-yl)-1,3,4-thiadiazol-2-yl)(tert-butoxycarbonyl)amino)-4-chloro-1H-indazole-1-carboxylate

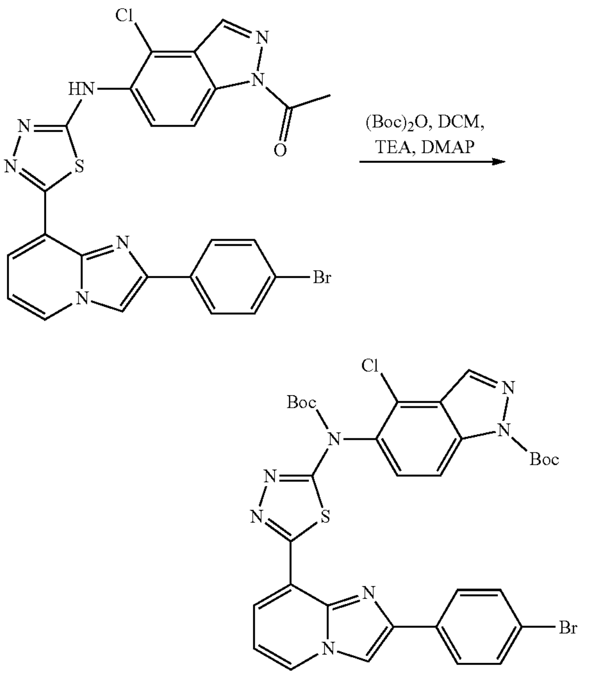

Into a 250-mL round-bottom flask, was placed a solution of N-[5-[2-(4-bromophenyl)imidazo[1,2-a]pyridin-8-yl]-1,3,4-thiadiazol-2-yl]-4-chloro-1H-indazol-5-amine (3.6 g, 2.41 mmol, 1.00 equiv, 35%) in 1.26 (mL), dichloromethane (100 mL), TEA (2.2 g, 21.74 mmol, 8.00 equiv), $(Boc)_2O$ (2.1 g, 9.62 mmol, 4.00 equiv), and 4-dimethylaminopyridine (20 mg, 0.16 mmol, 0.10 equiv). The resulting solution was stirred overnight at room temperature then concentrated under vacuum. The residue was applied onto a silica gel column and eluted with ethyl acetate/petroleum ether (10:90-70:30). This resulted in 1.2 g (69%) of tert-butyl 5-([5-[2-(4-bromophenyl)imidazo[1,2-a]pyridin-8-yl]-1,3,4-thiadiazol-2-yl][(tert-butoxy)carbonyl]amino)-4-chloro-1H-indazole-1-carboxylate as alight yellow solid.

Part 7—Synthesis of Tert-Butyl 5-((tert-butoxycarbonyl)(5-(2-(4-(1-ethoxyvinyl)phenyl)imidazo[1,2-a]pyridin-8-yl)-1,3,4-thiadiazol-2-yl)amino)-4-chloro-1H-indazole-1-carboxylate

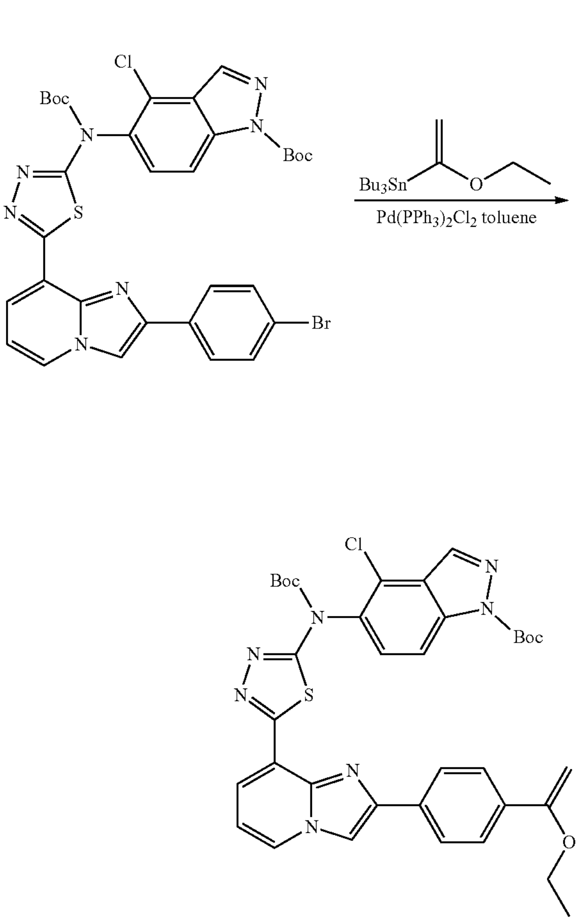

Into a 100-mL one round-bottom flask purged and maintained with an inert atmosphere of nitrogen, was placed tert-butyl 5-([5-[2-(4-bromophenyl)imidazo[1,2-a]pyridin-8-yl]-1,3,4-thiadiazol-2-yl][(tert-butoxy)carbonyl]amino)-4-chloro-1H-indazole-1-carboxylate (1.2 g, 1.66 mmol, 1.00 equiv), toluene (20 mL), tributyl(1-ethoxyethenyl)stannane (750 mg, 2.08 mmol, 1.20 equiv), dichloropalladium; bis (triphenylphosphane) (120 mg, 0.17 mmol, 0.10 equiv). The resulting solution was stirred for 2 h at 110° C. in an oil bath. The resulting mixture was concentrated under vacuum. The residue was applied onto a silica gel column with ethyl acetate/petroleum ether (2:1). This resulted in 1.1 g of tert-butyl 5-[[(tert-butoxy)carbonyl](5-[2-[4-(1-ethoxyethenyl)phenyl]imidazo[1,2-a]pyridin-8-yl]-1,3,4-thiadiazol-2-yl)amino]-4-chloro-1H-indazole-1-carboxylate as a brown solid.

Part 8—Synthesis of 1-(4-(8-(5-((4-chloro-1H-indazol-5-yl)amino)-1,3,4-thiadiazol-2-yl)imidazo[1,2-a]pyridin-2-yl)phenyl)ethan-1-one

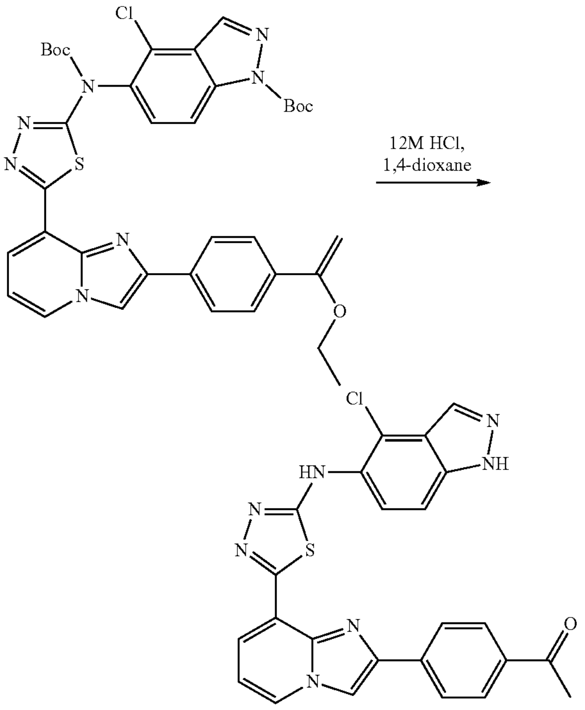

Into a 100-mL round-bottom flask, was placed tert-butyl 5-[[(tert-butoxy)carbonyl](5-[2-[4-(1-ethoxyethenyl)phenyl]imidazo[1,2-a]pyridin-8-yl]-1,3,4-thiadiazol-2-yl)amino]-4-chloro-1H-indazole-1-carboxylate (200 mg, 0.28 mmol, 1.00 equiv), 1,4-dioxane (4 mL), and 12 M aqueous HCl (2 mL). The solution was then stirred for 1 h at rt, resulting a precipitation which was collected by filtration and washed with EtOAc (15 mL), ethyl ether (20 mL) and DCM (20 mL) consequently. The solid was then dried in an oven under reduced pressure. The residue was dissolved in 5 mL of DMF and purified by prep-HPLC. This resulted in 5.2 mg (4%) of 1-[4-(8-[5-[(4-chloro-1H-indazol-5-yl)amino]-1,3,4-thiadiazol-2-yl]imidazo[1,2-a]pyridin-2-yl)phenyl]ethan-1-one as a green solid. (ES, m/z): $[M+H]^+$486. $^1H$ NMR (400 MHz, DMSO-$d_6$, ppm): δ 13.43 (s, 1H), 10.03 (s, 1H), 8.75-8.66 (m, 2H), 8.24-8.09 (m, 4H), 8.09-7.95 (m, 3H), 7.60 (d, J=9.0 Hz, 1H), 7.12 (t, J=7.0 Hz, 1H), 2.61 (s, 3H).

Example 52—Synthesis of Additional N-(1H-Indazol-5-yl)-1,3,4-thiadiazol-2-amine Compounds The compounds in Table 10 were prepared based on procedures described in Example 51.

TABLE 10

| Example No. | Chemical Structure | Physical Characterization Data |
|---|---|---|
| 52A | 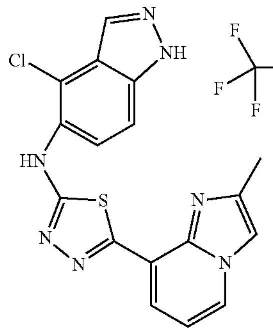 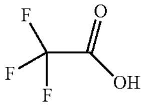 | (ES, m/z): $[M + H]^+$ 381.06 $^1H$ NMR (400 MHz, DMSO-$d_6$) δ 13.55 (s, 1H), 10.30 (s, 1H), 8.80 (s, 1H), 8.19 (d, J = 6.8 Hz, 2H), 8.09 (s, 1H), 7.93 (d, J = 8.8 Hz, 1H), 7.64 (d, J = 8.9 Hz, 1H), 7.36 (s, 1H), 2.49 (s, 3H) |
| 52B | 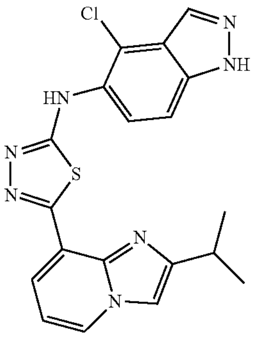 [SMILES: CC(C)c1cn2cccc(-c3nnc(Nc4ccc5[nH]ncc5c4Cl)s3)c2n1] | (ES, m/z): $[M + H]^+$ 410.21 $^1H$ NMR (400 MHz, DMSO-$d_6$, ppm) δ 13.41 (br s, 1H), 9.90 (br s, 1H), 8.58 (dd, J = 6.67, 1.09 Hz, 1H), 8.11 (s, 1H), 8.04 (dd, J = 7.25, 0.97 Hz, 1H), 7.98 (d, J = 8.86 Hz, 1H), 7.83 (d, J = 0.62 Hz, 1H), 7.58 (dd, J = 8.85, 0.77 Hz, 1H), 7.00 (m, 1H), 3.03 (sept, J = 6.61 Hz, 1H), 1.26 (t, J = 6.88 Hz, 6H) |
| 52C | 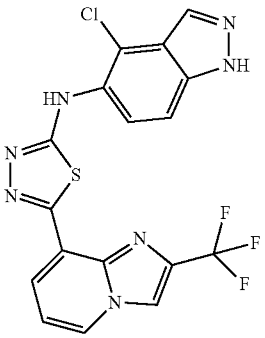 TFA | (ES, m/z): 436.08 $[M + H]^+$. $^1H$ NMR (400 MHz, DMSO-$d_6$) δ 13.44 (br s, 1H), 10.01 (br s, 1H), 8.71 (m, 2H), 8.28 (d, J = 7.50 Hz, 1H), 8.12 (s, 1H), 7.99 (d, J = 8.70 Hz, 1H), 7.59 (d, J = 8.93 Hz, 1H), 7.25 (m, 1H) |
| 52D | 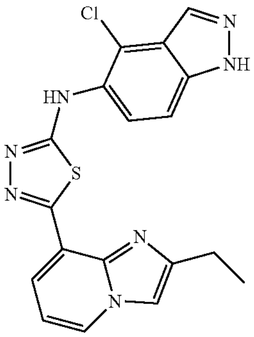 [SMILES: CCc1cn2cccc(-c3nnc(Nc4ccc5[nH]ncc5c4Cl)s3)c2n1] | (ES, m/z): $[M + H]^+$ 396.17. $^1H$ NMR (400 MHz, DMSO-$d_6$) δ 13.42 (br s, 1H), 9.91 (br s, 1H), 8.58 (dd, J = 6.67, 1.06 Hz, 1H), 8.11 (s, 1H), 8.04 (dd, J = 7.19, 0.62 Hz, 1H), 7.95 (d, J = 8.87 Hz, 1H), 7.84 (s, 1H), 7.58 (dd, J = 8.84, 0.74 Hz, 1H), 7.08 (m, 1H), 2.73 (q, J = 7.55 Hz, 2H), 1.26 (t, J = 7.54 Hz, 3H) |

TABLE 10-continued

| Example No. | Chemical Structure | Physical Characterization Data |
| --- | --- | --- |
| 52E | 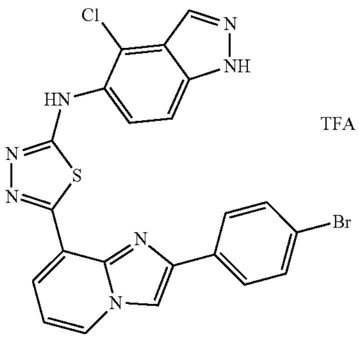 TFA | (ES, m/z): [M + H]$^+$ 521.98. $^1$H NMR (400 MHz, DMSO-$d_6$) δ 13.35 (br s, 1H), 10.00 (br s, 1H). 8.66 (dd, J = 6.70, 0.99 Hz, 1H), 8.60 (s, 1H), 8.13 - 8.11 (m, 2H), 8.02 (d, J = 8.90 Hz, 1H), 7.97 (d, J = 8.51 Hz, 2H), 7.68 (d, J = 8.53 Hz, 2H), 7.63 (dd, J = 8.89, 0.86 Hz, 1H), 7.10 (m, 1H) |
| 52F | 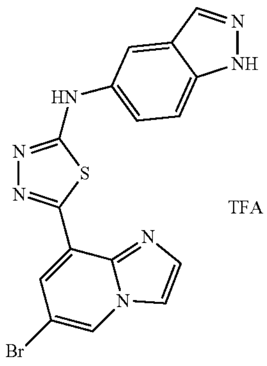 TFA | (ES, m/z): [M + H]$^+$ 412.03. $^1$H NMR (400 MHz, DMSO-$d_6$) δ 13.03 (br s, 1H), 10.55 (br s, 1H), 9.07 (s, 1H), 8.23 (d, J = 1.40 Hz, 1H), 8.16 (s, 1H), 8.08 (d, J = 6.97 Hz, 1H), 7.75 (s, 1H), 7.56 (d, J = 8.86 Hz, 1H), 7.42 (dd, J = 8.91, 1.98 Hz, 1H) |
| 52G | 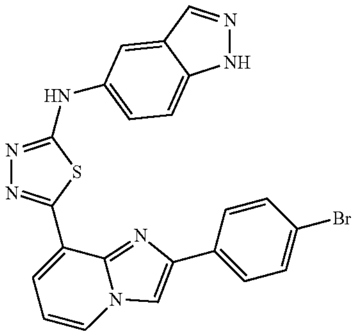 | (ES, m/z): [M + H]$^+$ 488.08. $^1$H NMR (400 MHz, DMSO-$d_6$) δ 12.98 (br s, 1H), 10.52 (br s, 1H), 8.67 (d, J = 6.56 Hz, 1H), 8.61 (s, 1H), 8.37 (s, 1H), 8.17 (d, J = 7.12 Hz, 1H), 8.05 (s, 1H), 8.00 (d, J = 8.42 Hz, 2H), 7.69 (d, J = 8.42 Hz, 2H), 7.54 (d, J = 8.84 Hz, 1H), 7.46 (d, J = 8.84 Hz, 1H), 7.11 (m, 1H) |

Example 53—Synthesis of Butyl (4-chloro-1H-indazol-5-yl)(5-(3-(2-(4-fluorophenyl)acetamido)phenyl)-1,3,4-thiadiazol-2-yl)carbamate

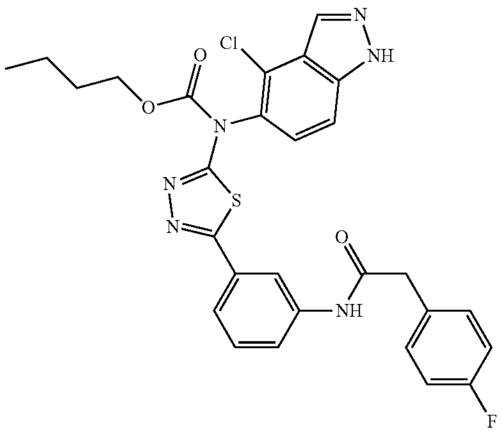 [SMILES: CCCCOC(=O)N(c1nnc(-c2cccc(NC(=O)Cc3ccc(F)cc3)c2)s1)c1ccc2[nH]ncc2c1Cl]

Part 1—Synthesis of Tert-Butyl 5-((butoxycarbonyl)(5-(3-nitrophenyl)-1,3,4-thiadiazol-2-yl)amino)-4-chloro-1H-indazole-1-carboxylate

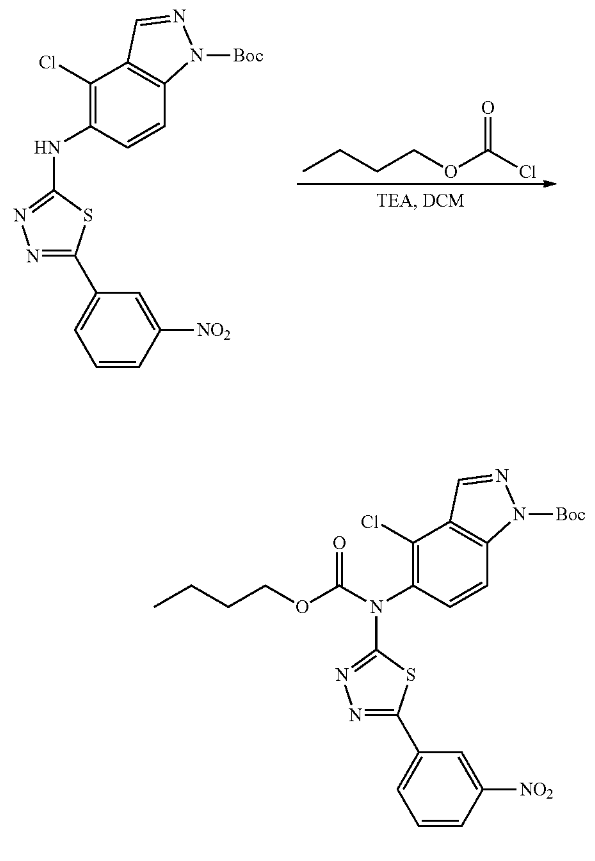

Into a 100-mL round-bottom flask, was placed a solution of tert-butyl 4-chloro-5-[[5-(3-nitrophenyl)-1,3,4-thiadiazol-2-yl]amino]-1H-indazole-1-carboxylate (800 mg, 1.69 mmol, 1.00 equiv) in dichloromethane (20 mL), butyl chloroformate (461 mg, 3.38 mmol, 2.00 equiv), and triethylamine (342 mg, 3.38 mmol, 2.00 equiv). The resulting solution was stirred for 2 h at room temperature then concentrated under vacuum. This resulted in 1.0 g (crude) of tert-butyl 5-[(butoxycarbonyl)[5-(3-nitrophenyl)-1,3,4-thiadiazol-2-yl]amino]-4-chloro-1H-indazole-1-carboxylate as a brown solid.

Part 2—Synthesis of Tert-Butyl 5-((5-(3-aminophenyl)-1,3,4-thiadiazol-2-yl)(butoxycarbonyl)amino)-4-chloro-1H-indazole-1-carboxylate

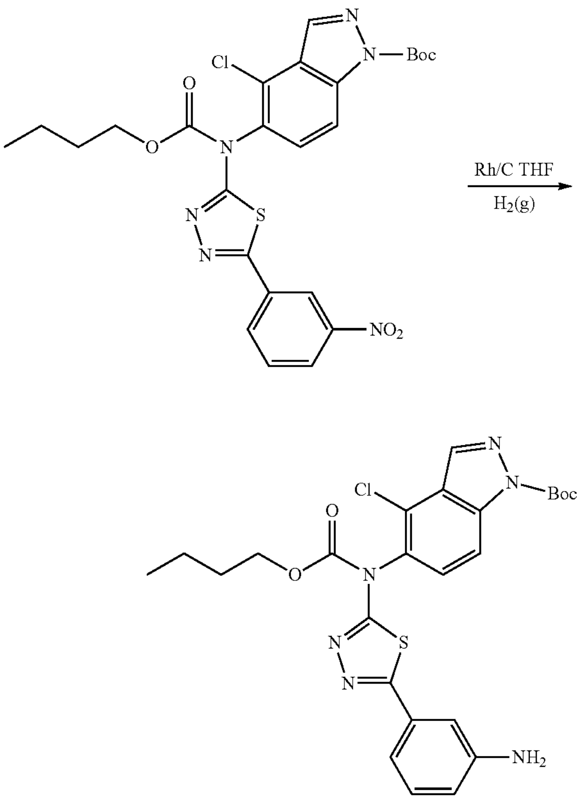

Into a 100-mL round-bottom flask, was placed a solution of tert-butyl 5-[(butoxycarbonyl)[5-(3-nitrophenyl)-1,3,4-thiadiazol-2-yl]amino]-4-chloro-1H-indazole-1-carboxylate (1.0 g, 1.75 mmol, 1.00 equiv) in tetrahydrofuran (40 mL), and Rh/C (1.0 g). The resulting solution was stirred under an atmosphere of hydrogen overnight at room temperature. The solids were removed by filtration and the filtrate was concentrated under vacuum. This resulted in 0.8 g (84%) of tert-butyl 5-[[5-(3-aminophenyl)-1,3,4-thiadiazol-2-yl](butoxycarbonyl)amino]-4-chloro-1H-indazole-1-carboxylate as a brown solid.

Part 3—Synthesis of Tert-Butyl 5-((butoxycarbonyl)(5-(3-(2-(4-fluorophenyl)acetamido)phenyl)-1,3,4-thiadiazol-2-yl)amino)-4-chloro-1H-indazole-1-carboxylate

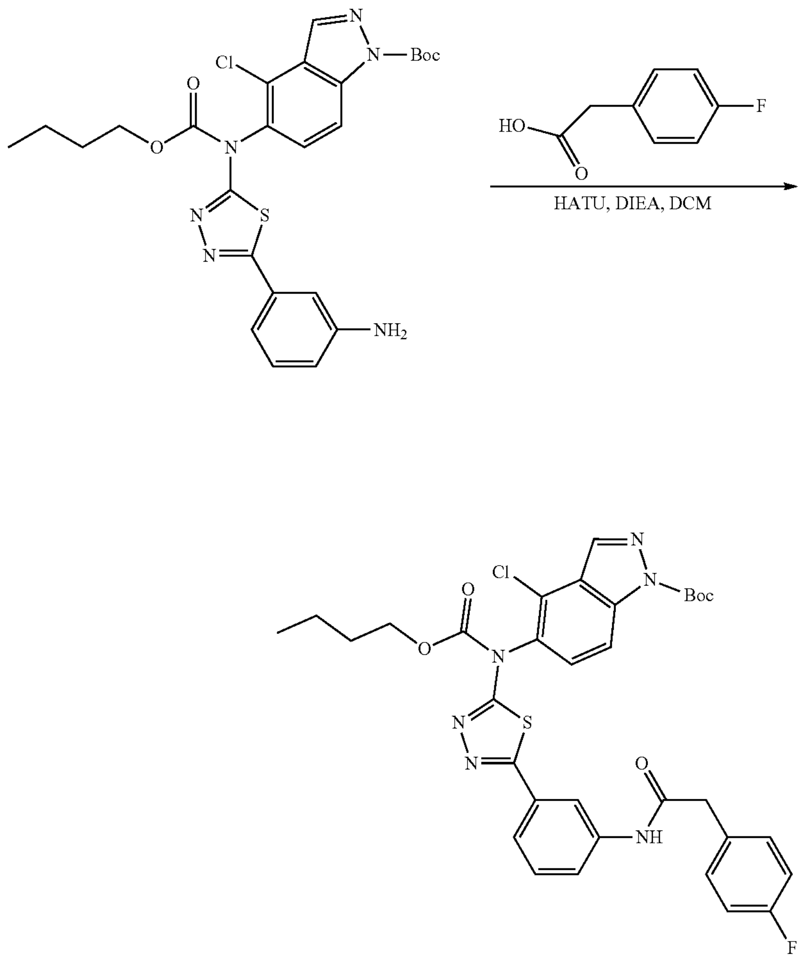

Into a 100-mL round-bottom flask, was placed a solution of tert-butyl 5-[[5-(3-aminophenyl)-1,3,4-thiadiazol-2-yl](butoxycarbonyl)amino]-4-chloro-1H-indazole-1-carboxylate (500 mg, 0.92 mmol, 1.00 equiv) in tetrahydrofuran (50 mL), 2-(4-fluorophenyl)acetic acid (284 mg, 1.84 mmol, 2.00 equiv), HATU (454.5 mg, 1.20 mmol, 1.30 equiv), and DIEA (475 mg, 3.68 mmol, 4.00 equiv). The resulting solution was stirred overnight at room temperature. The reaction was then quenched by the addition of 30 mL of water. The resulting mixture was extracted with 2×50 mL of ethyl acetate and the organic layers combined and dried over anhydrous sodium sulfate then concentrated under vacuum. This resulted in 300 mg (48%) of tert-butyl 5-[(butoxycarbonyl)(5-[3-[2-(4-fluorophenyl)acetamido]phenyl]-1,3,4-thiadiazol-2-yl)amino]-4-chloro-1H-indazole-1-carboxylate as light yellow oil.

Part 4—Synthesis of Butyl (4-chloro-1H-indazol-5-yl)(5-(3-(2-(4-fluorophenyl)acetamido)-phenyl)-1,3,4-thiadiazol-2-yl)carbamate

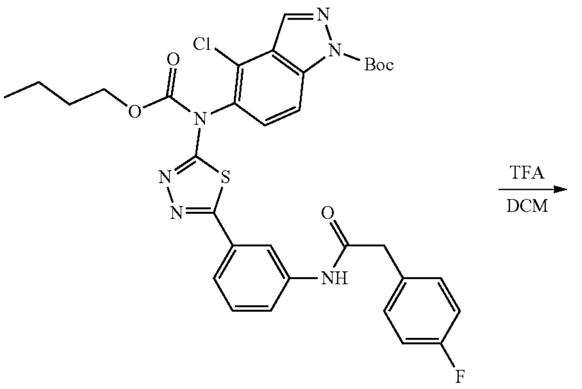

-continued

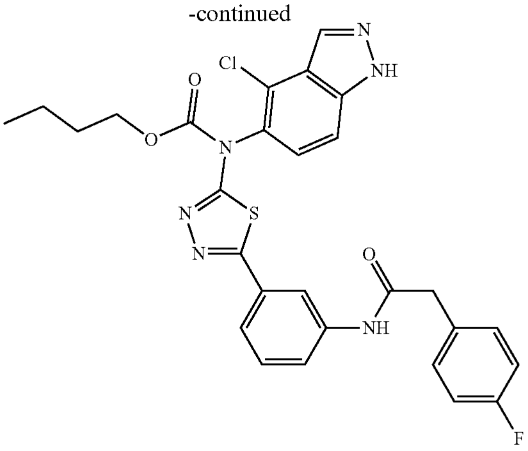

Into a 100-mL round-bottom flask, was placed a solution of tert-butyl 5-[(butoxycarbonyl)(5-[3-[2-(4-fluorophenyl) acetamido]phenyl]-1,3,4-thiadiazol-2-yl)amino]-4-chloro-1H-indazole-1-carboxylate (300 mg, 0.44 mmol, 1.00 equiv) in dichloromethane (20 mL). This was followed by the addition of trifluoroacetic acid (8 mL) dropwise with stirring at room temperature in 1 min. The resulting solution was stirred for 2 h at room temperature. The resulting mixture was concentrated under vacuum. The crude product was purified by Prep-HPLC with the following conditions (2#-AnalyseHPLC-SHIMADZU(HPLC-10)): Column, XBridge C18 OBD Prep Column, 100, 5, 19 mm×250 mm; mobile phase, Water (0.05% TFA) and ACN (10.0% ACN up to 30.0% ACN in 8 min); Detector, UV 254 nm. This resulted in 49.4 mg (19%) of butyl N-(4-chloro-1H-indazol-5-yl)-N-(5-[3-[2-(4-fluorophenyl)acetamido]phenyl]-1,3,4-thiadiazol-2-yl)carbamate trifluoroacetic acid solvate as a off-white solid. (ES, m/z): $[M+H]^+$578.13. $^1H$ NMR (400 MHz, DMSO-$d_6$, ppm) δ 13.65 (s, 1H), 10.40 (s, 1H), 8.27-8.18 (m, 2H), 7.78-7.64 (m, 2H), 7.63-7.53 (m, 2H), 7.51-7.40 (m, 1H), 7.40-7.28 (m, 2H), 7.22-7.04 (m, 2H), 4.32-4.12 (m, 2H), 3.66 (s, 2H), 1.52-1.40 (m, 2H), 1.24-1.05 (m, 2H), 0.73 (t, J=7.4 Hz, 3H).

Example 54—Synthesis of Additional Compounds

The compounds in Table 11 were prepared based on procedures described in Example 53.

TABLE 11

| Example No. | Chemical Structure | Physical Characterization Data |
|---|---|---|
| 54A | 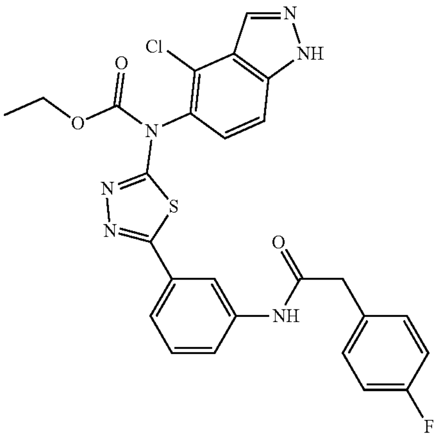 [SMILES: CCOC(=O)N(c1nnc(-c2cccc(NC(=O)Cc3ccc(F)cc3)c2)s1)c1ccc2[nH]ncc2c1Cl] | (ES, m/z): $[M + H]^+$ 550.10. $^1H$ NMR (400 MHz, DMSO-$d_6$) δ 13.70 - 13.63 (m. 1H), 10.40 (s, 1H), 8.27 - 8.18 (m, 2H), 7.78 - 7.70 (m, 1H), 7.70 - 7.64 (m, 1H) 7.63 - 7.53 (m, 2H), 7.45 (t, J = 8.0 Hz, 1H), 7.40 - 7.31 (m, 2H), 7.22 - 7.08 (m, 2H), 4.37 - 4.16 (m, 2H), 3.66 (s, 2H), 1.12 (t, J = 7.1 Hz, 3H) |
| 54B | 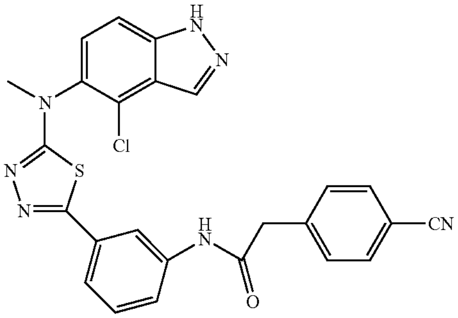 [SMILES: CN(c1nnc(-c2cccc(NC(=O)Cc3ccc(C#N)cc3)c2)s1)c1ccc2[nH]ncc2c1Cl] | (ES, m/z): $[M + H]^+$ 500. $^1H$ NMR (DMSO-$d_6$, 400 MHz, ppm): δ 13.15 (s, 1H), 10.40 (s, 1H), 8.28 (d, J = 1.0 Hz, 1H), 8.07 (t, J = 1.8 Hz, 1H), 7.83 - 7.77 (m, 2H), 7.72 (dd, J = 8.6, 1.0 Hz, 1H), 7.62 (td, J = 6.5, 6.0, 3.0 Hz, 2H), 7.55 - 7.50 (m, 2H), 7.42 - 7.33 (m, 2H), 3.78 (s, 2H), 3.53 (s, 3H) |

TABLE 11-continued

| Example No. | Chemical Structure | Physical Characterization Data |
| --- | --- | --- |
| 54C | 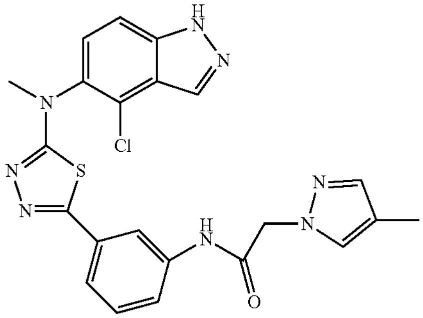 | (ES, m/z): $[M + H]^+$ 479. $^1H$ NMR ($DMSO-d_6$, 400 MHz, ppm): δ 10.44 (s, 1H), 8.25 (s, 1H), 8.08 (s, 1H), 7.70 (d, J = 8.3 Hz, 1H), 7.61 (dt, J = 7.4, 1.9 Hz, 1H), 7.54 (d, J = 9.9 Hz, 1H), 7.51 (s, 1H), 7.43 - 7.34 (m, 2H), 7.25 (s, 1H), 4.92 (s, 2H), 3.53 (s, 3H), 2.02 (s, 3H) |
| 54D | 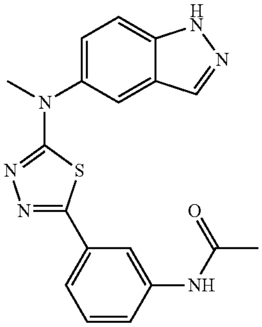 [SMILES: CC(=O)Nc1cccc(-c2nnc(N(C)c3ccc4[nH]ncc4c3)s2)c1] | (ES, m/z): $[M + H]^+$ 364.42. $^1H$ NMR ($DMSO-d_6$, 400 MHz, ppm): δ 13.32 - 13.23 (m, 1H), 10.05 (s, 1H), 8.12 (d, J = 1.0 Hz, 1H), 8.02 (d, J = 2.0 Hz, 1H), 7.94 (d, J = 1.9 Hz, 1H), 7.67 (d, J = 8.8 Hz, 1H), 7.59 (dt, J = 6.7, 2.2 Hz, 1H), 7.46 (dd, J = 8.8, 2.0 Hz, 1H), 7.37 - 7.27 (m, 2H), 3.55 (s, 3H), 2.01 (s, 3H) |
| 54E | 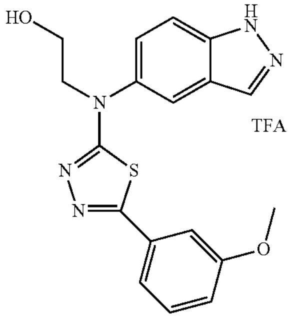 [SMILES: COc1cccc(-c2nnc(N(CCO)c3ccc4[nH]ncc4c3)s2)c1] TFA | (ES, m/z): $[M + H]^+$ 368. $^1H$ NMR ($DMSO-d_6$, 400 MHz, ppm): δ 13.01 (s, 1H), 8.00 (d, 1H, J = 0.8), 7.55 - 7.53 (m, 1H), 7.40 - 7.36 (m, 2H), 7.24 - 7.22 (m, 1H), 7.17 - 7.16 (m, 1H), 7.09 - 7.03 (m, 2H), 4.23 - 4.20 (m, 2H), 3.87 - 3.84 (m, 2H), 3.79 (s, 3H) |

Example 55—Synthesis of N-(4-Chloro-1H-indazol-5-yl)-5-(1-(2-(dimethylamino)ethyl)-1H-benzo[d]imidazol-4-yl)-1,3,4-thiadiazol-2-amine

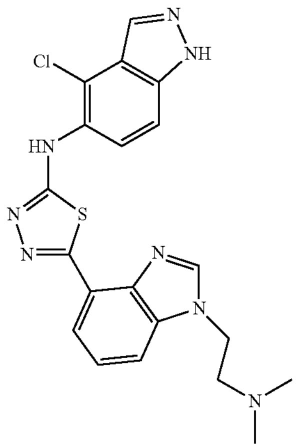 [SMILES: CN(C)CCn1cnc2c(-c3nnc(Nc4ccc5[nH]ncc5c4Cl)s3)cccc21]

Part 1—Synthesis of Methyl 1H-benzo[d]imidazole-4-carboxylate

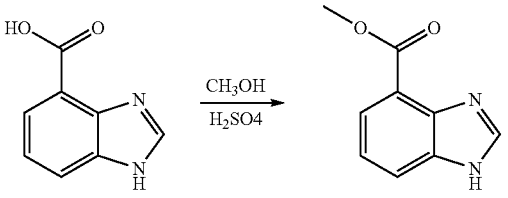

Into a 250-mL round-bottom flask, was placed a solution of 1H-1,3-benzodiazole-4-carboxylic acid (4.0 g, 24.67 mmol, 1.00 equiv) in methanol (60 mL), and sulfuric acid (6 mL). The resulting solution was stirred overnight at room temperature then concentrated under vacuum. The resulting solution was diluted with 30 mL of sodium chloride (aq) then extracted with EtOAc (2×30 mL) and the organic layers were combined. The pH value of the aqueous layer was adjusted to >7 with $NaHCO_3$ (2M) and was extracted with EtOAc (2×30 mL). All EtOAc solutions were then combined and concentrated under reduced pressure to provide methyl 1H-1,3-benzodiazole-4-carboxylate as a red solid (2.5 g, 58% yield).

Part 2—Synthesis of Methyl 1-[2-(dimethylamino) ethyl]-1H-1,3-benzodiazole-4-carboxylate

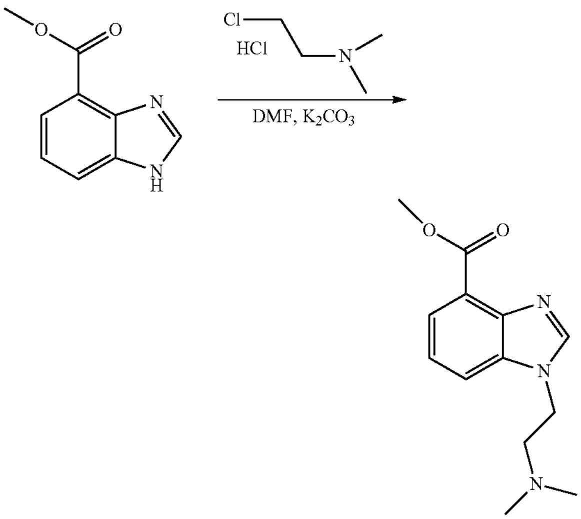

Into a 100-mL round-bottom flask, was placed a solution of methyl 1H-1,3-benzodiazole-4-carboxylate (500 mg, 2.84 mmol, 1.00 equiv) in N,N-dimethylformamide (60 mL), potassium carbonate (1.1 g, 7.96 mmol, 3.00 equiv), and (2-chloroethyl)dimethylamine hydrochloride (523.6 mg, 3.64 mmol, 1.00 equiv). The resulting solution was stirred overnight at 60° C. in an oil bath then allowed to cool and diluted with 40 mL of sodium chloride (aq). The resulting mixture was extracted with 2×40 mL of ethyl acetate and the organic layers combined and dried over anhydrous sodium sulfate then concentrated under vacuum. The residue was applied onto a silica gel column and eluted with ethyl acetate/petroleum ether (1:2). This resulted in 100 mg (14%) of methyl 1-[2-(dimethylamino)ethyl]-1H-1,3-benzodiazole-4-carboxylate as a solid.

Part 3—Synthesis of 1-[2-(dimethylamino)ethyl]-1H-1,3-benzodiazole-4-carbohydrazide

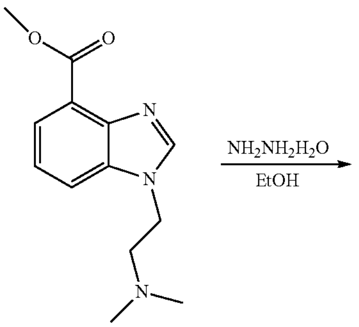

-continued

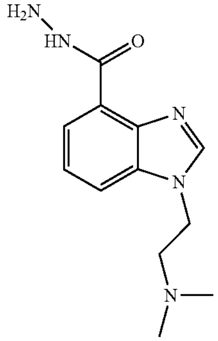

Into a 50-mL round-bottom flask, was placed a solution of methyl 1-[2-(dimethylamino)ethyl]-1H-1,3-benzodiazole-4-carboxylate (100 mg, 0.40 mmol, 1.00 equiv) in ethanol (20 mL), and hydrazine hydrate (202 mg, 4.04 mmol, 10.00 equiv). The resulting solution was stirred overnight at 80° C. in an oil bath then concentrated under vacuum. This resulted in 100 mg (100%) of 1-[2-(dimethylamino)ethyl]-1H-1,3-benzodiazole-4-carbohydrazide as a brown solid.

Part 4—Synthesis of N-[[(4-chloro-1H-indazol-5-yl) carbamothioyl]amino]-1-[2-(dimethylamino)ethyl]-1H-1,3-benzodiazole-4-carboxamide

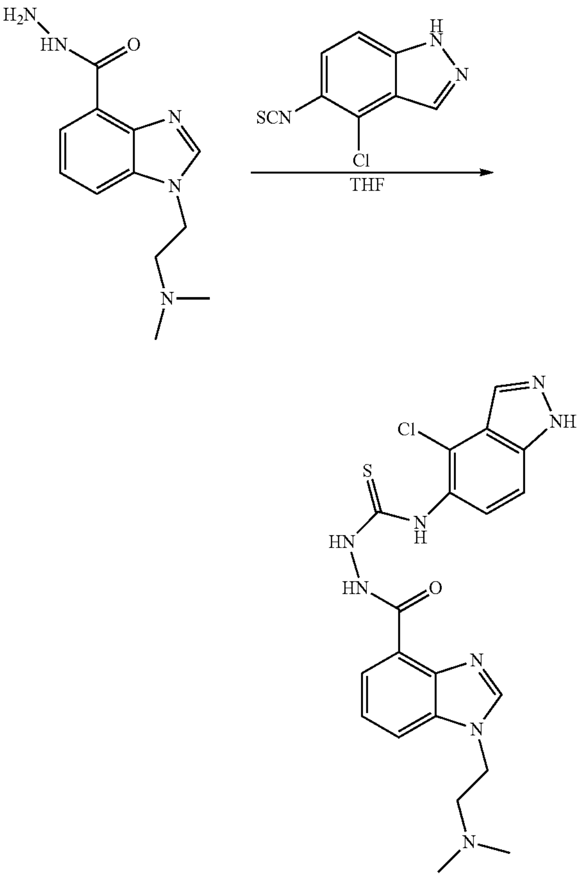

Into a round-bottom flask, was placed a solution of 1-[2-(dimethylamino)ethyl]-1H-1,3-benzodiazole-4-carbohydrazide (100 mg, 0.40 mmol, 1.00 equiv) in THF (20 mL), and 4-chloro-5-isothiocyanato-1H-indazole (84 mg, 0.40 mmol, 1.00 equiv). The resulting solution was stirred overnight at room temperature then concentrated under vacuum. This resulted in 150 mg (81%) of N-[[(4-chloro-1H-indazol-5-yl)carbamothioyl]amino]-1-[2-(dimethylamino)ethyl]-1H-1,3-benzodiazole-4-carboxamide as a light yellow solid.

Part 5—Synthesis of 4-chloro-N-(5-[1-[2-(dimethylamino)ethyl]-1H-1,3-benzodiazol-4-yl]-1,3,4-thiadiazol-2-yl)-1H-indazol-5-amine

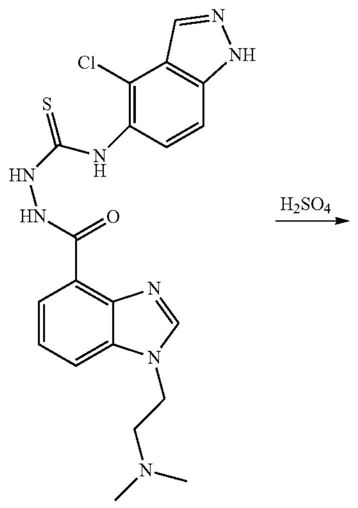

-continued

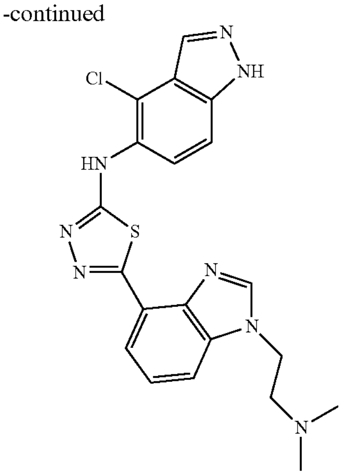

Into a 50-mL round-bottom flask, was placed a solution of N-[[(4-chloro-1H-indazol-5-yl)carbamothioyl]amino]-1-[2-(dimethylamino)ethyl]-1H-1,3-benzodiazole-4-carboxamide (100 mg, 0.22 mmol, 1.00 equiv) in sulfuric acid (6 mL). The resulting solution was stirred for 4 h at 60° C. in an oil bath. The reaction was then quenched by the addition of 40 mL of water/ice. The pH value of the solution was adjusted to >7 with sodium bicarbonate (aq) (2 M). The solids were removed by filtration and the filtrate was concentrated under vacuum. The crude product was purified by Prep-HPLC with the following conditions (2#-AnalyseHPLC-SHIMADZU (HPLC-10)): Column, XBridge Shield RP18 OBD Column, 5 um, 19*150 mm; mobile phase, Water (0.05% $NH_3H_2O$) and ACN (26.0% ACN up to 46.0% in 8 min); Detector, UV 254 nm. This resulted in 46.4 mg (48%) of 4-chloro-N-(5-[1-[2-(dimethylamino)ethyl]-1H-1,3-benzodiazol-4-yl]-1,3,4-thiadiazol-2-yl)-1H-indazol-5-amine as a solid. ES, m/z): $[M+H]^+$438.11. $^1H$ NMR (300 MHz, DMSO-$d_6$) δ 13.43 (s, 1H), 9.86 (s, 1H), 8.31 (s, 1H), 8.11 (s, 1H), 8.05-7.96 (m, 1H), 7.83 (d, J=8.9 Hz, 1H), 7.71 (d, J=8.0 Hz, 1H), 7.62-7.52 (m, 1H), 7.34 (t, J=7.9 Hz, 1H), 4.35 (t, J=6.2 Hz, 2H), 2.62 (s, 2H), 2.15 (s, 6H).

Example 56—Synthesis of Additional N-(1H-Indazol-5-yl)-1,3,4-thiadiazol-2-amine Compounds The compounds in Table 12 were prepared based on procedures described in Example 55.

TABLE 12

| Example No. | Chemical Structure | Physical Characterization Data |
|---|---|---|
| 56A | 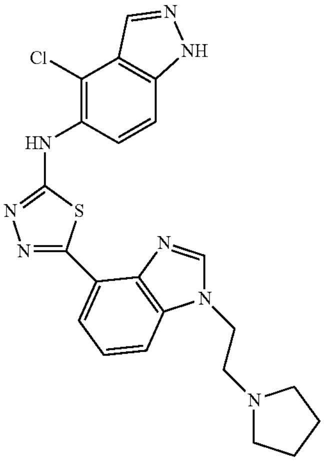 [SMILES: Clc1c(Nc2nnc(-c3cccc4c3ncn4CCN3CCCC3)s2)ccc2[nH]ncc12] | (ES, m/z): $[M + H]^+$ 464.13. $^1H$ NMR (400 MHz, DMSO-$d_6$) δ 13.45 (s, 1H), 10.05 (s, 1H), 8.31 (s, 1H), 8.13 (s, 1H), 7.87 (d, J = 8.8 Hz, 1H), 7.80 (dd, J = 8.0, 1.1 Hz, 1H), 7.63 - 7.56 (m, 1H), 7.43 - 7.36 (m, 1H), 7.29 (t, J = 7.8 Hz, 1H), 4.49 (t, J = 6.9 Hz, 2H), 2.36 (t, J = 6.8 Hz, 2H), 2.26 (d, J = 6.0 Hz, 4H), 1.60 - 1.52 (m, 4H). |

TABLE 12-continued

| Example No. | Chemical Structure | Physical Characterization Data |
| --- | --- | --- |
| 56B | 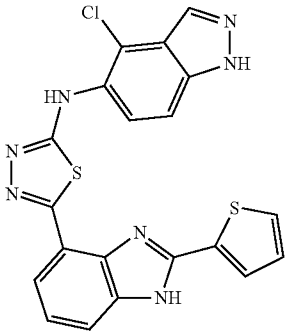 [SMILES: Clc1c(Nc2nnc(-c3cccc4[nH]c(-c5cccs5)nc34)s2)ccc2[nH]ncc12] | (ES, m/z): 450.00, 452.00 $[M + H]^+$. $^1H$ NMR (400 MHz, DMSO-$d_6$) δ 13.42 (s, 1H), 13.29 (s, 1H), 9.90 (s, 1H), 8.I1 (s, 1H), 8.02 – 7.97 (m, 2H), 7.87 (dd, J = 3.64, 1.00 Hz, 1H), 7.77 (dd, J = 4.99, 0.98 Hz, 1H), 7.60 – 7.56 (m, 2H), 7.35 – 7.23 (m, 2H). |
| 56C | 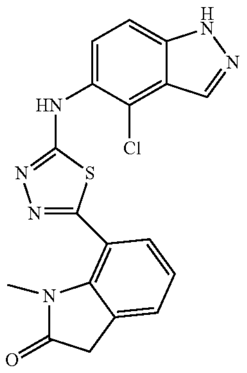 [SMILES: CN1C(=O)Cc2cccc(-c3nnc(Nc4ccc5[nH]ncc5c4Cl)s3)c21] | (ES, m/z): $[M + H]^+$ 397. $^1H$ NMR (DMSO-$d_6$, 400 MHz, ppm): δ 13.42 (s, 1H), 9.98 (s, 1H), 8.11 (s, 1H), 7.97 – 7.95 (m, 1H), 7.59 – 7.57 (d, J = 8.8, 1H), 7.39 – 7.38 (m, 1H), 7.30 – 7.28 (m, 1H), 7.10 – 7.06 (m, 1H), 3.64 (s, 2H), 2.93 (s, 3H). |
| 56D | 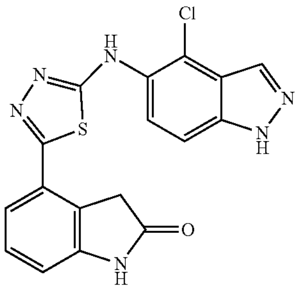 [SMILES: O=C1Cc2c(cccc2-c2nnc(Nc3ccc4[nH]ncc4c3Cl)s2)N1] | (ES, m/z): $[M + H]^+$ 382.95. $^1H$ NMR (DMSO-$d_6$, 400 MHz, ppm): δ 10.58 (s, 1H), 9.80 (s, 1H), 8.14 (s, 1H), 7.89 – 7.86 (d, J = 8.8 Hz, 1H), 7.61 – 7.59 (d, J = 8.8 Hz, 1H), 7.32 – 7.28 (m, 2H), 6.92 – 6.90 (m, 1H), 3.70 (s, 2H). |
| 56E | 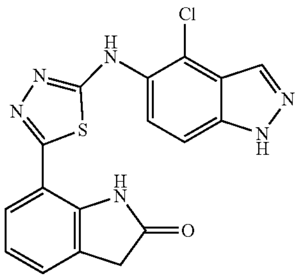 [SMILES: O=C1Cc2cccc(-c3nnc(Nc4ccc5[nH]ncc5c4Cl)s3)c2N1] | (ES, m/z): $[M + H]^+$ 382.95. $^1H$ NMR ($CDCl_3$, 400 MHz, ppm): δ 8.15 (s, 1H), 7.89 – 7.87 (d, J = 8.8 Hz, 1H), 7.62 – 7.60 (d, J = 8.8 Hz, 1H). 7.43 – 7.41 (d, J = 7.6 Hz, 1H). 7.33 – 7.31 (d, J = 7.2 Hz, 1H), 7.09 – 7.05 (t, J = 7.8 Hz, 1H), 3.64 (s, 2H). |

TABLE 12-continued

| Example No. | Chemical Structure | Physical Characterization Data |
|---|---|---|
| 56F | 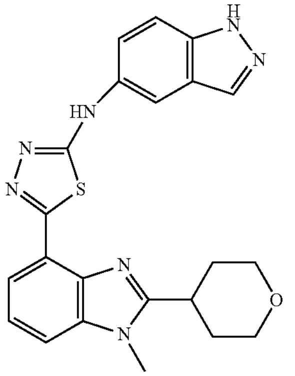 [SMILES: Cn1c(C2CCOCC2)nc2c(-c3nnc(Nc4ccc5[nH]ncc5c4)s3)cccc21] | (ES, m/z): $[M + H]^+$ 432. $^1H$ NMR (DMSO-$d_6$, 400 MHz, ppm): δ 12.98 (s, 1H), 10.39 (s, 1H), 8.40 (s, 1H), 8.05 - 8.03 (m, 2H), 7.66 - 7.64 (m, 1H), 7.54 - 7.52 (m, 1H), 7.46 - 7.43 (m, 1H), 7.37 - 7.34 (m, 1H), 4.04 - 4.01 (m, 2H), 3.68 (s, 3H), 3.59 - 3.53 (m, 2H), 3.41 - 3.34 (m, 1H), 1.98 - 1.91 (m, 4H). |
| 56G | 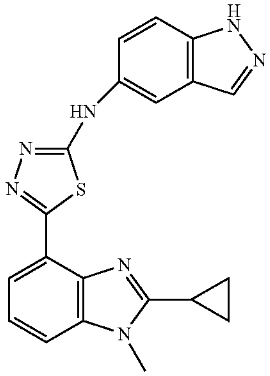 [SMILES: Cn1c(C2CC2)nc2c(-c3nnc(Nc4ccc5[nH]ncc5c4)s3)cccc21] | (ES, m/z): $[M + H]^+$ 388. $^1H$ NMR (DMSO-$d_6$ + $D_2O$, 400 MHz, ppm): δ 8.34 (d, J = 1.6 Hz, 1H), 8.10 (d, J = 0.8 Hz, 1H), 7.90 - 7.86 (m, 2H), 7.62 - 7.56 (m, 2H), 7.49 - 7.46 (m, 1H), 4.02 (s, 3H), 2.46 - 2.42 (m, 1H), 1.35 - 1.33 (m, 4H). |
| 56H | 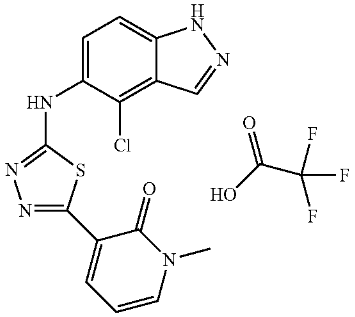 | ES, m/z): $[M + H]^+$ 359. $^1H$ NMR (DMSO-$d_6$, 400 MHz, ppm): δ 13.42 (s, 1H), 9.76 (s, 1H), 8.37 (dd, J = 7.3, 2.0 Hz, 1H), 8.11 (d, J = 1.0 Hz, 1H), 7.89 (dd, J = 6.6, 2.0 Hz, 1H), 7.79 (d, J = 8.9 Hz, 1H), 7.56 (dd, J = 8.9, 1.0 Hz, 1H), 6.50 (t, J = 7.0 Hz, 1H), 3.54 (s, 3H). |

Example 57—Synthesis of N-(5-(5-((4-Chloro-1H-indazol-5-yl)amino)-1,3,4-thiadiazol-2-yl)-1-methyl-2-oxo-1,2-dihydropyridin-3-yl)acetamide

Part 1—Synthesis of 6-hydroxy-5-nitronicotinic Acid

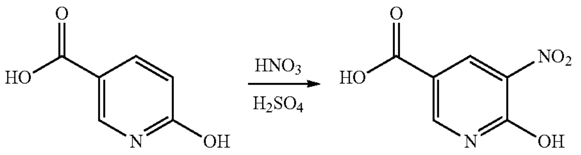

Into a 2000-mL round-bottom flask, was placed sulfuric acid (150 mL). This was followed by the addition of 6-hydroxypyridine-3-carboxylic acid (50 g, 359.43 mmol, 1.00 equiv), in portions at 0° C. in 5 min. To this was added $HNO_3$ (34.7 mL, 2.00 equiv) at 0° C. in 10 min. The resulting solution was stirred for 3 h at room temperature. The reaction was then quenched by the addition of 300 g of crush ice. The solids were collected by filtration. The solid was dried in an oven under reduced pressure. This resulted in 18.2 g (28%) of 6-hydroxy-5-nitropyridine-3-carboxylic acid as a gray solid.

Part 2—Synthesis of Methyl 6-hydroxy-5-nitronicotinate

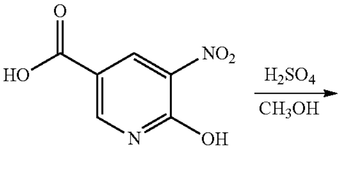

-continued

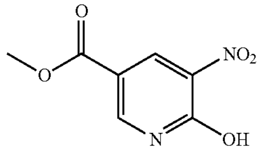

Into a 1000-mL round-bottom flask was placed a solution of 6-hydroxy-5-nitropyridine-3-carboxylic acid (16 g, 86.91 mmol, 1.00 equiv) in methanol (450 mL). This was followed by the addition of sulfuric acid (9 mL). The resulting solution was stirred for overnight at 65° C. The resulting mixture was concentrated under vacuum. The resulting solution was diluted with 300 mL of $H_2O$. The solids were collected by filtration. The solid was dried in an oven under reduced pressure. This resulted in 14.2 g (82%) of methyl 6-hydroxy-5-nitropyridine-3-carboxylate as a light brown solid.

Part 3—Synthesis of Methyl 1-methyl-5-nitro-6-oxo-1,6-dihydropyridine-3-carboxylate

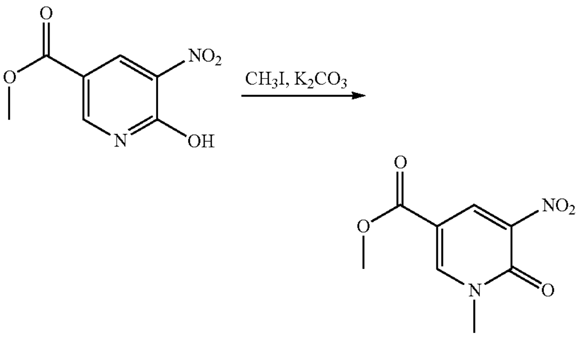

Into a 100-mL sealed tube, was placed a solution of methyl 6-hydroxy-5-nitropyridine-3-carboxylate (1.2 g, 6.06 mmol, 1.00 equiv) in N,N-dimethylformamide (15 mL). This was followed by the addition of $CH_3I$ (1.72 g, 12.12 mmol, 2.00 equiv) at room temperature. To this was added potassium carbonate (2.5 g, 18.09 mmol, 3.00 equiv) at room temperature. The resulting solution was stirred overnight at 80° C. in an oil bath. The residue was applied onto a silica gel column with dichloromethane/methanol (20:1). The collected fractions were combined and concentrated under vacuum. This resulted in 450 mg (35%) of methyl 1-methyl-5-nitro-6-oxo-1,6-dihydropyridine-3-carboxylate as a yellow solid.

Part 4—Synthesis of 1-methyl-5-nitro-6-oxo-1,6-dihydropyridine-3-carboxylic Acid

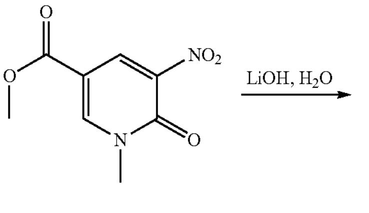

-continued

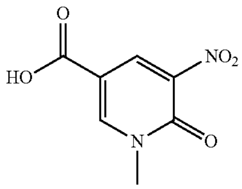

Into a 100-mL round-bottom flask, was placed a solution of methyl 1-methyl-5-nitro-6-oxo-1,6-dihydropyridine-3-carboxylate (450 mg, 2.12 mmol, 1.00 equiv) in methanol (6 mL). This was followed by the addition of a solution of lithium hydroxide (178 mg, 4.24 mmol, 2.00 equiv) in water (2 mL) at room temperature. The resulting solution was stirred overnight at room temperature. The resulting solution was extracted with 2×50 mL of ethyl acetate and the aqueous layers combined. The pH value of the solution was adjusted to 2 with hydrogen chloride(aq) (1 mol/L). The resulting solution was extracted with 3×50 mL of ethyl acetate and the organic layers combined and concentrated under vacuum. This resulted in 300 mg (71%) of 1-methyl-5-nitro-6-oxo-1,6-dihydropyridine-3-carboxylic acid as a brown solid.

Part 5—Synthesis of Tert-Butyl 2-(1-methyl-5-nitro-6-oxo-1,6-dihydropyridine-3-carbonyl)hydrazine-1-carboxylate

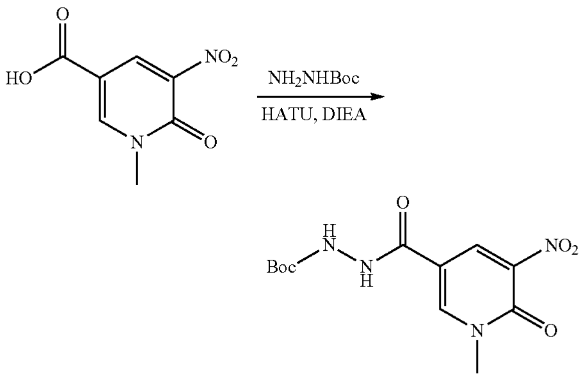

Into a 50-mL round-bottom flask, was placed a solution of 1-methyl-5-nitro-6-oxo-1,6-dihydropyridine-3-carboxylic acid (300 mg, 1.51 mmol, 1.00 equiv) in N,N-dimethylformamide (10 mL). This was followed by the addition of HATU (864 mg, 2.27 mmol, 1.50 equiv) at room temperature. To this was added DIEA (586 mg, 4.53 mmol, 3.00 equiv) at room temperature. To the mixture was added (tert-butoxy)carbohydrazide (300 mg, 2.27 mmol, 1.50 equiv) at room temperature. The resulting solution was stirred overnight at room temperature. The residue was applied onto a silica gel column with dichloromethane/methanol (10:1). The collected fractions were combined and concentrated under vacuum. This resulted in 330 mg (70%) of 5-[([[(tert-butoxy)carbonyl]amino]amino)carbonyl]-1-methyl-3-nitro-1,2-dihydropyridin-2-one as brown oil.

Part 6—Synthesis of 1-methyl-5-nitro-6-oxo-1,6-dihydropyridine-3-carbohydrazide Hydrochloride

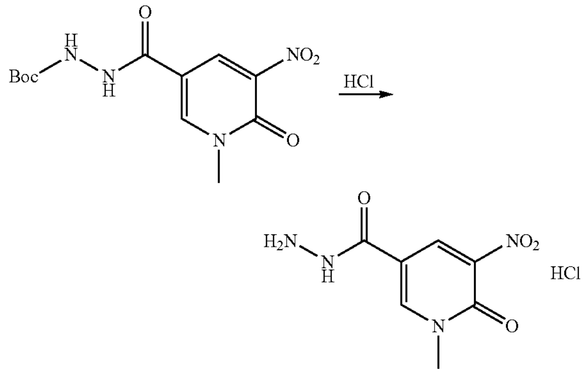

Into a 25-mL round-bottom flask, was placed 5-[([[(tert-butoxy)carbonyl]amino]amino)carbonyl]-1-methyl-3-nitro-1,2-dihydropyridin-2-one (330 mg, 1.06 mmol, 1.00 equiv). This was followed by the addition of hydrogen chloride in dioxane (8 mL) at room temperature. The resulting solution was stirred overnight at room temperature. The solids were collected by filtration. This resulted in 210 mg (80%) of 1-methyl-5-nitro-6-oxo-1,6-dihydropyridine-3-carbohydrazide hydrochloride as a off-white solid.

Part 7—Synthesis of N-(4-chloro-1H-indazol-5-yl)-2-(1-methyl-5-nitro-6-oxo-1,6-dihydropyridine-3-carbonyl)hydrazine-1-carbothioamide

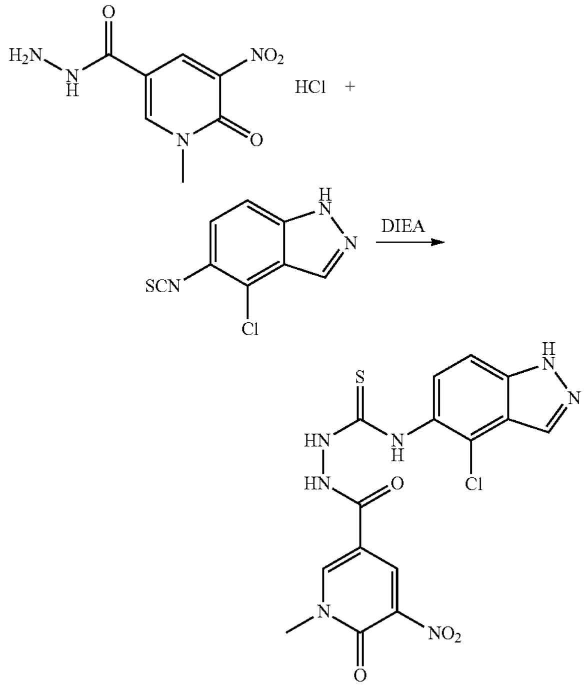

Into a 50-mL round-bottom flask, was placed a solution of 4-chloro-5-isothiocyanato-1H-indazole (169 mg, 0.81 mmol, 1.00 equiv) in dichloromethane (6 mL). This was followed by the addition of 1-methyl-5-nitro-6-oxo-1,6-dihydropyridine-3-carbohydrazide hydrochloride (200 mg, 0.80 mmol, 1.00 equiv) at room temperature. To this was added DIEA (312 mg, 2.41 mmol, 3.00 equiv) at room temperature. The resulting solution was stirred overnight at room temperature. The resulting mixture was concentrated under vacuum. This resulted in 339 mg (100%) of N-[[(4-chloro-1H-indazol-5-yl)carbamothioyl]amino]-1-methyl-5-nitro-6-oxo-1,6-dihydropyridine-3-carboxamide as brown crude oil.

Part 8—Synthesis of 5-(5-((4-chloro-1H-indazol-5-yl)amino)-1,3,4-thiadiazol-2-yl)-1-methyl-3-nitropyridin-2(1H)-one

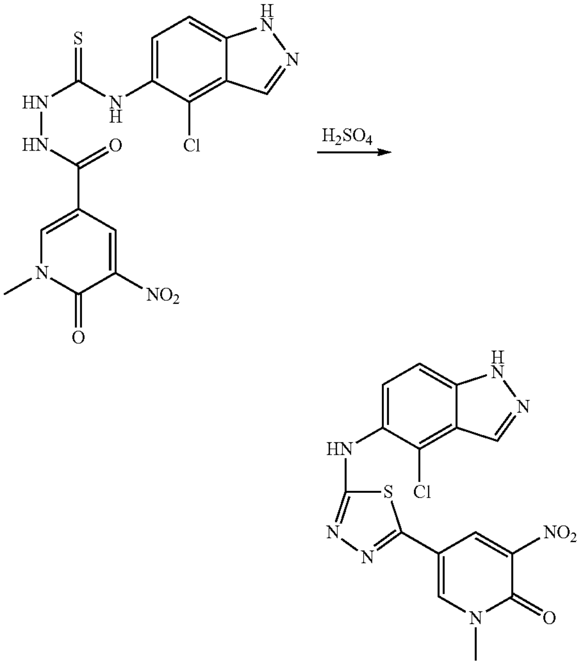

Into a 25-mL round-bottom flask, was placed N-[[(4-chloro-1H-indazol-5-yl)carbamothioyl]amino]-1-methyl-5-nitro-6-oxo-1,6-dihydropyridine-3-carboxamide (300 mg, 0.71 mmol, 1.00 equiv). This was followed by the addition of sulfuric acid (2 mL, 50.00 equiv) dropwise with stirring at 0° C. The resulting solution was stirred overnight at room temperature. The pH value of the solution was adjusted to 9 with sodium bicarbonate(aq). The solids were collected by filtration. This resulted in 250 mg (87%) of 5-[5-[(4-chloro-1H-indazol-5-yl)amino]-1,3,4-thiadiazol-2-yl]-1-methyl-3-nitro-1,2-dihydropyridin-2-one as a brown solid.

Part 9—Synthesis of Tert-Butyl 5-((tert-butoxycarbonyl)(5-(1-methyl-5-nitro-6-oxo-1,6-dihydropyridin-3-yl)-1,3,4-thiadiazol-2-yl)amino)-4-chloro-1H-indazole-1-carboxylate

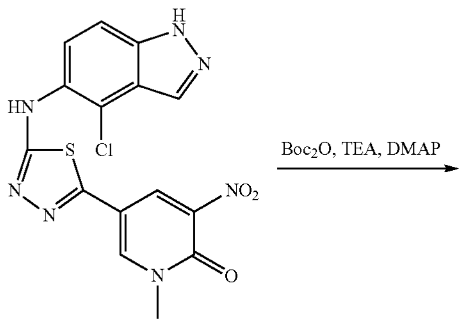

-continued

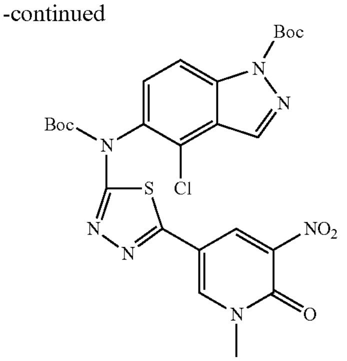

Into a 100-mL round-bottom flask, was placed a solution of 5-[5-[(4-chloro-1H-indazol-5-yl)amino]-1,3,4-thiadiazol-2-yl]-1-methyl-3-nitro-1,2-dihydropyridin-2-one (250 mg, 0.62 mmol, 1.00 equiv) in dichloromethane (15 mL). This was followed by the addition of Boc2O (402 mg, 1.84 mmol, 3.00 equiv) at room temperature. To this was added TEA (188 mg, 1.86 mmol, 3.00 equiv) at room temperature. To the mixture was added 4-dimethylaminopyridine (38 mg, 0.31 mmol, 0.50 equiv) at room temperature. The resulting solution was stirred overnight at room temperature. The residue was applied onto a silica gel column with ethyl acetate/petroleum ether (2:1). The collected fractions were combined and concentrated under vacuum. This resulted in 200 mg (53%) of tert-butyl 5-[[(tert-butoxy)carbonyl][5-(1-methyl-5-nitro-6-oxo-1,6-dihydropyridin-3-yl)-1,3,4-thiadiazol-2-yl]amino]-4-chloro-1H-indazole-1-carboxylate as a yellow solid.

Part 10—Synthesis of Tert-Butyl 5-((5-(5-amino-1-methyl-6-oxo-1,6-dihydropyridin-3-yl)-1,3,4-thiadiazol-2-yl)(tert-butoxycarbonyl)amino)-4-chloro-1H-indazole-1-carboxylate

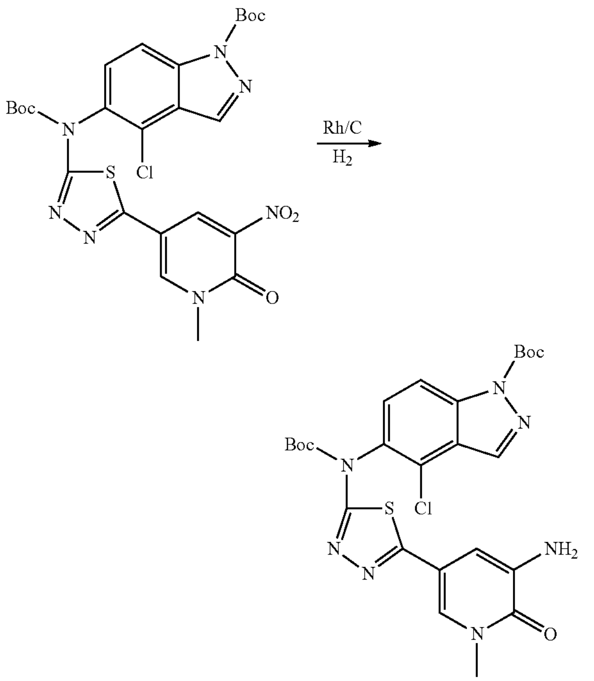

Into a 50-mL round-bottom flask purged and maintained with an inert atmosphere of hydrogen, was placed tert-butyl 5-[[(tert-butoxy)carbonyl][5-(1-methyl-5-nitro-6-oxo-1,6-dihydropyridin-3-yl)-1,3,4-thiadiazol-2-yl]amino]-4-chloro-1H-indazole-1-carboxylate (200 mg, 0.33 mmol, 1.00 equiv). This was followed by the addition of Rh/C (100 mg) at room temperature. The resulting solution was stirred under a hydrogen atmosphere overnight at room temperature. The solids were filtered out. The resulting mixture was concentrated under vacuum. This resulted in 160 mg (84%) of tert-butyl 5-[[5-(5-amino-1-methyl-6-oxo-1,6-dihydropyridin-3-yl)-1,3,4-thiadiazol-2-yl][(tert-butoxy)carbonyl]amino]-4-chloro-1H-indazole-1-carboxylate as a yellow green solid.

Part 11—Synthesis of Tert-Butyl 5-((5-(5-acetamido-1-methyl-6-oxo-1,6-dihydropyridin-3-yl)-1,3,4-thiadiazol-2-yl)(tert-butoxycarbonyl)amino)-4-chloro-1H-indazole-1-carboxylate

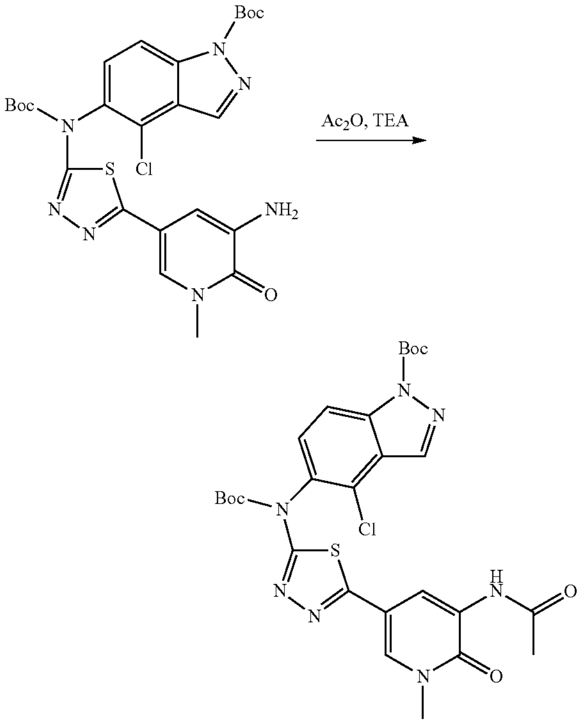

Into a 25-mL round-bottom flask, was placed a solution of tert-butyl 5-[[5-(5-amino-1-methyl-6-oxo-1,6-dihydropyridin-3-yl)-1,3,4-thiadiazol-2-yl][(tert-butoxy)carbonyl]amino]-4-chloro-1H-indazole-1-carboxylate (60 mg, 0.10 mmol, 1.00 equiv) in dichloromethane (5 mL). This was followed by the addition of acetic anhydride (21.4 mg, 0.21 mmol, 2.00 equiv) at room temperature. To this was added TEA (31.7 mg, 0.31 mmol, 3.00 equiv) at room temperature. The resulting solution was stirred overnight at room temperature. The residue was applied onto a silica gel column with ethyl acetate/petroleum ether (2:1). The collected fractions were combined and concentrated under vacuum. This resulted in 45 mg (70%) of tert-butyl 5-[[(tert-butoxy)carbonyl][5-(5-acetamido-1-methyl-6-oxo-1,6-dihydropyridin-3-yl)-1,3,4-thiadiazol-2-yl]amino]-4-chloro-1H-indazole-1-carboxylate as brown oil.

Part 12—Synthesis of N-(5-(5-((4-chloro-1H-indazol-5-yl)amino)-1,3,4-thiadiazol-2-yl)-1-methyl-2-oxo-1,2-dihydropyridin-3-yl)acetamide

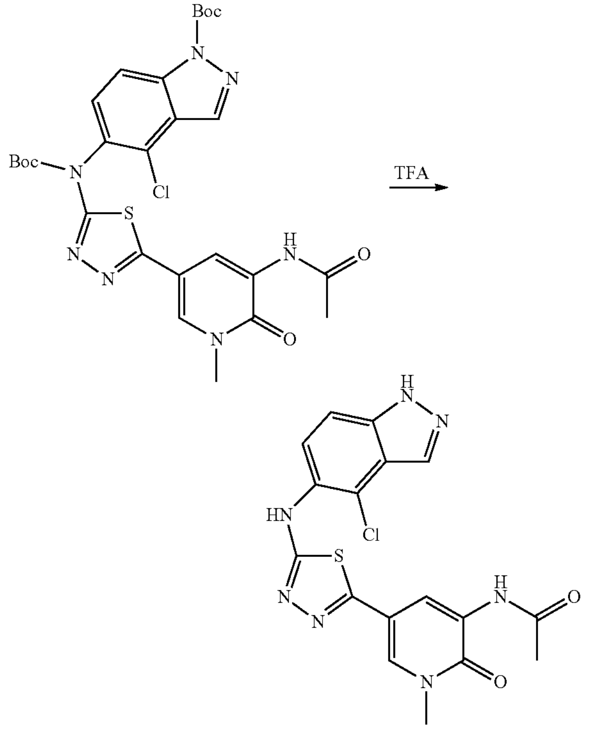

Into a 25-mL round-bottom flask, was placed a solution of tert-butyl 5-[[(tert-butoxy)carbonyl][5-(5-acetamido-1-methyl-6-oxo-1,6-dihydropyridin-3-yl)-1,3,4-thiadiazol-2-yl]amino]-4-chloro-1H-indazole-1-carboxylate (40 mg, 0.06 mmol, 1.00 equiv) in dichloromethane (4 mL). This was followed by the addition of trifluoroacetic acid (0.5 mL) at room temperature. The resulting solution was stirred overnight at room temperature. The resulting mixture was concentrated under vacuum. The crude product was purified by Prep-HPLC with the following conditions: Column, XBridge Prep OBD C18 Column, 19*250 mm, 5 um; mobile phase, Waters (0.05% NH3H2O) and ACN (20.0% ACN up to 39.0% in 8 min); Detector, UV 254 nm. This resulted in 11.7 mg (43%) of N-(5-[5-[(4-chloro-1H-indazol-5-yl)amino]-1,3,4-thiadiazol-2-yl]-1-methyl-2-oxo-1,2-dihydropyridin-3-yl)acetamide as a white solid. ES, m/z): $[M+H]^+$, 416. $^1$H NMR (400 MHz, DMSO-$d_6$, ppm) δ 13.47 (s, 1H), 9.96 (s, 1H), 9.43 (s, 1H), 8.78 (d, J=2.4 Hz, 1H), 8.15 (s, 1H), 8.00 (d, J=2.4 Hz, 1H), 7.82 (d, J=8.6 Hz, 1H), 7.60 (d, J=8.8 Hz, 1H), 3.56 (s, 3H), 2.16 (s, 3H).

Example 58—Synthesis of Additional N-(1H-Indazol-5-yl)-1,3,4-thiadiazol-2-amine Compounds The compounds in Table 13 were prepared based on procedures described in Example 57.

TABLE 13

| Example No. | Chemical Structure | Physical Characterization Data |
|---|---|---|
| 58A | 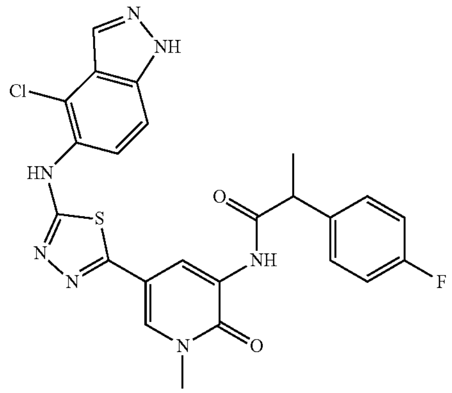 [SMILES: CC(C(=O)Nc1cc(-c2nnc(Nc3ccc4[nH]ncc4c3Cl)s2)cn(C)c1=O)c1ccc(F)cc1] | (ES, m/z): $[M + H]^+$, 524. $^1$H NMR (400 MHz, DMSO-$d_6$, ppm) δ 9.42 (s, 1H), 8.75 (d, J = 2.4 Hz, 1H), 8.12 (d, J = 1.0 Hz, 1H), 7.97 (d, J = 2.4 Hz, 1H), 7.77 (d, J = 8.8 Hz, 1H), 7.57 (dd, J = 8.9, 1.0 Hz, 1H), 7.48 - 7.38 (m, 2H), 7.19 - 7.09 (m, 2H), 4.26 (q, J = 7.0 Hz, 1H), 3.51 (s, 3H), 1.37 (d, J = 7.0 Hz, 3H). |
| 58B | 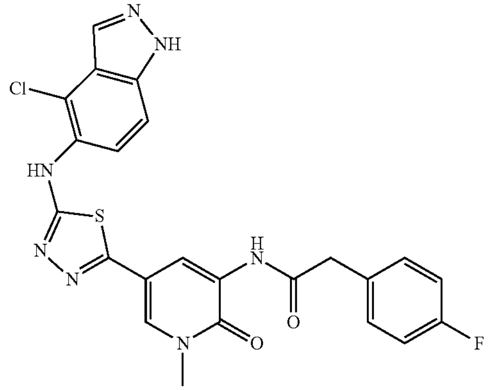 [SMILES: Cn1cc(-c2nnc(Nc3ccc4[nH]ncc4c3Cl)s2)cc(NC(=O)Cc2ccc(F)cc2)c1=O] | (ES, m/z): $[M + H]^+$, 510.3. $^1$H NMR (400 MHz, DMSO-$d_6$, ppm) δ 13.45 (s, 1H), 9.97 (s, 1H), 9.54 (s, 1H), 8.74 (d, J = 2.4 Hz, 1H), 8.12 (s, 1H), 7.98 (d, J = 2.5 Hz, 1H), 7.77 (d, J = 8.9 Hz, 1H), 7.57 (dd, J = 8.9, 1.0 Hz, 1H), 7.42 - 7.32 (m, 2H), 7.18 - 7.08 (m, 2H), 3.83 (s, 2H), 3.54 (s, 3H). |

Example 59—Synthesis of 5-(5-((4-Chloro-1H-indazol-5-yl)amino)-1,3,4-thiadiazol-2-yl)-1-isopropyl-2-oxo-1,2-dihydropyridine-3-carbonitrile

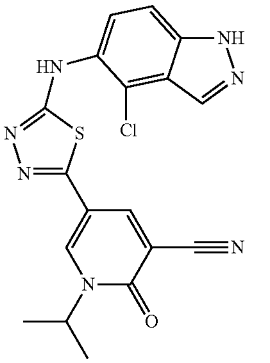

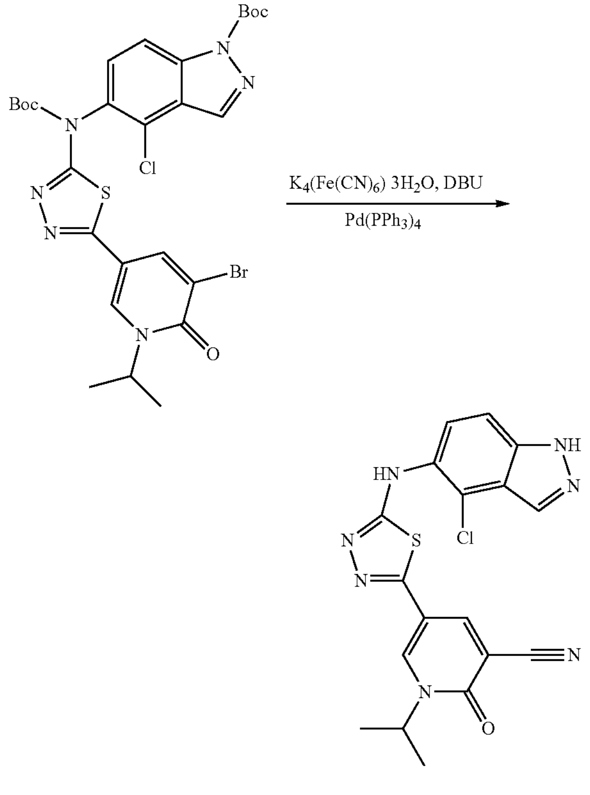

Into a 25-mL round-bottom flask purged and maintained with an inert atmosphere of nitrogen, was placed a solution of tert-butyl 5-([5-[5-bromo-6-oxo-1-(propan-2-yl)-1,6-dihydropyridin-3-yl]-1,3,4-thiadiazol-2-yl][(tert-butoxy)carbonyl]amino)-4-chloro-1H-indazole-1-carboxylate (100 mg, 0.15 mmol, 1.00 equiv) in tert-Butanol (3 mL) and $H_2O$ (2 mL). This was followed by the addition of $K_4(Fe(CN)_6).3H_2O$ (25.4 mg, 0.40 equiv) at room temperature. To this mixture was added DBU (5.7 mg, 0.04 mmol, 0.25 equiv) at room temperature followed by $Pd(PPh_3)_4$ (17.4 mg, 0.02 mmol, 0.10 equiv). The resulting solution was stirred overnight at 85° C. in an oil bath. After allowing to cool, the residue was applied onto a silica gel column and eluted with ethyl acetate/petroleum ether (3:1). The product was further purified by Prep-HPLC with the following conditions (2#-AnalyseHPLC-SHIMADZU(HPLC-10)): Column, Gemini-NX C18 AXAI Packed, 21.2*150 mm 5um; mobile phase, Water (0.05% $NH_3$) and ACN (24.0% ACN up to 48.0% in 8 min); Detector, UV 220 nm. This resulted in 5.7 mg (9%) of 5-[5-[(4-chloro-1H-indazol-5-yl)amino]-1,3,4-thiadiazol-2-yl]-2-oxo-1-(propan-2-yl)-1,2-dihydropyridine-3-carbonitrile as a yellow solid. (ES, m/z): $[M+H]^+$, 412. $^1H$ NMR (400 MHz, DMSO-$d_6$, ppm) δ 13.33 (s, 1H), 9.97 (s, 1H), 8.47 (d, J=2.5 Hz, 1H), 8.29 (s, 1H), 8.06 (s, 1H), 7.64 (d, J=8.7 Hz, 1H), 7.51 (d, J=8.8 Hz, 1H), 5.01 (h, J=6.6 Hz, 1H), 1.37 (d, J=6.8 Hz, 6H).

Example 60—Synthesis of 3-Bromo-5-(5-((4-chloro-1H-indazol-5-yl)amino)-1,3,4-thiadiazol-2-yl)-1-(2-(dimethylamino)ethyl)pyridin-2(1H)-one

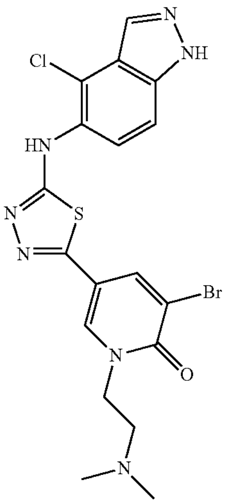 [SMILES: CN(C)CCn1cc(-c2nnc(Nc3ccc4[nH]ncc4c3Cl)s2)cc(Br)c1=O]

Part 1—Synthesis of Methyl 5-bromo-1-(2-(dimethylamino)ethyl)-6-oxo-1,6-dihydropyridine-3-carboxylate

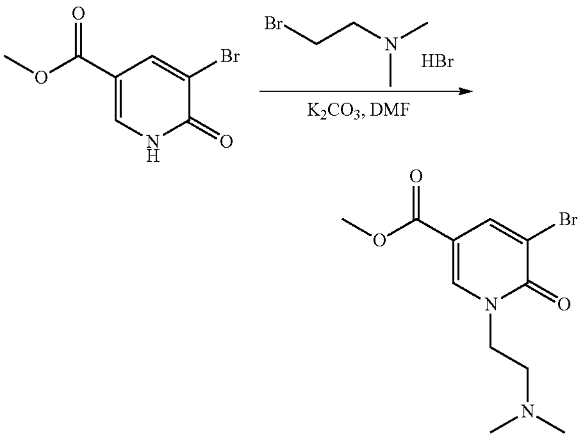

Into a 25-mL round-bottom flask was placed a solution of methyl 5-bromo-6-oxo-1,6-dihydropyridine-3-carboxylate (291 mg, 1.25 mmol, 1.00 equiv) in DMF (11 mL) and $K_2CO_3$ (862.5 mg, 6.24 mmol, 5.00 equiv). The resulting solution was stirred for 20 min at room temperature. (2-Bromoethyl)dimethylamine hydrobromide (585 mg, 2.51 mmol, 2.00 equiv) was added and the resulting solution was allowed to react, with stirring, for an additional 10 h at 100° C. then diluted with 50 mL of ethyl acetate. The resulting mixture was washed with 2×45 mL of water and 45 mL of brine. The organic phase was concentrated under vacuum. This resulted in 255 mg (67%) of methyl 5-bromo-1-[2-(dimethylamino)ethyl]-6-oxo-1,6-dihydropyridine-3-carboxylate as an off-white solid.

Part 2—Synthesis of 5-bromo-1-(2-(dimethylamino)ethyl)-6-oxo-1,6-dihydropyridine-3-carboxylic Acid

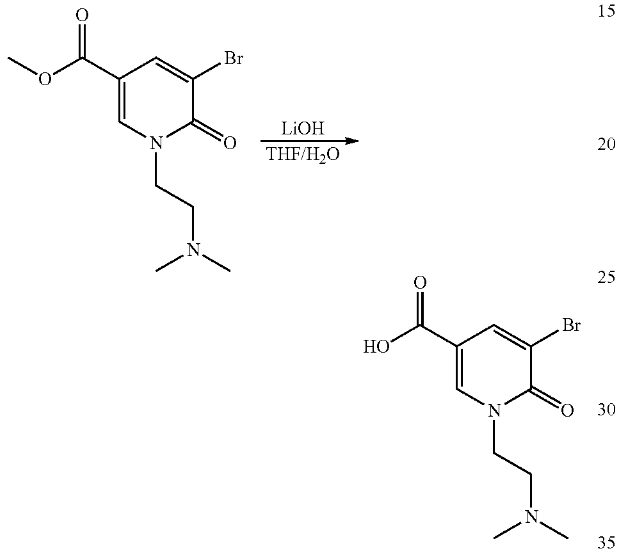

Into a 25-mL round-bottom flask was placed a solution of methyl 5-bromo-1-[2-(dimethylamino)ethyl]-6-oxo-1,6-dihydropyridine-3-carboxylate (255 mg, 0.84 mmol, 1.00 equiv) in 1:1 THF:$H_2O$ (10 mL). This was followed by the addition of a solution of LiOH.$H_2O$ (158.8 mg, 3.78 mmol, 4.50 equiv) in $H_2O$ (2 mL) dropwise with stirring. The resulting solution was stirred for 2 h at room temperature. The pH value of the solution was adjusted to 4 with HCl (1 mol/L). The resulting mixture was concentrated under vacuum and purified by preparative-TLC (4:1 DCM:MeOH). This resulted in 200 mg (82%) of 5-bromo-1-[2-(dimethylamino)ethyl]-6-oxo-1,6-dihydropyridine-3-carboxylic acid as yellow oil.

Part 3—Synthesis of Tert-Butyl 2-(5-bromo-1-(2-(dimethylamino)ethyl)-6-oxo-1,6-dihydropyridine-3-carbonyl)hydrazine-1-carboxylate

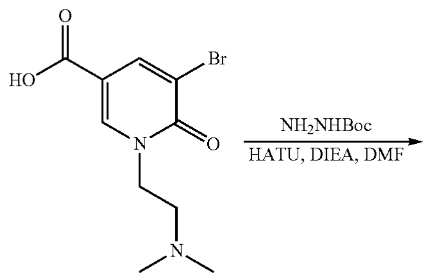

-continued

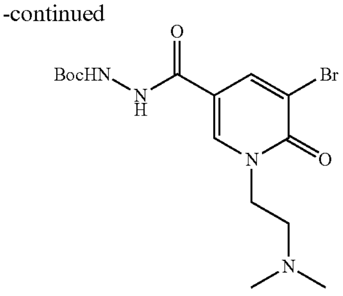

Into a 25-mL round-bottom flask was placed a solution of 5-bromo-1-[2-(dimethylamino)ethyl]-6-oxo-1,6-dihydropyridine-3-carboxylic acid (230 mg, 0.80 mmol, 1.00 equiv) in DMF (5 mL), (tert-butoxy)carbohydrazide (115 mg, 0.87 mmol, 1.10 equiv), HATU (393 mg, 1.03 mmol, 1.30 equiv) and DIEA (205 mg, 1.59 mmol, 2.00 equiv). The resulting solution was stirred for 10 h at room temperature then diluted with 65 mL of ethyl acetate. The resulting mixture was washed with 2×50 mL of water and 50 mL of brine. The organic phase was concentrated under vacuum and purified by preparative-TLC (10:1 DCM:MeOH). This resulted in 140 mg (44%) of 5-bromo-N-(tert-butoxy)carbonyl]-1-[2-(dimethylamino)ethyl]-6-oxo-1,6-dihydropyridine-3-carbohydrazide as a yellow oil.

Part 4—Synthesis of 5-bromo-1-(2-(dimethylamino)ethyl)-6-oxo-1,6-dihydropyridine-3-carbohydrazide Hydrochloride

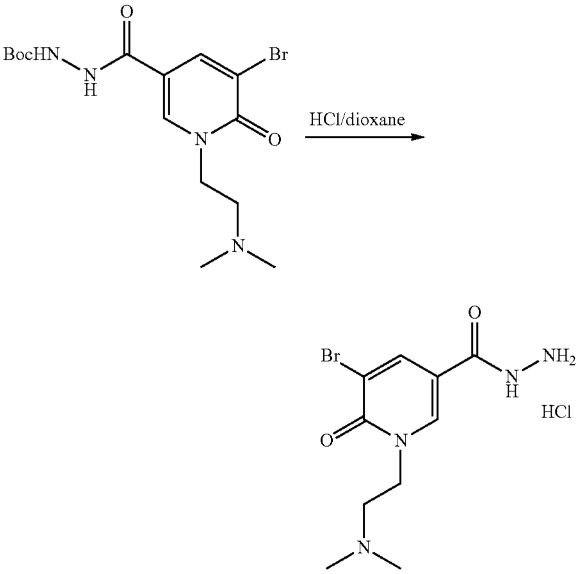 [SMILES: CN(C)CCn1cc(C(=O)NNC(=O)OC(C)(C)C)cc(Br)c1=O ; CN(C)CCn1cc(C(=O)NN)cc(Br)c1=O ; Cl]

Into a 25-mL round-bottom flask was placed 5-bromo-N-(tert-butoxy)carbonyl]-1-[2-(dimethylamino)ethyl]-6-oxo-1,6-dihydropyridine-3-carbohydrazide (120 mg, 0.30 mmol, 1.00 equiv) and HCl/dioxane (15 mL). The resulting solution was stirred for 1 h at room temperature. The resulting mixture was concentrated under vacuum. The residue was washed with 5 mL of ethyl acetate. The solids were collected by filtration. This resulted in 110 mg (98%) of 5-bromo-1-[2-(dimethylamino)ethyl]-6-oxo-1,6-dihydropyridine-3-carbohydrazide hydrochloride as an off-white solid.

Part 5—Synthesis of 2-(5-bromo-1-(2-(dimethylamino)ethyl)-6-oxo-1,6-dihydropyridine-3-carbonyl)-N-(4-chloro-1H-indazol-5-yl)hydrazine-1-carbothioamide

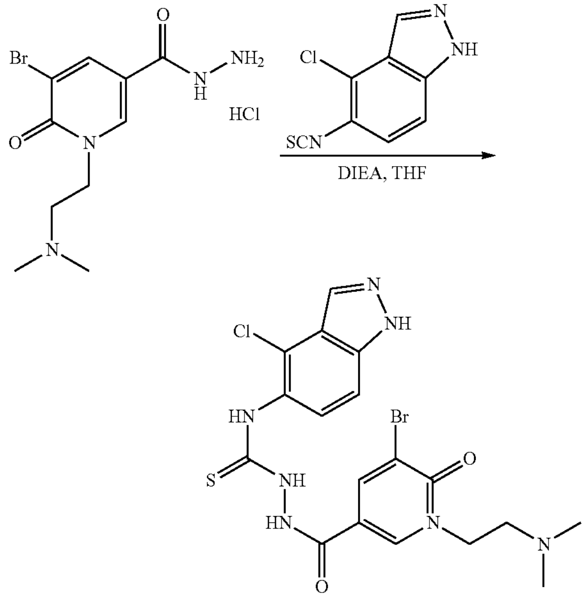

Into a 25-mL round-bottom flask was placed 5-bromo-1-[2-(dimethylamino)ethyl]-6-oxo-1,6-dihydropyridine-3-carbohydrazide hydrochloride (110 mg, 0.29 mmol, 1.00 equiv), THF (8 mL), DIEA (79 mg, 0.61 mmol, 2.00 equiv) and 4-chloro-5-isothiocyanato-1H-indazole (64.1 mg, 0.31 mmol, 1.00 equiv). The resulting solution was stirred for 2 h at room temperature then concentrated under vacuum. The residue was purified by preparative-TLC (4:1 DCM:MeOH). This resulted in 112 mg of 5-bromo-N-[[(4-chloro-1H-indazol-5-yl)carbamothioyl]amino]-1-[2-(dimethylamino)ethyl]-6-oxo-1,6-dihydropyridine-3-carboxamide as a yellow solid.

Part 6—Synthesis of 3-bromo-5-(5-((4-chloro-1H-indazol-5-yl)amino)-1,3,4-thiadiazol-2-yl)-1-(2-(dimethylamino)ethyl)pyridin-2(1H)-one

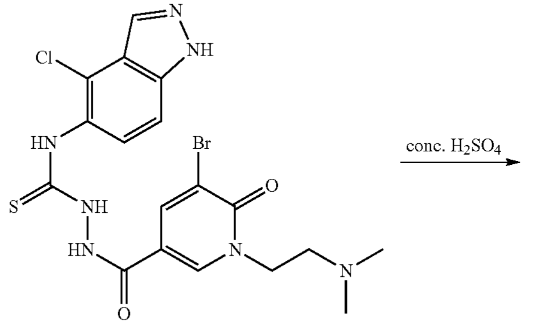

-continued

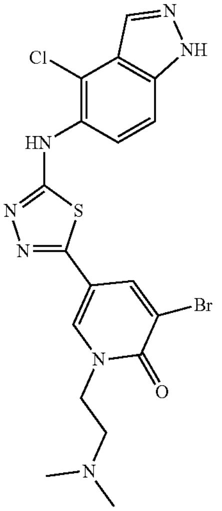

Into a 10-mL round-bottom flask was placed 5-bromo-N-[[(4-chloro-1H-indazol-5-yl)carbamothioyl]amino]-1-[2-(dimethylamino)ethyl]-6-oxo-1,6-dihydropyridine-3-carboxamide (112 mg, 0.27 mmol, 1.00 equiv) and concentrated sulfuric acid (2.5 mL). The resulting solution was stirred for 1 h at room temperature. The reaction was then quenched by pouring it into 20 g of crush ice. The pH value of the solution was adjusted to 9 with $NH_3.H_2O$ (1 M). The resulting solution was extracted with 3×15 mL of ethyl acetate and the organic layers combined and concentrated under vacuum. The product was purified by Prep-HPLC with the following conditions (2#-Analyse HPLC-SHIMADZU(HPLC-10)): Column: X-Select CSH Prep C18 OBD Column, 5 um, 19*150 mm; mobile phase: Water (0.05% $NH_3$) and ACN (10.0% ACN up to 55.0% in 8 min); Detector: UV 254 nm. This resulted in 9.7 mg (6%) of 3-bromo-5-[5-[(4-chloro-1H-indazol-5-yl)amino]-1,3,4-thiadiazol-2-yl]-1-[2-(dimethylamino)ethyl]-1,2-dihydropyridin-2-one as a light yellow solid. (ES, m/z): $[M+H]^+$, 495.8. $^1H$ NMR (400 MHz, DMSO-$d_6$, ppm) δ 13.46 (s, 1H), 10.04 (s, 1H), 8.30 (d, J=2.4 Hz, 1H), 8.25 (d, J=2.4 Hz, 1H), 8.13 (s, 1H), 7.77 (d, J=8.8 Hz, 1H), 7.58 (dd, J=8.8, 1.1 Hz, 1H), 4.08 (t, J=6.3 Hz, 2H), 2.52 (d, J=6.2 Hz, 2H), 2.15 (s, 6H).

Example 61—Synthesis of Additional N-(1H-indazol-5-yl)-1,3,4-thiadiazol-2-amine Compounds The compounds in Table 13 were prepared based on procedures described in Example 60.

TABLE 13

| Example No. | Chemical Structure | Physical Characterization Data |
|---|---|---|
| 61A | 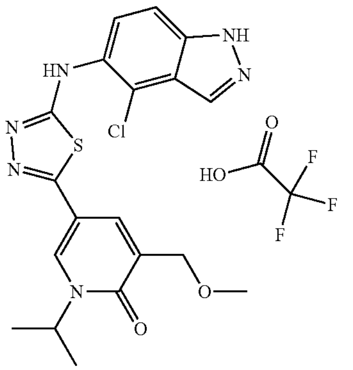 | (ES, m/z): [M − TFA + H]+ 431. $^1$H NMR (400 MHz, DMSO-$d_6$, ppm) δ 13.51 (s, 1H), 10.00 (s, 1H), 8.15 (s, 1H), 8.01 (d, J = 2.4 Hz, 1H), 7.83 − 7.74 (m, 2H), 7.60 (d, J = 8.8 Hz, 1H), 5.10 − 5.05 (m, 1H), 4.30 (s, 2H), 3.39 (s, 3H), 1.35 (d, J = 6.8 Hz, 6H). |
| 61B | 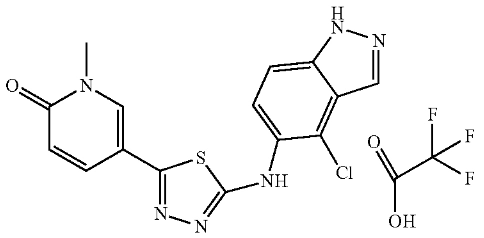 | (ES, m/z): [M − TFA + H]+ 359.10 $^1$H NMR (400 MHz, DMSO-$d_6$, ppm) δ 13.45 (s, 1H), 9.95 (s, 1H), 8.25 (d, J = 2.4 Hz, 1H), 8.12 (s, 1H), 7.87 − 7.90 (m, 1H), 7.79 (d, J = 8.4 Hz, 1H), 7.57 (d, J = 8.8 Hz, 1H), 6.48 (d, J = 9.6 Hz, 1H), 3.46 (s, 3H). |
| 61C | 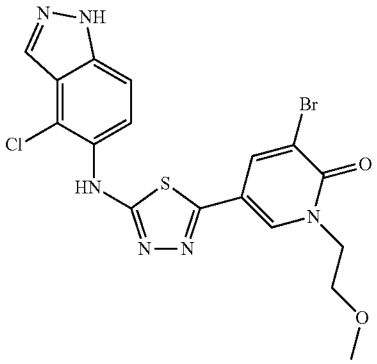 [SMILES: COCCn1cc(-c2nnc(Nc3ccc4[nH]ncc4c3Cl)s2)cc(Br)c1=O] | (ES, m/z): [M + H]+ 481. $^1$H NMR (400 MHz, DMSO-$d_6$, ppm) δ 13.46 (s, 1H), 9.97 (s, 1H), 8.31 (d, J = 2.4 Hz, 1H), 8.23 (d, J = 2.4 Hz, 1H), 8.13 (s, 1H), 7.78 (d, J = 8.8 Hz, 1H), 7.58 (dd, J = 8.8, 1.0 Hz, 1H), 4.19 (t, J = 5.4 Hz, 2H), 3.59 (t, J = 5.3 Hz, 2H), 3.22 (s, 3H). |
| 61D | 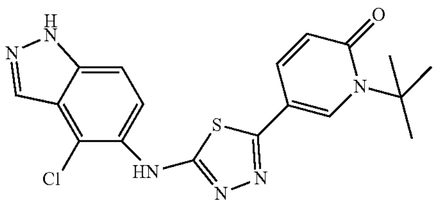 [SMILES: CC(C)(C)n1cc(-c2nnc(Nc3ccc4[nH]ncc4c3Cl)s2)ccc1=O] | (ES, m/z): [M + H]+ 401. $^1$H NMR (400 MHz, DMSO-$d_6$, ppm) δ 13.47 (s, 1H), 9.92 (s, 1H), 8.13 (s, 1H), 8.03 (d, J = 2.4 Hz, 1H), 7.86 − 7.71 (m, 2H), 7.58 (d, J = 8.9 Hz, 1H), 6.43 (d, J = 9.4 Hz, 1H), 1.64 (s, 9H). |
| 61E | 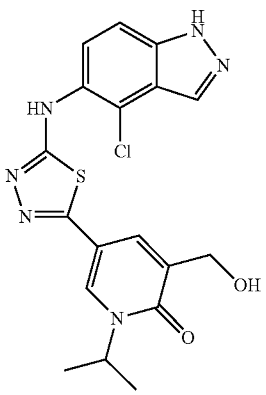 [SMILES: CC(C)n1cc(-c2nnc(Nc3ccc4[nH]ncc4c3Cl)s2)cc(CO)c1=O] | (ES, m/z): [M + H]+ 417. $^1$H NMR (400 MHz, DMSO-$d_6$, ppm) δ 13.48 (s, 1H), 9.90 (s, 1H), 8.15 (d, J = 1.0 Hz, 1H), 7.97 (d, J = 2.5 Hz, 1H), 7.88 (dt, J = 2.6, 1.4 Hz, 1H), 7.78 (d, J = 9.2 Hz, 1H), 7.61 (dd, J = 8.8, 1.0 Hz, 1H), 5.26 (t, J = 5.6 Hz, 1H), 5.08 (p, J = 6.8 Hz, 1H), 4.37 (d, J = 5.7 Hz, 2H), 1.35 (d, J = 6.8 Hz, 6H). |

TABLE 13-continued

| Example No. | Chemical Structure | Physical Characterization Data |
| --- | --- | --- |
| 61F | 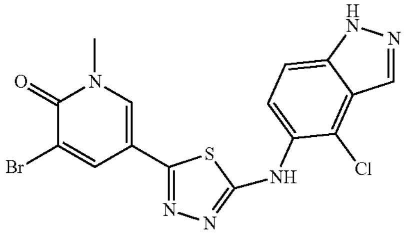 [SMILES: Cn1cc(-c2nnc(Nc3ccc4[nH]ncc4c3Cl)s2)cc(Br)c1=O] | (ES, m/z): $[M + H]^+$ 438.9. $^1H$ NMR (400 MHz, DMSO-$d_6$, ppm) δ 13.46 (s, 1H), 10.09 (s, 1H), 8.32 - 8.35 (m, 2H), 8.15 (d, J = 9.6 Hz, 1H), 7.79 (d, J = 8.8 Hz, 1H), 7.59 (d, J = 8.8 Hz, H), 3.57 (s, 3H). |
| 61G | 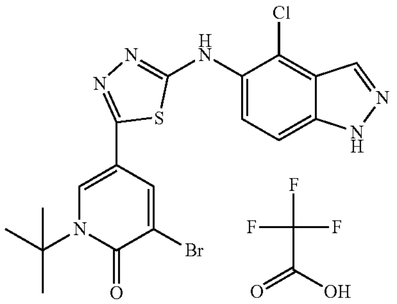 | (ES, m/z): $[M + H]^+$ 480.85. $^1H$ NMR (400 MHz, DMSO-$d_6$, ppm) δ 13.51 (s, 0.2H), 10.00 (s, 0.4H), 8.34 (s, 1H), 8.15 (s, 1H), 8.08 (s, 1H), 7.81 - 7.78 (d, J = 8.7 Hz, 1H), 7.61 - 7.58 (d, J = 9 Hz, 1H), 1.65 (s, 9H). |
| 61H | 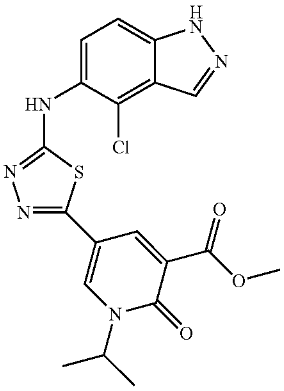 [SMILES: COC(=O)c1cc(-c2nnc(Nc3ccc4[nH]ncc4c3Cl)s2)cn(C(C)C)c1=O] | (ES, m/z): $[M + H]^+$ 445. $^1H$ NMR (400 MHz, DMSO-$d_6$, ppm) δ 13.50 (s, 1H), 10.05 (s, 1H), 8.40 (d, J = 2.7 Hz, 1H), 8.35 - 8.30 (m, 1H), 8.16 (s, 1H), 7.78 (d, J = 8.7 Hz, 1H), 7.61 (d, J = 8.8 Hz, 1H), 5.07 (p, J = 6.7 Hz, 1H), 3.79 (s, 3H), 1.37 (d, J = 6.8 Hz, 6H). |
| 61I | 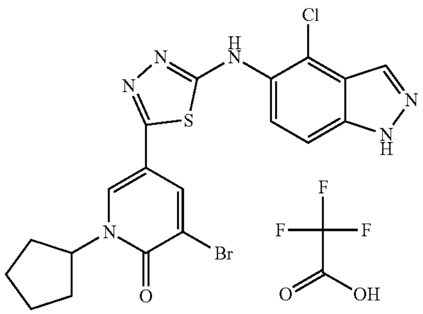 | (ES, m/z): $[M + H]^+$ 492.95. $^1H$ NMR (400 MHz, DMSO-$d_6$, ppm) δ 13.48 (s, 1H), 10.04 (s, 1H), 8.31 (s, 1H), 8.15 (s, 1H), 8.11 (s, 1H), 7.78 - 7.75 (d, J = 9.2 Hz, 1H), 7.61 - 7.59 (d, J = 8.8 Hz, 1H), 5.08 - 5.00 (m, 1H), 2.02 - 1.99 (m, 2H), 1.83 (s, 4H), 1.63 (s, 2H). |

TABLE 13-continued

| Example No. | Chemical Structure | Physical Characterization Data |
|---|---|---|
| 61J | 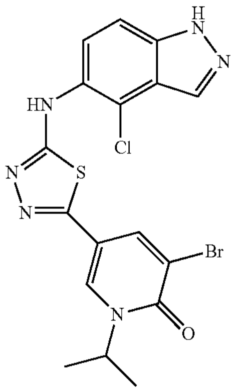 [SMILES: CC(C)n1cc(-c2nnc(Nc3ccc4[nH]ncc4c3Cl)s2)cc(Br)c1=O] | (ES, m/z): $[M + H]^+$ 465. $^1H$ NMR (400 MHz, DMSO-$d_6$, ppm) δ 13.46 (s, 1H), 10.01 (s, 1H), 8.29 (d, J = 2.3 Hz, 1H), 8.14 - 8.10 (m, 2H), 7.74 (d. J = 8.7 Hz, 1H), 7.58 (dd, J = 8.8, 1.1 Hz, 1H), 5.02 (p, J = 6.8 Hz, 1H), 1.35 (d, J = 6.8 Hz, 6H). |
| 61K | 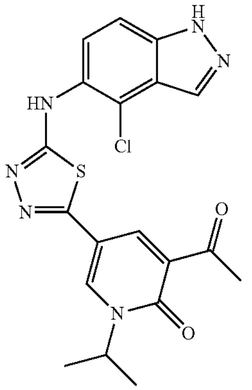 [SMILES: CC(=O)c1cc(-c2nnc(Nc3ccc4[nH]ncc4c3Cl)s2)cn(C(C)C)c1=O] | (ES, m/z): $[M + H]^+$ 429. $^1H$ NMR (400 MHz, DMSO-$d_6$, ppm) δ 10.01 (s, 1H), 8.36 (d, J = 2.8 Hz, 1H), 8.30 (d, J = 2.7 Hz, 1H), 8.15 - 8.10 (m, 1H), 7.79 - 7.73 (m, 1H), 7.58 (dd, J = 8.8, 1.0 Hz, 1H), 5.12 (h, J = 6.8 Hz, 1H), 2.58 (s, 3H), 1.37 (d, J = 6.8 Hz, 6H). |

Example 62—Synthesis of 4-(5-((4-Chloro-1H-indazol-5-yl)amino)-1,3,4-thiadiazol-2-yl)-1-isopropylpyridin-2(1H)-one

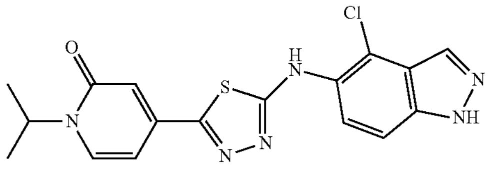 [SMILES: CC(C)n1ccc(-c2nnc(Nc3ccc4[nH]ncc4c3Cl)s2)cc1=O]

Part 1—Synthesis of Methyl 1-isopropyl-2-oxo-1,2-dihydropyridine-4-carboxylate

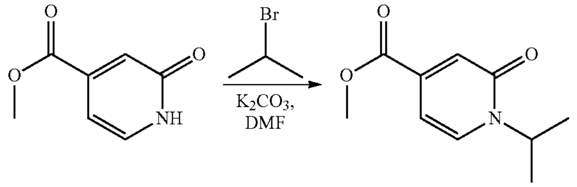

Into a 50-mL round-bottom flask, was placed methyl 2-oxo-1,2-dihydropyridine-4-carboxylate (1 g, 6.53 mmol, 1.00 equiv), N,N-dimethylformamide (20 mL), sodium carbonate (2080 mg, 19.62 mmol, 3.00 equiv), and 2-bromopropane (2400 mg, 19.51 mmol, 3.00 equiv). The resulting solution was stirred overnight at 100° C. in an oil bath then concentrated under vacuum. This resulted in 198.1 mg (16%) of methyl 2-oxo-1-(propan-2-yl)-1,2-dihydropyridine-4-carboxylate as light yellow oil.

Part 2—Synthesis of 1-isopropyl-2-oxo-1,2-dihydropyridine-4-carbohydrazide

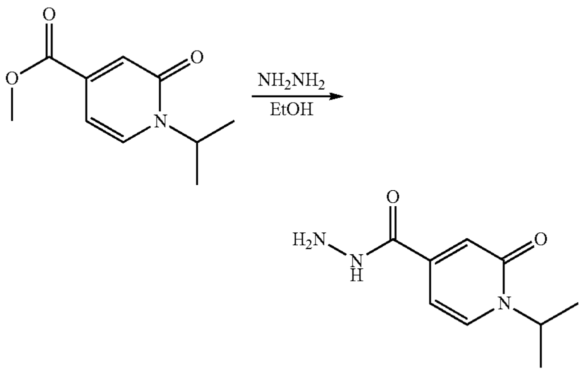

Into a 25-mL round-bottom flask, was placed methyl 2-oxo-1-(propan-2-yl)-1,2-dihydropyridine-4-carboxylate (160 mg, 0.82 mmol, 1.00 equiv), ethanol (3 mL), and hydrazine (3 mL). The resulting solution was stirred for 3 h at 80° C. in an oil bath. The resulting mixture was concentrated under vacuum. This resulted in 160 mg (100%) of 2-oxo-1-(propan-2-yl)-1,2-dihydropyridine-4-carbohydrazide as a white solid.

Part 3—Synthesis of N-(4-chloro-1H-indazol-5-yl)-2-(1-isopropyl-2-oxo-1,2-dihydropyridine-4-carbonyl)hydrazine-1-carbothioamide

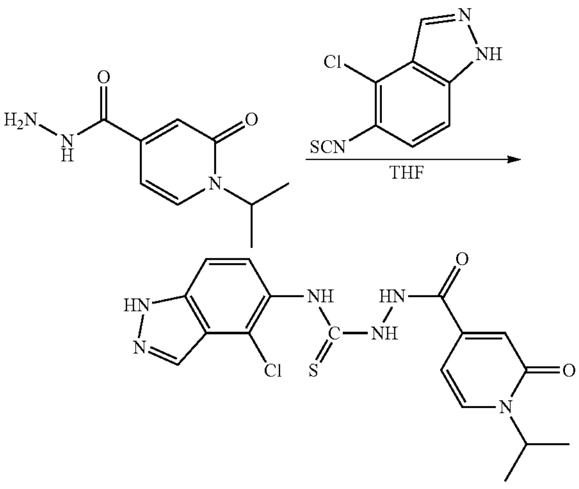

Into a 25-mL round-bottom flask, was placed 2-oxo-1-(propan-2-yl)-1,2-dihydropyridine-4-carbohydrazide (195 mg, 1.00 mmol, 1.00 equiv), tetrahydrofuran (5 mL), and 4-chloro-5-isothiocyanato-1H-indazole (210 mg, 1.00 mmol, 1.00 equiv). The resulting solution was stirred overnight at room temperature then concentrated under vacuum. This resulted in 400 mg (99%) of N-[[(4-chloro-1H-indazol-5-yl)carbamothioyl]amino]-2-oxo-1-(propan-2-yl)-1,2-dihydropyridine-4-carboxamide as a yellow solid.

Part 4—Synthesis of 4-(5-((4-chloro-1H-indazol-5-yl)amino)-1,3,4-thiadiazol-2-yl)-1-isopropylpyridin-2(1H)-one

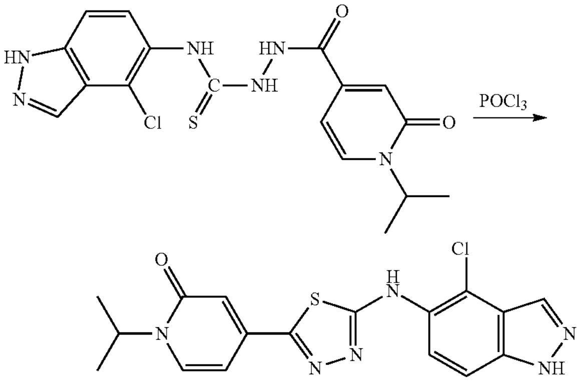

Into a 25-mL round-bottom flask, was placed N-[[(4-chloro-1H-indazol-5-yl)carbamothioyl]amino]-2-oxo-1-(propan-2-yl)-1,2-dihydropyridine-4-carboxamide (340 mg, 0.84 mmol, 1.00 equiv), and $POCl_3$ (5 mL). The resulting solution was stirred overnight at room temperature. The reaction was then quenched by the addition of 100 mL of water/ice. The pH value of the solution was adjusted to 8 with sodium bicarbonate (saturate). The solids were collected by filtration then dried in an oven under reduced pressure. The residue was dissolved in of DMF. The crude product was purified by Prep-HPLC with the following conditions (2#-AnalyseHPLC-SHIMADZU(HPLC-10)): Column: XBridge Shield RP18 OBD Column, 5 um, 19*150 mm; Mobile Phase A: Water (10 mM $NH_4HCO_3$), Mobile Phase B: ACN; Flow rate: 20 mL/min; Gradient: 48% B to 63% B in 7 min; Detector: 254 nm. This resulted in 42.9 mg (13%) of 4-[5-[(4-chloro-1H-indazol-5-yl)amino]-1,3,4-thiadiazol-2-yl]-1-(propan-2-yl)-1,2-dihydropyridin-2-one as a light yellow solid. (ES, m/z): $[M+H]^+$387. $^1H$ NMR (400 MHz, DMSO-$d_6$, ppm): δ 13.47 (s, 1H), 10.22 (s, 1H), 8.22 (dd, J=5.4, 0.7 Hz, 1H), 8.13 (s, 1H), 7.82 (d, J=8.8 Hz, 1H), 7.58 (dd, J=8.8, 1.0 Hz, 1H), 7.34 (dd, J=5.4, 1.5 Hz, 1H), 7.07-6.97 (m, 1H), 5.26 (p, J=6.2 Hz, 1H), 1.29 (d, J=6.1 Hz, 6H).

Example 63—Synthesis of 4-(5-((4-Chloro-1H-indazol-5-yl)amino)-1,3,4-thiadiazol-2-yl)-1-methylpyridin-2(1H)-one

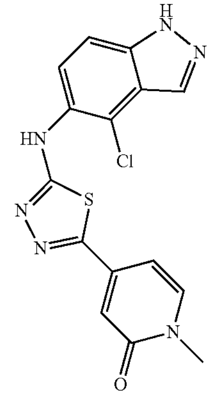 [SMILES: Cn1ccc(-c2nnc(Nc3ccc4[nH]ncc4c3Cl)s2)cc1=O]

The title compound was prepared based on procedures described in Example 62. Physical characterization data for the title compound is as follows: (ES, m/z): $[M+H]^+$359. $^1H$ NMR (400 MHz, DMSO-$d_6$, ppm) δ 13.36 (s, 1H), 9.82 (s, 1H), 10.02 (s, 1H), 8.11 (s, 1H), 7.76 (t, J=15.2 Hz, 2H), 7.56 (d, J=8.8 Hz, 1H), 6.68 (d, J=7.2 Hz, 1H), 6.61 (s, 1H), 3.30 (s, 3H).

Example 64—Synthesis of 1-(2,3-Dihydroxypropyl)-3-[5-(1H-indazol-5-ylamino)-1,3,4-thiadiazol-2-yl]pyridin-2-one

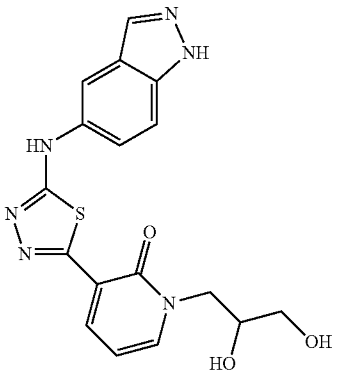 [SMILES: O=c1c(-c2nnc(Nc3ccc4[nH]ncc4c3)s2)cccn1CC(O)CO]

The title compound was prepared based on procedures described in Example 57. Physical characterization data for the title compound is as follows: (ES, m/z): $[M+H]^+$ 385. $^1H$ NMR (400 MHz, DMSO-$d_6$, ppm) δ 12.65 (br s, 1H), 10.31 (br s, 1H), 8.47-8.44 (m, 1H), 8.23 (d, 1H), 8.05 (s, 1H), 7.86-7.84 (m, 1H), 7.53 (d, 1H), 7.43-7.40 (m, 1H), 6.57-6.51 (m, 1H), 4.44-4.40 (m, 1H), 3.86-3.66 (m, 2H), 3.46-3.35 (m, 2H).

Example 65—Synthesis of 3-(5-((1H-Indazol-5-yl)amino)-1,3,4-thiadiazol-2-yl)-1-allylpyridin-2(1H)-one

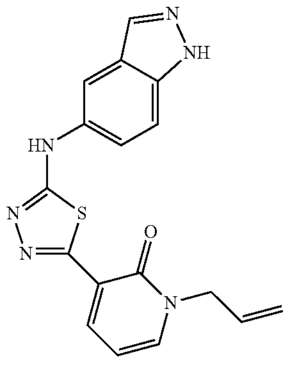 [SMILES: C=CCn1cccc(-c2nnc(Nc3ccc4[nH]ncc4c3)s2)c1=O]

The title compound was prepared based on procedures described in Example 57. Physical characterization data for the title compound is as follows: (ES, m/z): $[M+H]^+$ 351. $^1H$ NMR (400 MHz, DMSO-$d_6$, ppm) δ 10.30 (s, 1H), 8.47-8.45 (m, 1H), 8.24 (d, 1H), 8.04 (s, 1H), 7.93-7.91 (m, 1H), 7.53 (d, 1H), 7.42-7.40 (m, 1H), 6.58 (t, 1H), 6.06-5.97 (m, 1), 58.25-5.12 (m, 2H), 4.68 (d, 2H).

Example 66—Synthesis of N-(4-(5-((1H-Indazol-5-yl)amino)-1,3,4-thiadiazol-2-yl)pyrimidin-2-yl)-1-methyl-1H-pyrazole-4-carboxamide 2,2,2-trifluoroacetic Acid Solvate

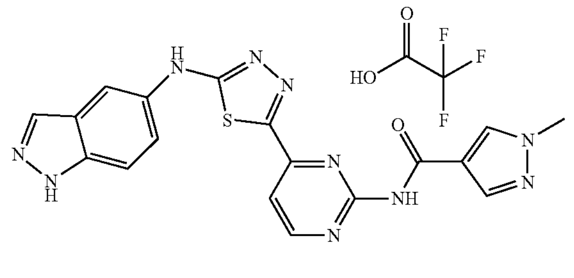

Part 1—Synthesis of 1-methyl-1H-pyrazole-4-carbonyl Chloride

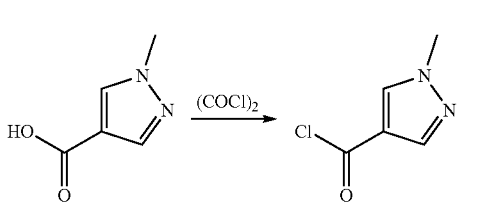

Into a 100-mL round-bottom flask was placed a solution of 1-methyl-1H-pyrazole-4-carboxylic acid (300 mg, 2.38 mmol, 1.00 equiv) in dichloromethane (10 mL), and oxalyl chloride (604 mg, 4.72 mmol, 2.00 equiv). The resulting solution was stirred overnight at room temperature then concentrated under vacuum. This resulted in 300 mg (87%) of 1-methyl-1H-pyrazole-4-carbonyl chloride as a yellow solid.

Part 2—Synthesis of Methyl 2-(1-methyl-1H-pyrazole-4-carboxamido)pyrimidine-4-carboxylate

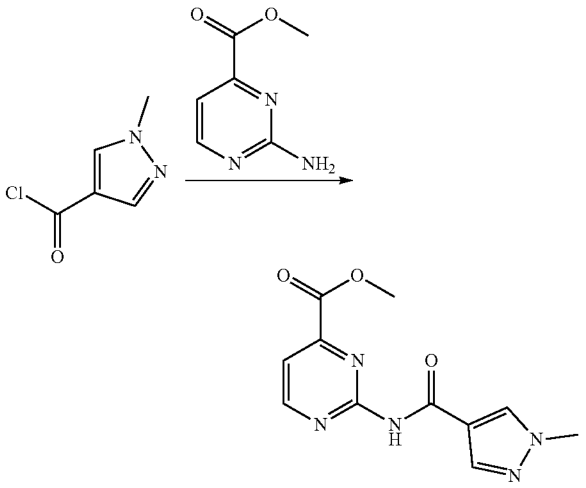

Into a 100-mL round-bottom flask was placed a solution of methyl 2-aminopyrimidine-4-carboxylate (1 g, 6.53 mmol, 1.00 equiv) in pyridine (20 mL), and 1-methyl-1H-pyrazole-4-carbonyl chloride (1 g, 6.92 mmol, 1.05 equiv). The resulting solution was stirred overnight at room temperature then concentrated under vacuum. The residue was applied onto a silica gel column and eluted with dichloromethane/methanol (20:1). This resulted in 1 g (59%) of methyl 2-(1-methyl-1H-pyrazole-4-amido)pyrimidine-4-carboxylate as a white solid.

Part 3—Synthesis of 2-(1-methyl-1H-pyrazole-4-carboxamido)pyrimidine-4-carboxylic Acid

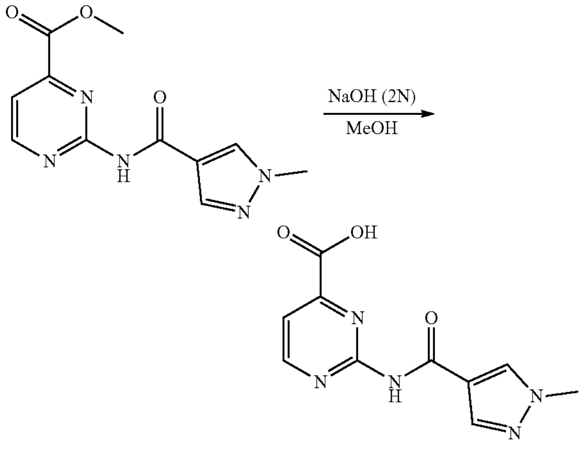

Into a 100-mL round-bottom flask was placed a solution of methyl 2-(1-methyl-1H-pyrazole-4-amido)pyrimidine-4-carboxylate (900 mg, 3.45 mmol, 1.00 equiv) in tetrahydrofuran (20 mL), and sodium hydroxide (2 N) (9 mL). The resulting solution was stirred overnight at room temperature. The pH value of the solution was adjusted to 4 with aqueous HCl (1 M) then concentrated under vacuum. The residue was dissolved in 100 mL of methanol and the solids were removed by filtration. The filtrate was concentrated under vacuum. This resulted in 500 mg (59%) of 2-(1-methyl-1H-pyrazole-4-amido)pyrimidine-4-carboxylic acid as a yellow solid.

Part 4—Synthesis of Tert-Butyl 2-(2-(1-methyl-1H-pyrazole-4-carboxamido)pyrimidine-4-carbonyl) hydrazine-1-carboxylate

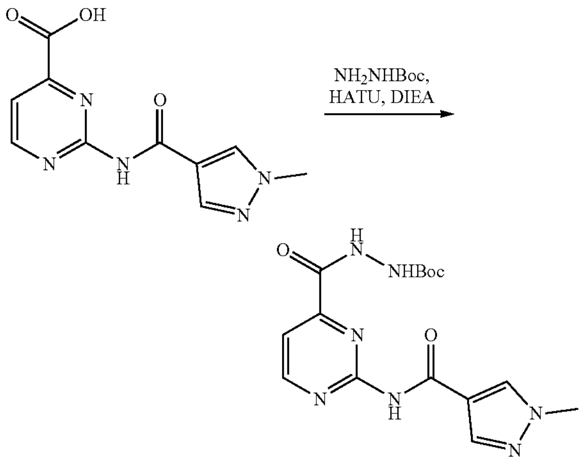

Into a 100-mL round-bottom flask was placed a solution of 2-(1-methyl-1H-pyrazole-4-amido)pyrimidine-4-carboxylic acid (600 mg, 2.43 mmol, 1.00 equiv) in dichloromethane (20 mL), $NH_2NHBoc$ (385 mg, 1.20 equiv), HATU (1.38 g, 3.63 mmol, 1.50 equiv), and DIEA (939 mg, 7.27 mmol, 3.00 equiv). The resulting solution was stirred overnight at room temperature then concentrated under vacuum. The residue was applied onto a silica gel column and eluted with dichloromethane/methanol (0:1). This resulted in 250 mg (29%) of N-[4-[([[(tert-butoxy)carbonyl]amino]amino) carbonyl]pyrimidin-2-yl]-1-methyl-1H-pyrazole-4-carboxamide as a yellow solid.

Part 5—Synthesis of N-(4-(hydrazinecarbonyl)pyrimidin-2-yl)-1-methyl-1H-pyrazole-4-carboxamide

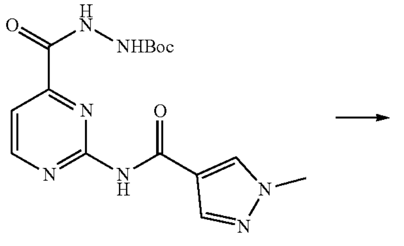

-continued

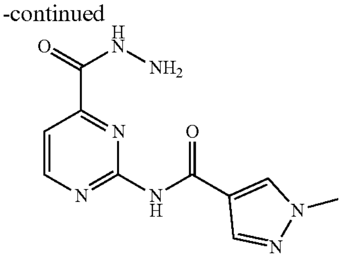

Into a 100-mL round-bottom flask was placed a solution of N-(4-[N-(tert-butoxy)carbonyl]hydrazinecarbonyl]pyrimidin-2-yl)-1-methyl-1H-pyrazole-4-carboxamide (450 mg, 1.25 mmol, 1.00 equiv) in hydrogen chloride/MeOH (10 mL). The resulting solution was stirred overnight at room temperature. The resulting mixture was concentrated under vacuum. This resulted in 200 mg (61%) of N-[4-(hydrazinecarbonyl)pyrimidin-2-yl]-1-methyl-1H-pyrazole-4-carboxamide as a yellow solid.

Part 6—Synthesis of N-(4-(5-((1H-indazol-5-yl) amino)-1,3,4-thiadiazol-2-yl)pyrimidin-2-yl)-1-methyl-1H-pyrazole-4-carboxamide

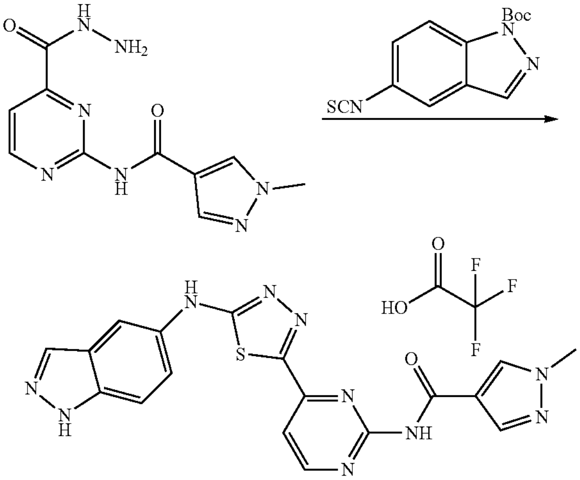

Into a 10-mL round-bottom flask was placed a solution of N-[4-(hydrazinecarbonyl)pyrimidin-2-yl]-1-methyl-1H-pyrazole-4-carboxamide (200 mg, 0.77 mmol, 1.00 equiv) in dichloromethane (5 mL), TEA (78 mg, 0.77 mmol, 1.00 equiv), and tert-butyl 5-isothiocyanato-1H-indazole-1-carboxylate (211 mg, 0.76 mmol, 1.00 equiv). The resulting solution was stirred overnight at room temperature then concentrated under vacuum. The residue was dissolved in 5 mL of concentrated sulfuric acid (98%). The resulting solution was stirred overnight at room temperature then poured into 100 mL of ice-water. The pH value of the solution was adjusted to 8 with sodium carbonate (aq). The solids were removed by filtration. The crude product was purified by Prep-HPLC with the following conditions (Prep-HPLC-007): Column, XBridge Prep C18 OBD Column, 5 um, 19*150 mm; mobile phase, water (0.05% TFA) and ACN (10.0% ACN up to 35.0% in 10 min); Detector, UV 254 nm. This resulted in 17 mg (4%) of N-(4-[5-[(1H-indazol-5-yl) amino]-1,3,4-thiadiazol-2-yl]pyrimidin-2-yl)-1-methyl-1H-pyrazole-4-carboxamide; trifluoroacetic acid solvate as a orange solid. (ES, m/z): $[M-TFA+H]^+$ 419.2. $^1H$ NMR (400 MHz, DMSO-$d_6$, ppm) δ 13.09 (s, 1H); 10.79 (s, 2H); 8.81 (d, J=5.2 Hz, 1H); 8.42 (s, 1H); 8.21 (d, J=1.6 Hz, 1H); 8.09 (s, 2H); 7.81 (d, J=4.8 Hz, 1H); 7.58 (d, J=8.8 Hz, 1H); 7.43-7.45 (m, 1H); 3.89 (s, 3H).

Example 67—Synthesis of 5-(2-Aminopyrimidin-4-yl)-N-(1H-indazol-5-yl)-1,3,4-thiadiazol-2-amine

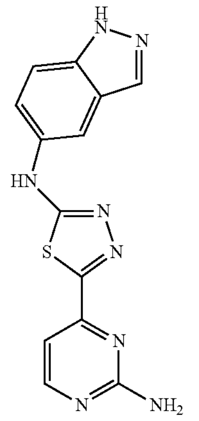 [SMILES: Nc1nccc(-c2nnc(Nc3ccc4[nH]ncc4c3)s2)n1]

The title compound was prepared based on procedures described in Example 66. Physical characterization data for the title compound is as follows: (ES, m/z): $[M+H]^+$ 311.1. $^1H$ NMR (400 MHz, DMSO-$d_6$, ppm) δ 13.10 (s, 1H); 8.37 (d, J=5.2 Hz, 1H); 8.21 (s, 1H); 8.07 (s, 1H); 7.56 (d, J=8.8 Hz, 1H); 7.41-7.44 (m, 1H); 7.22 (d, J=4.8 Hz, 1H); 6.91 (s, 2H).

Example 68—Synthesis of N-(6-(5-((1H-Indazol-5-yl)amino)-1,3,4-thiadiazol-2-yl)pyrazin-2-yl)-1-methyl-1H-pyrazole-4-carboxamide 2,2,2-trifluoroacetic Acid Solvate

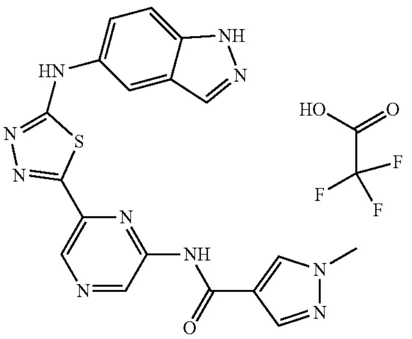

Part 1—Synthesis of Methyl 6-(1-methyl-1H-pyrazole-4-carboxamido)pyrazine-2-carboxylate

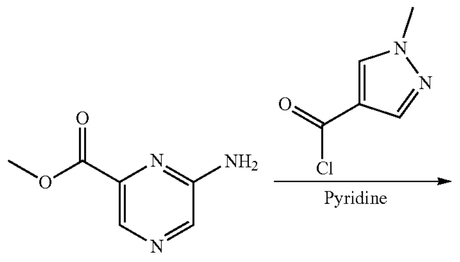

-continued

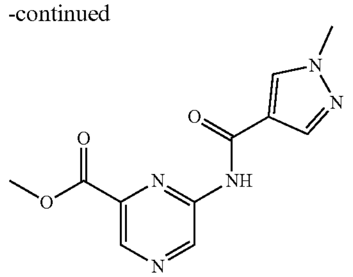

Into a 50-mL round-bottom flask was placed pyridine (25 mL), methyl 6-aminopyrazine-2-carboxylate (1 g, 6.53 mmol, 1.00 equiv) and 1-methyl-1H-pyrazole-4-carbonyl chloride (1.13 g, 7.82 mmol, 1.20 equiv). The resulting solution was stirred for 2 h at 25° C. in an oil bath. The resulting mixture was concentrated under vacuum at 55° C. for 1 h. This resulted in 1.72 g (93% purity) of methyl 6-(1-methyl-1H-pyrazole-4-amido)pyrazine-2-carboxylate as a yellow solid.

Part 2—Synthesis of N-(6-(hydrazinecarbonyl)pyrazin-2-yl)-1-methyl-1H-pyrazole-4-carboxamide

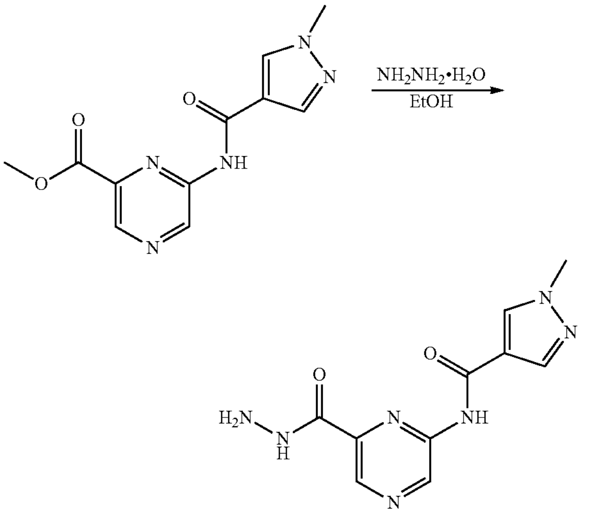

Into a 250-mL round-bottom flask was placed EtOH (60 mL), methyl 6-(1-methyl-1H-pyrazole-4-amido)pyrazine-2-carboxylate (1.7 g, 6.51 mmol, 1.00 equiv) and $NH_2NH_2.H_2O$ (8.2 g, 20.00 equiv). The resulting solution was stirred for 4 h at 78° C. in an oil bath. The reaction mixture was cooled to 0° C. with a water/ice bath. The solids were collected by filtration. The crude product was purified by re-crystallization from ethanol. This resulted in 700 mg (41%) of N-[6-(hydrazinecarbonyl)pyrazin-2-yl]-1-methyl-1H-pyrazole-4-carboxamide as an off-white solid.

Part 3—Synthesis of Tert-Butyl 5-(2-(6-(1-methyl-1H-pyrazole-4-carboxamido)pyrazine-2-carbonyl)hydrazine-1-carbothioamido)-1H-indazole-1-carboxylate

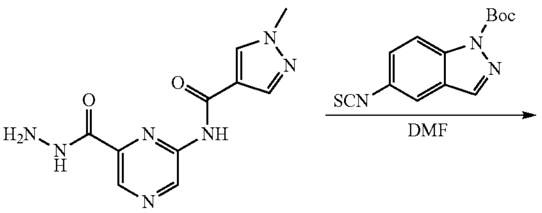

-continued

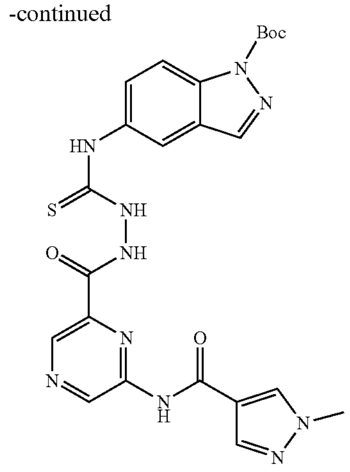

Into a 50-mL round-bottom flask was placed DMF (20 mL), N-[6-(hydrazinecarbonyl)pyrazin-2-yl]-1-methyl-1H-pyrazole-4-carboxamide (200 mg, 0.77 mmol, 1.00 equiv) and tert-butyl-5-isothiocyanato-1H-indazole-1-carboxylate (210 mg, 0.76 mmol, 1.00 equiv). The resulting solution was stirred for 4 h at 30° C. then concentrated under vacuum. This resulted in 416 mg (92% purity) of tert-butyl 5-[([[6-(1-methyl-1H-pyrazole-4-amido)pyrazin-2-yl]formohydrazido]methanethioyl)amino]-1H-indazole-1-carboxylate as an orange solid.

Part 4—Synthesis of N-(6-(5-((1H-indazol-5-yl)amino)-1,3,4-thiadiazol-2-yl)pyrazin-2-yl)-1-methyl-1H-pyrazole-4-carboxamide 2,2,2-trifluoroacetic Acid Solvate

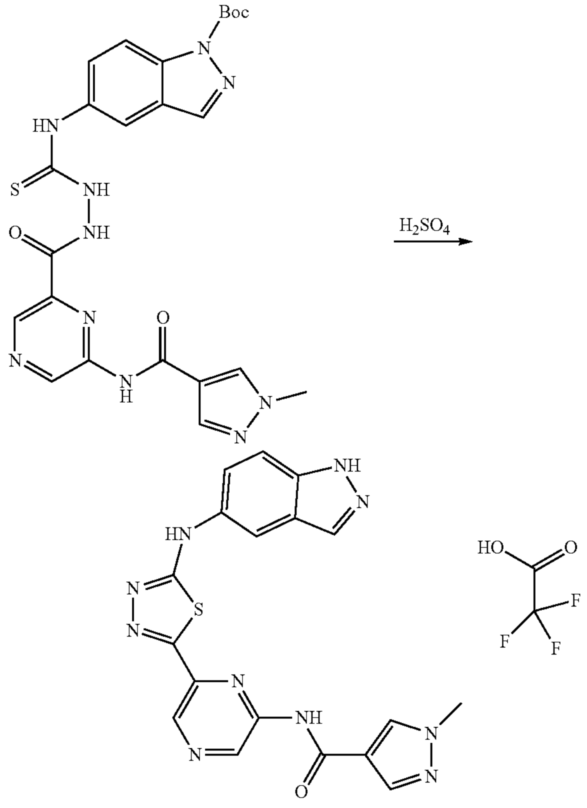

Into a 25-mL round-bottom flask was placed 2-N-[[(1H-indazol-5-yl)carbamothioyl]amino]-6-C-1-methyl-1H-pyrazole-4-pyrazine-2,6-dicarboxamide (200 mg, 0.46 mmol, 1.00 equiv). Sulfuric acid (10 mL) was added dropwise with stirring in a water/ice bath. The resulting suspension was stirred for 2 h at 30° C. The reaction was then quenched by pouring into 20 mL of crush ice. Solids precipitated and collected by filtration. The filter cake was washed with aq. $NaHCO_3$ and then purified by Prep-HPLC: Column: Gemini-NX 5u C18 110A, AXIA Packed 150×21.2 mm; Mobile Phase A: Water (0.05% TFA), Mobile Phase B: ACN; Gradient: 50% B to 80% B in 8 min; Detector, 254 nm. This resulted in 13.5 mg (6%) of N-(6-[5-[(1H-indazol-5-yl)amino]-1,3,4-thiadiazol-2-yl]pyrazin-2-yl)-1-methyl-1H-pyrazole-4-carboxamide trifluoroacetic acid solvate as an orange solid. (ES, m/z): $[M+H]^+$ 419.05. $^1H$ NMR (400 MHz, DMSO-$d_6$, ppm) δ 13.08 (br, s, 1H), 10.87 (s, 1H), 10.76 (s, 1H), 9.42 (s, 1H), 9.04 (s, 1H), 8.52 (s, 1H), 8.18-8.24 (m, 2H), 8.08 (s, 1H), 7.43-7.59 (m, 2H), 4.08 (s, 3H).

Example 69—Synthesis of 5-(6-Aminopyrazin-2-yl)-N-(1H-indazol-5-yl)-1,3,4-thiadiazol-2-amine

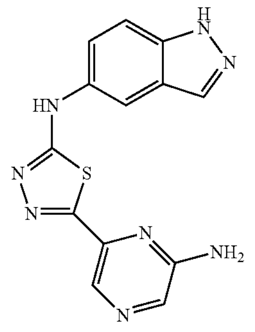 [SMILES: Nc1cncc(-c2nnc(Nc3ccc4[nH]ncc4c3)s2)n1]

The title compound was prepared based on procedures described in Example 68. Physical characterization data for the title compound is as follows: (ES, m/z): $[M+H]^+$311. $^1H$ NMR (400 MHz, DMSO-$d_6$) δ 13.03 (s, 1H), 10.58 (s, 1H), 8.41 (m, 2H), 8.22 (s, 1H), 8.06 (s, 1H), 7.91 (s, 1H), 7.56 (d, J=8.8 Hz, 1H), 7.41 (d, J=8 Hz, 1H), 6.79 (s, 1H).

Example 70—Synthesis of 5-(2-(4-Bromophenyl)-5,6,7,8-tetrahydroimidazo[1,2-a]pyridin-8-yl)-N-(4-chloro-1H-indazol-5-yl)-1,3,4-thiadiazol-2-amine

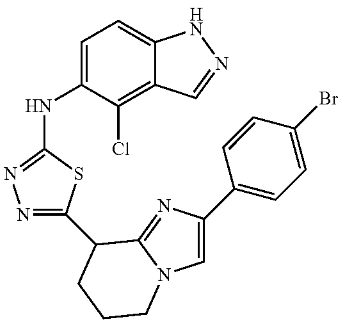 [SMILES: Clc1c(Nc2nnc(C3CCCn4cc(-c5ccc(Br)cc5)nc43)s2)ccc2[nH]ncc12]

Part 1—Synthesis of Methyl 2-(4-bromophenyl)-5,6,7,8-tetrahydroimidazo[1,2-a]pyridine-8-carboxylate

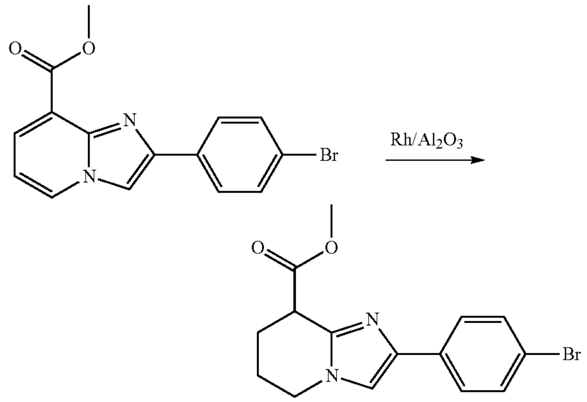

Into a 30-mL pressure tank reactor (0.5 MPa) purged and maintained with an inert atmosphere of hydrogen, was placed a solution of methyl 2-(4-bromophenyl)imidazo[1,2-a]pyridine-8-carboxylate (500 mg, 1.51 mmol, 1.00 equiv) in AcOH (15 mL), and Rh/$Al_2O_3$ (250 mg, 0.50 equiv). The resulting mixture was stirred overnight at room temperature. The solids were removed by filtration and filtrate was concentrated under vacuum. The resulting solution was diluted with 60 mL of DCM then washed with 2×30 mL of sodium bicarbonate (aq). The organic layer was dried over anhydrous sodium sulfate and concentrated under vacuum. This resulted in 380 mg (75%) of methyl 2-(4-bromophenyl)-5H,6H,7H,8H-imidazo[1,2-a]pyridine-8-carboxylate as a white solid.

Part 2—Synthesis of 2-(4-bromophenyl)-5,6,7,8-tetrahydroimidazo[1,2-a]pyridine-8-carbohydrazide

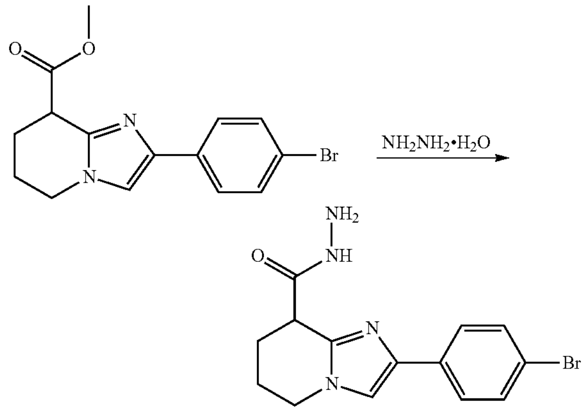

Into a 100-mL round-bottom flask, was placed a solution of methyl 2-(4-bromophenyl)-5H,6H,7H,8H-imidazo[1,2-a]pyridine-8-carboxylate (350 mg, 1.04 mmol, 1.00 equiv) in ethanol (12 mL), and $NH_2NH_2.H_2O$ (1.56 g, 30.00 equiv). The resulting solution was stirred overnight at room temperature then concentrated under vacuum. The crude product was purified by re-crystallization from ethanol. This resulted in 280 mg (80%) of 2-(4-bromophenyl)-5H,6H,7H,8H-imidazo[1,2-a]pyridine-8-carbohydrazide as a white solid.

Part 3—Synthesis of 5-(2-(4-bromophenyl)-5,6,7,8-tetrahydroimidazo[1,2-a]pyridin-8-yl)-N-(4-chloro-1H-indazol-5-yl)-1,3,4-thiadiazol-2-amine

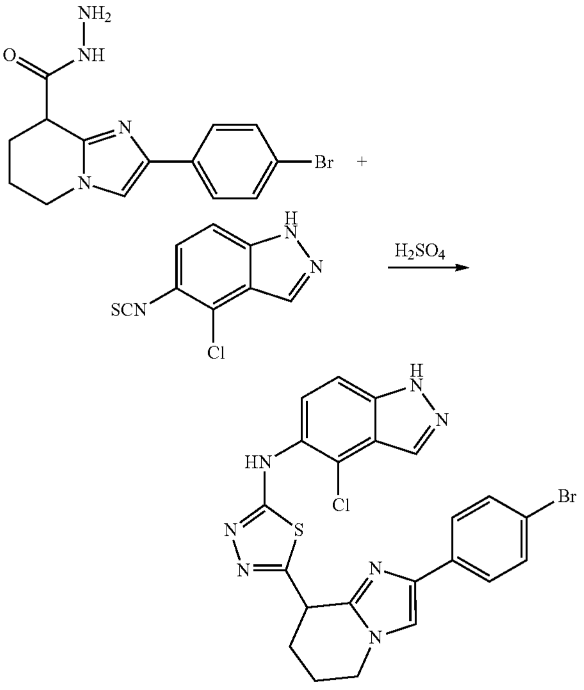

Into a 100-mL round-bottom flask, was placed a solution of 2-(4-bromophenyl)-5H,6H,7H,8H-imidazo[1,2-a]pyridine-8-carbohydrazide (150 mg, 0.45 mmol, 1.00 equiv) in dichloromethane (6 mL), and 4-chloro-5-thiocyanato-1H-indazole (100 mg, 0.48 mmol, 1.00 equiv). Concentrated sulfuric acid (1.32 g, 13.46 mmol, 30.00 equiv) was added dropwise with stirring at 0° C. The resulting solution was stirred for 1.5 days at room temperature. The reaction was then quenched by the addition of 30 mL of water/ice. The solids were collected by filtration. The crude product was purified by Prep-HPLC with the following conditions (2#-AnalyseHPLC-SHIMADZU(HPLC-10)): Column, XBridge Shield RP18 OBD Column, 5 um, 19*150 mm; mobile phase, Water (10 mM $NH_4HCO_3$) and ACN (40.0% ACN up to 55.0% in 8 min); Detector, UV 220 nm. This resulted in 82.6 mg (35%) of N-[5-[2-(4-bromophenyl)-5H,6H,7H,8H-imidazo[1,2-a]pyridin-8-yl]-1,3,4-thiadiazol-2-yl]-4-chloro-1H-indazol-5-amine as a pink solid. (ES, m/z): [M+1] 526. $^1$H NMR (400 MHz, DMSO-$d_6$ ppm) δ 13.39 (s, 1H), 9.69 (s, 1H), 8.09 (s, 1H), 7.88-7.85 (m, 1H), 7.68-7.64 (m, 3H), 7.55-7.49 (m, 3H), 4.61-4.57 (m, 1H), 4.07-4.03 (m, 2H), 2.33-2.21 (m, 2H), 2.07-2.05 (m, 2H).

Example 71—Synthesis of Additional N-(1H-Indazol-5-yl)-1,3,4-thiadiazol-2-amine Compounds The compounds in Table 14 were prepared based on procedures described in Example 70.

TABLE 14
| Example No. | Chemical Structure | Physical Characterization Data |
|---|---|---|
| 71A | 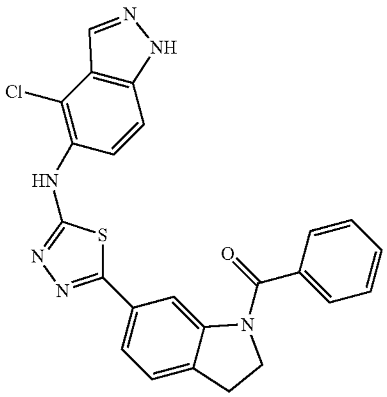 [SMILES: O=C(c1ccccc1)N1CCc2ccc(-c3nnc(Nc4ccc5[nH]ncc5c4Cl)s3)cc21] | (ES, m/z): [M + H]+ 472.1. $^1$H NMR (400 MHz, DMSO-$d_6$ ppm) δ 8.12 (d, J = 1.0 Hz, 1H), 7.84 (d, J = 8.9 Hz, 1H), 7.66 – 7.31 (m, 9H), 4.04 (t, J = 8.2 Hz, 2H), 3.11 (t, J = 8.3 Hz, 2H). |
| 71B | 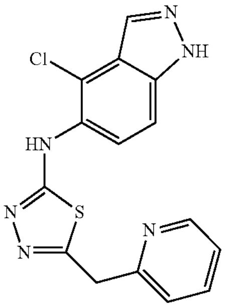 [SMILES: Clc1c(Nc2nnc(Cc3ccccn3)s2)ccc2[nH]ncc12] | (ES, m/z): [M + H]+ 345. $^1$H NMR (400 MHz, DMSO-$d_6$ ppm) δ 13.41 (br s, 1H), 9.65 (br s, 1H), 8.54 – 8.52 (m, 1H), 8.09 (s, 1H), 7.81 – 7.27 (m, 5H), 4.38 (s, 2H). |
| 71C | 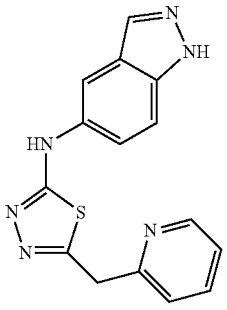 [SMILES: c1ccc(Cc2nnc(Nc3ccc4[nH]ncc4c3)s2)nc1] | (ES, m/z): [M + H]+ 309. $^1$H NMR (400 MHz, DMSO-$d_6$ ppm) δ 12.96 (s, 1H), 10.15 (s, 1H), 8.56 – 8.54 (m, 1H), 8.18 (s, lH), 8.02 (s, 1H), 7.81 – 776 (m, 1H), 7.51 – 7.28 (m, 4H), 7.21 (br s, 1H), 4.43 (s, 2H). |
| 71D | 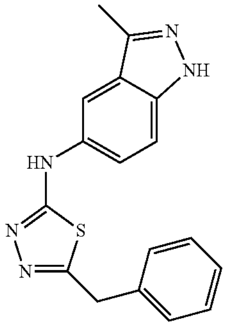 [SMILES: Cc1n[nH]c2ccc(Nc3nnc(Cc4ccccc4)s3)cc12] | (ES, m/z): [M + H]+ 322. $^1$H NMR (400 MHz, DMSO-$d_6$ ppm) δ 11.50 (br s, 1H), 10.08 (br s, 1H), 8.08 (s, 1H), 7.56 (s, 1H), 7.43 – 7.25 (m, 7H), 4.26 (s, 2H), 2.46 (s, 3H). |

TABLE 14-continued
| Example No. | Chemical Structure | Physical Characterization Data |
|---|---|---|
| 71E | 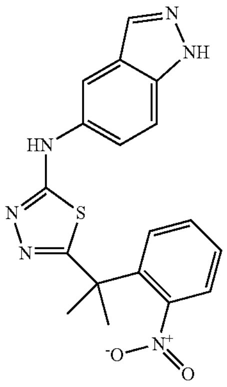 | (ES, m/z): $[M + H]^+$ 381. $^1H$ NMR (400 MHz, DMSO-$d_6$ ppm) δ 12.98 (s, 1H), 10.31 (s, 1H), 10.22 (s, 1H), 8.13 (s, 1H), 8.06 - 7.32 (m, 7H), 1.83 (s, 6H). |
| 71F | 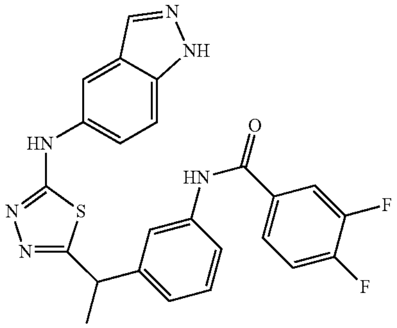 [SMILES: CC(c1cccc(NC(=O)c2ccc(F)c(F)c2)c1)c1nnc(Nc2ccc3[nH]ncc3c2)s1] | (ES, m/z): $[M + H]^+$ 477. $^1H$ NMR (400 MHz, DMSO-$d_6$ ppm) δ 12.97 (s, 1H), 10.32 (s, 1H), 10.18 (s, 1H), 8.15 (s, 1H), 8.06 - 7.11 (m, 11H), 4.50 (q, 1H), 1.68 (d, 3H). |
| 71G | 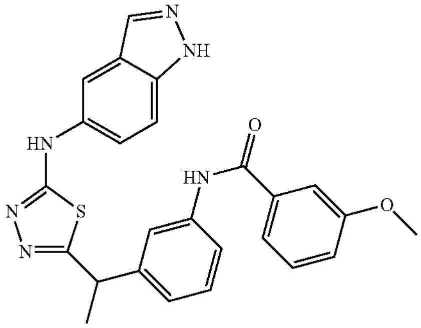 [SMILES: COc1cccc(C(=O)Nc2cccc(C(C)c3nnc(Nc4ccc5[nH]ncc5c4)s3)c2)c1] | (ES, m/z): $[M + H]^+$ 471. $^1H$ NMR (400 MHz, DMSO-$d_6$ ppm) δ 12.96 (s, 1H), 10.23 (s, 1H), 10.17 (s, 1H), 8.15 (s, 1H), 7.76 (s, 1H), 7.73 - 7.09 (m, 9H), 4.48 (q, 1H), 3.83 (s, 3H), 1.68 (d, 3H). |
| 71H | 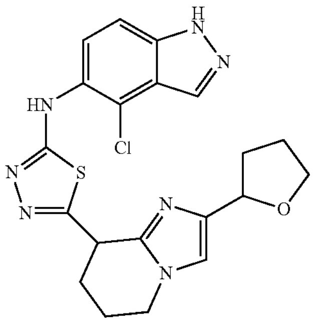 [SMILES: Clc1c(Nc2nnc(C3CCCn4cc(C5CCCO5)nc43)s2)ccc2[nH]ncc12] | (ES, m/z): $[M + H]^+$ 443. $^1H$ NMR (400 MHz, DMSO-$d_6$) δ 3.43 (s, 1H), 9.65 (s, 1H), 8.07 (s, 1H), 7.82 (d, J = 8, 1H), 7.52 (d, J = 8.8, 1H), 6.94 (s, 1H), 4.68 - 4.64 (m, 1H), 4.48 - 4.45 (m, 1H), 3.94 (d, J = 5.2, 2H), 3.80 - 3.76 (m, 1H), 3.66 - 3.62 (m, 1H), 2.29 - 2.27 (m, 1H), 2.17 - 2.10 (m, 1H), 2.04 - 1.94 (m, 3H), 1.92 - 1.81 (m, 3H). |

TABLE 14-continued
| Example No. | Chemical Structure | Physical Characterization Data |
| --- | --- | --- |
| 71I | 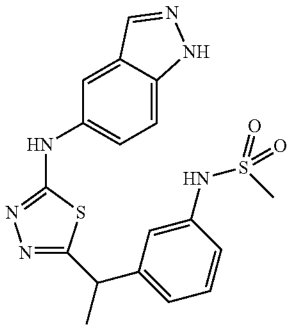 [SMILES: CC(c1cccc(NS(C)(=O)=O)c1)c1nnc(Nc2ccc3[nH]ncc3c2)s1] | (ES, m/z): $[M + H]^+$ 415. $^1H$ NMR (400 MHz, DMSO-$d_6$ ppm) δ 10.18 (br s, 1H), 9.76 (s, 1H), 8.14 (s, 1H), 8.01 (s, 1H), 7.51 – 7.08 (m, 6H), 4.48 (q, 1H). 2.98 (s, 3H), 1.65 (d, 3H). |
| 71J | 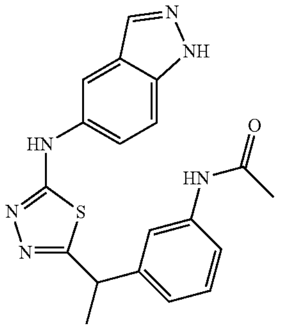 [SMILES: CC(=O)Nc1cccc(C(C)c2nnc(Nc3ccc4[nH]ncc4c3)s2)c1] | (ES, m/z): $[M + H]^+$ 379. $^1H$ NMR (400 MHz, DMSO-$d_6$ ppm) δ 12.96 (s, 1H), 10.16 (s, 1H), 9.94 (s, 1H), 8.15 (s, 1H), 7.54 – 7.48 (m, 3H), 7.34 – 7.24 (m, 2H), 7.02 (d, 1H), 4.45 (q, 1H), 2.01 (s, 3H), 1.64 (d, 3H). |
| 71K | 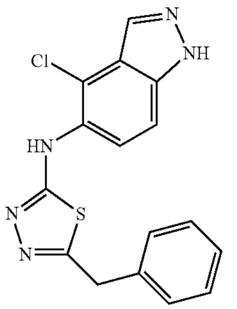 [SMILES: Clc1c(Nc2nnc(Cc3ccccc3)s2)ccc2[nH]ncc12] | (ES, m/z): $[M + H]^+$ 344. $^1H$ NMR (400 MHz, DMSO-$d_6$) δ 13.40 (s, 1H), 9.68 (s, 1H), 8.09 (s, 1H), 7.80 – 7.78 (m, 1H), 7.55 – 7.24 (m, 5H), 4.22 (s, 2H) |
| 71L | 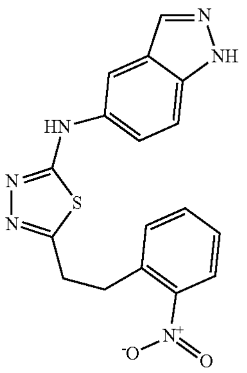 | (ES, m/z): $[M + H]^+$ 367. $^1H$ NMR (400 MHz, DMSO-$d_6$) δ 12.96 (s, 1H), 10.19 (s, 1H), 8.18 (s, 1H), 8.02 – 7.96 (m, 2H), 7.70 – 7.32 (m, 5H), 3.27 (s, 4H). |

TABLE 14-continued
| Example No. | Chemical Structure | Physical Characterization Data |
| --- | --- | --- |
| 71M | 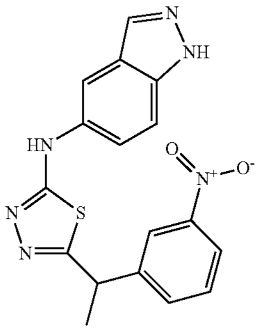 [SMILES: CC(c1cccc([N+](=O)[O-])c1)c1nnc(Nc2ccc3[nH]ncc3c2)s1] | (ES, m/z): [M + H]+ 367. $^1$H NMR (400 MHz, DMSO-$d_6$) δ 12.98 (s, 1H), 10.23 (s, 1H), 8.23 – 8.13 (m, 3H), 8.01 (s, 1H), 7.84 (d, 1H), 7.67 (t, 1H), 7.49 (d, 1H), 7.34 – 7.31 (m, 1H), 7.09 – 6.81 (m, 2H), 4.77 (q, 1H), 1.72 (d, 3H) |
| 71N | 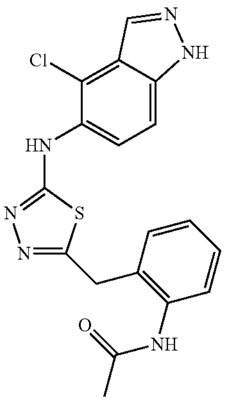 [SMILES: CC(=O)Nc1ccccc1Cc1nnc(Nc2ccc3[nH]ncc3c2Cl)s1] | (ES, m/z): [M + H]+ 401. $^1$H NMR (400 MHz, DMSO-$d_6$, ppm) δ 13.40 (s, 1H), 9.66 (s, 1H), 9.53 (s, 1H), 8.08 (s, 1H), 7.82 – 7.78 (m, 1H), 7.54 (d, 1H), 7.40 – 7.13 (m, 4H), 4.23 (s, 2H), 2.03 (s, 3H) |
| 71O | 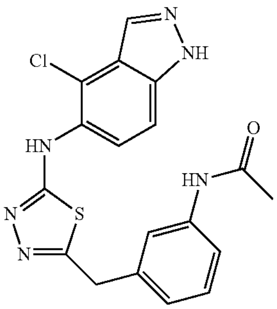 [SMILES: CC(=O)Nc1cccc(Cc2nnc(Nc3ccc4[nH]ncc4c3Cl)s2)c1] | (ES, m/z): [M + H]+ 401. $^1$H NMR (400 MHz, DMSO-$d_6$, ppm) δ 13.41 (br s, H), 9.93 (br s, 1H), 9.69 (br s, 1H), 8.09 (s, 1H), 7.82 – 7.79 (m, 1H), 7.55 – 7.48 (m, 3H), 7.26 – 7.22 (m, 1H), 6.98 – 6.95 (m, 1H), 4.18 (s, 2H), 2.01 (s, 3H) |
| 71P | 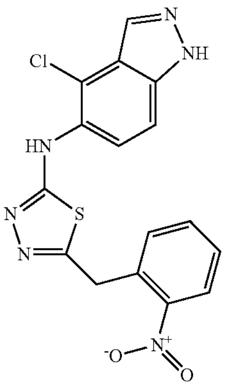 | (ES, m/z): [M + H]+ 389. $^1$H NMR (400 MHz, DMSO-$d_6$, ppm) δ 13.40 (br s, 1H), 9.73 (br s, 1H), 8.10 – 8.04 (m, 2H), 7.81 – 7.71 (m, 2H), 7.62 – 7.52 (m, 3H), 4.55 (s, 2H) |

TABLE 14-continued

| Example No. | Chemical Structure | Physical Characterization Data |
|---|---|---|
| 71Q | 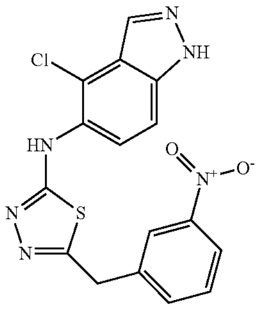 [SMILES: O=[N+]([O-])c1cccc(Cc2nnc(Nc3ccc4[nH]ncc4c3Cl)s2)c1] | (ES, m/z): $[M + H]^+$ 389. $^1H$ NMR (400 MHz, DMSO-$d_6$, ppm) δ 13.40 (br s, 1H), 9.74 (br s, 1H), 8.23 - 8.22 (m, 1H), 8.15 - 8.10 (m, 2H), 7.81 - 7.75 (m, 2H), 7.67 - 7.53 (m, 2H), 4.43 (s, 2H) |

Example 72—Synthesis of N-(4-Chloro-1H-indazol-5-yl)-5-(2-phenyl-5,6,7,8-tetrahydroimidazo[1,2-a]pyridin-8-yl)-1,3,4-thiadiazol-2-amine

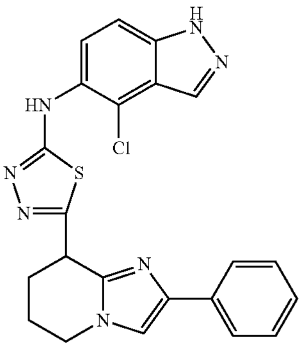 [SMILES: Clc1c(Nc2nnc(C3CCCn4cc(-c5ccccc5)nc43)s2)ccc2[nH]ncc12]

Part 1—Synthesis of Methyl 2-phenylimidazo[1,2-a]pyridine-8-carboxylate

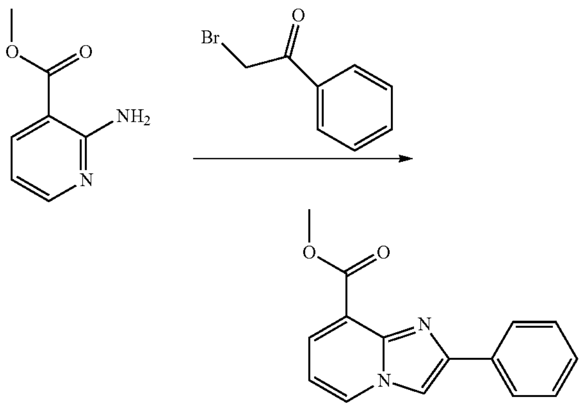

Into a 250-mL round-bottom flask, was placed methyl 2-aminopyridine-3-carboxylate (1 g, 6.57 mmol, 1.00 equiv), 2-butanone (80 mL), and 2-bromo-1-phenylethan-1-one (1.5 g, 7.54 mmol, 1.10 equiv). The resulting solution was stirred overnight at 85° C. then concentrated under vacuum. The residue was applied onto a silica gel column and eluted with ethyl acetate/petroleum ether (1:3). This resulted in 1.1 g (66%) of methyl 2-phenylimidazo[1,2-a]pyridine-8-carboxylate as a light brown solid.

Part 2—Synthesis of Methyl 2-phenyl-5,6,7,8-tetrahydroimidazo[1,2-a]pyridine-8-carboxylate

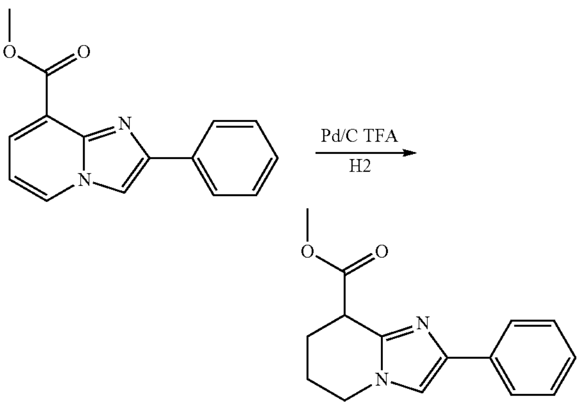

Into a 50-mL pressure tank reactor, was placed methyl 2-phenylimidazo[1,2-a]pyridine-8-carboxylate (1100 mg, 4.36 mmol, 1.00 equiv), methanol (8 mL), palladium on carbon (700 mg), and acetic acid (0.2 mL). The reaction mixture was exposed to 5 atmospheres of hydrogen and stirred overnight at 60° C. The solids were removed by filtration and the filtrate was concentrated under vacuum. This resulted in 900 mg (81%) of methyl 2-phenyl-5,6,7,8-imidazo[1,2-a]pyridine-8-carboxylate as a yellow solid.

Part 3—Synthesis of 2-phenyl-5,6,7,8-tetrahydroimidazo[1,2-a]pyridine-8-carbohydrazide

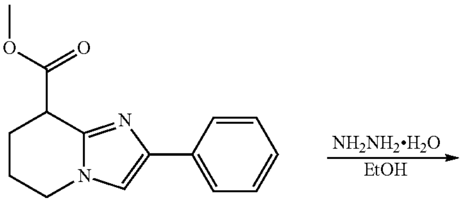

-continued

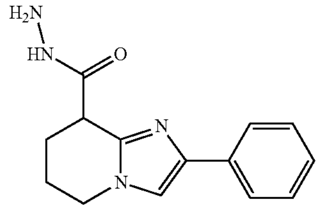

Into a 100-mL round-bottom flask, was placed methyl 2-phenyl-5H,6H,7H,8H-imidazo[1,2-a]pyridine-8-carboxylate (600 mg, 2.34 mmol, 1.00 equiv), ethanol (20 mL), and hydrazine hyrate (1.2 g, 10.00 equiv). The resulting solution was stirred overnight at 90° C. then concentrated under vacuum. This resulted in 468 mg (78%) of 2-phenyl-5H,6H,7H,8H-imidazo[1,2-a]pyridine-8-carbohydrazide as a yellow solid.

Part 4—Synthesis of N-(4-chloro-1H-indazol-5-yl)-2-(2-phenyl-5,6,7,8-tetrahydroimidazo[1,2-a]pyridine-8-carbonyl)hydrazine-1-carbothioamide

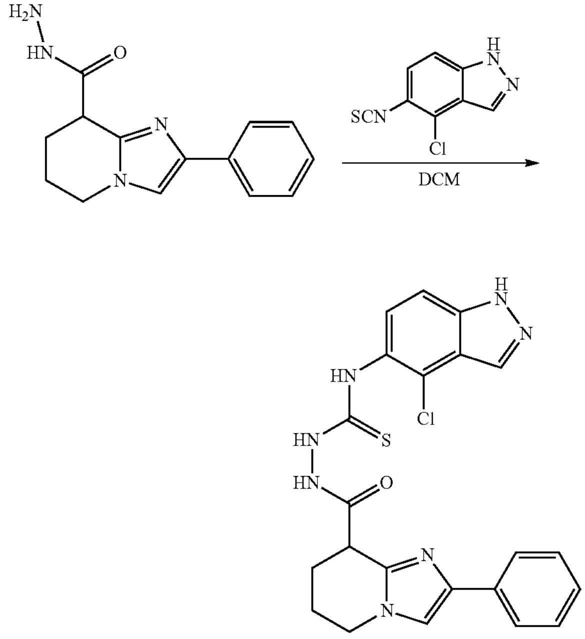

Into a 100-mL round-bottom flask, was placed 2-phenyl-5H,6H,7H,8H-imidazo[1,2-a]pyridine-8-carbohydrazide (200 mg, 0.78 mmol, 1.00 equiv), dichloromethane (20 mL), and 4-chloro-5-thiocyanato-1H-indazole (163.6 mg, 0.78 mmol, 1.00 equiv). The resulting solution was stirred overnight at room temperature then concentrated under vacuum. This resulted in 267 mg (73%) of N-[[(4-chloro-1H-indazol-5-yl)carbamothioyl]amino]-2-phenyl-5H,6H,7H,8H-imidazo[1,2-a]pyridine-8-carboxamide as a yellow solid.

Part 5—Synthesis of N-(4-chloro-1H-indazol-5-yl)-5-(2-phenyl-5,6,7,8-tetrahydroimidazo[1,2-a]pyridin-8-yl)-1,3,4-thiadiazol-2-amine

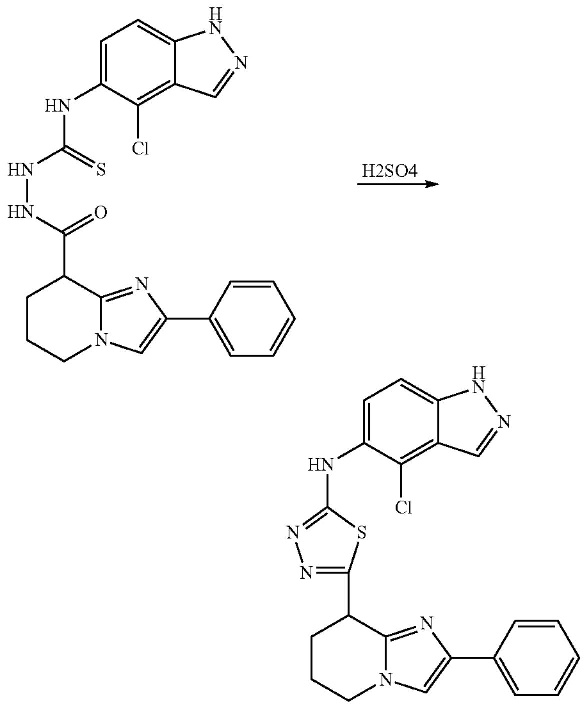

Into a 100-mL round-bottom flask, was placed N-[[(4-chloro-1H-indazol-5-yl)carbamothioyl]amino]-2-phenyl-5H,6H,7H,8H-imidazo[1,2-a]pyridine-8-carboxamide (200 mg, 0.43 mmol, 1.00 equiv), and concentrated sulfuric acid (1 g, 10.20 mmol, 23.75 equiv). The resulting solution was stirred for 2 h at room temperature then concentrated under vacuum. The crude product was purified by Prep-HPLC. This resulted in 18.8 mg (10%) of 4-chloro-N-(5-[2-phenyl-5H,6H,7H,8H-imidazo[1,2-a]pyridin-8-yl]-1,3,4-thiadiazol-2-yl)-1H-indazol-5-amine as a off-white solid. (ES, m/z): $[M+H]^+448$. $^1H$ NMR (400 MHz, DMSO-$d_6$, ppm) δ 8.07 (s, 1H), 7.83 (s, J=9.2 Hz, 1H), 7.69 (d, J=7.2 Hz, 2H), 7.53 (t, J=17.2 Hz, 1H), 7.31 (t, J=15.2 Hz, 2H), 7.17 (d, J=7.2 Hz, 1H), 4.58 (t, J=13.6 Hz, 1H), 4.04 (t, J=12. Hz, 2H), 2.31 (t, J=2.0 Hz, 1H), 2.25 (s, 1H), 2.04 (t, J=6.0 Hz, 2H).

Example 73—Synthesis of N-((1S,3R)-3-(5-((4-Chloro-1H-indazol-5-yl)amino)-1,3,4-thiadiazol-2-yl)cyclopentyl)acetamide 2,2,2-trifluoroacetic Acid Solvate

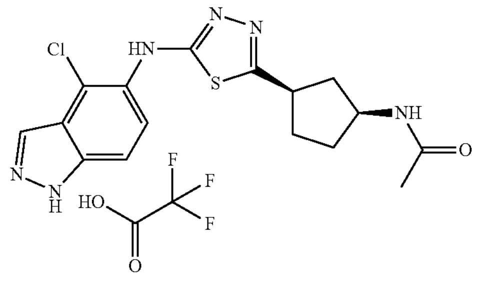

Part 1—Synthesis of Methyl (1R,3S)-3-aminocyclopentane-1-carboxylate

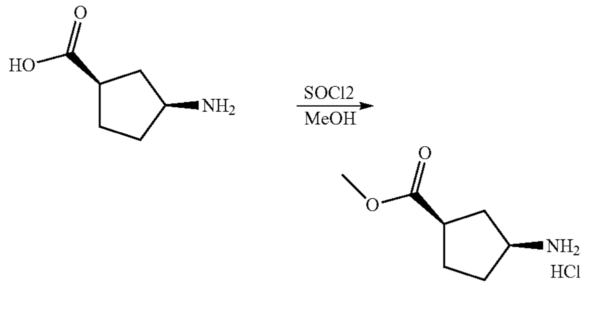

Into a 100-mL round-bottom flask, was placed a solution of (1R,3S)-3-aminocyclopentane-1-carboxylic acid (500 mg, 3.87 mmol, 1.00 equiv) in methanol (10 mL). This was followed by the addition of sulfuryl dichloride (921 mg, 7.74 mmol, 2.00 equiv) dropwise with stirring at 0° C. The resulting solution was stirred overnight at 70° C. then concentrated under vacuum. This resulted in 500 mg (90%) of methyl (1R,3S)-3-aminocyclopentane-1-carboxylate hydrochloride as colorless oil.

Part 2—Synthesis of Methyl (1R,3S)-3-acetamidocyclopentane-1-carboxylate

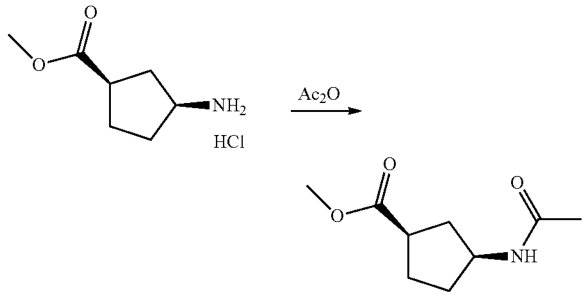

Into a 100-mL round-bottom flask, was placed a solution of methyl (1R,3S)-3-aminocyclopentane-1-carboxylate hydrochloride (500 mg, 3.49 mmol, 1.00 equiv) in dichloromethane (10 mL), triethylamine (1058 mg, 10.46 mmol, 3.00 equiv), and acetic anhydride (535 mg, 5.24 mmol, 1.50 equiv). The resulting solution was stirred overnight at room temperature then washed with 3x10 mL of water. The organic layer was dried over anhydrous sodium sulfate and concentrated under vacuum. This resulted in 500 mg (77%) of methyl (1R,3S)-3-acetamidocyclopentane-1-carboxylate as colorless oil.

Part 3—Synthesis of N-((1S,3R)-3-(hydrazinecarbonyl)cyclopentyl)acetamide

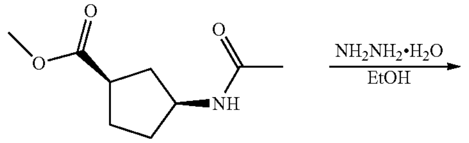

-continued

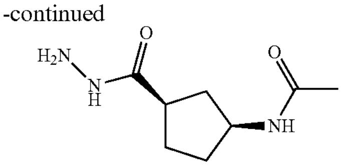

Into a 100-mL round-bottom flask, was placed a solution of methyl (1S,3R)-3-acetamidocyclopentane-1-carboxylate (500 mg, 2.70 mmol, 1.00 equiv) in ethanol (10 mL), and hydrazine hydrate (2 mL). The resulting solution was stirred overnight at 80° C. The resulting mixture was concentrated under vacuum. This resulted in 450 mg (90%) of N-[(1R,3S)-3-(hydrazinecarbonyl)cyclopentyl]acetamide as a white solid.

Part 4—Synthesis of N-((1S,3R)-3-(5-((4-chloro-1H-indazol-5-yl)amino)-1,3,4-thiadiazol-2-yl)cyclopentyl)acetamide 2,2,2-trifluoroacetic Acid Solvate

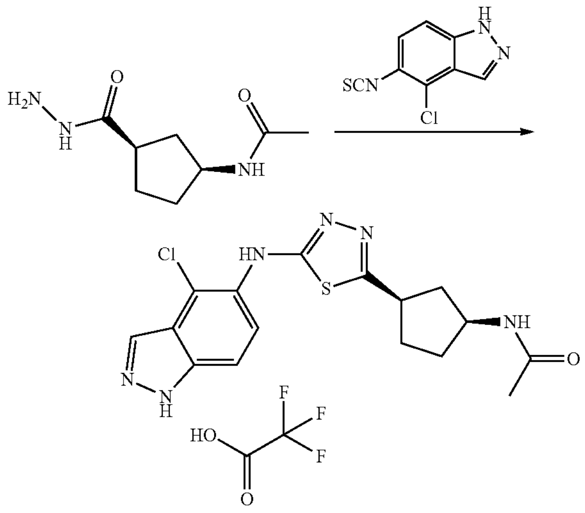

Into a 100-mL round-bottom flask, was placed a solution of N-[(1R,3S)-3-(hydrazinecarbonyl)cyclopentyl]acetamide (300 mg, 1.62 mmol, 1.00 equiv) in dichloromethane (10 mL), and 4-chloro-5-isothiocyanato-1H-indazole (340 mg, 1.62 mmol, 1.00 equiv). The resulting solution was stirred overnight at room temperature then concentrated under vacuum. The residue was dissolved in 3 mL of concentrate sulfuric acid, stirred overnight at room temperature then poured into ice-water (30 mL). The pH value of the solution was adjusted to 8 with sodium carbonate (aq). The resulting solution was extracted with 3x150 mL of ethyl acetate and the organic layers combined and dried over anhydrous sodium sulfate and concentrated under vacuum. The crude product was purified by Prep-HPLC with the following conditions (2#-AnalyseHPLC-SHIMADZU(HPLC-10)): Column, XBridge C18 OBD Prep Column, 100� 5 μm, 19 mmx250 mm; mobile phase, Water (0.05% TFA) and ACN (30.0% ACN up to 37.0% in 5 min); Detector, UV 254 nm. This resulted in 150 mg (19%) of N-[(1R,3S)-3-[5-[(4-chloro-1H-indazol-5-yl)amino]-1,3,4-thiadiazol-2-yl]cyclopentyl]acetamide trifluoroacetic acid solvate as a white solid. (ES, m/z): $[M-TFA+H]^+$377.00. $^1H$ NMR (400 MHz, DMSO-$d_6$, ppm) δ 8.11 (s, 1H), 7.94 (d, J=7.2 Hz, 1H), 7.79 (d, J=8.8 Hz, 1H), 7.54-7.57 (m, 1H), 4.07-4.13 (m, 1H), 3.34-3.39 (m, 1H), 2.54 (s, 0.3H), 2.33-2.39 (m, 1H), 2.03-2.06 (m, 1H), 1.80-1.94 (m, 2.4H), 1.77 (s, 3H), 1.51-1.66 (m, 2.3H).

Example 74—Synthesis of N-((1S,3R)-3-(5-((4-Chloro-1H-indazol-5-yl)amino)-1,3,4-thiadiazol-2-yl)cyclohexyl)acetamide

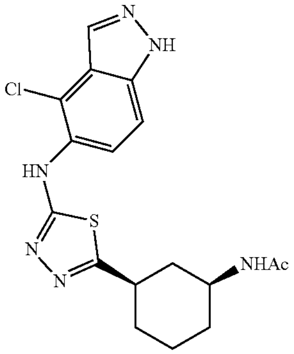 [SMILES: CC(=O)N[C@H]1CCC[C@@H](c2nnc(Nc3ccc4[nH]ncc4c3Cl)s2)C1]

The title compound was prepared based on procedures described in Example 73. Physical characterization data for the title compound is as follows: (ES, m/z): $[M+H]^+$ 391. $^1H$ NMR (400 MHz, DMSO-$d_6$) δ 13.47 (s, 1H); 9.67 (s, 1H), 8.11 (s 1H), 7.83-7.80 (m, 2H), 7.57-7.54 (m, 1H), 3.70-3.61 (m, 1H), 3.34 (s, 1H), 3.07-2.30 (m, 1H), 2.51-2.50 (m, 1H), 2.14-2.11 (m, 1H), 1.98-1.78 (m, 5H), 1.48-1.07 (m, 4H).

Example 75—Synthesis of Additional Compounds

The compounds in Table 15 were prepared based on procedures described herein.

TABLE 15

| Example No. | Chemical Structure |
|---|---|
| 75A | 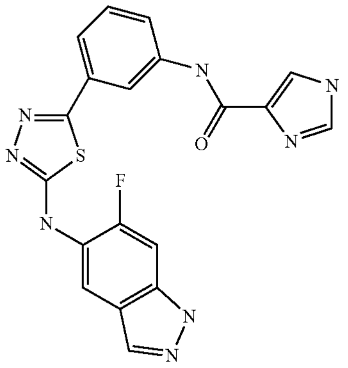 [SMILES: O=C(Nc1cccc(-c2nnc(Nc3cc4cn[nH]c4cc3F)s2)c1)c1c[nH]cn1] |

TABLE 15-continued

| Example No. | Chemical Structure |
|---|---|
| 75B | 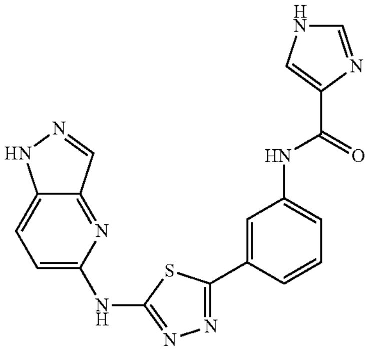 [SMILES: O=C(Nc1cccc(-c2nnc(Nc3ccc4[nH]ncc4n3)s2)c1)c1c[nH]cn1] |
| 75C | 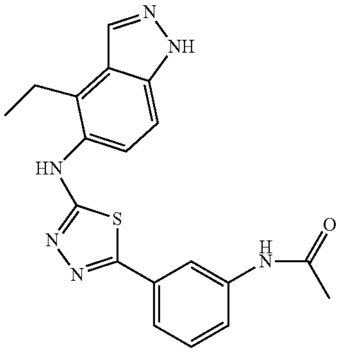 [SMILES: CCc1c(Nc2nnc(-c3cccc(NC(C)=O)c3)s2)ccc2[nH]ncc12] |
| 75D | 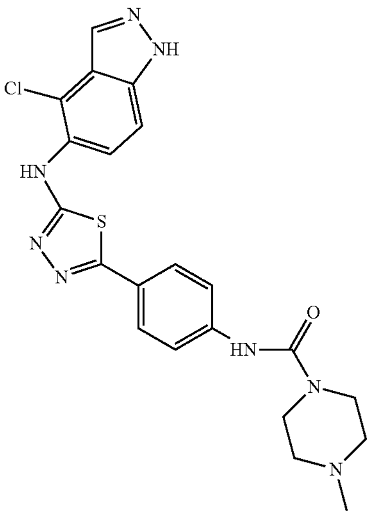 [SMILES: CN1CCN(C(=O)Nc2ccc(-c3nnc(Nc4ccc5[nH]ncc5c4Cl)s3)cc2)CC1] |
| 75E | 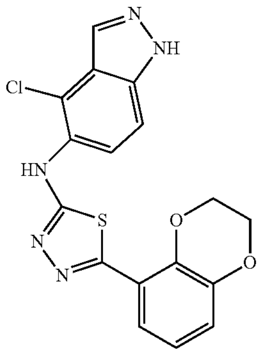 [SMILES: Clc1c(Nc2nnc(-c3cccc4c3OCCO4)s2)ccc2[nH]ncc12] |

TABLE 15-continued
| Example No. | Chemical Structure |
| --- | --- |
| 75F | 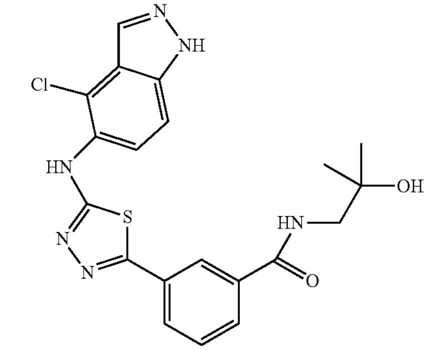 [SMILES: CC(C)(O)CNC(=O)c1cccc(-c2nnc(Nc3ccc4[nH]ncc4c3Cl)s2)c1] |
| 75G | 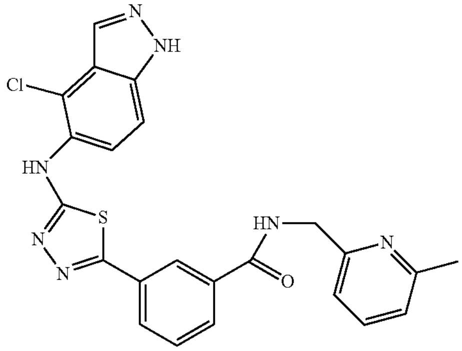 [SMILES: Cc1cccc(CNC(=O)c2cccc(-c3nnc(Nc4ccc5[nH]ncc5c4Cl)s3)c2)n1] |
| 75H | 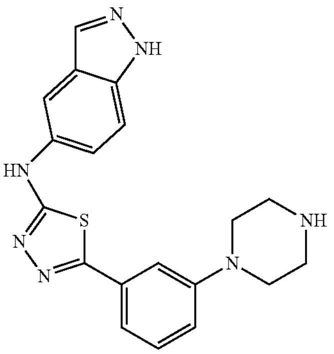 [SMILES: c1cc(-c2nnc(Nc3ccc4[nH]ncc4c3)s2)cc(N2CCNCC2)c1] |
| 75I | 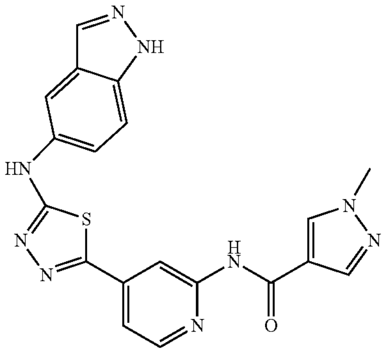 [SMILES: Cn1cc(C(=O)Nc2cc(-c3nnc(Nc4ccc5[nH]ncc5c4)s3)ccn2)cn1] |
TABLE 15-continued
| Example No. | Chemical Structure |
| --- | --- |
| 75J | 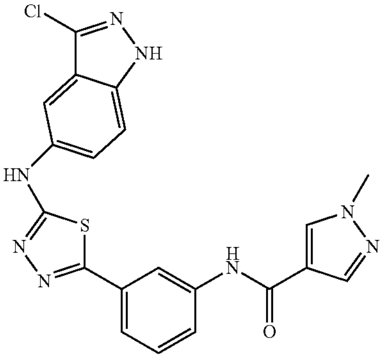 [SMILES: Cn1cc(C(=O)Nc2cccc(-c3nnc(Nc4ccc5[nH]nc(Cl)c5c4)s3)c2)cn1] |
| 75K | 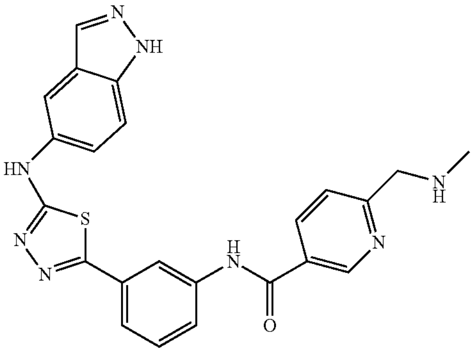 [SMILES: CNCc1ccc(C(=O)Nc2cccc(-c3nnc(Nc4ccc5[nH]ncc5c4)s3)c2)cn1] |
| 75L | 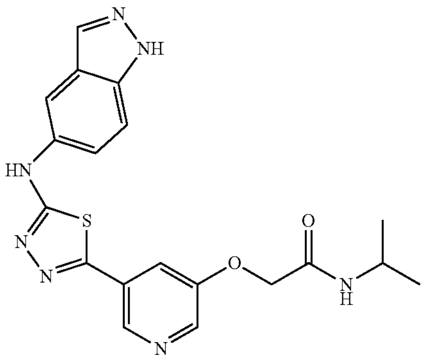 [SMILES: CC(C)NC(=O)COc1cncc(-c2nnc(Nc3ccc4[nH]ncc4c3)s2)c1] |
| 75M | 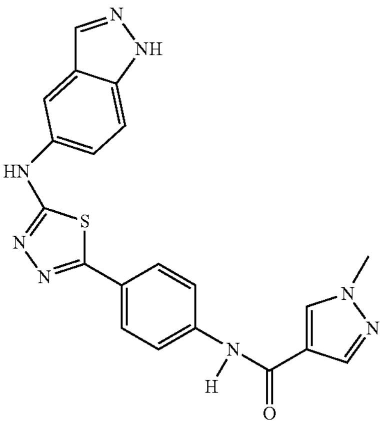 [SMILES: Cn1cc(C(=O)Nc2ccc(-c3nnc(Nc4ccc5[nH]ncc5c4)s3)cc2)cn1] |

TABLE 15-continued
| Example No. | Chemical Structure |
|---|---|
| 75N | 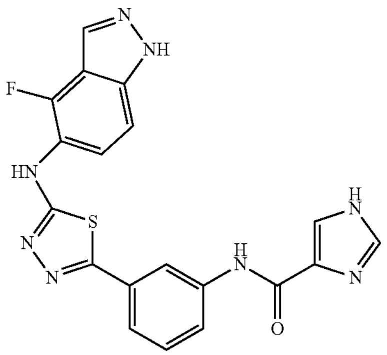 [SMILES: O=C(Nc1cccc(-c2nnc(Nc3ccc4[nH]ncc4c3F)s2)c1)c1c[nH]cn1] |
| 75O | 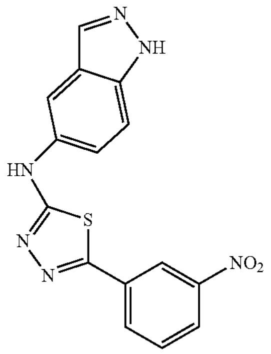 [SMILES: O=[N+]([O-])c1cccc(-c2nnc(Nc3ccc4[nH]ncc4c3)s2)c1] |
| 75P | 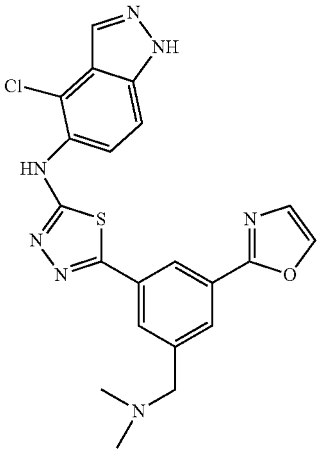 [SMILES: CN(C)Cc1cc(-c2ncco2)cc(-c2nnc(Nc3ccc4[nH]ncc4c3Cl)s2)c1] |
| 75Q | 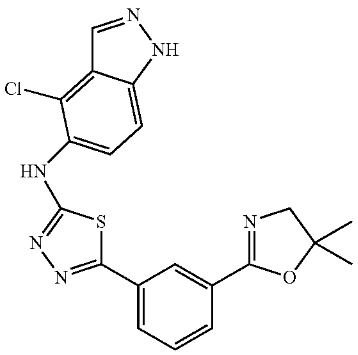 [SMILES: CC1(C)CN=C(c2cccc(-c3nnc(Nc4ccc5[nH]ncc5c4Cl)s3)c2)O1] |
TABLE 15-continued
| Example No. | Chemical Structure |
|---|---|
| 75R | 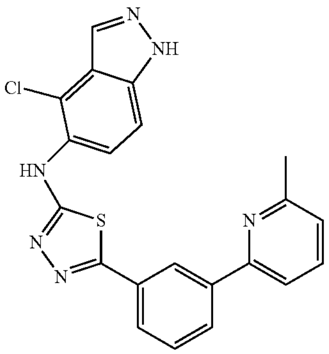 [SMILES: Cc1cccc(-c2cccc(-c3nnc(Nc4ccc5[nH]ncc5c4Cl)s3)c2)n1] |
| 75S | 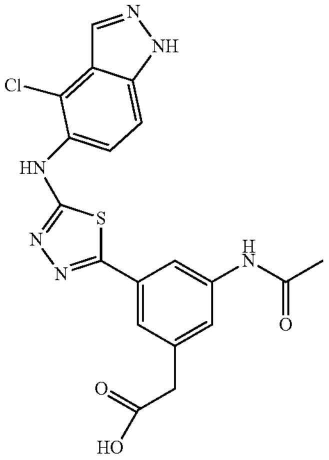 [SMILES: CC(=O)Nc1cc(CC(=O)O)cc(-c2nnc(Nc3ccc4[nH]ncc4c3Cl)s2)c1] |
| 75T | 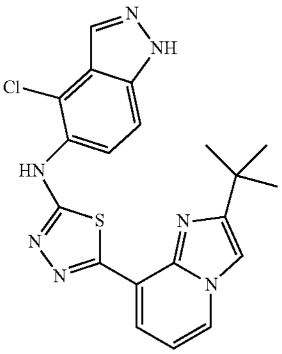 [SMILES: CC(C)(C)c1cn2cccc(-c3nnc(Nc4ccc5[nH]ncc5c4Cl)s3)c2n1] |
| 75U | 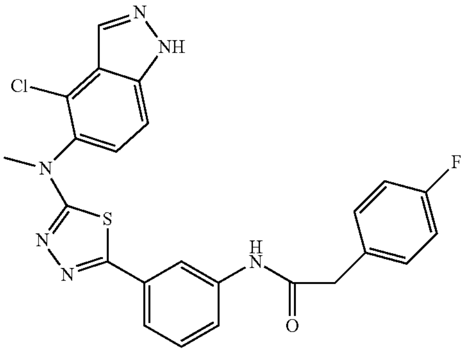 [SMILES: CN(c1nnc(-c2cccc(NC(=O)Cc3ccc(F)cc3)c2)s1)c1ccc2[nH]ncc2c1Cl] |

TABLE 15-continued

| Example No. | Chemical Structure |
| --- | --- |
| 75V | 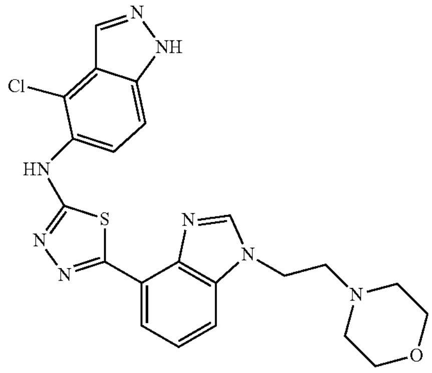 [SMILES: Clc1c(Nc2nnc(-c3cccc4c3ncn4CCN3CCOCC3)s2)ccc2[nH]ncc12] |
| 75W | 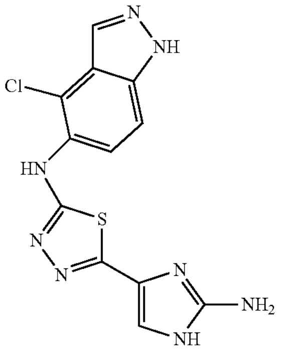 [SMILES: Nc1nc(-c2nnc(Nc3ccc4[nH]ncc4c3Cl)s2)c[nH]1] |

Example 76—Biological Assays for Inhibition of Rho-Associated Protein Kinase

Exemplary compounds were tested for ability to inhibit Rho-associated protein kinase isoform 1 (ROCK1) and Rho-associated protein kinase isoform 2 (ROCK2). Assay procedures and results are described below.

Part I—Procedures

Assays for ROCK inhibition were performed using the following protein constructs: glutathione S-transferase (GST)-tagged human ROCK1 catalytic domain 1-477 from Carna Biosciences (cat #01-109; apparent $K_m$ value for ATP is 10 μM) and GST-tagged human ROCK2 catalytic domain 1-553 from Carna Biosciences (Cat#01-110; apparent $K_m$ value for ATP is 15 μM). Protein constructs were purified from a baculovirus expression system. The peptide substrate was fluorescent LANCE® Ultra ULight-CREBtide: CKRREILSRRPSYRK (PerkinElmer, # TRF0107-D). Kinase reactions were carried out in in a 10 μL volume in 384-well plates: 50 nM ULight-CREBtide substrate, 2 nM constitutively active ROCK1 or ROCK2 kinase, and test compound in DMSO (or DMSO only for controls) were diluted into assay buffer containing 50 mM Tris-HCl (pH=7.5), 10 mM $MgCl_2$, 1 mM EGTA, 0.01% Tween-20, and 2 mM DTT such that the final concentration of DMSO was 0.5%. After a 90 minute incubation at room temperature on a shaker table, the kinase reaction was stopped by addition of 10 mM EDTA, and phosphorylation of the substrate was detected by adding 1 nM LANCE® Ultra Europium-anti-phospho-CREB (ser133) antibody (PerkinElmer, # TRF0200-D) and incubating for 60 minutes on a shaker at room temperature. The flurorescence resonance energy transfer (FRET) signals were read and analyzed on an Envision™ 2103 Multilabel Reader (Perkin Elmer). The concentration of test compound required to inhibit substrate phosphorylation by 50% (the $IC_{50}$) was calculated by non-linear regression using GraphPad PRIZM.

Part II—Results

Experimental results are provided in Tables 16 and 17 below. The symbol "++++" indicates an $IC_{50}$ less than 1 μM. The symbol "+++" indicates an $IC_{50}$ in the range of 1 μM to 15 μM. The symbol "++" indicates an $IC_{50}$ in the range of greater than 15 μM to 30 μM. The symbol "+" indicates an $IC_{50}$ greater than 30 μM. In this assay, 30 μM was the highest concentration of test compound analyzed.

TABLE 16

| Compound No. | Compound Structure* | $IC_{50}$ (μM) ROCK1 | $IC_{50}$ (μM) ROCK2 | Ratio of $IC_{50}$ of ROCK2 to ROCK1 |
| --- | --- | --- | --- | --- |
| A-1 | 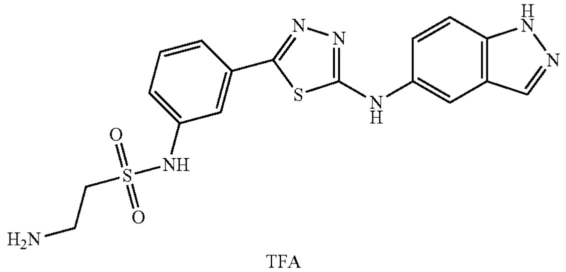 TFA | +++ | +++ | <5 |

TABLE 16-continued
| Compound No. | Compound Structure* | IC50 (μM) ROCK1 | ROCK2 | Ratio of IC50 of ROCK2 to ROCK1 |
|---|---|---|---|---|
| A-2 | 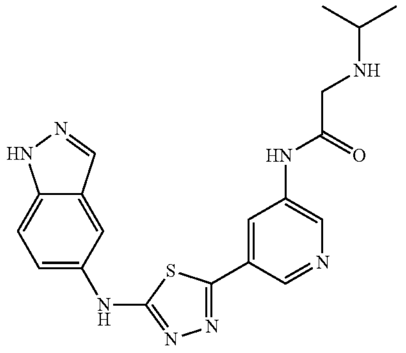 [SMILES: CC(C)NCC(=O)Nc1cncc(-c2nnc(Nc3ccc4[nH]ncc4c3)s2)c1] | +++ | ++++ | >5 |
| A-3 | 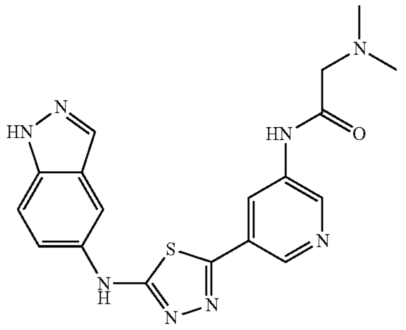 [SMILES: CN(C)CC(=O)Nc1cncc(-c2nnc(Nc3ccc4[nH]ncc4c3)s2)c1] | +++ | ++++ | <5 |
| A-4 | 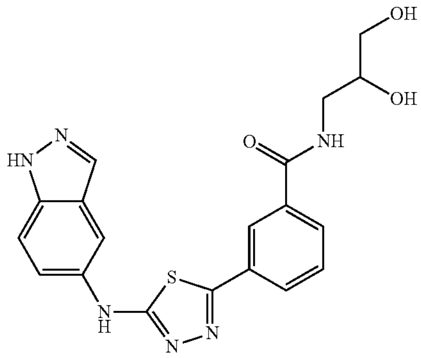 [SMILES: O=C(NCC(O)CO)c1cccc(-c2nnc(Nc3ccc4[nH]ncc4c3)s2)c1] | +++ | +++ | <5 |
| A-5 | 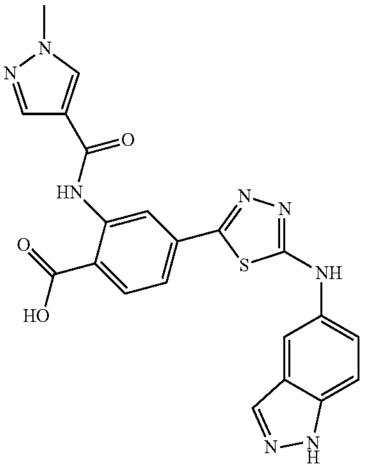 [SMILES: Cn1cc(C(=O)Nc2cc(-c3nnc(Nc4ccc5[nH]ncc5c4)s3)ccc2C(=O)O)cn1] | ++++ | ++++ | >5 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-6 | 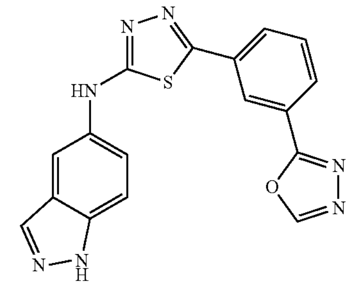 [SMILES: c1cc(-c2nnco2)cc(-c2nnc(Nc3ccc4[nH]ncc4c3)s2)c1] | + | + | <5 |
| A-7 | 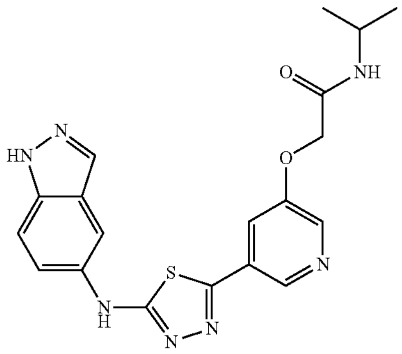 TFA | + | ++++ | >50 |
| A-8 | 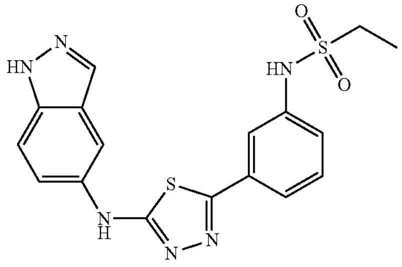 TFA | + | +++ | >5 |
| A-9 | 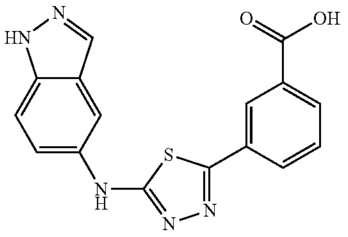 [SMILES: O=C(O)c1cccc(-c2nnc(Nc3ccc4[nH]ncc4c3)s2)c1] | ++ | +++ | >5 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-10 | 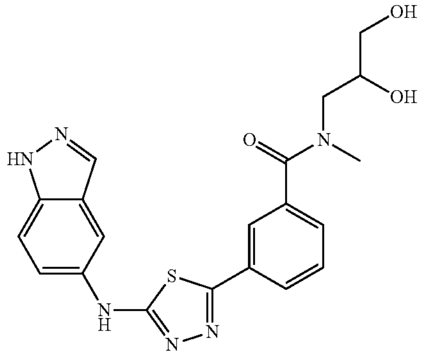 [SMILES: CN(CC(O)CO)C(=O)c1cccc(-c2nnc(Nc3ccc4[nH]ncc4c3)s2)c1] | ++ | +++ | <5 |
| A-11 | 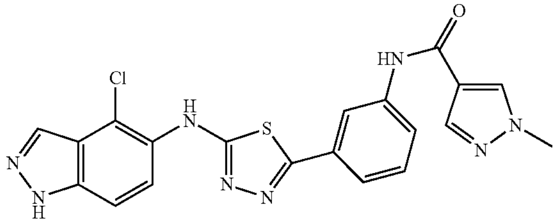 TFA | + | ++++ | >100 |
| A-12 | 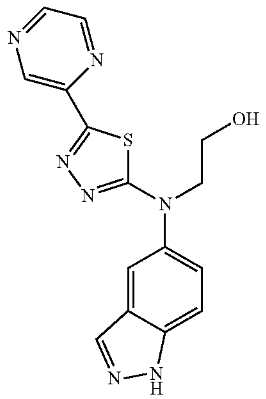 [SMILES: OCCN(c1ccc2[nH]ncc2c1)c1nnc(-c2cnccn2)s1] | + | + | <5 |
| A-13 | 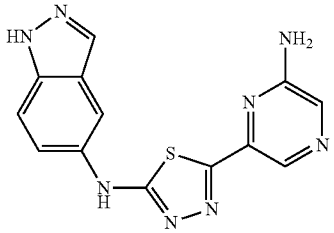 TFA | + | +++ | >5 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-14 | 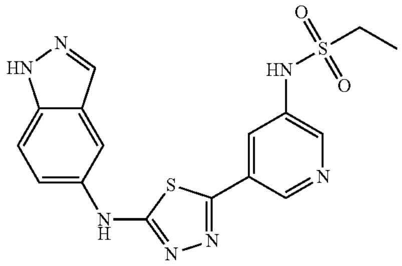 TFA | +++ | +++ | >5 |
| A-15 | 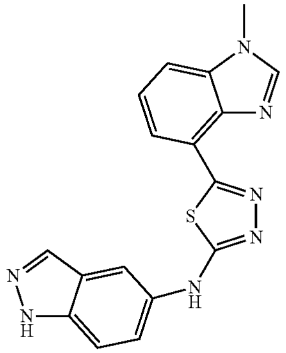 TFA | ++++ | ++++ | <5 |
| A-16 | 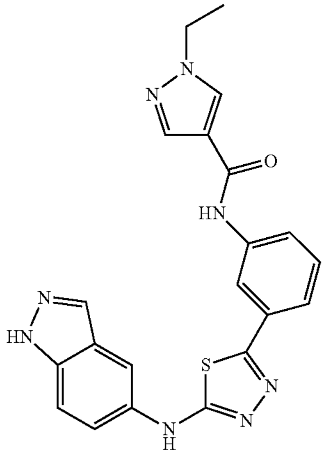 TFA | ++++ | ++++ | >5 |
| A-17 | 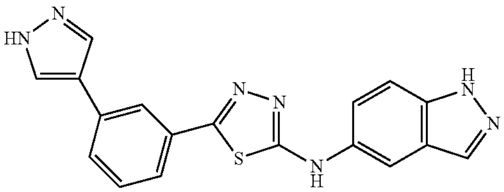 TFA | + | ++++ | >100 |

TABLE 16-continued
| Compound No. | Compound Structure* | IC50 (μM) ROCK1 | ROCK2 | Ratio of IC50 of ROCK2 to ROCK1 |
|---|---|---|---|---|
| A-18 | 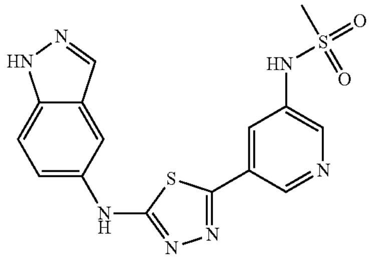 TFA | +++ | +++ | <5 |
| A-19 | 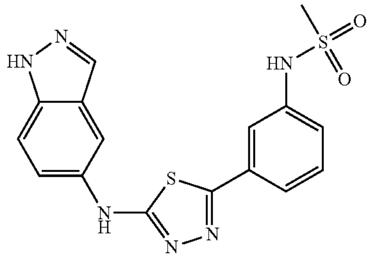 TFA | + | ++++ | >100 |
| A-20 | 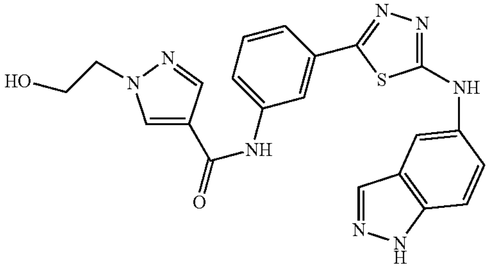 TFA | + | ++++ | >100 |
| A-21 | 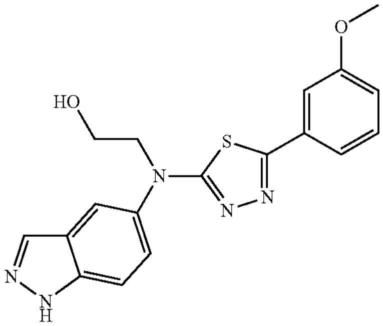 TFA | ++ | ++ | <5 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-22 | 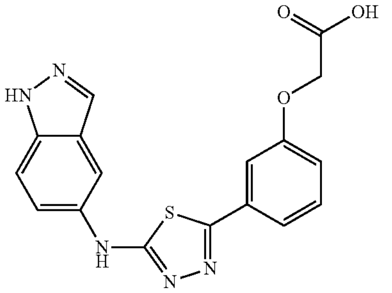 [SMILES: O=C(O)COc1cccc(-c2nnc(Nc3ccc4[nH]ncc4c3)s2)c1] | +++ | +++ | >5 |
| A-23 | 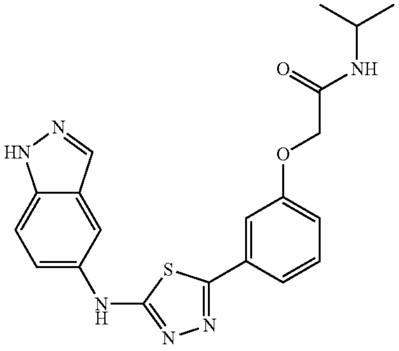 TFA | + | ++++ | >50 |
| A-24 | 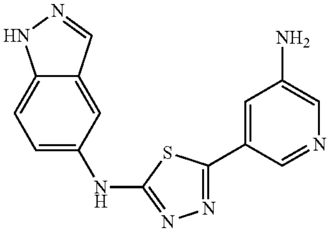 TFA | ++++ | ++++ | <5 |
| A-25 | 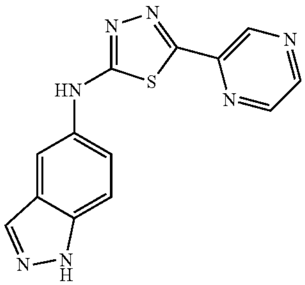 [SMILES: c1cnc(-c2nnc(Nc3ccc4[nH]ncc4c3)s2)cn1] | + | +++ | >5 |

TABLE 16-continued
| Compound No. | Compound Structure* | IC50 (μM) ROCK1 | ROCK2 | Ratio of IC50 of ROCK2 to ROCK1 |
|---|---|---|---|---|
| A-26 | 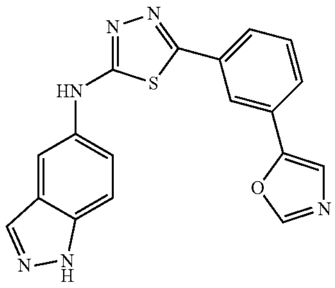 TFA | + | + | <5 |
| A-27 | 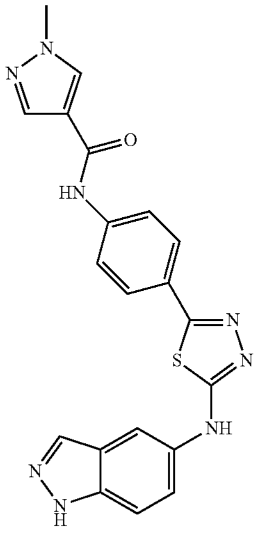 | + | + | <5 |
| A-28 | 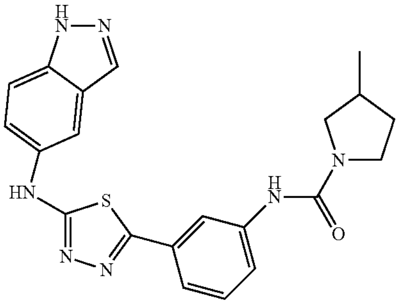 | ++++ | ++++ | >5 |
| A-29 | 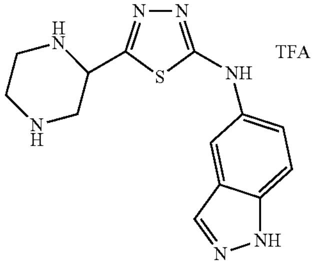 TFA | +++ | +++ | <5 |

TABLE 16-continued
| Compound No. | Compound Structure* | IC50 (μM) ROCK1 | ROCK2 | Ratio of IC50 of ROCK2 to ROCK1 |
|---|---|---|---|---|
| A-30 | 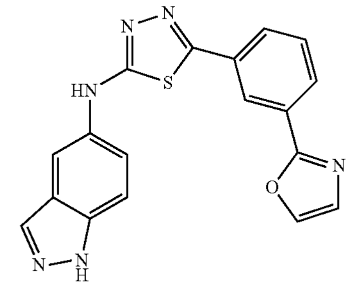 TFA | + | ++++ | >100 |
| A-31 | 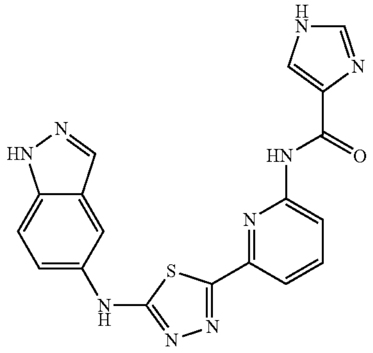 TFA | + | ++++ | >100 |
| A-32 | 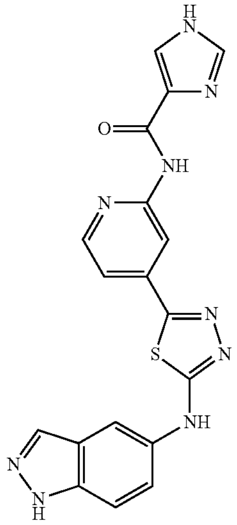 TFA | + | ++++ | >100 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-33 | 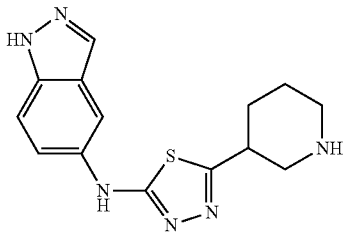 TFA | ++ | +++ | <5 |
| A-34 | 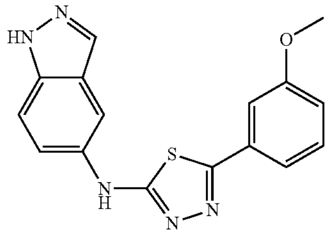 TFA | + | ++++ | >100 |
| A-35 | 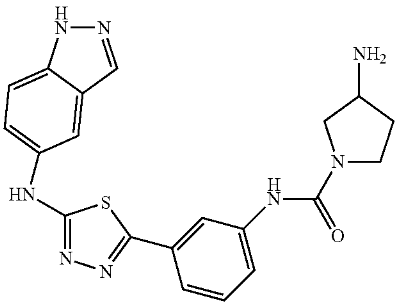 | +++ | ++++ | <5 |
| A-36 | 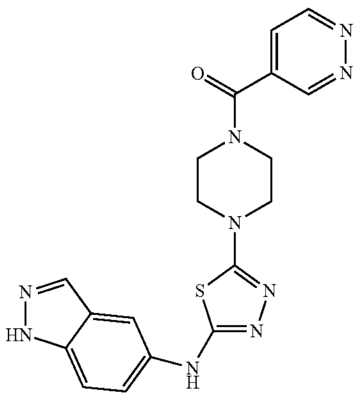 | + | +++ | >5 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-37 | 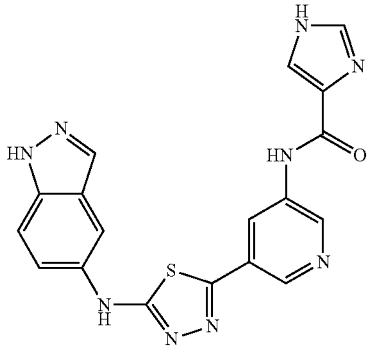 TFA | + | ++++ | >100 |
| A-38 | 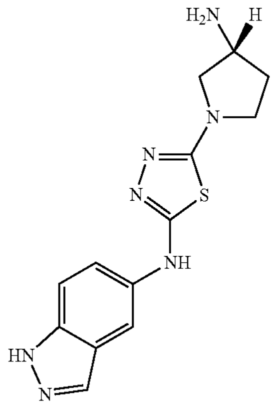 | +++ | +++ | <5 |
| A-39 | 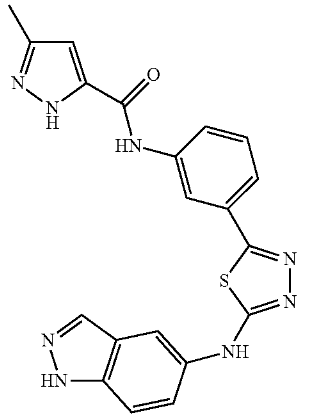 TFA | +++ | ++++ | >5 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-40 | 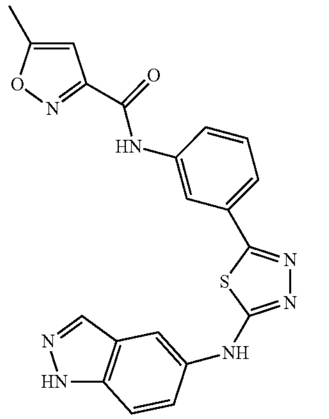 TFA | + | ++++ | >100 |
| A-41 | 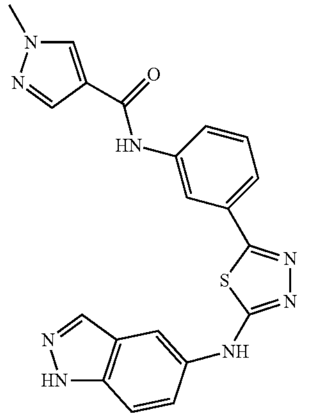 TFA | + | ++++ | >100 |
| A-42 | 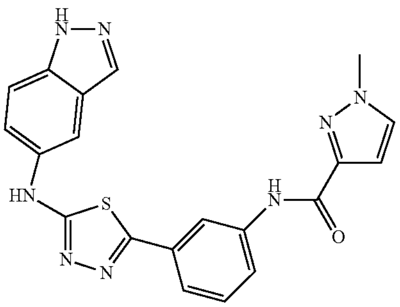 TFA | ++++ | ++++ | >5 |

TABLE 16-continued
| Compound No. | Compound Structure* | $IC_{50}$ (μM) ROCK1 | ROCK2 | Ratio of $IC_{50}$ of ROCK2 to ROCK1 |
|---|---|---|---|---|
| A-43 | 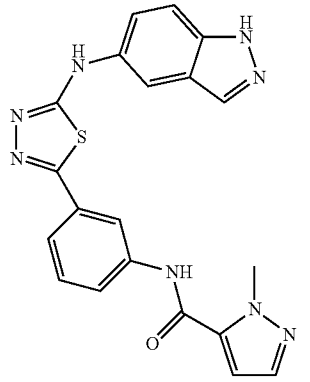 TFA | + | ++++ | >100 |
| A-44 | 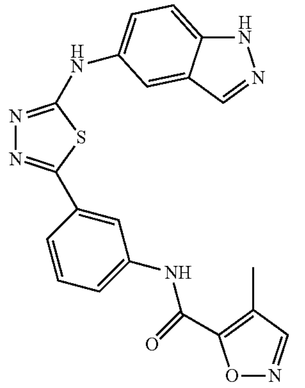 TFA | + | ++++ | >100 |
| A-45 | 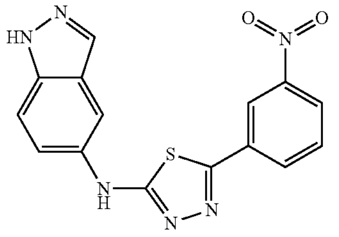 TFA | +++ | +++ | <5 |
| A-46 | 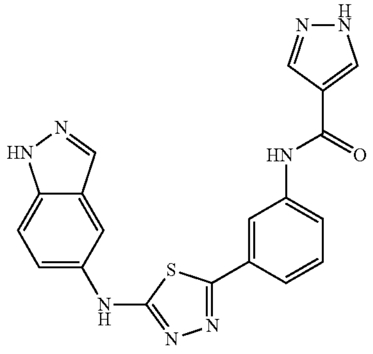 TFA | + | ++++ | >100 |

TABLE 16-continued
| Compound No. | Compound Structure* | $IC_{50}$ (μM) ROCK1 | $IC_{50}$ (μM) ROCK2 | Ratio of $IC_{50}$ of ROCK2 to ROCK1 |
|---|---|---|---|---|
| A-47 | 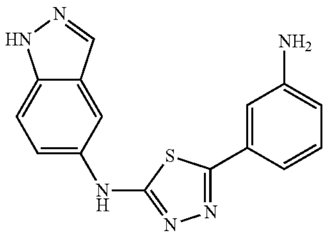 TFA | + | +++ | >5 |
| A-48 | 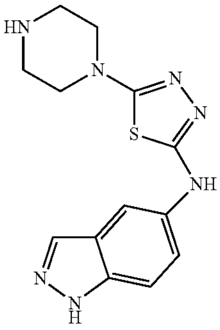 | +++ | +++ | <5 |
| A-49 | 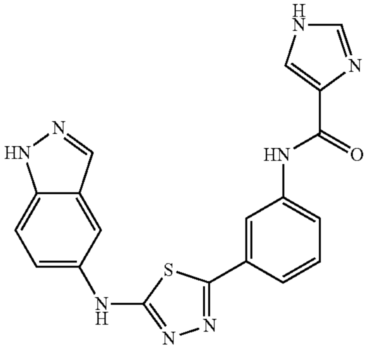 | + | ++++ | >100 |
| A-50 | 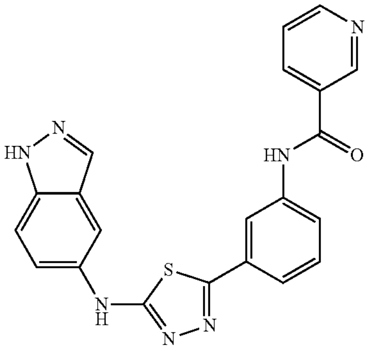 | + | ++++ | >100 |
*Compounds in the Table above depicted as the free base may contain a residual amount of 2,2,2-trifluoroacetic acid from the purification procedure used to prepare the compound.

TABLE 17

| Title Compound from Example No. | IC$_{50}$ (μM) ROCK1 | ROCK2 | Ratio of IC$_{50}$ of ROCK2 to ROCK1 |
|---|---|---|---|
| 34 | ++++ | ++++ | >50 |
| 35A | ++++ | ++++ | >5 |
| 35B | ++++ | ++++ | <5 |
| 35D | + | ++++ | >100 |
| 35E | +++ | ++++ | >50 |
| 35F | + | ++++ | >100 |
| 36 | ++++ | ++++ | >5 |
| 35G | ++++ | ++++ | >5 |
| 35H | +++ | ++++ | >5 |
| 35I | + | +++ | >5 |
| 35J | +++ | ++++ | >5 |
| 35K | +++ | ++++ | >5 |
| 35L | +++ | ++++ | >5 |
| 35M | +++ | ++++ | >5 |
| 35N | ++++ | ++++ | >5 |
| 35O | ++++ | ++++ | >5 |
| 75C | ++++ | ++++ | >5 |
| 35Q | + | ++++ | >100 |
| 35R | ++++ | ++++ | >5 |
| 75D | ++++ | ++++ | >5 |
| 35T | ++++ | ++++ | >5 |
| 35U | ++++ | ++++ | >5 |
| 35V | ++++ | ++++ | >5 |
| 35W | +++ | ++++ | >5 |
| 35X | +++ | ++++ | >50 |
| 35Y | ++++ | ++++ | >5 |
| 35Z | + | ++++ | >100 |
| 35AA | +++ | ++++ | >5 |
| 35AB | ++++ | ++++ | >5 |
| 35AC | +++ | ++++ | >5 |
| 35AD | +++ | ++++ | >5 |
| 75E | + | + | N/A |
| 35AE | ++++ | ++++ | <5 |
| 35AF | +++ | ++++ | >5 |
| 35AG | + | ++++ | >100 |
| 35AH | ++++ | ++++ | <5 |
| 35AI | ++++ | ++++ | >5 |
| 35AJ | + | ++++ | >75 |
| 35AK | ++++ | ++++ | <5 |
| 35AL | +++ | ++++ | >5 |
| 35AM | + | ++++ | >100 |
| 75F | +++ | ++++ | >5 |
| 35AO | + | ++++ | >100 |
| 35AP | ++++ | ++++ | <5 |
| 75G | ++++ | ++++ | <5 |
| 35AR | +++ | ++++ | >5 |
| 35AS | ++++ | ++++ | >50 |
| 35AU | + | ++++ | >100 |
| 35AV | +++ | ++++ | >5 |
| 35AW | ++++ | ++++ | >5 |
| 35AX | + | ++++ | >100 |
| 35AY | + | ++++ | >75 |
| 35AZ | + | +++ | >5 |
| 35BA | ++++ | ++++ | >5 |
| 35BB | + | ++++ | >100 |
| 35BC | + | ++++ | >75 |
| 35BD | + | ++++ | >100 |
| 35BE | + | ++++ | >100 |
| 35BF | +++ | ++++ | >5 |
| 35BG | + | ++++ | >100 |
| 35BH | ++++ | ++++ | >100 |
| 35BI | +++ | ++++ | >100 |
| 35BJ | ++++ | ++++ | >5 |
| 35BK | + | ++++ | >100 |
| 35BL | + | ++++ | >100 |
| 35BM | + | ++++ | >100 |
| 35BN | ++++ | ++++ | >5 |
| 35BO | ++++ | ++++ | >50 |
| 35BP | ++++ | ++++ | >5 |
| 35BQ | ++++ | ++++ | >5 |
| 35BR | + | ++++ | >100 |
| 35BS | ++++ | ++++ | <5 |
| 35BT | ++++ | ++++ | >5 |
| 75H | + | +++ | >5 |
| 35BU | ++++ | ++++ | >5 |
| 35BV | ++++ | ++++ | >50 |

TABLE 17-continued

| Title Compound from Example No. | IC$_{50}$ (μM) ROCK1 | ROCK2 | Ratio of IC$_{50}$ of ROCK2 to ROCK1 |
|---|---|---|---|
| 35BW | + | + | N/A |
| 75I | ++++ | ++++ | <5 |
| 35BY | + | ++++ | >100 |
| 75J | + | + | N/A |
| 35BZ | + | ++++ | >100 |
| 35CA | ++++ | ++++ | <5 |
| 35CB | + | ++++ | >100 |
| 75K | ++++ | ++++ | >5 |
| 35CD | +++ | +++ | <5 |
| 35CE | ++++ | ++++ | >5 |
| 35CF | +++ | ++++ | >5 |
| 35CG | ++++ | ++++ | >5 |
| 35CH | ++++ | ++++ | <5 |
| 35CI | ++++ | ++++ | <5 |
| 35CJ | + | ++++ | >5 |
| 35CK | ++++ | ++++ | >5 |
| 75L | + | ++++ | >75 |
| 35CL | ++ | +++ | >5 |
| 35CM | + | ++++ | >100 |
| 35CN | +++ | +++ | >5 |
| 35CO | +++ | +++ | >5 |
| 35CP | ++ | ++++ | >5 |
| 35CQ | + | ++++ | >100 |
| 35CR | + | ++++ | >5 |
| 35CS | ++++ | +++ | <5 |
| 75M | + | + | N/A |
| 35CT | + | ++++ | >5 |
| 75N | + | + | N/A |
| 75O | +++ | +++ | <5 |
| 35CU | + | +++ | >5 |
| 35CV | +++ | ++++ | >50 |
| 37 | + | ++++ | >100 |
| 38 | ++++ | ++++ | >5 |
| 39A | ++++ | ++++ | <5 |
| 39B | + | ++++ | >100 |
| 39C | +++ | ++++ | >75 |
| 39D | +++ | ++++ | >5 |
| 39E | + | ++++ | >100 |
| 40 | ++++ | ++++ | >5 |
| 42 | +++ | +++ | >5 |
| 75P | +++ | ++++ | >5 |
| 41C | ++++ | ++++ | >5 |
| 43 | +++ | ++++ | >5 |
| 41D | ++++ | ++++ | >50 |
| 45A | +++ | ++++ | >75 |
| 44 | ++++ | ++++ | >5 |
| 46A | ++++ | ++++ | >5 |
| 46B | + | ++++ | >100 |
| 46C | ++++ | ++++ | >5 |
| 46D | + | ++++ | >100 |
| 46E | + | ++++ | >100 |
| 46F | +++ | ++++ | >5 |
| 75Q | +++ | ++++ | >5 |
| 46H | + | ++++ | >100 |
| 46I | + | ++++ | >100 |
| 46J | + | ++++ | >100 |
| 75R | + | ++++ | >100 |
| 46L | + | ++++ | >100 |
| 46M | + | ++++ | >100 |
| 46N | ++++ | ++++ | >5 |
| 46O | + | ++++ | >100 |
| 46P | + | ++++ | >100 |
| 47 | + | ++++ | >100 |
| 48A | +++ | ++++ | >5 |
| 48B | +++ | ++++ | >50 |
| 48C | +++ | ++++ | >5 |
| 48D | +++ | ++++ | >5 |
| 48E | ++ | +++ | <5 |
| 48F | ++++ | ++++ | >5 |
| 48G | + | ++++ | >100 |
| 48H | ++++ | ++++ | >50 |
| 48I | ++++ | ++++ | >5 |
| 48J | ++++ | ++++ | >5 |
| 48K | + | ++++ | >100 |
| 48L | +++ | ++++ | >5 |
| 48M | ++++ | ++++ | >5 |

TABLE 17-continued

| Title Compound from Example No. | $IC_{50}$ (μM) ROCK1 | ROCK2 | Ratio of $IC_{50}$ of ROCK2 to ROCK1 |
|---|---|---|---|
| 48N | + | ++++ | >100 |
| 48O | + | ++++ | >100 |
| 48P | + | ++++ | >100 |
| 48Q | +++ | ++++ | >5 |
| 48R | ++++ | ++++ | >5 |
| 75S | ++++ | ++++ | >5 |
| 48T | ++++ | ++++ | >5 |
| 48U | ++++ | ++++ | >5 |
| 48V | ++++ | ++++ | >5 |
| 48W | ++++ | ++++ | >5 |
| 48X | + | +++ | >5 |
| 48Y | + | ++++ | >100 |
| 48Z | ++++ | ++++ | >5 |
| 48AA | ++++ | ++++ | >5 |
| 48AB | ++++ | ++++ | >5 |
| 48AC | ++++ | ++++ | >5 |
| 48AD | ++++ | ++++ | >5 |
| 48AE | ++++ | ++++ | >5 |
| 48AF | + | ++++ | >100 |
| 48AG | ++++ | ++++ | >50 |
| 50A | +++ | ++++ | >5 |
| 50B | +++ | ++++ | >100 |
| 50C | ++++ | ++++ | >5 |
| 50D | + | ++++ | >100 |
| 50E | + | ++++ | >100 |
| 51 | + | ++++ | >100 |
| 50F | ++++ | ++++ | >5 |
| 75T | + | + | N/A |
| 50G | ++++ | ++++ | <5 |
| 50H | +++ | ++++ | >5 |
| 52A | ++++ | ++++ | >5 |
| 52B | ++++ | ++++ | <5 |
| 52C | + | ++++ | >100 |
| 52D | ++++ | ++++ | >5 |
| 52E | + | ++++ | >100 |
| 52F | + | ++++ | >100 |
| 52G | + | ++++ | >100 |
| 49 | ++++ | ++++ | >5 |
| 53 | + | ++++ | >100 |
| 54A | + | +++ | >5 |
| 54B | + | ++ | <5 |
| 54C | +++ | +++ | <5 |
| 75U | + | + | N/A |
| 54D | +++ | +++ | <5 |
| 54E | ++ | ++ | <5 |
| 55 | ++++ | ++++ | >5 |
| 75V | + | + | N/A |
| 56A | + | +++ | >5 |
| 56B | + | ++++ | >100 |
| 56C | +++ | +++ | <5 |
| 56D | + | ++++ | >100 |
| 56E | + | ++++ | >50 |
| 56F | + | ++++ | >100 |
| 56G | + | ++++ | >100 |
| 75W | ++++ | ++++ | <5 |
| 56H | + | ++++ | >100 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound represented by Formula I:

(I)

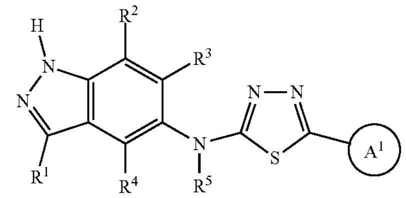

or a pharmaceutically acceptable salt thereof, or a solvate of the foregoing; wherein:

$R^1$ and $R^4$ each represent independently for each occurrence hydrogen, halogen, $C_1$-$C_3$ alkyl, $C_1$-$C_3$ haloalkyl, cyclopropyl, $C_2$-$C_4$ alkenyl, or cyano;

$R^2$ and $R^3$ each represent independently for each occurrence hydrogen, $C_1$-$C_3$ alkyl, cyclopropyl, or cyano;

$R^5$ is hydrogen, $C_1$-$C_6$ alkyl, $C_1$-$C_6$ hydroxyalkyl, or —$CO_2R^{12}$;

$R^6$ and $R^7$ each represent independently for each occurrence hydrogen, $C_1$-$C_6$ alkyl, $C_1$-$C_6$ hydroxyalkyl, or $C_3$-$C_6$ cycloalkyl; or $R^6$ and $R^7$ when attached to the same nitrogen atom may be taken together with the nitrogen atom to form a 3-7 membered ring optionally substituted with 1 or 2 $R^{12}$;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, —($C_1$-$C_6$ alkylene)-O—($C_1$-$C_6$ alkyl), or —($C_1$-$C_6$ alkylene)-N($R^6$)($R^7$); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N($R^6$)$_2$, and —($C_1$-$C_6$ alkylene)-$CO_2R^6$;

$R^{10}$ represents independently for each occurrence $C_1$-$C_6$ alkyl, $C_1$-$C_6$ haloalkyl, $C_3$-$C_6$ cycloalkyl, $C_1$-$C_6$ hydroxyalkyl, —($C_1$-$C_6$ alkylene)-O—($C_1$-$C_6$ alkyl), —($C_1$-$C_6$ alkylene)-N($R^8$)($R^9$), —($C_1$-$C_6$ alkylene)-$CO_2R^6$, —($C_1$-$C_6$ alkylene)-(3-7 membered heterocycloalkyl), or 3-7 membered heterocycloalkyl; wherein said cycloalkyl is optionally substituted by 1 or 2 $C_1$-$C_6$ alkyl;

$R^{11}$ represents independently for each occurrence a 5-6 membered heteroaryl or 3-7 membered heterocycloalkyl, each of which is optionally substituted with 1 or 2 occurrences of $Y^1$;

$R^{12}$ represents independently for each occurrence $C_1$-$C_6$ alkyl or $C_3$-$C_6$ cycloalkyl;

$A^1$ is a cyclic group selected from:

(i)

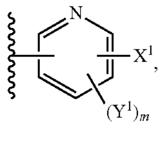
,
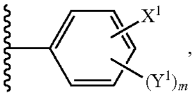
,

-continued

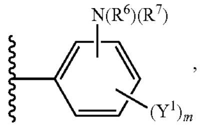

, or

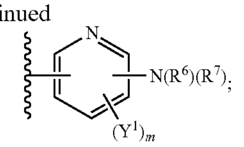

(ii)

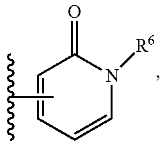

,

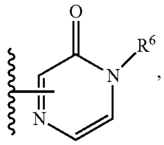

, or dihydropyridinyl, each being optionally substituted by $X^1$ and 0, 1, 2, or 3 occurrences of $Y^1$;

(iii) a heteroaryl selected from the group consisting a 8-10 membered bicyclic heteroaryl, a 5-membered heteroaryl, and a 6-membered heteroaryl containing at least two ring nitrogen atoms; wherein said heteroaryl is optionally substituted by 1, 2, or 3 substituents independently selected from the group consisting of $X^1$, $Y^1$, —($C_1$-$C_6$ alkylene)-$CO_2R^8$, —$N(R^6)(R^7)$, —O-(3-7 membered heterocyclyl), a 3-7 membered heterocycloalkyl, and $C_6$ aryl;

(iv) a 3-7 membered heterocycloalkyl, $C_3$-$C_7$ cycloalkyl, or 8-10 membered bicyclic partially unsaturated heterocyclyl, each optionally substituted by oxo, $C_6$ aryl, $X^1$, and 0, 1, 2, or 3 occurrences of $Y^1$; or (v) aralkyl or heteroaralkyl, each being optionally substituted by a $C_6$ aryl, $X^1$, and 0, 1, 2, or 3 occurrences of $Y^1$;

$X^1$ represents independently for each occurrence:

—$N(R^6)C(O)$-(3-7 membered heterocyclyl), —$N(R^6)C(O)$-phenyl, —$N(R^6)C(O)$-aralkyl, or —$N(R^6)C(O)$-heteroaralkyl; each of which is optionally substituted by 1, 2, or 3 substituents independently selected from the group consisting of $Y^1$ and —$N(R^8)(R^9)$;

—$CO_2R^8$, —$C(O)N(R^8)(R^9)$, —$C(O)R^{11}$, —$C(O)R^{12}$, —C(O)-(3-7 membered heterocyclyl), —$C(O)N(R^8)(R^{10})$, —$N(R^6)C(O)R^{10}$, —$N(R^{10})C(O)R^{10}$, —$N(R^6)CO_2R^{10}$, —$N(R^8)SO_2R^{10}$, —$N(R^6)$—($C_1$-$C_6$ alkylene)-$C(O)N(R^8)(R^9)$, —$N(R^6)$—C(O)—($C_1$-$C_6$ hydroxyalkylene)-$N(R^8)(R^9)$, —$N(R^6)$—C(O)-(2-6 membered heteroalkyl), —$N(R^6)C(O)N(R^6)(R^7)$, or —$NO_2$;

—O—($C_1$-$C_6$ alkylene)-$CO_2R^8$, —$OC(O)R^{12}$, —O—($C_1$-$C_6$ alkylene)-$C(O)N(R^8)(R^9)$, —O—($C_1$-$C_6$ alkylene)-$N(R^8)(R^9)$, —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;

—$SO_2R^{10}$, —$SO_2N(R^8)$-heteroaryl, cyano, or —$P(O)(OR^8)_2$;

5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of phenyl, and —$N(R^6)(R^7)$; or —($C_2$-$C_6$ alkylene)-aryl, —($C_2$-$C_6$ alkylene)-heterocyclyl, or —($C_1$-$C_6$ alkylene)-$COR^{12}$;

$Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, $C_2$-$C_6$ alkenyl, cyano, hydroxyl, —$CO_2R^8$, —$C(O)N(R^8)(R^9)$, —$N(R^6)C(O)R^{10}$, —$N(R^6)C(O)N(R^6)(R^7)$, —($C_1$-$C_6$ alkylene)-$CO_2R^8$, —($C_1$-$C_6$ alkylene)-O—($C_1$-$C_6$ alkyl), —($C_1$-$C_6$ alkylene)-$N(R^6)(R^7)$, —($C_1$-$C_6$ alkylene)-$N(R^6)S(O)_2R^{12}$, —($C_1$-$C_6$ alkylene)-S—$C(O)R^{12}$, —S—$R^{12}$, or 3-7 membered heterocycloalkyl; and m is 0, 1, 2, or 3.

2. The compound of claim 1, wherein the compound is a compound of Formula I or a pharmaceutically acceptable salt thereof.

3. The compound of claim 2, wherein $R^1$, $R^2$, and $R^3$ are independently hydrogen.

4. The compound of claim 2, wherein $R^4$ is chloro; and $R^5$ is hydrogen.

5. The compound of claim 4, wherein $R^6$ and $R^7$ are independently hydrogen or $C_1$-$C_6$ alkyl; and $R^8$ and $R^9$ each represent independently for each occurrence hydrogen, $C_1$-$C_6$ alkyl, $C_1$-$C_6$ hydroxyalkyl, or $C_3$-$C_6$ cycloalkyl.

6. The compound of claim 2, wherein $A^1$ is

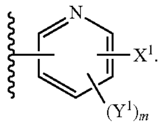

7. The compound of claim 2, wherein $A^1$ is

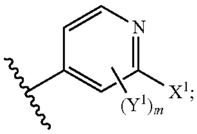

or $A^1$ is

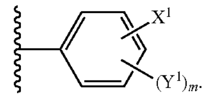

8. The compound of claim 2, wherein $X^1$ is —$N(R^6)C(O)$-(3-7 membered heterocyclyl) optionally substituted by 1, 2, or 3 substituents independently selected from the group consisting of $Y^1$ and —$N(R^8)(R^9)$.

9. The compound of claim 2, wherein $X^1$ is —$N(R^6)C(O)R^{10}$, —$N(R^{10})C(O)R^{10}$, —$N(R^6)CO_2R^{10}$, or —$N(R^8)SO_2R^{10}$.

10. The compound of claim 6, wherein $X^1$ is —$N(R^6)CO_2R^{10}$.

11. The compound of claim 2, wherein $X^1$ is a 5-6 membered heteroaryl optionally substituted with 1, 2, or 3 substituents independently selected from the group consisting of $Y^1$ and phenyl.

12. The compound of claim 2, wherein $Y^1$ represents independently for each occurrence halogen, $C_1$-$C_6$ alkyl, $C_1$-$C_6$ haloalkyl, $C_1$-$C_6$ hydroxyalkyl, —$CO_2R^8$, hydroxyl, or —($C_1$-$C_6$ alkylene)-$N(R^6)(R^7)$.

13. The compound of claim 1, wherein the compound is represented by Formula I-A:

(I-A)

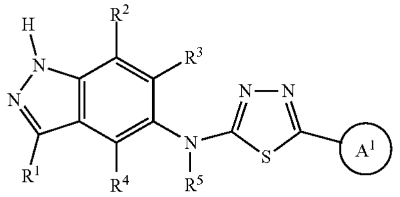

or a pharmaceutically acceptable salt thereof, or a solvate of the foregoing; wherein:

$R^1$, $R^2$, $R^3$, and $R^5$ are hydrogen;

$R^4$ is chloro or fluoro;

$R^6$ and $R^7$ each represent independently for each occurrence hydrogen or $C_1$-$C_3$ alkyl;

$R^8$ and $R^9$ each represent independently for each occurrence hydrogen or $C_1$-$C_3$ alkyl; or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, —$CO_2R^6$, —$N(R^6)_2$, and hydroxyl;

$R^{10}$ is $C_1$-$C_6$ alkyl, $C_1$-$C_6$ haloalkyl, $C_3$-$C_6$ cycloalkyl, or $C_1$-$C_6$ hydroxyalkyl;

$A^1$ is a cyclic group selected from:

(i)

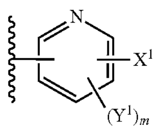

or

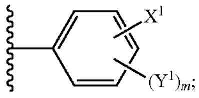

(ii)

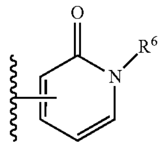

substituted by $X^1$ and 0, 1, 2, or 3 occurrences of $Y^1$; or (iii) a heteroaryl selected from the group consisting of a 8-10 membered bicyclic heteroaryl, a 5-membered heteroaryl, and a 6-membered heteroaryl containing at least two ring nitrogen atoms; wherein said heteroaryl is optionally substituted by 1, 2, or 3 substituents independently selected from the group consisting of $X^1$, $Y^1$, —($C_1$-$C_6$alkylene)-$CO_2R^8$, —$N(R^6)(R^7)$, —O-(3-7 membered heterocyclyl), a 3-7 membered heterocycloalkyl, and $C_6$ aryl;

$X^1$ represents independently for each occurrence:

—$N(R^6)C(O)$-(3-7 membered heterocyclyl) or —$N(R^6)C(O)$-phenyl, each of which is optionally substituted by 1, 2, or 3 substituents independently selected from the group consisting of $Y^1$ and —$N(R^8)(R^9)$;

—$CO_2R^8$, —$C(O)N(R^8)(R^9)$, —$N(R^6)C(O)R^{10}$, —$N(R^{10})C(O)R^{10}$, —$N(R^6)CO_2R^{10}$, or —$N(R^8)SO_2R^{10}$;

—O—($C_1$-$C_6$alkylene)-$CO_2R^8$, —O—($C_1$-$C_6$ alkylene)-$C(O)N(R^8)(R^9)$, —O—($C_1$-$C_6$ alkylene)-$N(R^8)(R^9)$, or —O—($C_1$-$C_6$ alkyl); or 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —$N(R^6)(R^7)$;

$Y^1$ represents independently for each occurrence halogen, $C_1$-$C_6$ alkyl, $C_1$-$C_6$ haloalkyl, $C_1$-$C_6$ hydroxyalkyl, —$CO_2R^8$, hydroxyl, or —($C_1$-$C_6$alkylene)-$N(R^6)(R^7)$; and m is 0, 1, 2, or 3.

14. The compound of claim 13, wherein the compound is a compound of Formula I-A or a pharmaceutically acceptable salt thereof.

15. The compound of claim 14, wherein $R^4$ is chloro.

16. The compound of claim 15, wherein $R^6$ and $R^7$ are independently hydrogen or methyl; and $R^8$ and $R^9$ each represent independently for each occurrence hydrogen or $C_1$-$C_3$ alkyl.

17. The compound of claim 14, wherein $A^1$ is

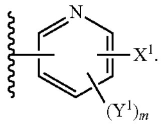

18. The compound of claim 16, wherein $A^1$ is

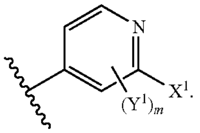

19. The compound of claim 14, wherein $A^1$ is

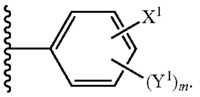

20. The compound of claim 14, wherein $A^1$ is

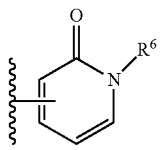

substituted by $X^1$ and 0, 1, 2, or 3 occurrences of $Y^1$.

21. The compound of claim 17, wherein $X^1$ is —$N(R^6)C(O)$-(3-7 membered heterocyclyl) optionally substituted by 1, 2, or 3 substituents independently selected from the group consisting of $Y^1$ and —$N(R^8)(R^9)$.

22. The compound of claim 14, wherein $X^1$ is —$N(R^6)C(O)R^{10}$, —$N(R^{10})C(O)R^{10}$, —$N(R^6)CO_2R^{10}$, or —$N(R^8)SO_2R^{10}$.

23. The compound of claim 17, wherein $X^1$ is —$N(R^6)CO_2R^{10}$.

24. The compound of claim 17, wherein $X^1$ is a 5-6 membered heteroaryl, 3-7 membered heterocycloalkyl, 3-7 membered oxo-heterocycloalkyl, or 8-10 membered bicyclic heterocyclyl, each of which is optionally substituted with 1, 2, or 3 substituents independently selected from the group consisting of $Y^1$, phenyl, and —N($R^6$)($R^7$).

25. The compound of claim 14, wherein m is 0.

26. A compound represented by Formula II-1:

(II-1)

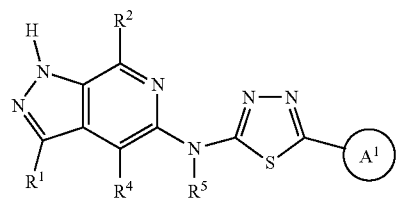

or a pharmaceutically acceptable salt thereof, or a solvate of the foregoing; wherein:

$R^1$ and $R^4$ each represent independently for each occurrence hydrogen, halogen, $C_1$-$C_3$ alkyl, $C_1$-$C_3$ haloalkyl, cyclopropyl, or cyano;

$R^2$ is hydrogen, $C_1$-$C_3$ alkyl, cyclopropyl, or cyano;

$R^5$ is hydrogen, $C_1$-$C_6$ alkyl, or $C_1$-$C_6$ hydroxyalkyl;

$R^6$ and $R^7$ each represent independently for each occurrence hydrogen, $C_1$-$C_6$ alkyl, or $C_3$-$C_6$ cycloalkyl; or $R^6$ and $R^7$ when attached to the same nitrogen atom may be taken together with the nitrogen atom to form a 3-7 membered ring;

$R^8$ and $R^9$ each represent independently for each occurrence hydrogen, $C_1$-$C_6$ alkyl, $C_1$-$C_6$ hydroxyalkyl, $C_1$-$C_3$ haloalkyl, $C_3$-$C_6$ cycloalkyl, or —($C_1$-$C_6$ alkylene)-O—($C_1$-$C_6$ alkyl); or $R^8$ and $R^9$ when attached to the same nitrogen atom may be taken together with the nitrogen atom to form a 3-7 membered ring optionally substituted by 1, 2, or 3 substituents independently selected from the group consisting of halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^6$, —C(O)N($R^6$)($R^7$), —N($R^6$)C(O)$R^6$, —N($R^6$)$_2$, and —($C_1$-$C_6$ alkylene)-$CO_2R^6$;

$R^{10}$ represents independently for each occurrence $C_1$-$C_6$ alkyl, $C_3$-$C_6$ cycloalkyl, $C_1$-$C_6$ hydroxyalkyl, or —($C_1$-$C_6$ alkylene)-N($R^8$)($R^9$);

$R^{11}$ represents independently for each occurrence a 5-6 membered heteroaryl or 3-7 membered heterocycloalkyl, each of which is optionally substituted with 1 or 2 occurrences of $Y^1$;

$A^1$ is a cyclic group selected from:

(i)

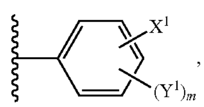
,
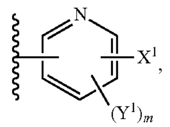

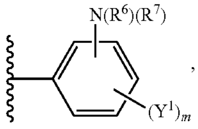
, or
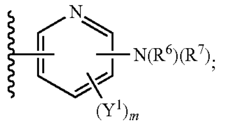

(ii) a heteroaryl selected from the group consisting a 8-10 membered bicyclic heteroaryl, a 5-membered heteroaryl, and a 6-membered heteroaryl containing at least two, ring nitrogen atoms; wherein said heteroaryl is optionally substituted by 1, 2, or 3 substituents independently selected from the group consisting of $X^1$, $Y^1$, —($C_1$-$C_6$ alkylene)-$CO_2R^8$, —N($R^6$)($R^7$), —O-(3-7 membered heterocyclyl), and a 3-7 membered heterocycloalkyl; or (iii) a 3-7 membered heterocycloalkyl optionally substituted by 1, 2, or 3 substituents independently selected from the group consisting of $X^1$ and $Y^1$;

$X^1$ represents independently for each occurrence:

—N($R^6$)C(O)-(3-7 membered heterocyclyl), —N($R^6$)C(O)-phenyl, —N($R^6$)C(O)-aralkyl, or —N($R^6$)C(O)-heteroaralkyl; each of which is optionally substituted by 1, 2, or 3 substituents independently selected from the group consisting of $Y^1$ and —N($R^8$)($R^9$);

—$CO_2R^8$, —C(O)N($R^8$)($R^9$), —C(O)$R^{11}$, —C(O)-(3-7 membered heterocyclyl), —C(O)N($R^8$)($R^{10}$), —N($R^6$)C(O)$R^{10}$, —N($R^6$)$CO_2R^{10}$, —N($R^8$)$SO_2R^{10}$, —N($R^6$)—($C_1$-$C_6$ alkylene)-C(O)N($R^8$)($R^9$), —N($R^6$)—C(O)—($C_1$-$C_6$ hydroxyalkylene)-N($R^8$)($R^9$), —N($R^6$)—C(O)-(2-6 membered heteroalkyl), or —$NO_2$;

—O—($C_1$-$C_6$ alkylene)-$CO_2R^8$, —O—($C_1$-$C_6$ alkylene)-C(O)N($R^8$)($R^9$), —O—($C_1$-$C_6$ alkylene)-N($R^8$)($R^9$), —O—($C_1$-$C_6$ alkyl), —O-(3-7 membered heterocyclyl), —O—($C_1$-$C_6$ alkylene)-aryl, or —O—($C_1$-$C_6$ alkylene)-heteroaryl;

—$SO_2R^{10}$, —$SO_2N(R^8)$-heteroaryl, or —P(O)($OR^8$)$_2$;

5-membered heteroaryl optionally substituted with 1, 2, or 3 occurrences of $Y^1$; or —($C_2$-$C_6$ alkylene)-aryl or —($C_2$-$C_6$ alkylene)-heteroaryl;

$Y^1$ represents independently for each occurrence halogen, $C_1$-$C_6$ alkyl, $C_1$-$C_6$ haloalkyl, $C_1$-$C_6$ hydroxyalkyl, $C_3$-$C_6$ cycloalkyl, $C_1$-$C_6$ alkoxyl, cyano, hydroxyl, —$CO_2R^8$, —C(O)N($R^8$)($R^9$), —N($R^6$)C(O)$R^{10}$, —($C_1$-$C_6$ alkylene)-$CO_2R^8$, or —($C_1$-$C_6$ alkylene)-O—($C_1$-$C_6$ alkyl); and m is 0, 1, 2, or 3.

27. A compound in any one of the following tables, wherein the compound is in solvated form, non-solvated form, or a pharmaceutically acceptable salt of any of the foregoing:

TABLE 1

| No. | Compound |
|---|---|
| I-1 | 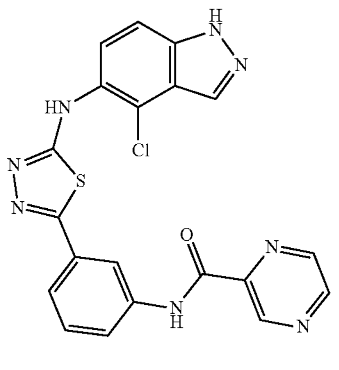 [SMILES: O=C(Nc1cccc(-c2nnc(Nc3ccc4[nH]ncc4c3Cl)s2)c1)c1cnccn1] |

TABLE 1-continued
| No. | Compound |
| --- | --- |
| I-2 | 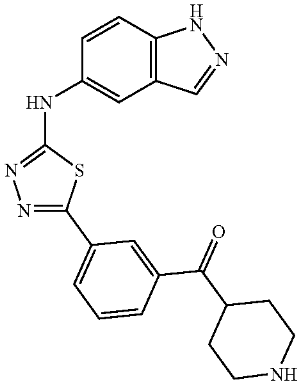 [SMILES: O=C(c1cccc(-c2nnc(Nc3ccc4[nH]ncc4c3)s2)c1)C1CCNCC1] |
| I-3 | 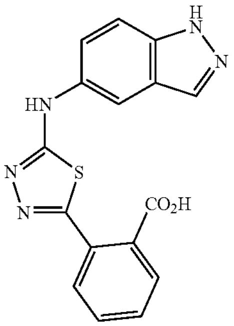 [SMILES: O=C(O)c1ccccc1-c1nnc(Nc2ccc3[nH]ncc3c2)s1] |
| I-4 | 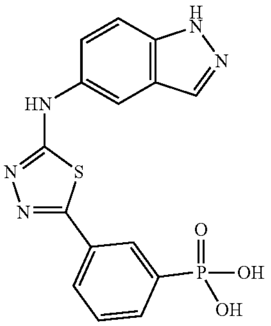 [SMILES: O=P(O)(O)c1cccc(-c2nnc(Nc3ccc4[nH]ncc4c3)s2)c1] |
| I-5 | 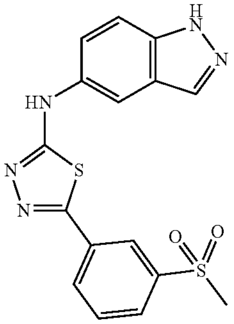 [SMILES: CS(=O)(=O)c1cccc(-c2nnc(Nc3ccc4[nH]ncc4c3)s2)c1] |
| I-6 | 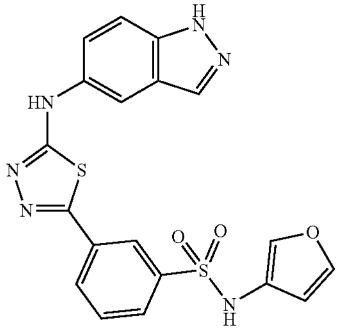 [SMILES: O=S(=O)(Nc1ccoc1)c1cccc(-c2nnc(Nc3ccc4[nH]ncc4c3)s2)c1] |
| I-7 | 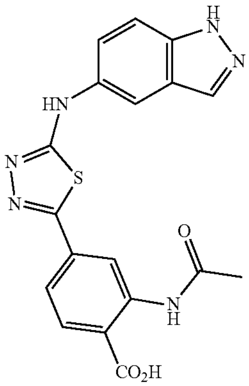 [SMILES: CC(=O)Nc1cc(-c2nnc(Nc3ccc4[nH]ncc4c3)s2)ccc1C(=O)O] |
| I-8 | 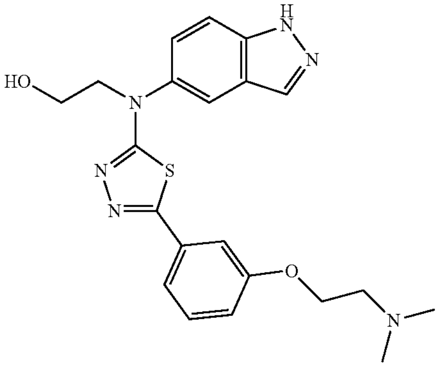 [SMILES: CN(C)CCOc1cccc(-c2nnc(N(CCO)c3ccc4[nH]ncc4c3)s2)c1] |
| I-9 | 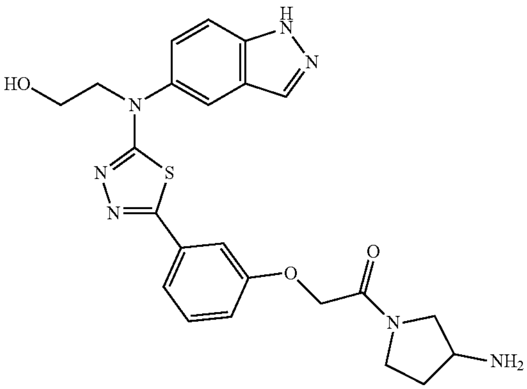 [SMILES: NC1CCN(C(=O)COc2cccc(-c3nnc(N(CCO)c4ccc5[nH]ncc5c4)s3)c2)C1] |

TABLE 1-continued
| No. | Compound |
|---|---|
| I-10 | 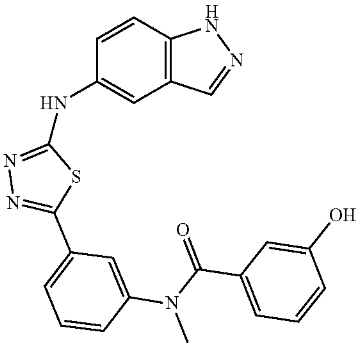 [SMILES: CN(C(=O)c1cccc(O)c1)c1cccc(-c2nnc(Nc3ccc4[nH]ncc4c3)s2)c1] |
| I-11 | 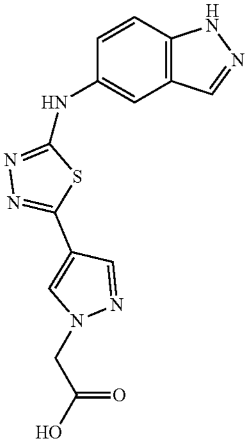 [SMILES: O=C(O)Cn1cc(-c2nnc(Nc3ccc4[nH]ncc4c3)s2)cn1] |
| I-12 | 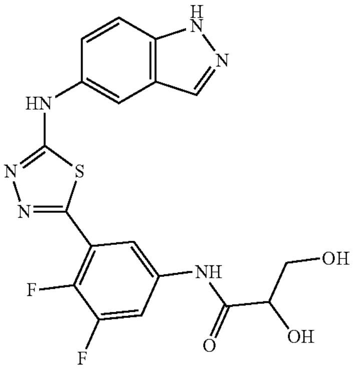 [SMILES: O=C(Nc1cc(F)c(F)c(-c2nnc(Nc3ccc4[nH]ncc4c3)s2)c1)C(O)CO] |
| I-13 | 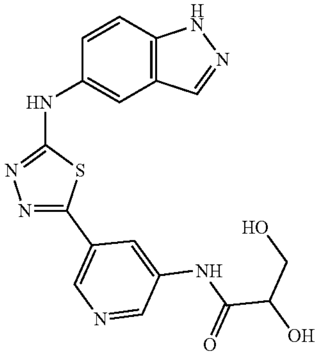 [SMILES: O=C(Nc1cncc(-c2nnc(Nc3ccc4[nH]ncc4c3)s2)c1)C(O)CO] |
TABLE 1-continued
| No. | Compound |
|---|---|
| I-14 | 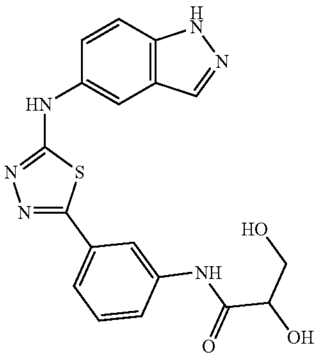 [SMILES: O=C(Nc1cccc(-c2nnc(Nc3ccc4[nH]ncc4c3)s2)c1)C(O)CO] |
| I-15 | 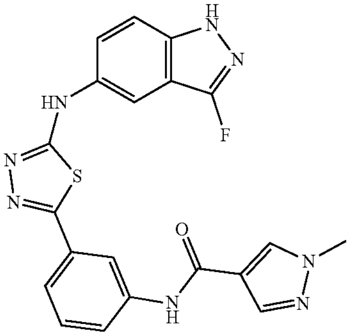 [SMILES: Cn1cc(C(=O)Nc2cccc(-c3nnc(Nc4ccc5[nH]nc(F)c5c4)s3)c2)cn1] |
| I-16 | 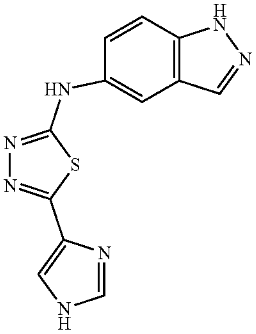 [SMILES: c1nc(-c2nnc(Nc3ccc4[nH]ncc4c3)s2)c[nH]1] |
| I-17 | 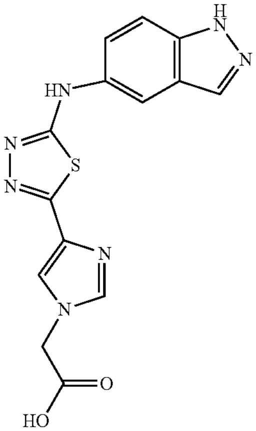 [SMILES: O=C(O)Cn1cnc(-c2nnc(Nc3ccc4[nH]ncc4c3)s2)c1] |

TABLE 1-continued
| No. | Compound |
|---|---|
| I-18 | 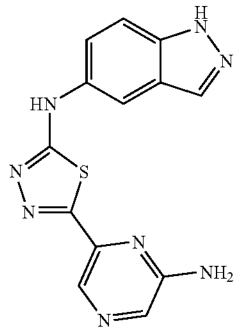 [SMILES: Nc1cncc(-c2nnc(Nc3ccc4[nH]ncc4c3)s2)n1] |
| I-19 | 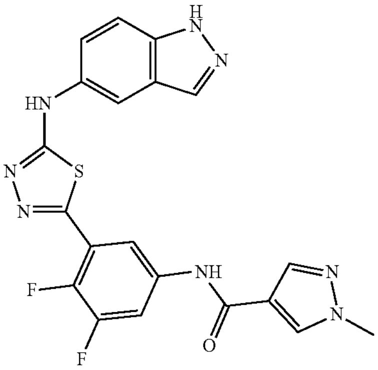 [SMILES: Cn1cc(C(=O)Nc2cc(F)c(F)c(-c3nnc(Nc4ccc5[nH]ncc5c4)s3)c2)cn1] |
| I-20 | 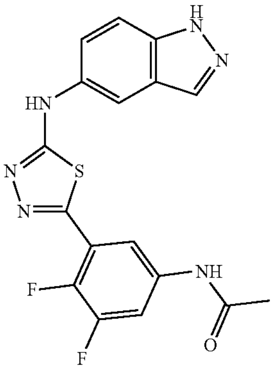 [SMILES: CC(=O)Nc1cc(F)c(F)c(-c2nnc(Nc3ccc4[nH]ncc4c3)s2)c1] |
| I-21 | 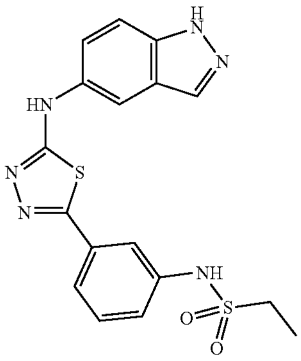 [SMILES: CCS(=O)(=O)Nc1cccc(-c2nnc(Nc3ccc4[nH]ncc4c3)s2)c1] |
TABLE 1-continued
| No. | Compound |
|---|---|
| I-22 | 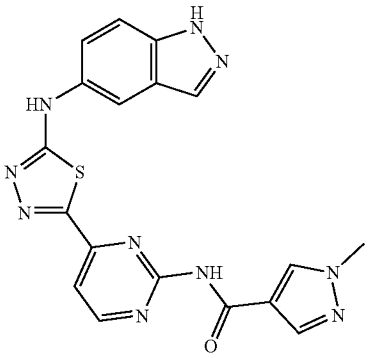 [SMILES: Cn1cc(C(=O)Nc2nccc(-c3nnc(Nc4ccc5[nH]ncc5c4)s3)n2)cn1] |
| I-23 | 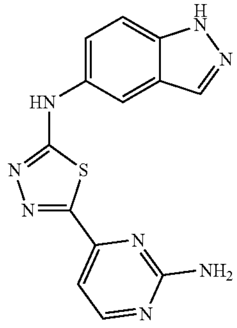 [SMILES: Nc1nccc(-c2nnc(Nc3ccc4[nH]ncc4c3)s2)n1] |
| I-24 | 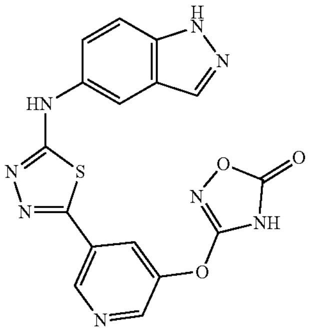 [SMILES: O=c1[nH]c(Oc2cncc(-c3nnc(Nc4ccc5[nH]ncc5c4)s3)c2)no1] |
| I-25 | 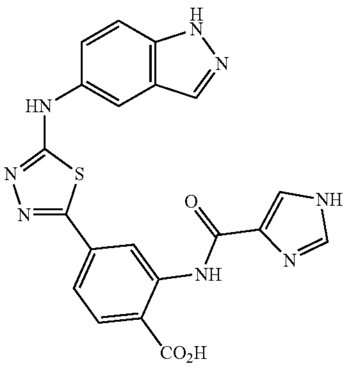 [SMILES: O=C(Nc1cc(-c2nnc(Nc3ccc4[nH]ncc4c3)s2)ccc1C(=O)O)c1c[nH]cn1] |

TABLE 1-continued
| No. | Compound |
| --- | --- |
| I-26 | 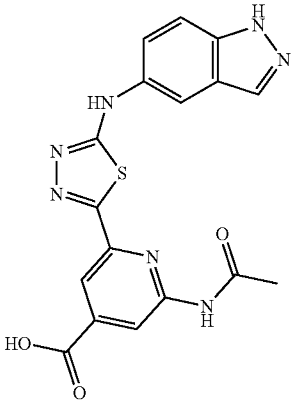 [SMILES: CC(=O)Nc1cc(C(=O)O)cc(-c2nnc(Nc3ccc4[nH]ncc4c3)s2)n1] |
| I-27 | 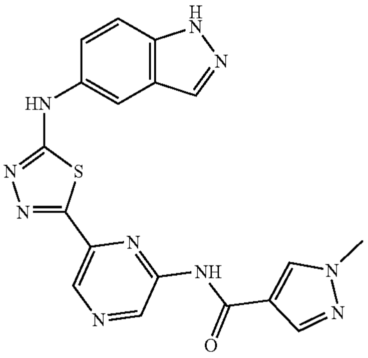 |
| I-28 | 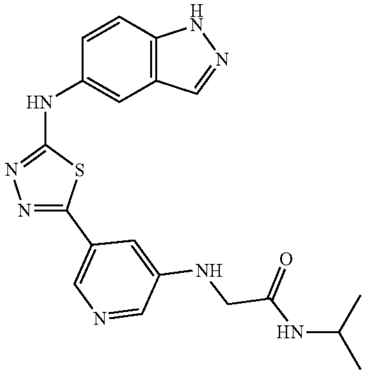 [SMILES: CC(C)NC(=O)CNc1cncc(-c2nnc(Nc3ccc4[nH]ncc4c3)s2)c1] |
| I-29 | 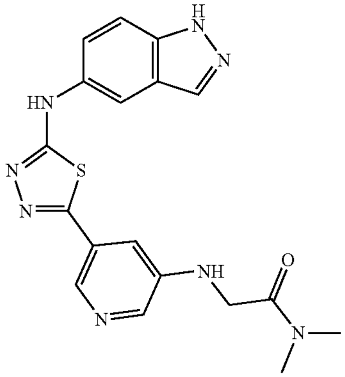 [SMILES: CN(C)C(=O)CNc1cncc(-c2nnc(Nc3ccc4[nH]ncc4c3)s2)c1] |
TABLE 1-continued
| No. | Compound |
| --- | --- |
| I-30 | 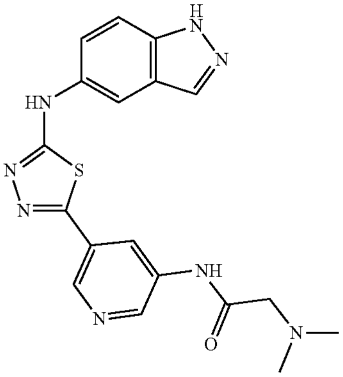 [SMILES: CN(C)CC(=O)Nc1cncc(-c2nnc(Nc3ccc4[nH]ncc4c3)s2)c1] |
| I-31 | 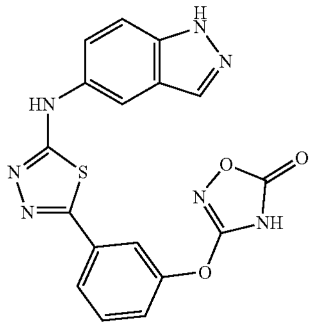 [SMILES: O=c1[nH]c(Oc2cccc(-c3nnc(Nc4ccc5[nH]ncc5c4)s3)c2)no1] |
| I-32 | 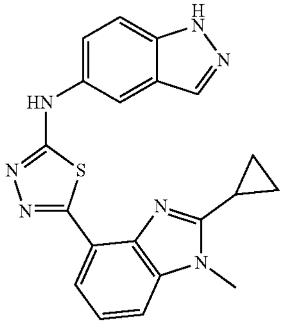 [SMILES: Cn1c(C2CC2)nc2c(-c3nnc(Nc4ccc5[nH]ncc5c4)s3)cccc21] |
| I-33 | 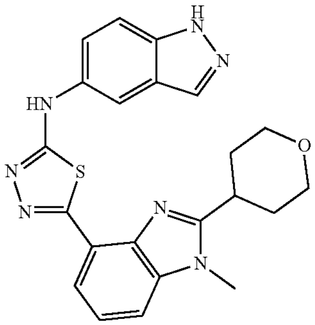 [SMILES: Cn1c(C2CCOCC2)nc2c(-c3nnc(Nc4ccc5[nH]ncc5c4)s3)cccc21] |

TABLE 1-continued
| No. | Compound |
|---|---|
| I-34 | 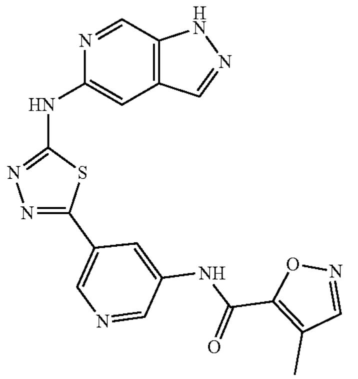 [SMILES: Cc1cnoc1C(=O)Nc1cncc(-c2nnc(Nc3cc4cn[nH]c4cn3)s2)c1] |
| I-35 | 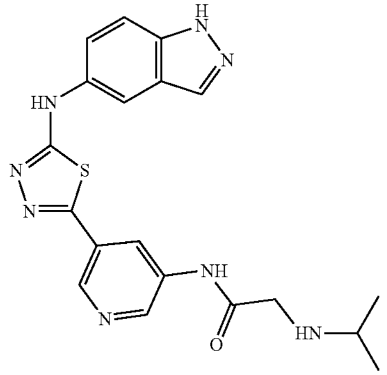 [SMILES: CC(C)NCC(=O)Nc1cncc(-c2nnc(Nc3ccc4[nH]ncc4c3)s2)c1] |
| I-36 | 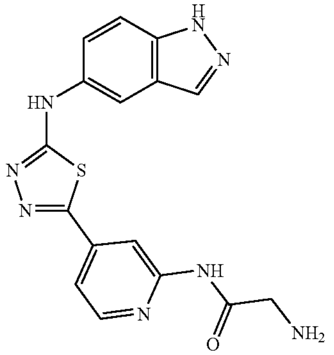 [SMILES: NCC(=O)Nc1cc(-c2nnc(Nc3ccc4[nH]ncc4c3)s2)ccn1] |
| I-37 | 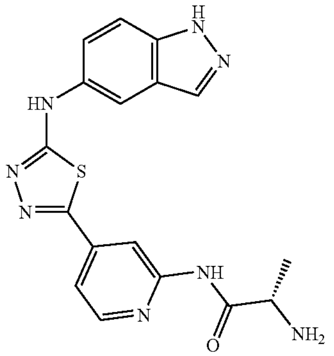 [SMILES: C[C@H](N)C(=O)Nc1cc(-c2nnc(Nc3ccc4[nH]ncc4c3)s2)ccn1] |
TABLE 1-continued
| No. | Compound |
|---|---|
| I-38 | 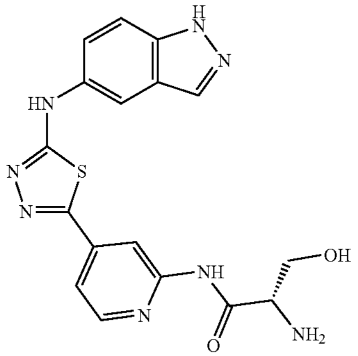 [SMILES: N[C@@H](CO)C(=O)Nc1cc(-c2nnc(Nc3ccc4[nH]ncc4c3)s2)ccn1] |
| I-39 | 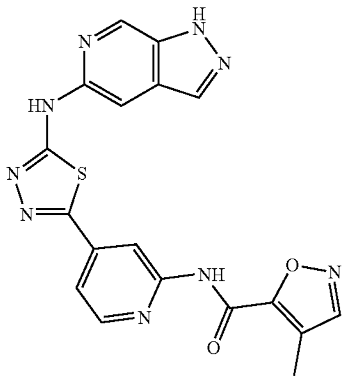 [SMILES: Cc1cnoc1C(=O)Nc1cc(-c2nnc(Nc3cc4cn[nH]c4cn3)s2)ccn1] |
| I-40 | 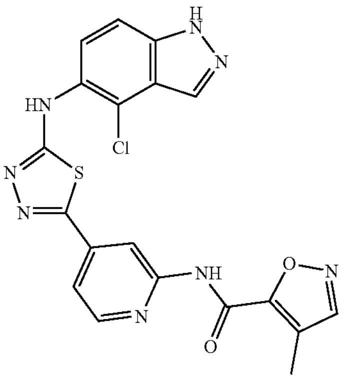 [SMILES: Cc1cnoc1C(=O)Nc1cc(-c2nnc(Nc3ccc4[nH]ncc4c3Cl)s2)ccn1] |
| I-41 | 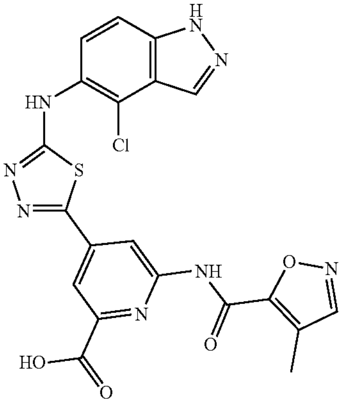 [SMILES: Cc1cnoc1C(=O)Nc1cc(-c2nnc(Nc3ccc4[nH]ncc4c3Cl)s2)cc(C(=O)O)n1] |

TABLE 1-continued
| No. | Compound |
| --- | --- |
| I-42 | 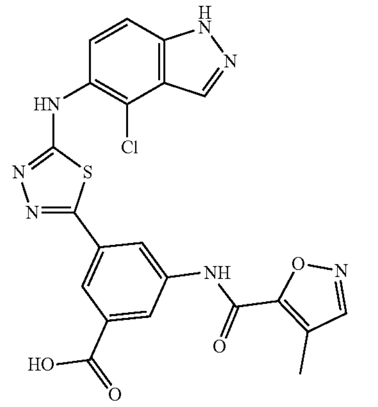 [SMILES: Cc1cnoc1C(=O)Nc1cc(C(=O)O)cc(-c2nnc(Nc3ccc4[nH]ncc4c3Cl)s2)c1] |
| I-43 | 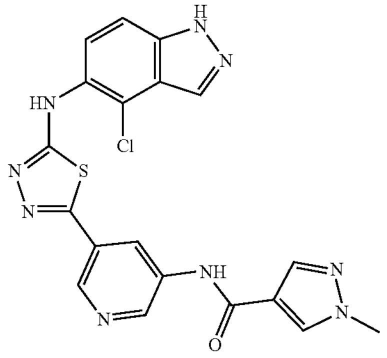 [SMILES: Cn1cc(C(=O)Nc2cncc(-c3nnc(Nc4ccc5[nH]ncc5c4Cl)s3)c2)cn1] |
| I-44 | 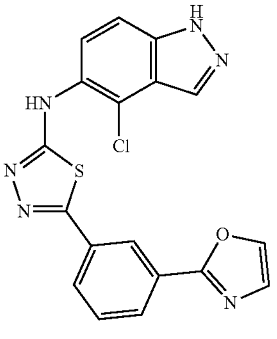 [SMILES: Clc1c(Nc2nnc(-c3cccc(-c4ncco4)c3)s2)ccc2[nH]ncc12] |
| I-45 | 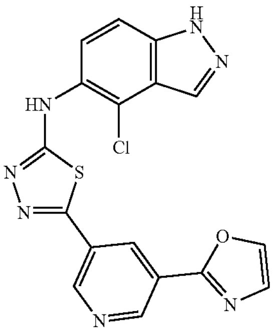 [SMILES: Clc1c(Nc2nnc(-c3cncc(-c4ncco4)c3)s2)ccc2[nH]ncc12] |
TABLE 1-continued
| No. | Compound |
| --- | --- |
| I-46 | 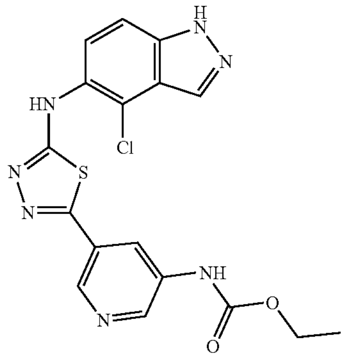 [SMILES: CCOC(=O)Nc1cncc(-c2nnc(Nc3ccc4[nH]ncc4c3Cl)s2)c1] |
| I-47 | 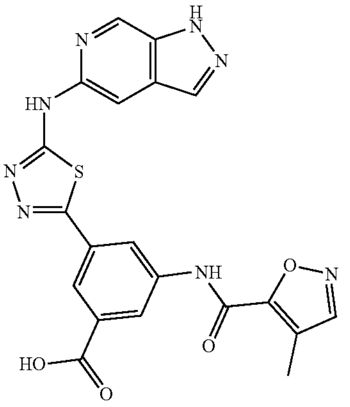 [SMILES: Cc1cnoc1C(=O)Nc1cc(C(=O)O)cc(-c2nnc(Nc3cc4cn[nH]c4cn3)s2)c1] |
| I-48 | 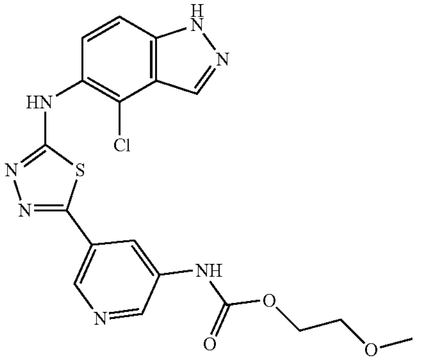 [SMILES: COCCOC(=O)Nc1cncc(-c2nnc(Nc3ccc4[nH]ncc4c3Cl)s2)c1] |
| I-49 | 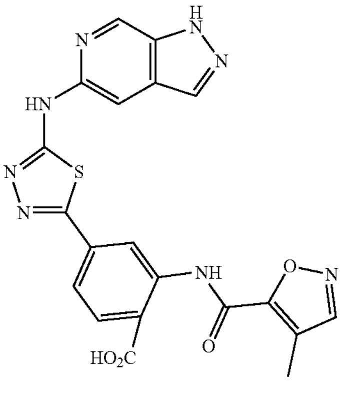 [SMILES: Cc1cnoc1C(=O)Nc1cc(-c2nnc(Nc3cc4cn[nH]c4cn3)s2)ccc1C(=O)O] |

TABLE 1-continued
| No. | Compound |
| --- | --- |
| I-50 | 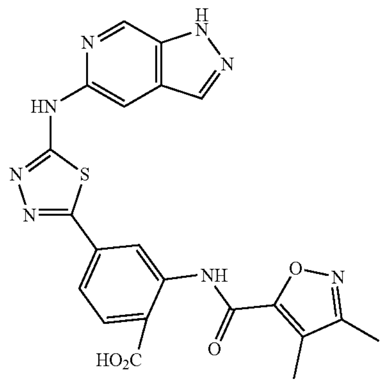 [SMILES: Cc1noc(C(=O)Nc2cc(-c3nnc(Nc4cc5cn[nH]c5cn4)s3)ccc2C(=O)O)c1C] |
| I-51 | 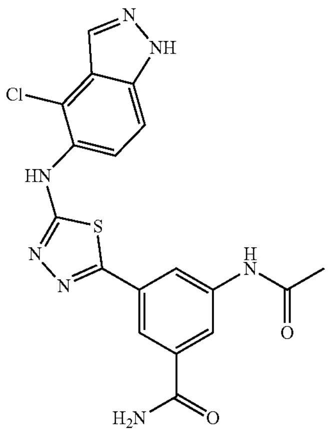 [SMILES: CC(=O)Nc1cc(C(N)=O)cc(-c2nnc(Nc3ccc4[nH]ncc4c3Cl)s2)c1] |
| I-52 | 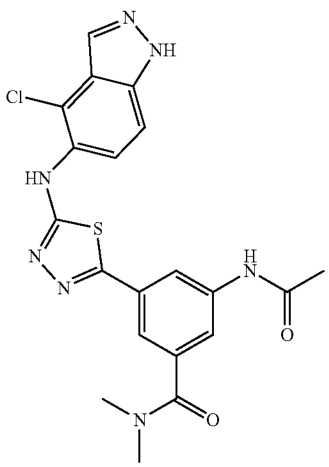 [SMILES: CC(=O)Nc1cc(C(=O)N(C)C)cc(-c2nnc(Nc3ccc4[nH]ncc4c3Cl)s2)c1] |
TABLE 1-continued
| No. | Compound |
| --- | --- |
| I-53 | 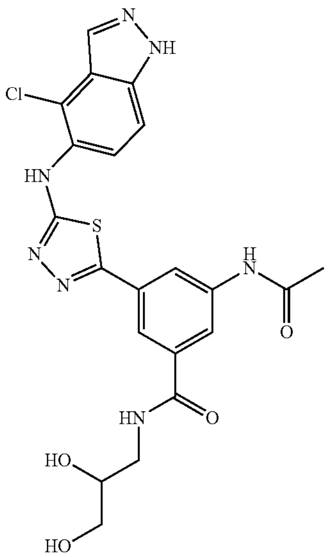 [SMILES: CC(=O)Nc1cc(C(=O)NCC(O)CO)cc(-c2nnc(Nc3ccc4[nH]ncc4c3Cl)s2)c1] |
| I-54 | 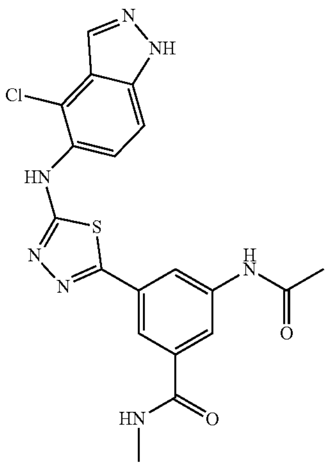 [SMILES: CNC(=O)c1cc(NC(C)=O)cc(-c2nnc(Nc3ccc4[nH]ncc4c3Cl)s2)c1] |
| I-55 | 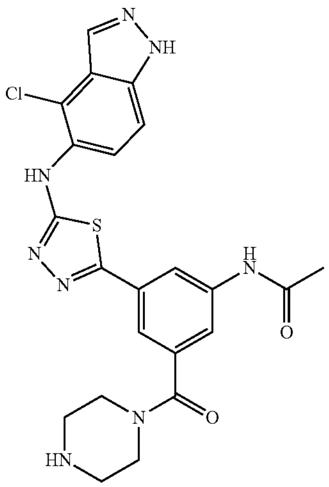 [SMILES: CC(=O)Nc1cc(C(=O)N2CCNCC2)cc(-c2nnc(Nc3ccc4[nH]ncc4c3Cl)s2)c1] |

TABLE 1-continued
| No. | Compound |
|---|---|
| I-56 | 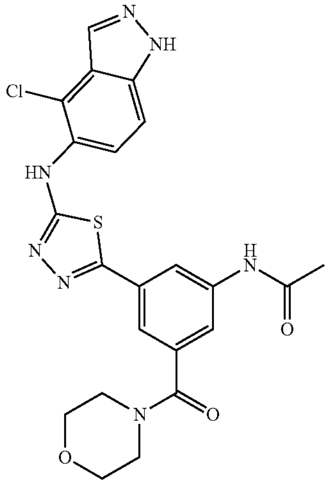 [SMILES: CC(=O)Nc1cc(C(=O)N2CCOCC2)cc(-c2nnc(Nc3ccc4[nH]ncc4c3Cl)s2)c1] |
| I-57 | 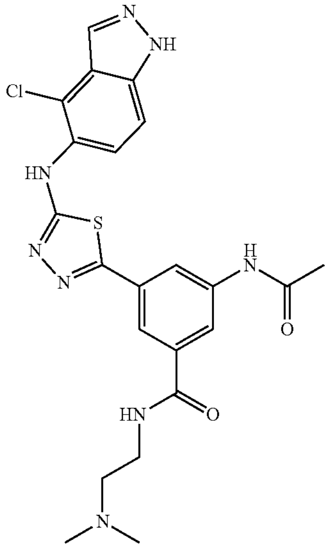 [SMILES: CC(=O)Nc1cc(C(=O)NCCN(C)C)cc(-c2nnc(Nc3ccc4[nH]ncc4c3Cl)s2)c1] |
| I-58 | 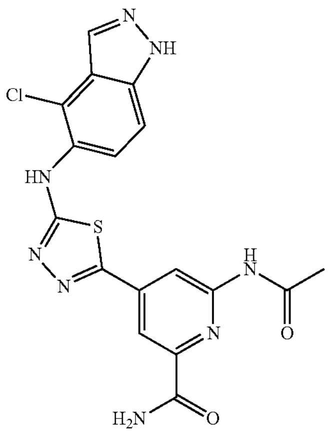 [SMILES: CC(=O)Nc1cc(-c2nnc(Nc3ccc4[nH]ncc4c3Cl)s2)cc(C(N)=O)n1] |
| I-59 | 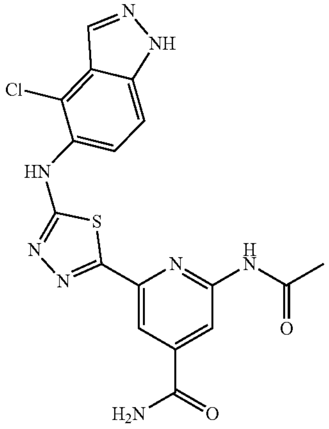 |
| I-60 | 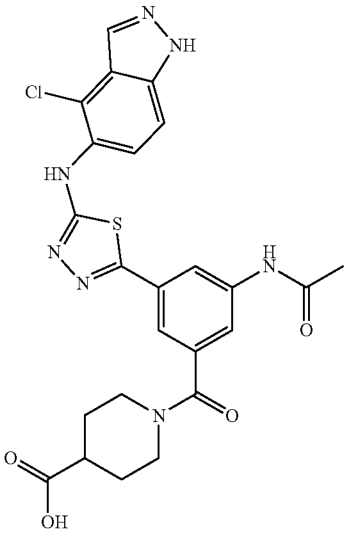 [SMILES: CC(=O)Nc1cc(C(=O)N2CCC(C(=O)O)CC2)cc(-c2nnc(Nc3ccc4[nH]ncc4c3Cl)s2)c1] |
| I-61 | 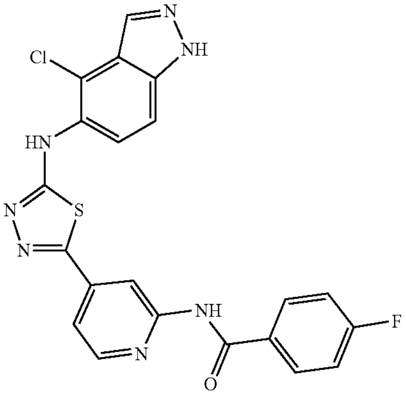 [SMILES: O=C(Nc1cc(-c2nnc(Nc3ccc4[nH]ncc4c3Cl)s2)ccn1)c1ccc(F)cc1] |

TABLE 1-continued
| No. | Compound |
|---|---|
| I-62 | 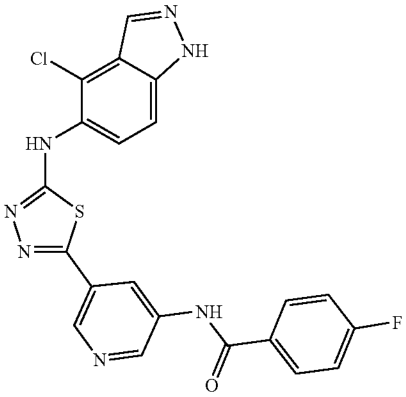 [SMILES: O=C(Nc1cncc(-c2nnc(Nc3ccc4[nH]ncc4c3Cl)s2)c1)c1ccc(F)cc1] |
| I-63 | 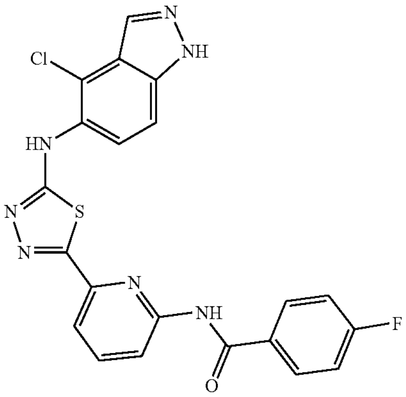 [SMILES: O=C(Nc1cccc(-c2nnc(Nc3ccc4[nH]ncc4c3Cl)s2)n1)c1ccc(F)cc1] |
| I-64 | 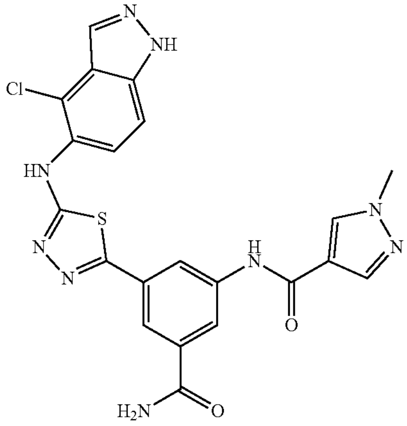 [SMILES: Cn1cc(C(=O)Nc2cc(C(N)=O)cc(-c3nnc(Nc4ccc5[nH]ncc5c4Cl)s3)c2)cn1] |
TABLE 1-continued
| No. | Compound |
|---|---|
| I-65 | 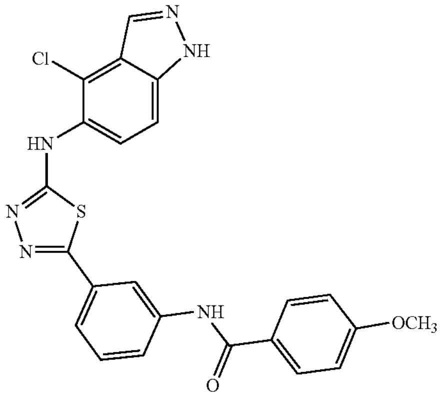 [SMILES: COc1ccc(C(=O)Nc2cccc(-c3nnc(Nc4ccc5[nH]ncc5c4Cl)s3)c2)cc1] |
| I-66 | 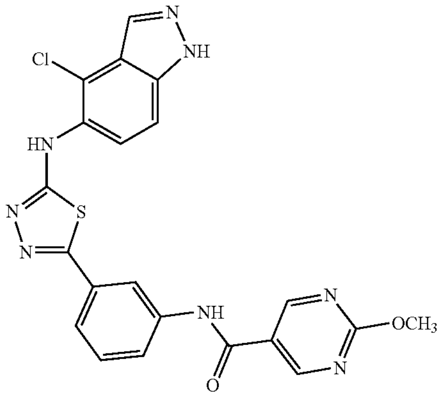 [SMILES: COc1ncc(C(=O)Nc2cccc(-c3nnc(Nc4ccc5[nH]ncc5c4Cl)s3)c2)cn1] |
| I-67 | 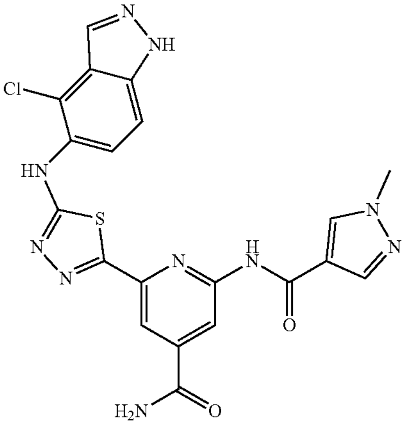 [SMILES: Cn1cc(C(=O)Nc2cc(C(N)=O)cc(-c3nnc(Nc4ccc5[nH]ncc5c4Cl)s3)n2)cn1] |

TABLE 1-continued
| No. | Compound |
| --- | --- |
| I-68 | 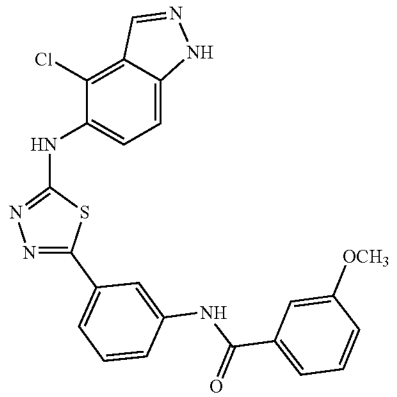 [SMILES: COc1cccc(C(=O)Nc2cccc(-c3nnc(Nc4ccc5[nH]ncc5c4Cl)s3)c2)c1] |
| I-69 | 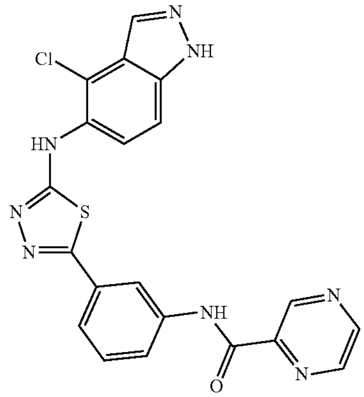 [SMILES: O=C(Nc1cccc(-c2nnc(Nc3ccc4[nH]ncc4c3Cl)s2)c1)c1cnccn1] |
| I-70 | 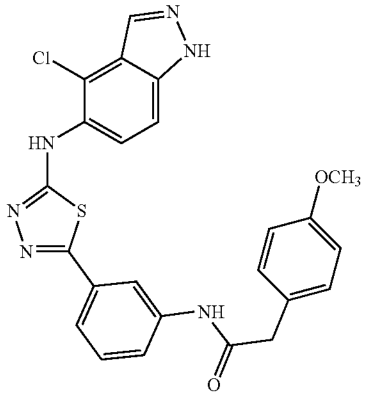 [SMILES: COc1ccc(CC(=O)Nc2cccc(-c3nnc(Nc4ccc5[nH]ncc5c4Cl)s3)c2)cc1] |
| I-71 | 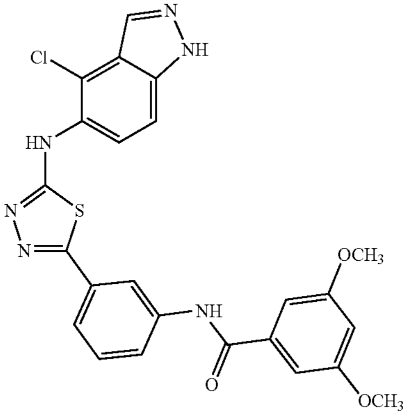 [SMILES: COc1cc(OC)cc(C(=O)Nc2cccc(-c3nnc(Nc4ccc5[nH]ncc5c4Cl)s3)c2)c1] |
TABLE 1-continued
| No. | Compound |
| --- | --- |
| I-72 | 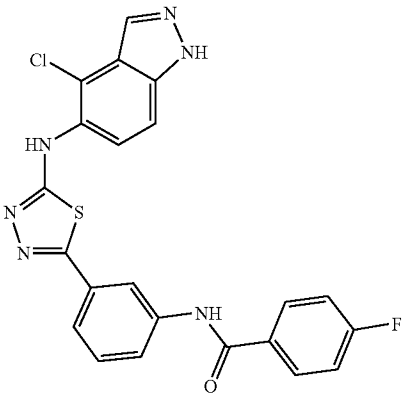 [SMILES: O=C(Nc1cccc(-c2nnc(Nc3ccc4[nH]ncc4c3Cl)s2)c1)c1ccc(F)cc1] |
| I-73 | 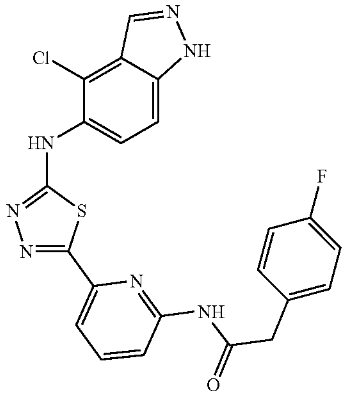 [SMILES: O=C(Cc1ccc(F)cc1)Nc1cccc(-c2nnc(Nc3ccc4[nH]ncc4c3Cl)s2)n1] |
| I-74 | 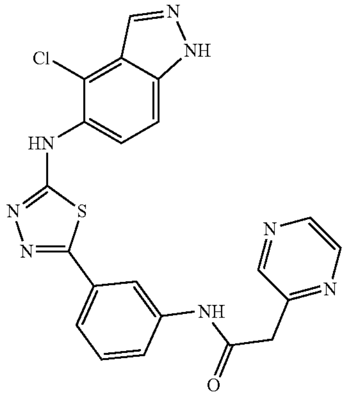 [SMILES: O=C(Cc1cnccn1)Nc1cccc(-c2nnc(Nc3ccc4[nH]ncc4c3Cl)s2)c1] |
| I-75 | 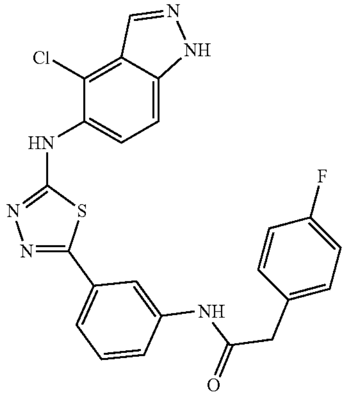 [SMILES: O=C(Cc1ccc(F)cc1)Nc1cccc(-c2nnc(Nc3ccc4[nH]ncc4c3Cl)s2)c1] |

TABLE 1-continued
| No. | Compound |
| --- | --- |
| I-76 | 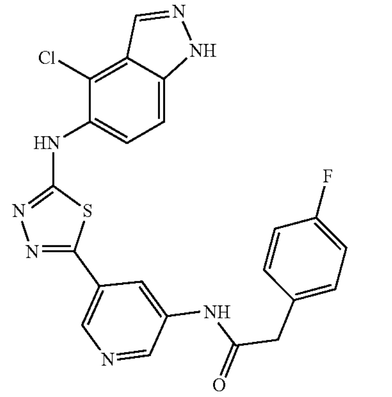 [SMILES: O=C(Cc1ccc(F)cc1)Nc1cncc(-c2nnc(Nc3ccc4[nH]ncc4c3Cl)s2)c1] |
| I-77 | 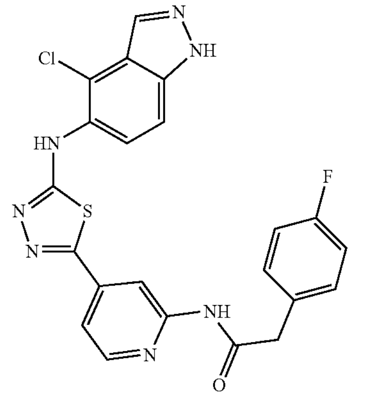 |
| I-78 | 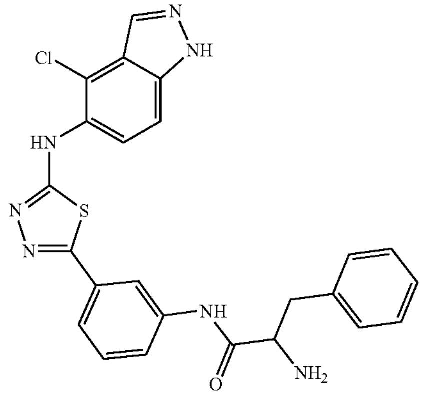 [SMILES: NC(Cc1ccccc1)C(=O)Nc1cccc(-c2nnc(Nc3ccc4[nH]ncc4c3Cl)s2)c1] |
| I-79 | 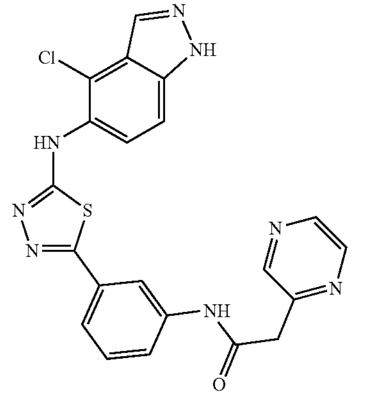 [SMILES: O=C(Cc1cnccn1)Nc1cccc(-c2nnc(Nc3ccc4[nH]ncc4c3Cl)s2)c1] |
TABLE 1-continued
| No. | Compound |
| --- | --- |
| I-80 | 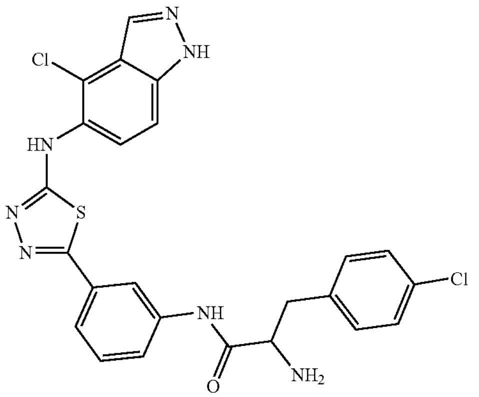 [SMILES: NC(Cc1ccc(Cl)cc1)C(=O)Nc1cccc(-c2nnc(Nc3ccc4[nH]ncc4c3Cl)s2)c1] |
| I-81 | 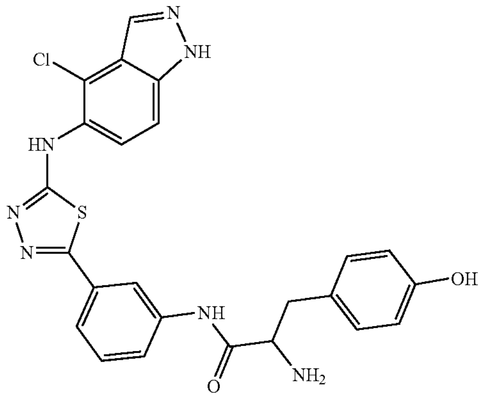 [SMILES: NC(Cc1ccc(O)cc1)C(=O)Nc1cccc(-c2nnc(Nc3ccc4[nH]ncc4c3Cl)s2)c1] |
| I-82 | 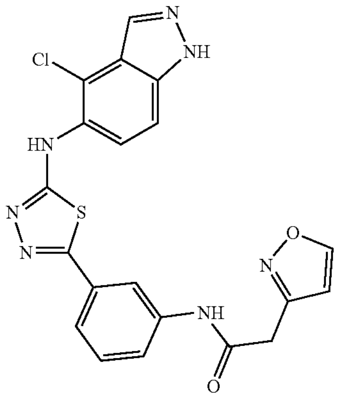 [SMILES: O=C(Cc1ccon1)Nc1cccc(-c2nnc(Nc3ccc4[nH]ncc4c3Cl)s2)c1] |
| I-83 | 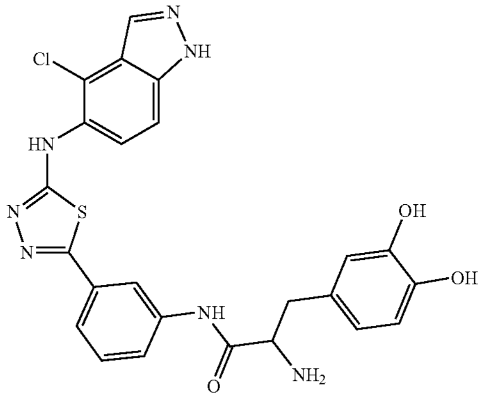 [SMILES: NC(Cc1ccc(O)c(O)c1)C(=O)Nc1cccc(-c2nnc(Nc3ccc4[nH]ncc4c3Cl)s2)c1] |

TABLE 1-continued
| No. | Compound |
|---|---|
| I-84 | 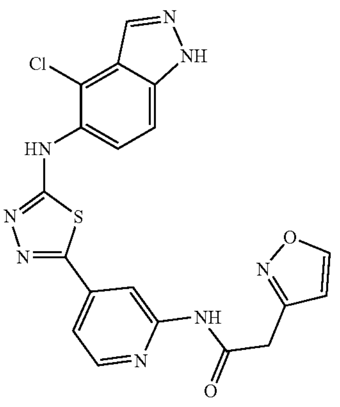 [SMILES: O=C(Cc1ccon1)Nc1cc(-c2nnc(Nc3ccc4[nH]ncc4c3Cl)s2)ccn1] |
| I-85 | 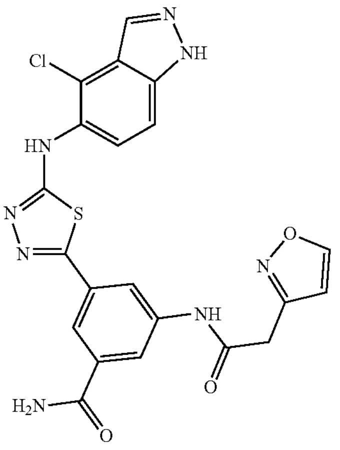 [SMILES: NC(=O)c1cc(NC(=O)Cc2ccon2)cc(-c2nnc(Nc3ccc4[nH]ncc4c3Cl)s2)c1] |
| I-86 | 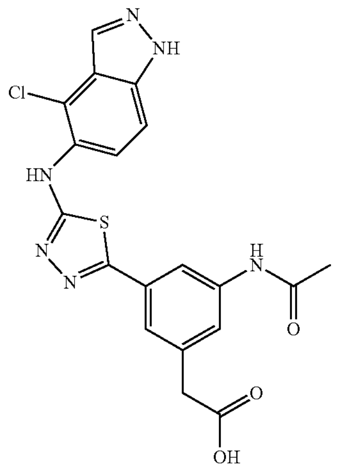 [SMILES: CC(=O)Nc1cc(CC(=O)O)cc(-c2nnc(Nc3ccc4[nH]ncc4c3Cl)s2)c1] |
TABLE 1-continued
| No. | Compound |
|---|---|
| I-87 | 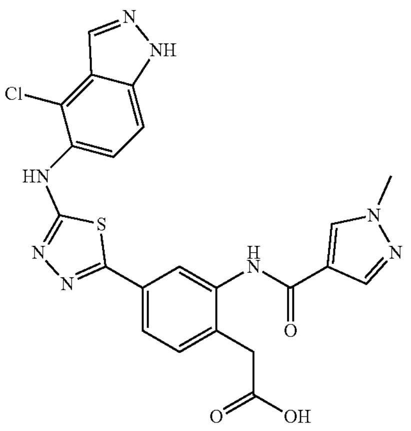 [SMILES: Cn1cc(C(=O)Nc2cc(-c3nnc(Nc4ccc5[nH]ncc5c4Cl)s3)ccc2CC(=O)O)cn1] |
| I-88 | 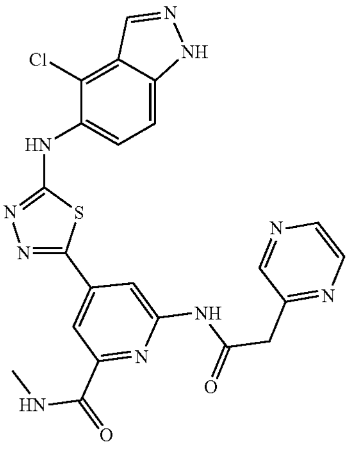 [SMILES: CNC(=O)c1cc(-c2nnc(Nc3ccc4[nH]ncc4c3Cl)s2)cc(NC(=O)Cc2cnccn2)n1] |
| I-89 | 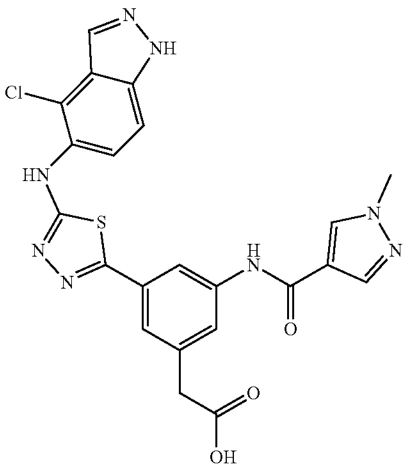 [SMILES: Cn1cc(C(=O)Nc2cc(CC(=O)O)cc(-c3nnc(Nc4ccc5[nH]ncc5c4Cl)s3)c2)cn1] |

TABLE 1-continued
| No. | Compound |
|---|---|
| I-90 | 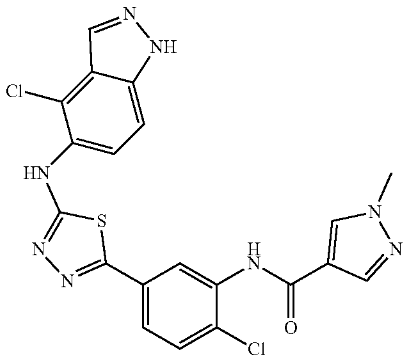 [SMILES: Cn1cc(C(=O)Nc2cc(-c3nnc(Nc4ccc5[nH]ncc5c4Cl)s3)ccc2Cl)cn1] |
TABLE 2
| Compound |
|---|
| 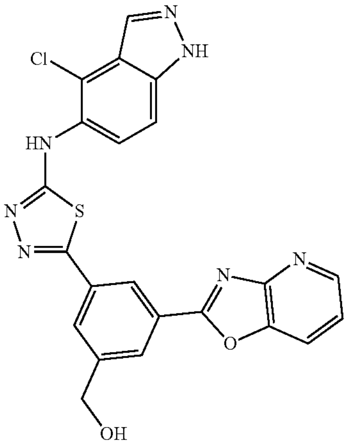 [SMILES: OCc1cc(-c2nc3ncccc3o2)cc(-c2nnc(Nc3ccc4[nH]ncc4c3Cl)s2)c1] |
| 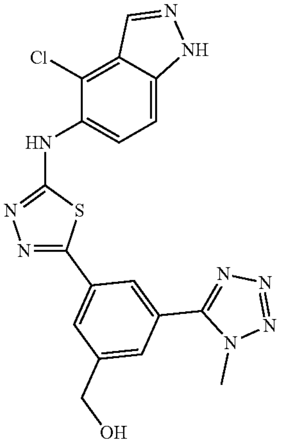 [SMILES: Cn1nnnc1-c1cc(CO)cc(-c2nnc(Nc3ccc4[nH]ncc4c3Cl)s2)c1] |
TABLE 2-continued
| Compound |
|---|
| 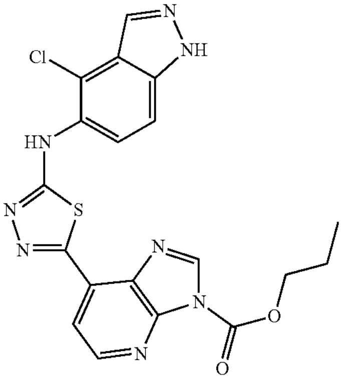 [SMILES: CCCOC(=O)n1cnc2c(-c3nnc(Nc4ccc5[nH]ncc5c4Cl)s3)ccnc21] |
| 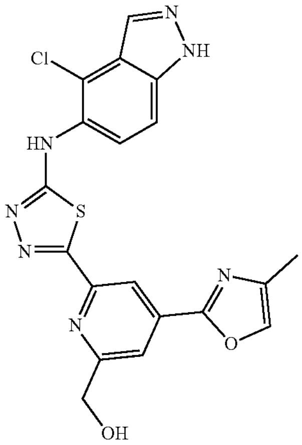 [SMILES: Cc1coc(-c2cc(CO)nc(-c3nnc(Nc4ccc5[nH]ncc5c4Cl)s3)c2)n1] |
| 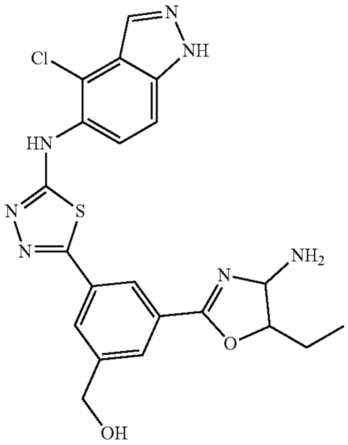 [SMILES: CCC1OC(c2cc(CO)cc(-c3nnc(Nc4ccc5[nH]ncc5c4Cl)s3)c2)=NC1N] |

TABLE 2-continued
| Compound |
| --- |
| 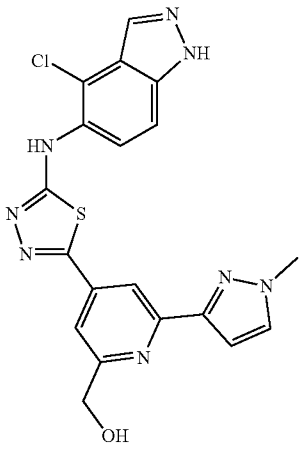 [SMILES: Cn1ccc(-c2cc(-c3nnc(Nc4ccc5[nH]ncc5c4Cl)s3)cc(CO)n2)n1] |
| 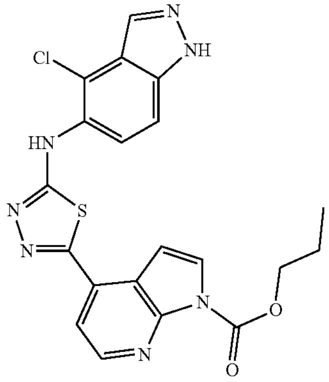 [SMILES: CCCOC(=O)n1ccc2c(-c3nnc(Nc4ccc5[nH]ncc5c4Cl)s3)ccnc21] |
| 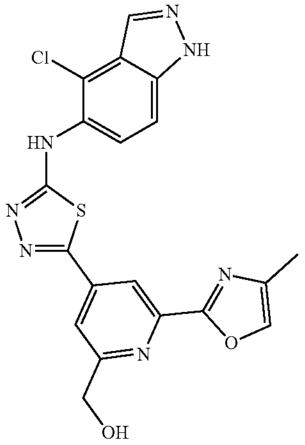 [SMILES: Cc1coc(-c2cc(-c3nnc(Nc4ccc5[nH]ncc5c4Cl)s3)cc(CO)n2)n1] |
TABLE 2-continued
| Compound |
| --- |
| 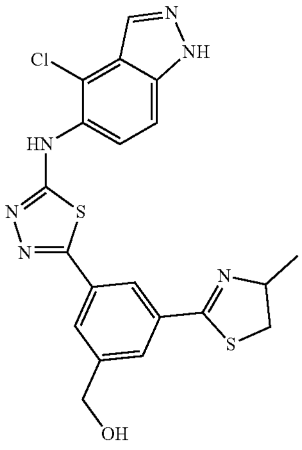 [SMILES: CC1CSC(c2cc(CO)cc(-c3nnc(Nc4ccc5[nH]ncc5c4Cl)s3)c2)=N1] |
| 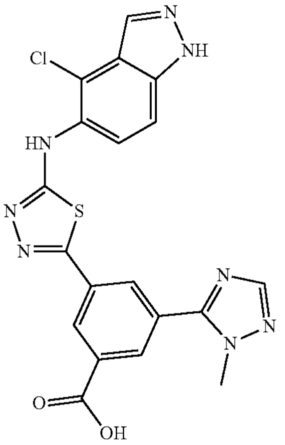 [SMILES: Cn1ncnc1-c1cc(C(=O)O)cc(-c2nnc(Nc3ccc4[nH]ncc4c3Cl)s2)c1] |
| 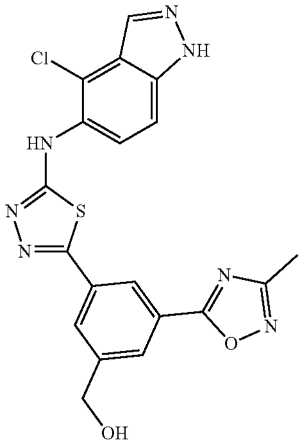 [SMILES: Cc1noc(-c2cc(CO)cc(-c3nnc(Nc4ccc5[nH]ncc5c4Cl)s3)c2)n1] |

TABLE 2-continued
| Compound |
| --- |
| 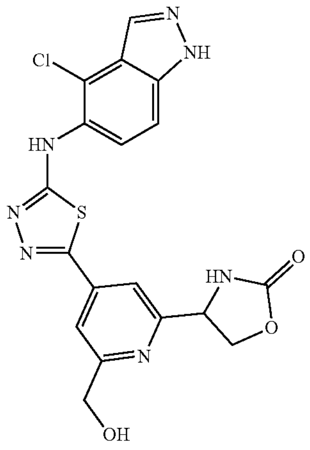 [SMILES: O=C1NC(c2cc(-c3nnc(Nc4ccc5[nH]ncc5c4Cl)s3)cc(CO)n2)CO1] |
| 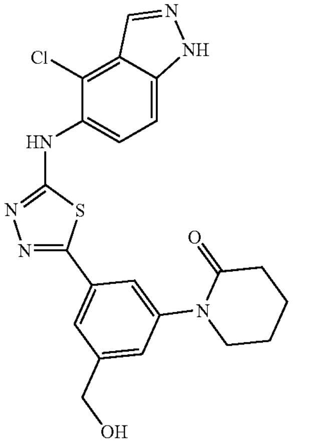 [SMILES: O=C1CCCCN1c1cc(CO)cc(-c2nnc(Nc3ccc4[nH]ncc4c3Cl)s2)c1] |
| 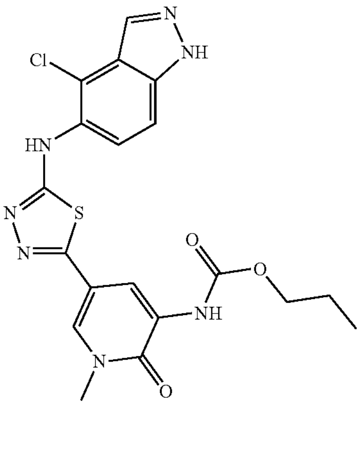 [SMILES: CCCOC(=O)Nc1cc(-c2nnc(Nc3ccc4[nH]ncc4c3Cl)s2)cn(C)c1=O] |
TABLE 2-continued
| Compound |
| --- |
| 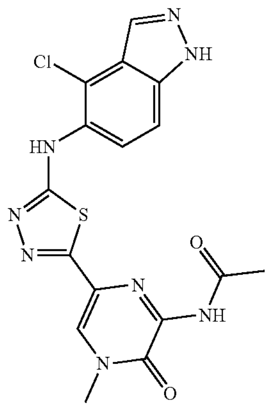 [SMILES: CC(=O)Nc1nc(-c2nnc(Nc3ccc4[nH]ncc4c3Cl)s2)cn(C)c1=O] |
| 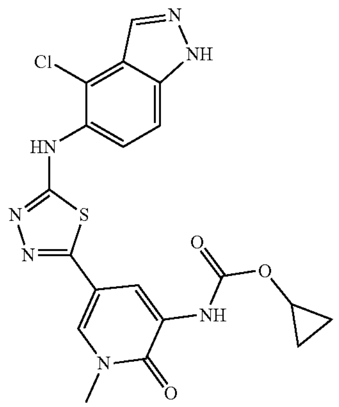 [SMILES: Cn1cc(-c2nnc(Nc3ccc4[nH]ncc4c3Cl)s2)cc(NC(=O)OC2CC2)c1=O] |
| 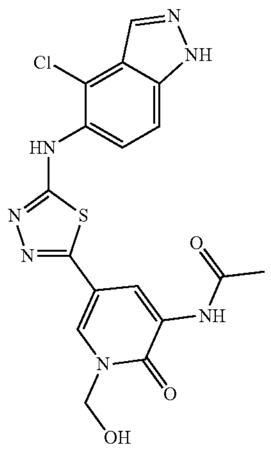 [SMILES: CC(=O)Nc1cc(-c2nnc(Nc3ccc4[nH]ncc4c3Cl)s2)cn(CO)c1=O] |

TABLE 2-continued
| Compound |
| --- |
| 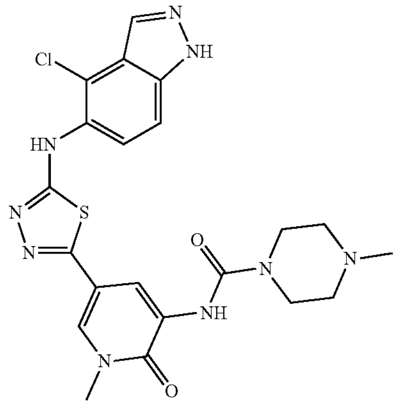 [SMILES: CN1CCN(C(=O)Nc2cc(-c3nnc(Nc4ccc5[nH]ncc5c4Cl)s3)cn(C)c2=O)CC1] |
| 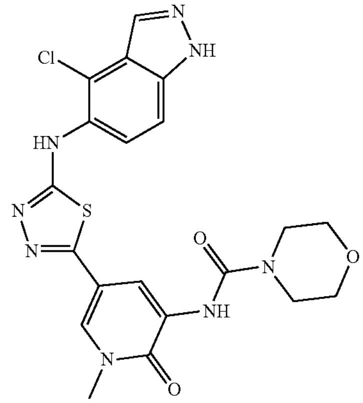 [SMILES: Cn1cc(-c2nnc(Nc3ccc4[nH]ncc4c3Cl)s2)cc(NC(=O)N2CCOCC2)c1=O] |
| 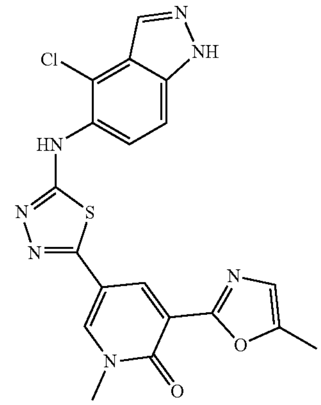 [SMILES: Cc1cnc(-c2cc(-c3nnc(Nc4ccc5[nH]ncc5c4Cl)s3)cn(C)c2=O)o1] |
TABLE 2-continued
| Compound |
| --- |
| 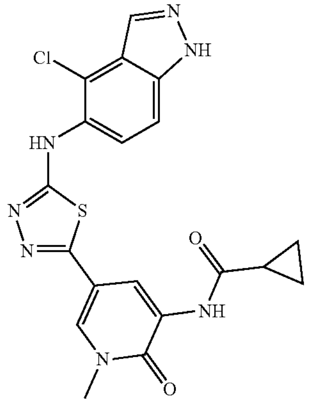 [SMILES: Cn1cc(-c2nnc(Nc3ccc4[nH]ncc4c3Cl)s2)cc(NC(=O)C2CC2)c1=O] |
| 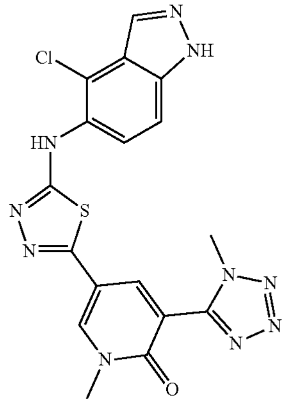 [SMILES: Cn1nnnc1-c1cc(-c2nnc(Nc3ccc4[nH]ncc4c3Cl)s2)cn(C)c1=O] |
| 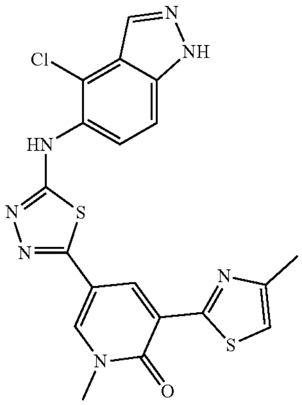 [SMILES: Cc1csc(-c2cc(-c3nnc(Nc4ccc5[nH]ncc5c4Cl)s3)cn(C)c2=O)n1] |

TABLE 2-continued
| Compound |
| --- |
| 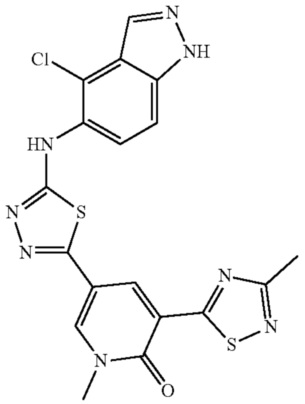 [SMILES: Cc1nsc(-c2cc(-c3nnc(Nc4ccc5[nH]ncc5c4Cl)s3)cn(C)c2=O)n1] |
| 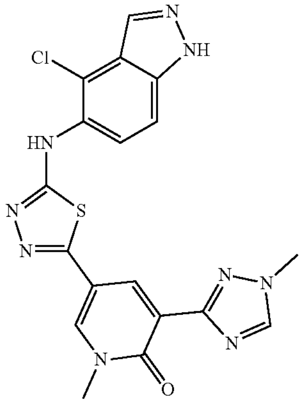 [SMILES: Cn1cnc(-c2cc(-c3nnc(Nc4ccc5[nH]ncc5c4Cl)s3)cn(C)c2=O)n1] |
| 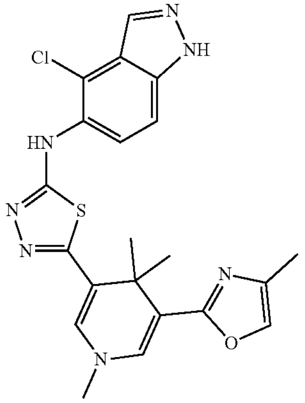 [SMILES: Cc1coc(C2=CN(C)C=C(c3nnc(Nc4ccc5[nH]ncc5c4Cl)s3)C2(C)C)n1] |
TABLE 2-continued
| Compound |
| --- |
| 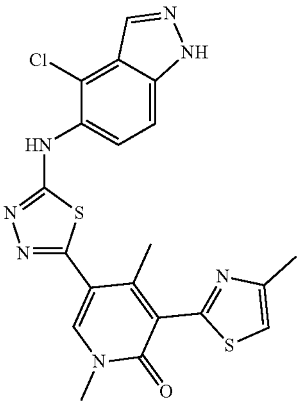 [SMILES: Cc1csc(-c2c(C)c(-c3nnc(Nc4ccc5[nH]ncc5c4Cl)s3)cn(C)c2=O)n1] |
| 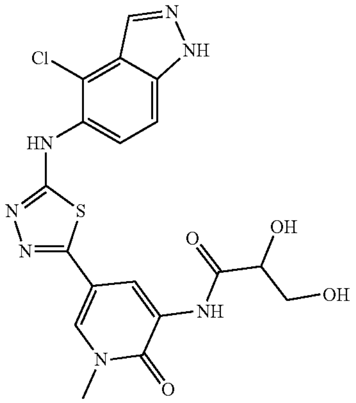 [SMILES: Cn1cc(-c2nnc(Nc3ccc4[nH]ncc4c3Cl)s2)cc(NC(=O)C(O)CO)c1=O] |
| 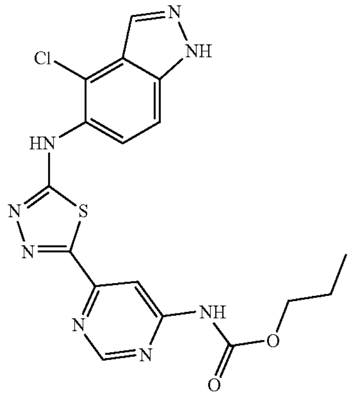 [SMILES: CCCOC(=O)Nc1cc(-c2nnc(Nc3ccc4[nH]ncc4c3Cl)s2)ncn1] |
| 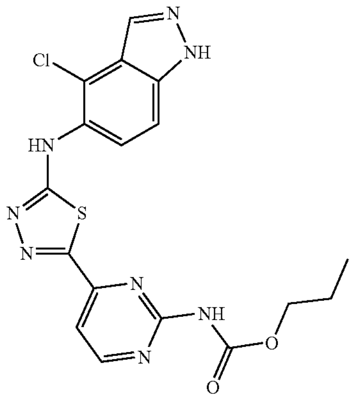 [SMILES: CCCOC(=O)Nc1nccc(-c2nnc(Nc3ccc4[nH]ncc4c3Cl)s2)n1] |

TABLE 2-continued
| Compound |
|---|
| 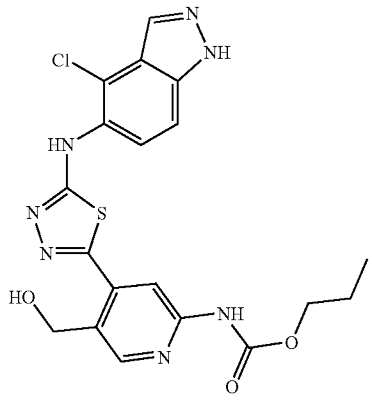 [SMILES: CCCOC(=O)Nc1cc(-c2nnc(Nc3ccc4[nH]ncc4c3Cl)s2)c(CO)cn1] |
| 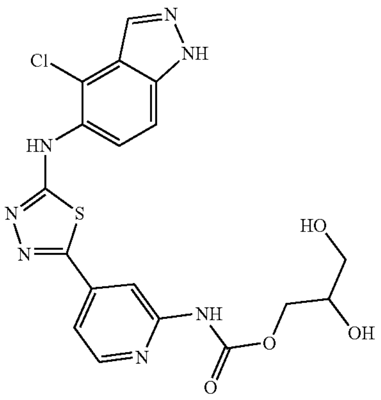 [SMILES: O=C(Nc1cc(-c2nnc(Nc3ccc4[nH]ncc4c3Cl)s2)ccn1)OCC(O)CO] |
| 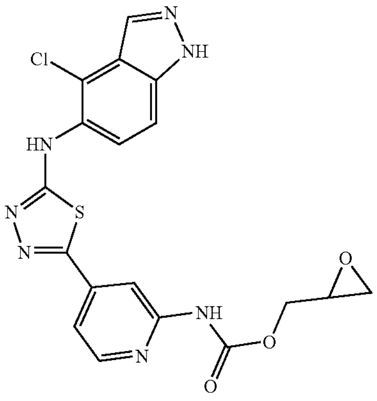 [SMILES: O=C(Nc1cc(-c2nnc(Nc3ccc4[nH]ncc4c3Cl)s2)ccn1)OCC1CO1] |
| 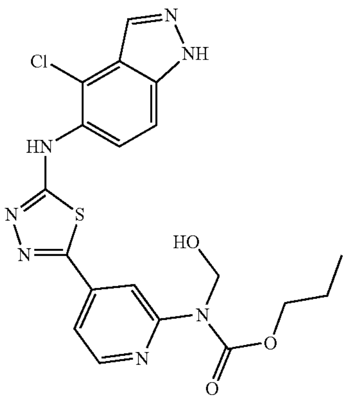 [SMILES: CCCOC(=O)N(CO)c1cc(-c2nnc(Nc3ccc4[nH]ncc4c3Cl)s2)ccn1] |
TABLE 2-continued
| Compound |
|---|
| 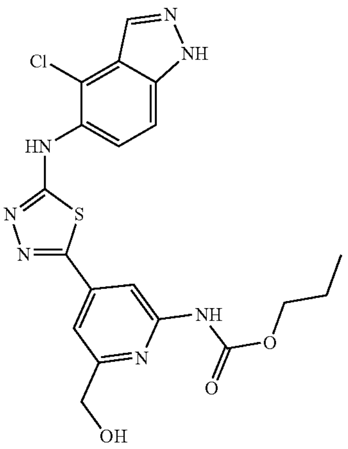 [SMILES: CCCOC(=O)Nc1cc(-c2nnc(Nc3ccc4[nH]ncc4c3Cl)s2)cc(CO)n1] |
| 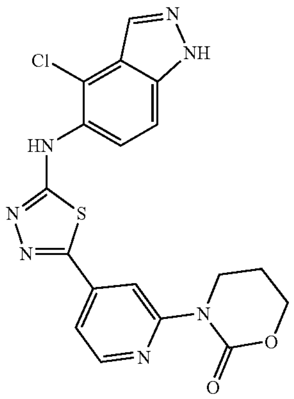 [SMILES: O=C1OCCCN1c1cc(-c2nnc(Nc3ccc4[nH]ncc4c3Cl)s2)ccn1] |
| 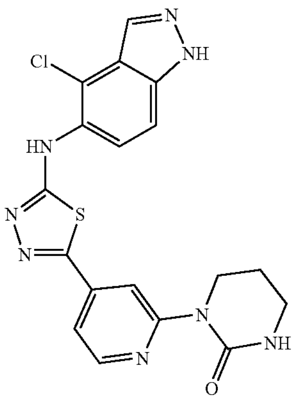 [SMILES: O=C1NCCCN1c1cc(-c2nnc(Nc3ccc4[nH]ncc4c3Cl)s2)ccn1] |

TABLE 2-continued
| Compound |
| --- |
| 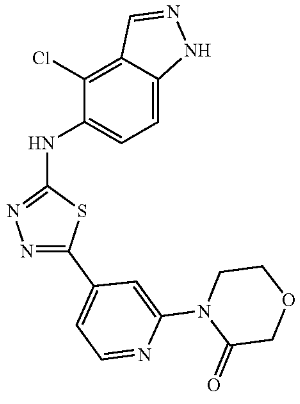 [SMILES: O=C1COCCN1c1cc(-c2nnc(Nc3ccc4[nH]ncc4c3Cl)s2)ccn1] |
| 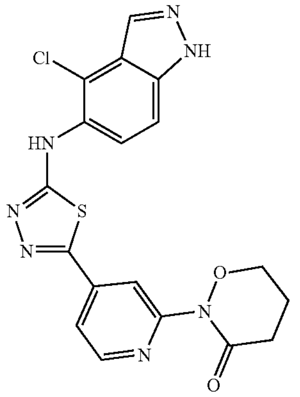 [SMILES: O=C1CCCON1c1cc(-c2nnc(Nc3ccc4[nH]ncc4c3Cl)s2)ccn1] |
| 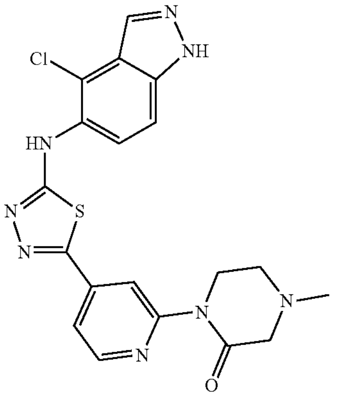 [SMILES: CN1CCN(c2cc(-c3nnc(Nc4ccc5[nH]ncc5c4Cl)s3)ccn2)C(=O)C1] |
| 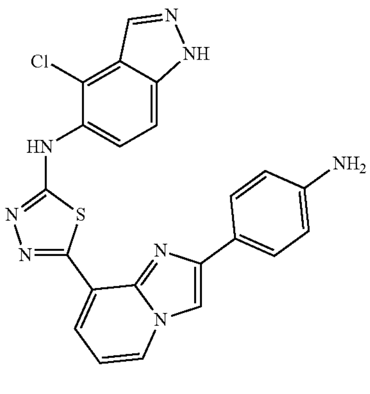 [SMILES: Nc1ccc(-c2cn3cccc(-c4nnc(Nc5ccc6[nH]ncc6c5Cl)s4)c3n2)cc1] |
TABLE 2-continued
| Compound |
| --- |
| 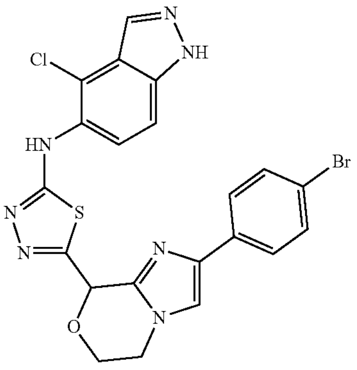 [SMILES: Clc1c(Nc2nnc(C3OCCn4cc(-c5ccc(Br)cc5)nc43)s2)ccc2[nH]ncc12] |
| 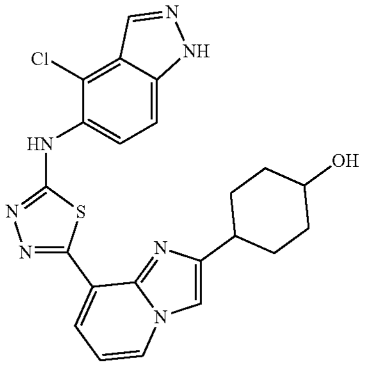 [SMILES: OC1CCC(c2cn3cccc(-c4nnc(Nc5ccc6[nH]ncc6c5Cl)s4)c3n2)CC1] |
| 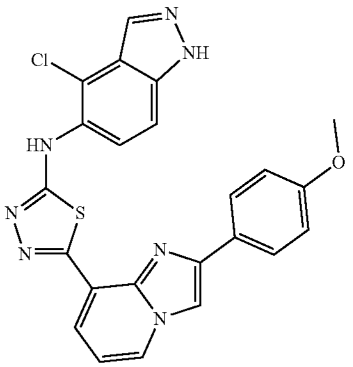 [SMILES: COc1ccc(-c2cn3cccc(-c4nnc(Nc5ccc6[nH]ncc6c5Cl)s4)c3n2)cc1] |
| 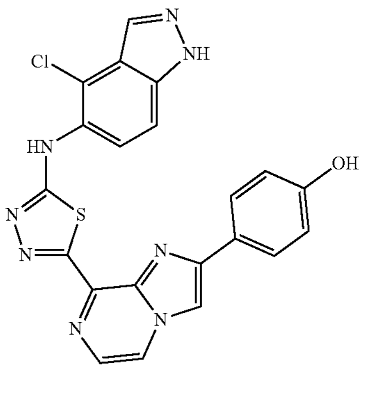 [SMILES: Oc1ccc(-c2cn3ccnc(-c4nnc(Nc5ccc6[nH]ncc6c5Cl)s4)c3n2)cc1] |

TABLE 2-continued
| Compound |
|---|
| 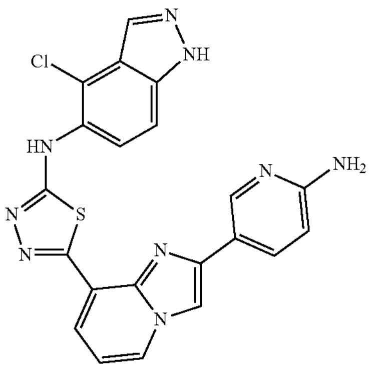 [SMILES: Nc1ccc(-c2cn3cccc(-c4nnc(Nc5ccc6[nH]ncc6c5Cl)s4)c3n2)cn1] |
| 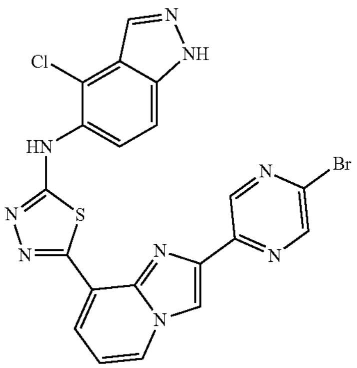 [SMILES: Clc1c(Nc2nnc(-c3cccn4cc(-c5cnc(Br)cn5)nc34)s2)ccc2[nH]ncc12] |
| 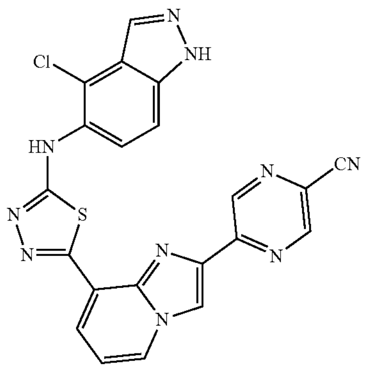 [SMILES: N#Cc1cnc(-c2cn3cccc(-c4nnc(Nc5ccc6[nH]ncc6c5Cl)s4)c3n2)cn1] |
| 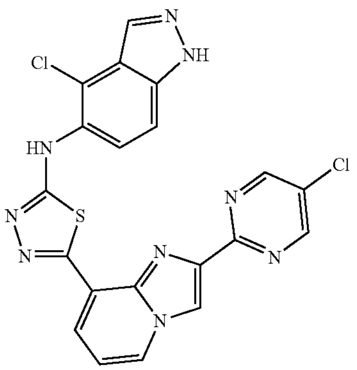 [SMILES: Clc1cnc(-c2cn3cccc(-c4nnc(Nc5ccc6[nH]ncc6c5Cl)s4)c3n2)nc1] |
TABLE 2-continued
| Compound |
|---|
| 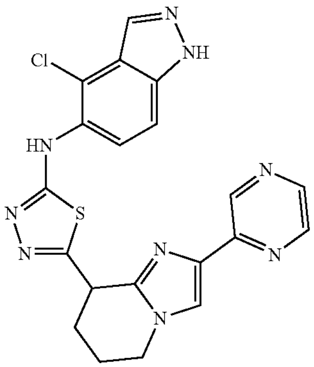 [SMILES: Clc1c(Nc2nnc(C3CCCn4cc(-c5cnccn5)nc43)s2)ccc2[nH]ncc12] |
| 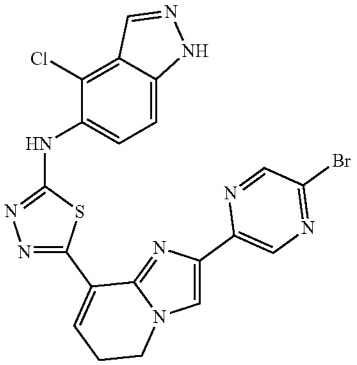 [SMILES: Clc1c(Nc2nnc(C3=CCCn4cc(-c5cnc(Br)cn5)nc43)s2)ccc2[nH]ncc12] |
| 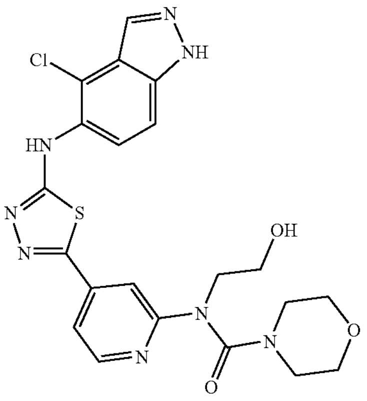 [SMILES: O=C(N1CCOCC1)N(CCO)c1cc(-c2nnc(Nc3ccc4[nH]ncc4c3Cl)s2)ccn1] |
| 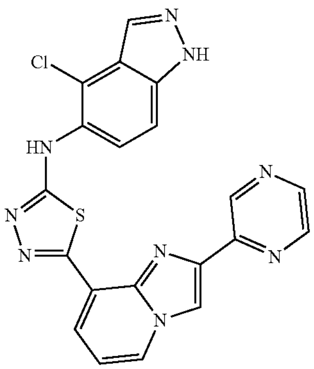 [SMILES: Clc1c(Nc2nnc(-c3cccn4cc(-c5cnccn5)nc34)s2)ccc2[nH]ncc12] |

TABLE 2-continued
| Compound |
|---|
| 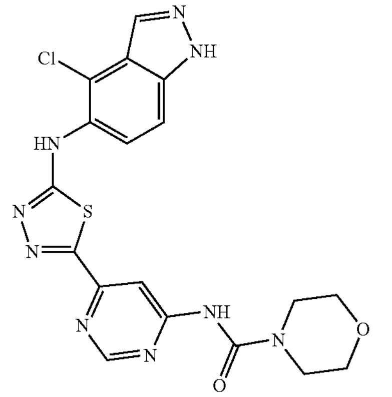 [SMILES: O=C(Nc1cc(-c2nnc(Nc3ccc4[nH]ncc4c3Cl)s2)ncn1)N1CCOCC1] |
| 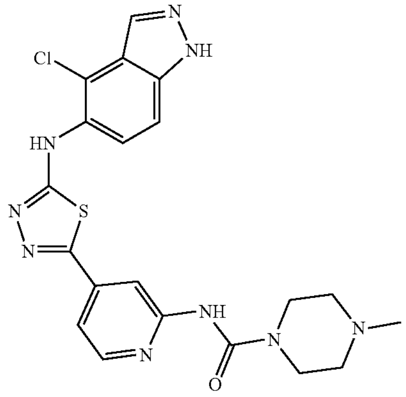 [SMILES: CN1CCN(C(=O)Nc2cc(-c3nnc(Nc4ccc5[nH]ncc5c4Cl)s3)ccn2)CC1] |
| 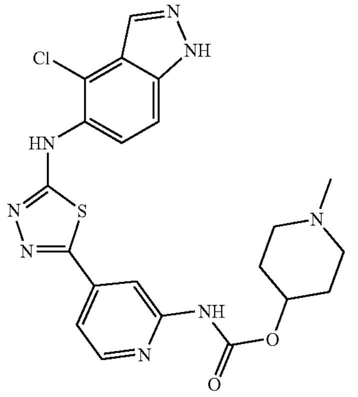 [SMILES: CN1CCC(OC(=O)Nc2cc(-c3nnc(Nc4ccc5[nH]ncc5c4Cl)s3)ccn2)CC1] |
| 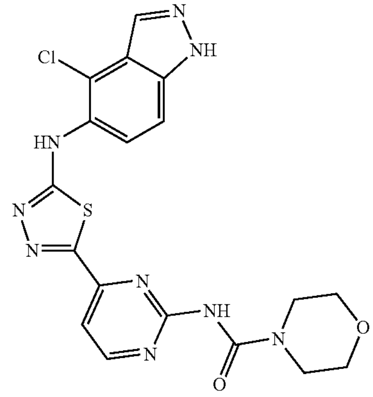 [SMILES: O=C(Nc1nccc(-c2nnc(Nc3ccc4[nH]ncc4c3Cl)s2)n1)N1CCOCC1] |
TABLE 2-continued
| Compound |
|---|
| 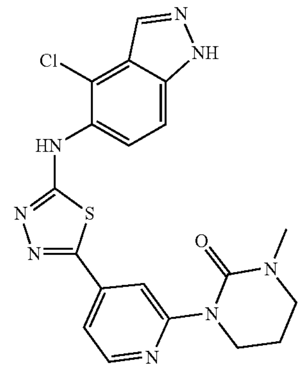 [SMILES: CN1CCCN(c2cc(-c3nnc(Nc4ccc5[nH]ncc5c4Cl)s3)ccn2)C1=O] |
| 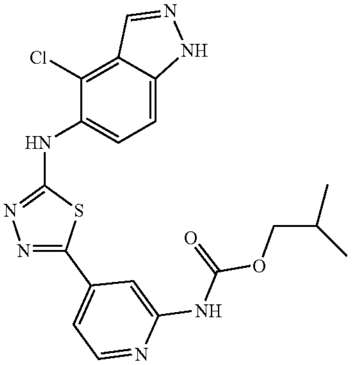 [SMILES: CC(C)COC(=O)Nc1cc(-c2nnc(Nc3ccc4[nH]ncc4c3Cl)s2)ccn1] |
| 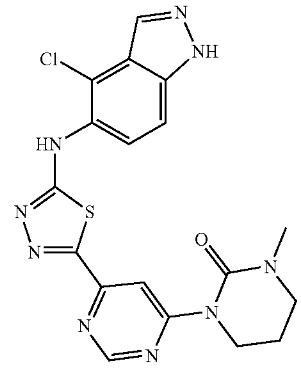 [SMILES: CN1CCCN(c2cc(-c3nnc(Nc4ccc5[nH]ncc5c4Cl)s3)ncn2)C1=O] |
| 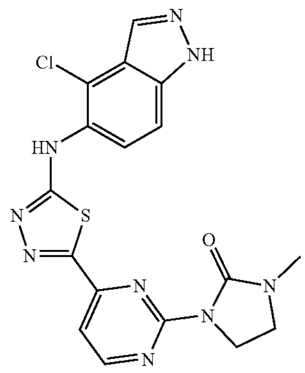 [SMILES: CN1CCN(c2nccc(-c3nnc(Nc4ccc5[nH]ncc5c4Cl)s3)n2)C1=O] |

TABLE 2-continued
| Compound |
|---|
| 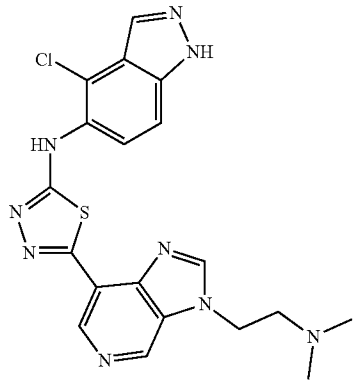 [SMILES: CN(C)CCn1cnc2c(-c3nnc(Nc4ccc5[nH]ncc5c4Cl)s3)cncc21] |
| 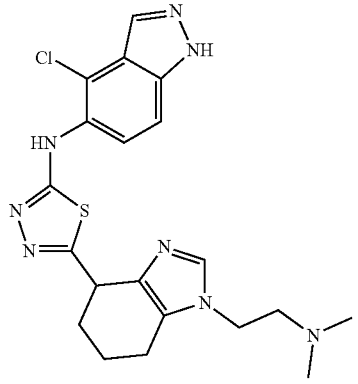 [SMILES: CN(C)CCn1cnc2c1CCCC2c1nnc(Nc2ccc3[nH]ncc3c2Cl)s1] |
| 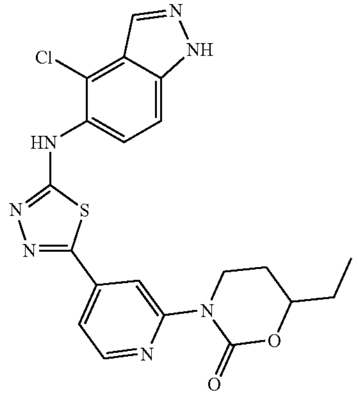 [SMILES: CCC1CCN(c2cc(-c3nnc(Nc4ccc5[nH]ncc5c4Cl)s3)ccn2)C(=O)O1] |
| 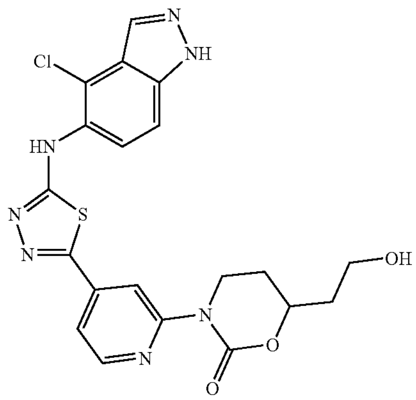 [SMILES: O=C1OC(CCO)CCN1c1cc(-c2nnc(Nc3ccc4[nH]ncc4c3Cl)s2)ccn1] |
TABLE 2-continued
| Compound |
|---|
| 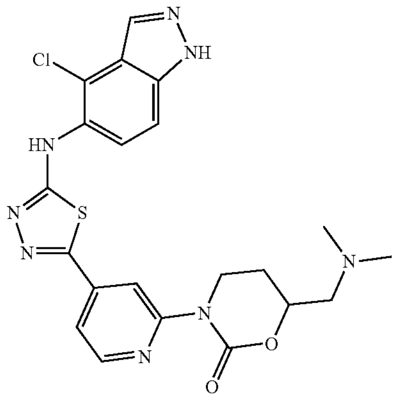 [SMILES: CN(C)CC1CCN(c2cc(-c3nnc(Nc4ccc5[nH]ncc5c4Cl)s3)ccn2)C(=O)O1] |
| 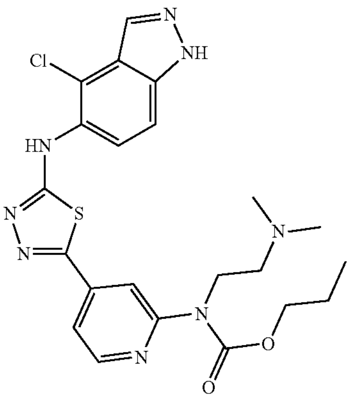 [SMILES: CCCOC(=O)N(CCN(C)C)c1cc(-c2nnc(Nc3ccc4[nH]ncc4c3Cl)s2)ccn1] |
| 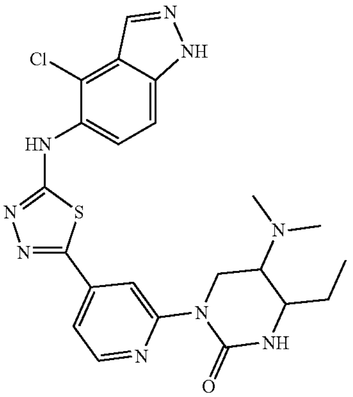 [SMILES: CCC1NC(=O)N(c2cc(-c3nnc(Nc4ccc5[nH]ncc5c4Cl)s3)ccn2)CC1N(C)C] |
| 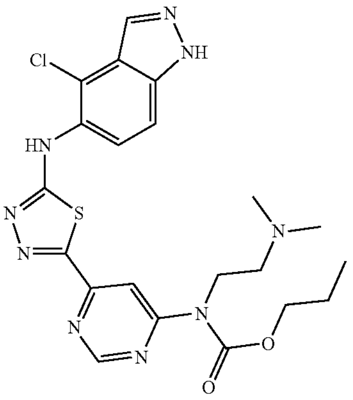 [SMILES: CCCOC(=O)N(CCN(C)C)c1cc(-c2nnc(Nc3ccc4[nH]ncc4c3Cl)s2)ncn1] |

TABLE 2-continued
| Compound |
| --- |
| 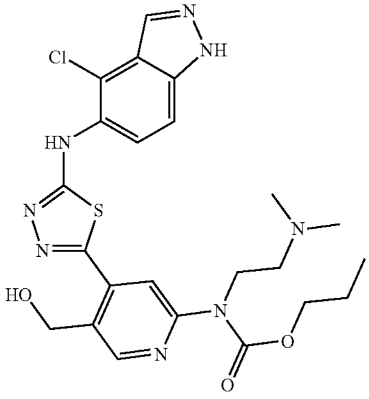 [SMILES: CCCOC(=O)N(CCN(C)C)c1cc(-c2nnc(Nc3ccc4[nH]ncc4c3Cl)s2)c(CO)cn1] |
| 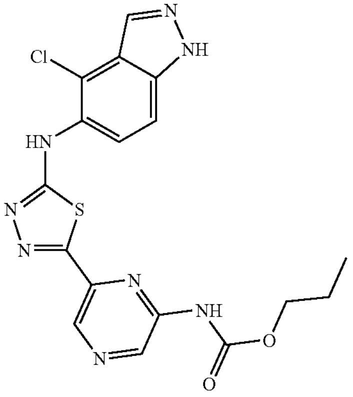 [SMILES: CCCOC(=O)Nc1cncc(-c2nnc(Nc3ccc4[nH]ncc4c3Cl)s2)n1] |
| 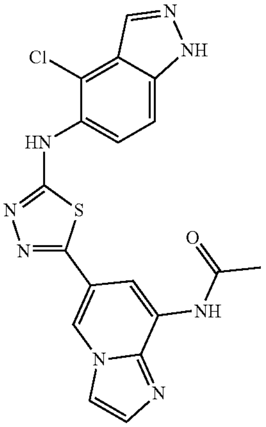 [SMILES: CC(=O)Nc1cc(-c2nnc(Nc3ccc4[nH]ncc4c3Cl)s2)cn2ccnc12] |
| 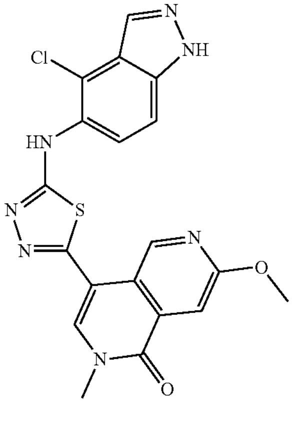 [SMILES: COc1cc2c(=O)n(C)cc(-c3nnc(Nc4ccc5[nH]ncc5c4Cl)s3)c2cn1] |
TABLE 2-continued
| Compound |
| --- |
| 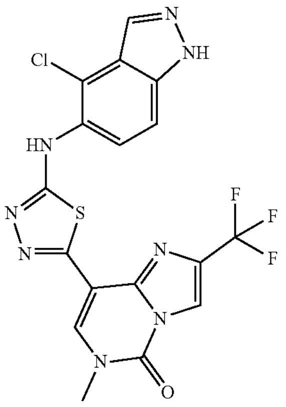 [SMILES: Cn1cc(-c2nnc(Nc3ccc4[nH]ncc4c3Cl)s2)c2nc(C(F)(F)F)cn2c1=O] |
| 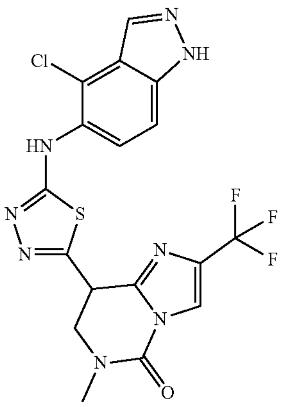 [SMILES: CN1CC(c2nnc(Nc3ccc4[nH]ncc4c3Cl)s2)c2nc(C(F)(F)F)cn2C1=O] |
| 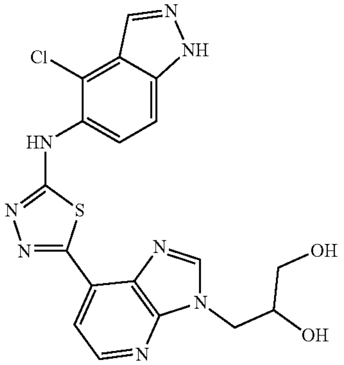 [SMILES: OCC(O)Cn1cnc2c(-c3nnc(Nc4ccc5[nH]ncc5c4Cl)s3)ccnc21] |
| 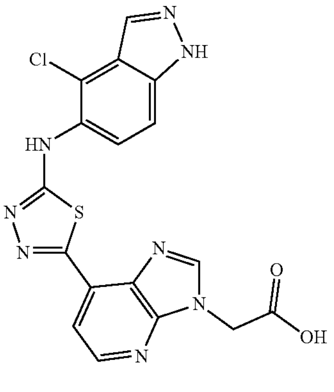 [SMILES: O=C(O)Cn1cnc2c(-c3nnc(Nc4ccc5[nH]ncc5c4Cl)s3)ccnc21] |

TABLE 2-continued
| Compound |
| --- |
| 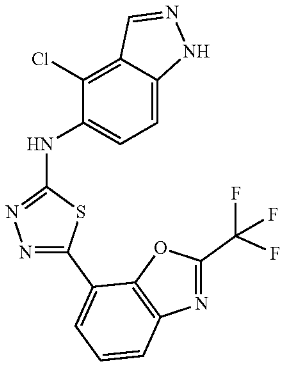 [SMILES: FC(F)(F)c1nc2cccc(-c3nnc(Nc4ccc5[nH]ncc5c4Cl)s3)c2o1] |
| 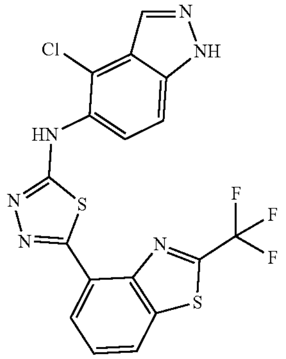 [SMILES: FC(F)(F)c1nc2c(-c3nnc(Nc4ccc5[nH]ncc5c4Cl)s3)cccc2s1] |
| 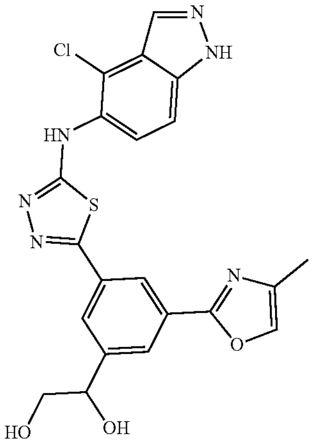 [SMILES: Cc1coc(-c2cc(-c3nnc(Nc4ccc5[nH]ncc5c4Cl)s3)cc(C(O)CO)c2)n1] |
| 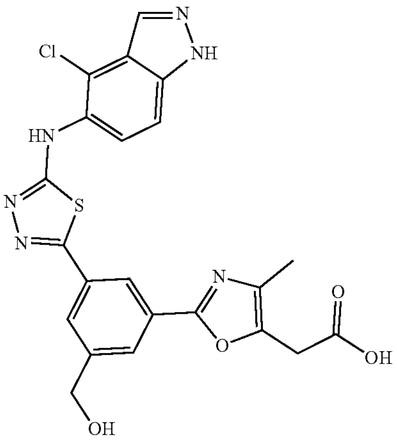 [SMILES: Cc1nc(-c2cc(CO)cc(-c3nnc(Nc4ccc5[nH]ncc5c4Cl)s3)c2)oc1CC(=O)O] |
TABLE 2-continued
| Compound |
| --- |
| 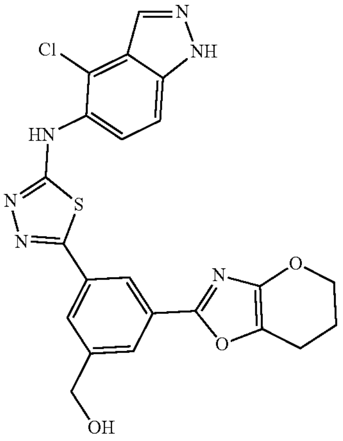 [SMILES: OCc1cc(-c2nc3c(o2)CCCO3)cc(-c2nnc(Nc3ccc4[nH]ncc4c3Cl)s2)c1] |
| 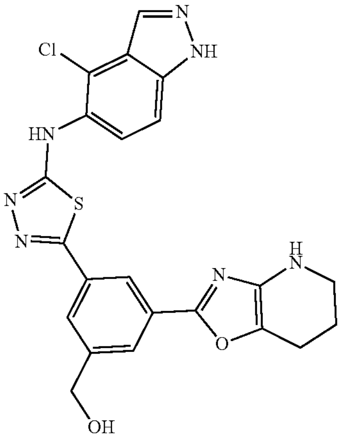 [SMILES: OCc1cc(-c2nc3c(o2)CCCN3)cc(-c2nnc(Nc3ccc4[nH]ncc4c3Cl)s2)c1] |
| 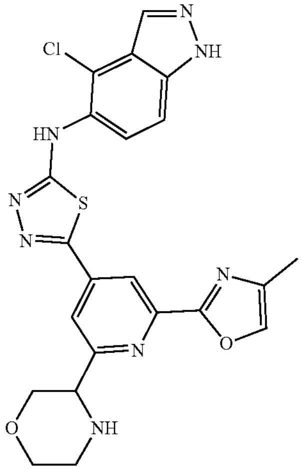 [SMILES: Cc1coc(-c2cc(-c3nnc(Nc4ccc5[nH]ncc5c4Cl)s3)cc(C3COCCN3)n2)n1] |

TABLE 2-continued
| Compound |
| --- |
| 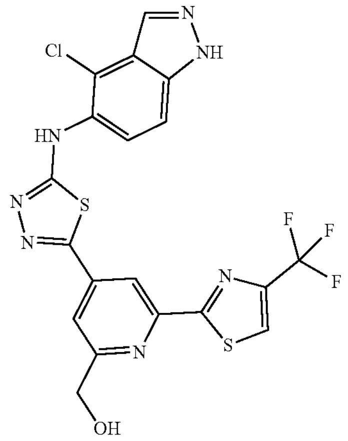 [SMILES: OCc1cc(-c2nnc(Nc3ccc4[nH]ncc4c3Cl)s2)cc(-c2nc(C(F)(F)F)cs2)n1] |
| 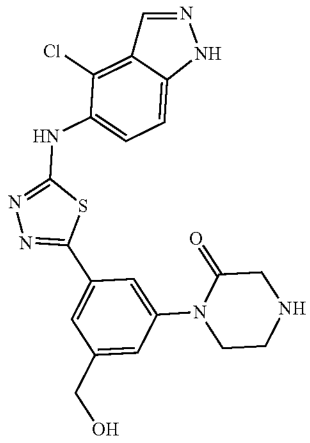 [SMILES: O=C1CNCCN1c1cc(CO)cc(-c2nnc(Nc3ccc4[nH]ncc4c3Cl)s2)c1] |
| 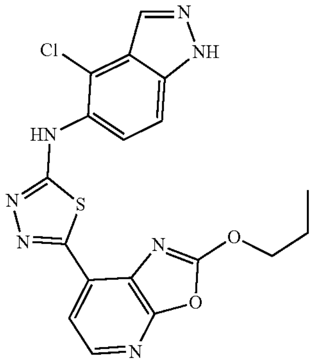 [SMILES: CCCOc1nc2c(-c3nnc(Nc4ccc5[nH]ncc5c4Cl)s3)ccnc2o1] |
| 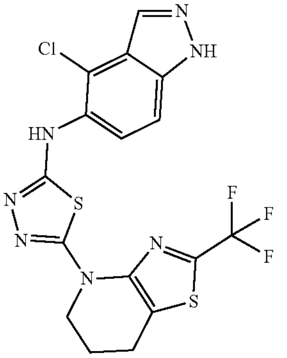 [SMILES: FC(F)(F)c1nc2c(s1)CCCN2c1nnc(Nc2ccc3[nH]ncc3c2Cl)s1] |
TABLE 2-continued
| Compound |
| --- |
| 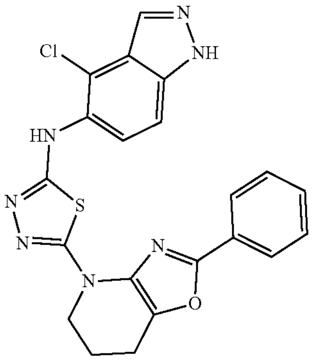 [SMILES: Clc1c(Nc2nnc(N3CCCc4oc(-c5ccccc5)nc43)s2)ccc2[nH]ncc12] |
| 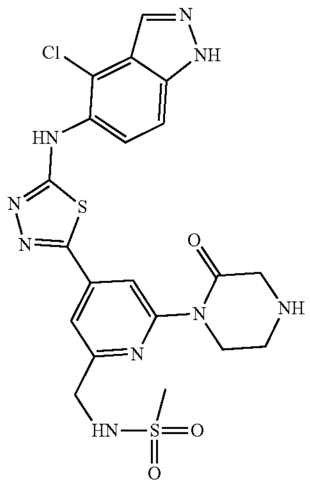 [SMILES: CS(=O)(=O)NCc1cc(-c2nnc(Nc3ccc4[nH]ncc4c3Cl)s2)cc(N2CCNCC2=O)n1] |
| 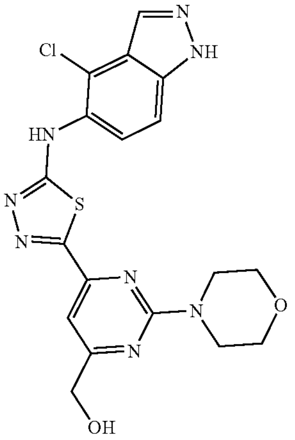 [SMILES: OCc1cc(-c2nnc(Nc3ccc4[nH]ncc4c3Cl)s2)nc(N2CCOCC2)n1] |

TABLE 2-continued
| Compound |
| --- |
| 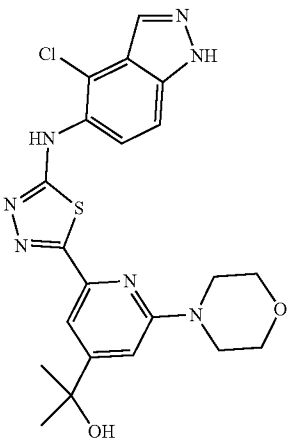 [SMILES: CC(C)(O)c1cc(-c2nnc(Nc3ccc4[nH]ncc4c3Cl)s2)nc(N2CCOCC2)c1] |
| 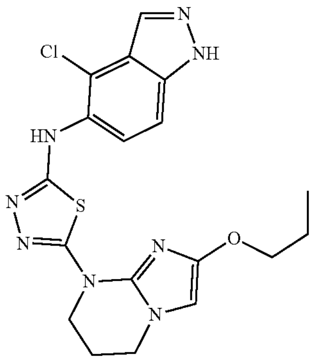 [SMILES: CCCOc1cn2c(n1)N(c1nnc(Nc3ccc4[nH]ncc4c3Cl)s1)CCC2] |
| 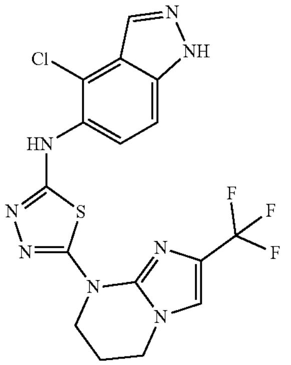 [SMILES: FC(F)(F)c1cn2c(n1)N(c1nnc(Nc3ccc4[nH]ncc4c3Cl)s1)CCC2] |
| 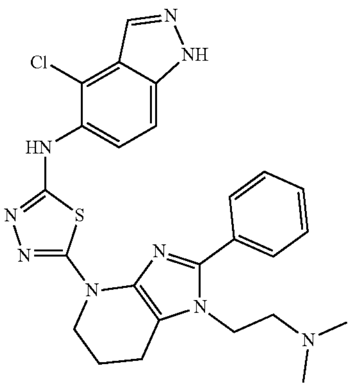 [SMILES: CN(C)CCn1c(-c2ccccc2)nc2c1CCCN2c1nnc(Nc2ccc3[nH]ncc3c2Cl)s1] |
TABLE 2-continued
| Compound |
| --- |
| 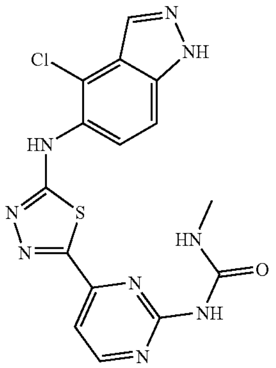 [SMILES: CNC(=O)Nc1nccc(-c2nnc(Nc3ccc4[nH]ncc4c3Cl)s2)n1] |
| 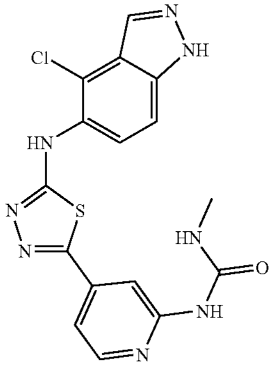 [SMILES: CNC(=O)Nc1cc(-c2nnc(Nc3ccc4[nH]ncc4c3Cl)s2)ccn1] |
| 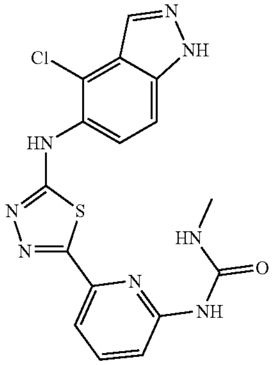 [SMILES: CNC(=O)Nc1cccc(-c2nnc(Nc3ccc4[nH]ncc4c3Cl)s2)n1] |
| 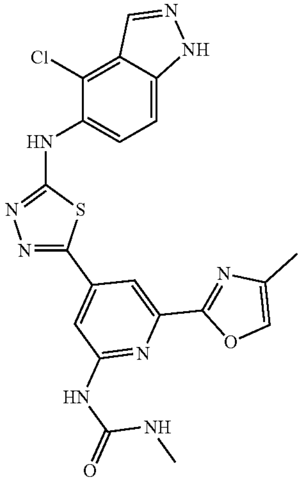 [SMILES: CNC(=O)Nc1cc(-c2nnc(Nc3ccc4[nH]ncc4c3Cl)s2)cc(-c2nc(C)co2)n1] |

TABLE 2-continued
| Compound |
| --- |
| 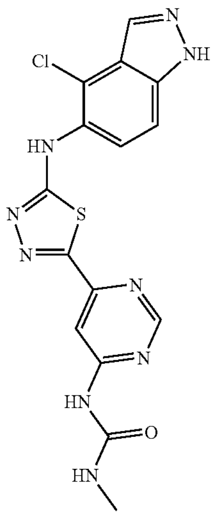 [SMILES: CNC(=O)Nc1cc(-c2nnc(Nc3ccc4[nH]ncc4c3Cl)s2)ncn1] |
| 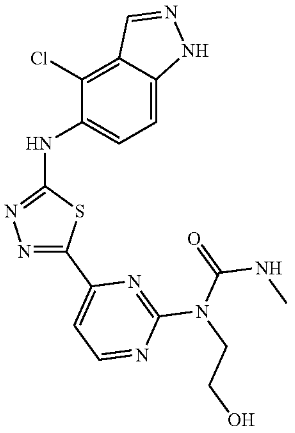 [SMILES: CNC(=O)N(CCO)c1nccc(-c2nnc(Nc3ccc4[nH]ncc4c3Cl)s2)n1] |
| 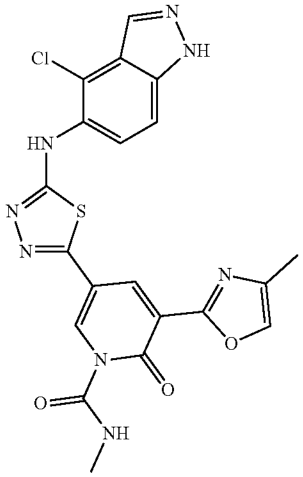 [SMILES: CNC(=O)n1cc(-c2nnc(Nc3ccc4[nH]ncc4c3Cl)s2)cc(-c2nc(C)co2)c1=O] |
TABLE 2-continued
| Compound |
| --- |
| 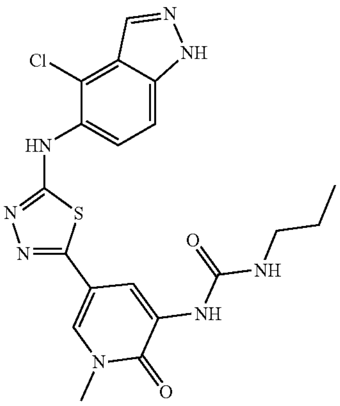 [SMILES: CCCNC(=O)Nc1cc(-c2nnc(Nc3ccc4[nH]ncc4c3Cl)s2)cn(C)c1=O] |
| 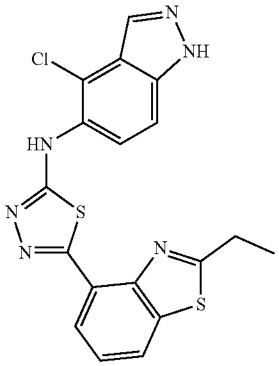 [SMILES: CCc1nc2c(-c3nnc(Nc4ccc5[nH]ncc5c4Cl)s3)cccc2s1] |
| 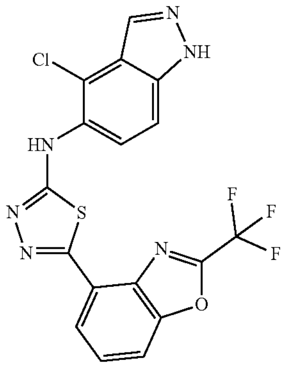 [SMILES: FC(F)(F)c1nc2c(-c3nnc(Nc4ccc5[nH]ncc5c4Cl)s3)cccc2o1] |
| 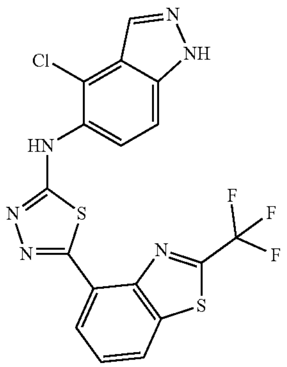 [SMILES: FC(F)(F)c1nc2c(-c3nnc(Nc4ccc5[nH]ncc5c4Cl)s3)cccc2s1] |

TABLE 2-continued
| Compound |
|---|
| 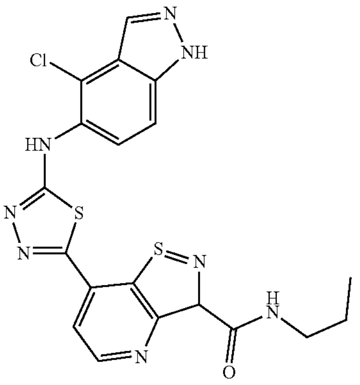 |
| 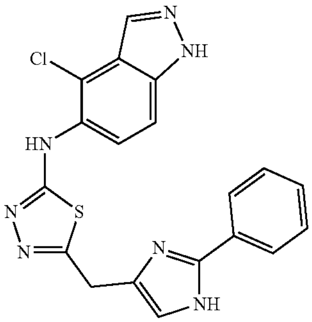 [SMILES: Clc1c(Nc2nnc(Cc3c[nH]c(-c4ccccc4)n3)s2)ccc2[nH]ncc12] |
| 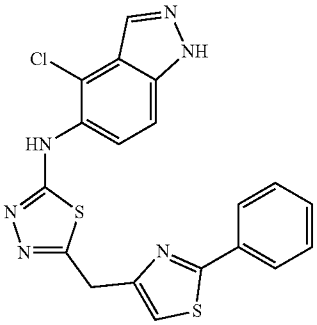 [SMILES: Clc1c(Nc2nnc(Cc3csc(-c4ccccc4)n3)s2)ccc2[nH]ncc12] |
| 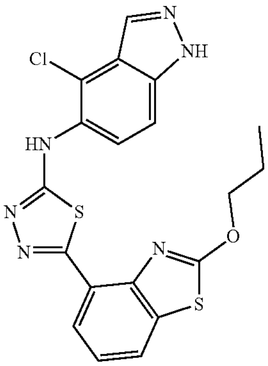 [SMILES: CCCOc1nc2c(-c3nnc(Nc4ccc5[nH]ncc5c4Cl)s3)cccc2s1] |
TABLE 2-continued
| Compound |
|---|
| 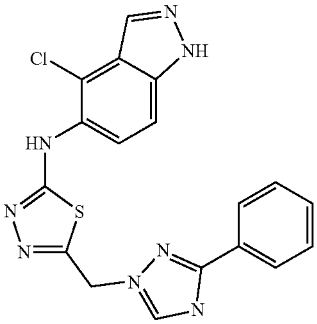 |
| 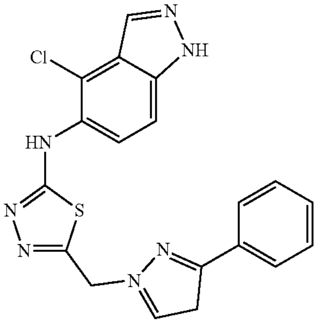 |
| 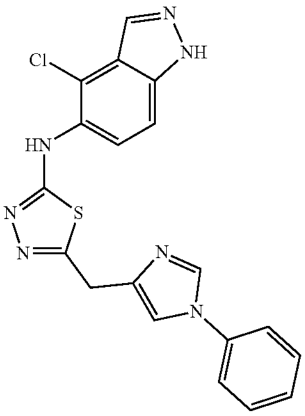 [SMILES: Clc1c(Nc2nnc(Cc3cn(-c4ccccc4)cn3)s2)ccc2[nH]ncc12] |
| 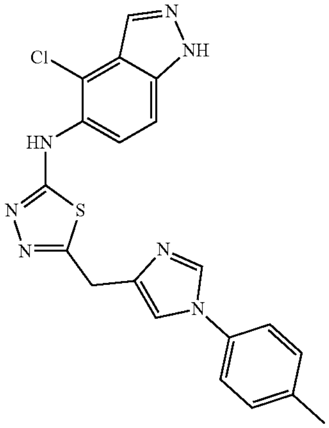 [SMILES: Cc1ccc(-n2cnc(Cc3nnc(Nc4ccc5[nH]ncc5c4Cl)s3)c2)cc1] |

TABLE 3
| Example No. | Chemical Structure |
| --- | --- |
| 35A | 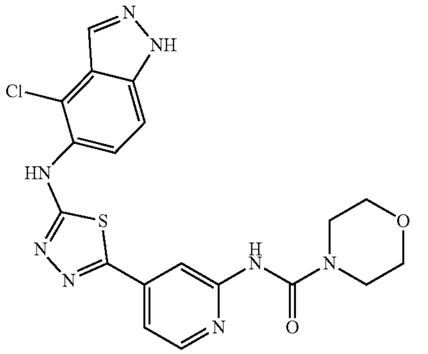 [SMILES: O=C(Nc1cc(-c2nnc(Nc3ccc4[nH]ncc4c3Cl)s2)ccn1)N1CCOCC1] |
| 35B | 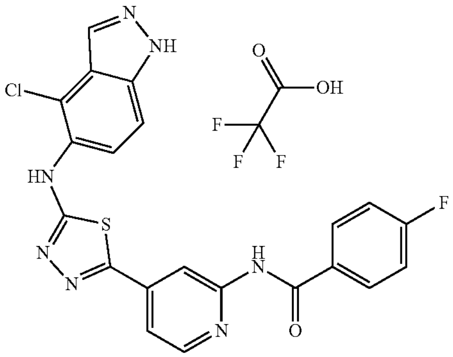 [SMILES: O=C(Nc1cc(-c2nnc(Nc3ccc4[nH]ncc4c3Cl)s2)ccn1)c1ccc(F)cc1 ; O=C(O)C(F)(F)F] |
| 35C | 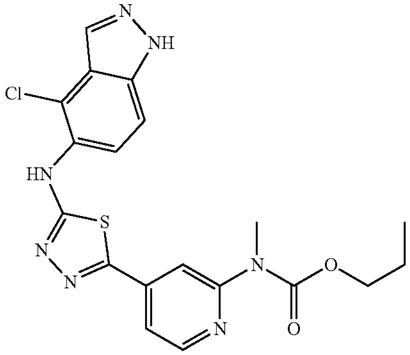 [SMILES: CCCOC(=O)N(C)c1cc(-c2nnc(Nc3ccc4[nH]ncc4c3Cl)s2)ccn1] |
| 35D | 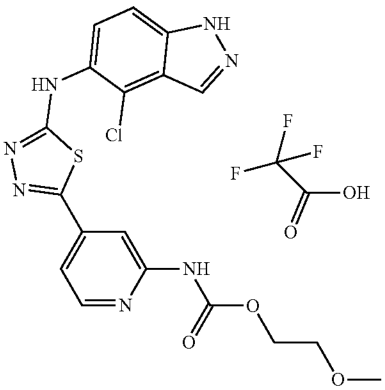 [SMILES: COCCOC(=O)Nc1cc(-c2nnc(Nc3ccc4[nH]ncc4c3Cl)s2)ccn1 ; O=C(O)C(F)(F)F] |
TABLE 3-continued
| Example No. | Chemical Structure |
| --- | --- |
| 35E | 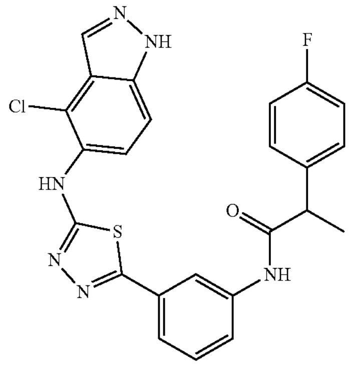 [SMILES: CC(C(=O)Nc1cccc(-c2nnc(Nc3ccc4[nH]ncc4c3Cl)s2)c1)c1ccc(F)cc1] |
| 35F | 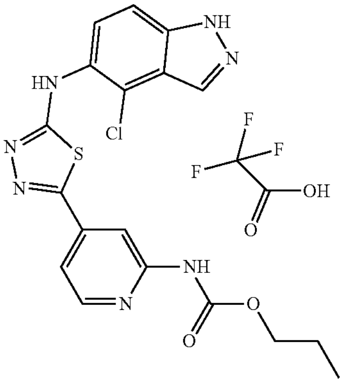 |
| 35G | 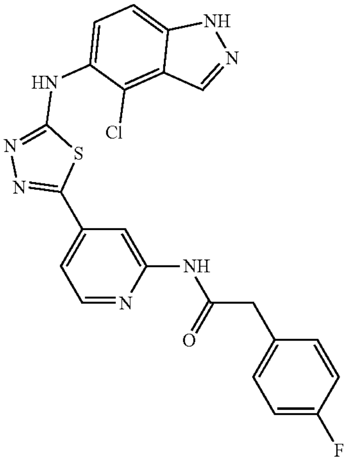 [SMILES: O=C(Cc1ccc(F)cc1)Nc1cc(-c2nnc(Nc3ccc4[nH]ncc4c3Cl)s2)ccn1] |

TABLE 3-continued
| Example No. | Chemical Structure |
|---|---|
| 35H | 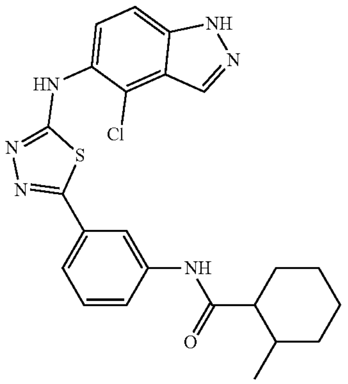 [SMILES: CC1CCCCC1C(=O)Nc1cccc(-c2nnc(Nc3ccc4[nH]ncc4c3Cl)s2)c1] |
| 35I | 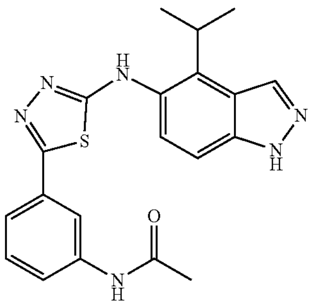 [SMILES: CC(=O)Nc1cccc(-c2nnc(Nc3ccc4[nH]ncc4c3C(C)C)s2)c1] |
| 35J | 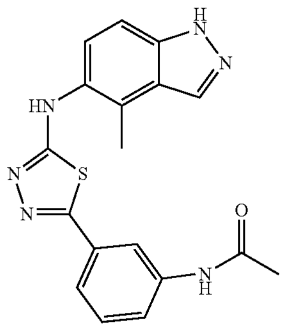 [SMILES: CC(=O)Nc1cccc(-c2nnc(Nc3ccc4[nH]ncc4c3C)s2)c1] |
| 35K | 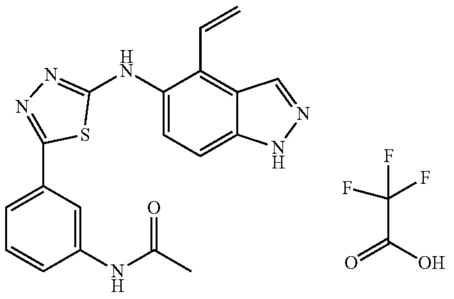 [SMILES: C=Cc1c(Nc2nnc(-c3cccc(NC(C)=O)c3)s2)ccc2[nH]ncc12 ; O=C(O)C(F)(F)F] |
TABLE 3-continued
| Example No. | Chemical Structure |
|---|---|
| 35L | 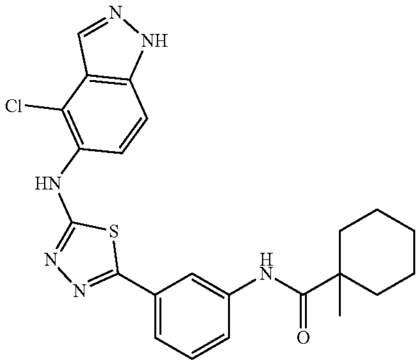 [SMILES: CC1(C(=O)Nc2cccc(-c3nnc(Nc4ccc5[nH]ncc5c4Cl)s3)c2)CCCCC1] |
| 35M | 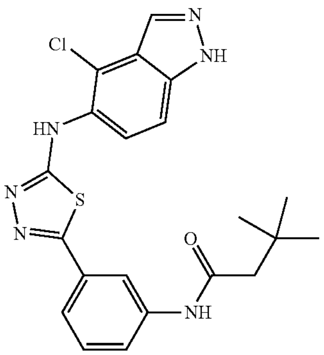 [SMILES: CC(C)(C)CC(=O)Nc1cccc(-c2nnc(Nc3ccc4[nH]ncc4c3Cl)s2)c1] |
| 35N | 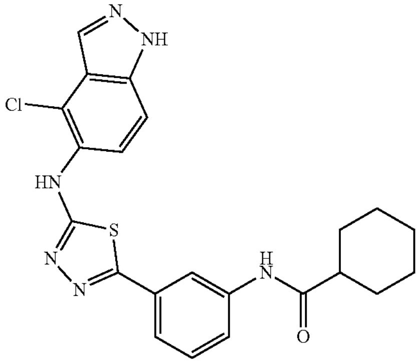 [SMILES: O=C(Nc1cccc(-c2nnc(Nc3ccc4[nH]ncc4c3Cl)s2)c1)C1CCCCC1] |
| 35O | 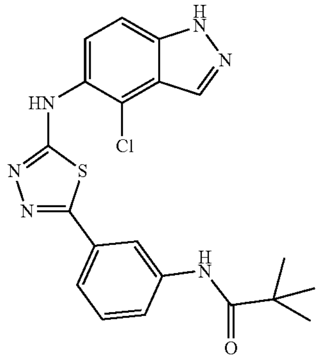 [SMILES: CC(C)(C)C(=O)Nc1cccc(-c2nnc(Nc3ccc4[nH]ncc4c3Cl)s2)c1] |

TABLE 3-continued
| Example No. | Chemical Structure |
|---|---|
| 35P | 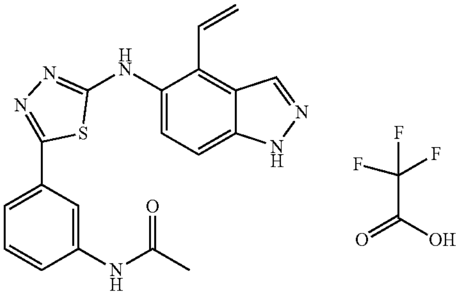 [SMILES: C=Cc1c(Nc2nnc(-c3cccc(NC(C)=O)c3)s2)ccc2[nH]ncc12 ; O=C(O)C(F)(F)F] |
| 35Q | 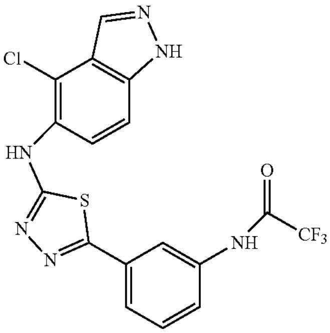 [SMILES: O=C(Nc1cccc(-c2nnc(Nc3ccc4[nH]ncc4c3Cl)s2)c1)C(F)(F)F] |
| 35R | 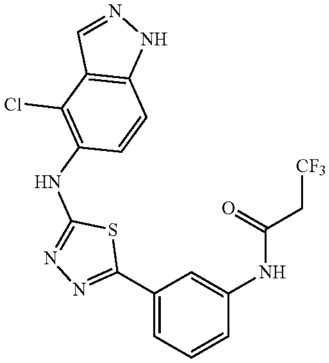 [SMILES: O=C(CC(F)(F)F)Nc1cccc(-c2nnc(Nc3ccc4[nH]ncc4c3Cl)s2)c1] |
| 35S | 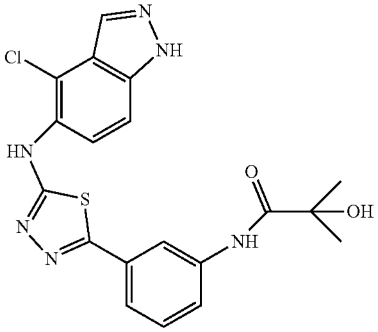 [SMILES: CC(C)(O)C(=O)Nc1cccc(-c2nnc(Nc3ccc4[nH]ncc4c3Cl)s2)c1] |
TABLE 3-continued
| Example No. | Chemical Structure |
|---|---|
| 35T | 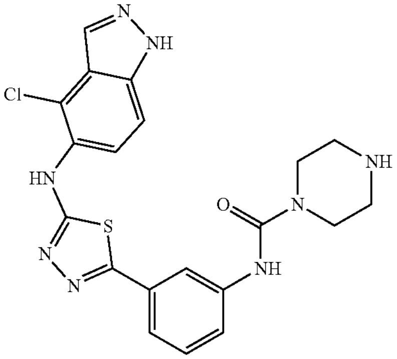 [SMILES: O=C(Nc1cccc(-c2nnc(Nc3ccc4[nH]ncc4c3Cl)s2)c1)N1CCNCC1] |
| 35U | 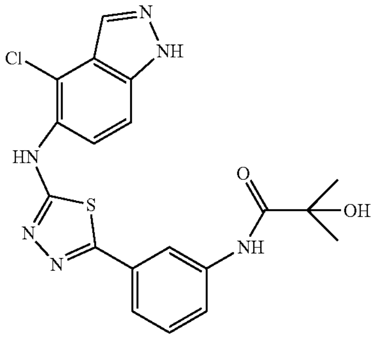 [SMILES: CC(C)(O)C(=O)Nc1cccc(-c2nnc(Nc3ccc4[nH]ncc4c3Cl)s2)c1] |
| 35V | 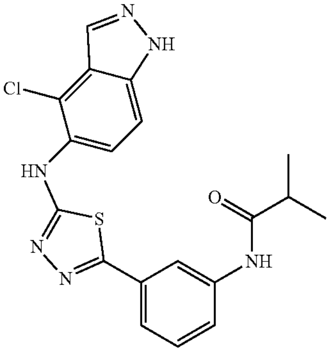 [SMILES: CC(C)C(=O)Nc1cccc(-c2nnc(Nc3ccc4[nH]ncc4c3Cl)s2)c1] |
| 35W | 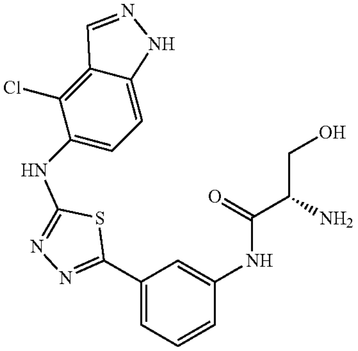 [SMILES: N[C@@H](CO)C(=O)Nc1cccc(-c2nnc(Nc3ccc4[nH]ncc4c3Cl)s2)c1] |

TABLE 3-continued
| Example No. | Chemical Structure |
|---|---|
| 35X | 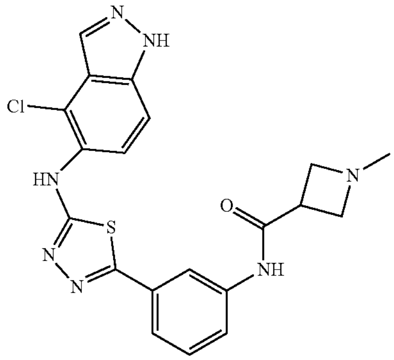 [SMILES: CN1CC(C(=O)Nc2cccc(-c3nnc(Nc4ccc5[nH]ncc5c4Cl)s3)c2)C1] |
| 35Y | 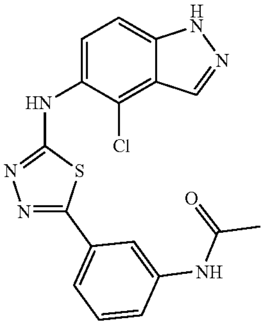 [SMILES: CC(=O)Nc1cccc(-c2nnc(Nc3ccc4[nH]ncc4c3Cl)s2)c1] |
| 35Z | 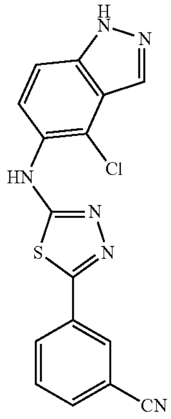 [SMILES: N#Cc1cccc(-c2nnc(Nc3ccc4[nH]ncc4c3Cl)s2)c1] |
| 35AA | 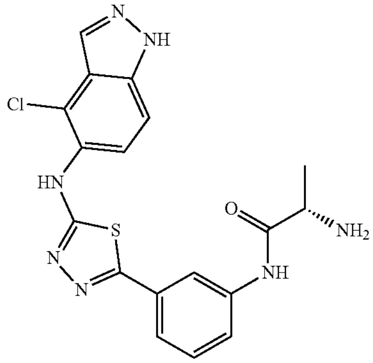 [SMILES: C[C@H](N)C(=O)Nc1cccc(-c2nnc(Nc3ccc4[nH]ncc4c3Cl)s2)c1] |
| 35AB | 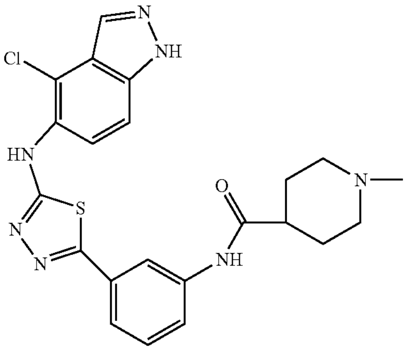 [SMILES: CN1CCC(C(=O)Nc2cccc(-c3nnc(Nc4ccc5[nH]ncc5c4Cl)s3)c2)CC1] |
| 35AC | 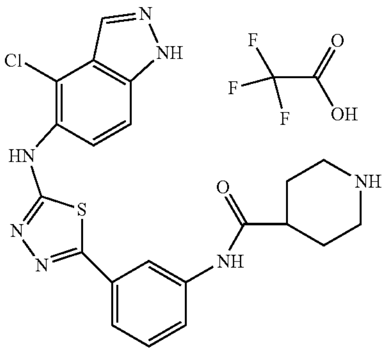 |
| 35AD | 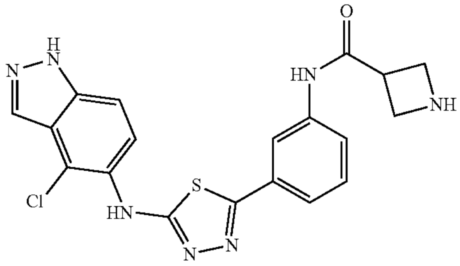 [SMILES: O=C(Nc1cccc(-c2nnc(Nc3ccc4[nH]ncc4c3Cl)s2)c1)C1CNC1] |
| 35AE | 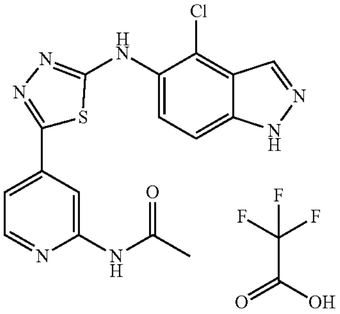 [SMILES: CC(=O)Nc1cc(-c2nnc(Nc3ccc4[nH]ncc4c3Cl)s2)ccn1 ; O=C(O)C(F)(F)F] |

TABLE 3-continued
| Example No. | Chemical Structure |
| --- | --- |
| 35AF | 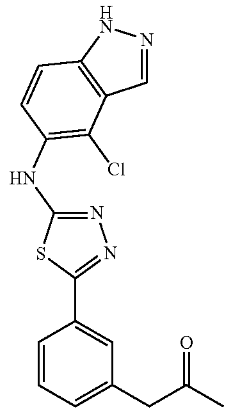 [SMILES: CC(=O)Cc1cccc(-c2nnc(Nc3ccc4[nH]ncc4c3Cl)s2)c1] |
| 35AG | 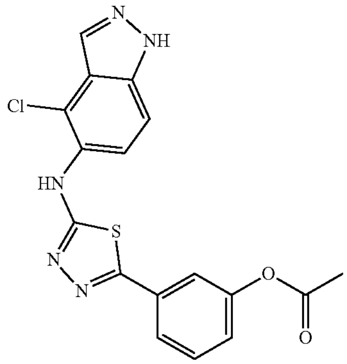 [SMILES: CC(=O)Oc1cccc(-c2nnc(Nc3ccc4[nH]ncc4c3Cl)s2)c1] |
| 35AH | 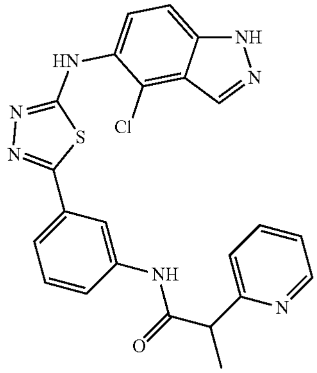 [SMILES: CC(C(=O)Nc1cccc(-c2nnc(Nc3ccc4[nH]ncc4c3Cl)s2)c1)c1ccccn1] |
| 35AI | 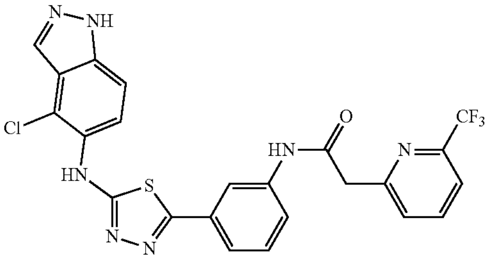 [SMILES: O=C(Cc1cccc(C(F)(F)F)n1)Nc1cccc(-c2nnc(Nc3ccc4[nH]ncc4c3Cl)s2)c1] |
TABLE 3-continued
| Example No. | Chemical Structure |
| --- | --- |
| 35AJ | 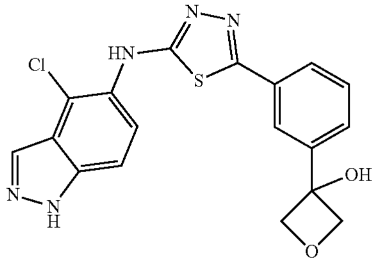 [SMILES: OC1(c2cccc(-c3nnc(Nc4ccc5[nH]ncc5c4Cl)s3)c2)COC1] |
| 35AK | 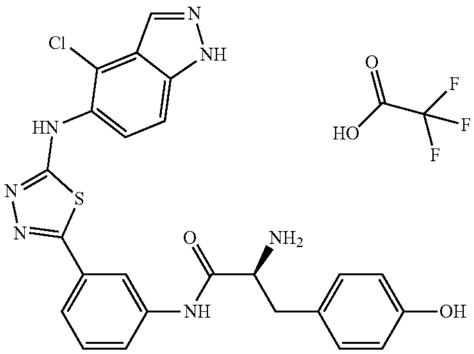 [SMILES: N[C@@H](Cc1ccc(O)cc1)C(=O)Nc1cccc(-c2nnc(Nc3ccc4[nH]ncc4c3Cl)s2)c1 ; O=C(O)C(F)(F)F] |
| 35AL | 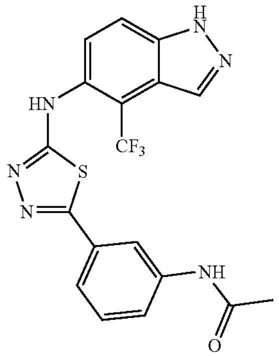 [SMILES: CC(=O)Nc1cccc(-c2nnc(Nc3ccc4[nH]ncc4c3C(F)(F)F)s2)c1] |
| 35AM | 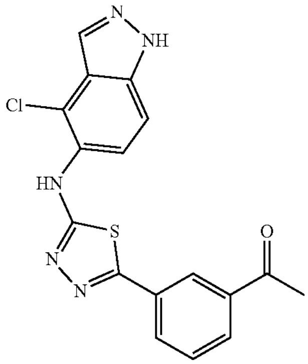 [SMILES: CC(=O)c1cccc(-c2nnc(Nc3ccc4[nH]ncc4c3Cl)s2)c1] |

TABLE 3-continued
| Example No. | Chemical Structure |
|---|---|
| 35AN | 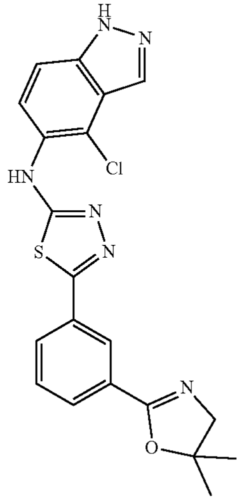 [SMILES: CC1(C)CN=C(c2cccc(-c3nnc(Nc4ccc5[nH]ncc5c4Cl)s3)c2)O1] |
| 35AO | 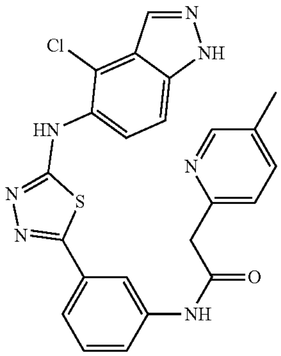 [SMILES: Cc1ccc(CC(=O)Nc2cccc(-c3nnc(Nc4ccc5[nH]ncc5c4Cl)s3)c2)nc1] |
| 35AP | 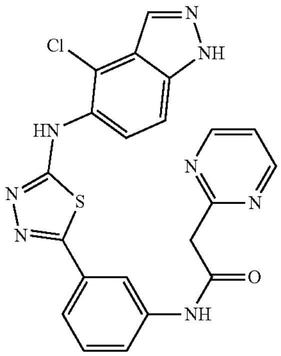 [SMILES: O=C(Cc1ncccn1)Nc1cccc(-c2nnc(Nc3ccc4[nH]ncc4c3Cl)s2)c1] |
| 35AQ | 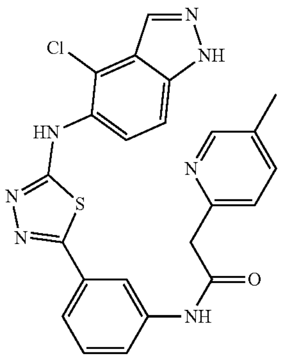 [SMILES: Cc1ccc(CC(=O)Nc2cccc(-c3nnc(Nc4ccc5[nH]ncc5c4Cl)s3)c2)nc1] |
TABLE 3-continued
| Example No. | Chemical Structure |
|---|---|
| 35AR | 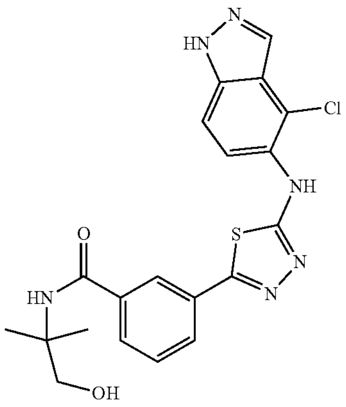 [SMILES: CC(C)(CO)NC(=O)c1cccc(-c2nnc(Nc3ccc4[nH]ncc4c3Cl)s2)c1] |
| 35AS | 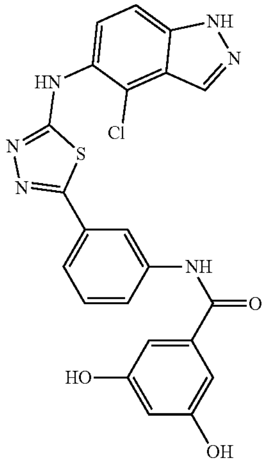 [SMILES: O=C(Nc1cccc(-c2nnc(Nc3ccc4[nH]ncc4c3Cl)s2)c1)c1cc(O)cc(O)c1] |
| 35AU | 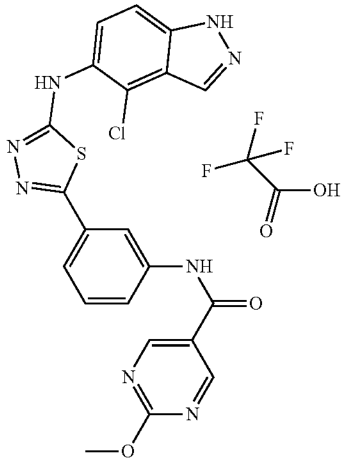 [SMILES: COc1ncc(C(=O)Nc2cccc(-c3nnc(Nc4ccc5[nH]ncc5c4Cl)s3)c2)cn1 ; O=C(O)C(F)(F)F] |

TABLE 3-continued
| Example No. | Chemical Structure |
|---|---|
| 35AV | 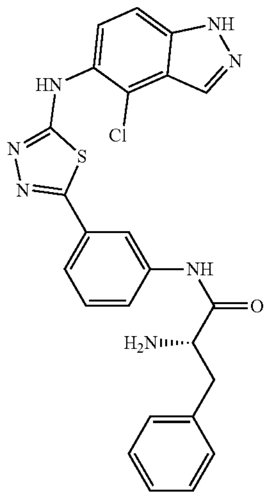 [SMILES: N[C@@H](Cc1ccccc1)C(=O)Nc1cccc(-c2nnc(Nc3ccc4[nH]ncc4c3Cl)s2)c1] |
| 35AW | 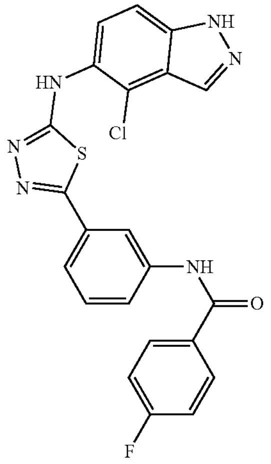 [SMILES: O=C(Nc1cccc(-c2nnc(Nc3ccc4[nH]ncc4c3Cl)s2)c1)c1ccc(F)cc1] |
| 35AX | 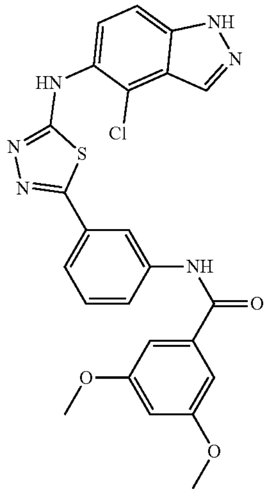 [SMILES: COc1cc(OC)cc(C(=O)Nc2cccc(-c3nnc(Nc4ccc5[nH]ncc5c4Cl)s3)c2)c1] |
TABLE 3-continued
| Example No. | Chemical Structure |
|---|---|
| 35AY | 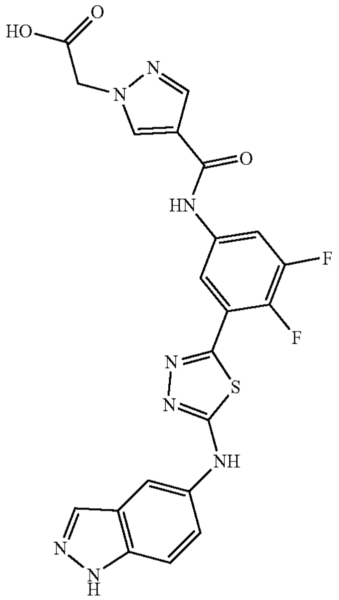 [SMILES: O=C(O)Cn1cc(C(=O)Nc2cc(F)c(F)c(-c3nnc(Nc4ccc5[nH]ncc5c4)s3)c2)cn1] |
| 35AZ | 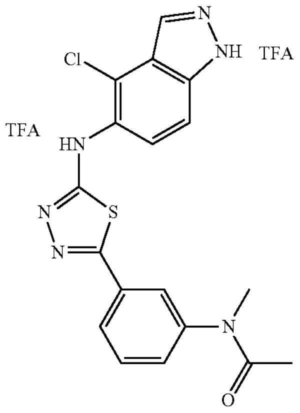 [SMILES: CC(=O)N(C)c1cccc(-c2nnc(Nc3ccc4[nH]ncc4c3Cl)s2)c1] |
| 35BA | 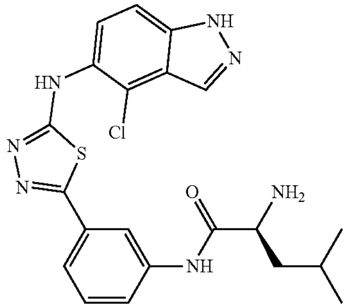 [SMILES: CC(C)C[C@H](N)C(=O)Nc1cccc(-c2nnc(Nc3ccc4[nH]ncc4c3Cl)s2)c1] |

TABLE 3-continued
| Example No. | Chemical Structure |
|---|---|
| 35BB | 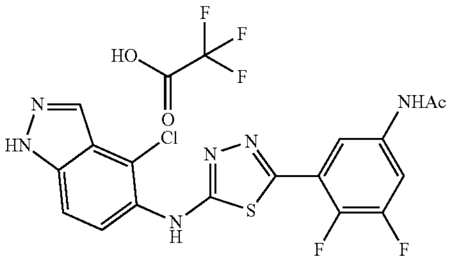 |
| 35BC | 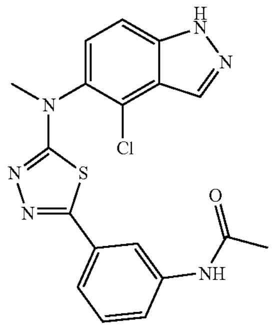 [SMILES: CC(=O)Nc1cccc(-c2nnc(N(C)c3ccc4[nH]ncc4c3Cl)s2)c1] |
| 35BD | 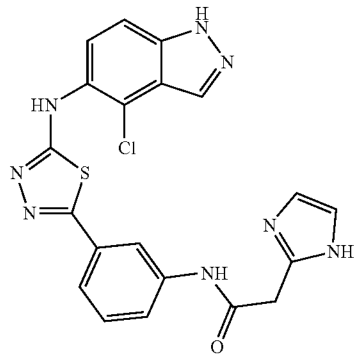 [SMILES: O=C(Cc1ncc[nH]1)Nc1cccc(-c2nnc(Nc3ccc4[nH]ncc4c3Cl)s2)c1] |
| 35BE | 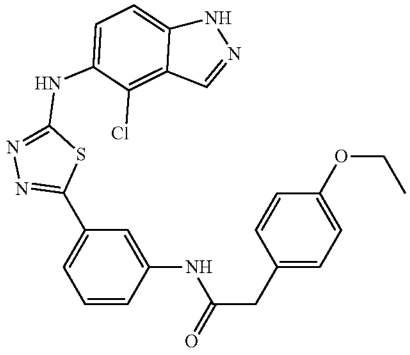 [SMILES: CCOc1ccc(CC(=O)Nc2cccc(-c3nnc(Nc4ccc5[nH]ncc5c4Cl)s3)c2)cc1] |
| 35BF | 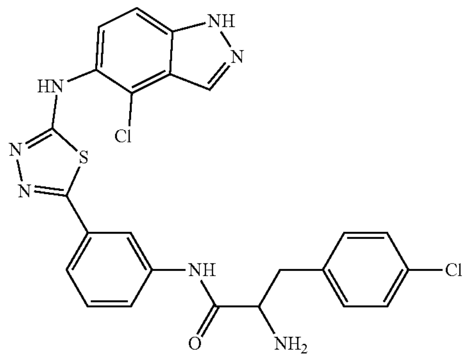 [SMILES: NC(Cc1ccc(Cl)cc1)C(=O)Nc1cccc(-c2nnc(Nc3ccc4[nH]ncc4c3Cl)s2)c1] |
| 35BG | 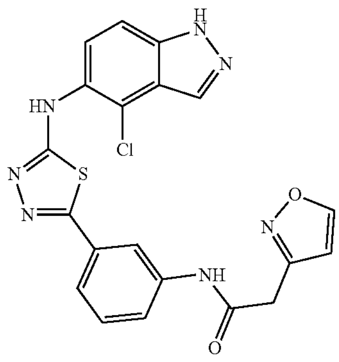 [SMILES: O=C(Cc1ccon1)Nc1cccc(-c2nnc(Nc3ccc4[nH]ncc4c3Cl)s2)c1] |
| 35BH | 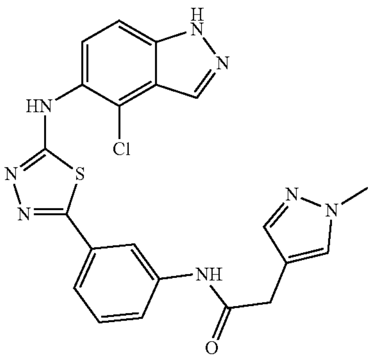 [SMILES: Cn1cc(CC(=O)Nc2cccc(-c3nnc(Nc4ccc5[nH]ncc5c4Cl)s3)c2)cn1] |
| 35BI | 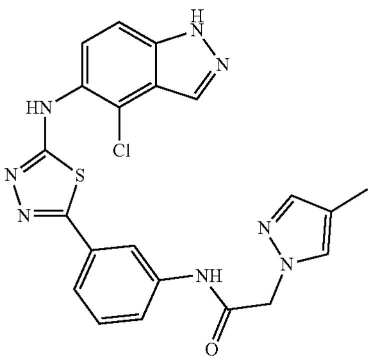 [SMILES: Cc1cnn(CC(=O)Nc2cccc(-c3nnc(Nc4ccc5[nH]ncc5c4Cl)s3)c2)c1] |

TABLE 3-continued
| Example No. | Chemical Structure |
|---|---|
| 35BJ | 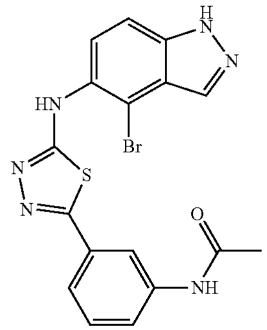 [SMILES: CC(=O)Nc1cccc(-c2nnc(Nc3ccc4[nH]ncc4c3Br)s2)c1] |
| 35BK | 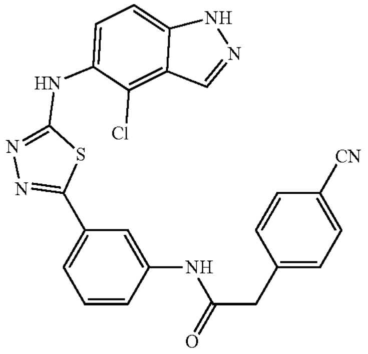 [SMILES: N#Cc1ccc(CC(=O)Nc2cccc(-c3nnc(Nc4ccc5[nH]ncc5c4Cl)s3)c2)cc1] |
| 35BL | 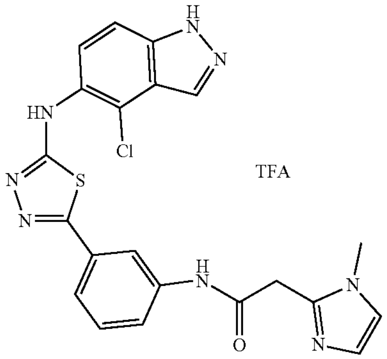 [SMILES: Cn1ccnc1CC(=O)Nc1cccc(-c2nnc(Nc3ccc4[nH]ncc4c3Cl)s2)c1] TFA |
| 35BM | 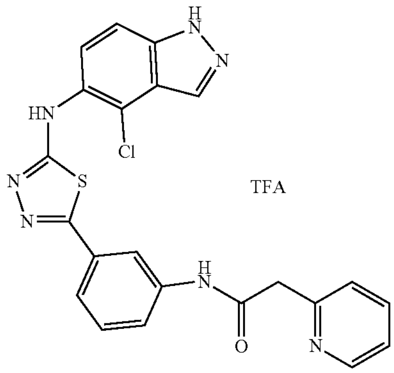 [SMILES: O=C(Cc1ccccn1)Nc1cccc(-c2nnc(Nc3ccc4[nH]ncc4c3Cl)s2)c1] TFA |
TABLE 3-continued
| Example No. | Chemical Structure |
|---|---|
| 35BN | 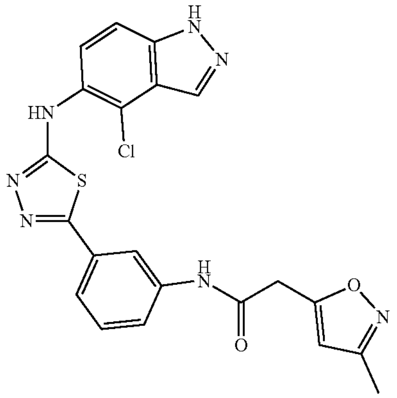 [SMILES: Cc1cc(CC(=O)Nc2cccc(-c3nnc(Nc4ccc5[nH]ncc5c4Cl)s3)c2)on1] |
| 35BO | 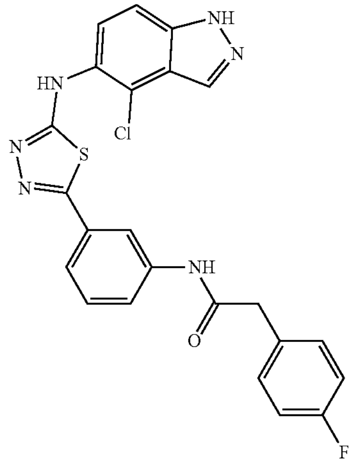 [SMILES: O=C(Cc1ccc(F)cc1)Nc1cccc(-c2nnc(Nc3ccc4[nH]ncc4c3Cl)s2)c1] |
| 35BP | 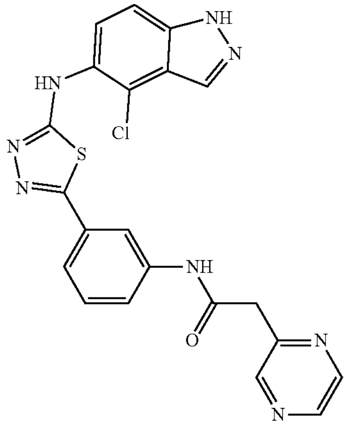 [SMILES: O=C(Cc1cnccn1)Nc1cccc(-c2nnc(Nc3ccc4[nH]ncc4c3Cl)s2)c1] |

TABLE 3-continued
| Example No. | Chemical Structure |
| --- | --- |
| 35BQ | 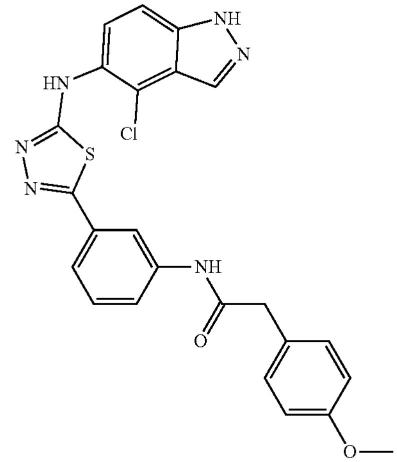 [SMILES: COc1ccc(CC(=O)Nc2cccc(-c3nnc(Nc4ccc5[nH]ncc5c4Cl)s3)c2)cc1] |
| 35BR | 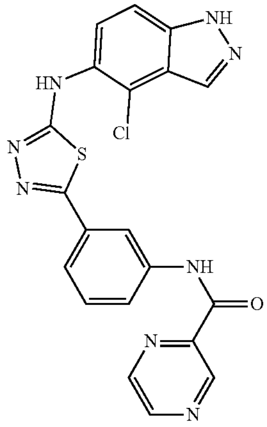 [SMILES: O=C(Nc1cccc(-c2nnc(Nc3ccc4[nH]ncc4c3Cl)s2)c1)c1cnccn1] |
| 35BS | 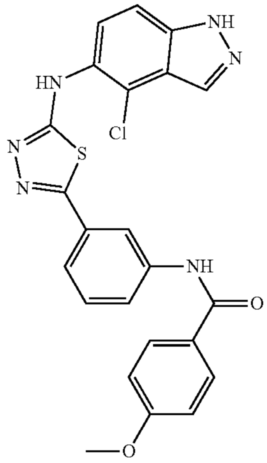 [SMILES: COc1ccc(C(=O)Nc2cccc(-c3nnc(Nc4ccc5[nH]ncc5c4Cl)s3)c2)cc1] |
TABLE 3-continued
| Example No. | Chemical Structure |
| --- | --- |
| 35BT | 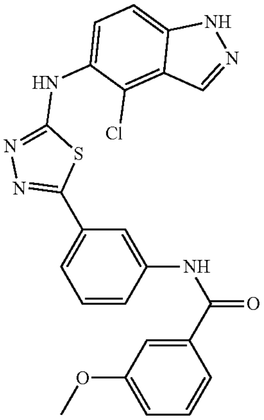 [SMILES: COc1cccc(C(=O)Nc2cccc(-c3nnc(Nc4ccc5[nH]ncc5c4Cl)s3)c2)c1] |
| 35BU | 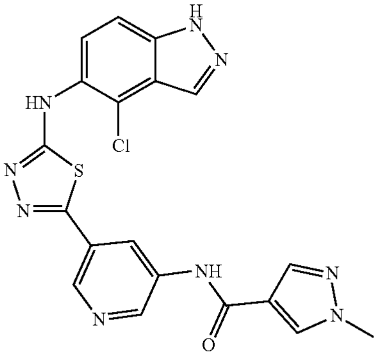 [SMILES: Cn1cc(C(=O)Nc2cncc(-c3nnc(Nc4ccc5[nH]ncc5c4Cl)s3)c2)cn1] |
| 35BV | 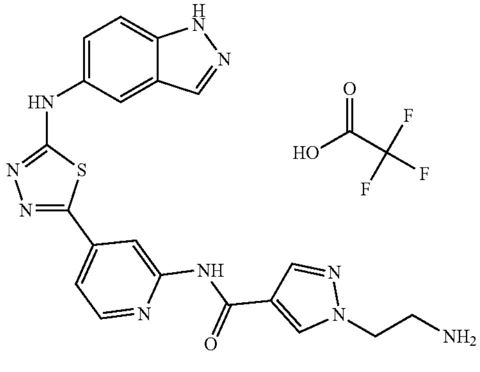 [SMILES: NCCn1cc(C(=O)Nc2cc(-c3nnc(Nc4ccc5[nH]ncc5c4)s3)ccn2)cn1 ; O=C(O)C(F)(F)F] |
| 35BW | 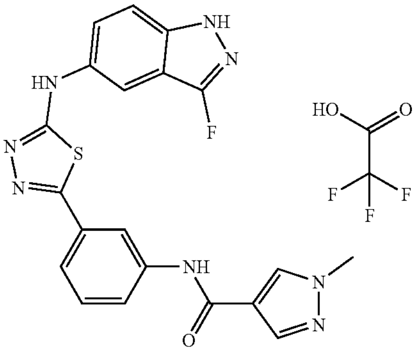 |

TABLE 3-continued
| Example No. | Chemical Structure |
|---|---|
| 35BX | 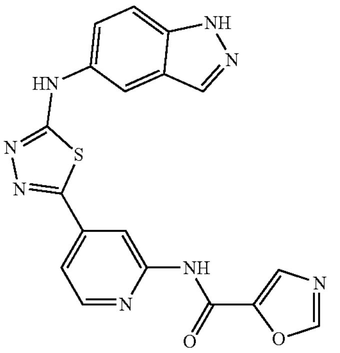 [SMILES: O=C(Nc1cc(-c2nnc(Nc3ccc4[nH]ncc4c3)s2)ccn1)c1cnco1] |
| 35BY | 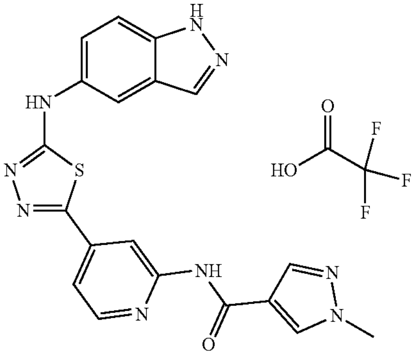 [SMILES: Cn1cc(C(=O)Nc2cc(-c3nnc(Nc4ccc5[nH]ncc5c4)s3)ccn2)cn1 ; O=C(O)C(F)(F)F] |
| 35BZ | 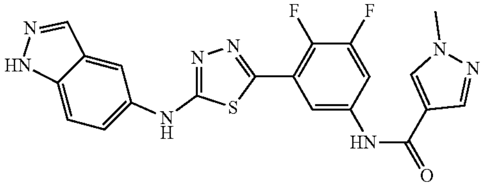 [SMILES: Cn1cc(C(=O)Nc2cc(F)c(F)c(-c3nnc(Nc4ccc5[nH]ncc5c4)s3)c2)cn1] |
| 35CA | 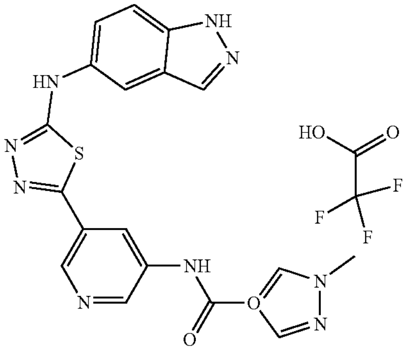 |
| 35CB | 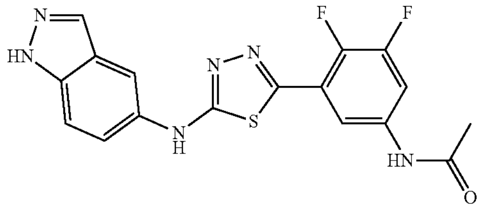 [SMILES: CC(=O)Nc1cc(F)c(F)c(-c2nnc(Nc3ccc4[nH]ncc4c3)s2)c1] |
| 35CC | 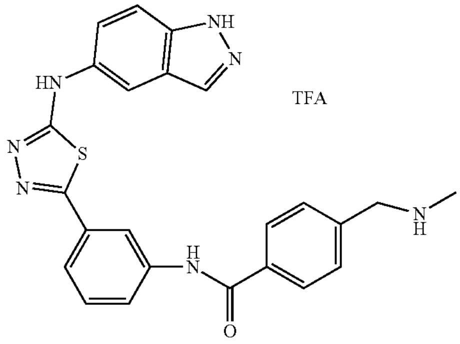 [SMILES: CNCc1ccc(C(=O)Nc2cccc(-c3nnc(Nc4ccc5[nH]ncc5c4)s3)c2)cc1] TFA |
| 35CD | 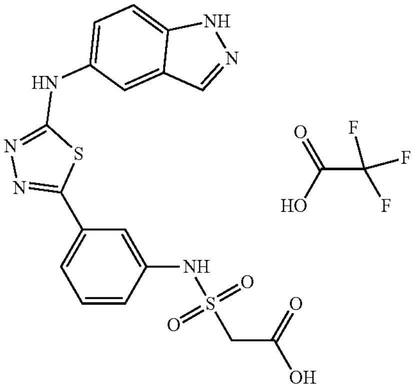 [SMILES: O=C(O)CS(=O)(=O)Nc1cccc(-c2nnc(Nc3ccc4[nH]ncc4c3)s2)c1 ; O=C(O)C(F)(F)F] |
| 35CE | 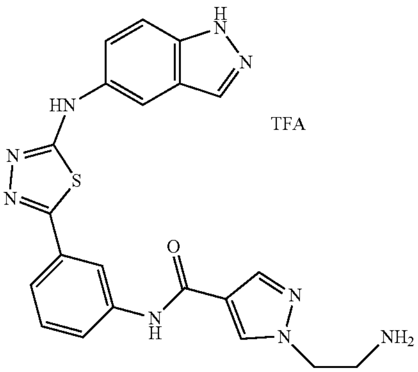 [SMILES: NCCn1cc(C(=O)Nc2cccc(-c3nnc(Nc4ccc5[nH]ncc5c4)s3)c2)cn1] TFA |
| 35CF | 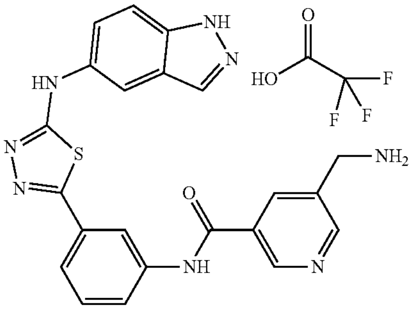 |

TABLE 3-continued
| Example No. | Chemical Structure |
|---|---|
| 35CG | 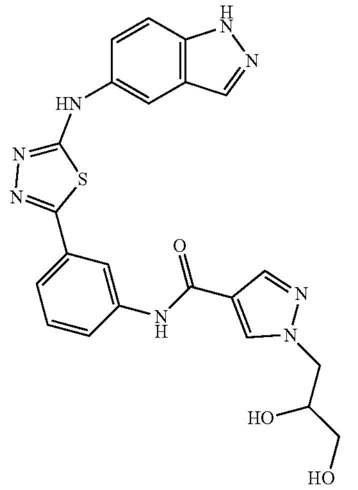 [SMILES: O=C(Nc1cccc(-c2nnc(Nc3ccc4[nH]ncc4c3)s2)c1)c1cnn(CC(O)CO)c1] |
| 35CH | 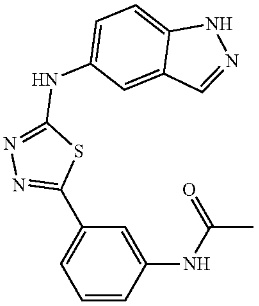 [SMILES: CC(=O)Nc1cccc(-c2nnc(Nc3ccc4[nH]ncc4c3)s2)c1] |
| 35CI | 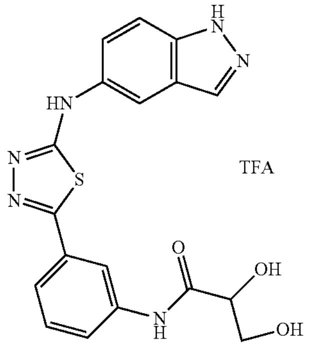 [SMILES: O=C(Nc1cccc(-c2nnc(Nc3ccc4[nH]ncc4c3)s2)c1)C(O)CO] TFA |
| 35CJ | 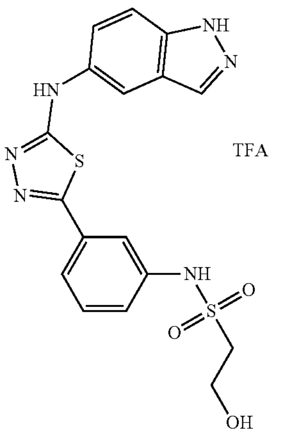 [SMILES: O=S(=O)(CCO)Nc1cccc(-c2nnc(Nc3ccc4[nH]ncc4c3)s2)c1] TFA |
| 35CK | 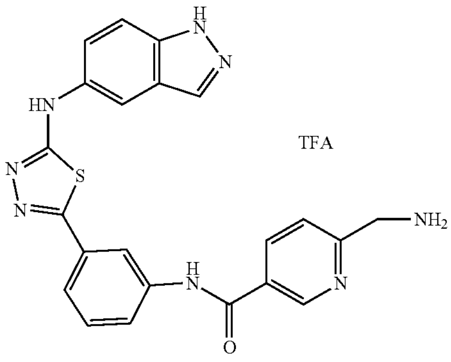 [SMILES: NCc1ccc(C(=O)Nc2cccc(-c3nnc(Nc4ccc5[nH]ncc5c4)s3)c2)cn1] TFA |
| 35CL | 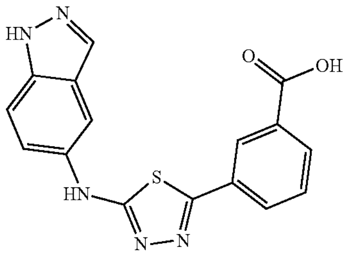 [SMILES: O=C(O)c1cccc(-c2nnc(Nc3ccc4[nH]ncc4c3)s2)c1] |
| 35CM | 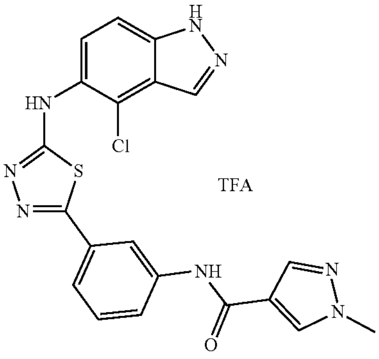 [SMILES: Cn1cc(C(=O)Nc2cccc(-c3nnc(Nc4ccc5[nH]ncc5c4Cl)s3)c2)cn1] TFA |
| 35CN | 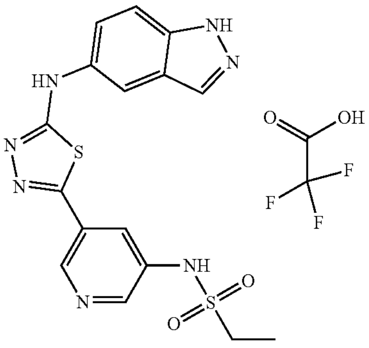 [SMILES: CCS(=O)(=O)Nc1cncc(-c2nnc(Nc3ccc4[nH]ncc4c3)s2)c1 ; O=C(O)C(F)(F)F] |

TABLE 3-continued
| Example No. | Chemical Structure |
| --- | --- |
| 35CO | 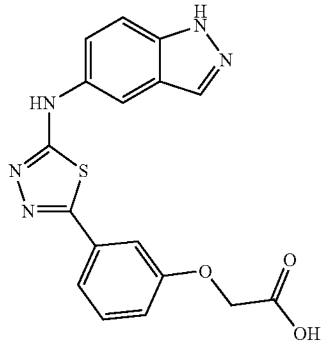 [SMILES: O=C(O)COc1cccc(-c2nnc(Nc3ccc4[nH]ncc4c3)s2)c1] |
| 35CP | 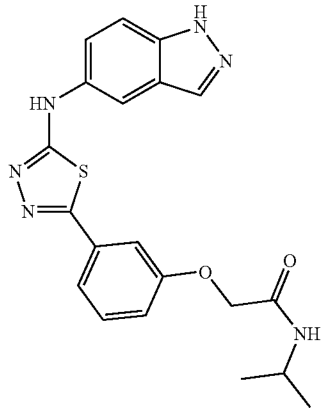 [SMILES: CC(C)NC(=O)COc1cccc(-c2nnc(Nc3ccc4[nH]ncc4c3)s2)c1] |
| 35CQ | 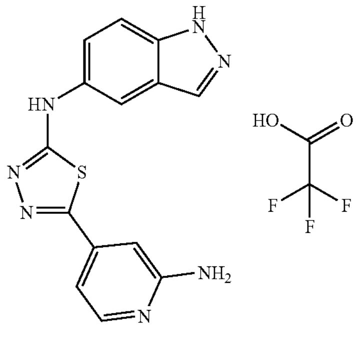 [SMILES: Nc1cc(-c2nnc(Nc3ccc4[nH]ncc4c3)s2)ccn1 ; O=C(O)C(F)(F)F] |
| 35CR | 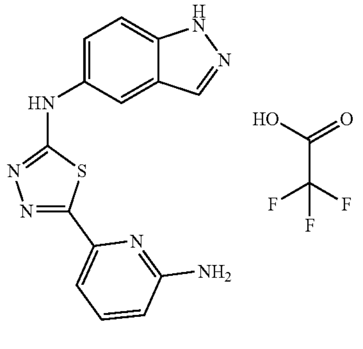 [SMILES: Nc1cccc(-c2nnc(Nc3ccc4[nH]ncc4c3)s2)n1 ; O=C(O)C(F)(F)F] |
TABLE 3-continued
| Example No. | Chemical Structure |
| --- | --- |
| 35CS | 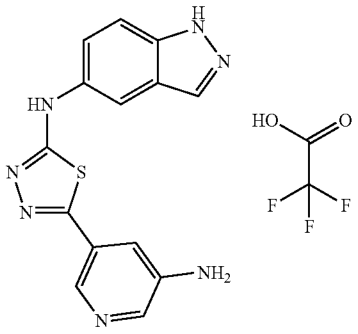 [SMILES: Nc1cncc(-c2nnc(Nc3ccc4[nH]ncc4c3)s2)c1 ; O=C(O)C(F)(F)F] |
| 35CT | 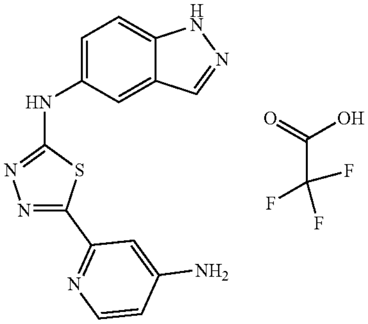 [SMILES: Nc1ccnc(-c2nnc(Nc3ccc4[nH]ncc4c3)s2)c1 ; O=C(O)C(F)(F)F] |
| 35CU | 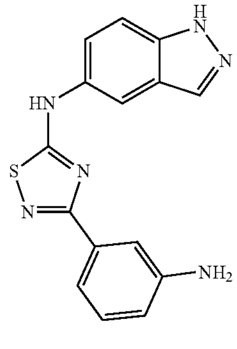 [SMILES: Nc1cccc(-c2nsc(Nc3ccc4[nH]ncc4c3)n2)c1] |
| 35CV | 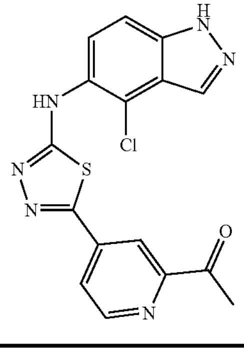 |

TABLE 4
| Example No. | Chemical Structure |
|---|---|
| 39A | 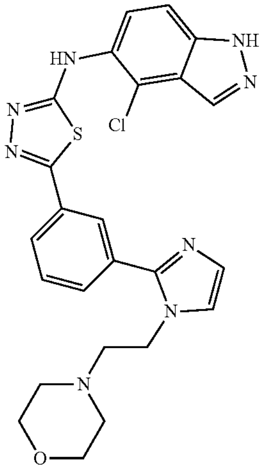 [SMILES: Clc1c(Nc2nnc(-c3cccc(-c4nccn4CCN4CCOCC4)c3)s2)ccc2[nH]ncc12] |
| 39B | 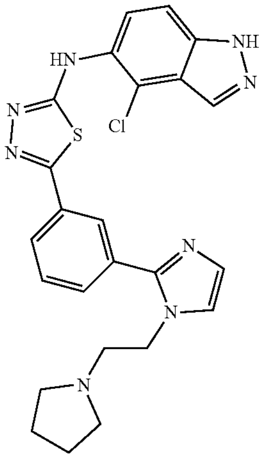 [SMILES: Clc1c(Nc2nnc(-c3cccc(-c4nccn4CCN4CCCC4)c3)s2)ccc2[nH]ncc12] |
| 39C | 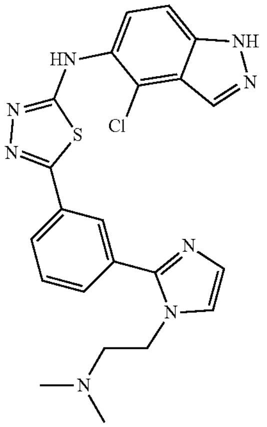 [SMILES: CN(C)CCn1ccnc1-c1cccc(-c2nnc(Nc3ccc4[nH]ncc4c3Cl)s2)c1] |
TABLE 4-continued
| Example No. | Chemical Structure |
|---|---|
| 39D | 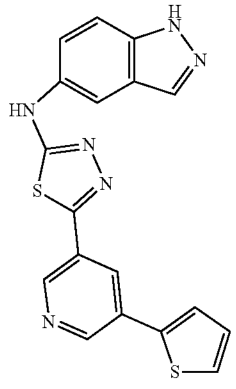 [SMILES: c1csc(-c2cncc(-c3nnc(Nc4ccc5[nH]ncc5c4)s3)c2)c1] |
| 39E | 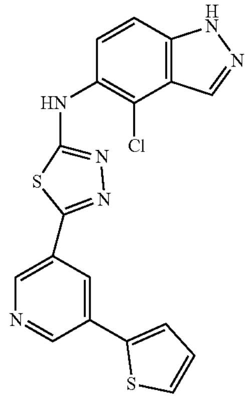 [SMILES: Clc1c(Nc2nnc(-c3cncc(-c4cccs4)c3)s2)ccc2[nH]ncc12] |
TABLE 5
| Example No. | Chemical Structure |
|---|---|
| 41A | 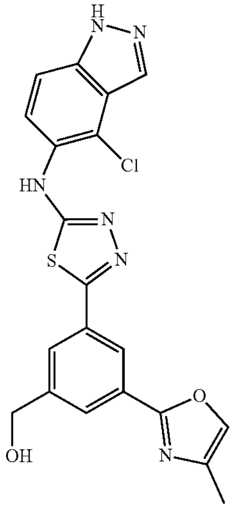 [SMILES: Cc1coc(-c2cc(CO)cc(-c3nnc(Nc4ccc5[nH]ncc5c4Cl)s3)c2)n1] |

TABLE 5-continued
| Example No. | Chemical Structure |
| --- | --- |
| 41B | 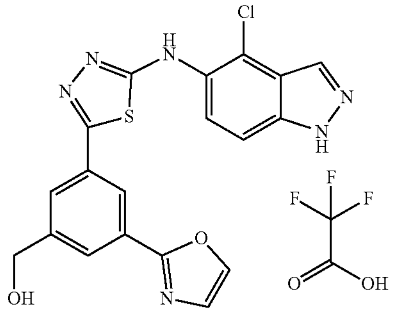 |
| 41C | 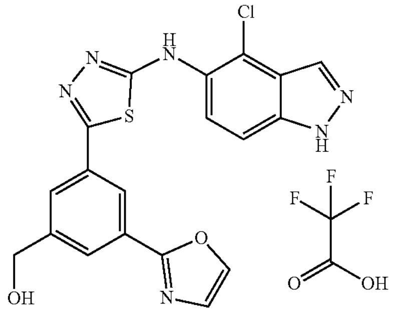 |
| 41D | 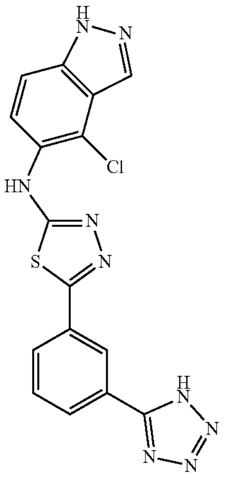 [SMILES: Clc1c(Nc2nnc(-c3cccc(-c4nnn[nH]4)c3)s2)ccc2[nH]ncc12] |
TABLE 6
| Example No. | Chemical Structure |
| --- | --- |
| 45A | 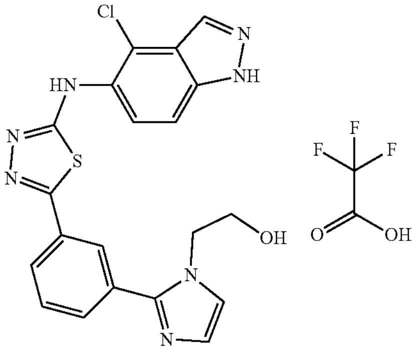 |
TABLE 7
| Example No. | Chemical Structure |
| --- | --- |
| 46A | 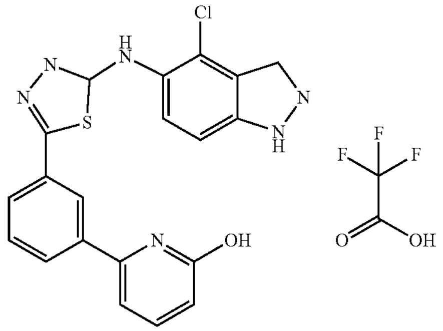 [SMILES: Oc1cccc(-c2cccc(C3=NNC(Nc4ccc5c(c4Cl)CNN5)S3)c2)n1 ; O=C(O)C(F)(F)F] |
| 46B | 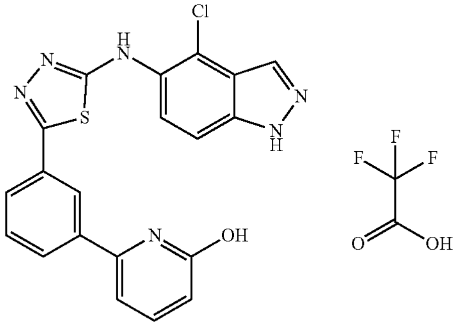 [SMILES: Oc1cccc(-c2cccc(-c3nnc(Nc4ccc5[nH]ncc5c4Cl)s3)c2)n1 ; O=C(O)C(F)(F)F] |
| 46C | 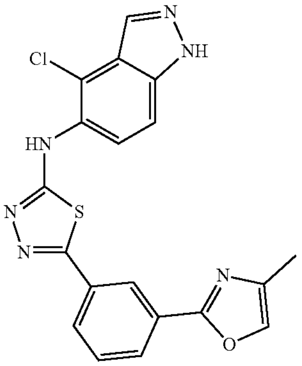 [SMILES: Cc1coc(-c2cccc(-c3nnc(Nc4ccc5[nH]ncc5c4Cl)s3)c2)n1] |
| 46D | 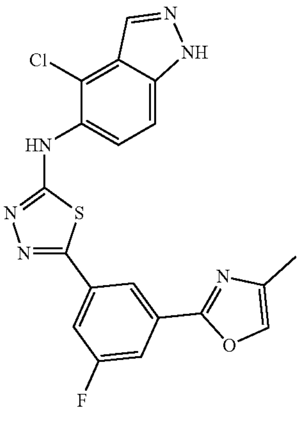 [SMILES: Cc1coc(-c2cc(F)cc(-c3nnc(Nc4ccc5[nH]ncc5c4Cl)s3)c2)n1] |

TABLE 7-continued
| Example No. | Chemical Structure |
| --- | --- |
| 46E | 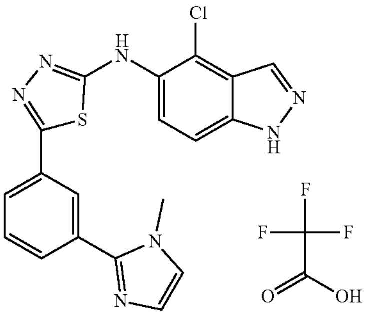 [SMILES: Cn1ccnc1-c1cccc(-c2nnc(Nc3ccc4[nH]ncc4c3Cl)s2)c1 ; O=C(O)C(F)(F)F] |
| 46F | 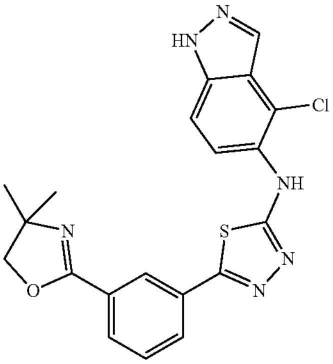 [SMILES: CC1(C)COC(c2cccc(-c3nnc(Nc4ccc5[nH]ncc5c4Cl)s3)c2)=N1] |
| 46G | 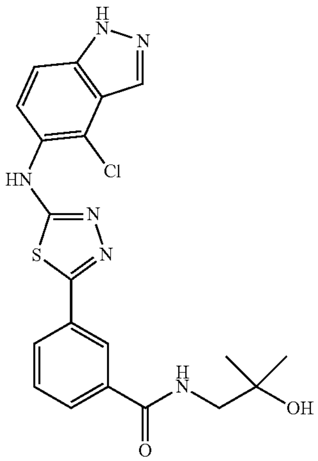 [SMILES: CC(C)(O)CNC(=O)c1cccc(-c2nnc(Nc3ccc4[nH]ncc4c3Cl)s2)c1] |
| 46H | 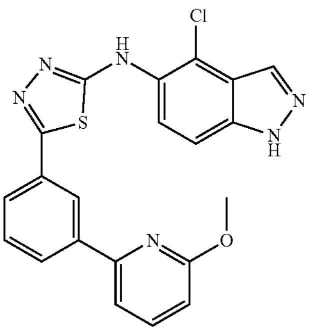 [SMILES: COc1cccc(-c2cccc(-c3nnc(Nc4ccc5[nH]ncc5c4Cl)s3)c2)n1] |
| 46I | 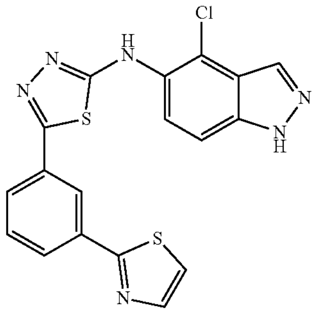 [SMILES: Clc1c(Nc2nnc(-c3cccc(-c4nccs4)c3)s2)ccc2[nH]ncc12] |
| 46J | 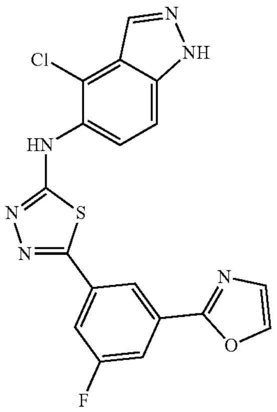 [SMILES: Fc1cc(-c2ncco2)cc(-c2nnc(Nc3ccc4[nH]ncc4c3Cl)s2)c1] |
| 46K | 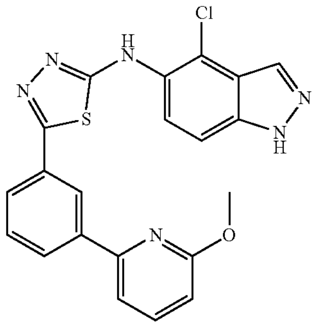 [SMILES: COc1cccc(-c2cccc(-c3nnc(Nc4ccc5[nH]ncc5c4Cl)s3)c2)n1] |
| 46L | 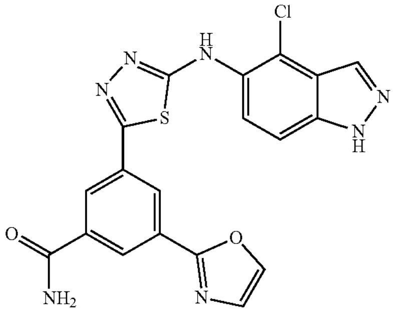 [SMILES: NC(=O)c1cc(-c2ncco2)cc(-c2nnc(Nc3ccc4[nH]ncc4c3Cl)s2)c1] |

TABLE 7-continued
| Example No. | Chemical Structure |
|---|---|
| 46M | 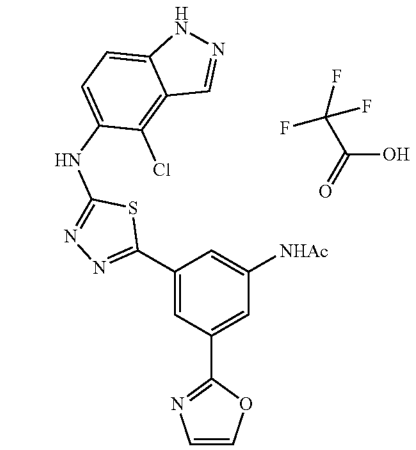 [SMILES: CC(=O)Nc1cc(-c2ncco2)cc(-c2nnc(Nc3ccc4[nH]ncc4c3Cl)s2)c1 ; O=C(O)C(F)(F)F] |
| 46N | 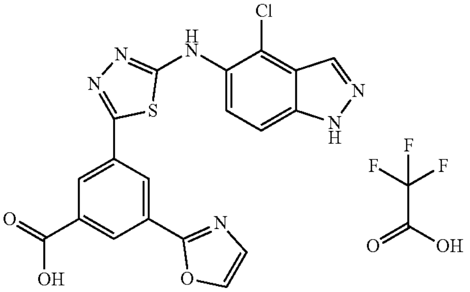 [SMILES: O=C(O)c1cc(-c2ncco2)cc(-c2nnc(Nc3ccc4[nH]ncc4c3Cl)s2)c1 ; O=C(O)C(F)(F)F] |
| 46O | 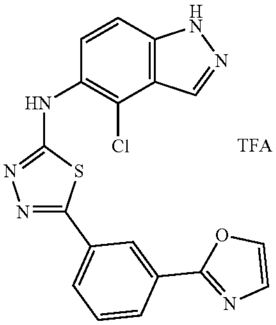 [SMILES: Clc1c(Nc2nnc(-c3cccc(-c4ncco4)c3)s2)ccc2[nH]ncc12] TFA |
| 46P | 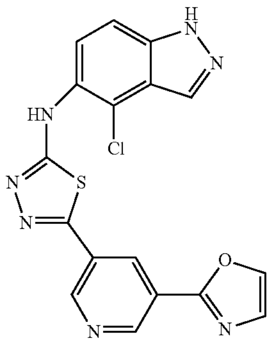 [SMILES: Clc1c(Nc2nnc(-c3cncc(-c4ncco4)c3)s2)ccc2[nH]ncc12] |
TABLE 8
| Example No. | Chemical Structure |
|---|---|
| 48A | 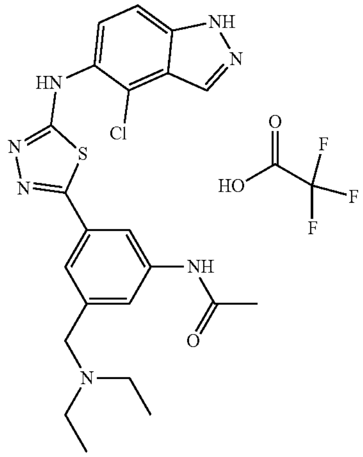 [SMILES: CCN(CC)Cc1cc(NC(C)=O)cc(-c2nnc(Nc3ccc4[nH]ncc4c3Cl)s2)c1 ; O=C(O)C(F)(F)F] |
| 48B | 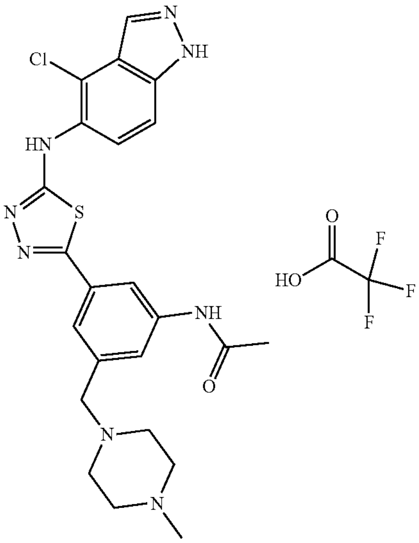 [SMILES: CC(=O)Nc1cc(CN2CCN(C)CC2)cc(-c2nnc(Nc3ccc4[nH]ncc4c3Cl)s2)c1 ; O=C(O)C(F)(F)F] |
| 48C | 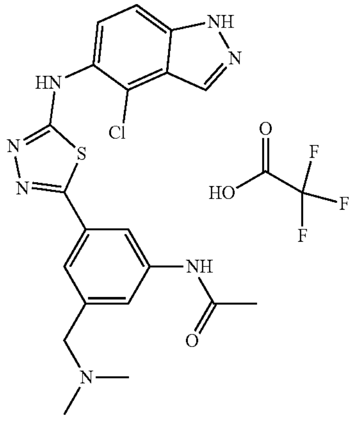 [SMILES: CC(=O)Nc1cc(CN(C)C)cc(-c2nnc(Nc3ccc4[nH]ncc4c3Cl)s2)c1 ; O=C(O)C(F)(F)F] |

TABLE 8-continued
| Example No. | Chemical Structure |
|---|---|
| 48D | 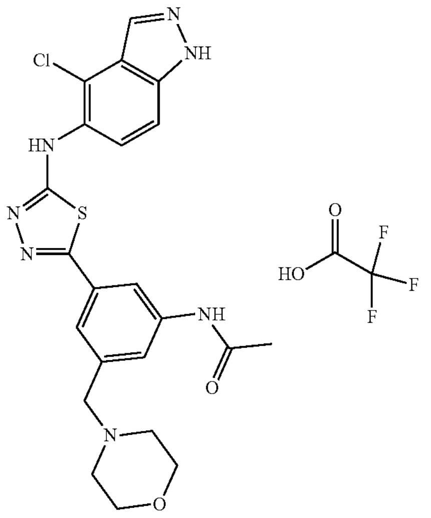 [SMILES: CC(=O)Nc1cc(CN2CCOCC2)cc(-c2nnc(Nc3ccc4[nH]ncc4c3Cl)s2)c1 ; O=C(O)C(F)(F)F] |
| 48E | 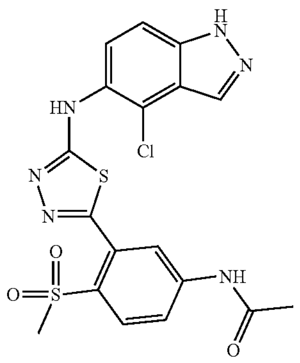 [SMILES: CC(=O)Nc1ccc(S(C)(=O)=O)c(-c2nnc(Nc3ccc4[nH]ncc4c3Cl)s2)c1] |
| 48F | 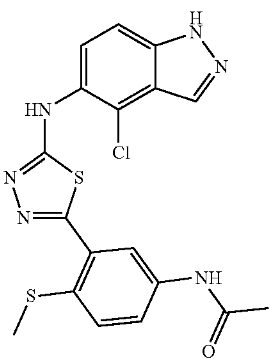 [SMILES: CSc1ccc(NC(C)=O)cc1-c1nnc(Nc2ccc3[nH]ncc3c2Cl)s1] |
TABLE 8-continued
| Example No. | Chemical Structure |
|---|---|
| 48G | 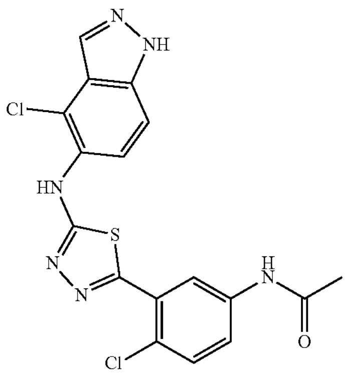 [SMILES: CC(=O)Nc1ccc(Cl)c(-c2nnc(Nc3ccc4[nH]ncc4c3Cl)s2)c1] |
| 48H | 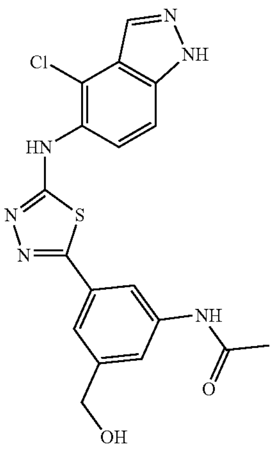 [SMILES: CC(=O)Nc1cc(CO)cc(-c2nnc(Nc3ccc4[nH]ncc4c3Cl)s2)c1] |
| 48I | 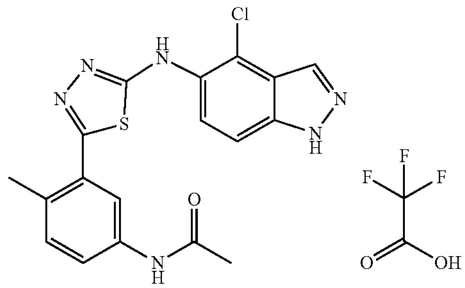 [SMILES: CC(=O)Nc1ccc(C)c(-c2nnc(Nc3ccc4[nH]ncc4c3Cl)s2)c1 ; O=C(O)C(F)(F)F] |
| 48J | 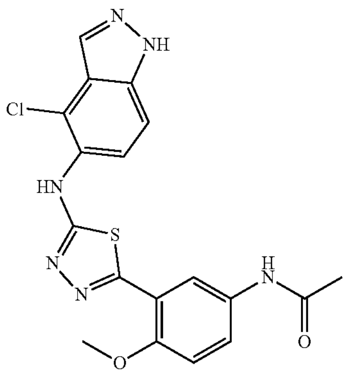 [SMILES: COc1ccc(NC(C)=O)cc1-c1nnc(Nc2ccc3[nH]ncc3c2Cl)s1] |

TABLE 8-continued
| Example No. | Chemical Structure |
|---|---|
| 48K | 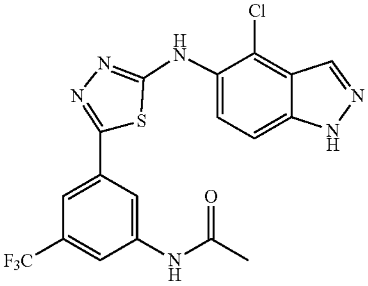 [SMILES: CC(=O)Nc1cc(-c2nnc(Nc3ccc4[nH]ncc4c3Cl)s2)cc(C(F)(F)F)c1] |
| 48L | 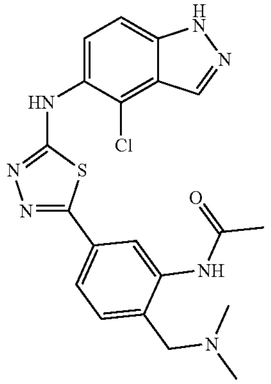 [SMILES: CC(=O)Nc1cc(-c2nnc(Nc3ccc4[nH]ncc4c3Cl)s2)ccc1CN(C)C] |
| 48M | 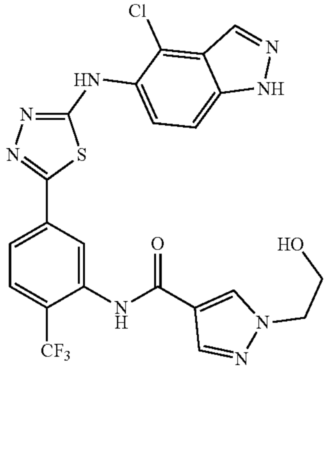 [SMILES: O=C(Nc1cc(-c2nnc(Nc3ccc4[nH]ncc4c3Cl)s2)ccc1C(F)(F)F)c1cnn(CCO)c1] |
| 48N | 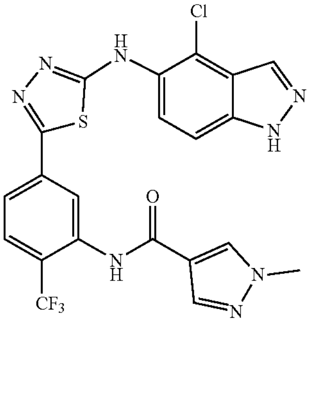 [SMILES: Cn1cc(C(=O)Nc2cc(-c3nnc(Nc4ccc5[nH]ncc5c4Cl)s3)ccc2C(F)(F)F)cn1] |
TABLE 8-continued
| Example No. | Chemical Structure |
|---|---|
| 48O | 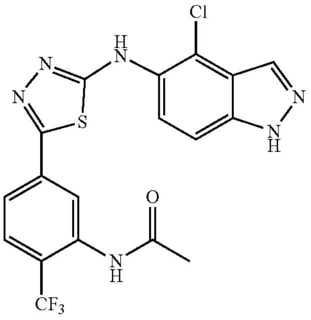 [SMILES: CC(=O)Nc1cc(-c2nnc(Nc3ccc4[nH]ncc4c3Cl)s2)ccc1C(F)(F)F] |
| 48P | 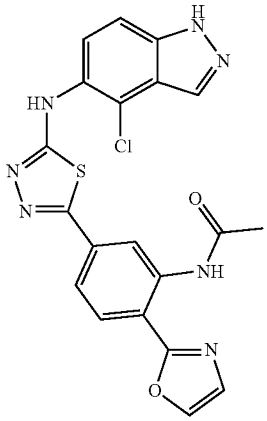 [SMILES: CC(=O)Nc1cc(-c2nnc(Nc3ccc4[nH]ncc4c3Cl)s2)ccc1-c1ncco1] |
| 48Q | 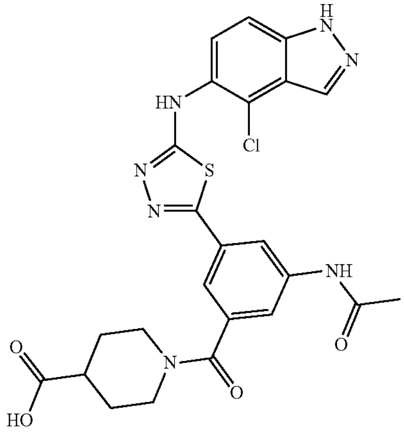 [SMILES: CC(=O)Nc1cc(C(=O)N2CCC(C(=O)O)CC2)cc(-c2nnc(Nc3ccc4[nH]ncc4c3Cl)s2)c1] |

TABLE 8-continued
| Example No. | Chemical Structure |
|---|---|
| 48R | 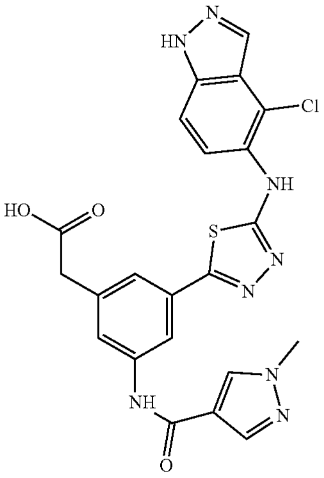 [SMILES: Cn1cc(C(=O)Nc2cc(CC(=O)O)cc(-c3nnc(Nc4ccc5[nH]ncc5c4Cl)s3)c2)cn1] |
| 48S | 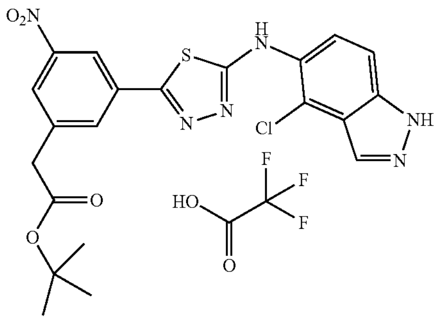 |
| 48T | 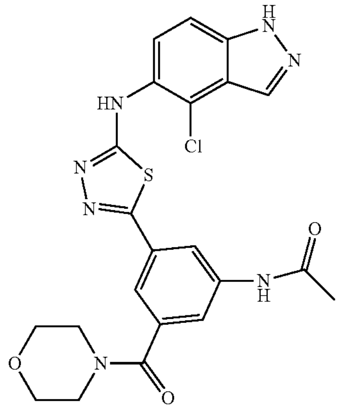 [SMILES: CC(=O)Nc1cc(C(=O)N2CCOCC2)cc(-c2nnc(Nc3ccc4[nH]ncc4c3Cl)s2)c1] |
| 48U | 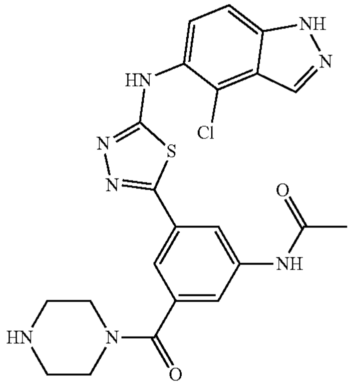 [SMILES: CC(=O)Nc1cc(C(=O)N2CCNCC2)cc(-c2nnc(Nc3ccc4[nH]ncc4c3Cl)s2)c1] |
TABLE 8-continued
| Example No. | Chemical Structure |
|---|---|
| 48V | 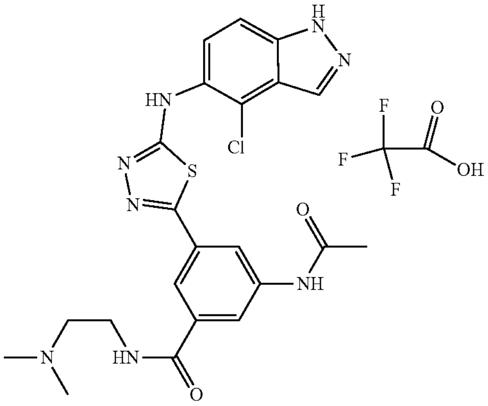 [SMILES: CC(=O)Nc1cc(C(=O)NCCN(C)C)cc(-c2nnc(Nc3ccc4[nH]ncc4c3Cl)s2)c1 ; O=C(O)C(F)(F)F] |
| 48W | 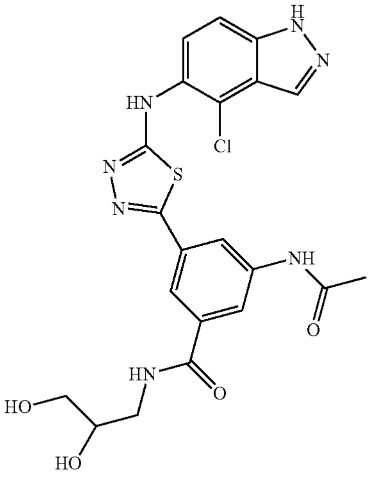 [SMILES: CC(=O)Nc1cc(C(=O)NCC(O)CO)cc(-c2nnc(Nc3ccc4[nH]ncc4c3Cl)s2)c1] |
| 48X | 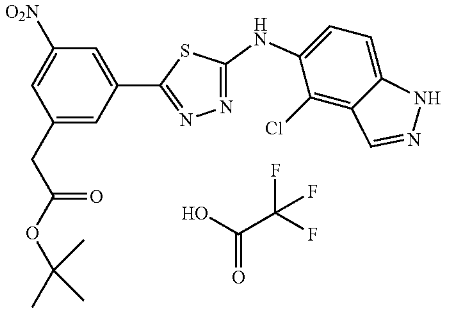 |
| 48Y | 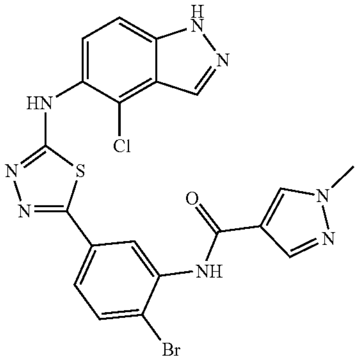 [SMILES: Cn1cc(C(=O)Nc2cc(-c3nnc(Nc4ccc5[nH]ncc5c4Cl)s3)ccc2Br)cn1] |

TABLE 8-continued
| Example No. | Chemical Structure |
|---|---|
| 48Z | 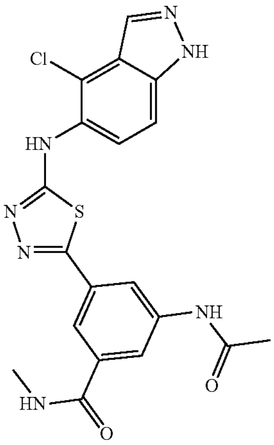 [SMILES: CNC(=O)c1cc(NC(C)=O)cc(-c2nnc(Nc3ccc4[nH]ncc4c3Cl)s2)c1] |
| 48AA | 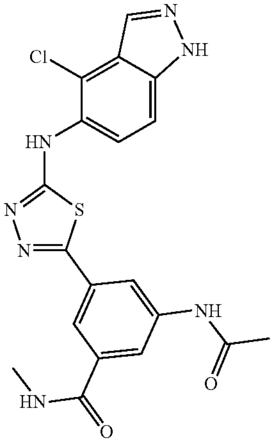 [SMILES: CNC(=O)c1cc(NC(C)=O)cc(-c2nnc(Nc3ccc4[nH]ncc4c3Cl)s2)c1] |
| 48AB | 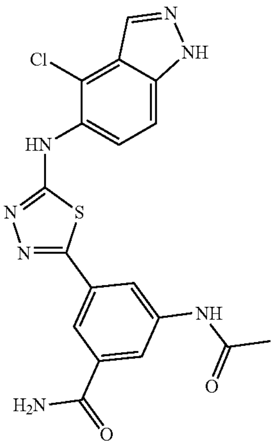 [SMILES: CC(=O)Nc1cc(C(N)=O)cc(-c2nnc(Nc3ccc4[nH]ncc4c3Cl)s2)c1] |
TABLE 8-continued
| Example No. | Chemical Structure |
|---|---|
| 48AC | 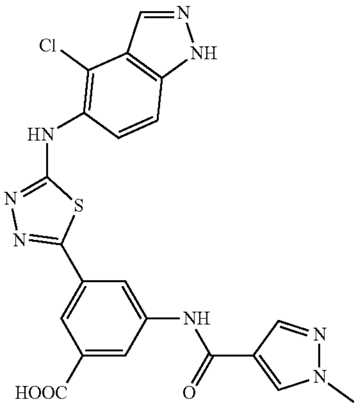 [SMILES: Cn1cc(C(=O)Nc2cc(C(=O)O)cc(-c3nnc(Nc4ccc5[nH]ncc5c4Cl)s3)c2)cn1] |
| 48AD | 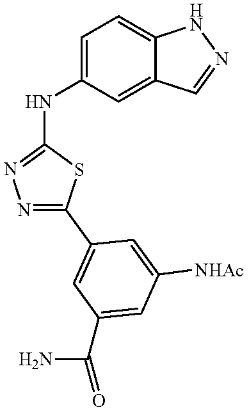 [SMILES: CC(=O)Nc1cc(C(N)=O)cc(-c2nnc(Nc3ccc4[nH]ncc4c3)s2)c1] |
| 48AE | 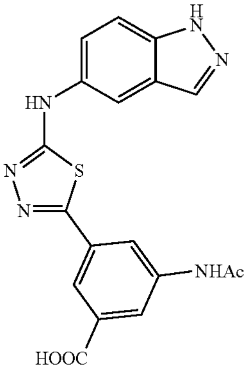 [SMILES: CC(=O)Nc1cc(C(=O)O)cc(-c2nnc(Nc3ccc4[nH]ncc4c3)s2)c1] |
| 48AF | 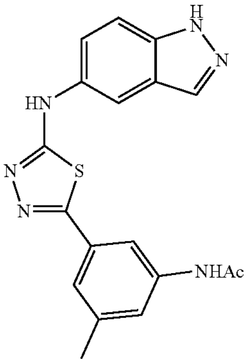 [SMILES: CC(=O)Nc1cc(C)cc(-c2nnc(Nc3ccc4[nH]ncc4c3)s2)c1] |

TABLE 8-continued
| Example No. | Chemical Structure |
|---|---|
| 48AG | 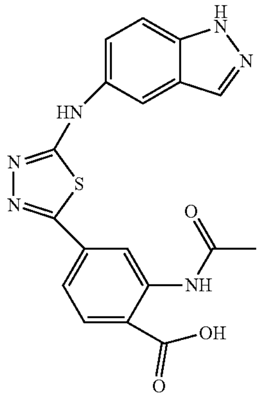 [SMILES: CC(=O)Nc1cc(-c2nnc(Nc3ccc4[nH]ncc4c3)s2)ccc1C(=O)O] |
TABLE 9
| Example No. | Chemical Structure |
|---|---|
| 50A | 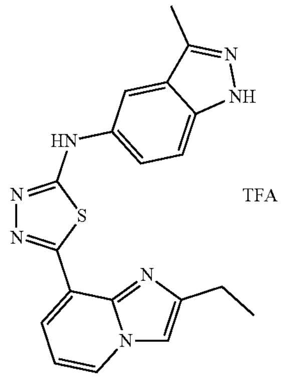 TFA |
| 50B* | 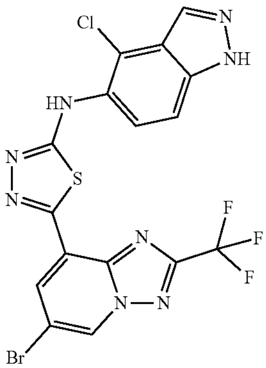 |
TABLE 9-continued
| Example No. | Chemical Structure |
|---|---|
| 50C | 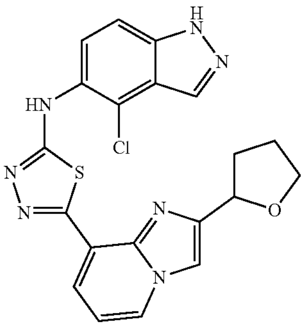 [SMILES: Clc1c(Nc2nnc(-c3cccn4cc(C5CCCO5)nc34)s2)ccc2[nH]ncc12] |
| 50D | 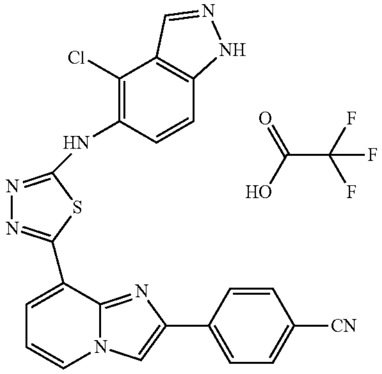 [SMILES: N#Cc1ccc(-c2cn3cccc(-c4nnc(Nc5ccc6[nH]ncc6c5Cl)s4)c3n2)cc1 ; O=C(O)C(F)(F)F] |
| 50E | 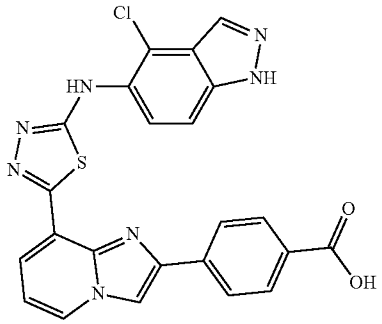 [SMILES: O=C(O)c1ccc(-c2cn3cccc(-c4nnc(Nc5ccc6[nH]ncc6c5Cl)s4)c3n2)cc1] |
| 50F | 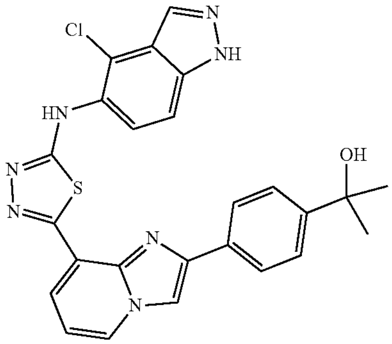 [SMILES: CC(C)(O)c1ccc(-c2cn3cccc(-c4nnc(Nc5ccc6[nH]ncc6c5Cl)s4)c3n2)cc1] |

TABLE 9-continued
| Example No. | Chemical Structure |
|---|---|
| 50G | 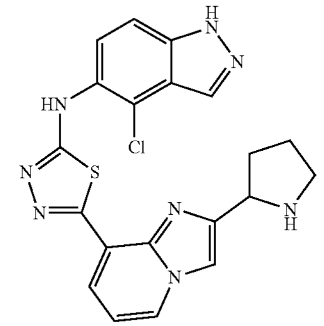 [SMILES: Clc1c(Nc2nnc(-c3cccn4cc(C5CCCN5)nc34)s2)ccc2[nH]ncc12] |
| 50H | 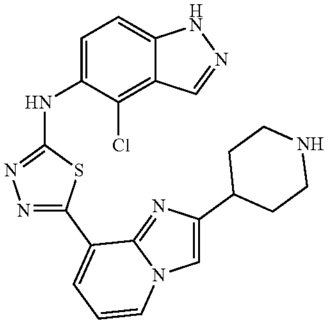 [SMILES: Clc1c(Nc2nnc(-c3cccn4cc(C5CCNCC5)nc34)s2)ccc2[nH]ncc12] |
TABLE 10
| Example No. | Chemical Structure |
|---|---|
| 52A | 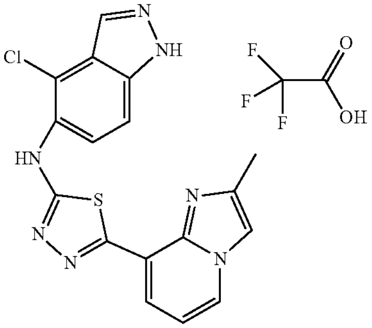 |
| 52B | 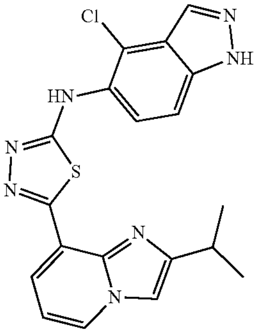 [SMILES: CC(C)c1cn2cccc(-c3nnc(Nc4ccc5[nH]ncc5c4Cl)s3)c2n1] |
TABLE 10-continued
| Example No. | Chemical Structure |
|---|---|
| 52C | 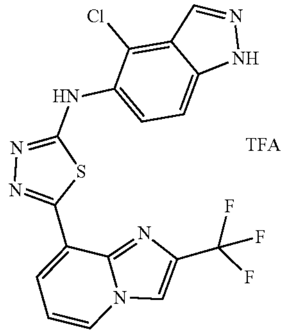 TFA |
| 52D | 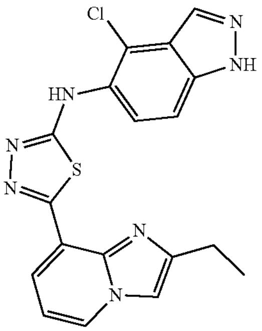 |
| 52E | 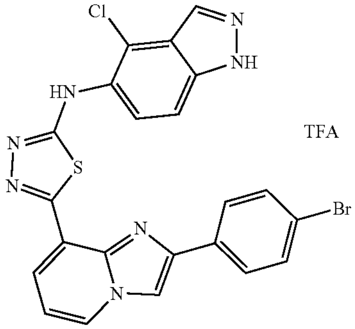 TFA |
| 52F | 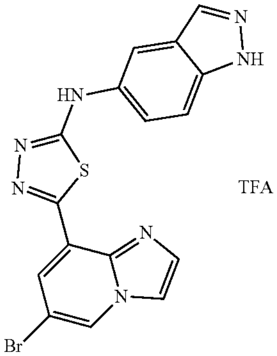 TFA |

TABLE 10-continued
| Example No. | Chemical Structure |
|---|---|
| 52G | 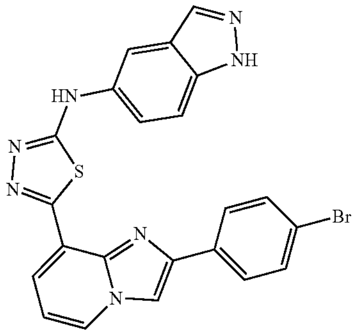 [SMILES: Brc1ccc(-c2cn3cccc(-c4nnc(Nc5ccc6[nH]ncc6c5)s4)c3n2)cc1] |
TABLE 11
| Example No. | Chemical Structure |
|---|---|
| 54A | 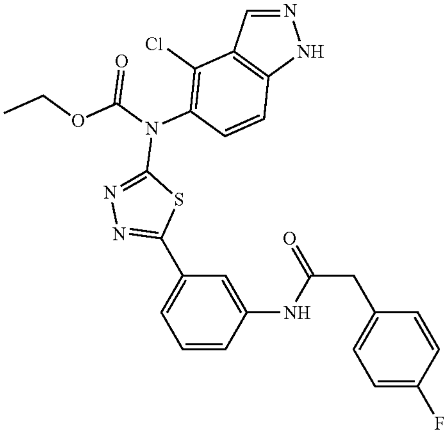 [SMILES: CCOC(=O)N(c1nnc(-c2cccc(NC(=O)Cc3ccc(F)cc3)c2)s1)c1ccc2[nH]ncc2c1Cl] |
| 54B | 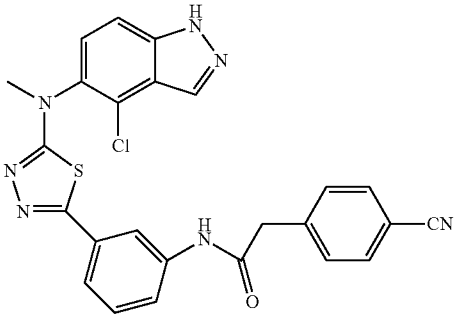 [SMILES: CN(c1nnc(-c2cccc(NC(=O)Cc3ccc(C#N)cc3)c2)s1)c1ccc2[nH]ncc2c1Cl] |
| 54C | 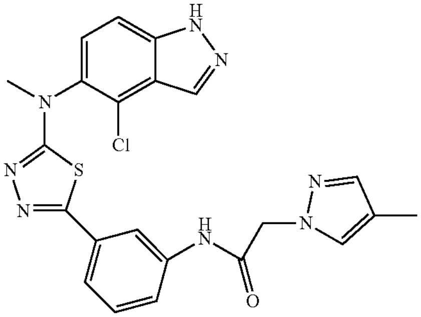 |
TABLE 11-continued
| Example No. | Chemical Structure |
|---|---|
| 54D | 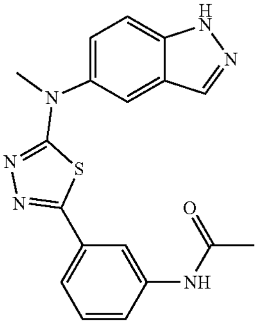 [SMILES: CC(=O)Nc1cccc(-c2nnc(N(C)c3ccc4[nH]ncc4c3)s2)c1] |
| 54E | 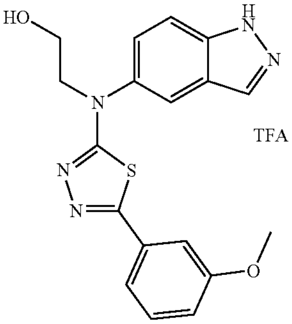 [SMILES: COc1cccc(-c2nnc(N(CCO)c3ccc4[nH]ncc4c3)s2)c1] TFA |
TABLE 12
| Example No. | Chemical Structure |
|---|---|
| 56A | 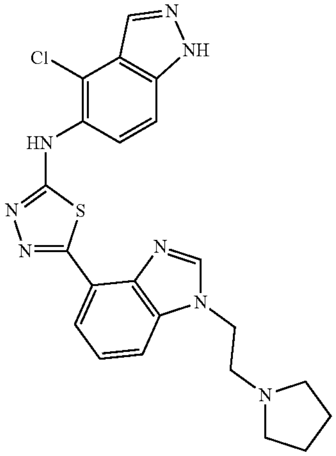 [SMILES: Clc1c(Nc2nnc(-c3cccc4c3ncn4CCN3CCCC3)s2)ccc2[nH]ncc12] |
| 56B | 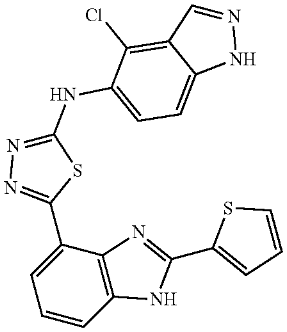 [SMILES: Clc1c(Nc2nnc(-c3cccc4[nH]c(-c5cccs5)nc34)s2)ccc2[nH]ncc12] |

TABLE 12-continued
| Example No. | Chemical Structure |
|---|---|
| 56C | 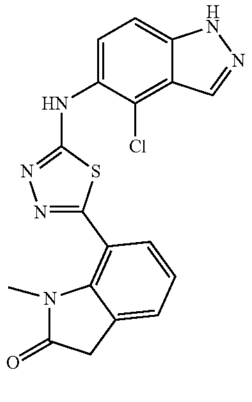 [SMILES: CN1C(=O)Cc2cccc(-c3nnc(Nc4ccc5[nH]ncc5c4Cl)s3)c21] |
| 56D | 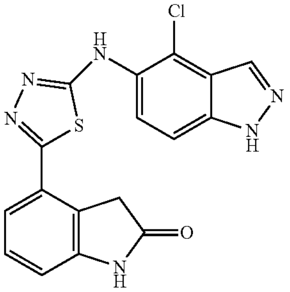 [SMILES: O=C1Cc2c(cccc2-c2nnc(Nc3ccc4[nH]ncc4c3Cl)s2)N1] |
| 56E | 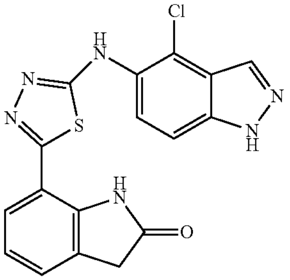 [SMILES: O=C1Cc2cccc(-c3nnc(Nc4ccc5[nH]ncc5c4Cl)s3)c2N1] |
| 56F | 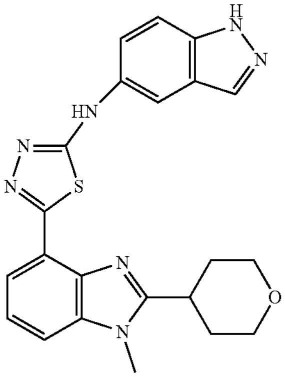 [SMILES: Cn1c(C2CCOCC2)nc2c(-c3nnc(Nc4ccc5[nH]ncc5c4)s3)cccc21] |
| 56G | 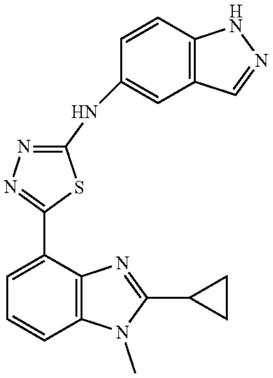 [SMILES: Cn1c(C2CC2)nc2c(-c3nnc(Nc4ccc5[nH]ncc5c4)s3)cccc21] |
| 56H | 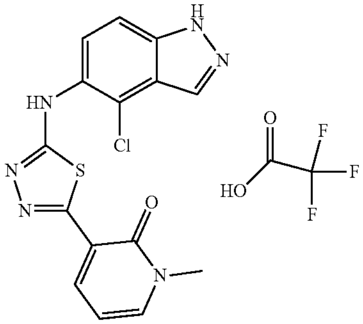 [SMILES: Cn1cccc(-c2nnc(Nc3ccc4[nH]ncc4c3Cl)s2)c1=O ; O=C(O)C(F)(F)F] |
TABLE 13
| Example No. | Chemical Structure |
|---|---|
| 58A | 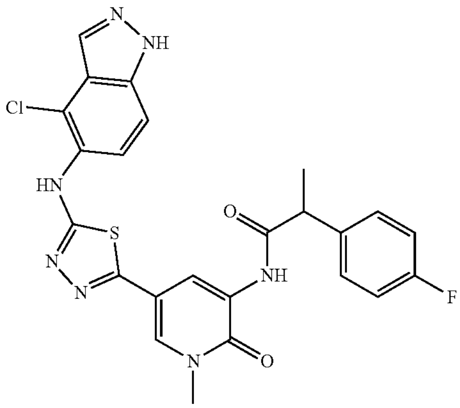 [SMILES: CC(C(=O)Nc1cc(-c2nnc(Nc3ccc4[nH]ncc4c3Cl)s2)cn(C)c1=O)c1ccc(F)cc1] |

TABLE 13-continued
| Example No. | Chemical Structure |
|---|---|
| 58B | 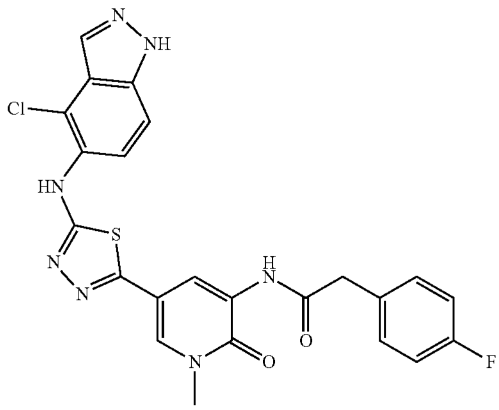 [SMILES: Cn1cc(-c2nnc(Nc3ccc4[nH]ncc4c3Cl)s2)cc(NC(=O)Cc2ccc(F)cc2)c1=O] |
TABLE 13A
| Example No. | Chemical Structure |
|---|---|
| 61A | 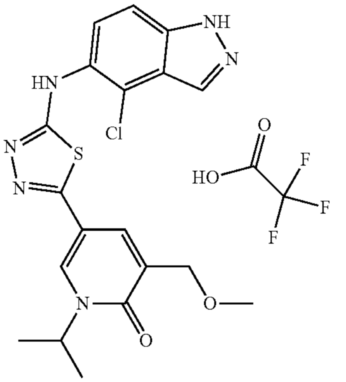 [SMILES: COCc1cc(-c2nnc(Nc3ccc4[nH]ncc4c3Cl)s2)cn(C(C)C)c1=O ; O=C(O)C(F)(F)F] |
| 61B | 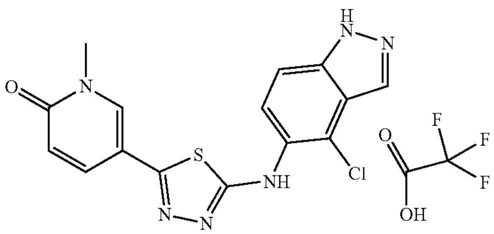 |
| 61C | 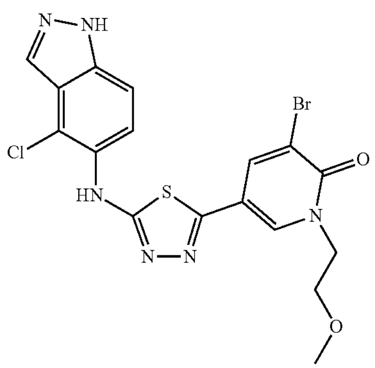 [SMILES: COCCn1cc(-c2nnc(Nc3ccc4[nH]ncc4c3Cl)s2)cc(Br)c1=O] |
TABLE 13A-continued
| Example No. | Chemical Structure |
|---|---|
| 61D | 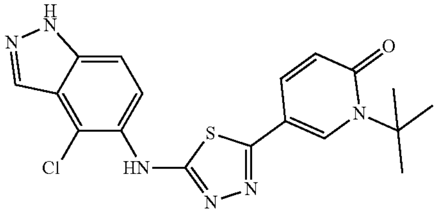 [SMILES: CC(C)(C)n1cc(-c2nnc(Nc3ccc4[nH]ncc4c3Cl)s2)ccc1=O] |
| 61E | 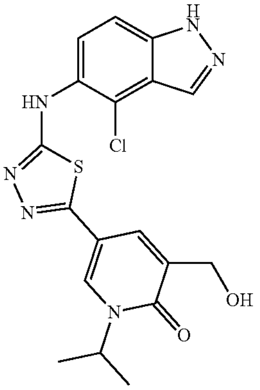 [SMILES: CC(C)n1cc(-c2nnc(Nc3ccc4[nH]ncc4c3Cl)s2)cc(CO)c1=O] |
| 61F | 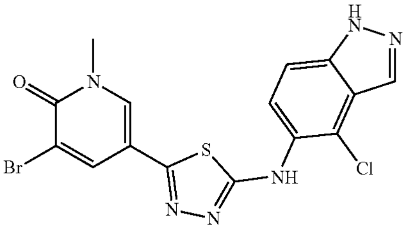 [SMILES: Cn1cc(-c2nnc(Nc3ccc4[nH]ncc4c3Cl)s2)cc(Br)c1=O] |
| 61G | 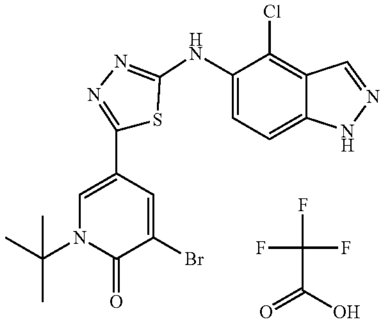 [SMILES: CC(C)(C)n1cc(-c2nnc(Nc3ccc4[nH]ncc4c3Cl)s2)cc(Br)c1=O ; O=C(O)C(F)(F)F] |
| 61H | 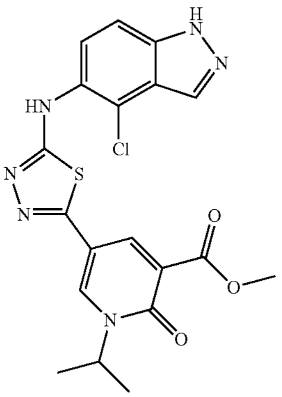 [SMILES: COC(=O)c1cc(-c2nnc(Nc3ccc4[nH]ncc4c3Cl)s2)cn(C(C)C)c1=O] |

TABLE 13A-continued
| Example No. | Chemical Structure |
| --- | --- |
| 61I | 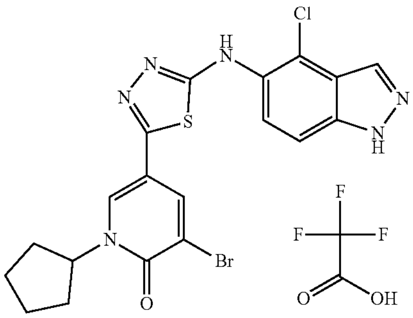 [SMILES: O=c1c(Br)cc(-c2nnc(Nc3ccc4[nH]ncc4c3Cl)s2)cn1C1CCCC1 ; O=C(O)C(F)(F)F] |
| 61J | 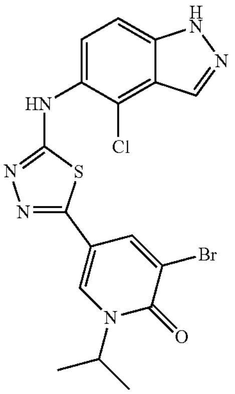 [SMILES: CC(C)n1cc(-c2nnc(Nc3ccc4[nH]ncc4c3Cl)s2)cc(Br)c1=O] |
| 61K | 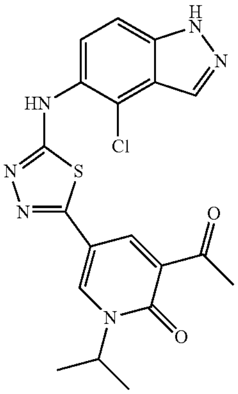 [SMILES: CC(=O)c1cc(-c2nnc(Nc3ccc4[nH]ncc4c3Cl)s2)cn(C(C)C)c1=O] |
TABLE 14
| Example No. | Chemical Structure |
| --- | --- |
| 71A | 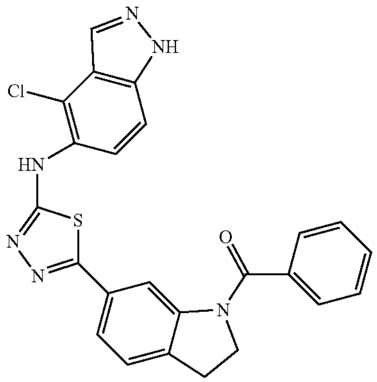 [SMILES: O=C(c1ccccc1)N1CCc2ccc(-c3nnc(Nc4ccc5[nH]ncc5c4Cl)s3)cc21] |
| 71B | 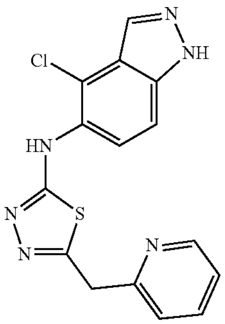 [SMILES: Clc1c(Nc2nnc(Cc3ccccn3)s2)ccc2[nH]ncc12] |
| 71C | 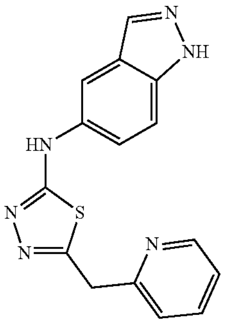 [SMILES: c1ccc(Cc2nnc(Nc3ccc4[nH]ncc4c3)s2)nc1] |
| 71D | 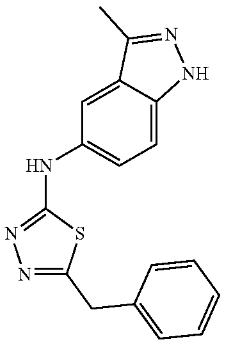 [SMILES: Cc1n[nH]c2ccc(Nc3nnc(Cc4ccccc4)s3)cc12] |

TABLE 14-continued
| Example No. | Chemical Structure |
|---|---|
| 71E | 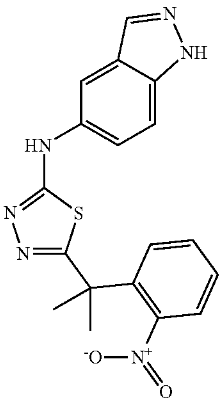 |
| 71F | 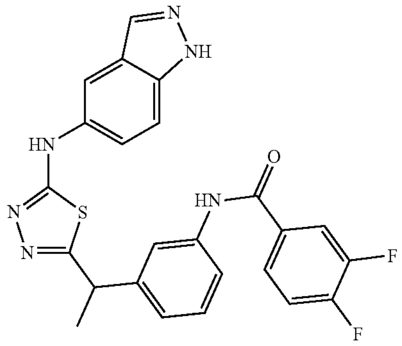 [SMILES: CC(c1cccc(NC(=O)c2ccc(F)c(F)c2)c1)c1nnc(Nc2ccc3[nH]ncc3c2)s1] |
| 71G | 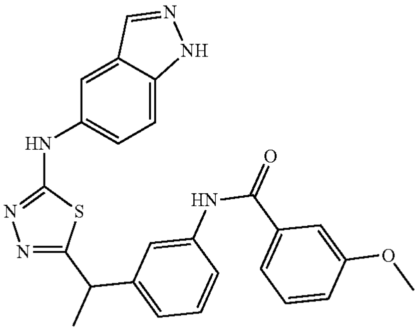 [SMILES: COc1cccc(C(=O)Nc2cccc(C(C)c3nnc(Nc4ccc5[nH]ncc5c4)s3)c2)c1] |
| 71H | 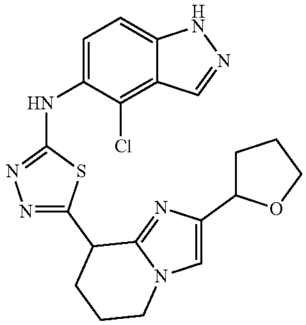 [SMILES: Clc1c(Nc2nnc(C3CCCn4cc(C5CCCO5)nc43)s2)ccc2[nH]ncc12] |
TABLE 14-continued
| Example No. | Chemical Structure |
|---|---|
| 71I | 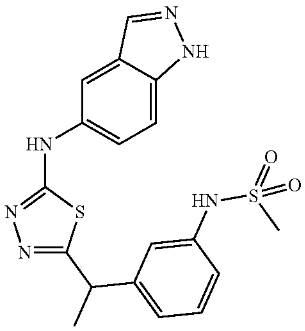 [SMILES: CC(c1cccc(NS(C)(=O)=O)c1)c1nnc(Nc2ccc3[nH]ncc3c2)s1] |
| 71J | 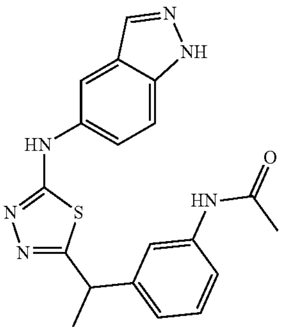 [SMILES: CC(=O)Nc1cccc(C(C)c2nnc(Nc3ccc4[nH]ncc4c3)s2)c1] |
| 71K | 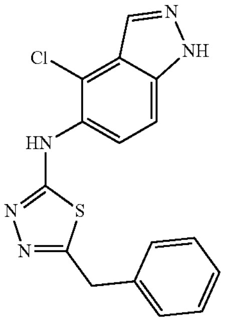 [SMILES: Clc1c(Nc2nnc(Cc3ccccc3)s2)ccc2[nH]ncc12] |
| 71L | 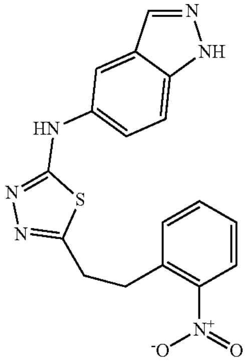 |

TABLE 14-continued
| Example No. | Chemical Structure |
|---|---|
| 71M | 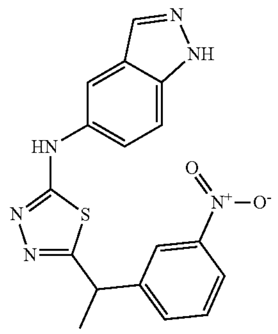 [SMILES: CC(c1cccc([N+](=O)[O-])c1)c1nnc(Nc2ccc3[nH]ncc3c2)s1] |
| 71N | 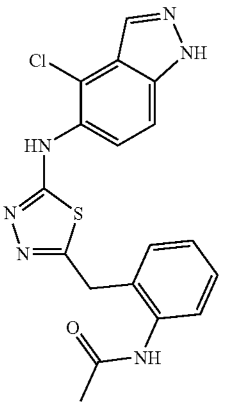 [SMILES: CC(=O)Nc1ccccc1Cc1nnc(Nc2ccc3[nH]ncc3c2Cl)s1] |
| 71O | 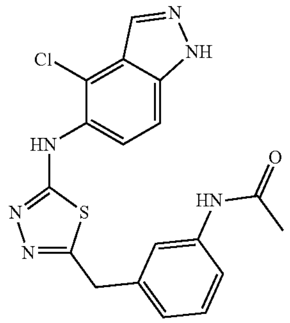 [SMILES: CC(=O)Nc1cccc(Cc2nnc(Nc3ccc4[nH]ncc4c3Cl)s2)c1] |
| 71P | 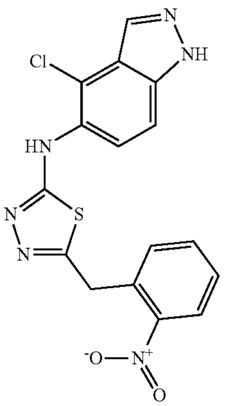 |
| 71Q | 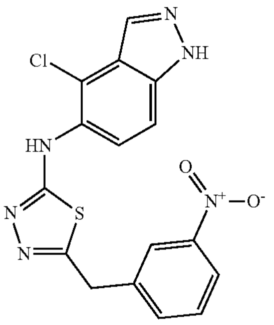 [SMILES: O=[N+]([O-])c1cccc(Cc2nnc(Nc3ccc4[nH]ncc4c3Cl)s2)c1] |
TABLE 15
| Example No. | Chemical Structure |
|---|---|
| 75A | 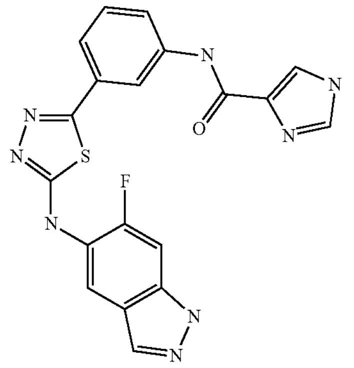 [SMILES: O=C(Nc1cccc(-c2nnc(Nc3cc4cn[nH]c4cc3F)s2)c1)c1c[nH]cn1] |
| 75B | 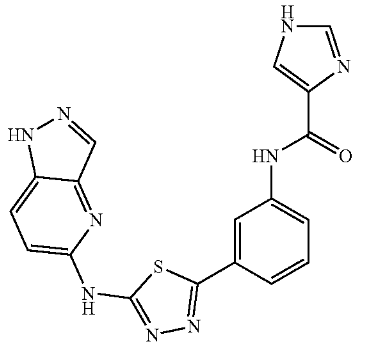 [SMILES: O=C(Nc1cccc(-c2nnc(Nc3ccc4[nH]ncc4n3)s2)c1)c1c[nH]cn1] |
| 75C | 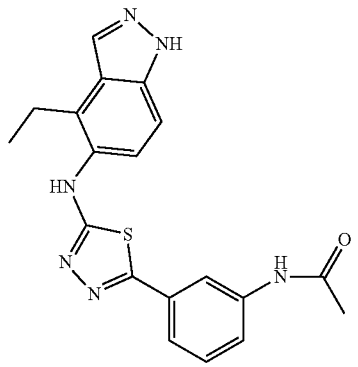 [SMILES: CCc1c(Nc2nnc(-c3cccc(NC(C)=O)c3)s2)ccc2[nH]ncc12] |

TABLE 15-continued
| Example No. | Chemical Structure |
|---|---|
| 75D | 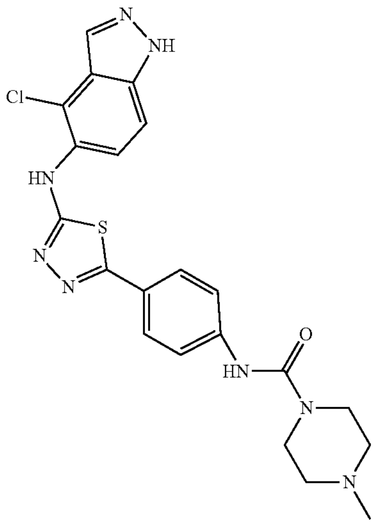 [SMILES: CN1CCN(C(=O)Nc2ccc(-c3nnc(Nc4ccc5[nH]ncc5c4Cl)s3)cc2)CC1] |
| 75E | 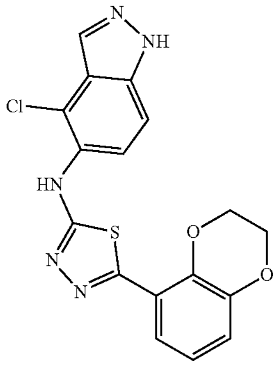 [SMILES: Clc1c(Nc2nnc(-c3cccc4c3OCCO4)s2)ccc2[nH]ncc12] |
| 75F | 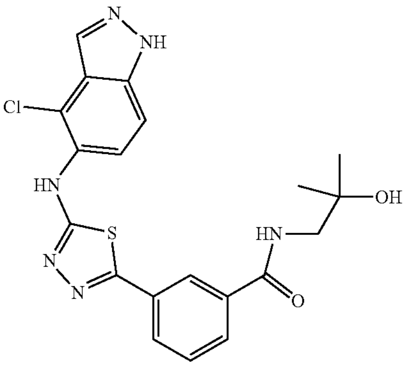 [SMILES: CC(C)(O)CNC(=O)c1cccc(-c2nnc(Nc3ccc4[nH]ncc4c3Cl)s2)c1] |
| 75G | 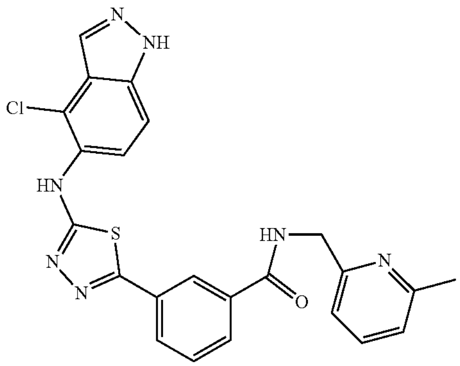 [SMILES: Cc1cccc(CNC(=O)c2cccc(-c3nnc(Nc4ccc5[nH]ncc5c4Cl)s3)c2)n1] |
| 75H | 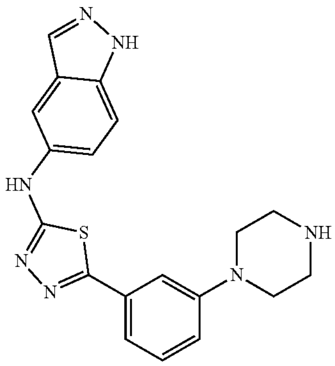 [SMILES: c1cc(-c2nnc(Nc3ccc4[nH]ncc4c3)s2)cc(N2CCNCC2)c1] |
| 75I | 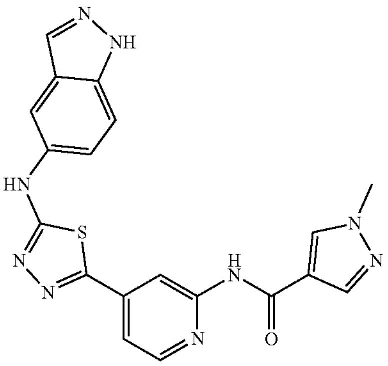 [SMILES: Cn1cc(C(=O)Nc2cc(-c3nnc(Nc4ccc5[nH]ncc5c4)s3)ccn2)cn1] |
| 75J | 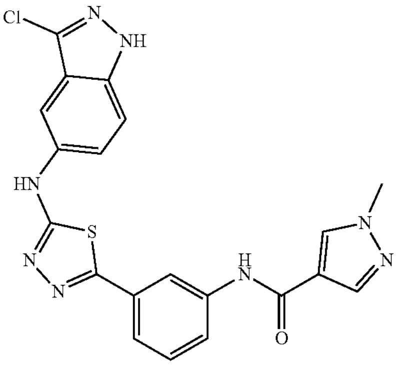 [SMILES: Cn1cc(C(=O)Nc2cccc(-c3nnc(Nc4ccc5[nH]nc(Cl)c5c4)s3)c2)cn1] |

TABLE 15-continued
| Example No. | Chemical Structure |
| --- | --- |
| 75K | 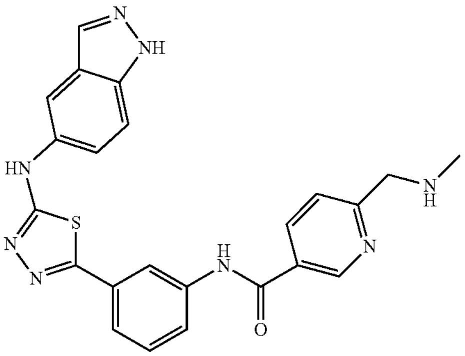 [SMILES: CNCc1ccc(C(=O)Nc2cccc(-c3nnc(Nc4ccc5[nH]ncc5c4)s3)c2)cn1] |
| 75L | 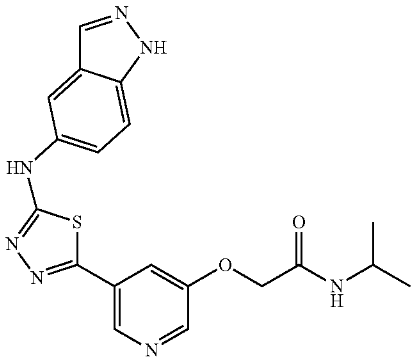 [SMILES: CC(C)NC(=O)COc1cncc(-c2nnc(Nc3ccc4[nH]ncc4c3)s2)c1] |
| 75M | 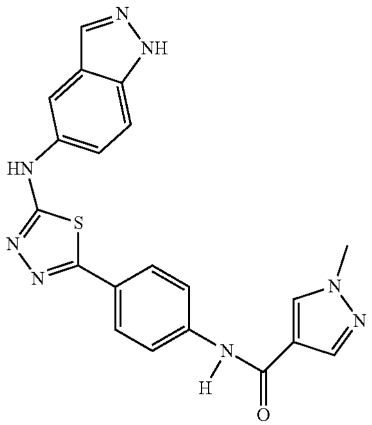 [SMILES: Cn1cc(C(=O)Nc2ccc(-c3nnc(Nc4ccc5[nH]ncc5c4)s3)cc2)cn1] |
| 75N | 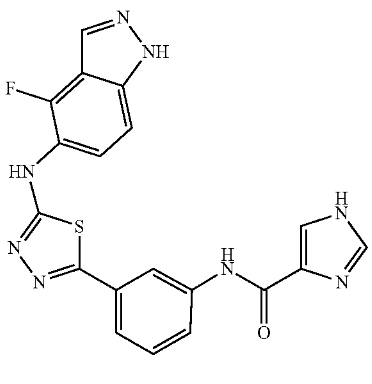 [SMILES: O=C(Nc1cccc(-c2nnc(Nc3ccc4[nH]ncc4c3F)s2)c1)c1c[nH]cn1] |
| 75O | 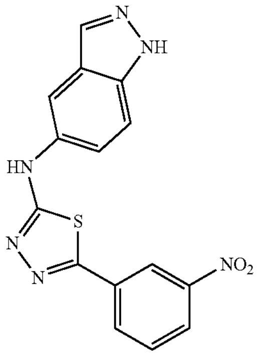 [SMILES: O=[N+]([O-])c1cccc(-c2nnc(Nc3ccc4[nH]ncc4c3)s2)c1] |
| 75P | 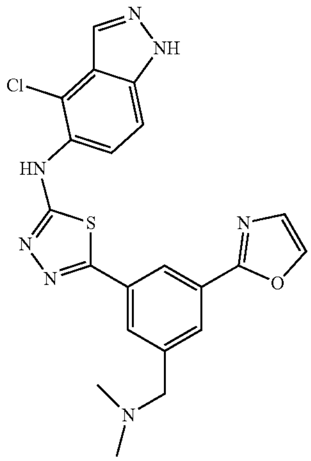 [SMILES: CN(C)Cc1cc(-c2ncco2)cc(-c2nnc(Nc3ccc4[nH]ncc4c3Cl)s2)c1] |
| 75Q | 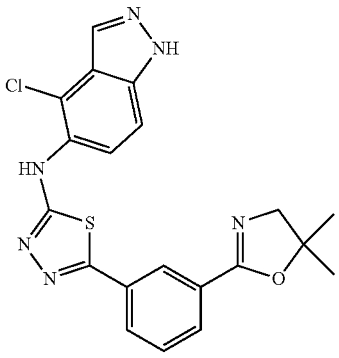 [SMILES: CC1(C)CN=C(c2cccc(-c3nnc(Nc4ccc5[nH]ncc5c4Cl)s3)c2)O1] |
| 75R | 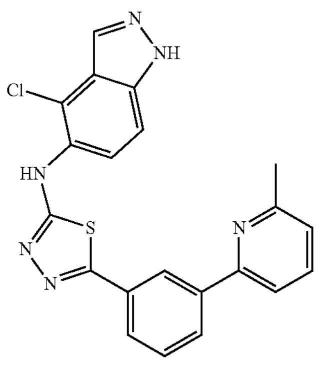 [SMILES: Cc1cccc(-c2cccc(-c3nnc(Nc4ccc5[nH]ncc5c4Cl)s3)c2)n1] |

TABLE 15-continued
| Example No. | Chemical Structure |
|---|---|
| 75S | 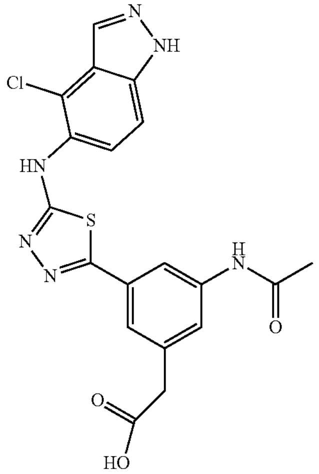 [SMILES: CC(=O)Nc1cc(CC(=O)O)cc(-c2nnc(Nc3ccc4[nH]ncc4c3Cl)s2)c1] |
| 75T | 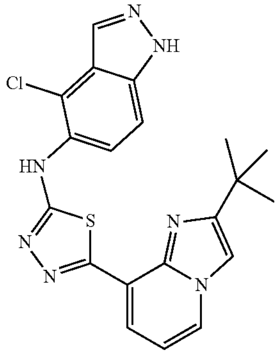 [SMILES: CC(C)(C)c1cn2cccc(-c3nnc(Nc4ccc5[nH]ncc5c4Cl)s3)c2n1] |
| 75U | 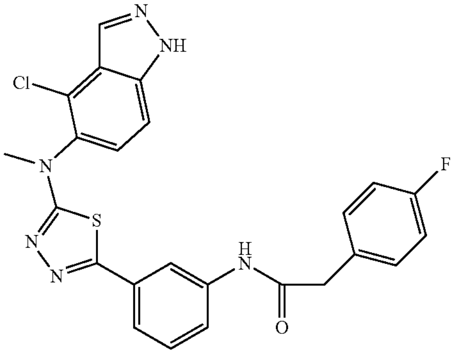 [SMILES: CN(c1nnc(-c2cccc(NC(=O)Cc3ccc(F)cc3)c2)s1)c1ccc2[nH]ncc2c1Cl] |
| 75V | 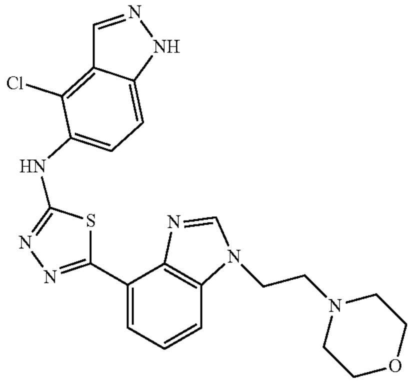 [SMILES: Clc1c(Nc2nnc(-c3cccc4c3ncn4CCN3CCOCC3)s2)ccc2[nH]ncc12] |
| 75W | 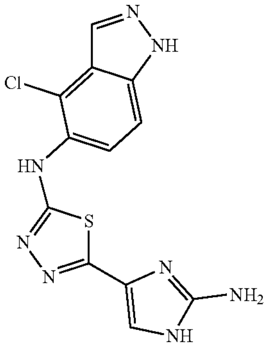 [SMILES: Nc1nc(-c2nnc(Nc3ccc4[nH]ncc4c3Cl)s2)c[nH]1] |
TABLE 16
| Compound No. | Compound Structure |
|---|---|
| A-1 | 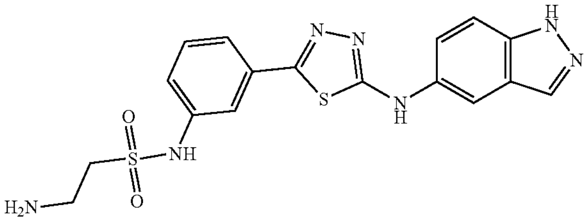 [SMILES: NCCS(=O)(=O)Nc1cccc(-c2nnc(Nc3ccc4[nH]ncc4c3)s2)c1] |

TABLE 16-continued
| Compound No. | Compound Structure |
|---|---|
| A-2 | 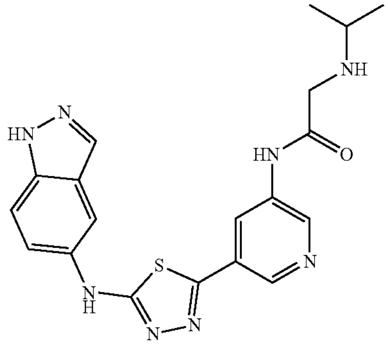 [SMILES: CC(C)NCC(=O)Nc1cncc(-c2nnc(Nc3ccc4[nH]ncc4c3)s2)c1] |
| A-3 | 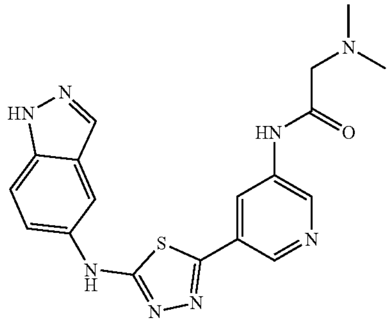 [SMILES: CN(C)CC(=O)Nc1cncc(-c2nnc(Nc3ccc4[nH]ncc4c3)s2)c1] |
| A-4 | 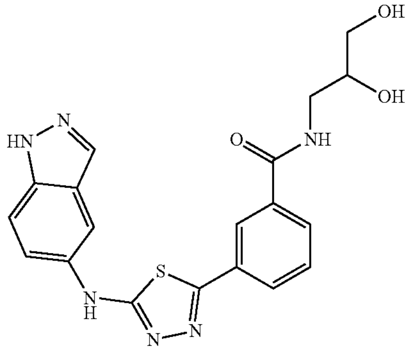 [SMILES: O=C(NCC(O)CO)c1cccc(-c2nnc(Nc3ccc4[nH]ncc4c3)s2)c1] |
| A-5 | 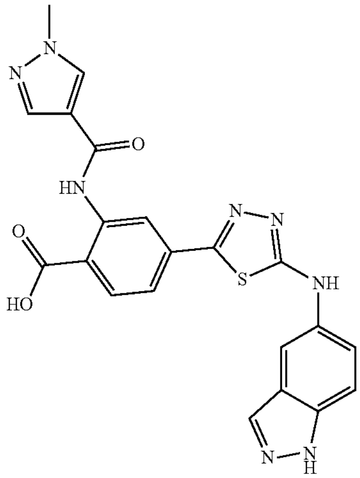 [SMILES: Cn1cc(C(=O)Nc2cc(-c3nnc(Nc4ccc5[nH]ncc5c4)s3)ccc2C(=O)O)cn1] |

TABLE 16-continued
| Compound No. | Compound Structure |
| --- | --- |
| A-6 | 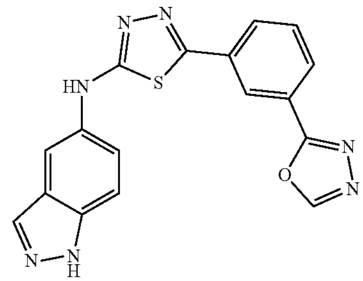 [SMILES: c1cc(-c2nnco2)cc(-c2nnc(Nc3ccc4[nH]ncc4c3)s2)c1] |
| A-7 | 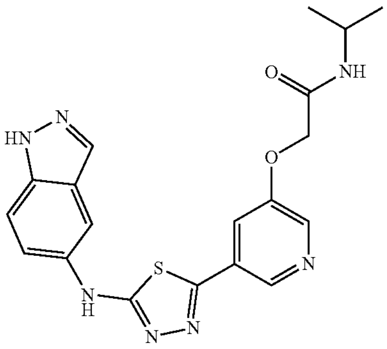 TFA |
| A-8 | 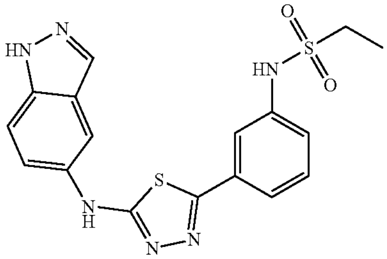 TFA |
| A-9 | 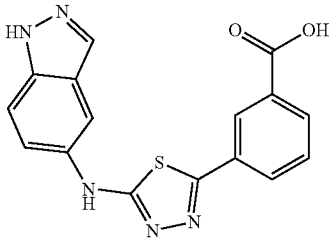 [SMILES: O=C(O)c1cccc(-c2nnc(Nc3ccc4[nH]ncc4c3)s2)c1] |
| A-10 | 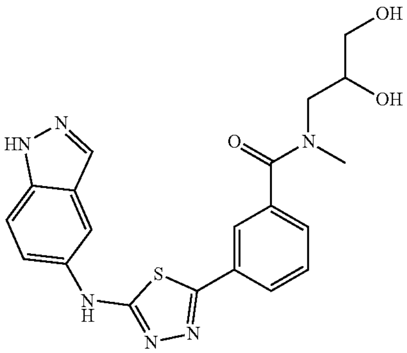 [SMILES: CN(CC(O)CO)C(=O)c1cccc(-c2nnc(Nc3ccc4[nH]ncc4c3)s2)c1] |

TABLE 16-continued
| Compound No. | Compound Structure |
|---|---|
| A-11 | 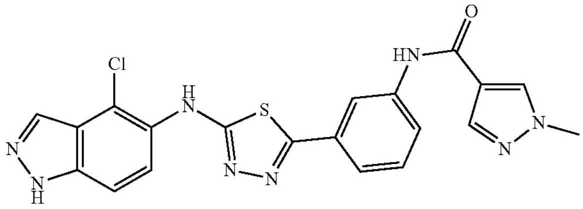 TFA |
| A-12 | 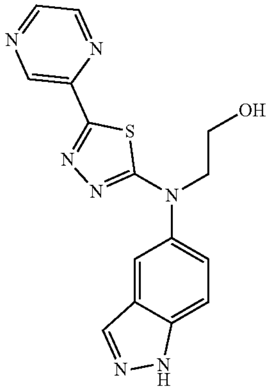 |
| A-13 | 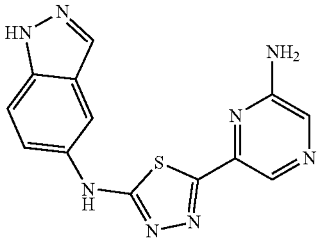 TFA |
| A-14 | 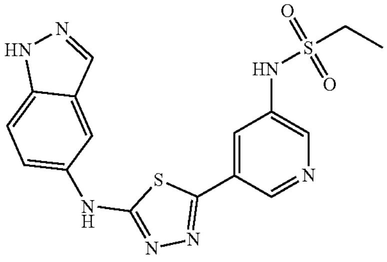 TFA |

TABLE 16-continued
| Compound No. | Compound Structure |
| --- | --- |
| A-15 | 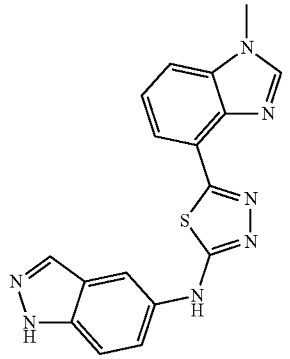 TFA |
| A-16 | 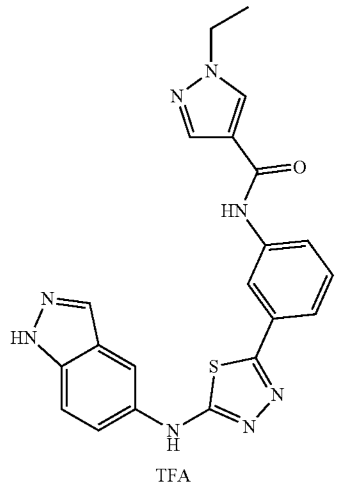 TFA |
| A-17 | 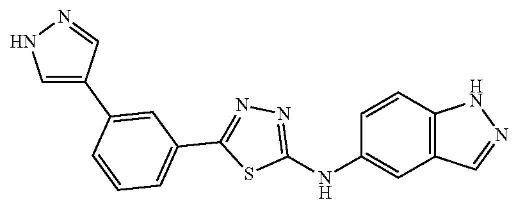 TFA |
| A-18 | 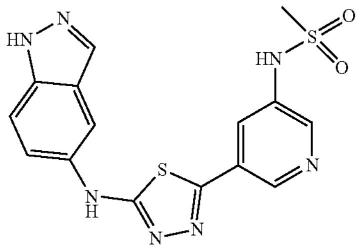 TFA |

TABLE 16-continued
| Compound No. | Compound Structure |
| --- | --- |
| A-19 | 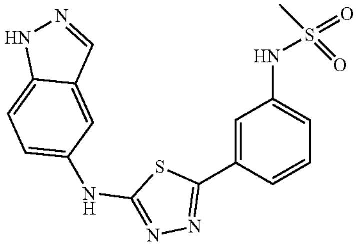 TFA |
| A-20 | 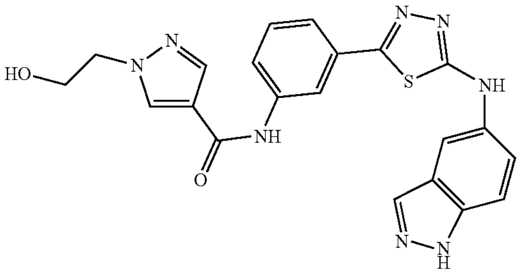 TFA |
| A-21 | 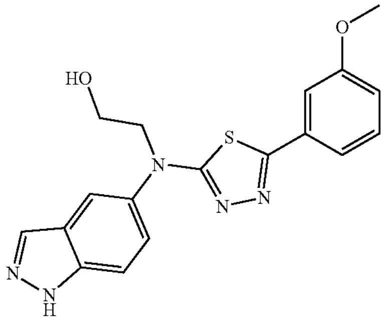 TFA |
| A-22 | 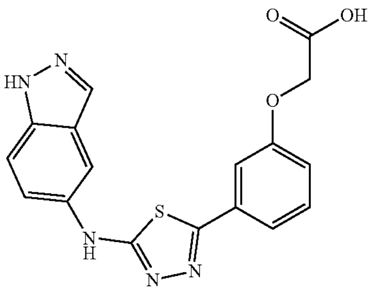 TFA |

TABLE 16-continued
| Compound No. | Compound Structure |
|---|---|
| A-23 | 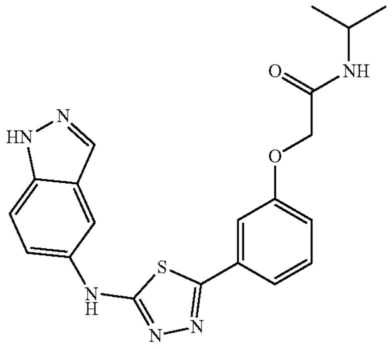 TFA |
| A-24 | 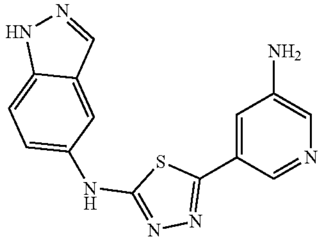 TFA |
| A-25 | 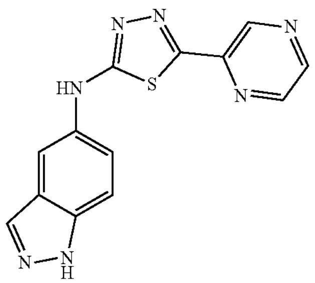 |
| A-26 | 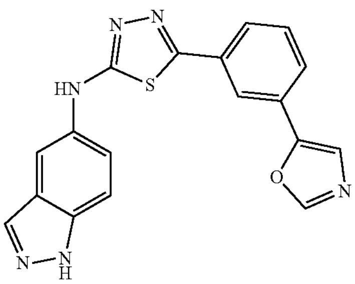 TFA |

TABLE 16-continued
| Compound No. | Compound Structure |
|---|---|
| A-27 | 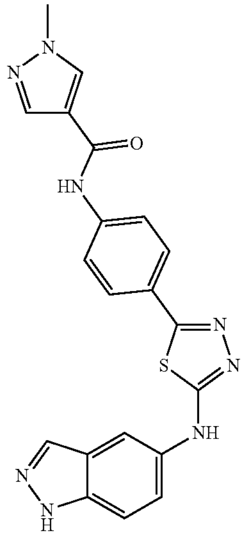 [SMILES: Cn1cc(C(=O)Nc2ccc(-c3nnc(Nc4ccc5[nH]ncc5c4)s3)cc2)cn1] |
| A-28 | 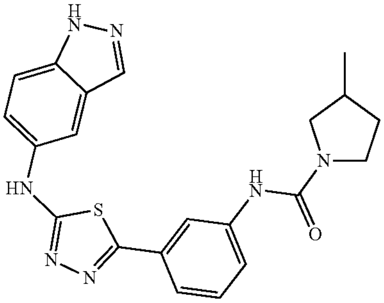 TFA |
| A-29 | 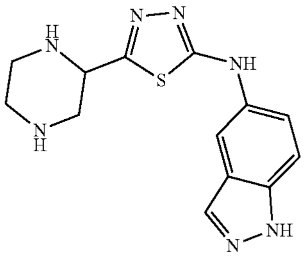 TFA |
| A-30 | 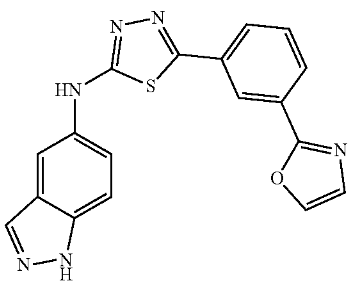 TFA |

TABLE 16-continued
| Compound No. | Compound Structure |
|---|---|
| A-31 | 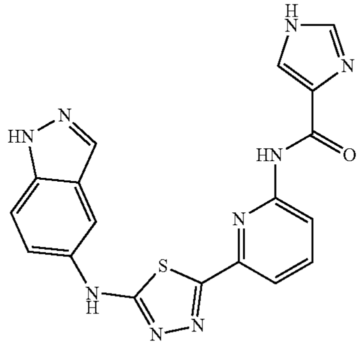 TFA |
| A-32 | 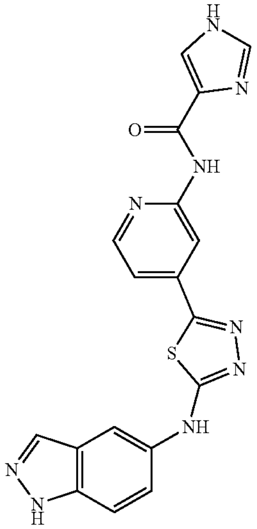 TFA |
| A-33 | 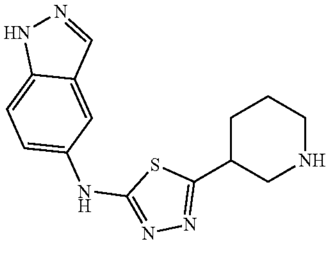 TFA |
| A-34 | 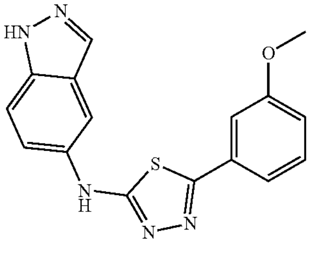 TFA |

TABLE 16-continued
| Compound No. | Compound Structure |
|---|---|
| A-35 | 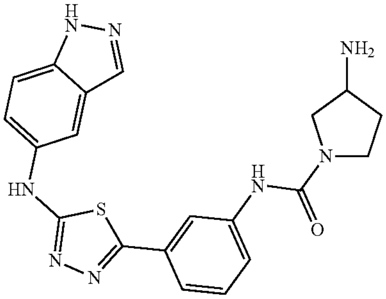 TFA |
| A-36 | 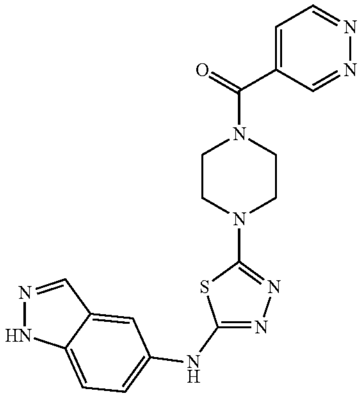 |
| A-37 | 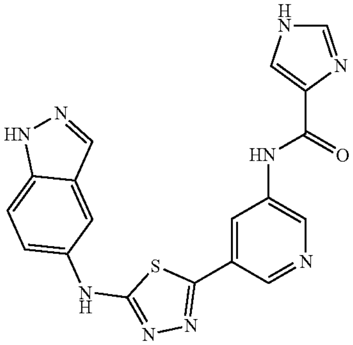 TFA |
| A-38 | 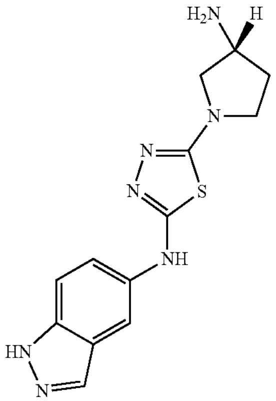 |

TABLE 16-continued
| Compound No. | Compound Structure |
|---|---|
| A-39 | 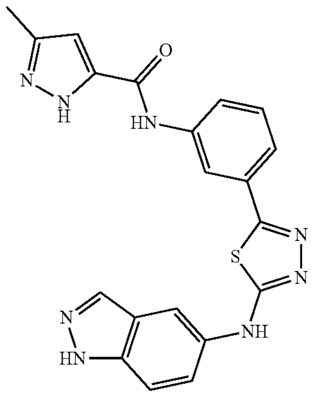 TFA |
| A-40 | 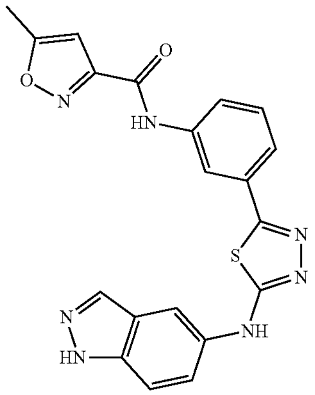 TFA |
| A-41 | 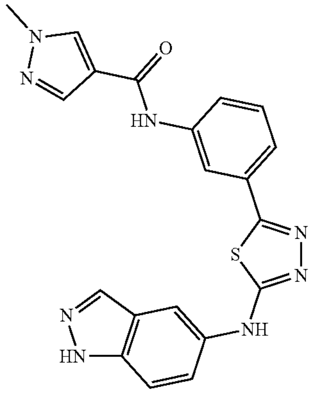 TFA |

TABLE 16-continued
| Compound No. | Compound Structure |
|---|---|
| A-42 | 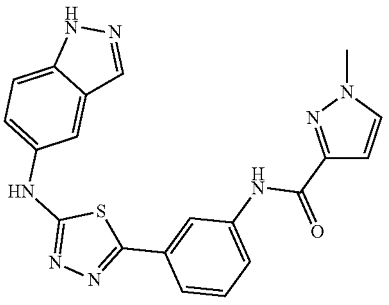 TFA |
| A-43 | 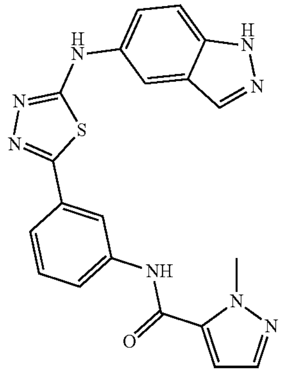 TFA |
| A-44 | 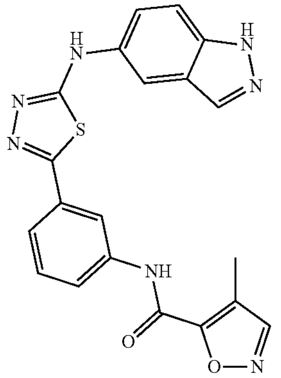 TFA |

TABLE 16-continued
| Compound No. | Compound Structure |
|---|---|
| A-45 | 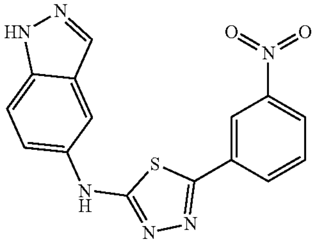 TFA |
| A-46 | 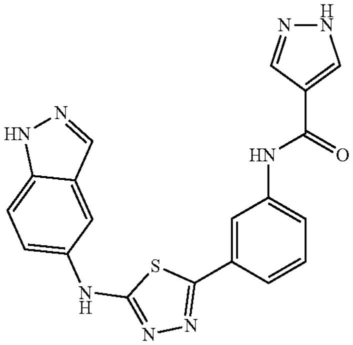 TFA |
| A-47 | 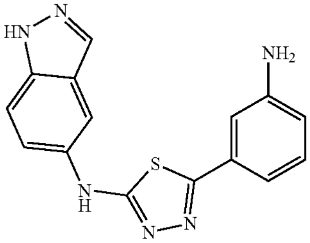 TFA |
| A-48 | 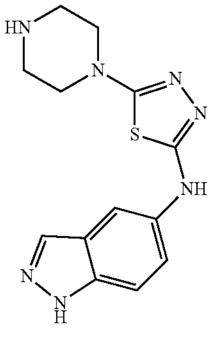 |

TABLE 16-continued
| Compound No. | Compound Structure |
|---|---|
| A-49 | 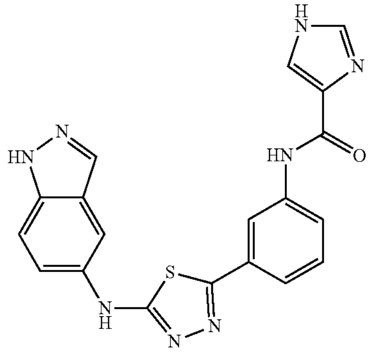 [SMILES: O=C(Nc1cccc(-c2nnc(Nc3ccc4[nH]ncc4c3)s2)c1)c1c[nH]cn1] |
| A-50 | 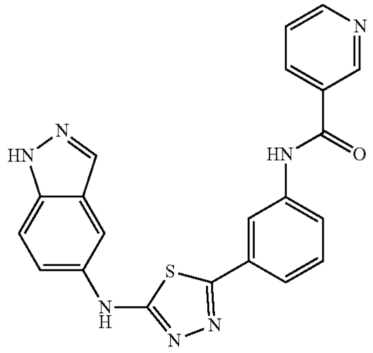 [SMILES: O=C(Nc1cccc(-c2nnc(Nc3ccc4[nH]ncc4c3)s2)c1)c1cccnc1] |
TABLE 17
| Example No. | Compound Structure |
|---|---|
| 34 | 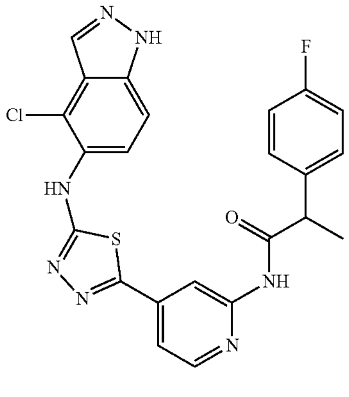 [SMILES: CC(C(=O)Nc1cc(-c2nnc(Nc3ccc4[nH]ncc4c3Cl)s2)ccn1)c1ccc(F)cc1] |
TABLE 17-continued
| Example No. | Compound Structure |
|---|---|
| 36 | 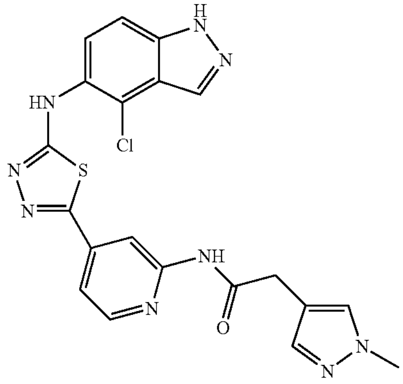 [SMILES: Cn1cc(CC(=O)Nc2cc(-c3nnc(Nc4ccc5[nH]ncc5c4Cl)s3)ccn2)cn1] |

TABLE 17-continued
| Example No. | Compound Structure |
|---|---|
| 37 | 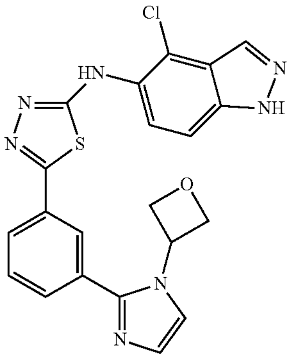 [SMILES: Clc1c(Nc2nnc(-c3cccc(-c4nccn4C4COC4)c3)s2)ccc2[nH]ncc12] |
| 38 | 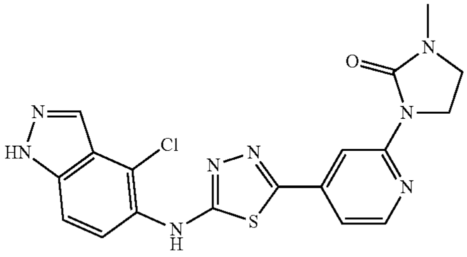 [SMILES: CN1CCN(c2cc(-c3nnc(Nc4ccc5[nH]ncc5c4Cl)s3)ccn2)C1=O] |
| 40 | 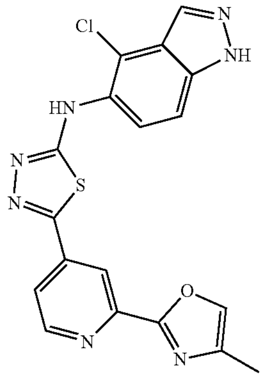 [SMILES: Cc1coc(-c2cc(-c3nnc(Nc4ccc5[nH]ncc5c4Cl)s3)ccn2)n1] |
| 42 | 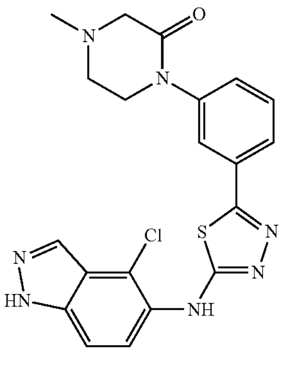 [SMILES: CN1CCN(c2cccc(-c3nnc(Nc4ccc5[nH]ncc5c4Cl)s3)c2)C(=O)C1] |
TABLE 17-continued
| Example No. | Compound Structure |
|---|---|
| 44 | 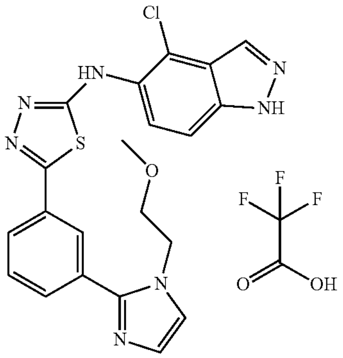 [SMILES: COCCn1ccnc1-c1cccc(-c2nnc(Nc3ccc4[nH]ncc4c3Cl)s2)c1 ; O=C(O)C(F)(F)F] |
| 47 | 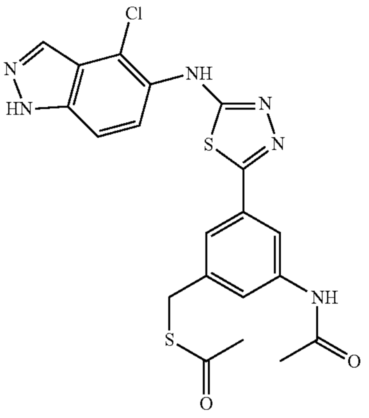 [SMILES: CC(=O)Nc1cc(CSC(C)=O)cc(-c2nnc(Nc3ccc4[nH]ncc4c3Cl)s2)c1] |
| 51 | 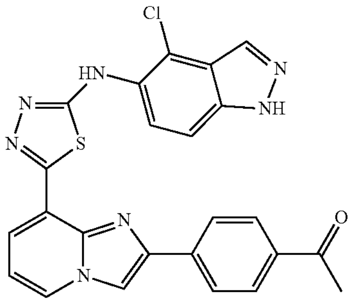 [SMILES: CC(=O)c1ccc(-c2cn3cccc(-c4nnc(Nc5ccc6[nH]ncc6c5Cl)s4)c3n2)cc1] |
| 49 | 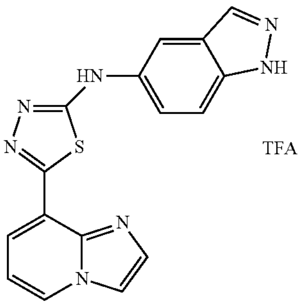 [SMILES: c1cc(-c2nnc(Nc3ccc4[nH]ncc4c3)s2)c2nccn2c1] TFA |

TABLE 17-continued

| Example No. | Compound Structure |
| --- | --- |
| 53 | 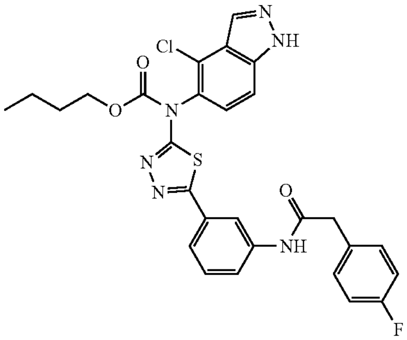 [SMILES: CCCCOC(=O)N(c1nnc(-c2cccc(NC(=O)Cc3ccc(F)cc3)c2)s1)c1ccc2[nH]ncc2c1Cl] |
| 55 | 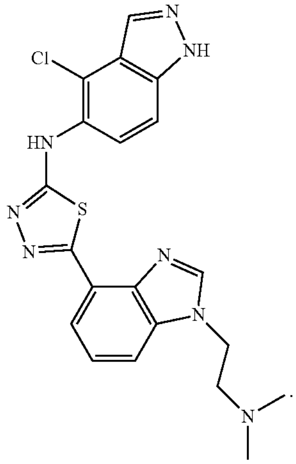 [SMILES: CN(C)CCn1cnc2c(-c3nnc(Nc4ccc5[nH]ncc5c4Cl)s3)cccc21] |

28. The compound of claim 1, wherein the compound is at least a five-fold more potent inhibitor of Rho-associated protein kinase isoform 2 than Rho-associated protein kinase isoform 1.

29. A pharmaceutical composition comprising a compound of claim 1 and a pharmaceutically acceptable carrier.

30. A method of treating a Rho-associated protein kinase isoform 2 disorder selected from the group consisting of an inflammatory disorder, immune disorder, fibrotic disorder, and cardiovascular disorder, comprising administering to a patient in need thereof a therapeutically effective amount of a compound of claim 1 to treat the disorder.

31. The method of claim 30, wherein the disorder is scleroderma, psoriasis, nonalcoholic steatohepatitis, giant cell arteritis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, ulcerative colitis, asthma, uveitis, rheumatoid arthritis, or epidermal hyperplasia.

32. A method of inhibiting a Rho-associated protein kinase isoform 2, comprising exposing a Rho-associated protein kinase isoform 2 to a compound of claim 1 to inhibit said Rho-associated protein kinase isoform 2.

* * * * *